US012464944B2

(12) United States Patent
Gao et al.

(10) Patent No.: US 12,464,944 B2
(45) Date of Patent: Nov. 4, 2025

(54) HETEROCYCLIC COMPOUND CONTAINING HETEROATOM SUBSTITUTED FLUORENE AND OPTOELECTRONIC DEVICE

(71) Applicant: Wuhan Tianma Micro-Electronics Co., Ltd., Wuhan (CN)

(72) Inventors: Wei Gao, Shanghai (CN); Wenpeng Dai, Shanghai (CN); Lei Zhang, Shanghai (CN); You Gao, Shanghai (CN); Lu Zhai, Shanghai (CN)

(73) Assignee: Wuhan Tianma Micro-Electronics Co., Ltd., Wuhan (CN)

( * ) Notice: Subject to any disclaimer, the term of this patent is extended or adjusted under 35 U.S.C. 154(b) by 942 days.

(21) Appl. No.: 17/667,346

(22) Filed: Feb. 8, 2022

(65) Prior Publication Data

US 2023/0172057 A1 Jun. 1, 2023

(30) Foreign Application Priority Data

Nov. 30, 2021 (CN) ......................... 202111452323.0

(51) Int. Cl.

| | |
|---|---|
| ***C07D 491/147*** | (2006.01) |
| ***C07D 491/048*** | (2006.01) |
| ***C07D 495/04*** | (2006.01) |
| ***C07D 519/00*** | (2006.01) |
| ***C09K 11/06*** | (2006.01) |
| ***H10K 85/60*** | (2023.01) |
| *H10K 50/15* | (2023.01) |
| *H10K 50/18* | (2023.01) |
| *H10K 50/844* | (2023.01) |

(52) U.S. Cl.

CPC ....... *H10K 85/636* (2023.02); *C07D 491/048* (2013.01); *C07D 495/04* (2013.01); *C07D 519/00* (2013.01); *C09K 11/06* (2013.01); *H10K 85/633* (2023.02); *C09K 2211/1018* (2013.01); *H10K 50/15* (2023.02); *H10K 50/18* (2023.02); *H10K 50/844* (2023.02); *H10K 85/615* (2023.02); *H10K 85/622* (2023.02); *H10K 85/626* (2023.02); *H10K 85/657* (2023.02); *H10K 85/6572* (2023.02); *H10K 85/6574* (2023.02)

(58) Field of Classification Search

None

See application file for complete search history.

(56) References Cited

U.S. PATENT DOCUMENTS

| | | | | |
|---|---|---|---|---|
| 2018/0179238 A1 | | 6/2018 | Banglin et al. | |
| 2019/0097138 A1 | | 3/2019 | Lee et al. | |
| 2023/0157159 A1 | * | 5/2023 | Kim | H10K 85/633 257/40 |
| 2024/0199559 A1 | * | 6/2024 | Li | C07D 269/02 |

FOREIGN PATENT DOCUMENTS

| | | | | | |
|---|---|---|---|---|---|
| CN | 107936957 A | | 4/2018 | |
| CN | 105884786 B | | 8/2018 | |
| CN | 111662225 A | | 9/2020 | |
| CN | 111675698 A | | 9/2020 | |
| CN | 111848534 A | * | 10/2020 | C07D 253/10 |
| CN | 112778320 A | | 5/2021 | |
| CN | 113582938 A | | 11/2021 | |
| CN | 113620819 A | | 11/2021 | |
| KR | 20140133405 A | * | 11/2014 | C07D 491/14 |
| KR | 20210142561 A | * | 11/2021 | C07D 491/048 |
| WO | 20200027389 A1 | | 2/2020 | |

OTHER PUBLICATIONS

Machine translation of WO 2020/027389, translation generated Feb. 2025, 20 pages. (Year: 2025).*

* cited by examiner

*Primary Examiner* — Robert S Loewe

(74) *Attorney, Agent, or Firm* — Anova Law Group, PLLC

(57) ABSTRACT

A heterocyclic compound containing heteroatom substituted fluorene and an optoelectronic device are provided. The heterocyclic compound includes a structure in Formula I:

Formula I

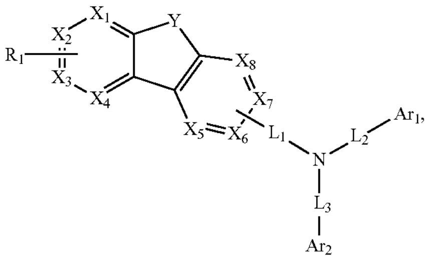

where Y is selected from O or S; at least one of $X_1$, $X_2$, $X_3$, $X_4$, $X_5$, $X_6$, $X_7$ and $X_8$ is a N atom, and rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group condensed with adjacent groups; and $R_2$ is selected from a hydrogen atom, a deuterium atom, a substituted or unsubstituted C1-C5 alkyl group, a halogen, a cyano group, or an amino group.

16 Claims, 1 Drawing Sheet

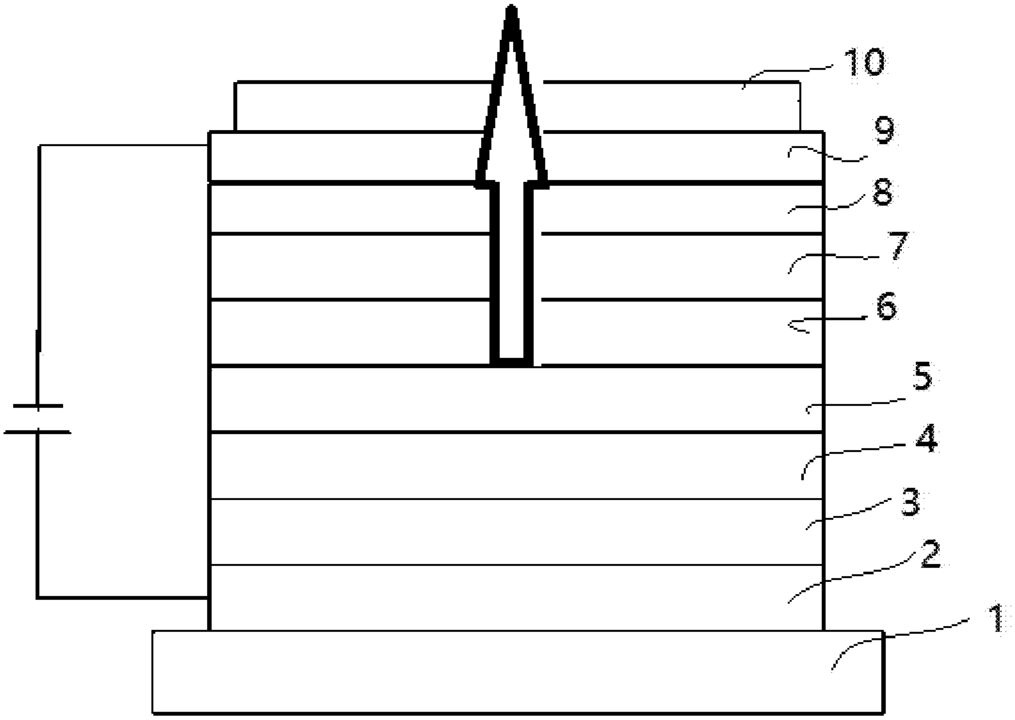
10
9
8
7
6
5
4
3
2
1

HETEROCYCLIC COMPOUND CONTAINING HETEROATOM SUBSTITUTED FLUORENE AND OPTOELECTRONIC DEVICE

CROSS-REFERENCE TO RELATED APPLICATION

This application claims the priority of Chinese patent application No. 202111452323.0, filed on Nov. 30, 2021, the entirety of which is incorporated herein by reference.

FIELD

The present disclosure generally relates to the field of organic electroluminescent material technology and, more particularly, relates to a heterocyclic compound containing heteroatom substituted fluorene and an optoelectronic device.

BACKGROUND

According to a direction of light emitted by an organic light-emitting layer, organic light-emitting diode (OLED) display can be divided into a bottom-emitting OLED display and a top-emitting OLED display. In the bottom-emitting OLED display, light emits towards a direction facing the substrate, a reflective electrode is formed over the organic light-emitting layer, and a transparent electrode is formed under the organic light-emitting layer. If the OLED display is an active matrix OLED display, a portion of the thin film transistors formed therein does not transmit light, such that a light-emitting area is reduced. On the other hand, in the top-emitting OLED display, the transparent electrode is formed over the organic light-emitting layer, and the reflective electrode is formed under the organic light-emitting layer, such that light emits towards a direction opposite to the substrate, thereby increasing the light transmission area and improving the brightness.

Currently, a refractive index of an OLED device cannot meet market demand, and the light extraction effect is insufficient. The difference in measured refractive indices for respective wavelength regions of the blue light, green light, and red light is substantially large. Therefore, not all the light emitted by the blue, green, and red light-emitting devices can simultaneously obtain the high light extraction efficiency.

In view of the low light extraction efficiency of an existing OLED device, a capping layer (CPL), e.g., a light extraction material, needs to be added in the device structure. According to the principles of optical absorption and refraction, a refractive index of a material of the surface capping layer is as high as possible.

SUMMARY

One aspect of the present disclosure provides a heterocyclic compound containing heteroatom substituted fluorene. The heterocyclic compound includes a structure in Formula I:

Formula I

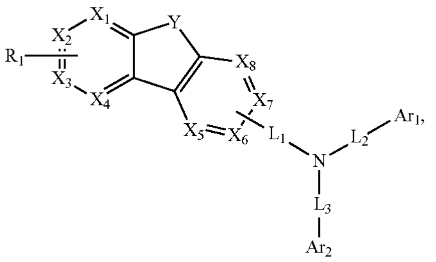

where Y is selected from O or S; at least one of $X_1$, $X_2$, $X_3$, $X_4$, $X_5$, $X_6$, $X_7$ and $X_8$ is a N atom, and rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group condensed with adjacent groups; and $R_2$ is selected from a hydrogen atom, a deuterium atom, a substituted or unsubstituted C1-C5 alkyl group, a halogen, a cyano group, or an amino group.

Another aspect of the present disclosure provides a display panel. The display panel includes an organic light-emitting device. The organic light-emitting device includes an anode, a cathode, and an organic thin layer disposed between the anode and the cathode. The cathode is covered with a capping layer, and the capping layer includes any one or a combination of at least two of heterocyclic compounds. Each heterocyclic compound includes a structure in Formula I:

Formula I

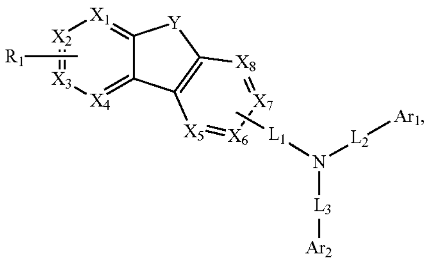

where Y is selected from O or S; at least one of $X_1$, $X_2$, $X_3$, $X_4$, $X_5$, $X_6$, $X_7$ and $X_8$ is a N atom, and rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group condensed with adjacent groups; and $R_2$ is selected from a hydrogen atom, a deuterium atom, a substituted or unsubstituted C1-C5 alkyl group, a halogen, a cyano group, or an amino group.

Another aspect of the present disclosure provides a display device. The display device includes a display panel. The display panel includes an organic light-emitting device. The organic light-emitting device includes an anode, a cathode, and an organic thin layer disposed between the anode and the cathode. The cathode is covered with a capping layer, and the capping layer includes any one or a combination of at least two of heterocyclic compounds. Each heterocyclic compound includes a structure in Formula I:

Formula I

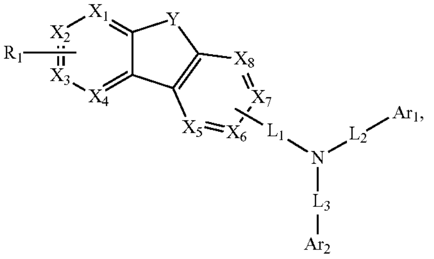

where Y is selected from O or S; at least one of $X_1$, $X_2$, $X_3$, $X_4$, $X_5$, $X_6$, $X_7$ and $X_8$ is a N atom, and rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group condensed with adjacent groups; and $R_2$ is selected from a hydrogen atom, a deuterium atom, a substituted or unsubstituted C1-C5 alkyl group, a halogen, a cyano group, or an amino group.

Other aspects of the present disclosure can be understood by those skilled in the art in light of the description, the claims, and the drawings of the present disclosure.

BRIEF DESCRIPTION OF THE DRAWINGS

To more clearly illustrate the embodiments of the present disclosure, the drawings will be briefly described below. The drawings in the following description are certain embodiments of the present disclosure, and other drawings may be obtained by a person of ordinary skill in the art in view of the drawings provided without creative efforts.

The figure illustrates a schematic diagram of an exemplary organic light-emitting device consistent with disclosed embodiments of the present disclosure.

DETAILED DESCRIPTION OF THE DISCLOSURE

Reference will now be made in detail to exemplary embodiments of the disclosure, which are illustrated in the accompanying drawings. Wherever possible, the same reference numbers will be used throughout the drawings to refer to the same or the alike parts. The described embodiments are some but not all of the embodiments of the present disclosure. Based on the disclosed embodiments, persons of ordinary skill in the art may derive other embodiments consistent with the present disclosure, all of which are within the scope of the present disclosure.

Similar reference numbers and letters represent similar terms in the following FIGURES, such that once an item is defined in one FIGURE, it does not need to be further discussed in subsequent FIGURES.

The present disclosure provides a heterocyclic compound containing heteroatom substituted fluorene. The heterocyclic compound containing heteroatom substituted fluorene may have a structure shown in Formula I:

Formula I

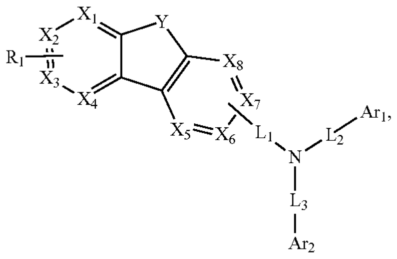

where Y may be selected from O or S; at least one of $X_1$, $X_2$, $X_3$, $X_4$, $X_5$, $X_6$, $X_7$ and $X_8$ may be a N atom, and the rest may be $CR_2$; $L_1$, $L_2$, and $L_3$ may be independently selected from single bond, substituted or unsubstituted aromatic groups; $Ar_1$ and $Ar_2$ may be independently selected from substituted or unsubstituted aromatic groups or heteroaryl groups; $R_1$ may be selected from a hydrogen atom, a deuterium atom, or an aromatic group or a heteroaryl group condensed with adjacent groups; and $R_2$ may be selected from a hydrogen atom, a deuterium atom, a substituted or unsubstituted C1-C5 alkyl group, a halogen, a cyano group, or an amino group.

The present disclosure provides a heterocyclic compound containing heteroatom substituted fluorene and an optoelectronic device. The prepared heterocyclic compound may have a substantially high refractive index in the entire visible light region. The difference in measured refractive indices of the heterocyclic compound for respective wavelength regions of blue light, green light, and red light may be substantially small, and the light extraction efficiency of the heterocyclic compound in a blue light device, a green light device and a red light device may be substantially high, thereby achieving a substantially high device efficiency. In the present disclosure, by introducing heteroatom substituted fluorene in the molecular structure, although the molecular volume change is substantially small, the polarizability of the molecule may be greatly improved, which may comprehensively improve the refractive index of the heterocyclic compound in wavelength regions of the blue light, green light, and red light.

In one embodiment, the substituent of the aromatic group or heteroaryl group may be selected from a C1-C10 alkyl group or a C1-C10 alkoxy group.

In one embodiment, any one, two or three of $X_1$, $X_2$, $X_3$, $X_4$, $X_5$, $X_6$, $X_7$, and $X_8$ may be a N atom, and the rest may be $CR_2$.

In one embodiment, the $R_2$ may be a hydrogen atom, a deuterium atom, F, Cl, Br, a cyano group, or a trifluoromethyl group.

In one embodiment, the heteroatom substituted fluorene in Formula I may have any one of the following structures:

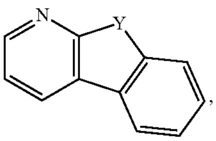,
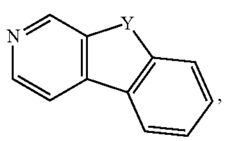,
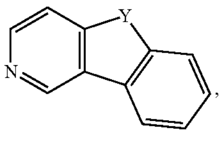,
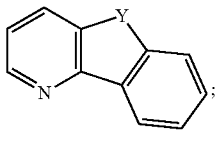;

where Y may be selected from O or S, and the above structure may be connected to $L_1$ through any carbon atom.

In one embodiment, the heteroatom substituted fluorene in Formula I may have any one of the following structures:

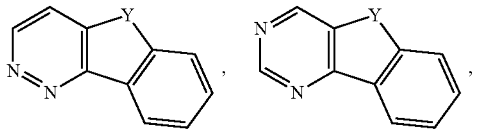
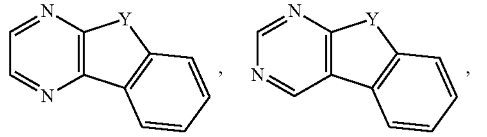
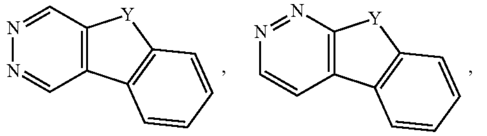
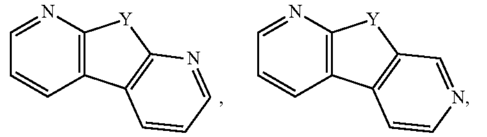
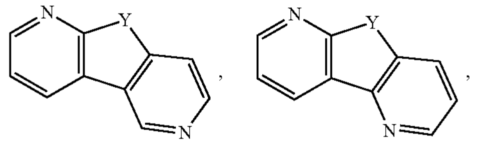
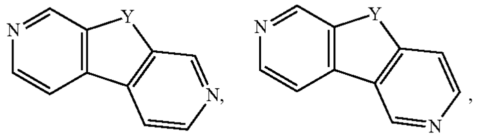
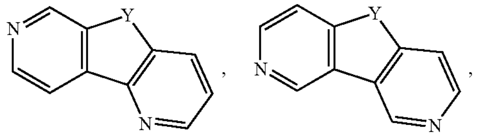
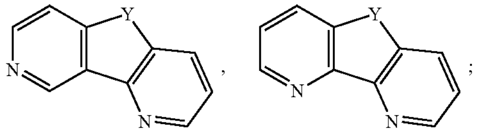

where Y may be selected from O or S, and the above structure may be connected to $L_1$ through any carbon atom.

In one embodiment, the heteroatom substituted fluorene in Formula I may have any one of the following structures:

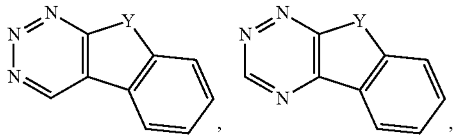
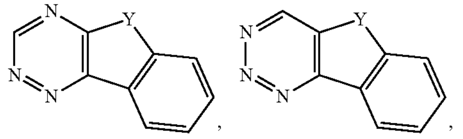

-continued

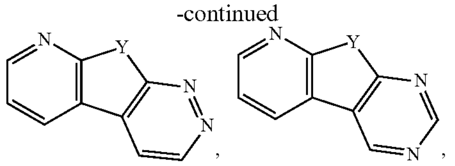
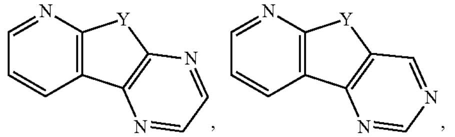
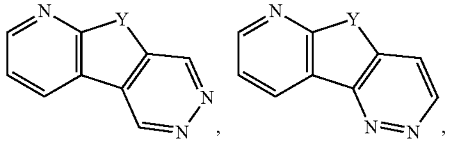
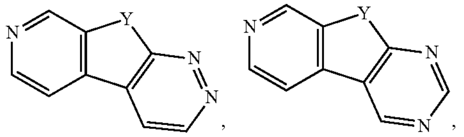
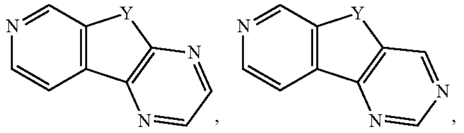
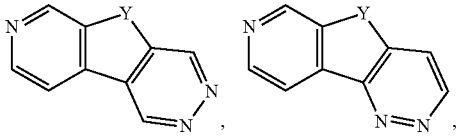
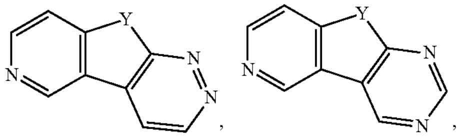
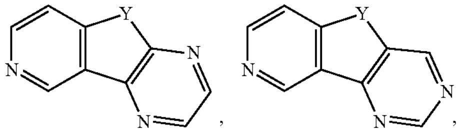
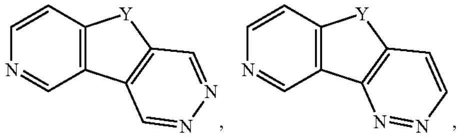
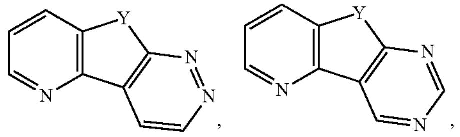
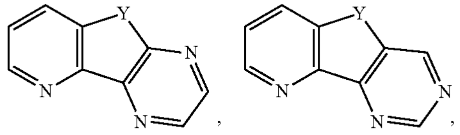
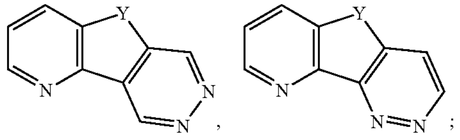

where Y may be selected from O or S, and the above structure may be connected to $L_1$ through any carbon atom.

In one embodiment, the heteroatom substituted fluorene in Formula I may have any one of the following structures:
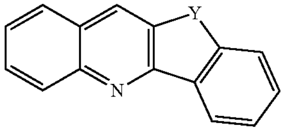
,
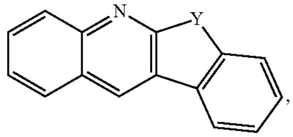
,
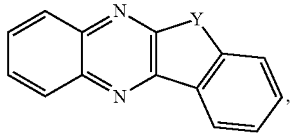
,
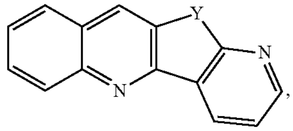
,
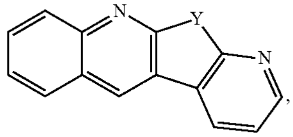
,
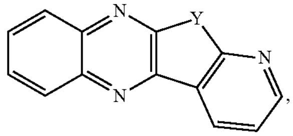
,
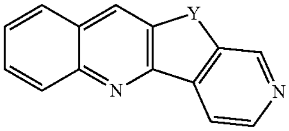
,
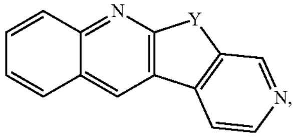
,
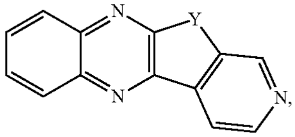
,
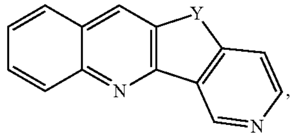
,
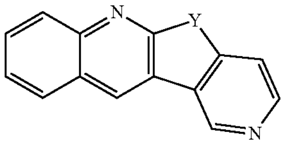
,
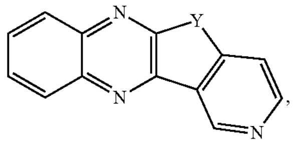
,
-continued
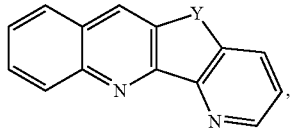
,
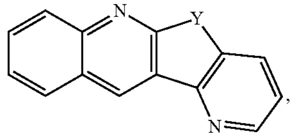
,
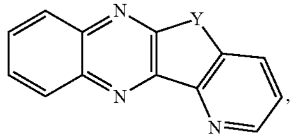
,
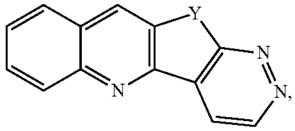
,
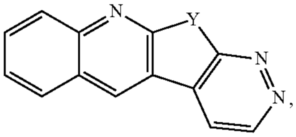
,
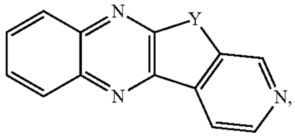
,
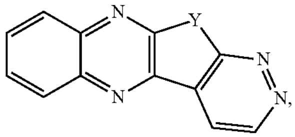
,
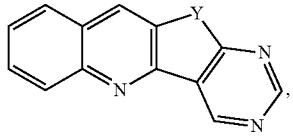
,
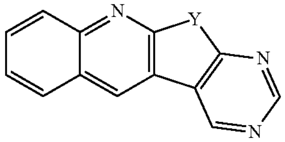
,
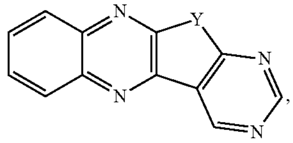
,
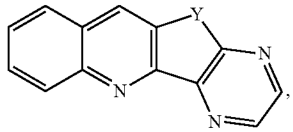
,
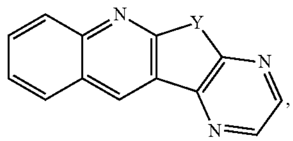
, -continued
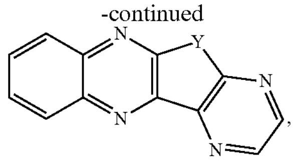
,
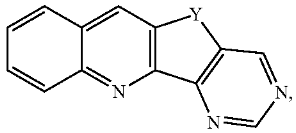
,
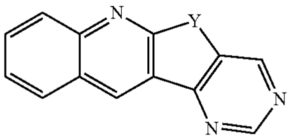
,
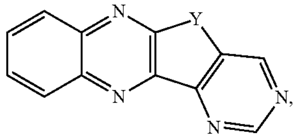
,
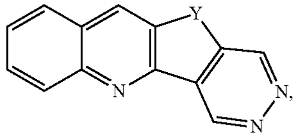
,
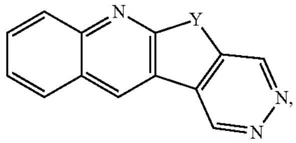
,
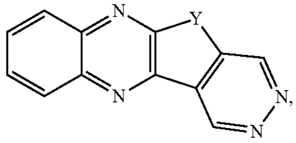
,
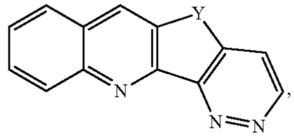
,
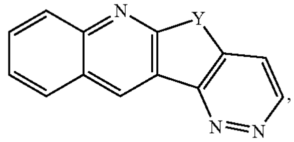
,
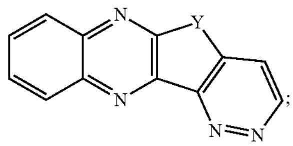
;
where Y may be selected from O or S, and the above structure may be connected to $L_1$ through any carbon atom.
The above heteroatom substituted fluorene may refer to the following structure in the structural formula:
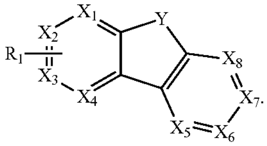
.
In one embodiment, the heterocyclic compound may have any one of the following structures:
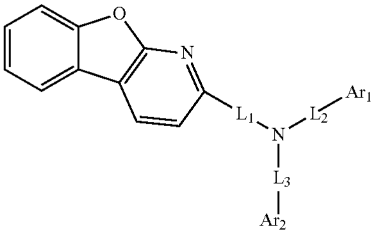
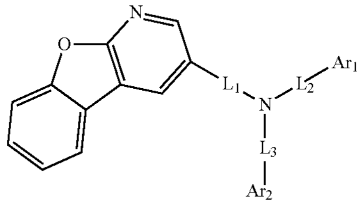
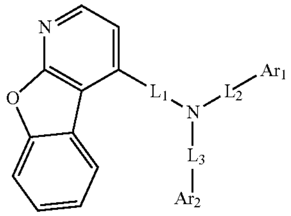
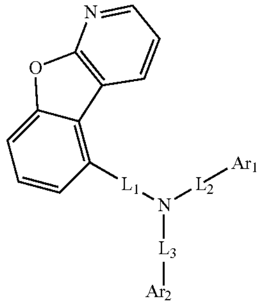
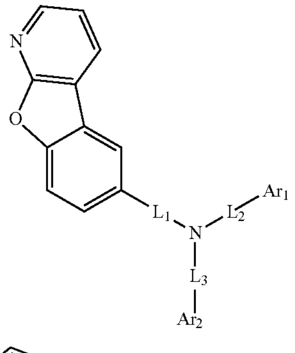
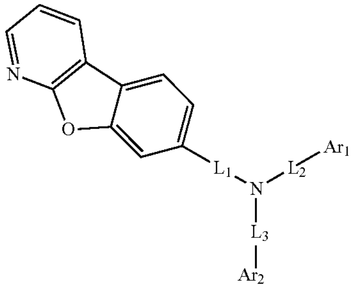

-continued
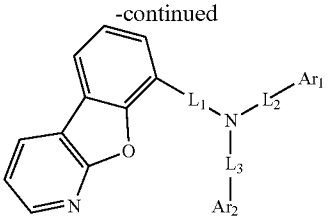
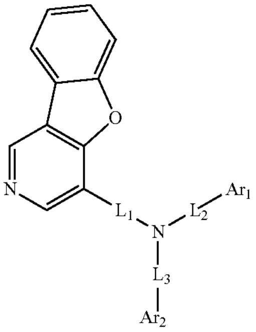
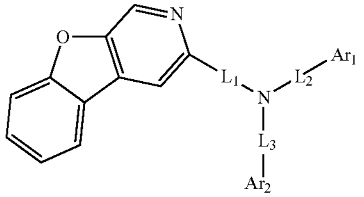
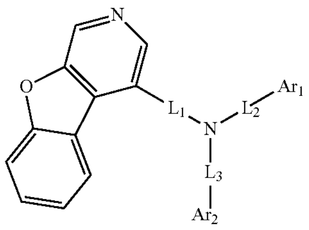
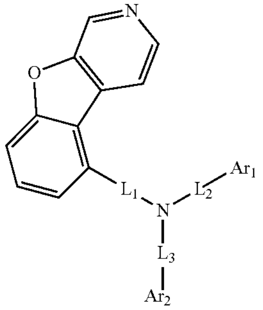
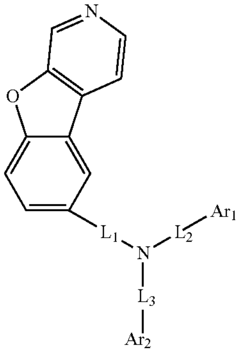
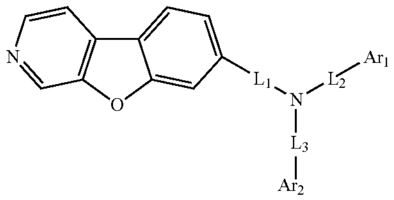
-continued
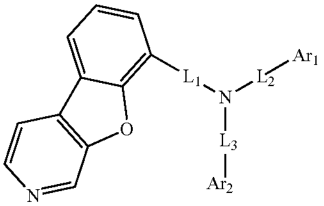
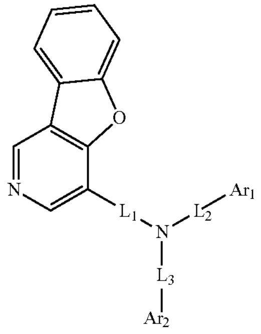
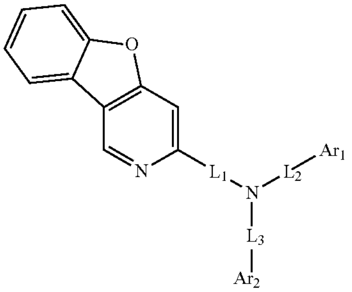
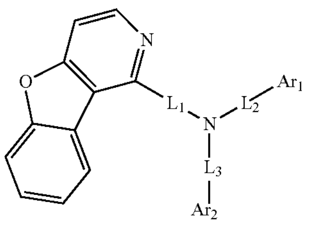
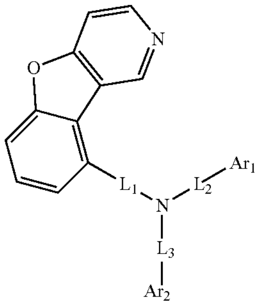
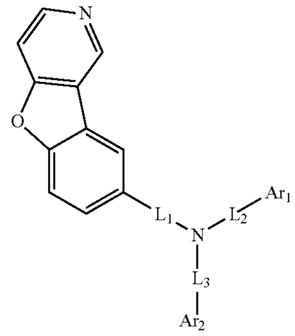
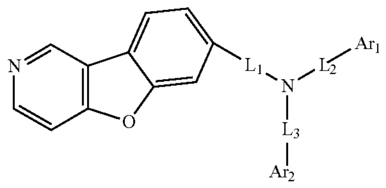

-continued
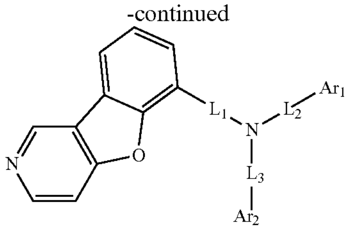
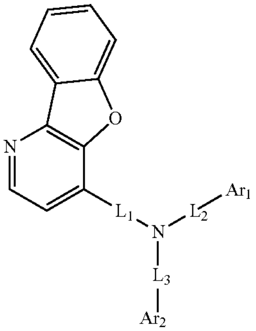
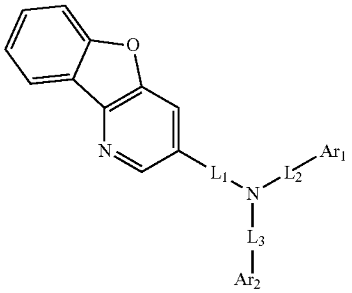
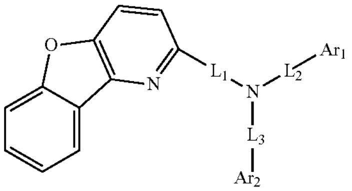
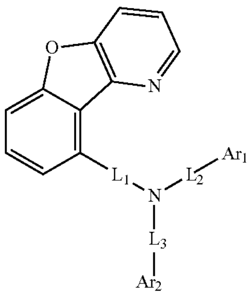
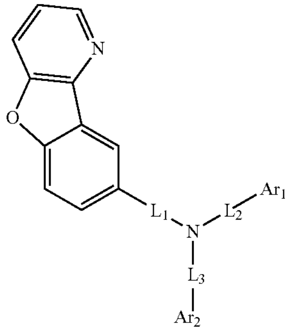
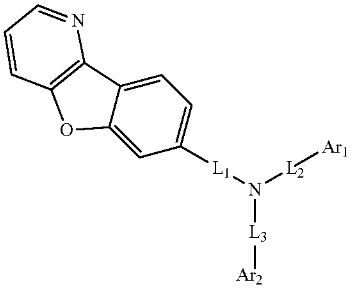
-continued
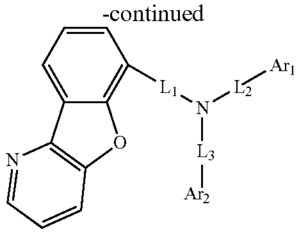
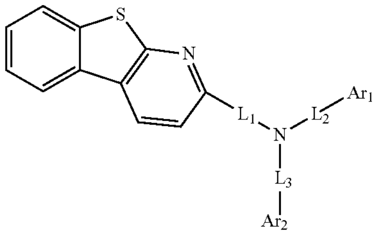
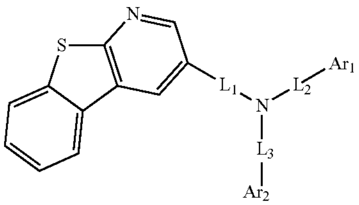
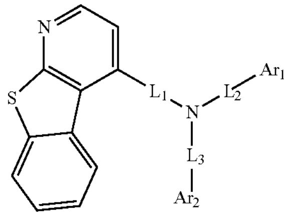
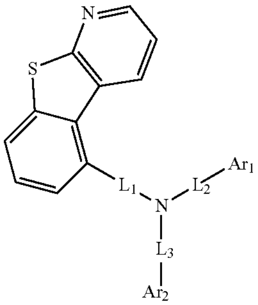
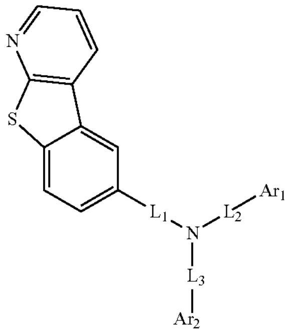
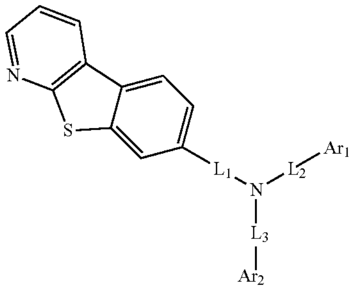

-continued
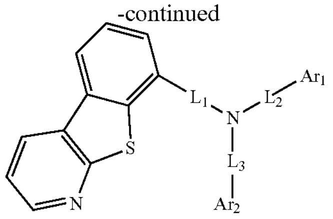
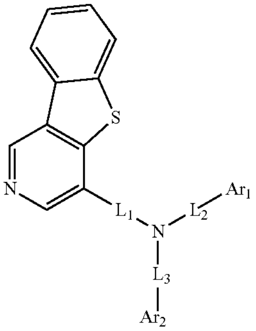
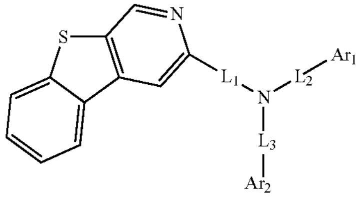
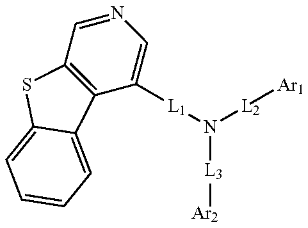
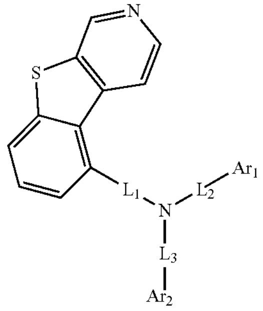
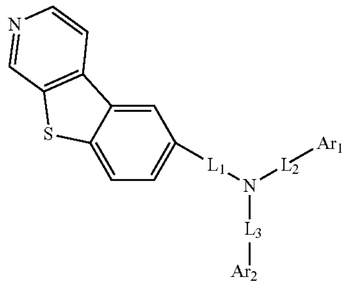
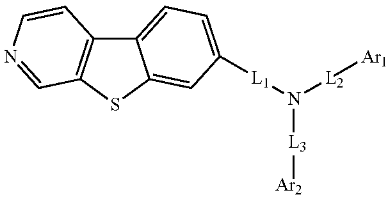
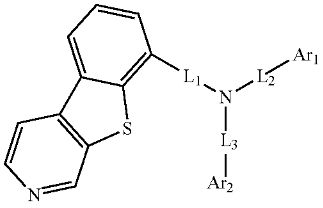
-continued
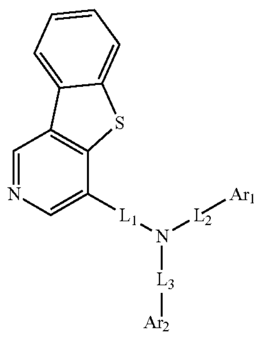
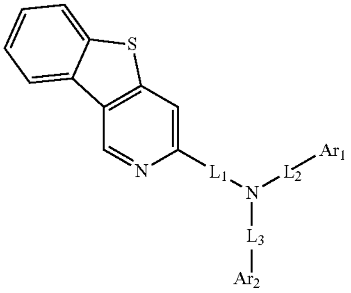
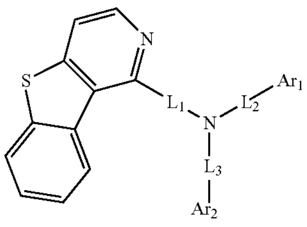
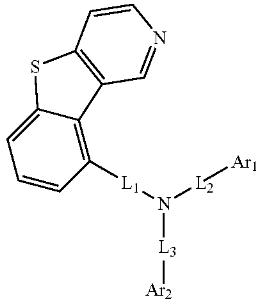
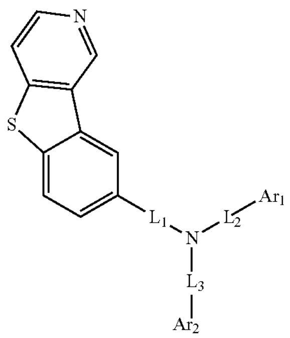
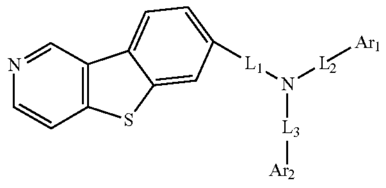
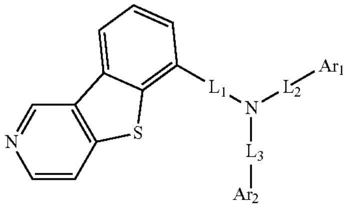

-continued
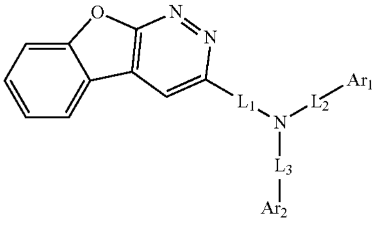
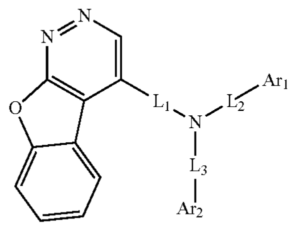
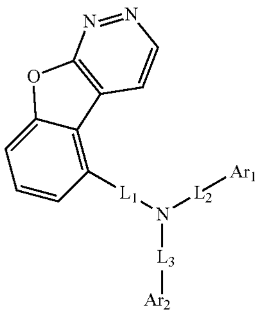
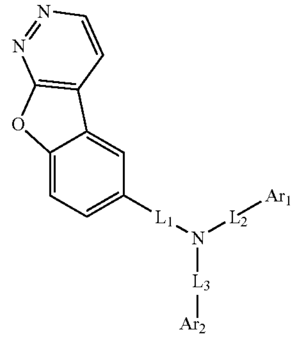
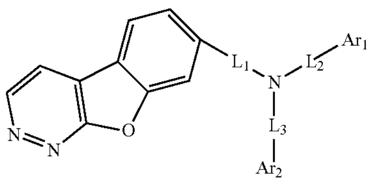
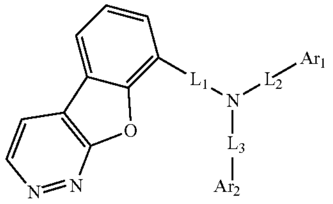
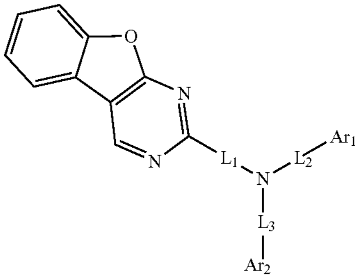
-continued
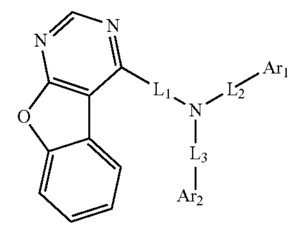
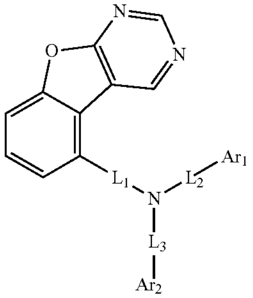
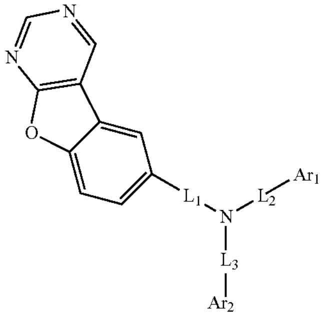
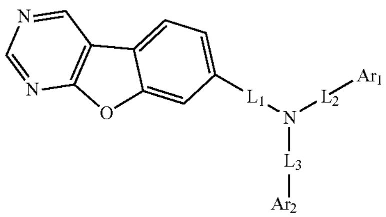
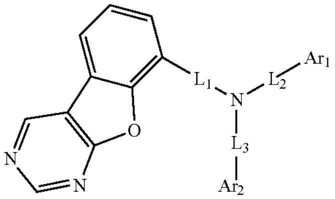
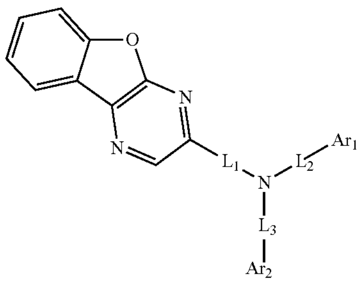
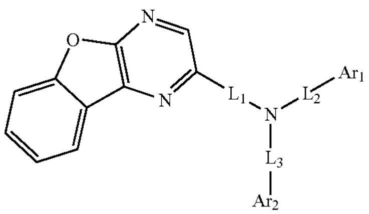

-continued
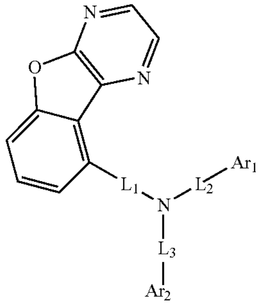
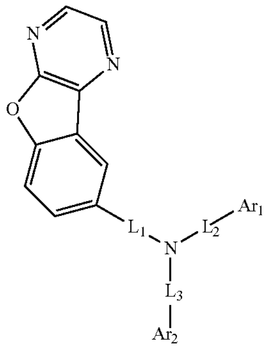
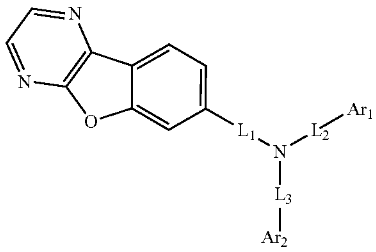
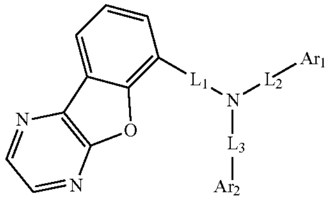
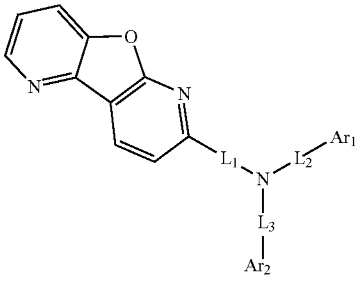
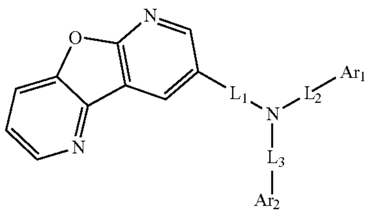
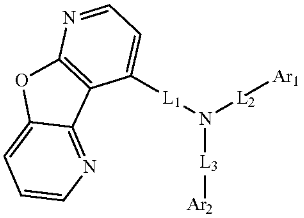
-continued
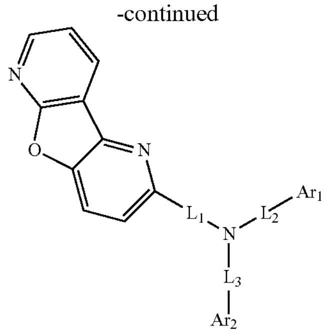
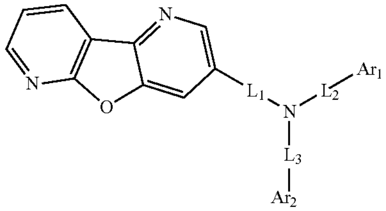
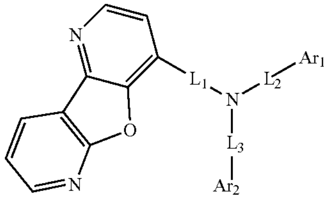
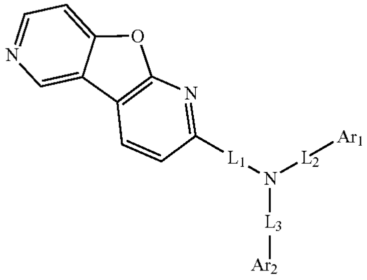
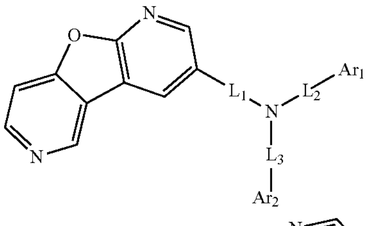
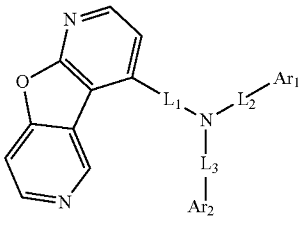
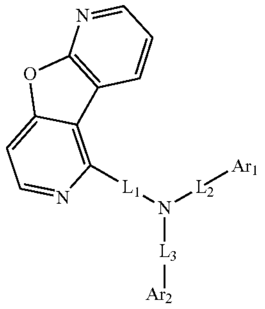

-continued
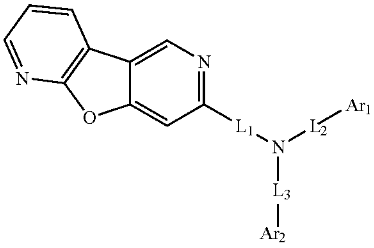
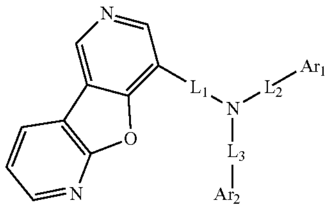
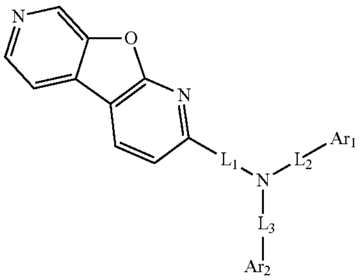
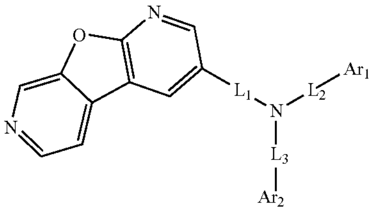
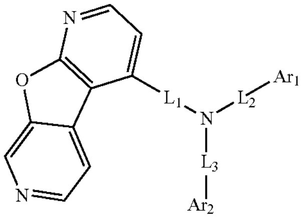
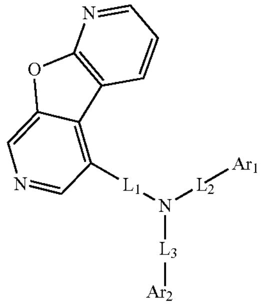
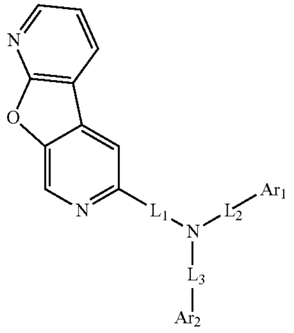
-continued
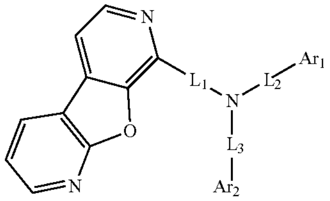
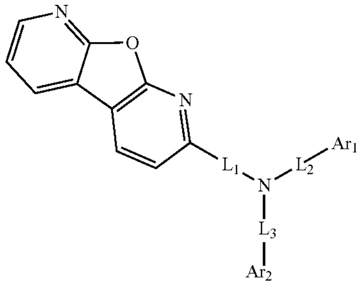
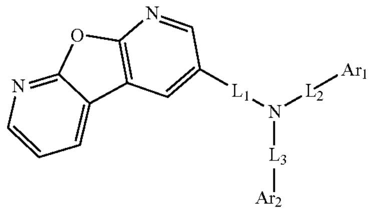
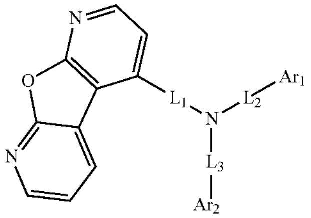
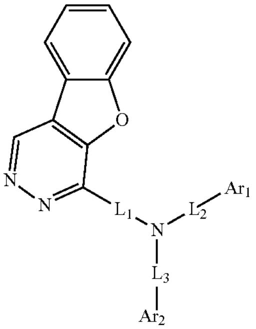
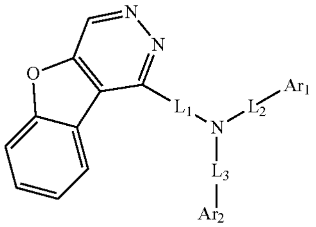
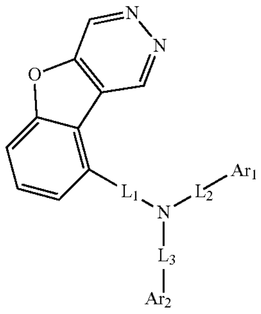

-continued
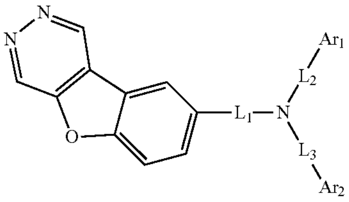
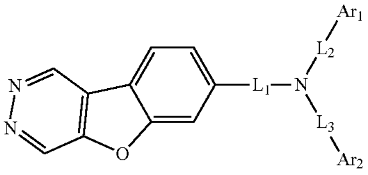
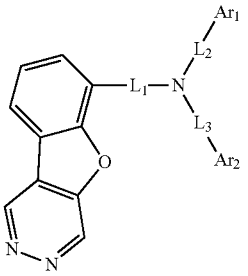
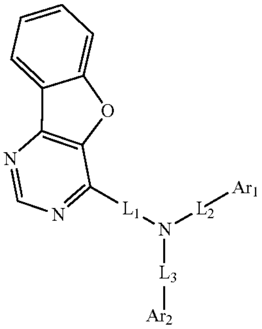
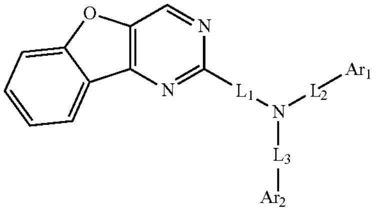
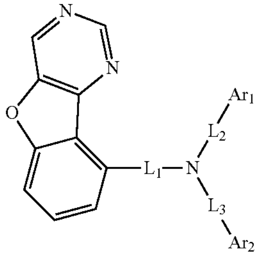
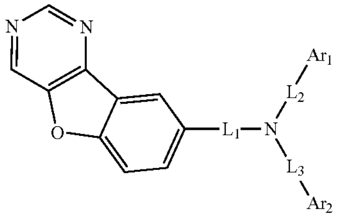
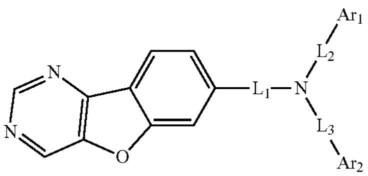
-continued
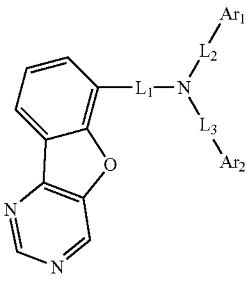
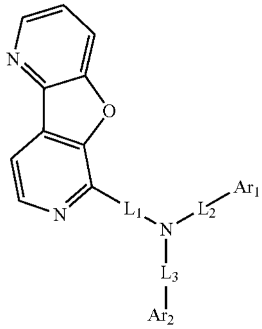
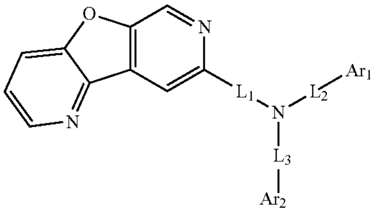
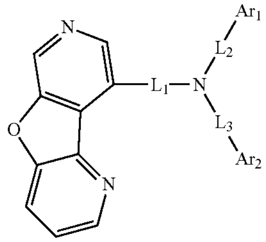
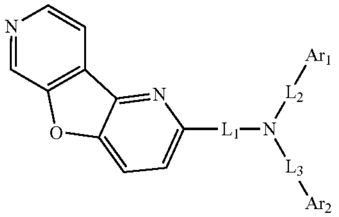
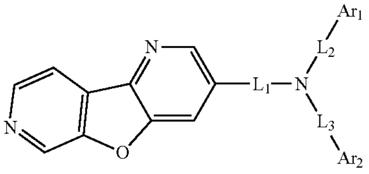
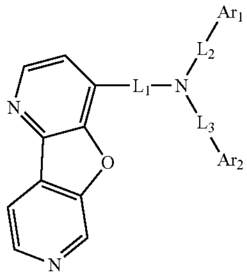
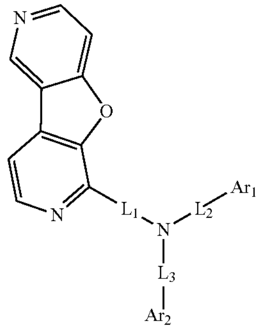
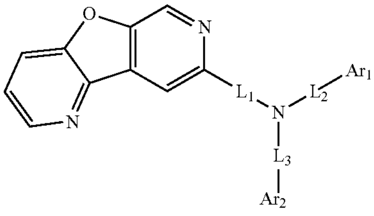

-continued
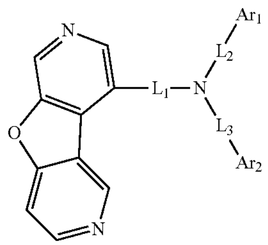
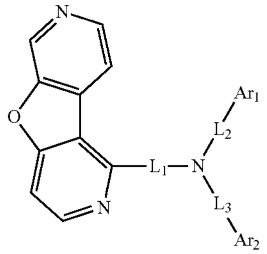
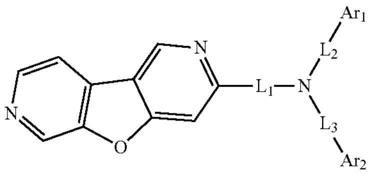
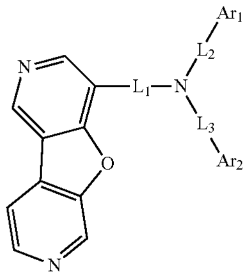
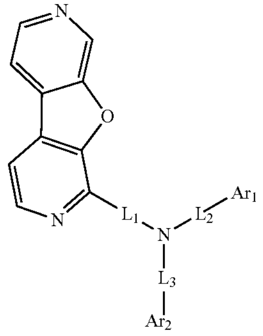
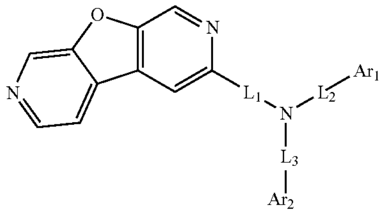
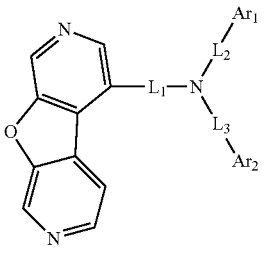
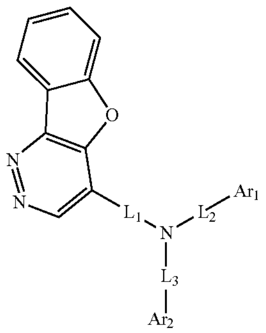
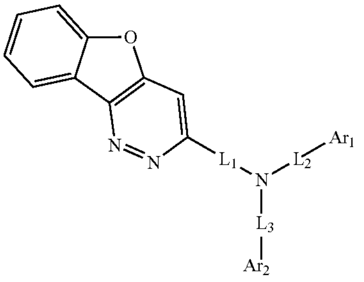
-continued
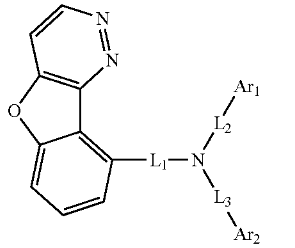
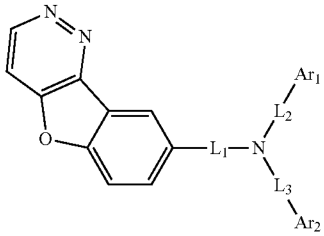
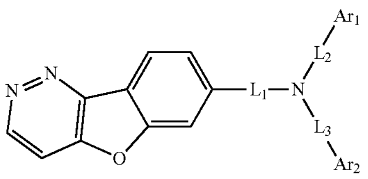
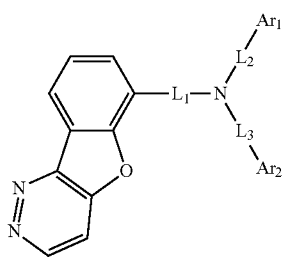
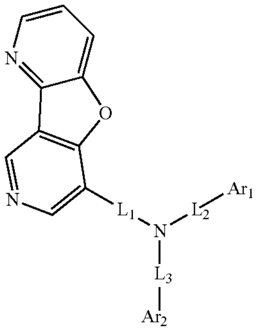
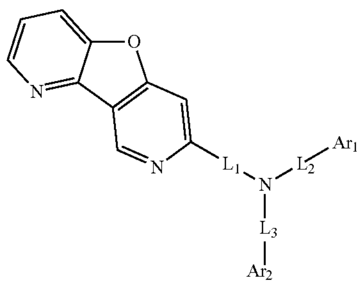
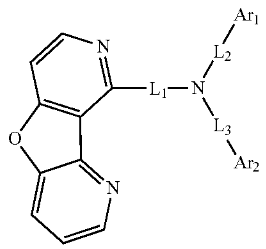

-continued
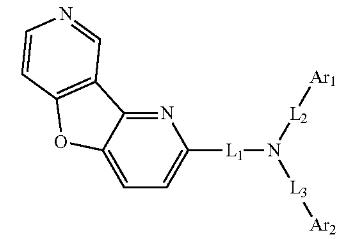
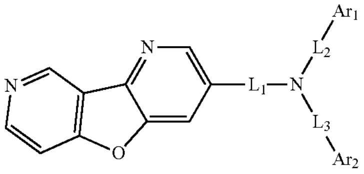
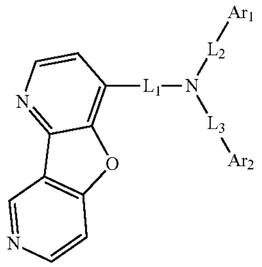
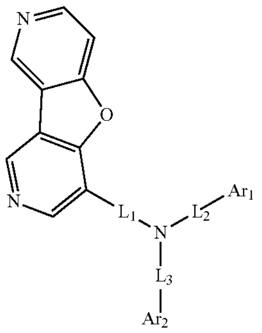
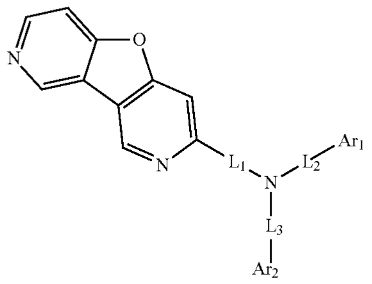
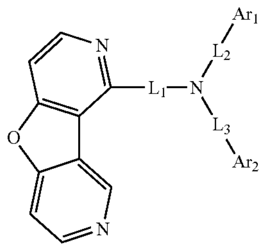
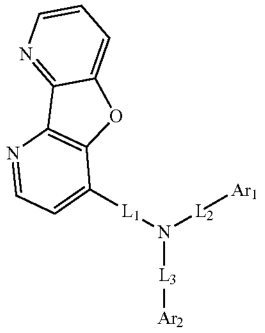
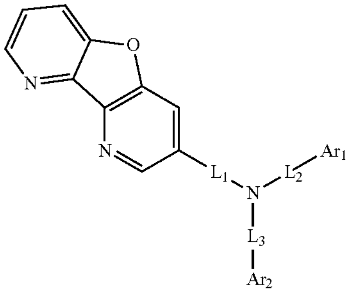
-continued
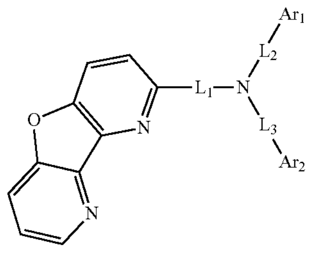
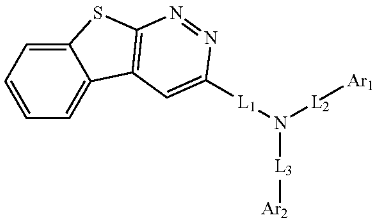
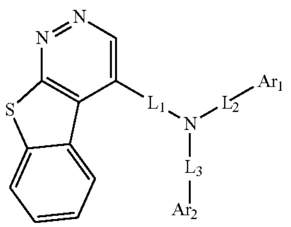
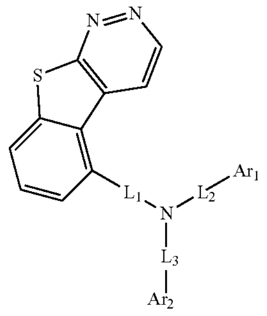
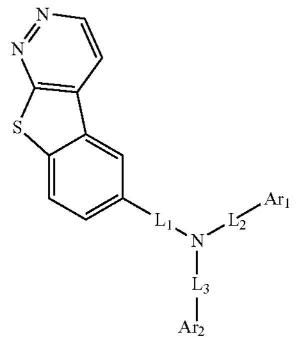
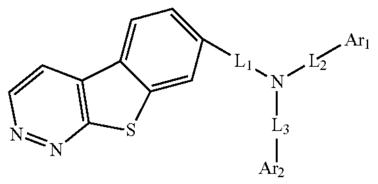
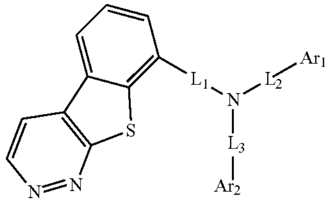

-continued
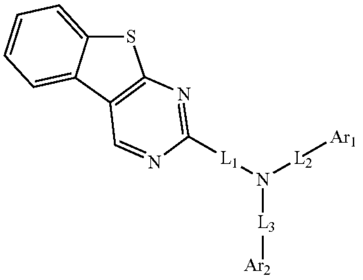
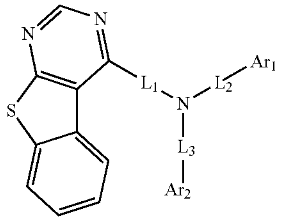
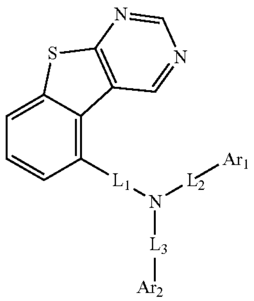
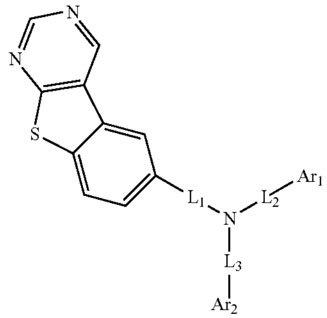
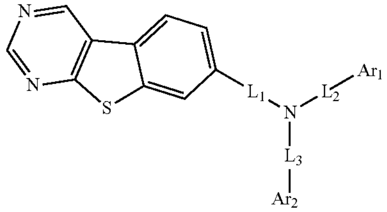
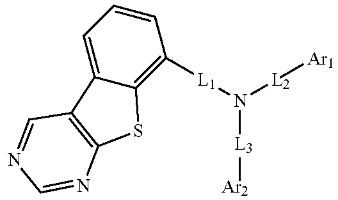
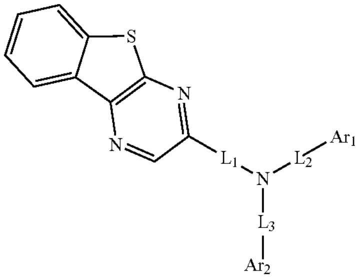
-continued
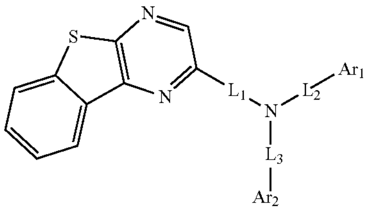
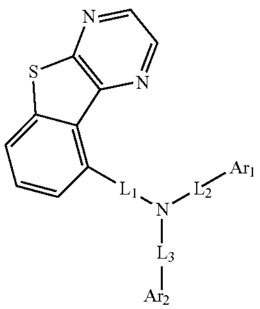
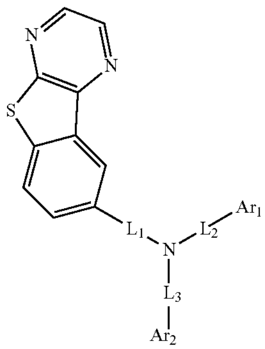
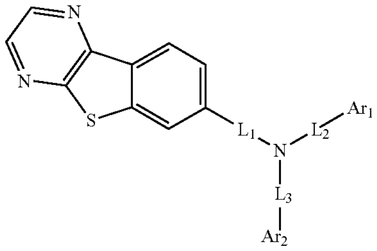
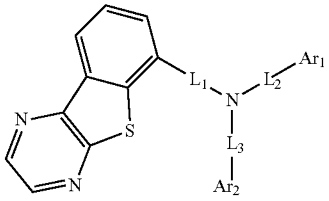
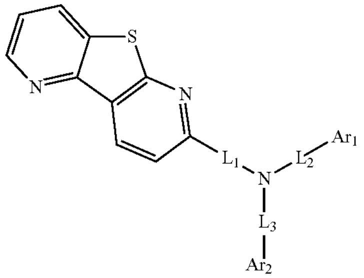
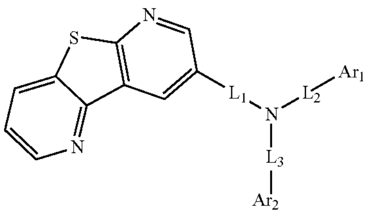
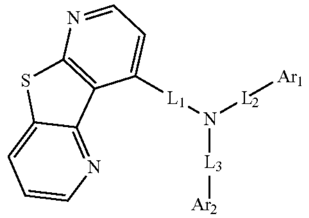

-continued

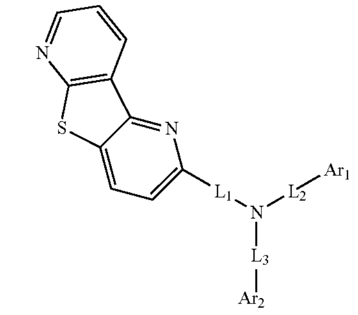

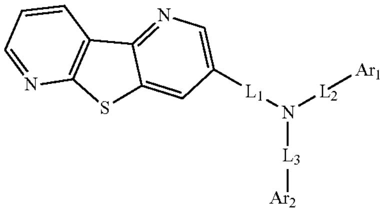

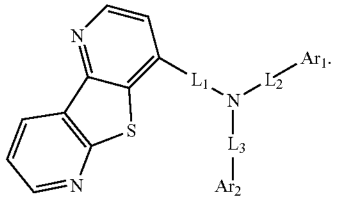

In one embodiment, the $L_1$, $L_2$, and $L_3$ may be independently selected from single bond, substituted or unsubstituted aromatic groups. The substituent of the aromatic group may be selected from deuterium atom.

In one embodiment, the $L_1$, $L_2$, and $L_3$ may be independently selected from phenylene, biphenylene, terphenylene, naphthylene, anthrylene, phenanthrylene, pyrenylene, fluoranthene, triphenylene or fluorenylene.

In one embodiment, the $L_1$, $L_2$, and $L_3$ may be independently selected from any one of the following structures:

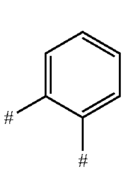
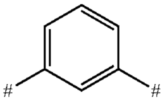
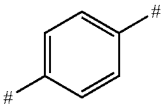
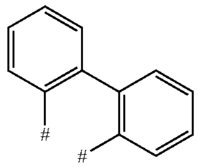
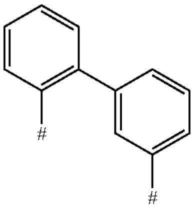
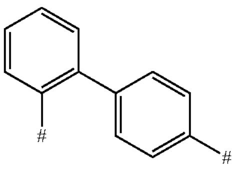
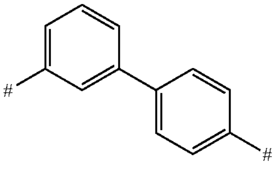

-continued

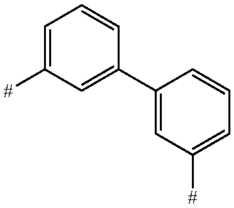
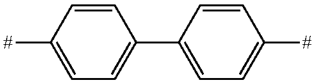
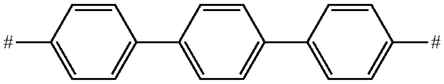
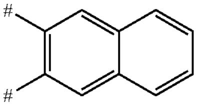
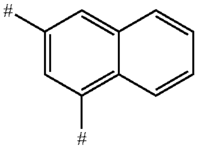
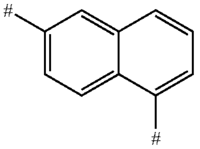
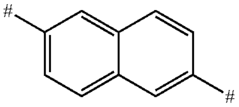
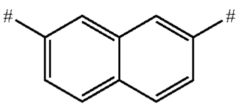
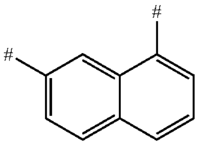
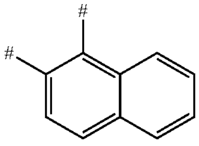
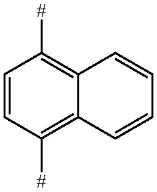
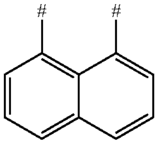
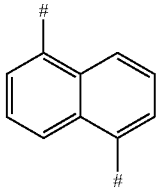
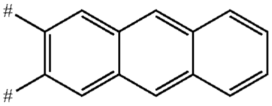
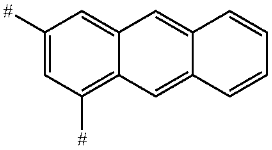
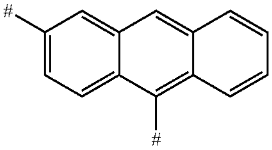
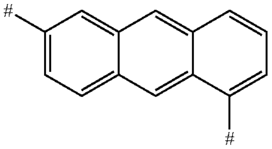
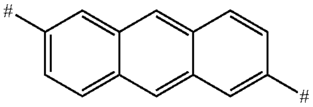
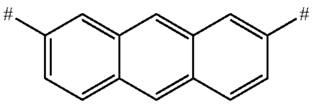

-continued
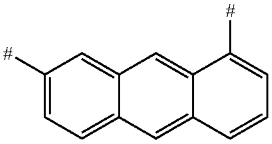
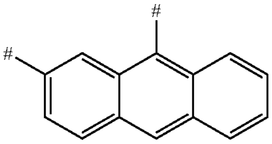
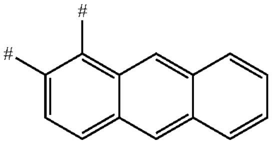
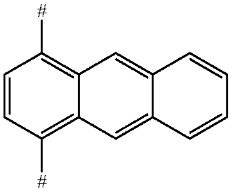
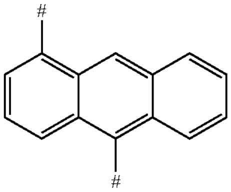
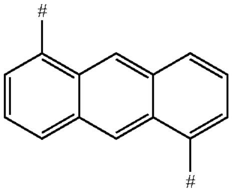
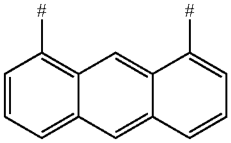
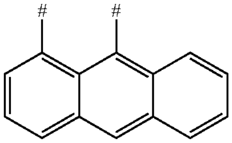
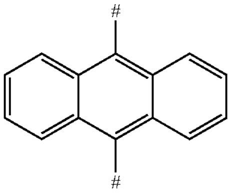
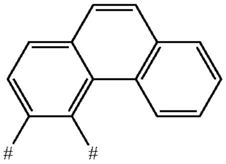
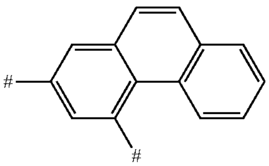
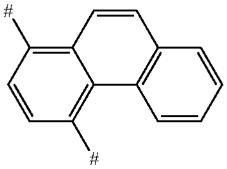
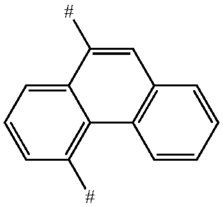
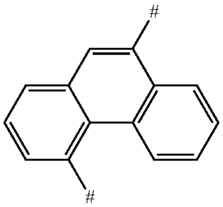
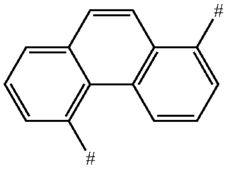
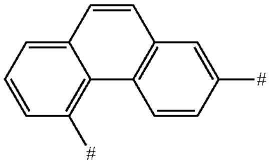
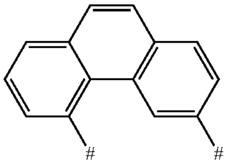
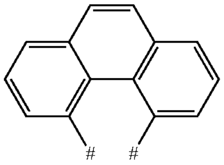
-continued
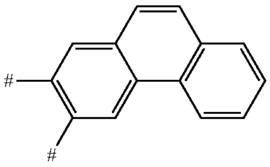
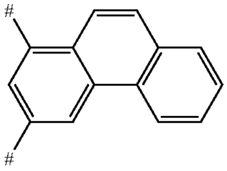
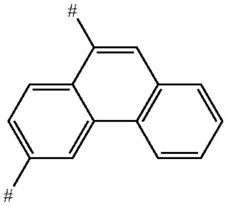
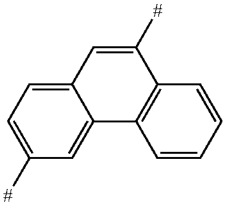
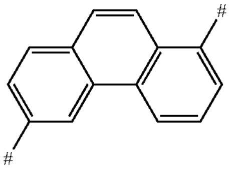
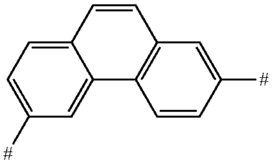
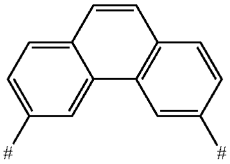
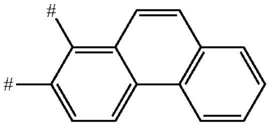
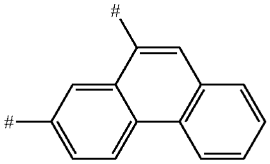
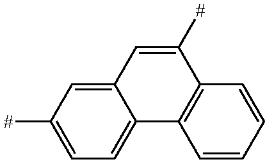
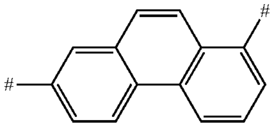
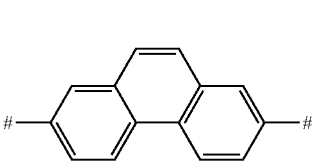
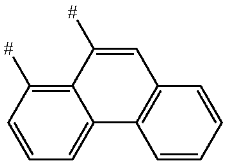
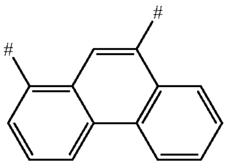
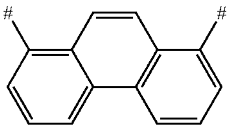
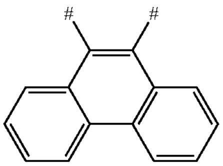
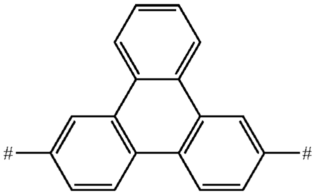

-continued

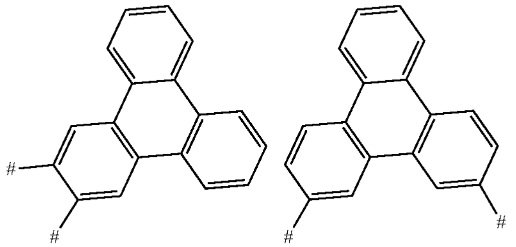

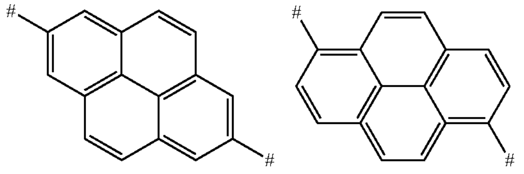

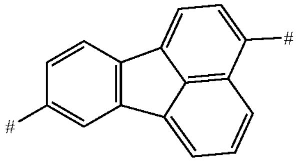

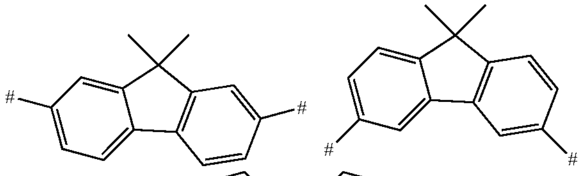

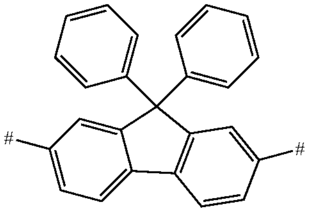

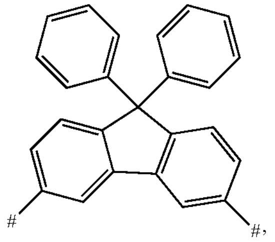

where #may represent a connection position.

In one embodiment, the $Ar_1$ and $Ar_2$ may be independently selected from substituted or unsubstituted aromatic groups or heteroaryl groups. The substituent of the aforementioned aromatic group or heteroaryl group may be selected from a deuterium atom.

In one embodiment, the $Ar_1$ and $Ar_2$ may be independently selected from substituted or unsubstituted condensed aromatic groups or condensed heteroaryl groups. The substituent of the aforementioned condensed aromatic group or condensed heteroaryl group may be selected from a deuterium atom.

In one embodiment, the $Ar_1$ and $Ar_2$ may be independently selected from phenyl, biphenyl, terphenyl, naphthyl, anthracenyl, phenanthryl, pyrenyl, fluoranthene, triphenylene, fluorenyl, pyrrolyl, furyl, thienyl, pyridyl, pyrimidinyl, pyridazinyl, triazinyl, benzofuranyl, benzothienyl, dibenzofuranyl, dibenzothienyl, oxazolyl, oxadiazolyl, thiazolyl, thiadiazolyl, benzoxazolyl, benzothiazolyl, imidazolyl, pyrazolyl, indolyl, quinolinyl, isoquinolinyl, purinyl, isoxazolyl, isothiazole, pyrone, pyrazinyl, thienofuranyl, thienopyrrolyl, pyrrolopyridyl, pyridopyrimidinyl, pyrazolooxazolyl, pyrazinopyridazinyl, imidazothiazolyl or coumarin.

In one embodiment, the $Ar_1$ and $Ar_2$ may be independently selected from any one of the following structures:

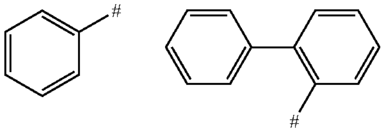

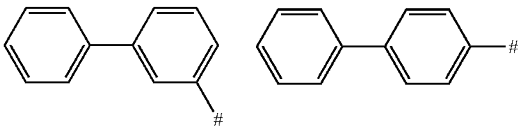

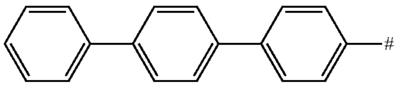

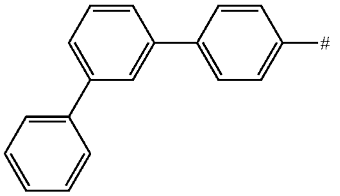

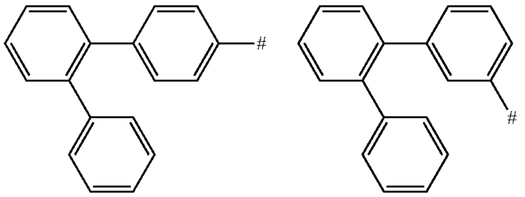

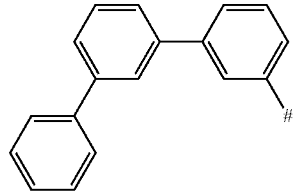

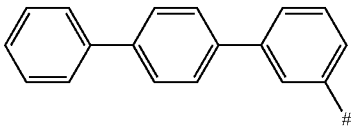

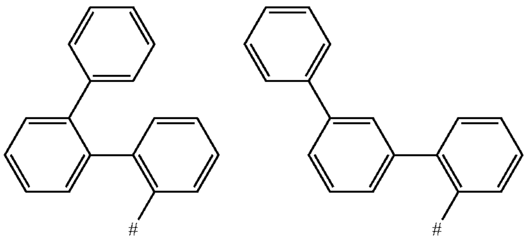

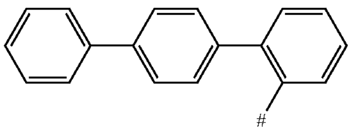

-continued
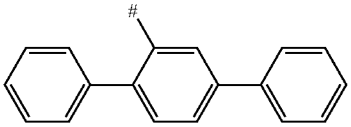
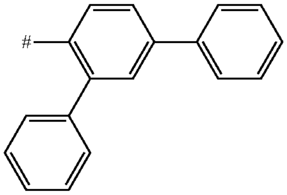
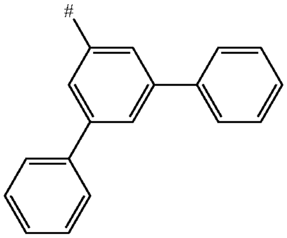
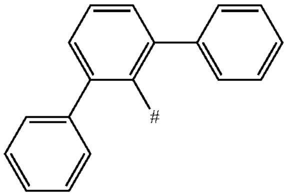
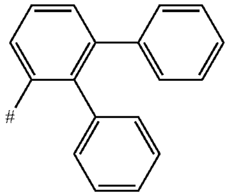
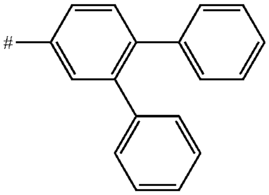
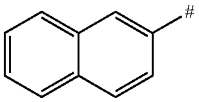
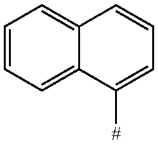
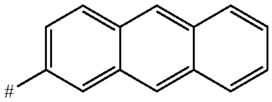
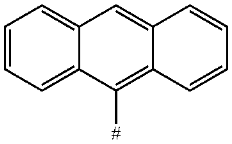
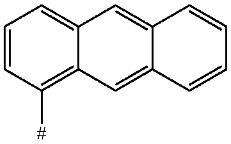
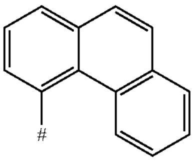
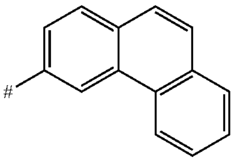
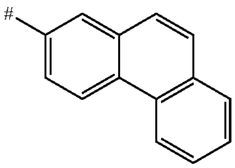
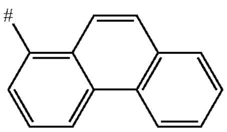
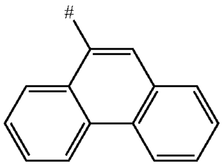
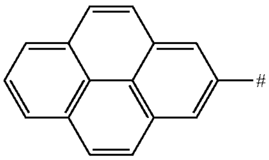
-continued
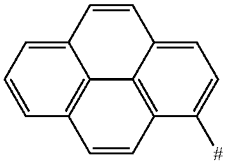
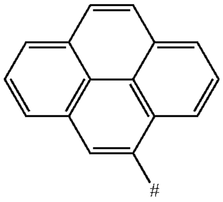
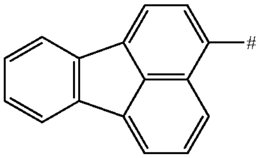
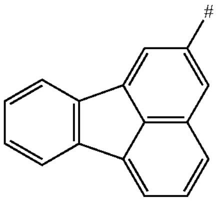
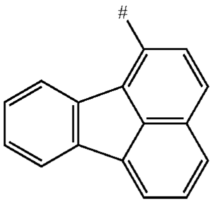
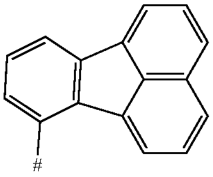
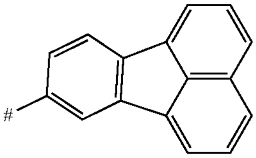
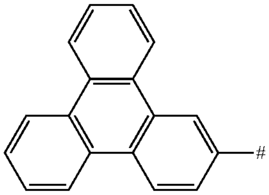
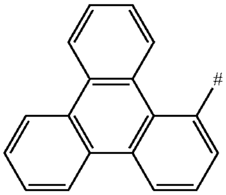
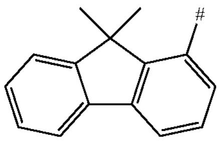
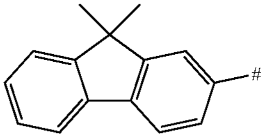
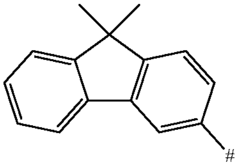
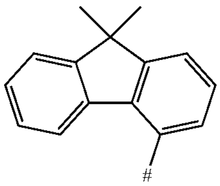
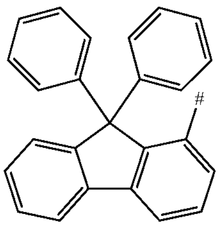
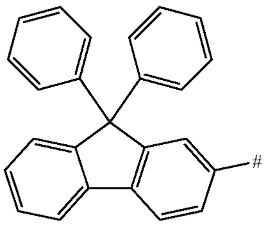
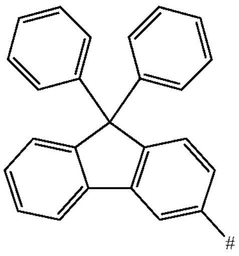

-continued
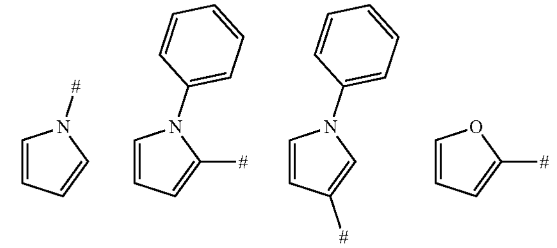
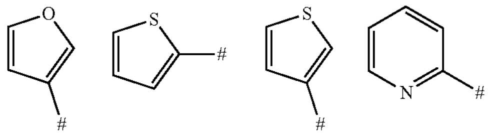
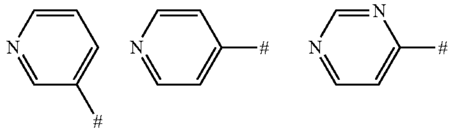
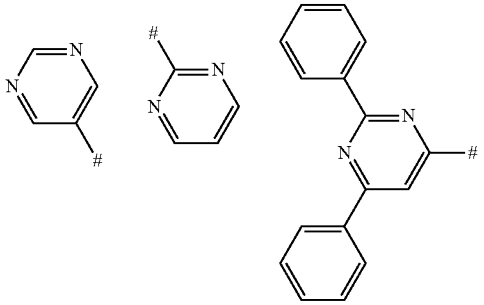
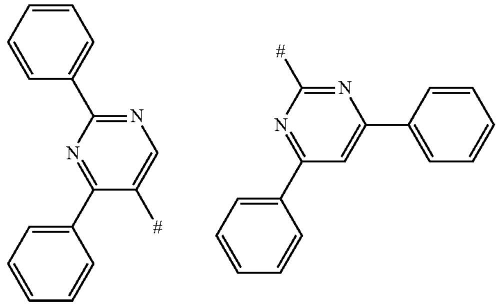
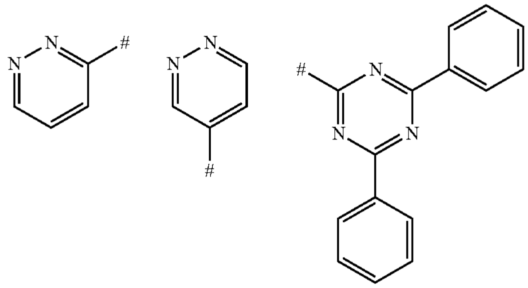
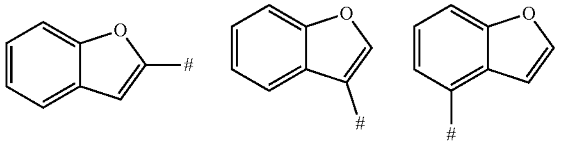
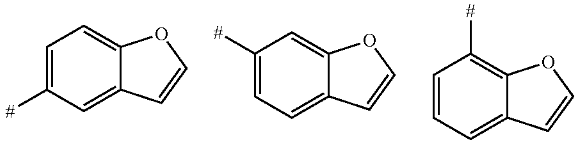
-continued
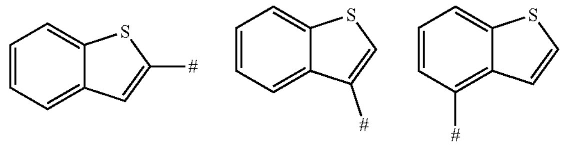
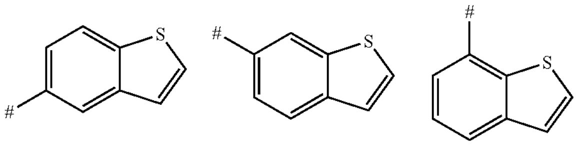
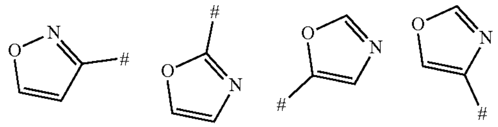
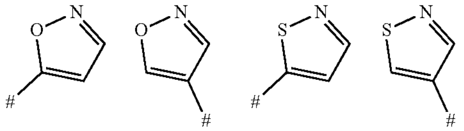
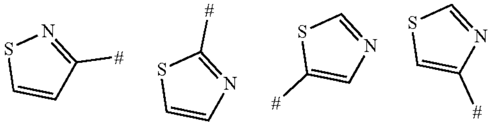
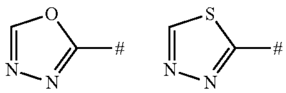
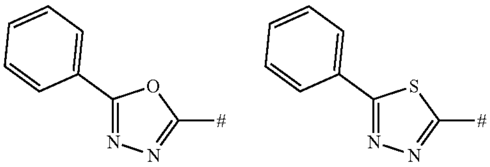
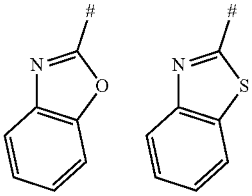
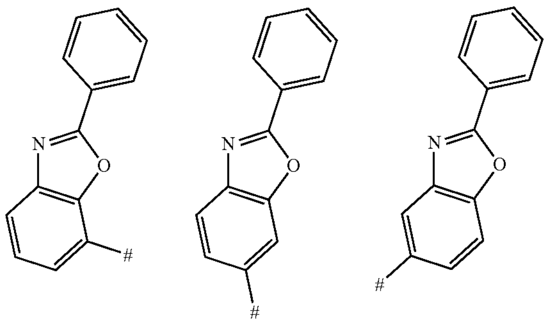

-continued
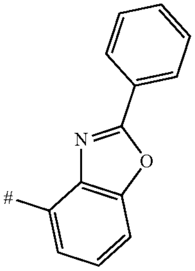
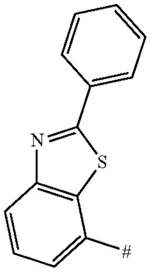
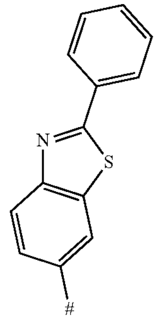
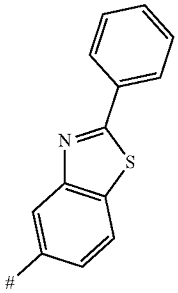
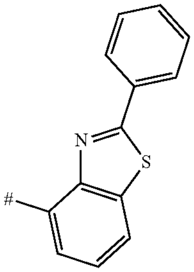
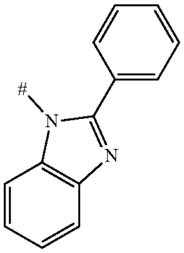
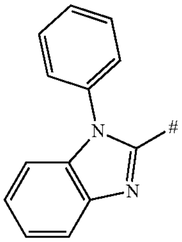
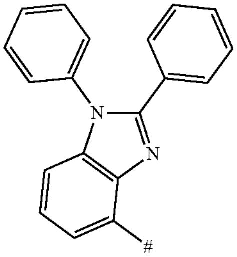
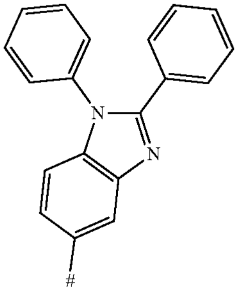
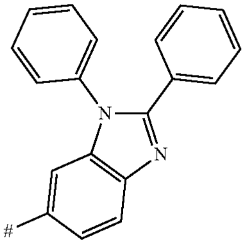
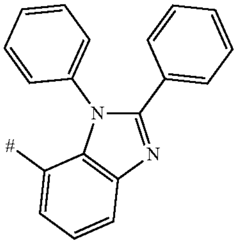
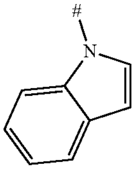
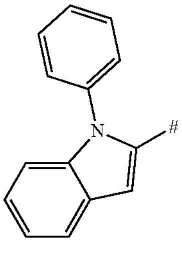
-continued
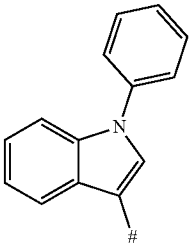
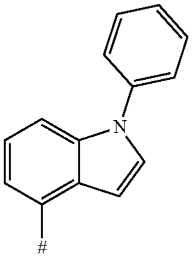
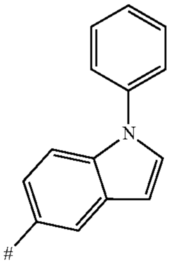
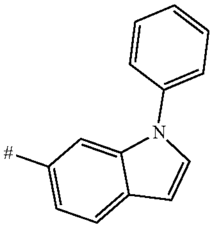
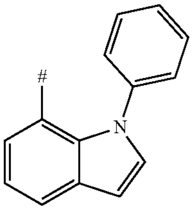
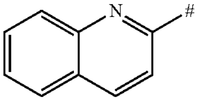
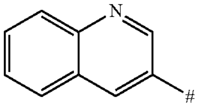
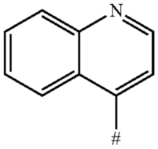
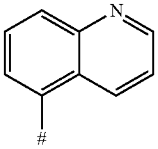
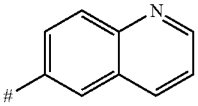
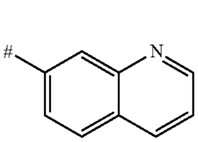
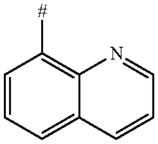
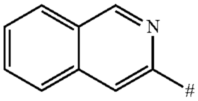
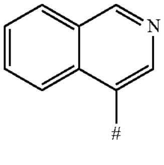
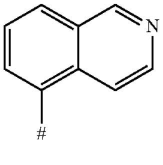
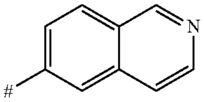
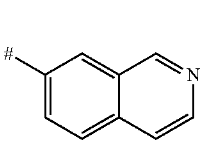
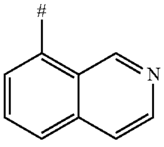
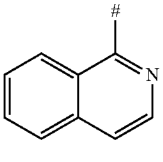
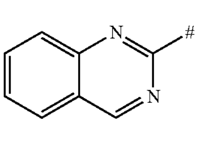

-continued
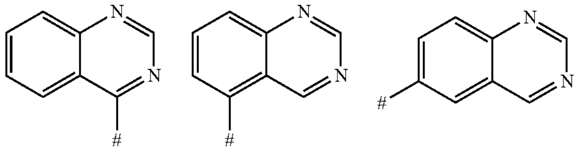
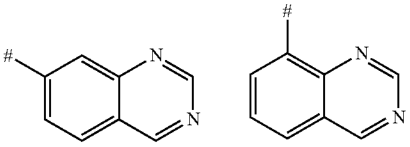
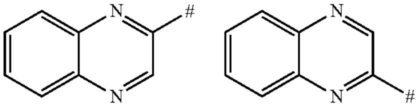
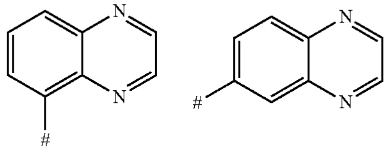
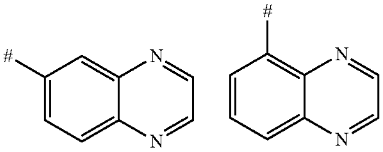
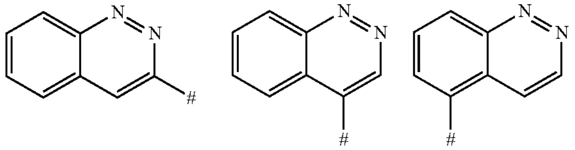
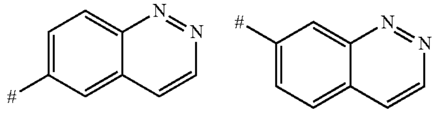
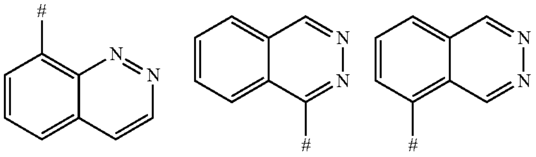
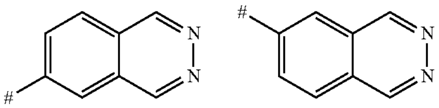
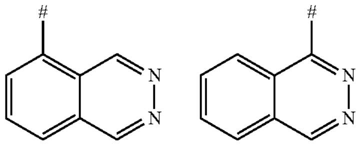
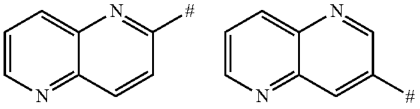
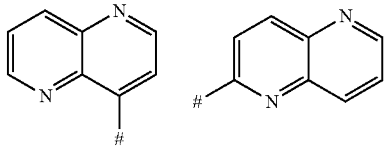
-continued
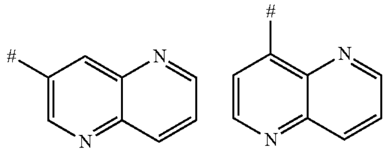
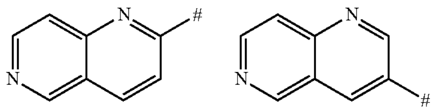
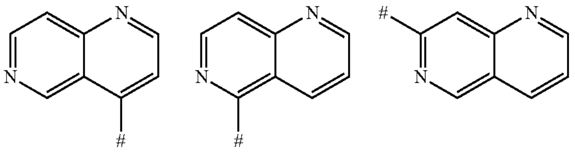
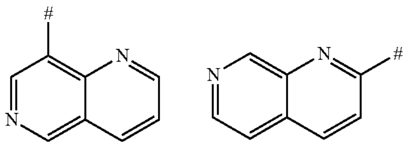
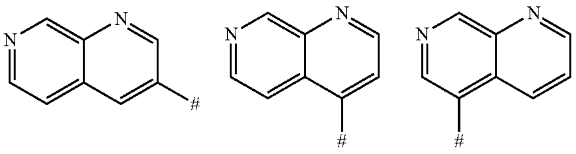
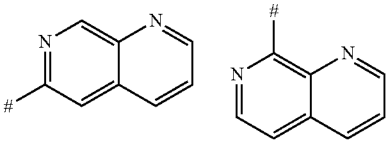
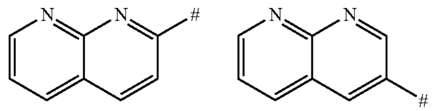
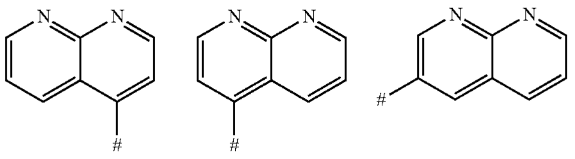
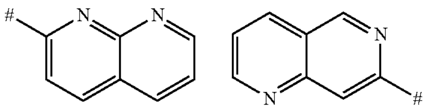
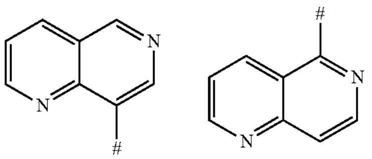
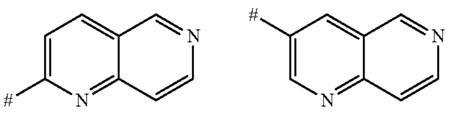
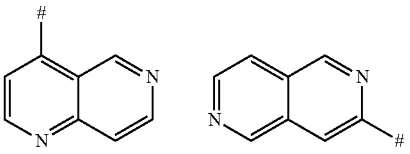

-continued
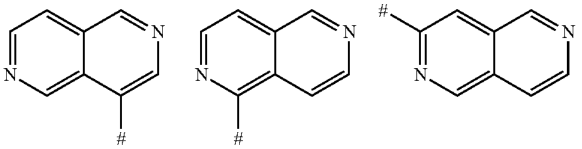
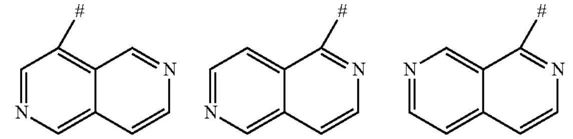
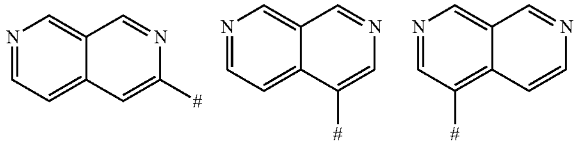
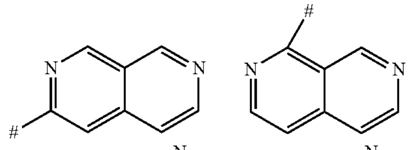
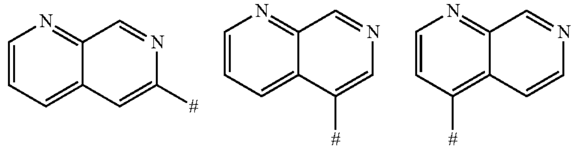
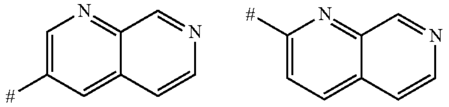
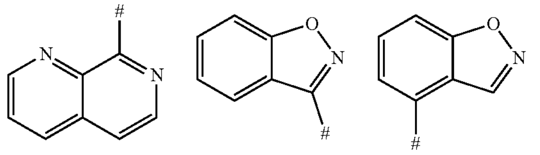
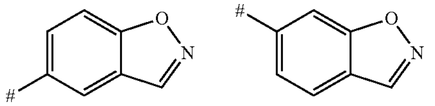
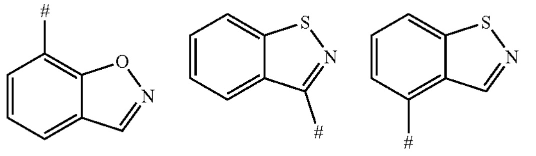
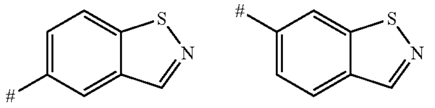
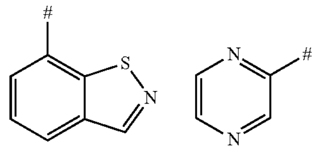
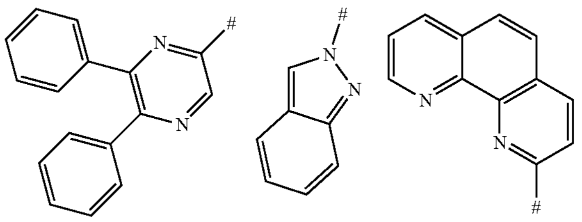
-continued
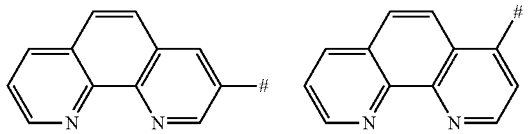
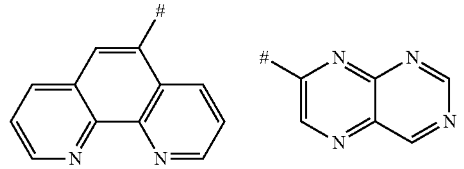
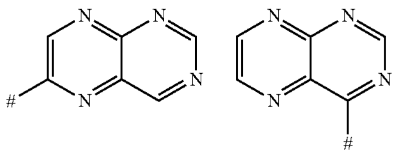
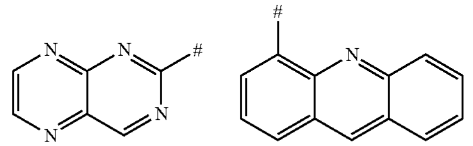
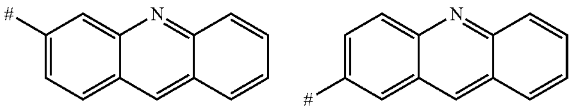
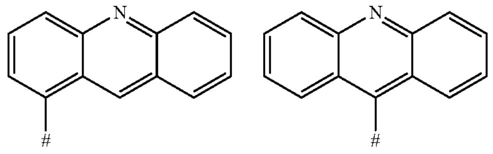
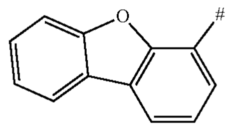
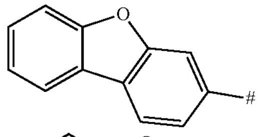
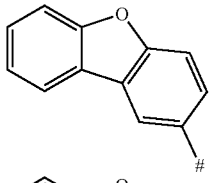
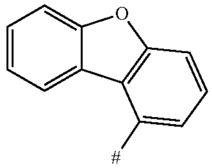
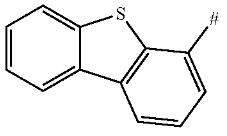

-continued
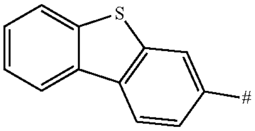
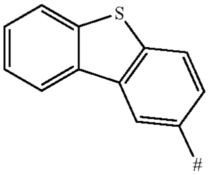
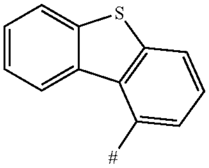
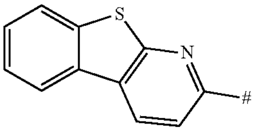
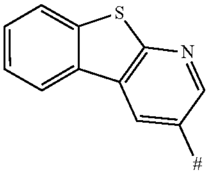
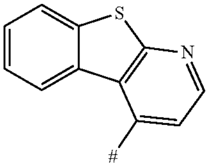
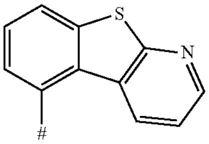
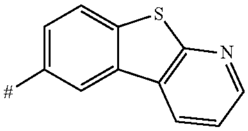
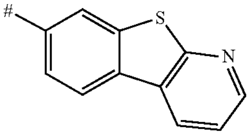
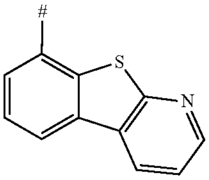
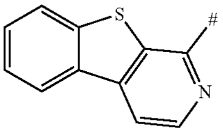
-continued
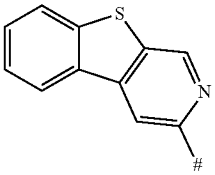
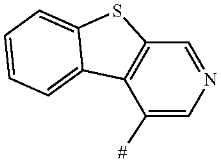
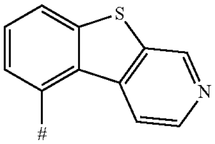
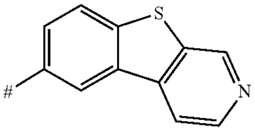
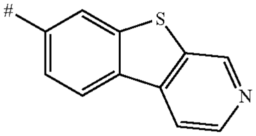
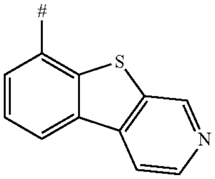
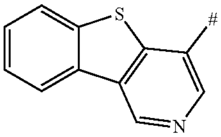
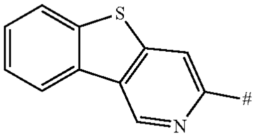
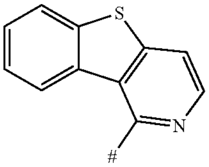
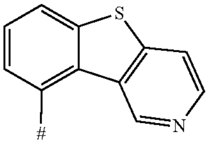
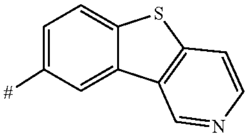

-continued
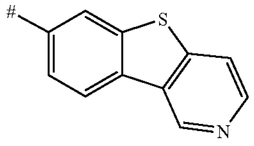
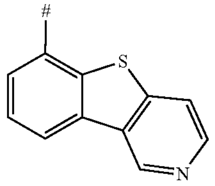
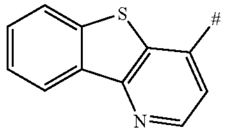
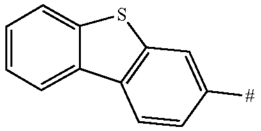
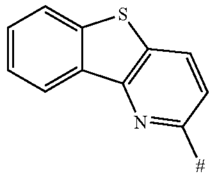
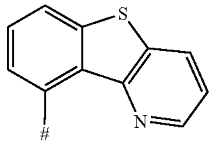
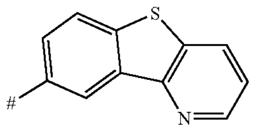
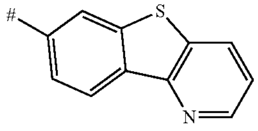
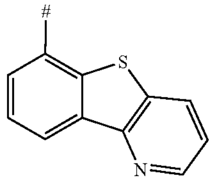
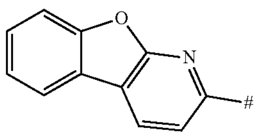
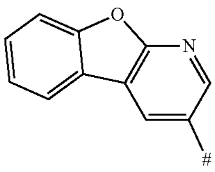
-continued
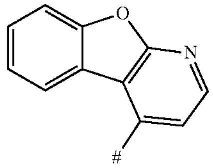
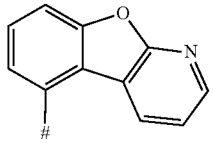
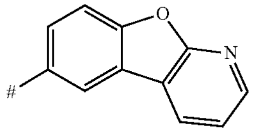
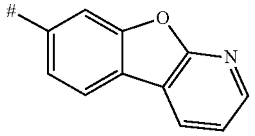
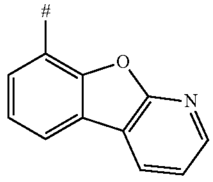
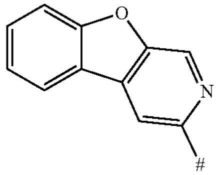
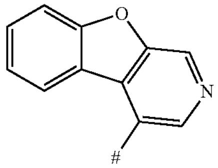
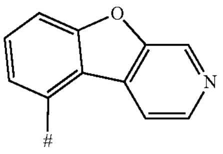
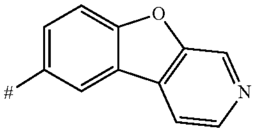
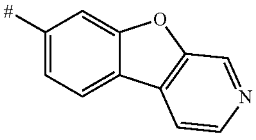
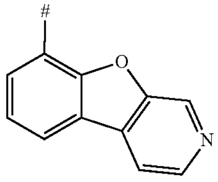

-continued
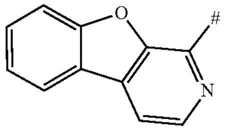
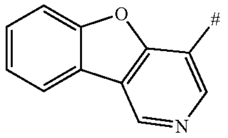
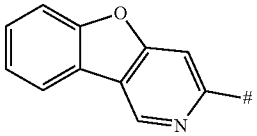
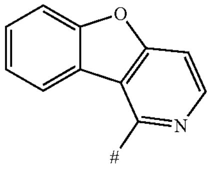
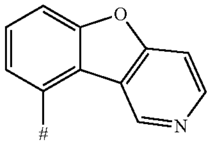
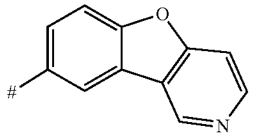
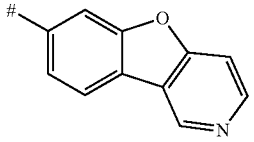
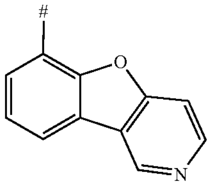
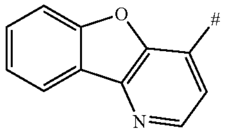
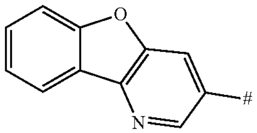
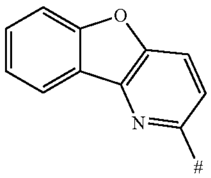
-continued
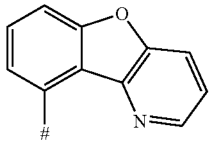
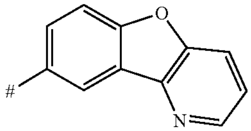
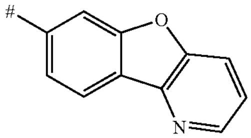
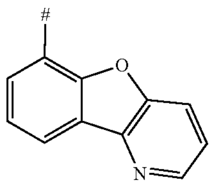
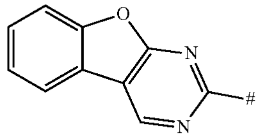
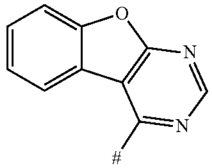
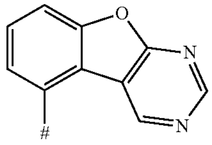
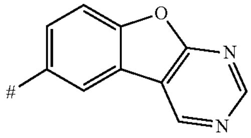
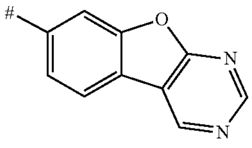
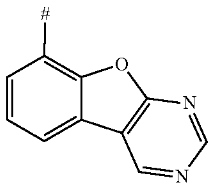
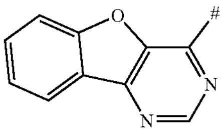

-continued
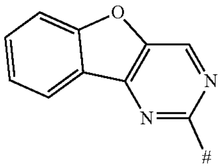
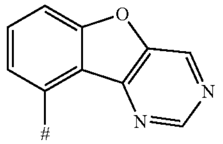
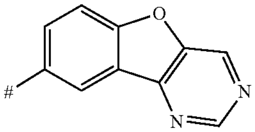
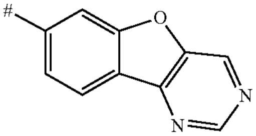
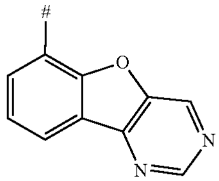
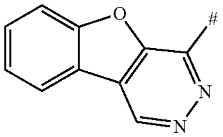
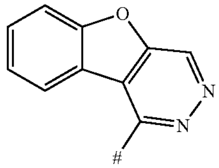
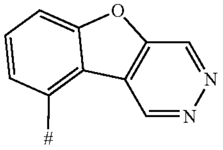
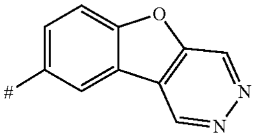
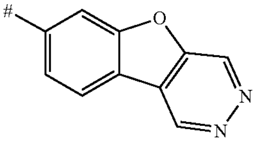
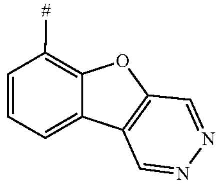
-continued
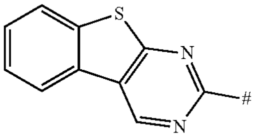
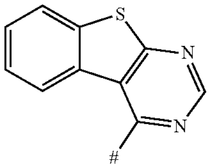
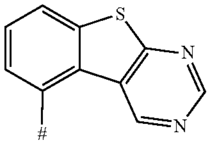
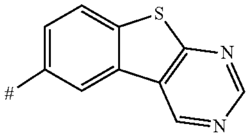
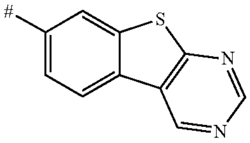
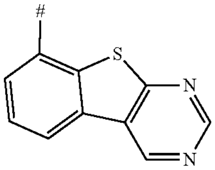
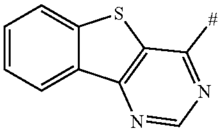
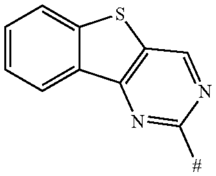
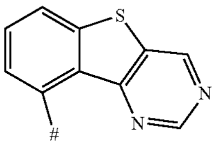
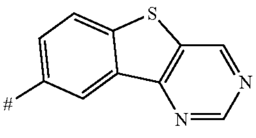
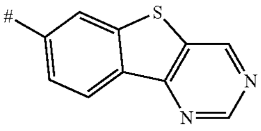

-continued
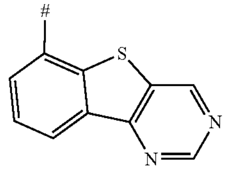
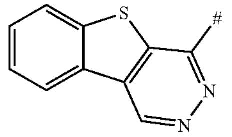
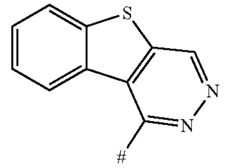
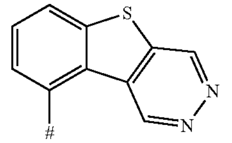
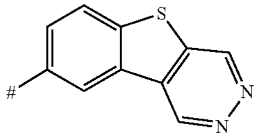
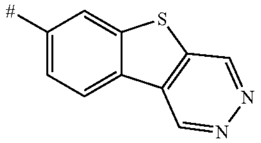
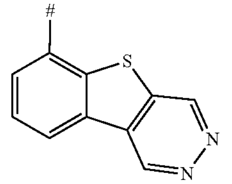
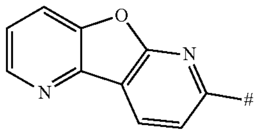
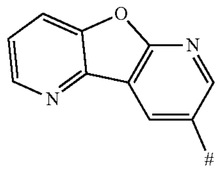
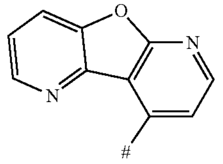
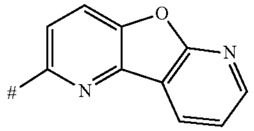
-continued
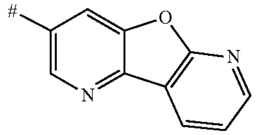
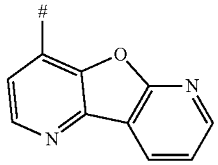
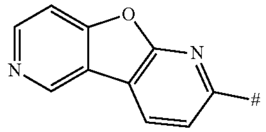
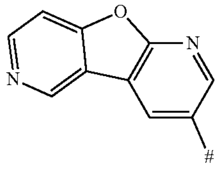
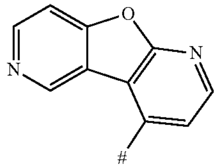
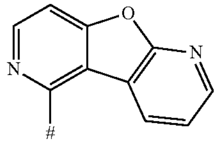
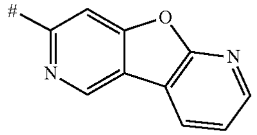
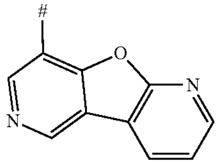
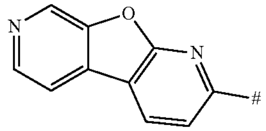
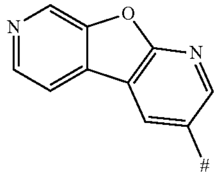
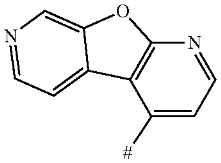

-continued
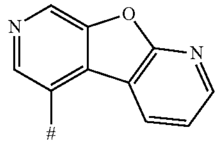
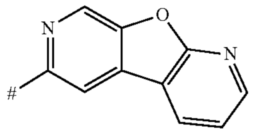
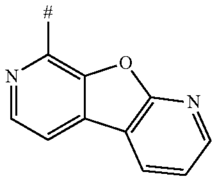
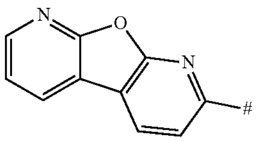
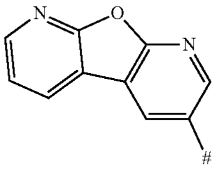
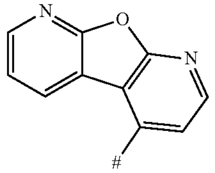
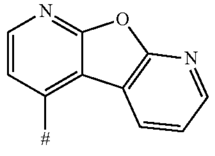
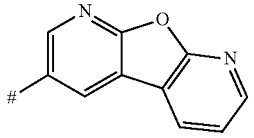
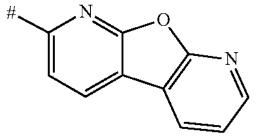
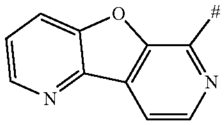
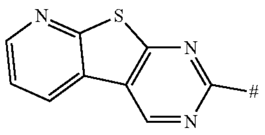
-continued
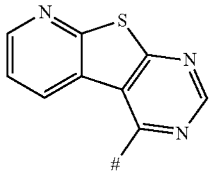
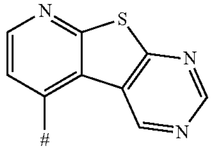
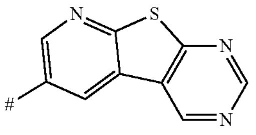
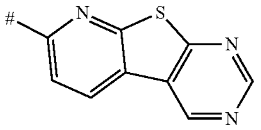
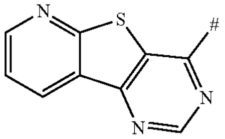
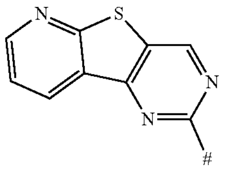
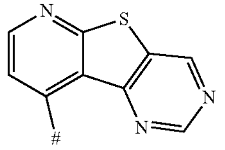
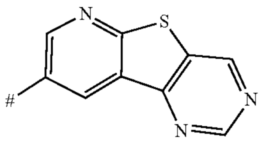
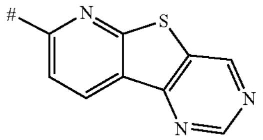
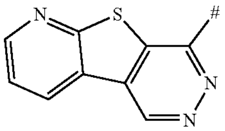
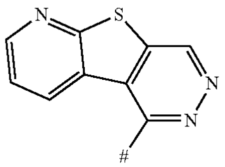

-continued
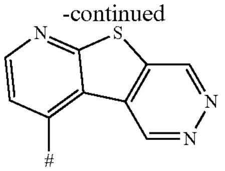
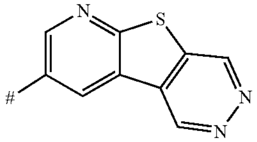
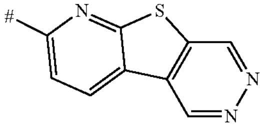
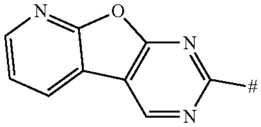
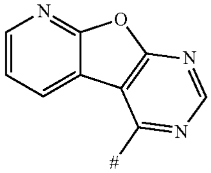
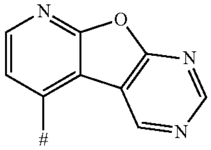
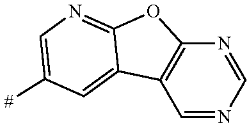
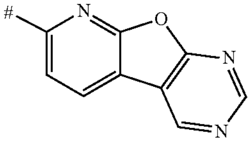
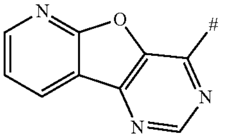
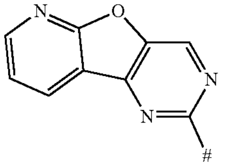
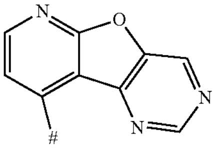
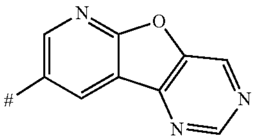
-continued
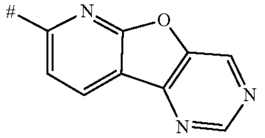
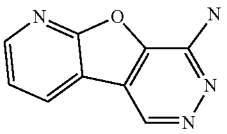
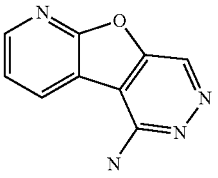
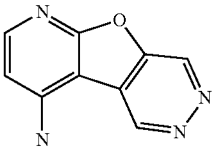
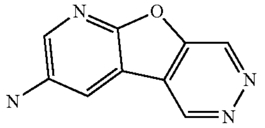
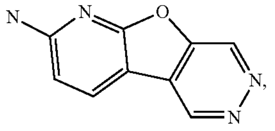
where #may represent a connection position.
In one embodiment, the heterocyclic compound may have any one of the following structures:
M001
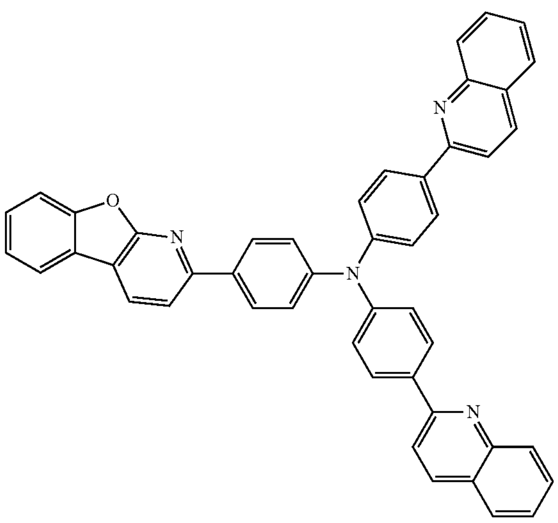

-continued
M002
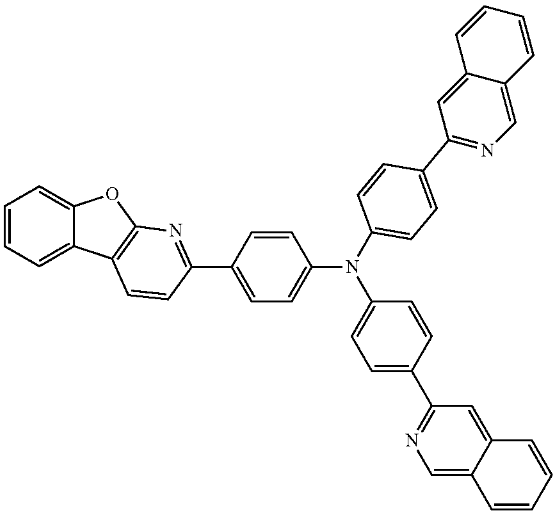
M003
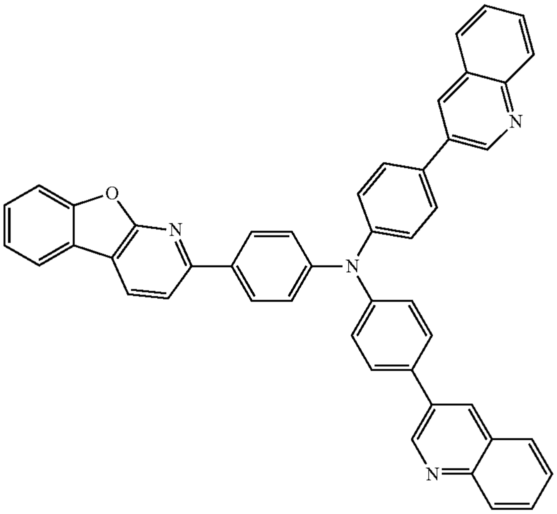
M004
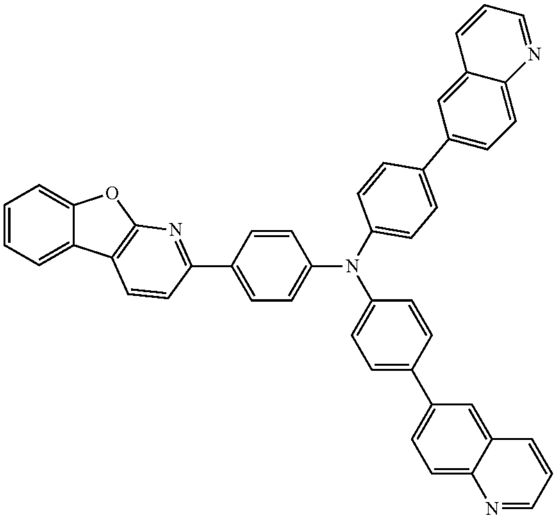
-continued
M005
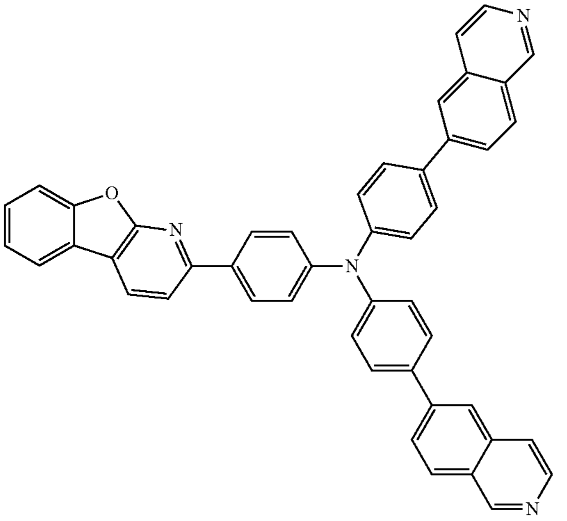
M006
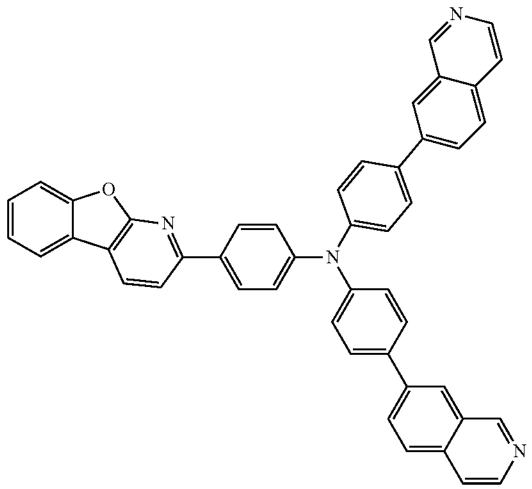
M007
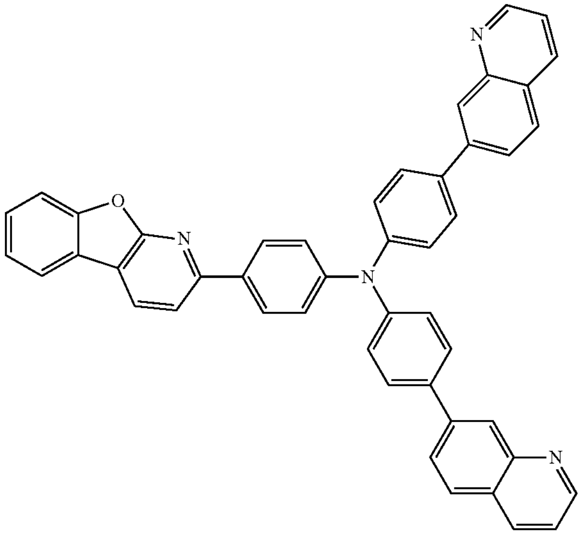

-continued
M008
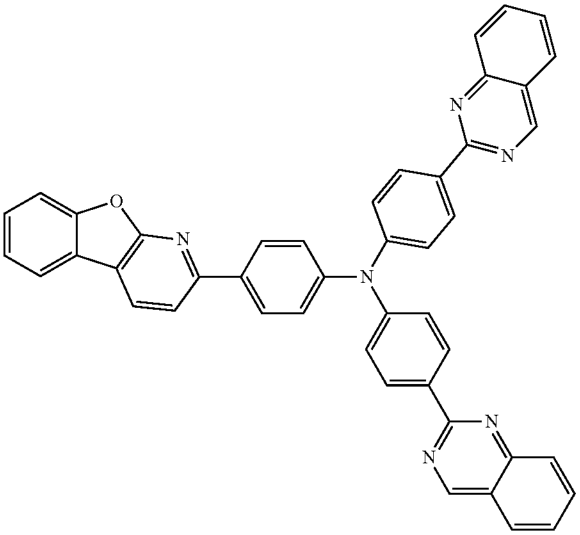
M009
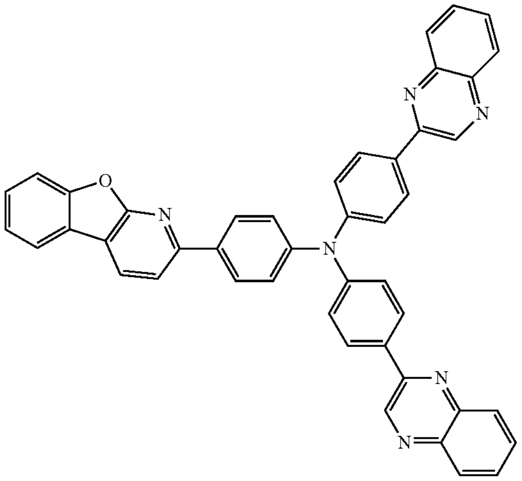
M010
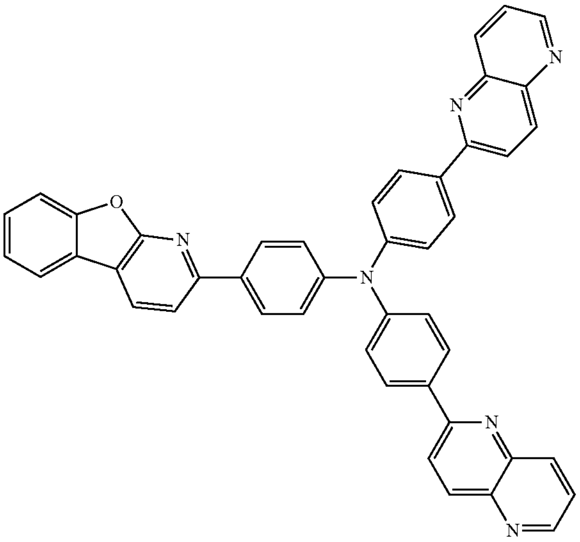
-continued
M011
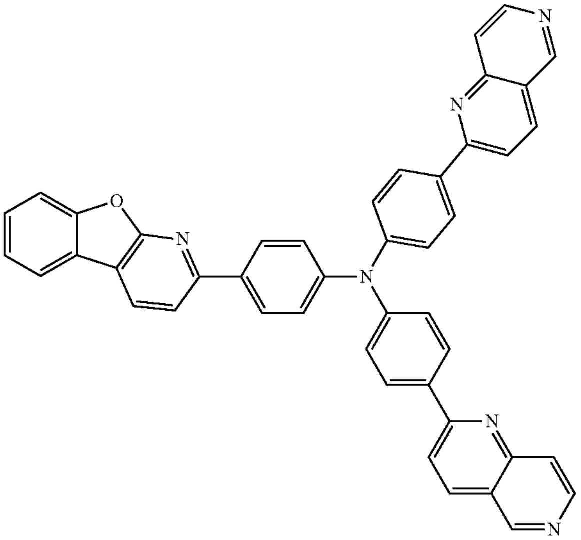
M012
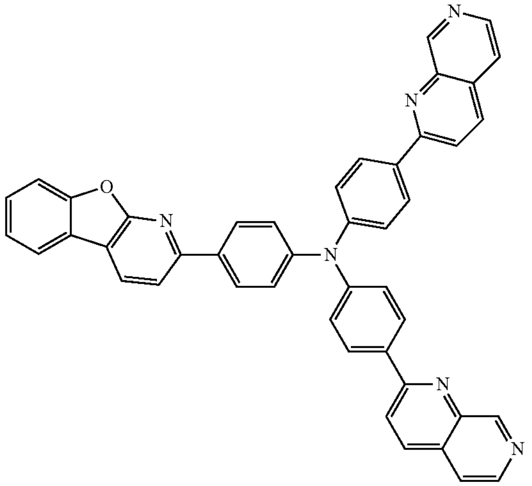
M013
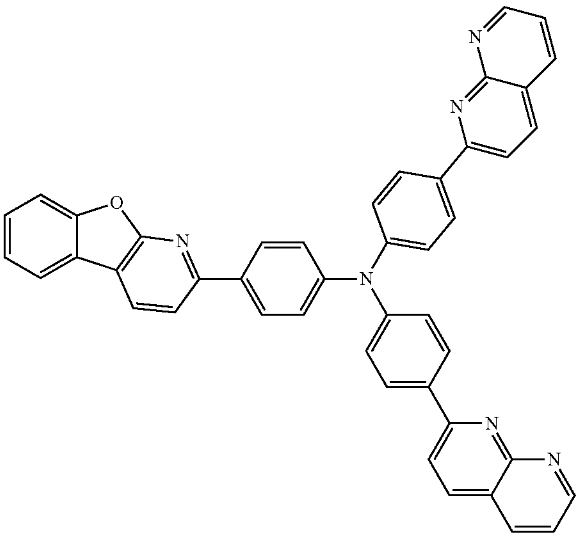

-continued
M014
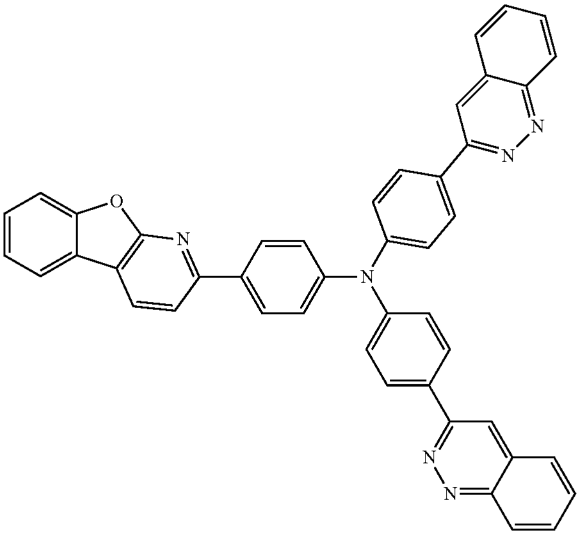
M015
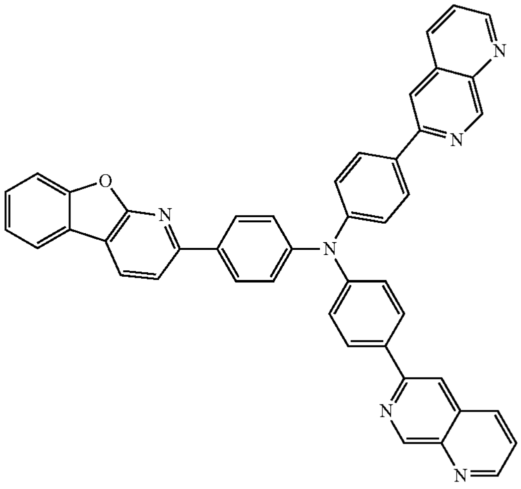
M016
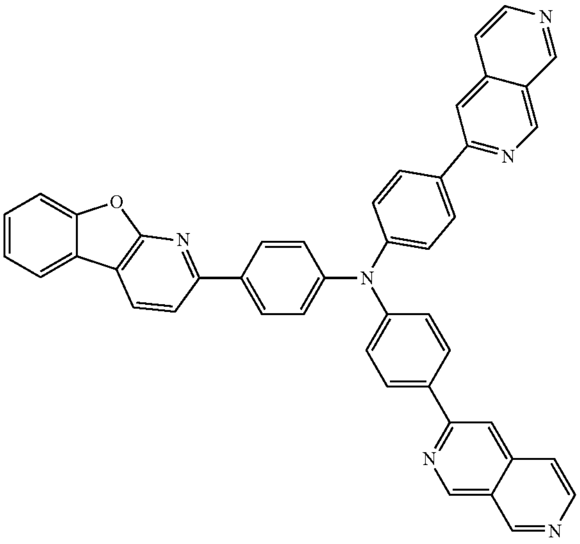
-continued
M017
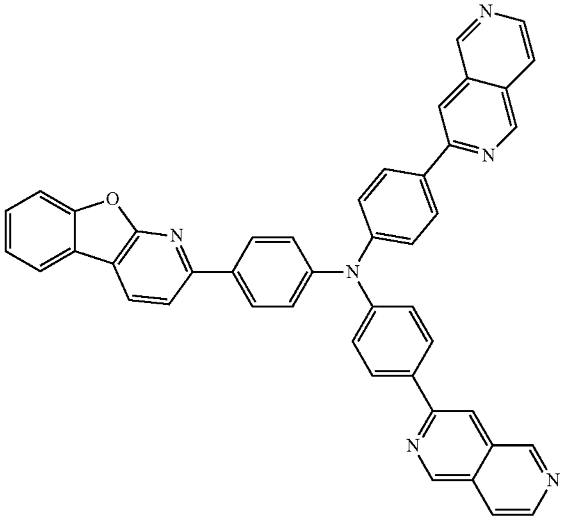
M018
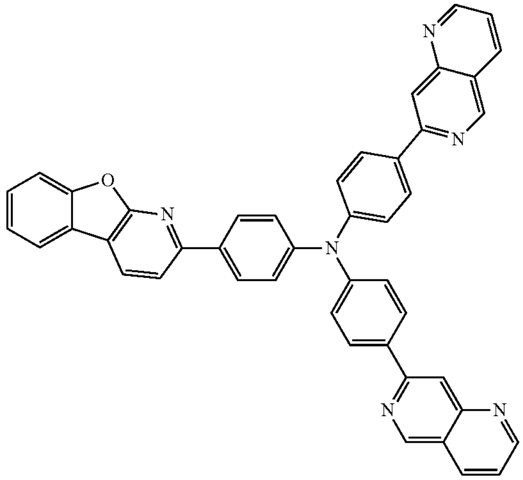
M019
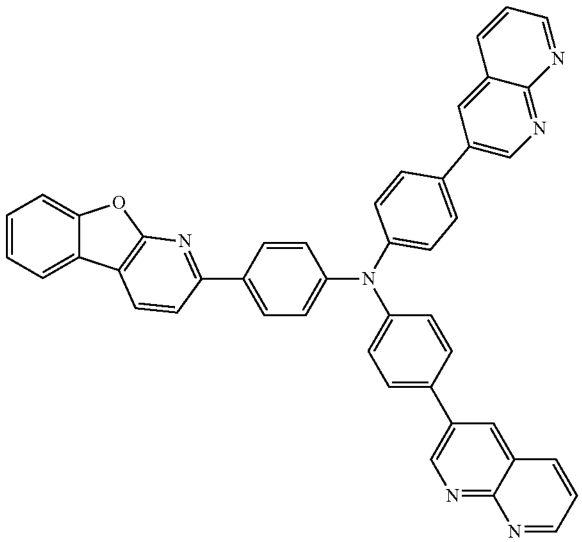

-continued
M020
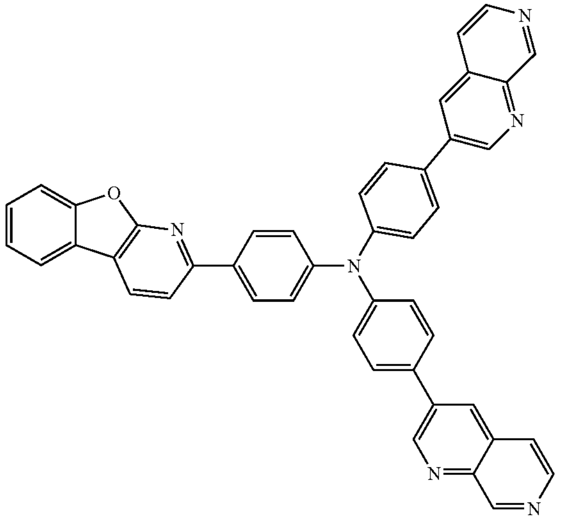
M021
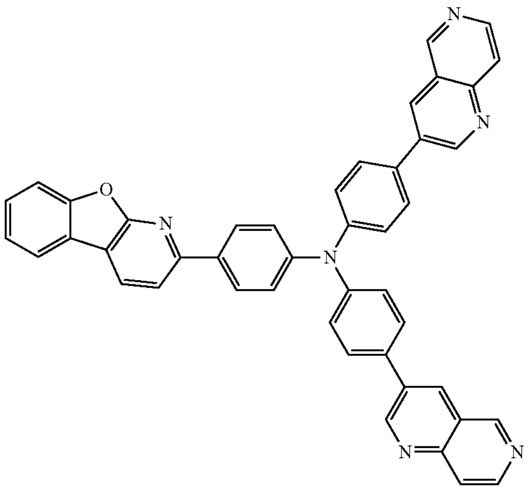
M022
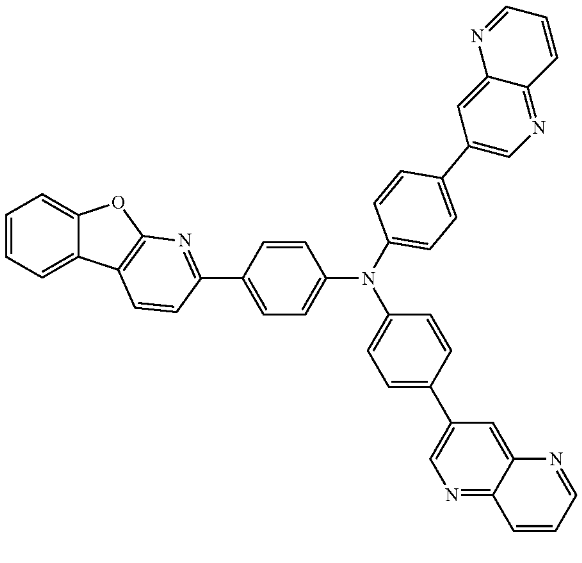
-continued
M023
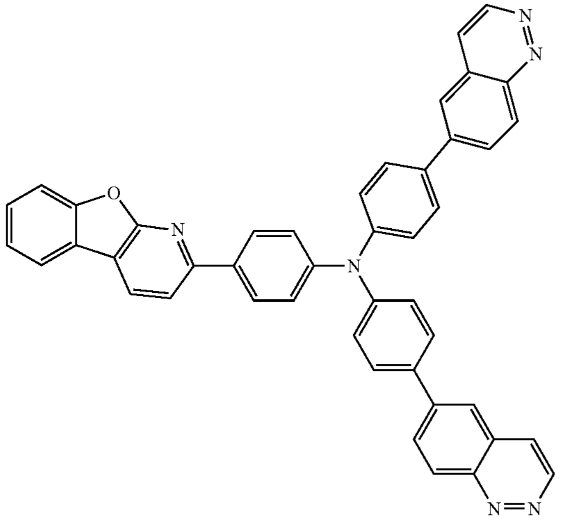
M024
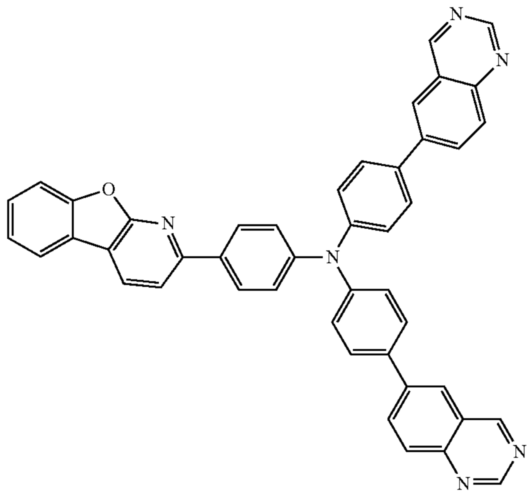
M025
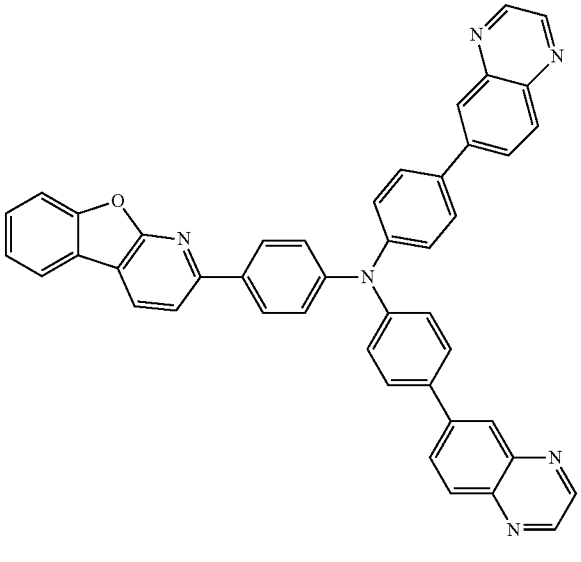

-continued
M026
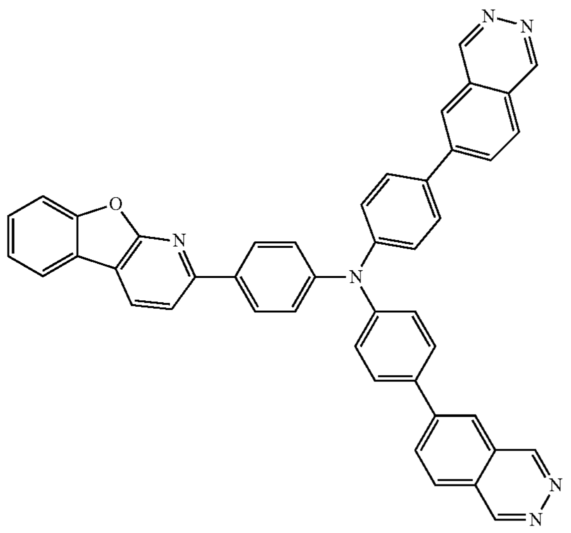
M027
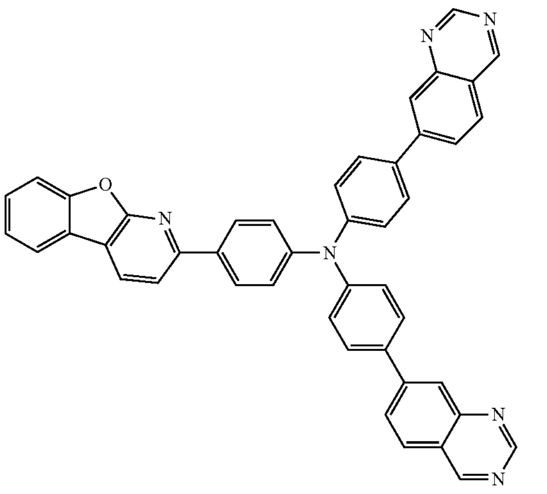
M028
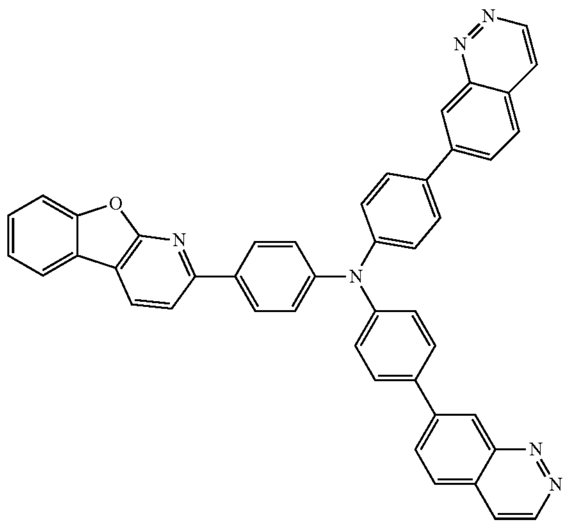
-continued
M029
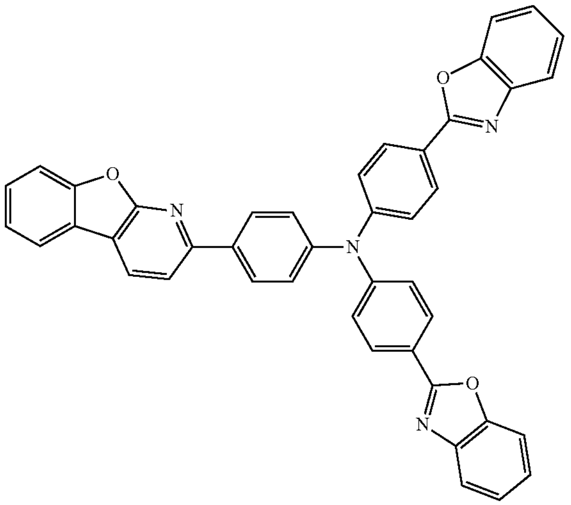
M030
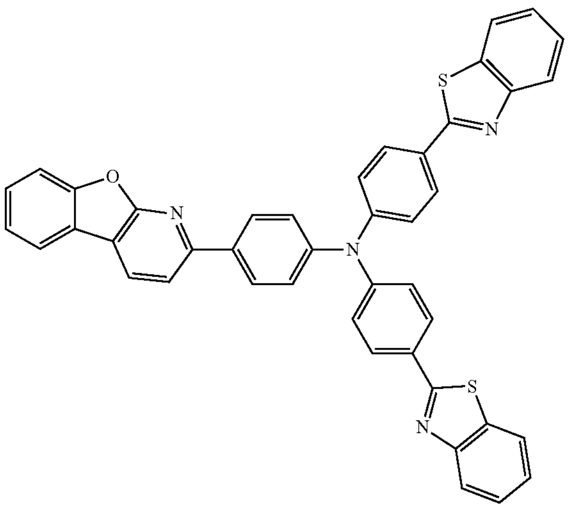
M031
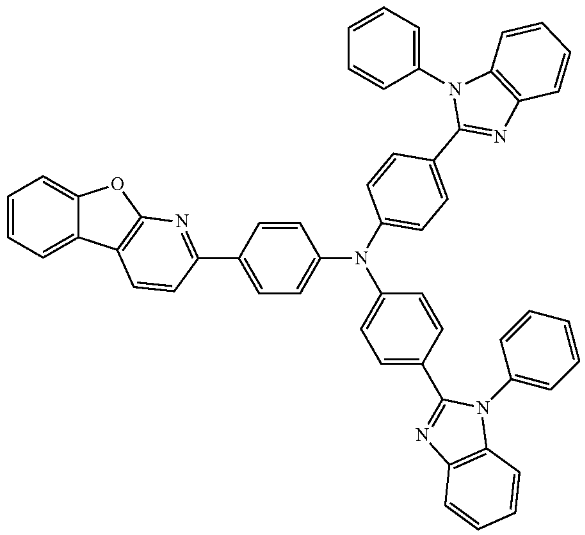

-continued
M032
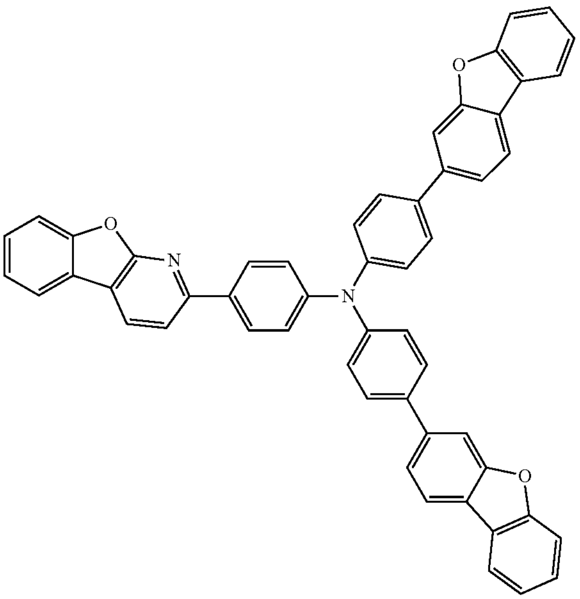
M033
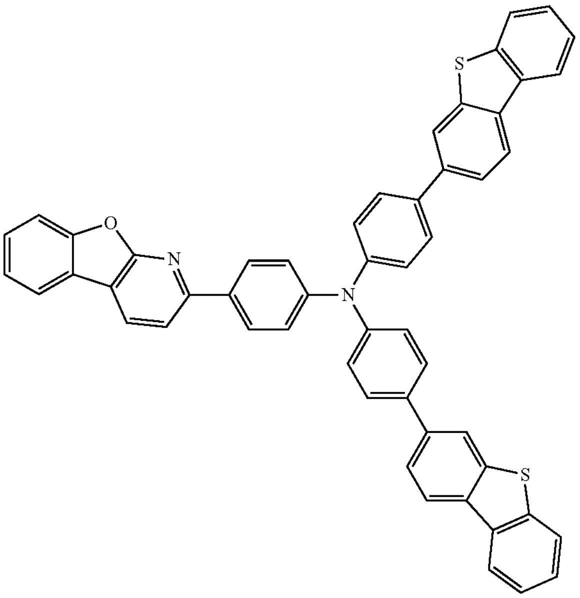
-continued
M034
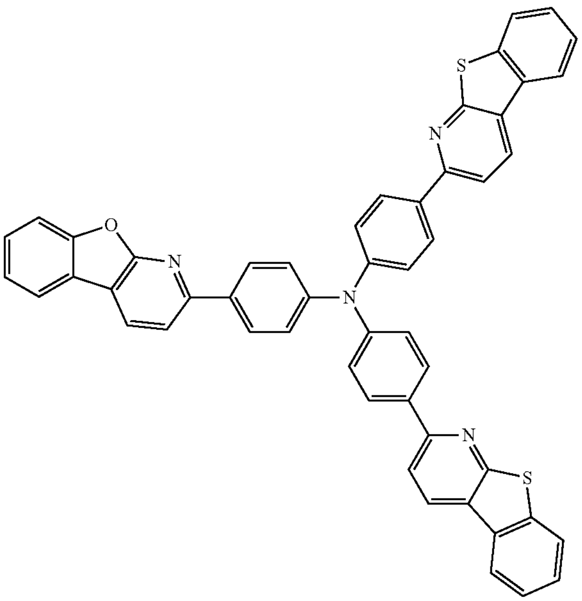
M035
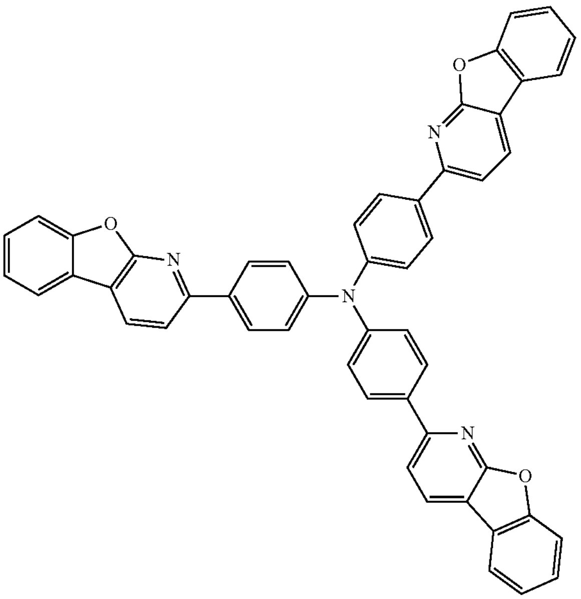

-continued
M036
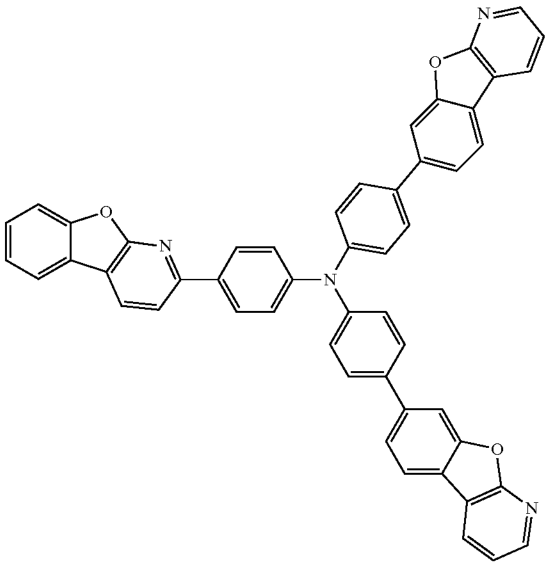
M037
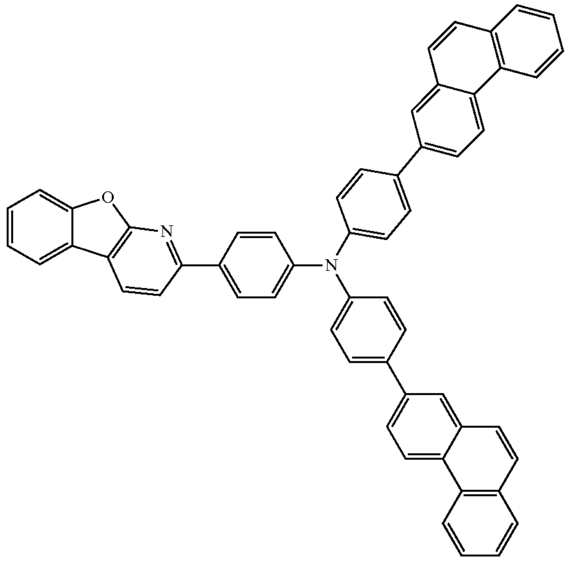
-continued
M038
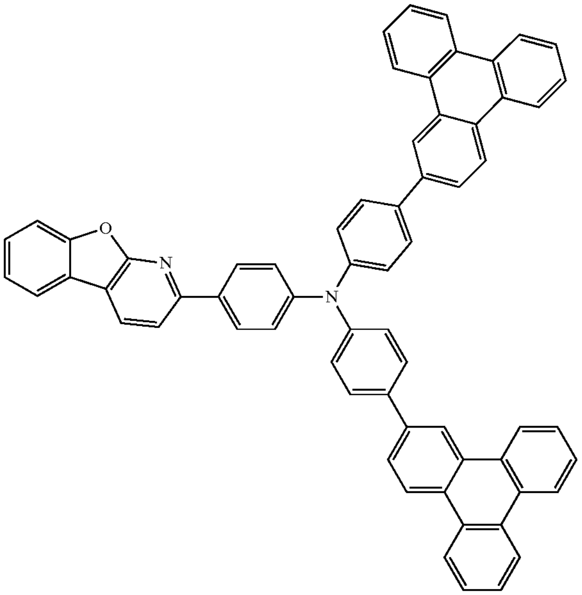
M039
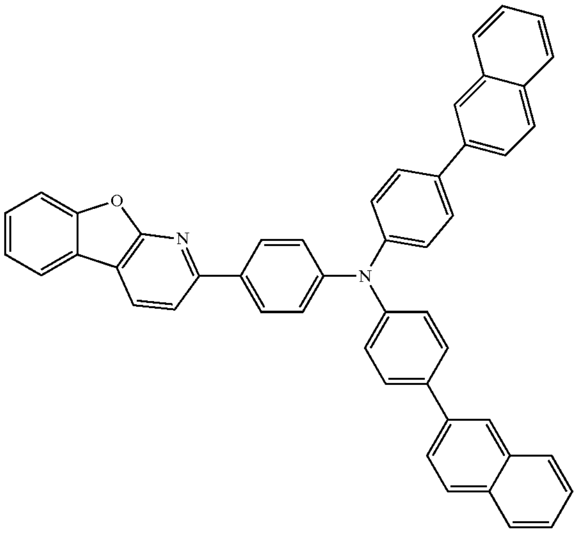

M040
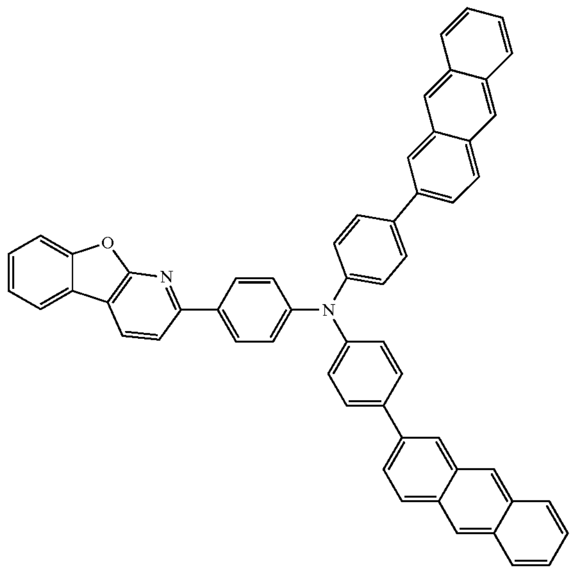
M041
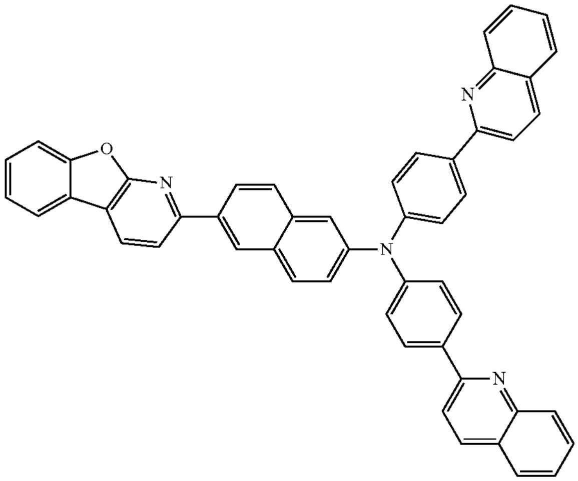
M042
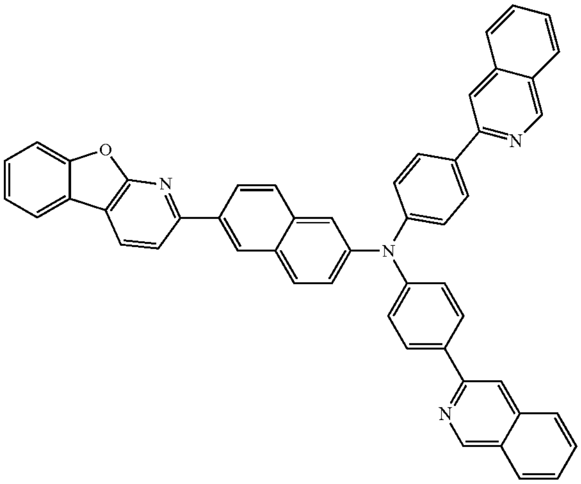
M043
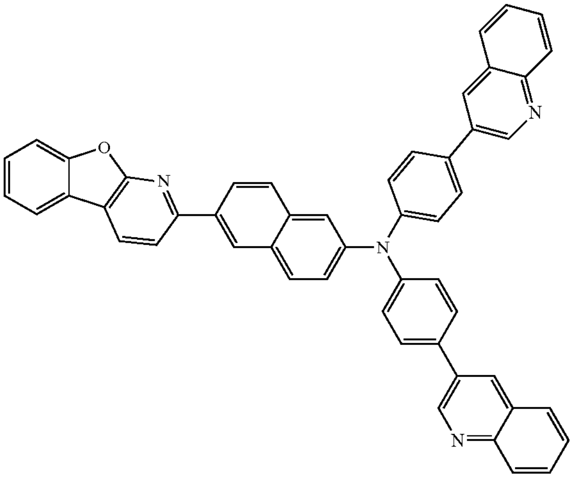
M044
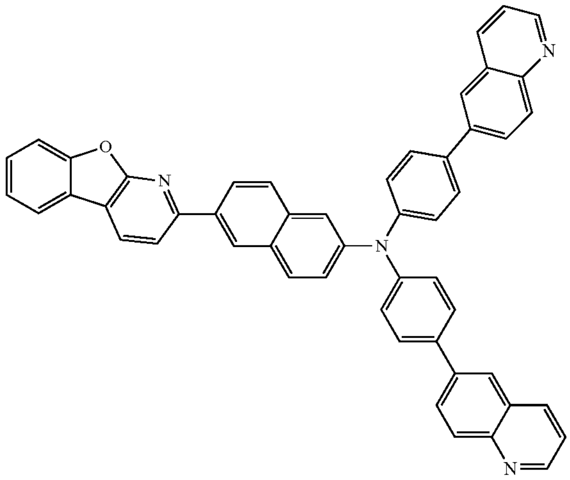
M045
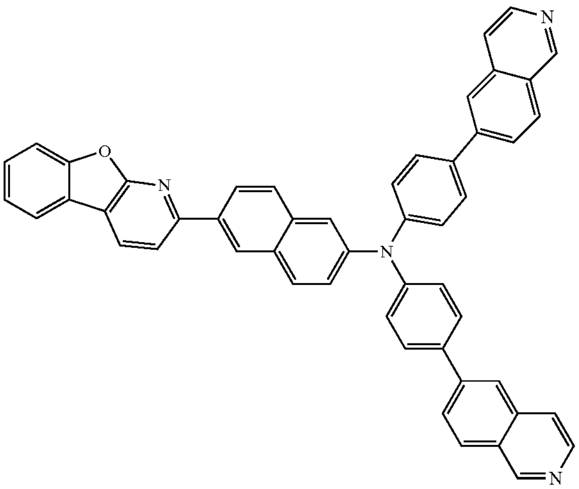

-continued
M046
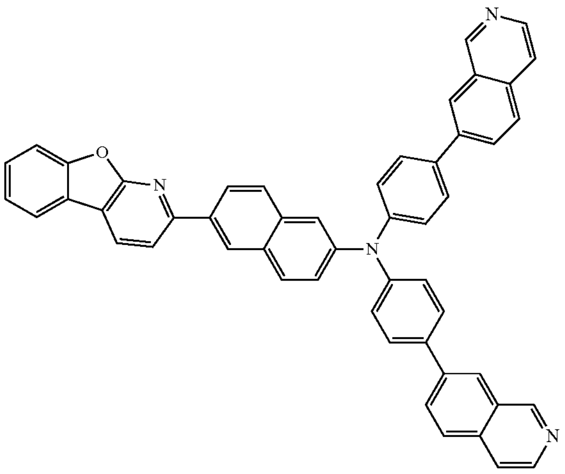
M047
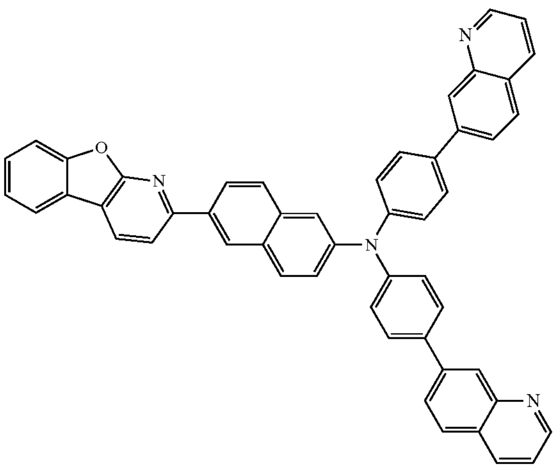
M048
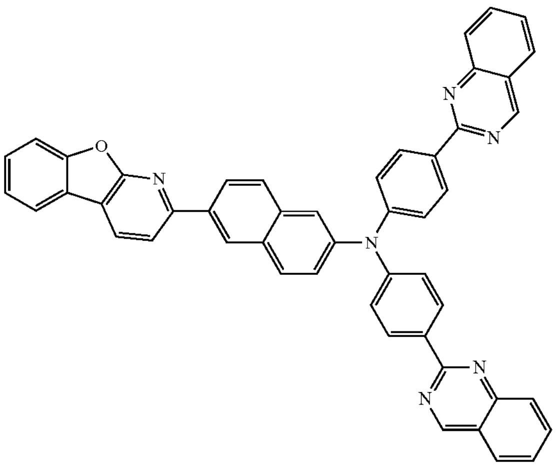
-continued
M049
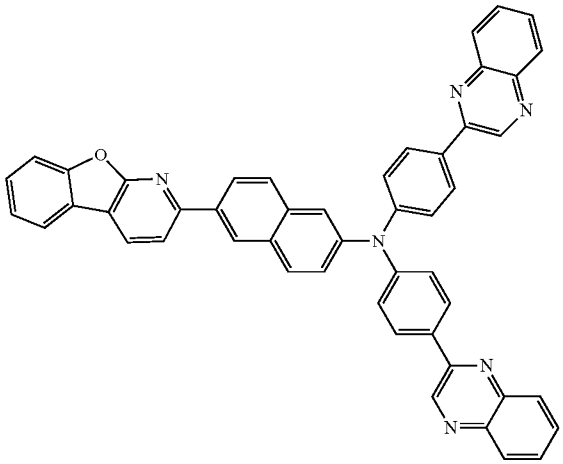
M50
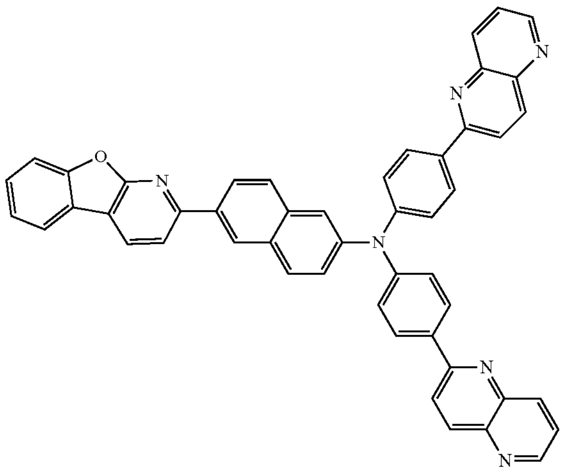
M051
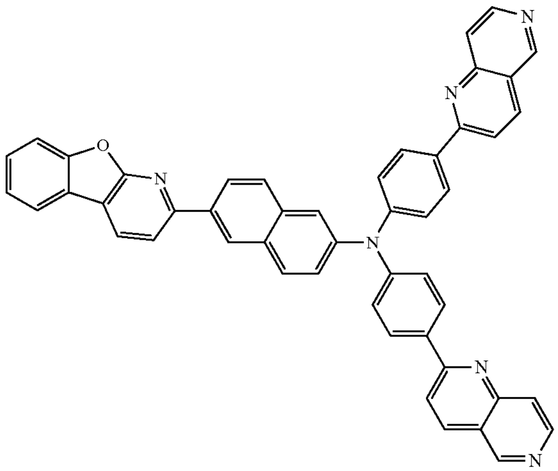

-continued
M052
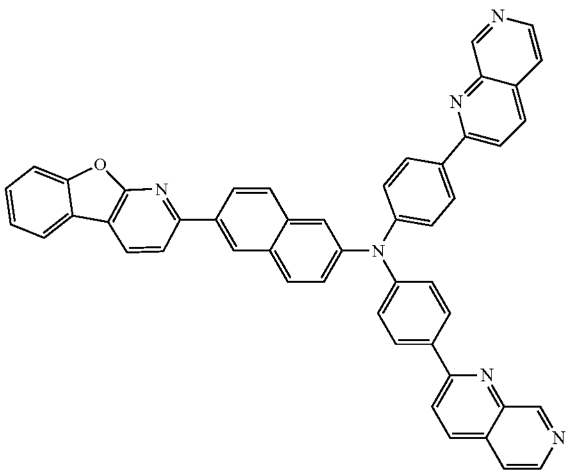
M53
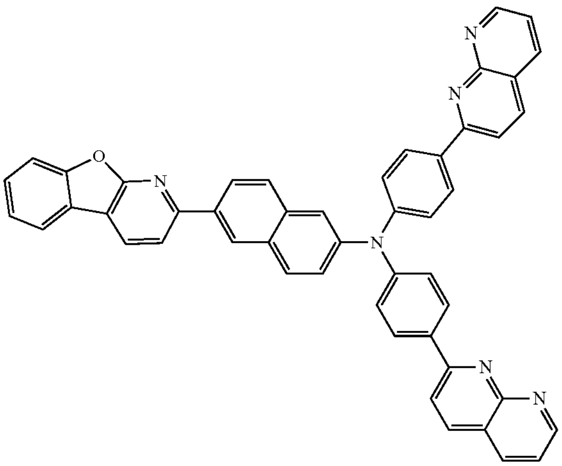
M054
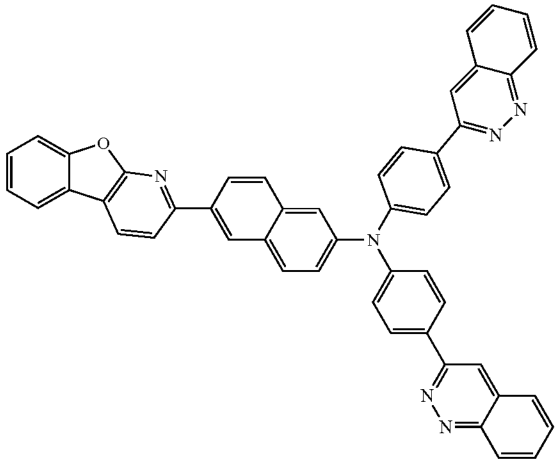
-continued
M055
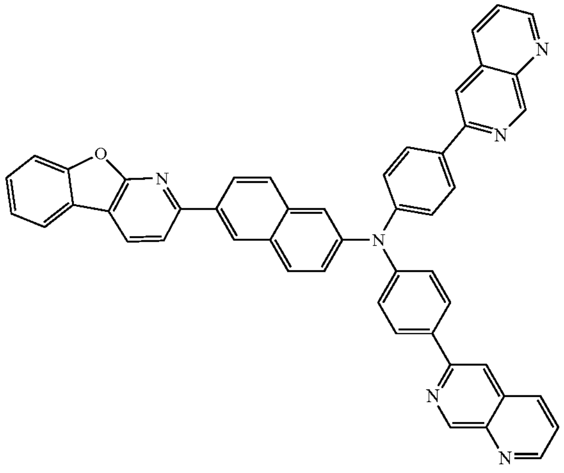
M56
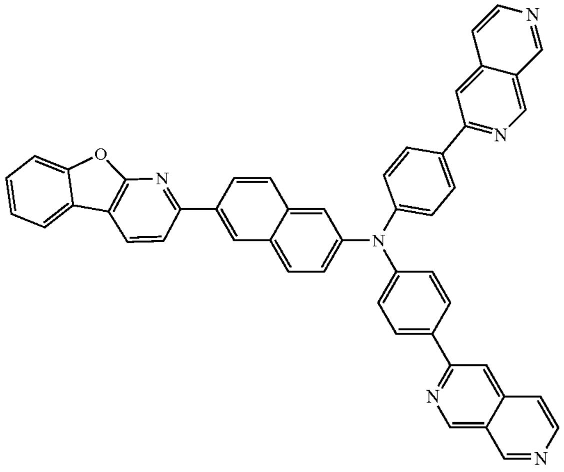

-continued
M057
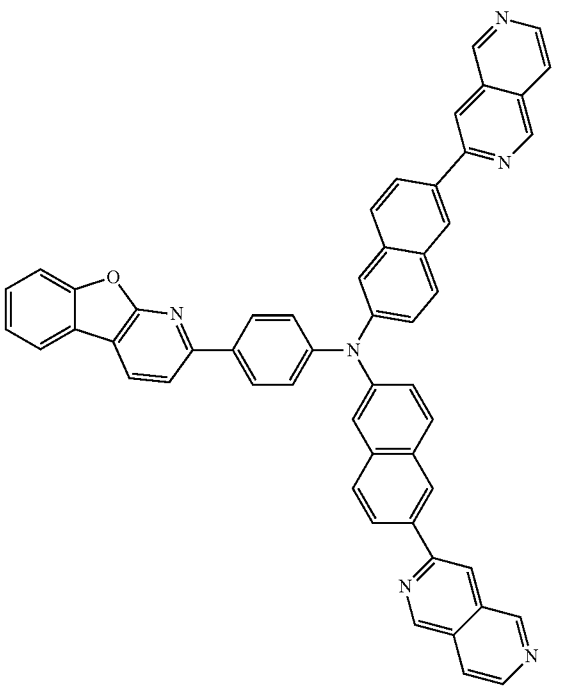
M058
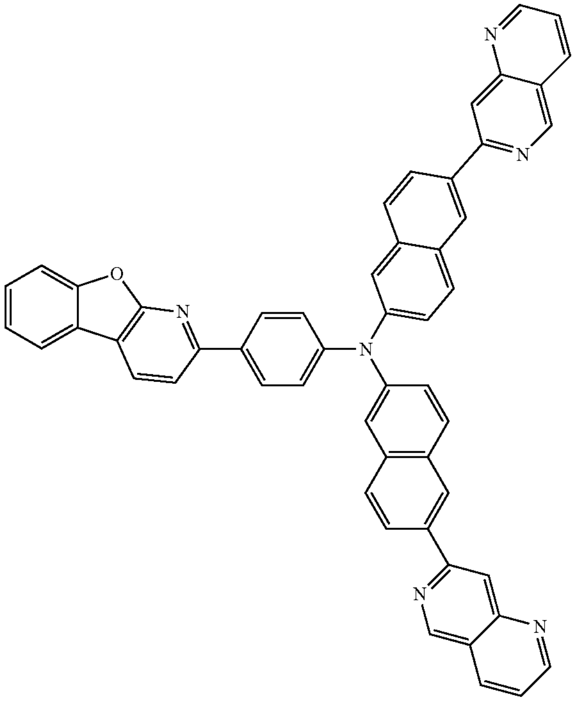
-continued
M059
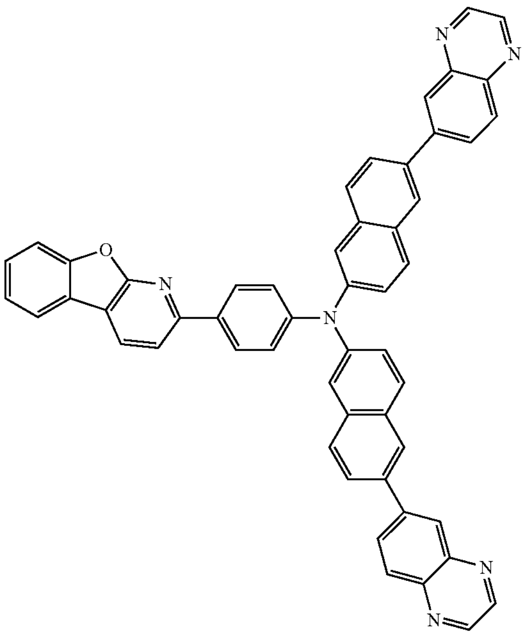
M060
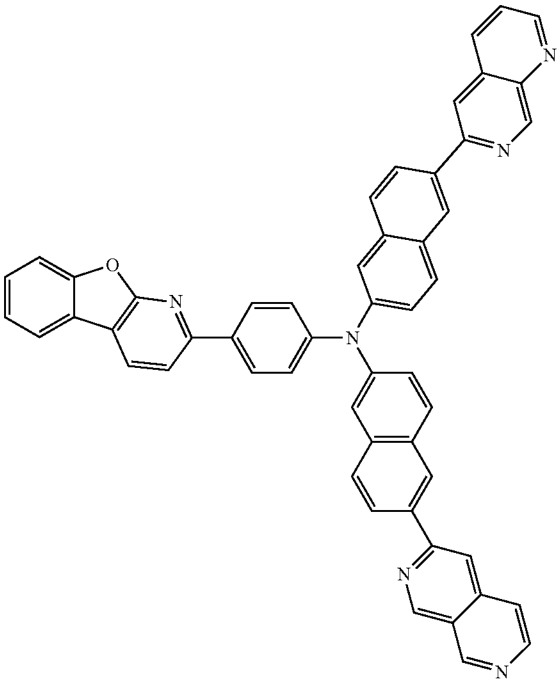

-continued
M061
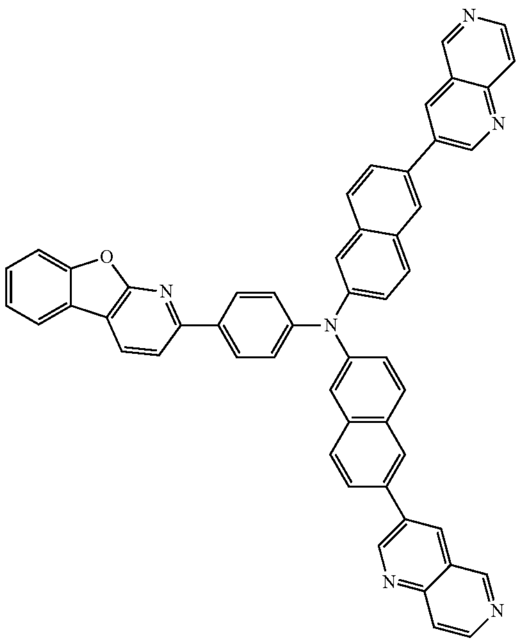
M062
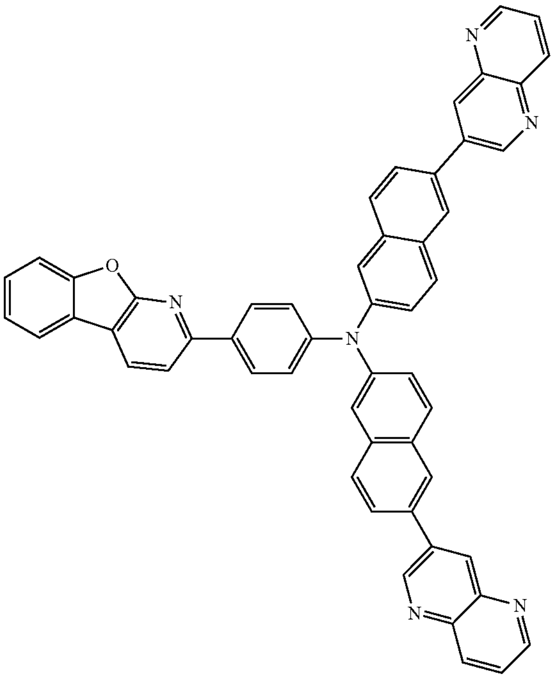
-continued
M063
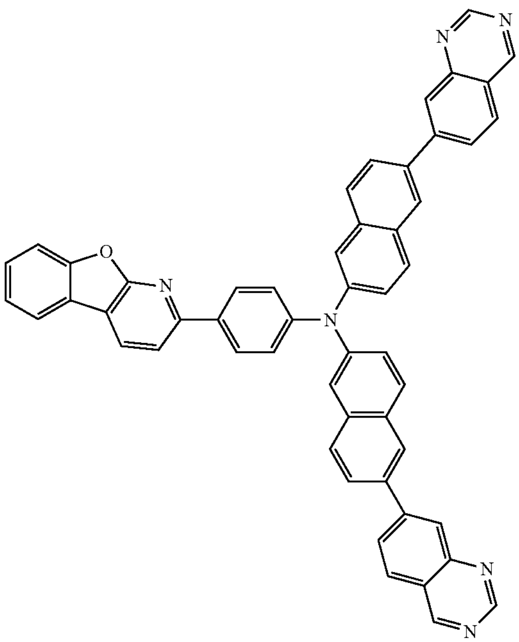
M064
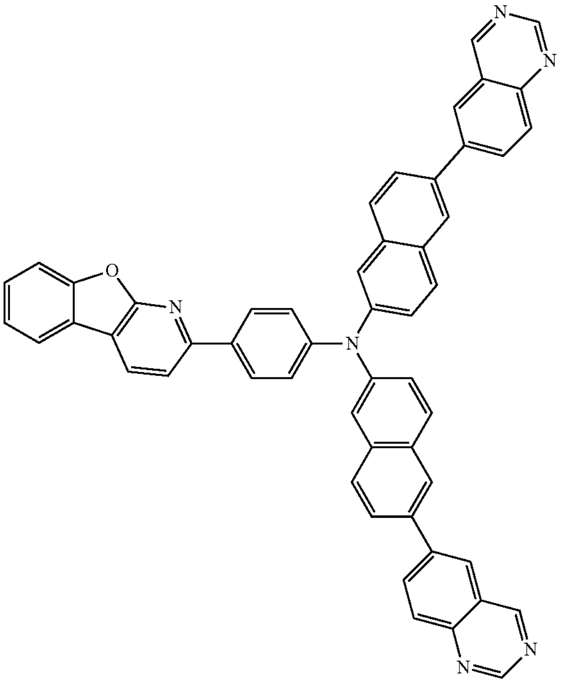

-continued
M065
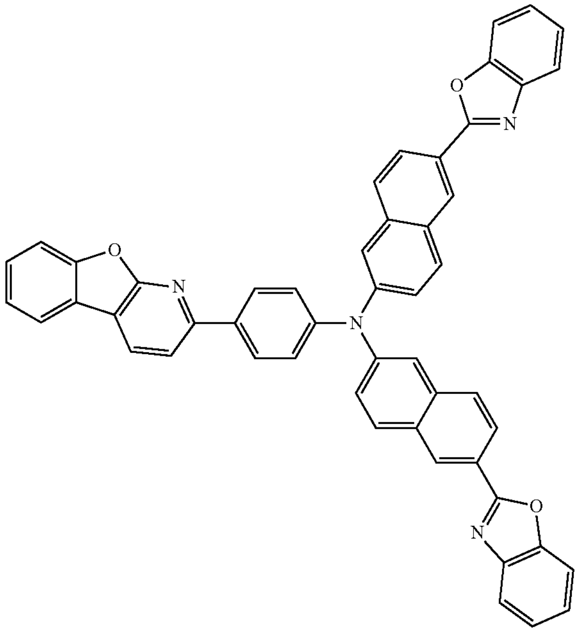
M066
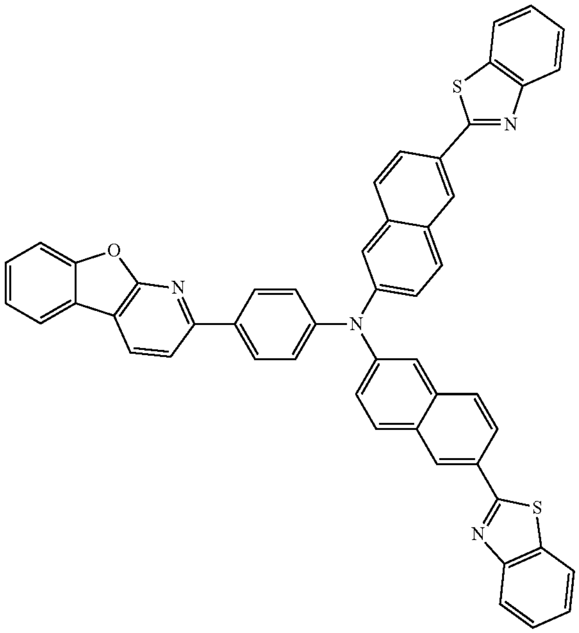
-continued
M067
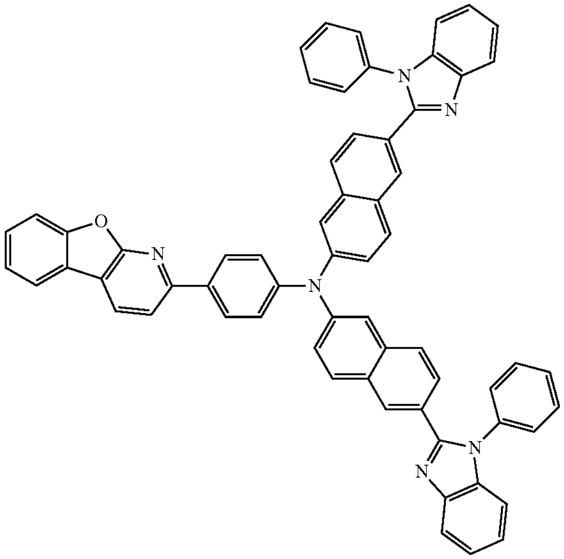
M068
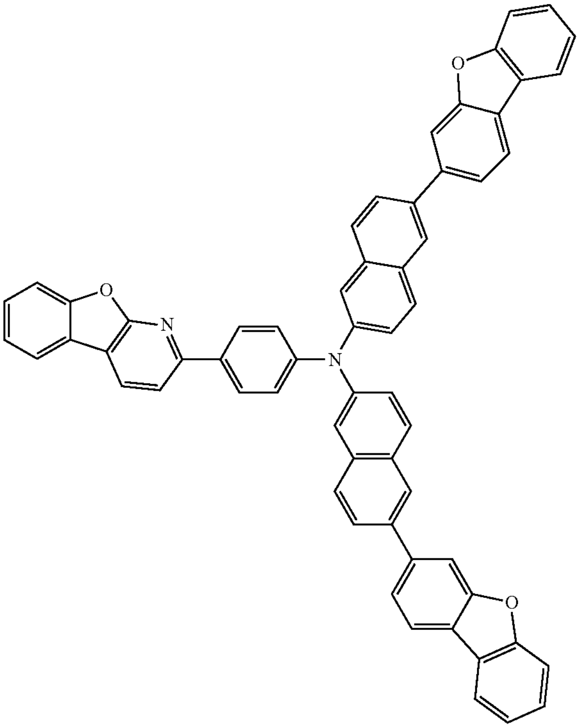

-continued
M069
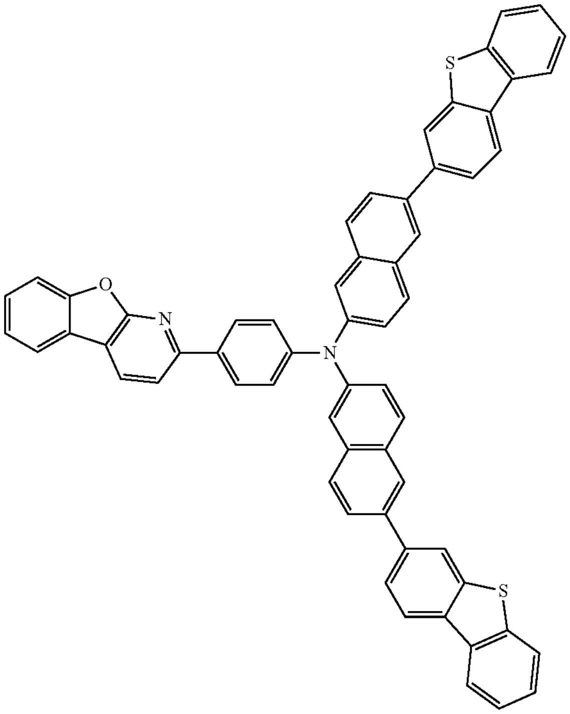
M070
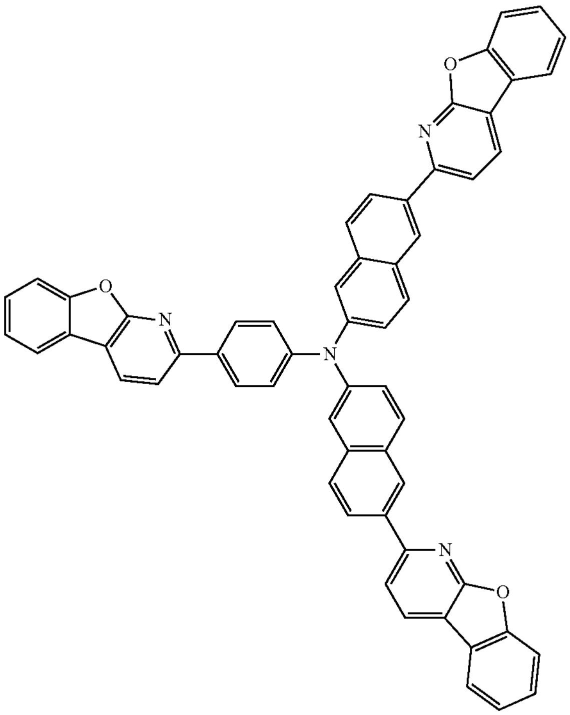
-continued
M071
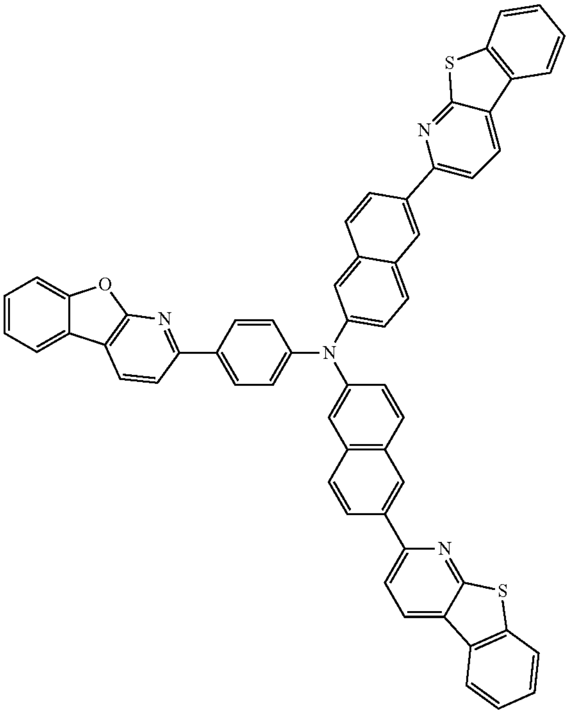
M072
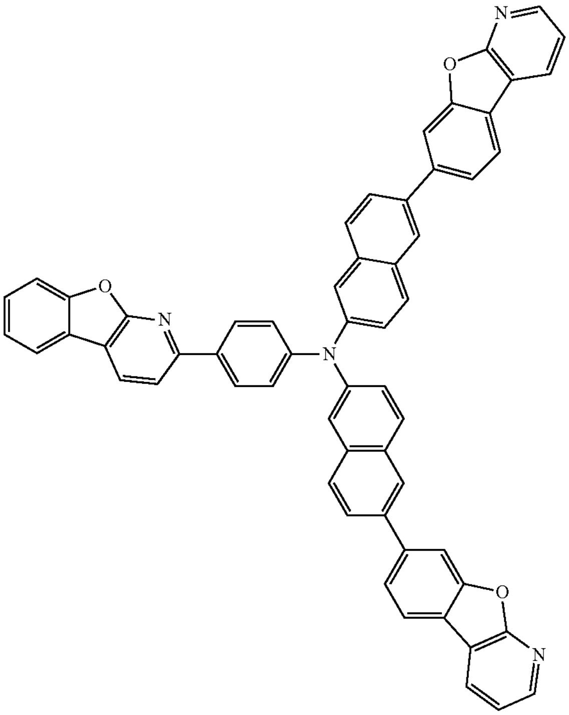

-continued
M073
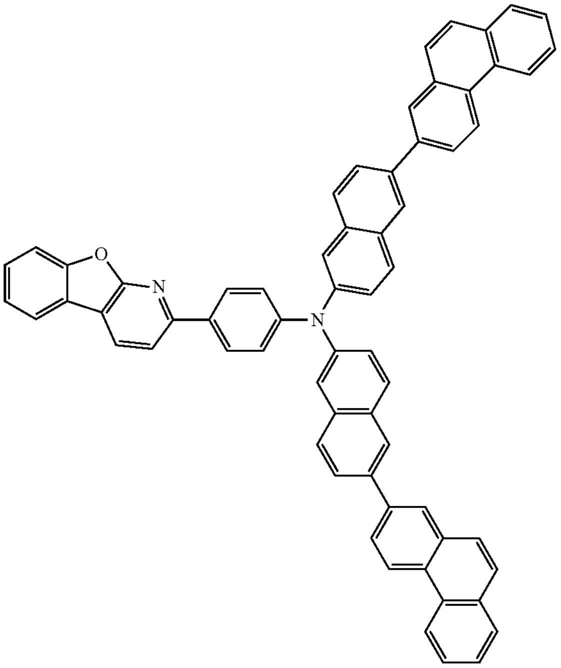
M074
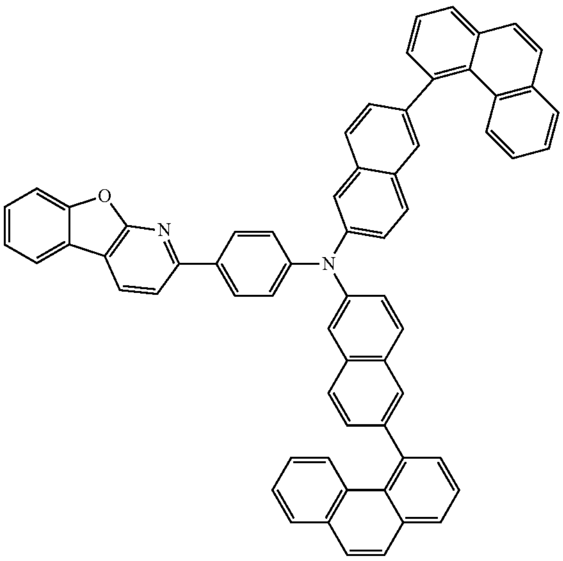
-continued
M075
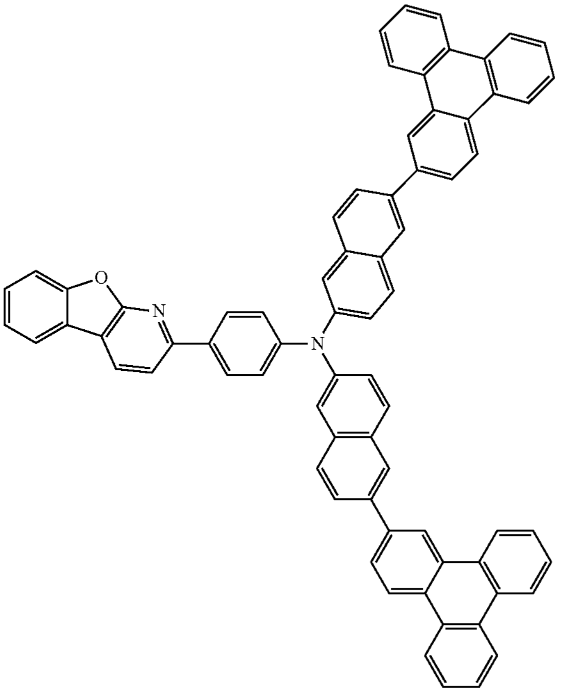
M076
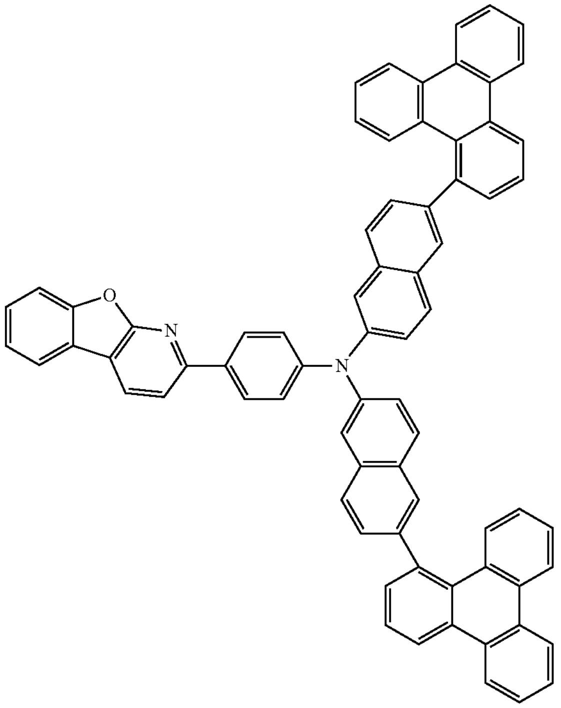

-continued
M077
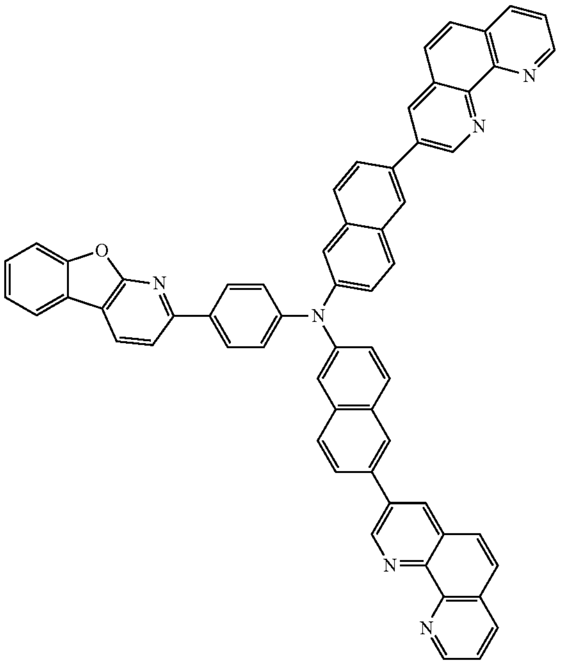
M078
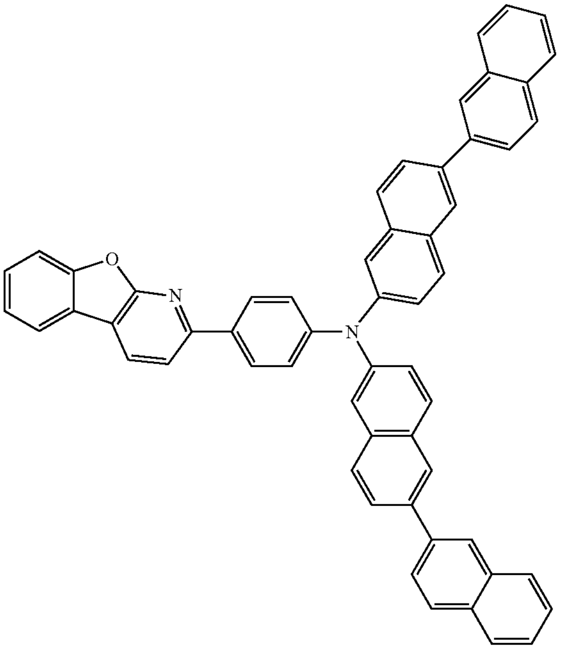
-continued
M079
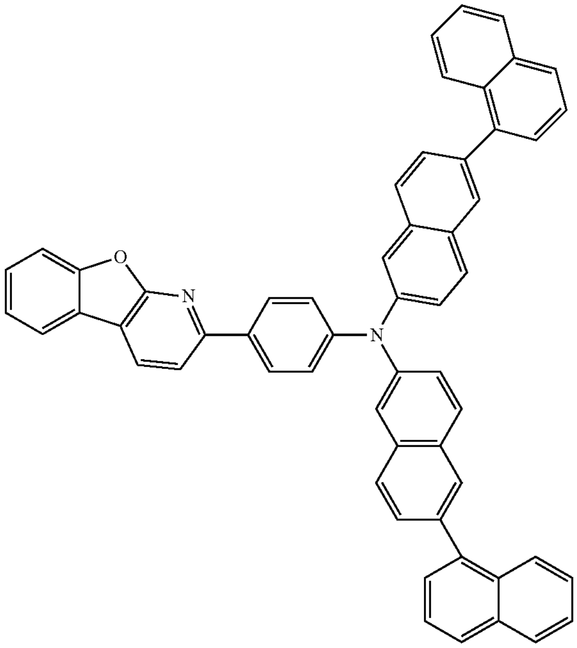
M080
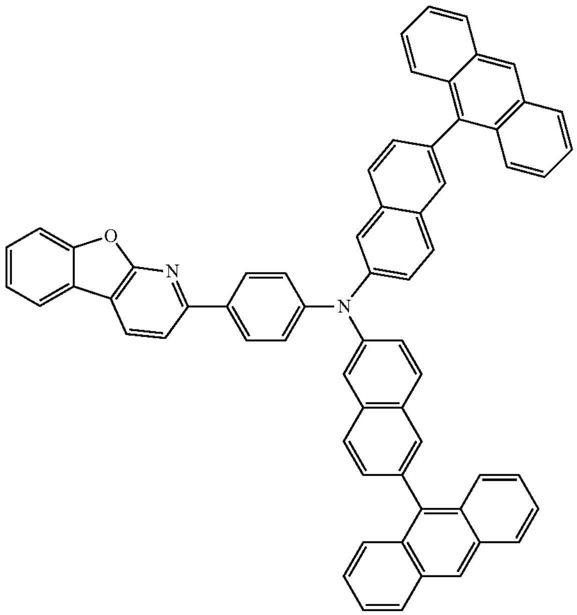

-continued
M081
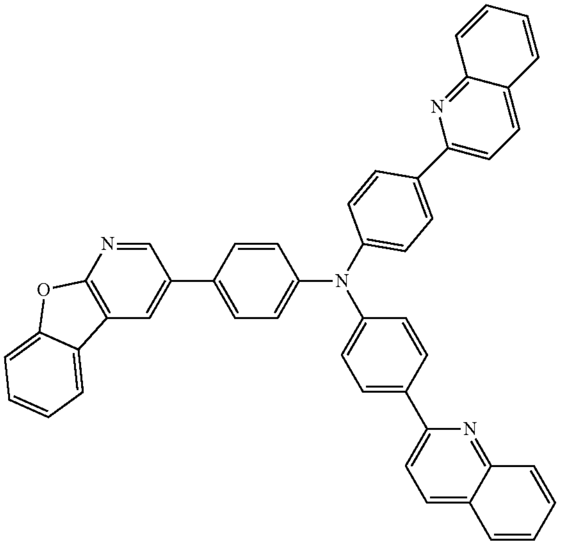
M082
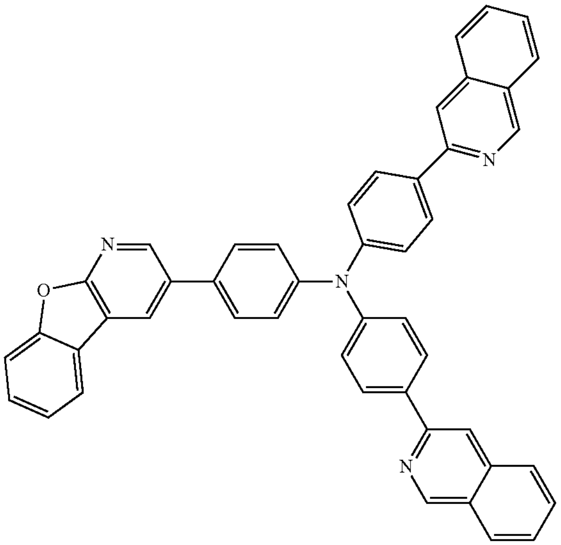
-continued
M083
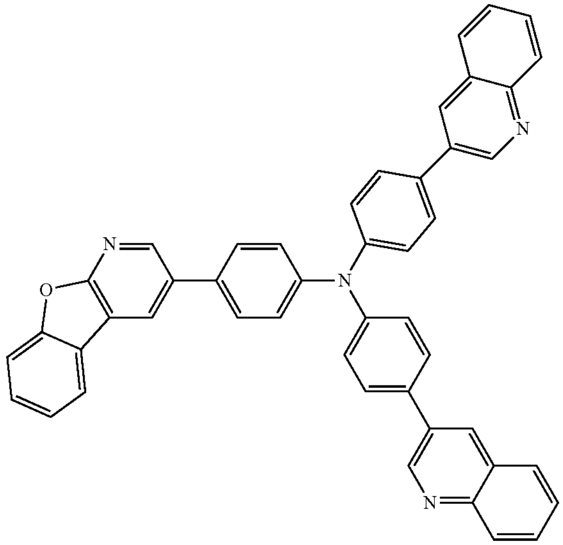
M084
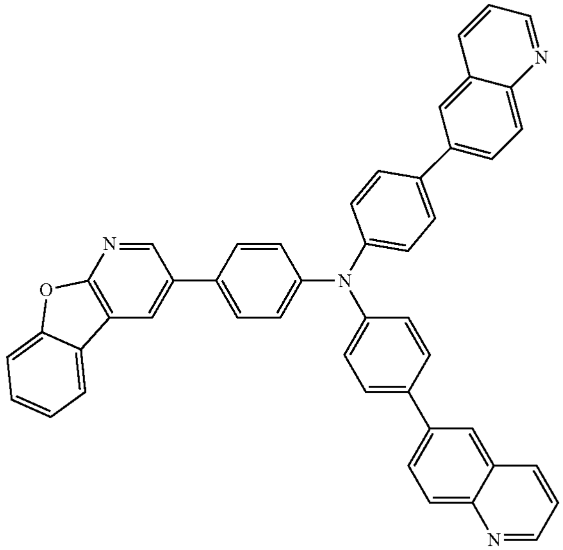

-continued
M085
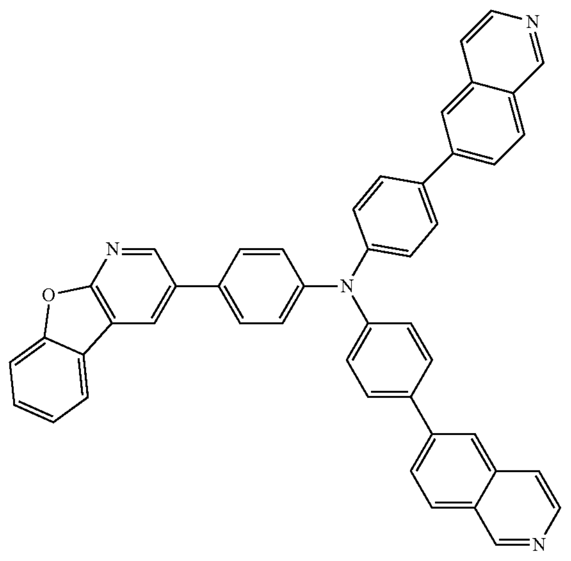
M086
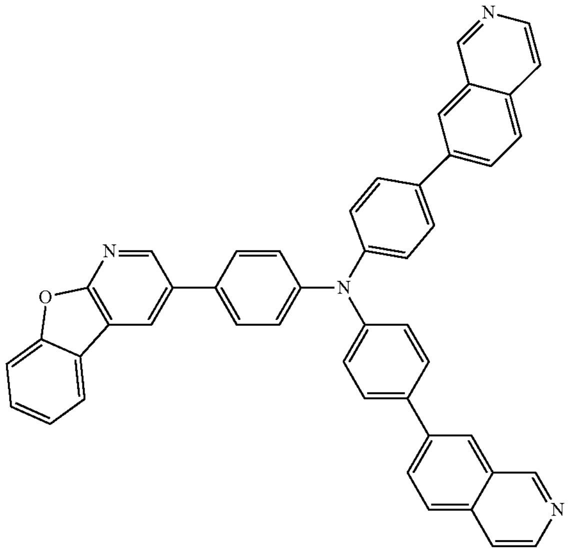
-continued
M087
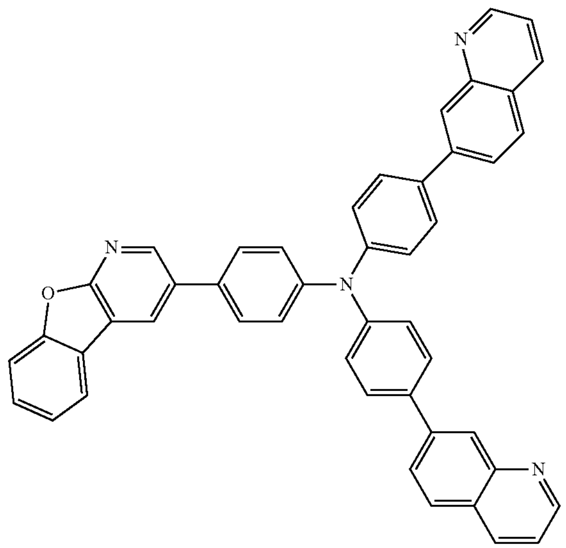
M088
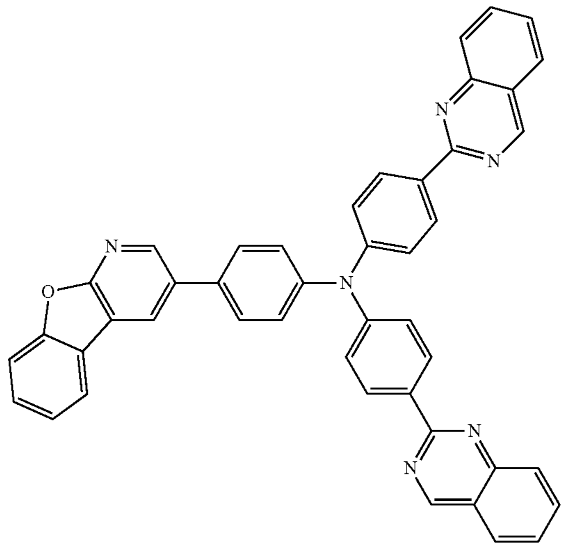

-continued
M089
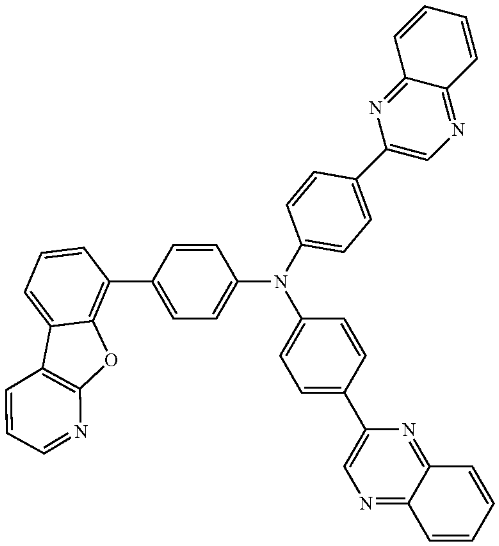
M090
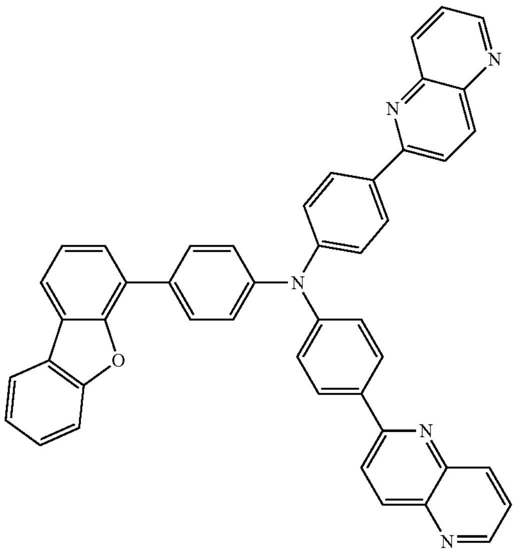
-continued
M091
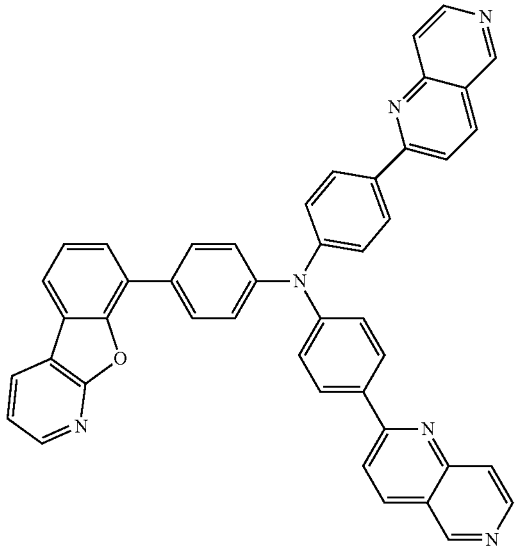
M092
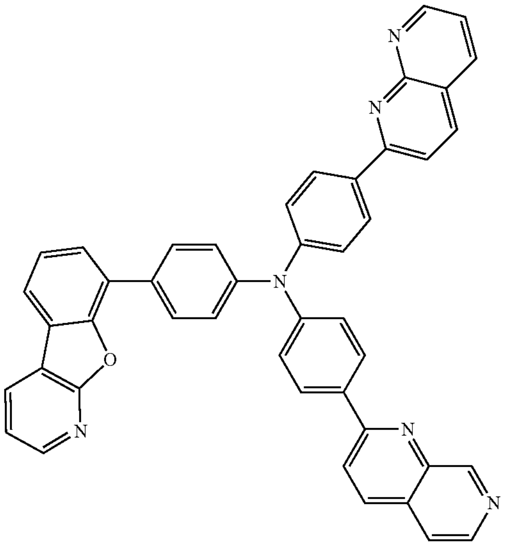

-continued
M093
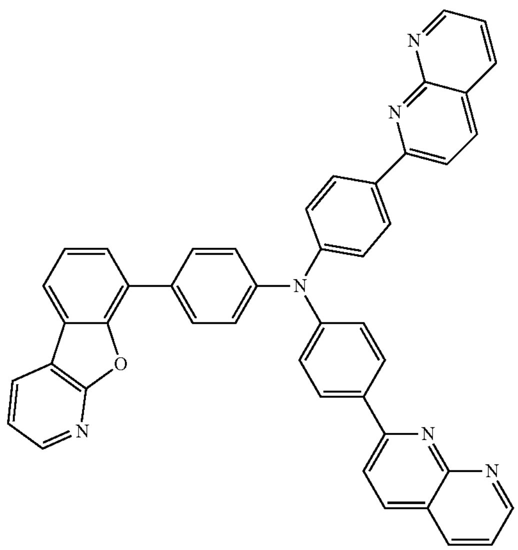
M094
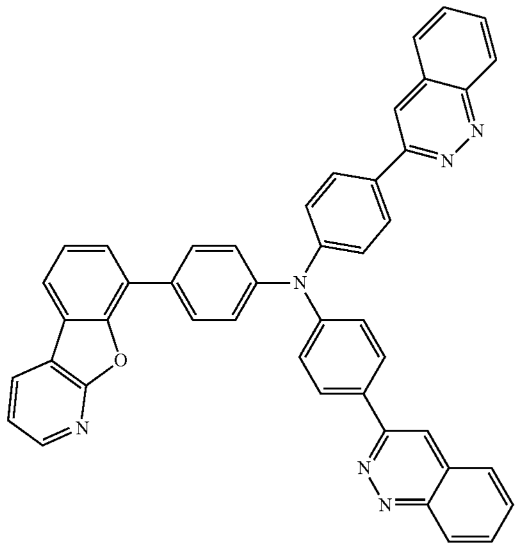
-continued
M095
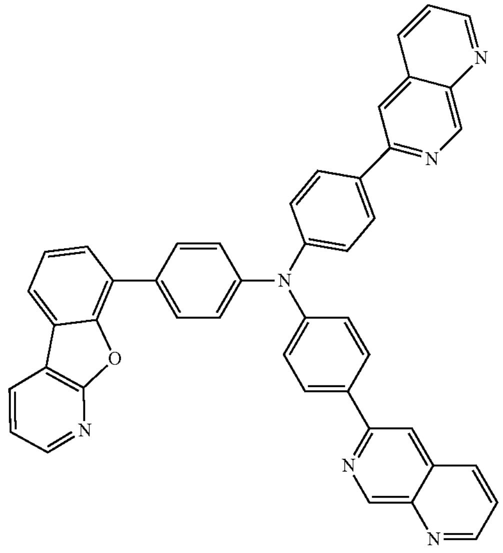
M096
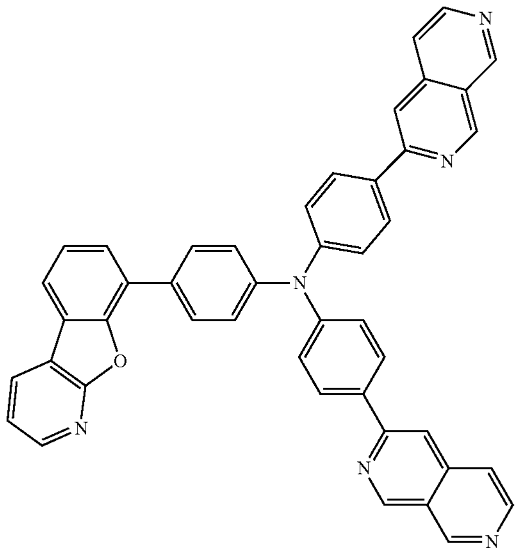
M097
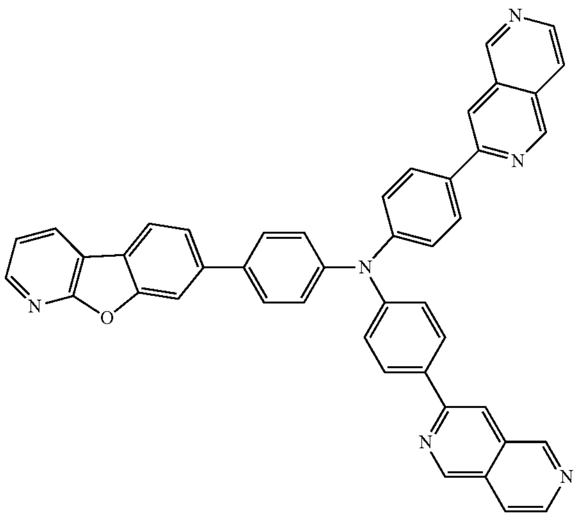

-continued
M098
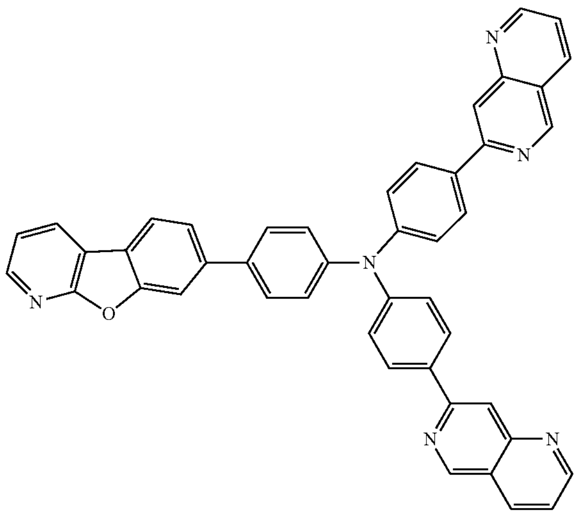
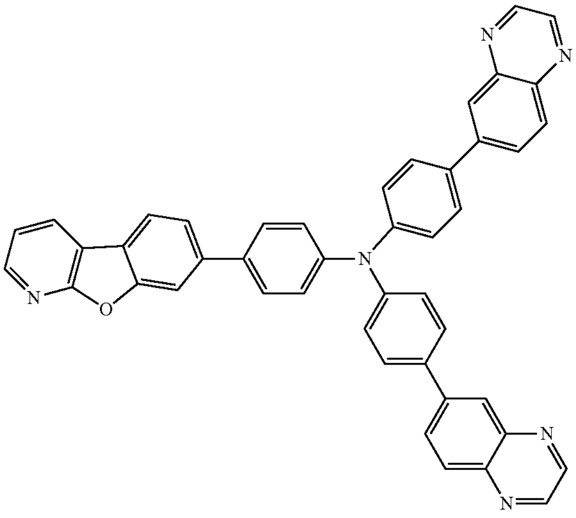
M100
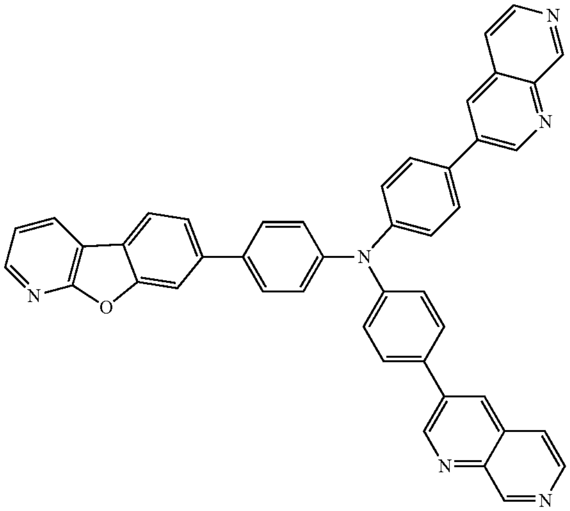
-continued
M101
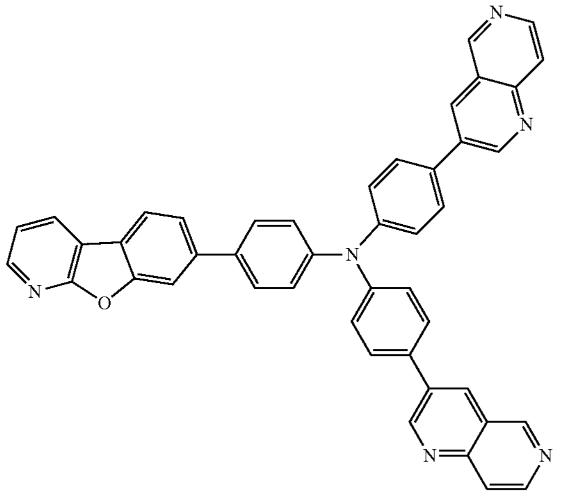
M102
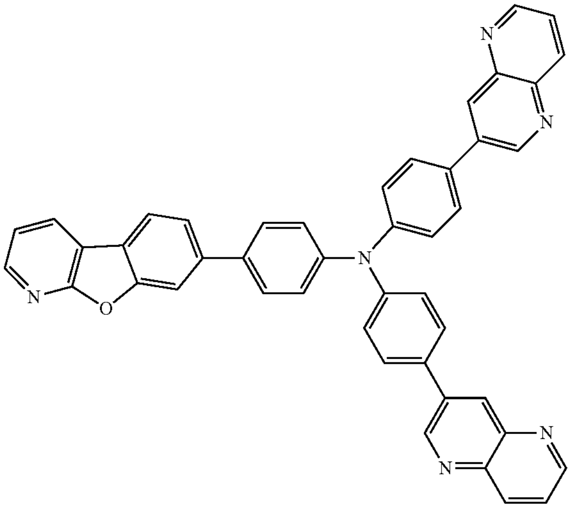
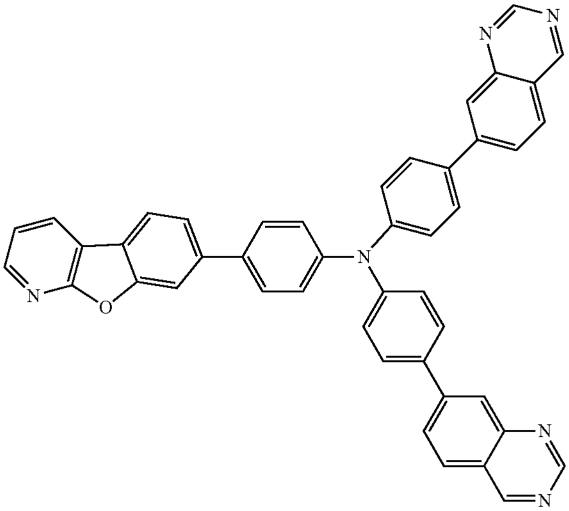

M104
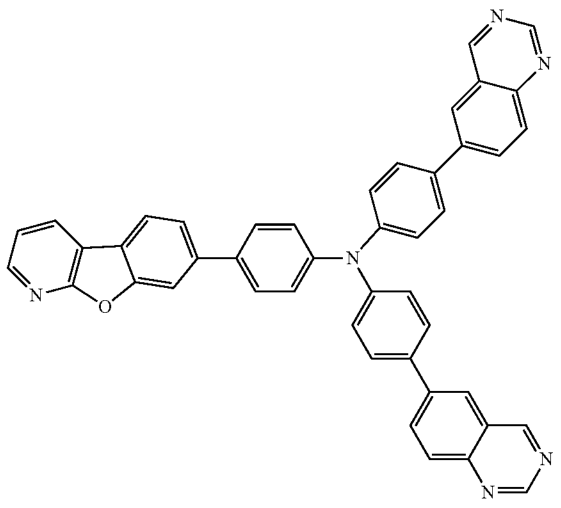
M105
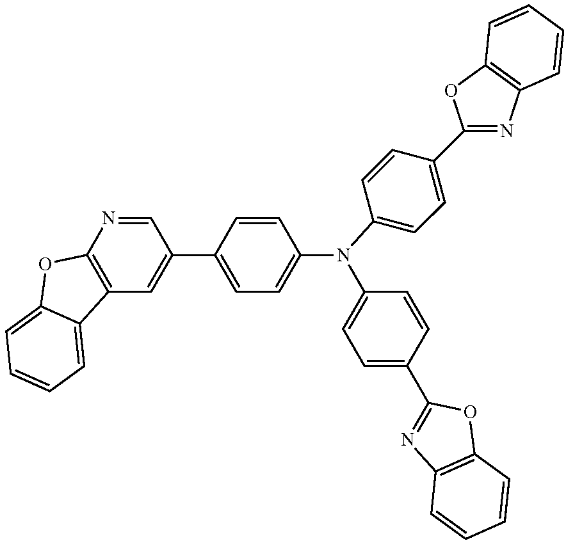
M106
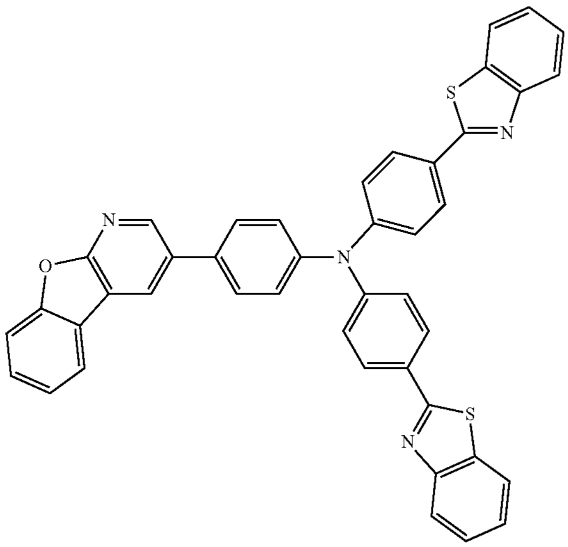
M107
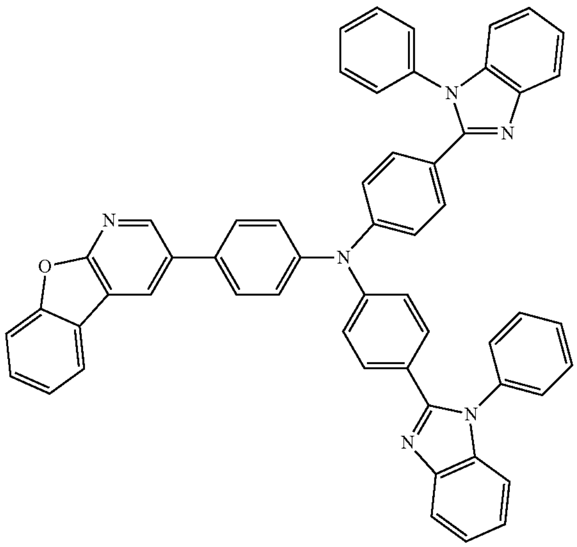
M108
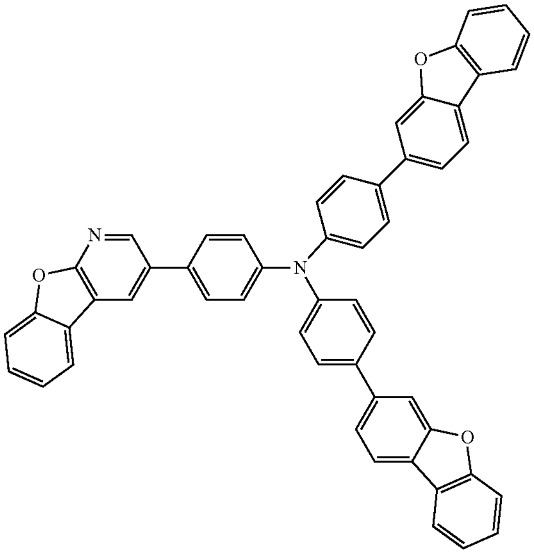

M109
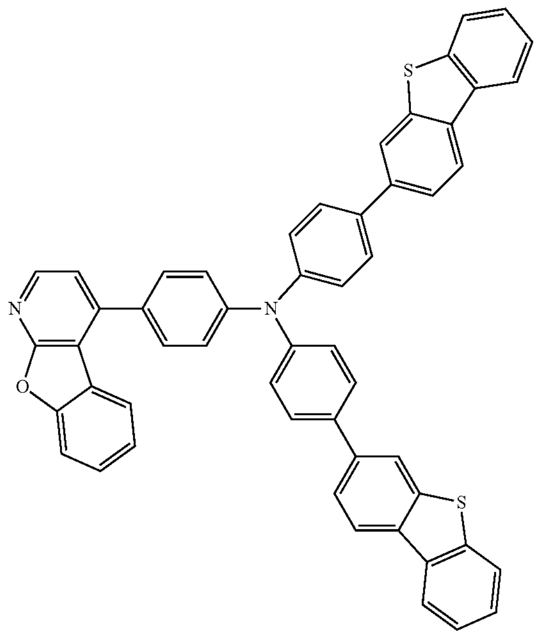
M110
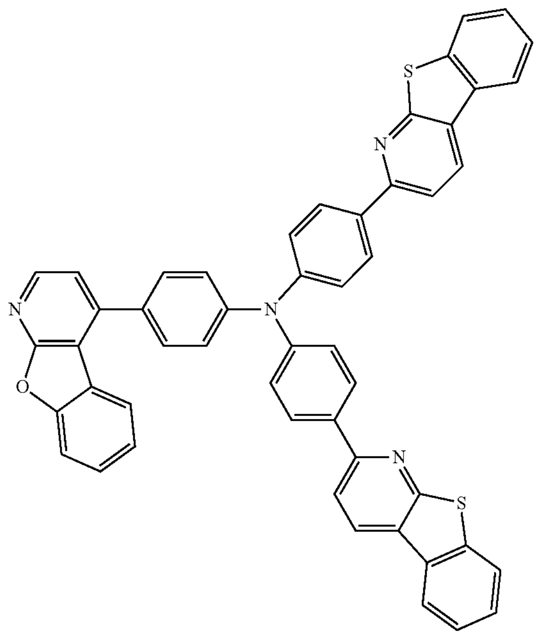
M111
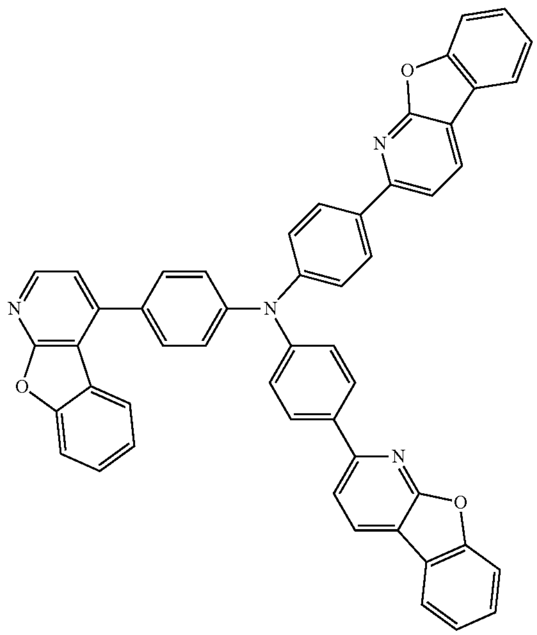
M112
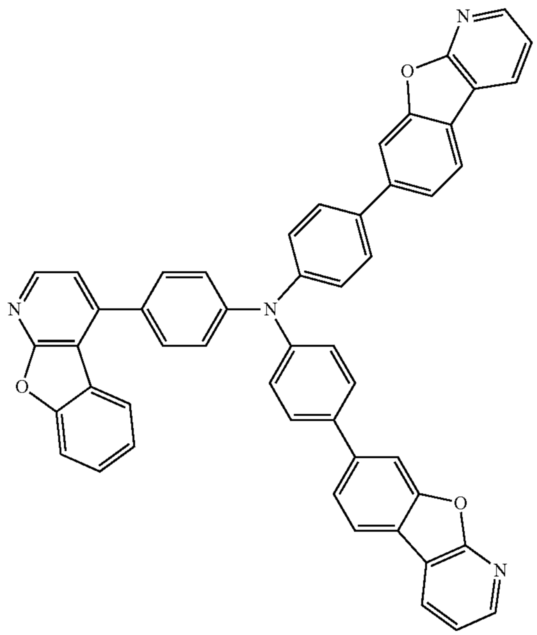

-continued
M113
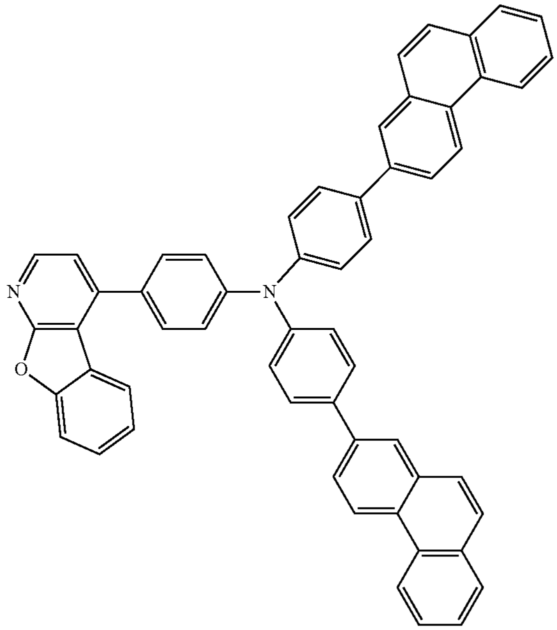
M114
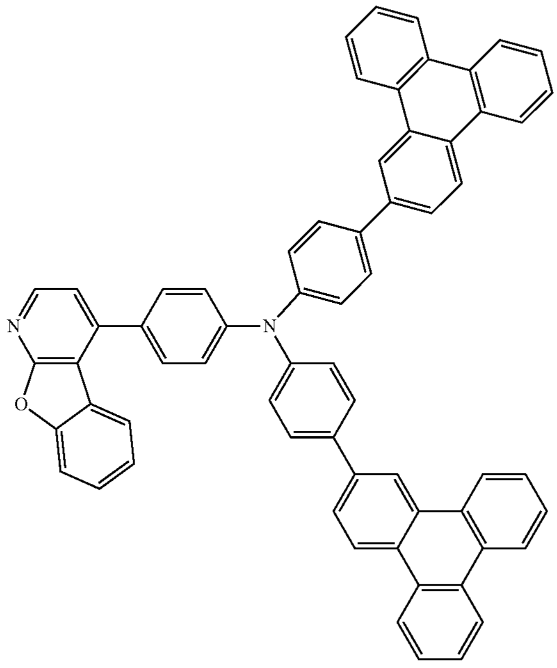
-continued
M115
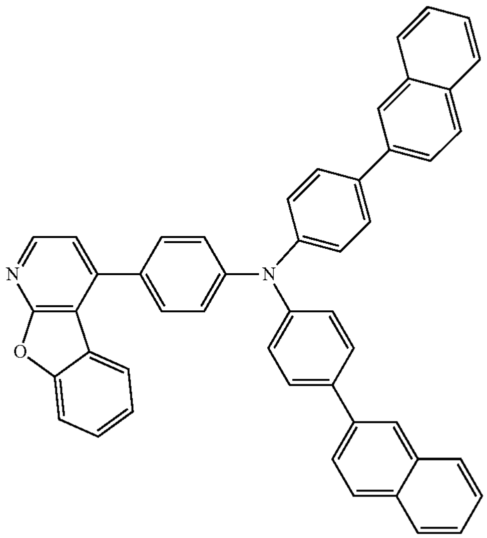
M116
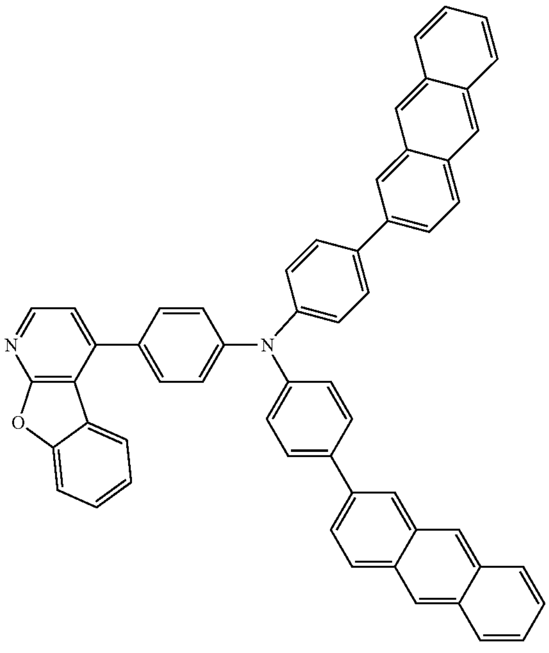

-continued
M117
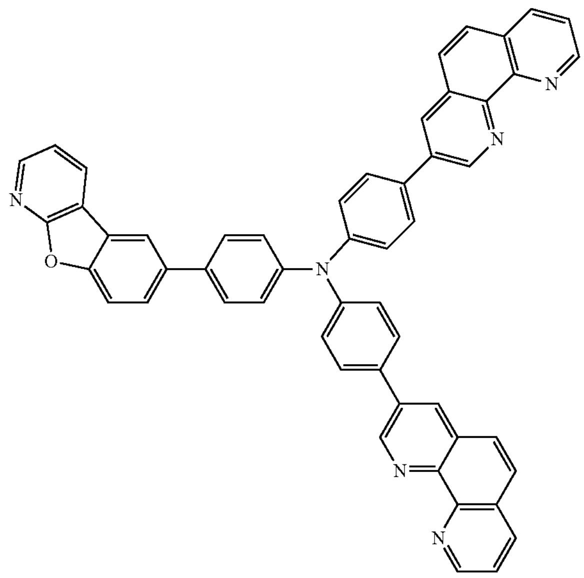
M118
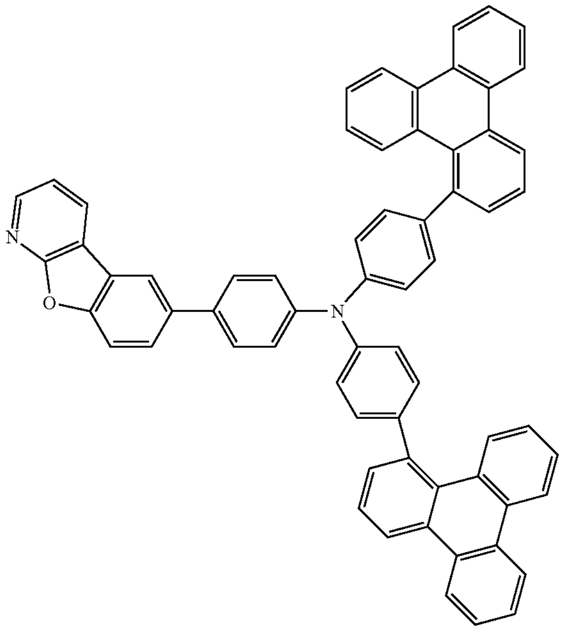
-continued
M119
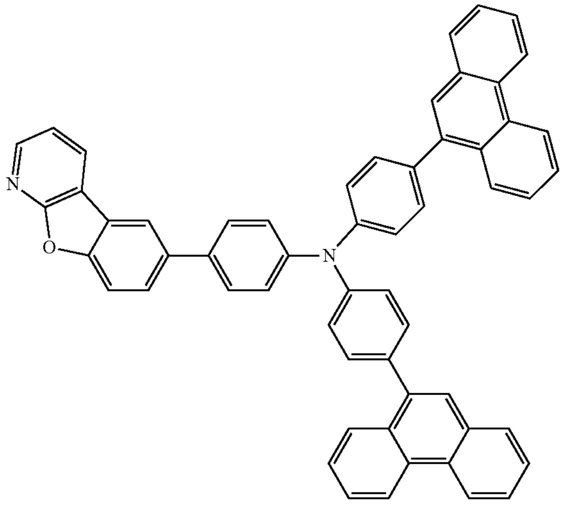
M120
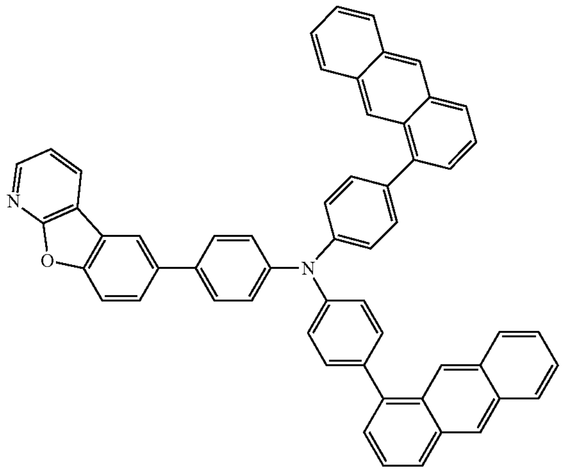
M121
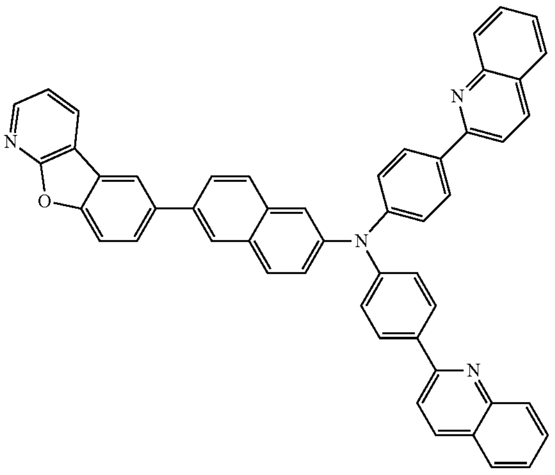

-continued
M122
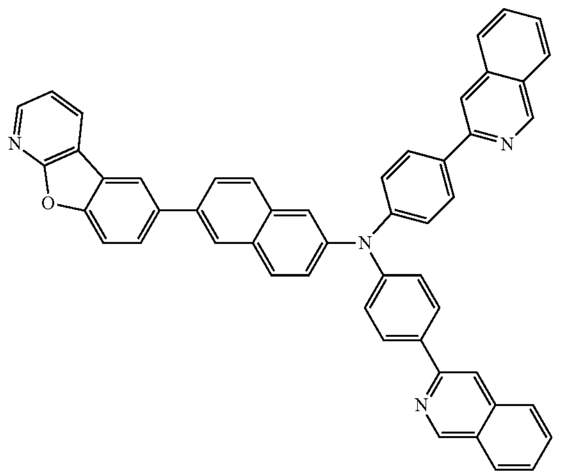
M123
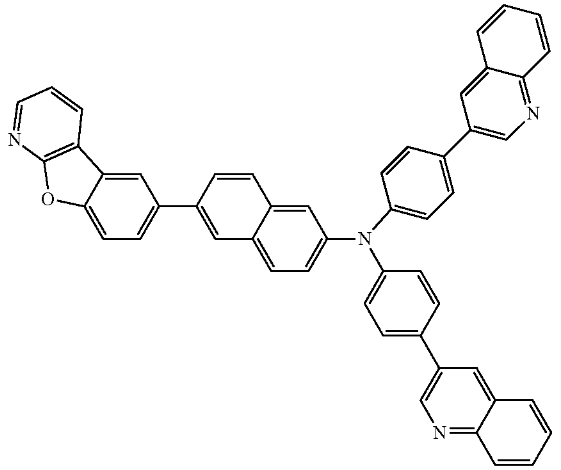
M124
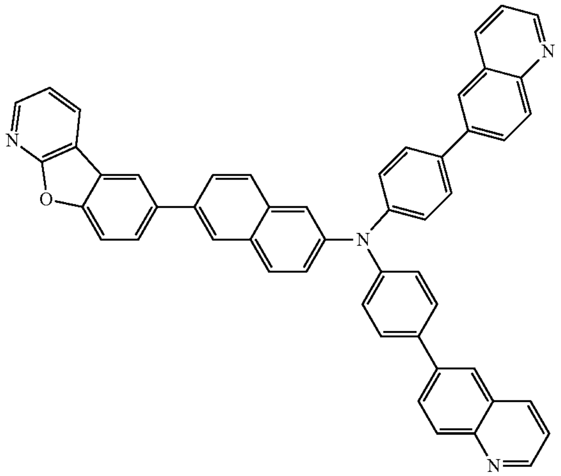
-continued
M125
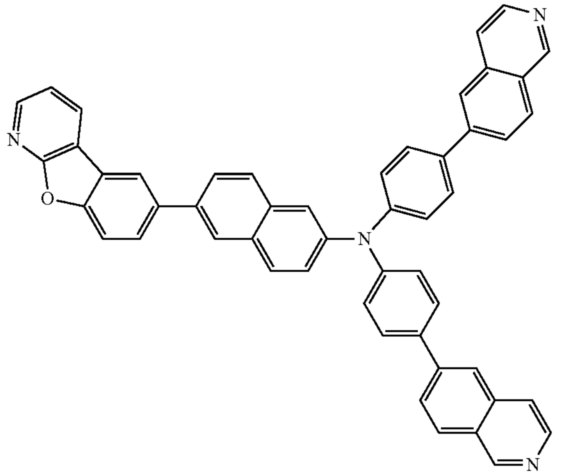
M126
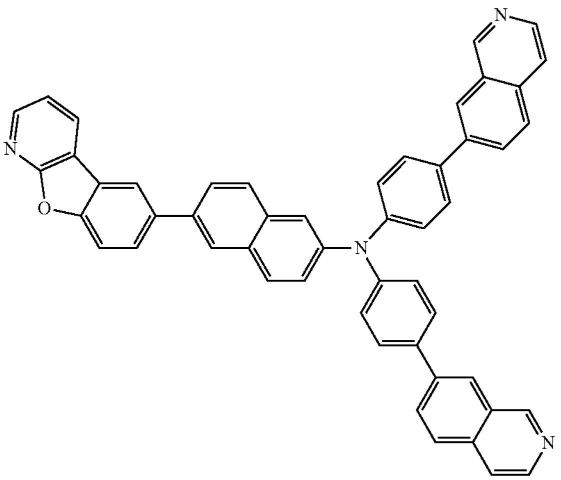
M127
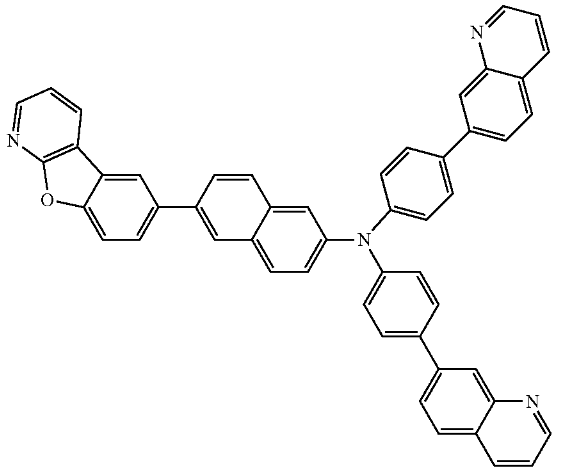

-continued
M128
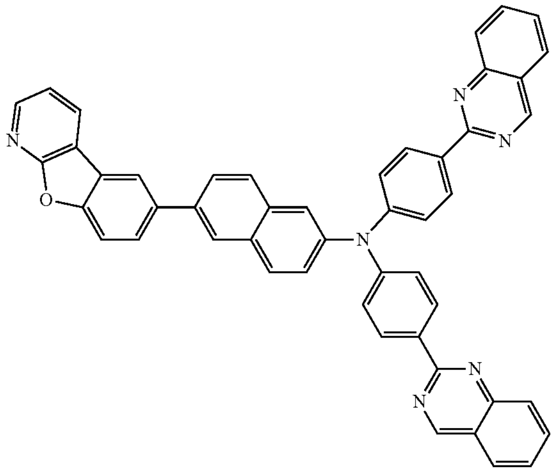
M129
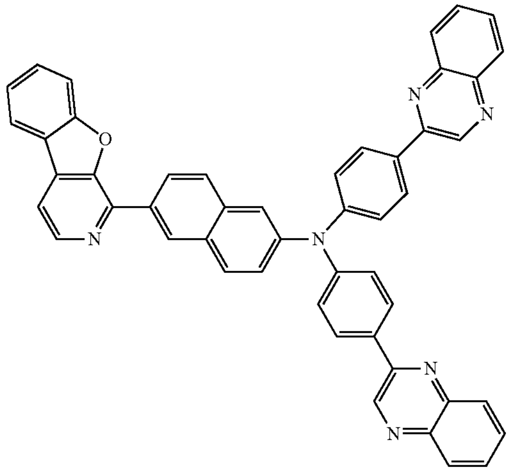
M130
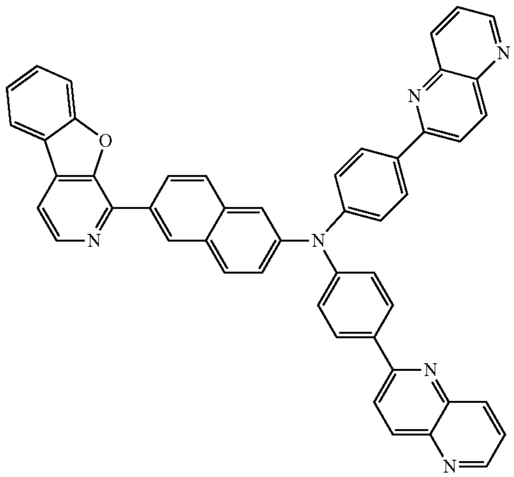
-continued
M131
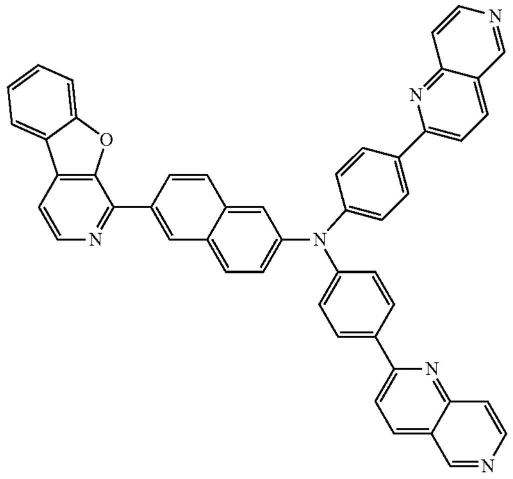
M132
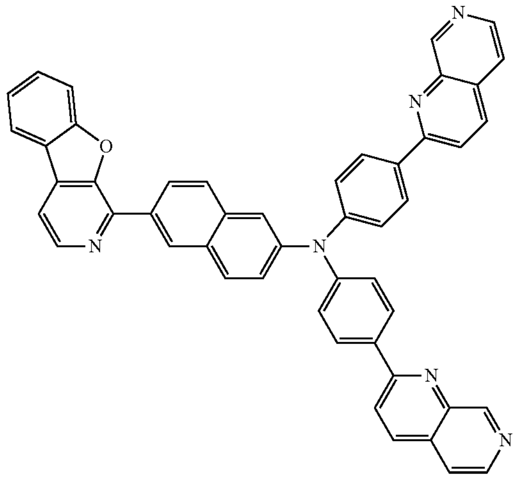
M133
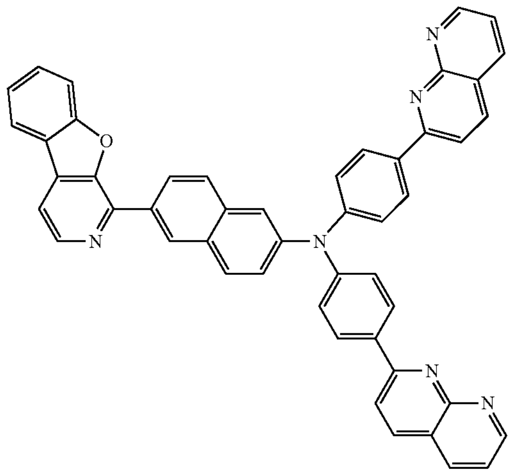

-continued
M134
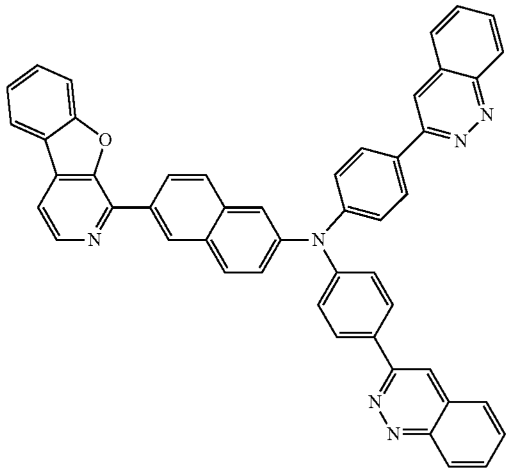
M135
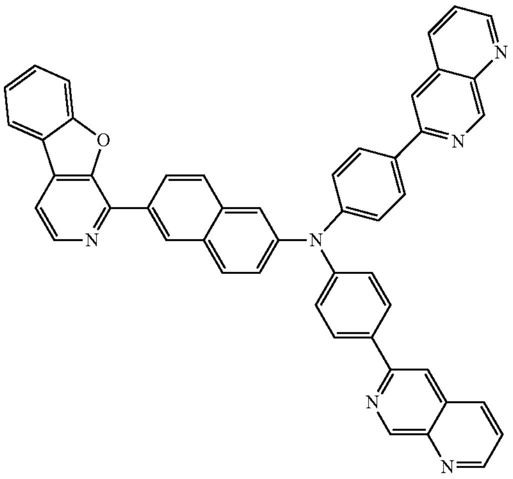
M136
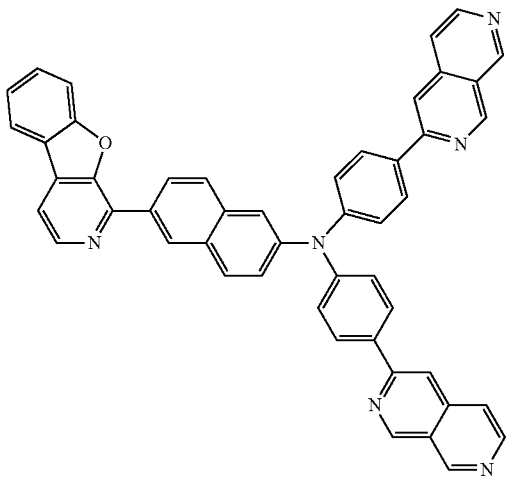
-continued
M137
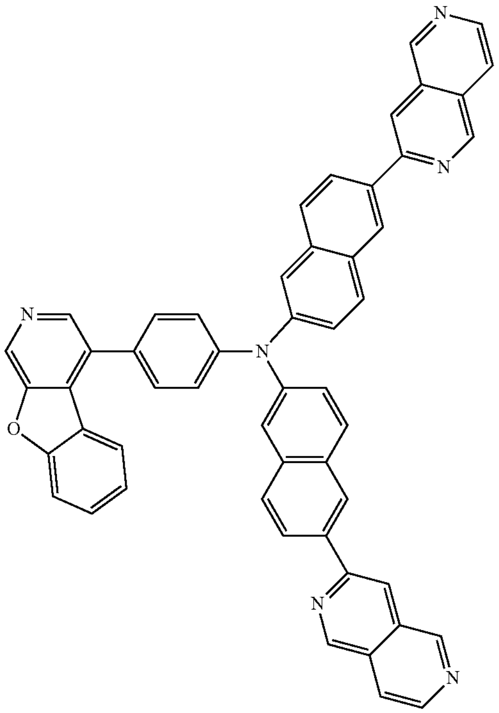
M138
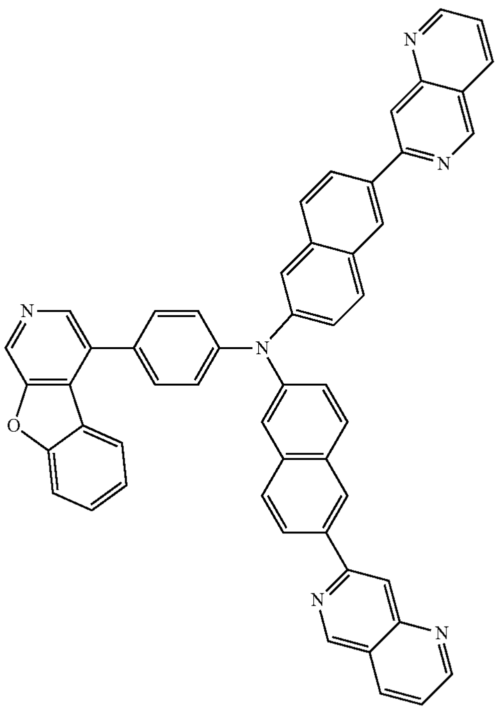

-continued
M139
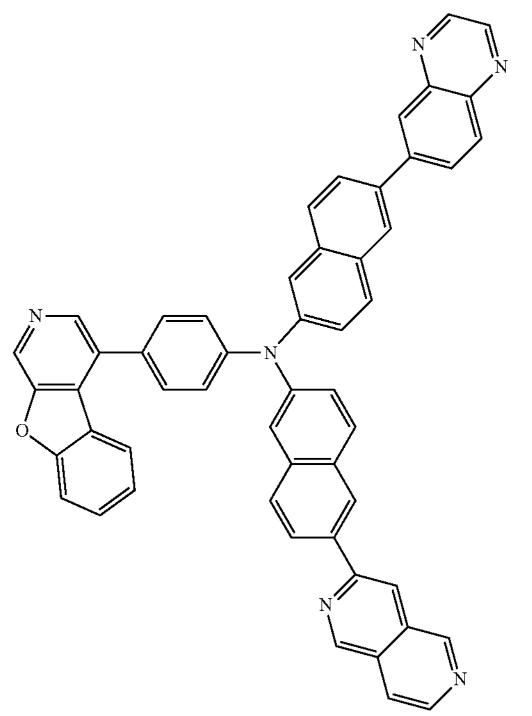
M140
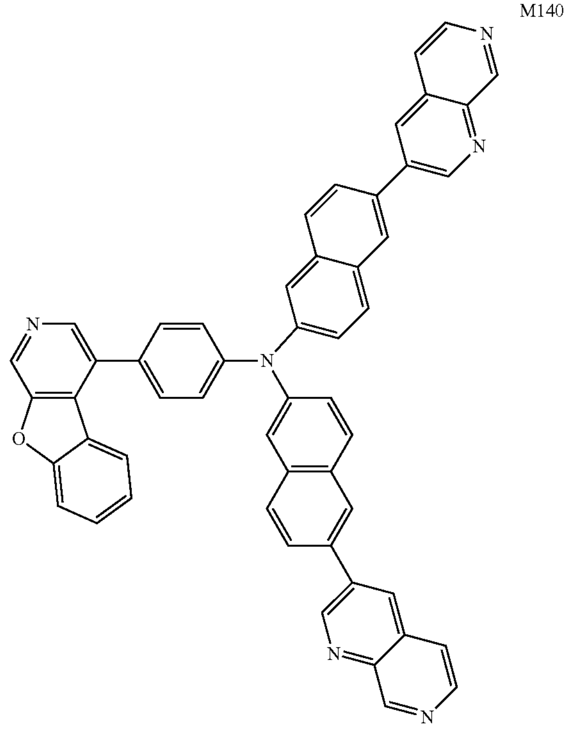
-continued
M141
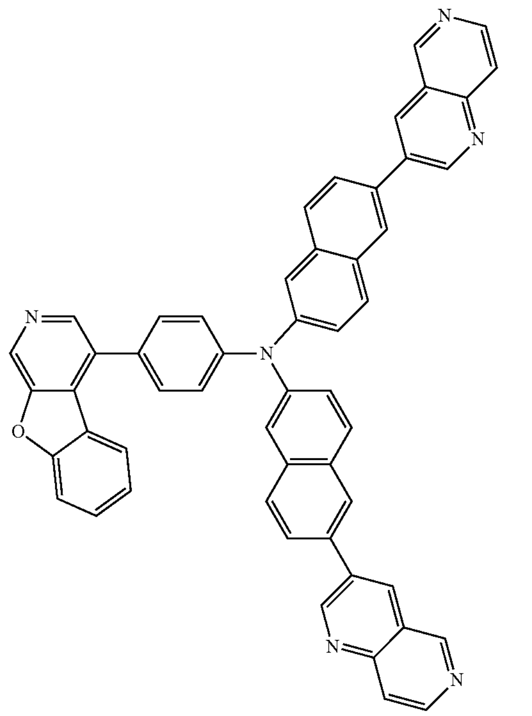
M142
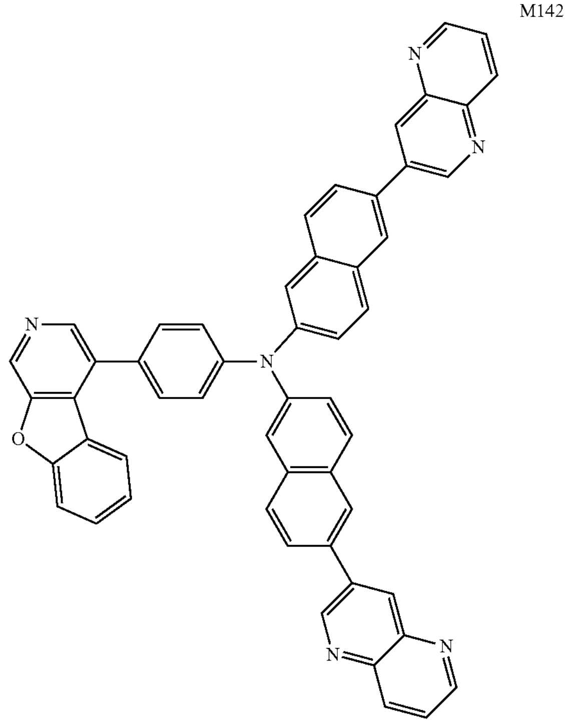

-continued
M143
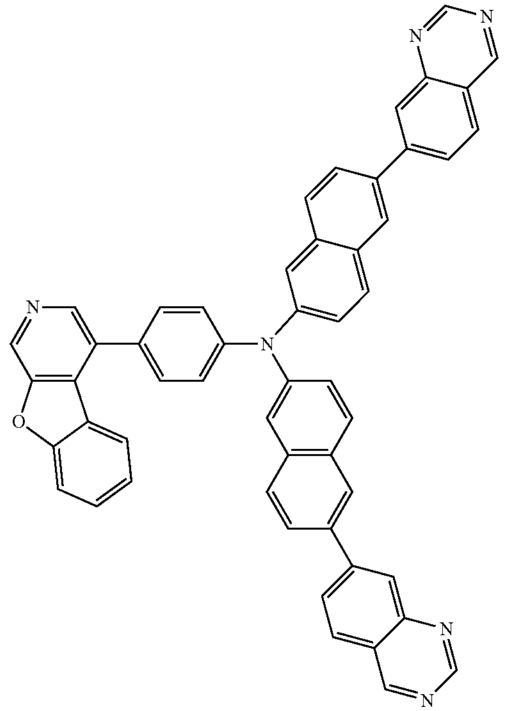
M144
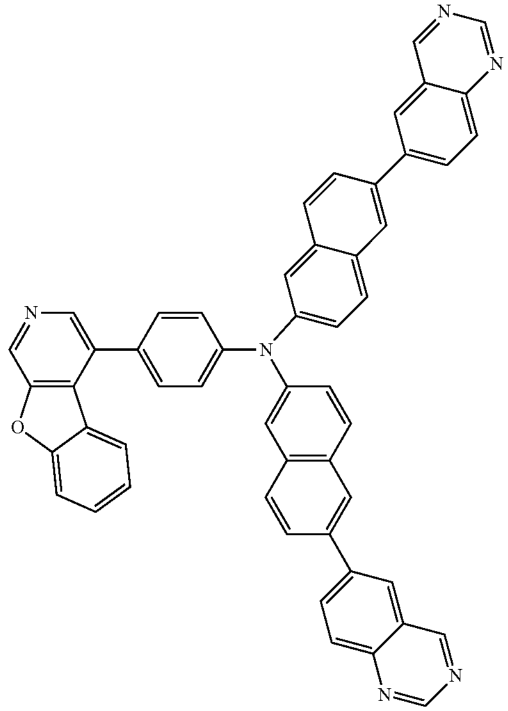
-continued
M145
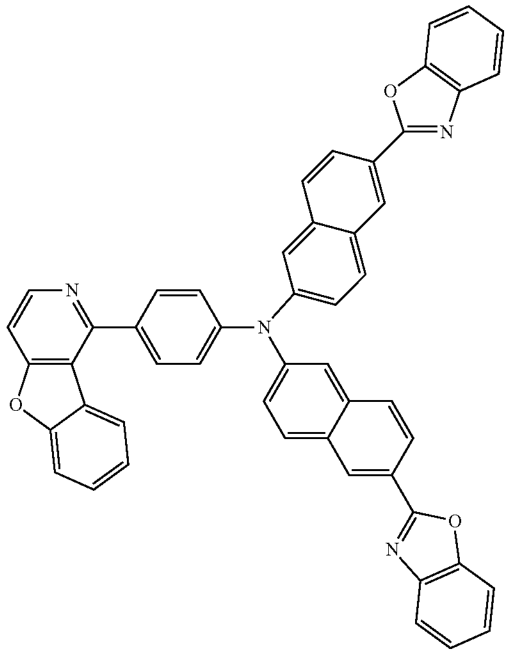
M146
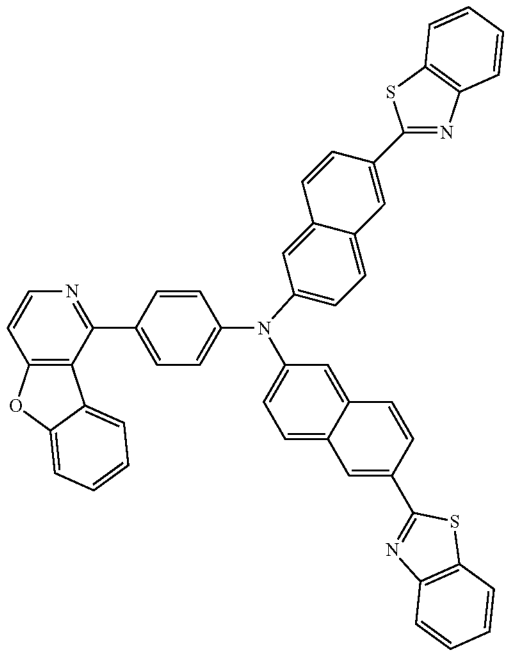

M147
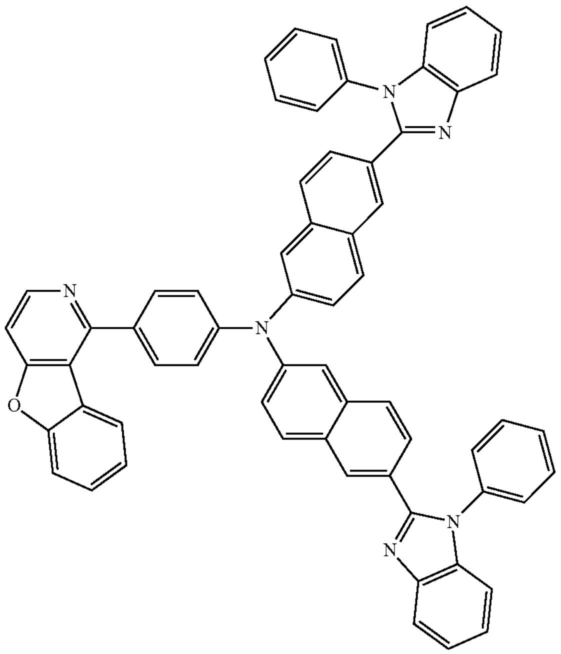
M148
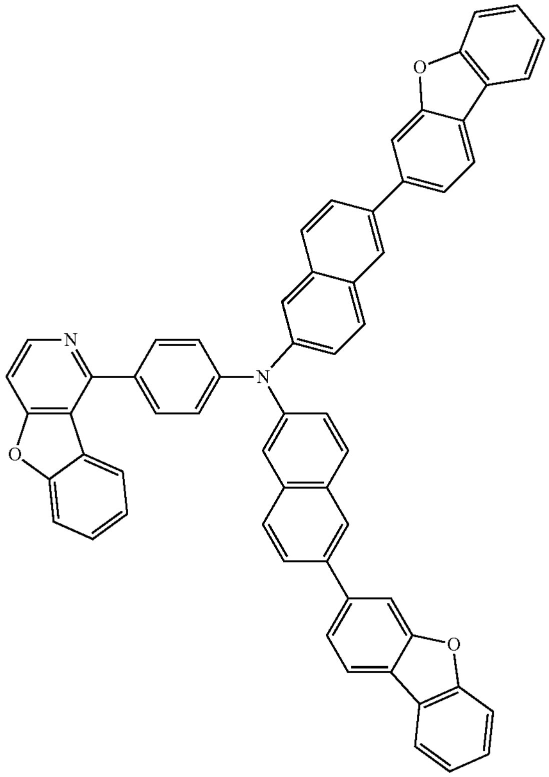
M149
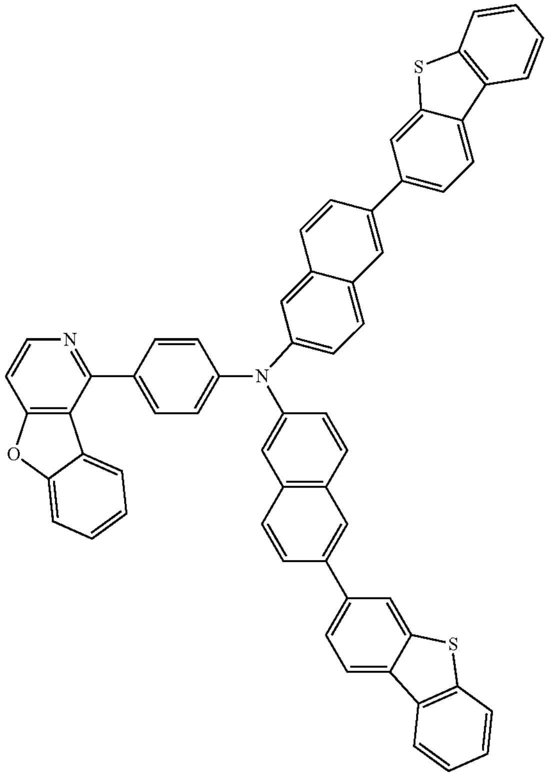
M150
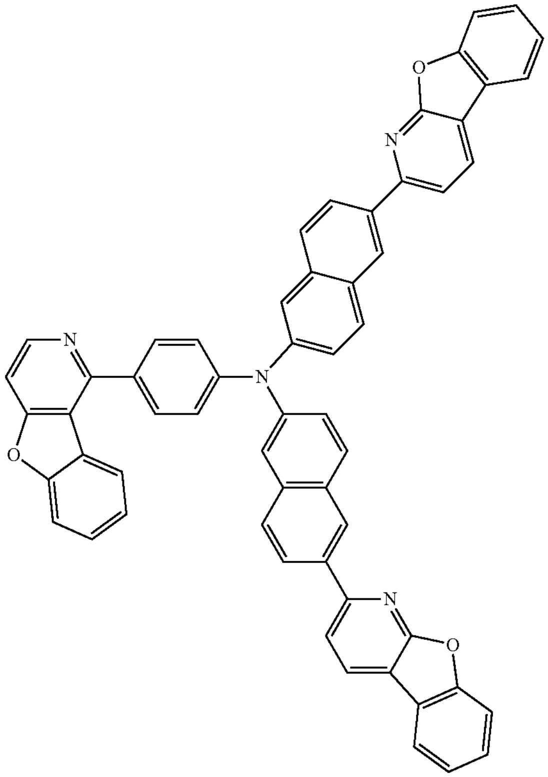

-continued
M151
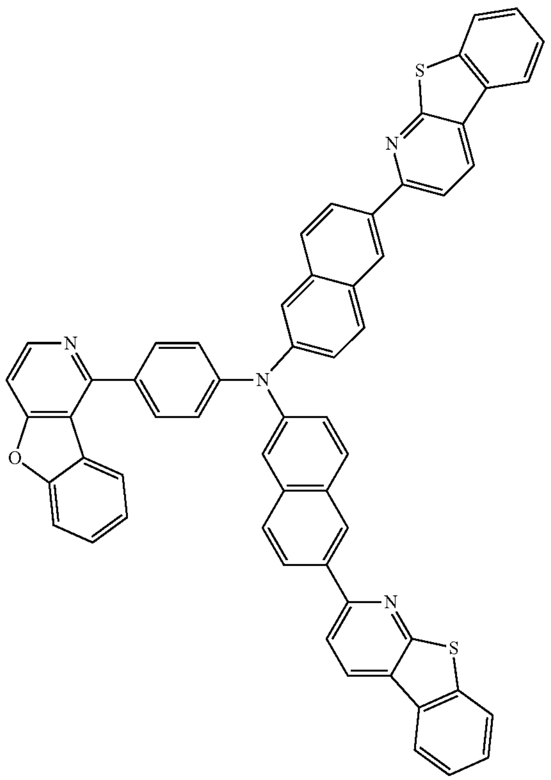
M152
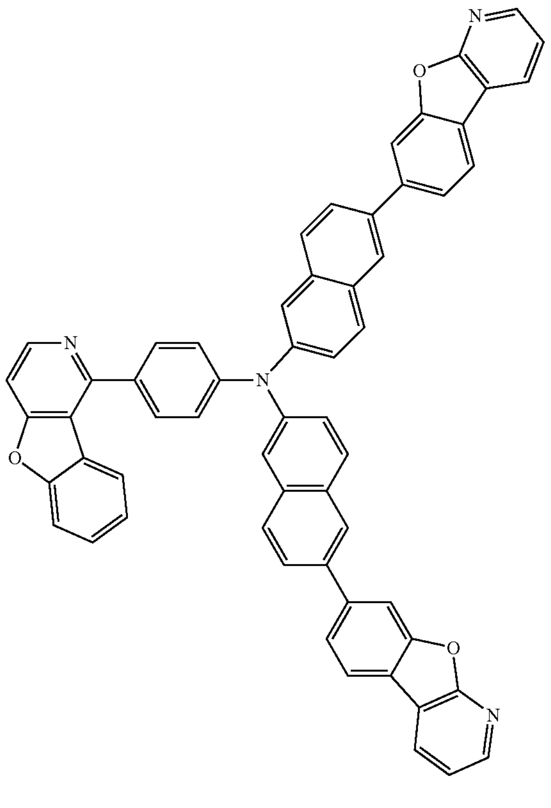
-continued
M153
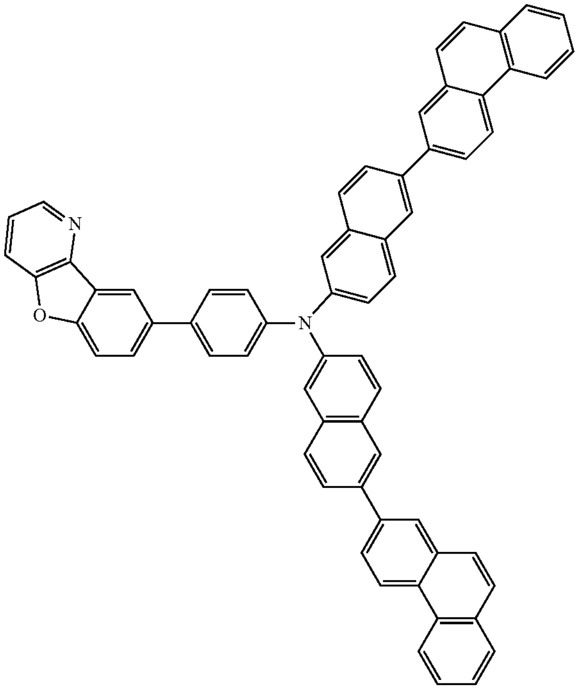
M154
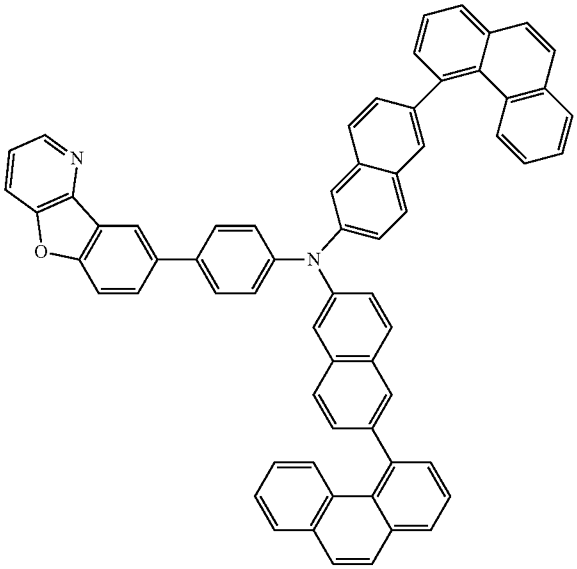

-continued
M155
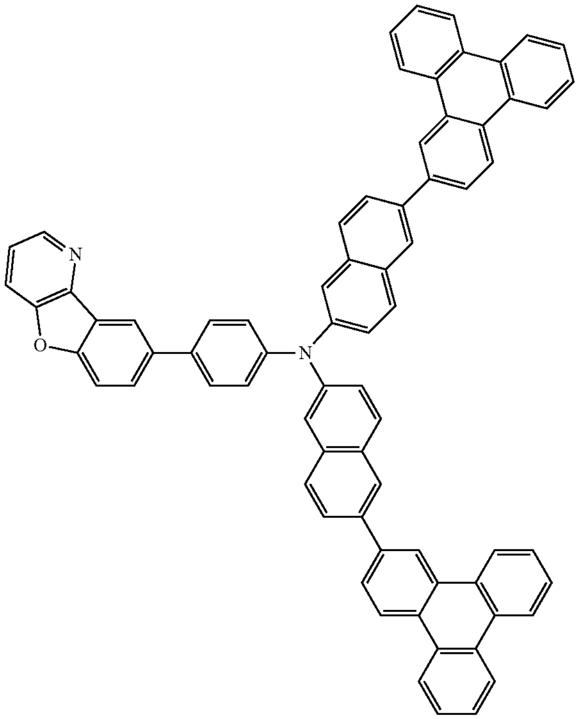
M156
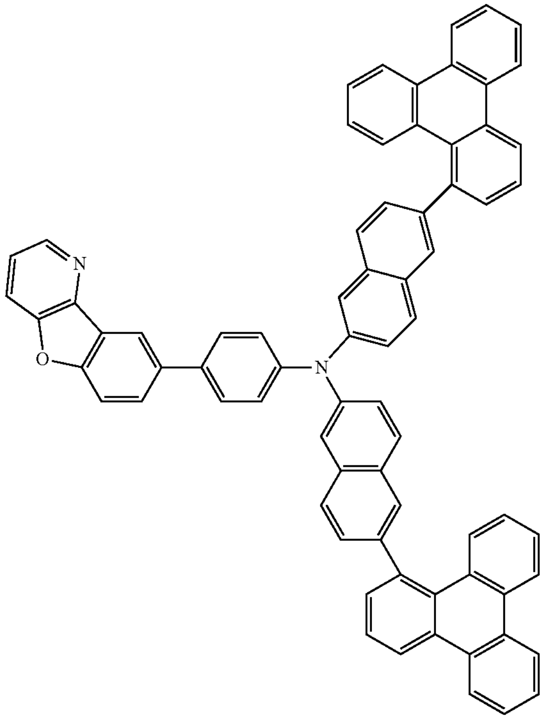
-continued
M157
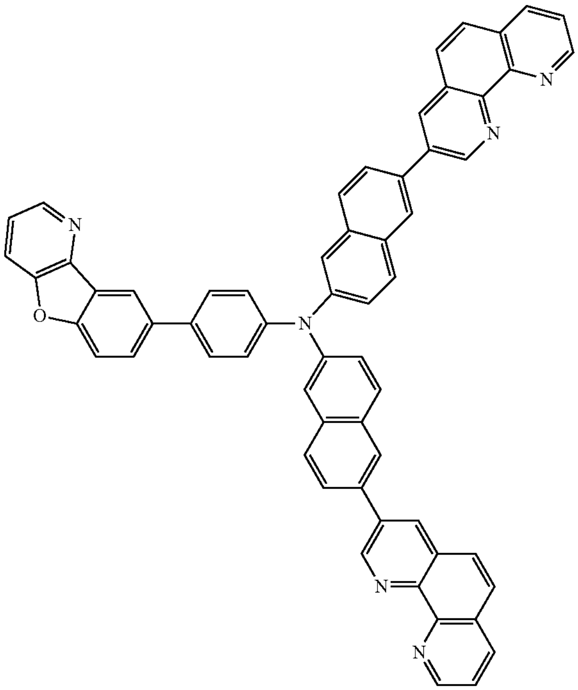
N158
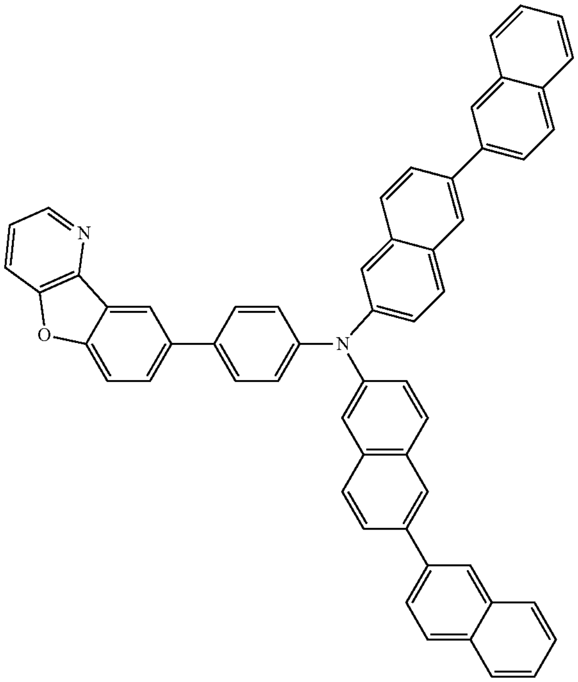

-continued
M159
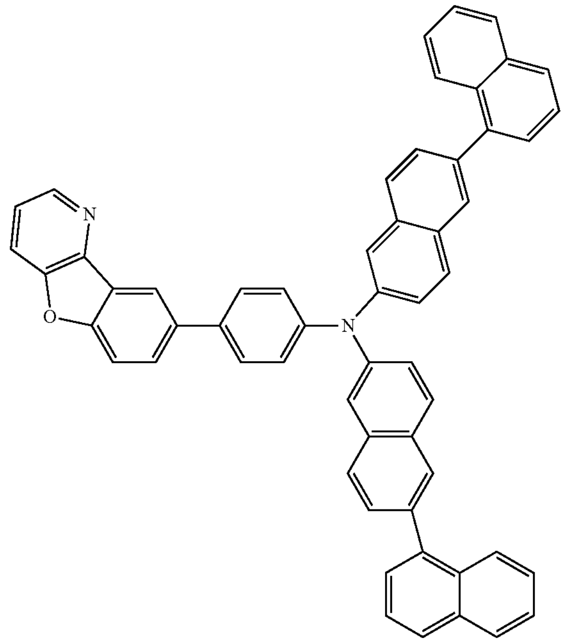
M160
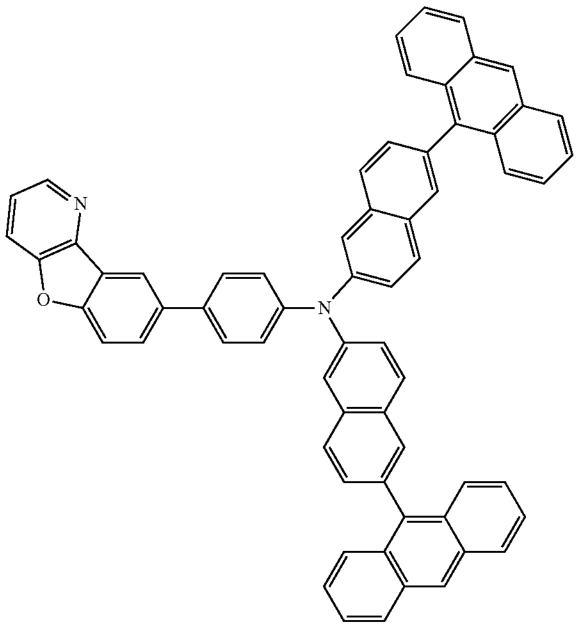
-continued
M161
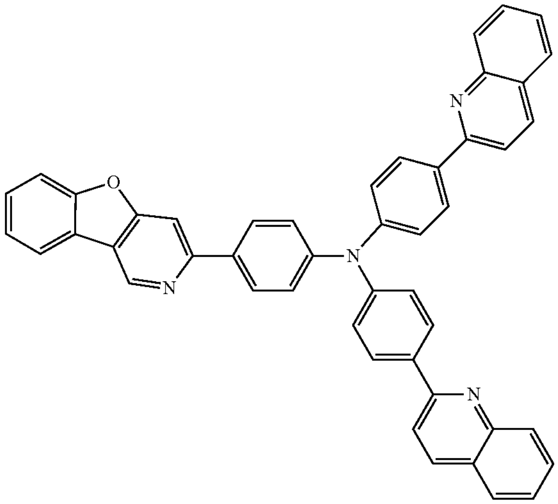
M162
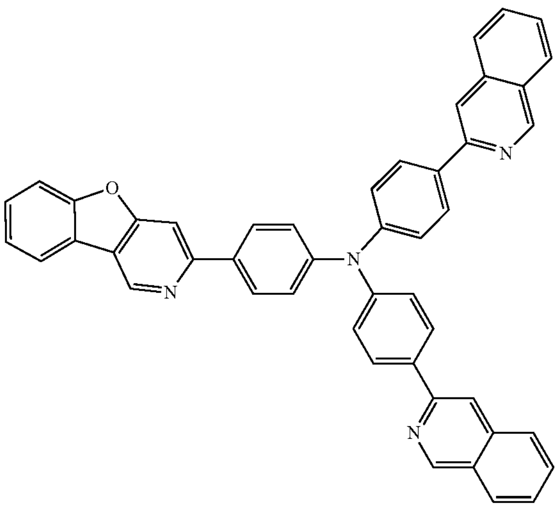
M163
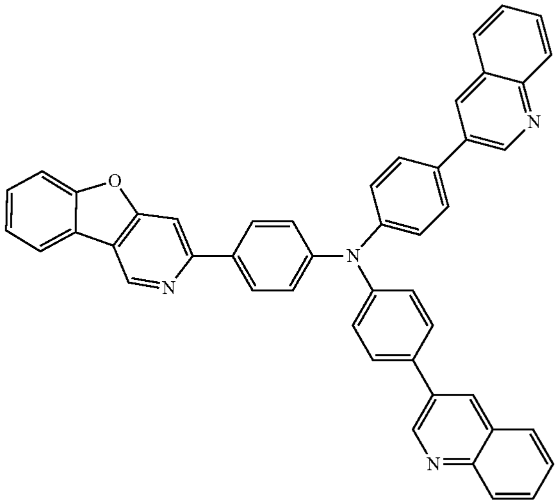

-continued
M164
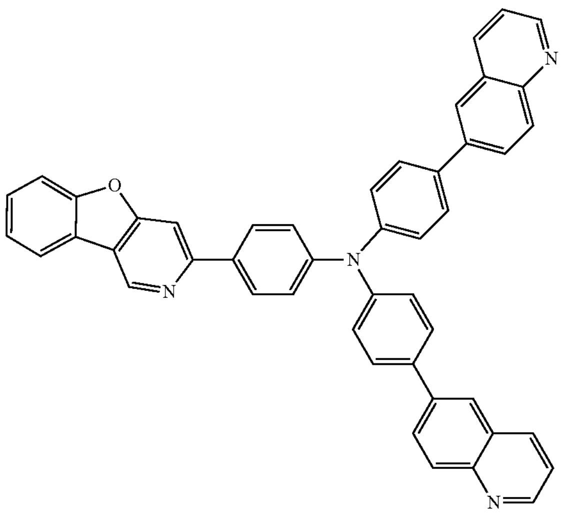
M165
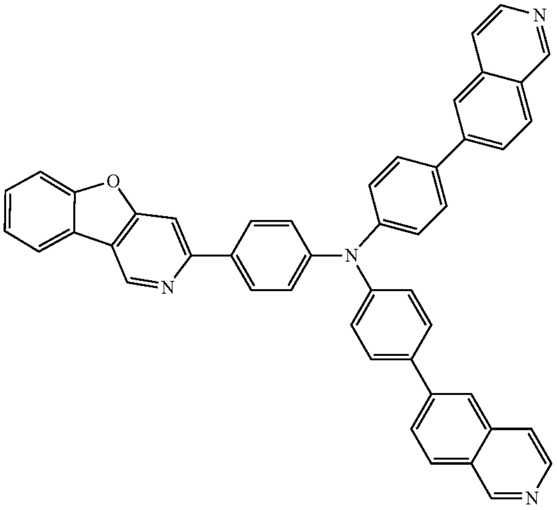
M166
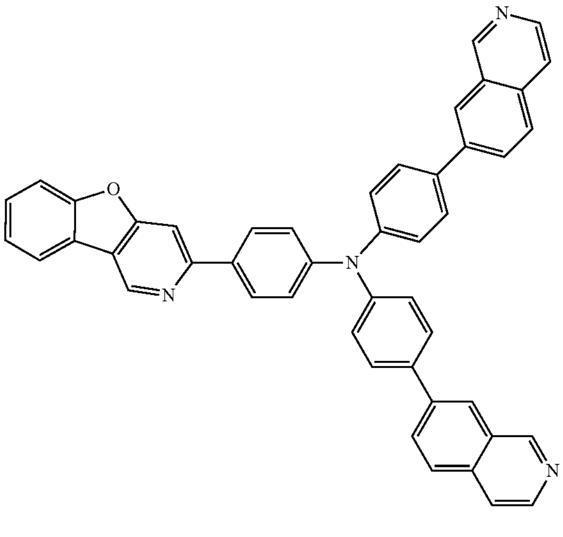
-continued
M167
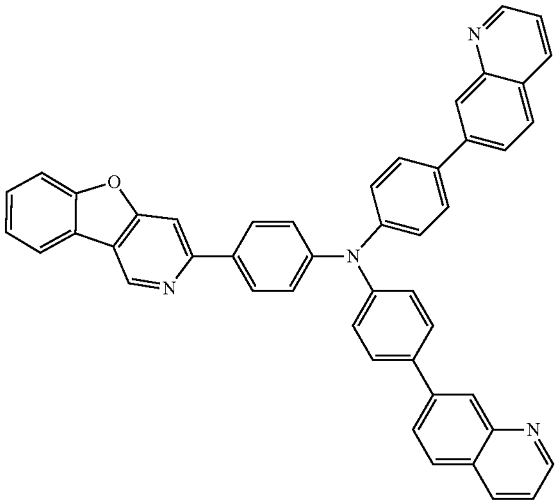
M168
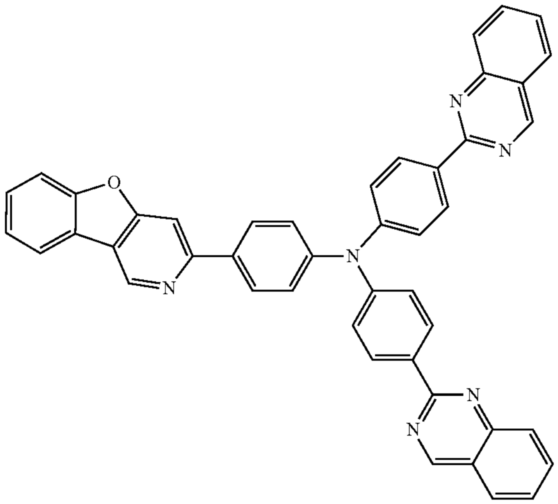
M169
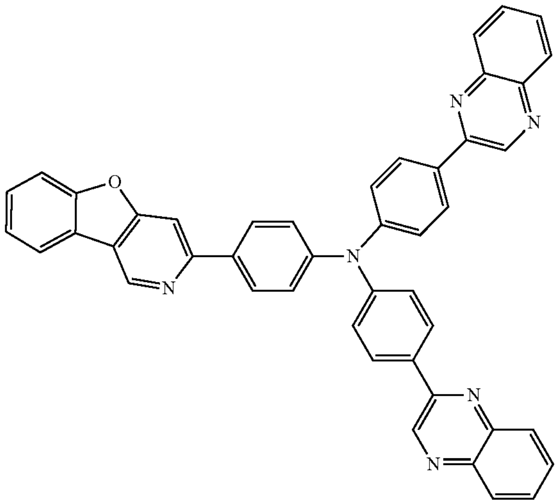

-continued
M170
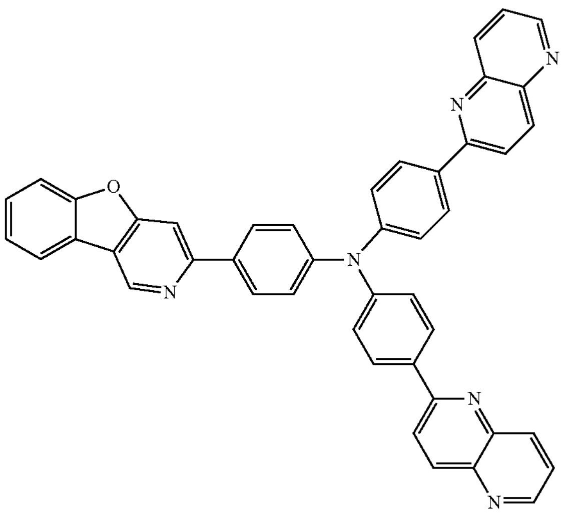
M171
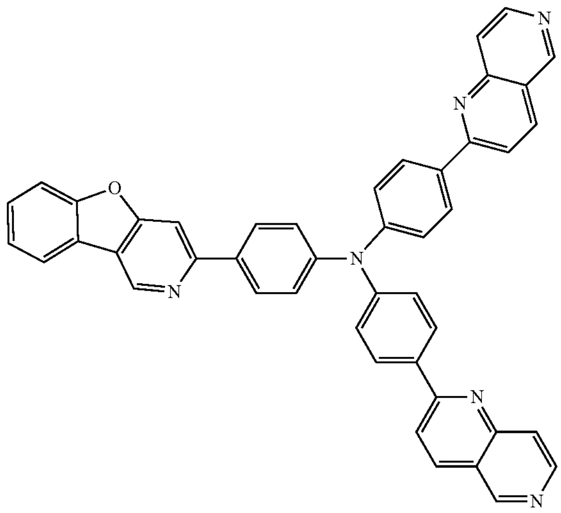
M172
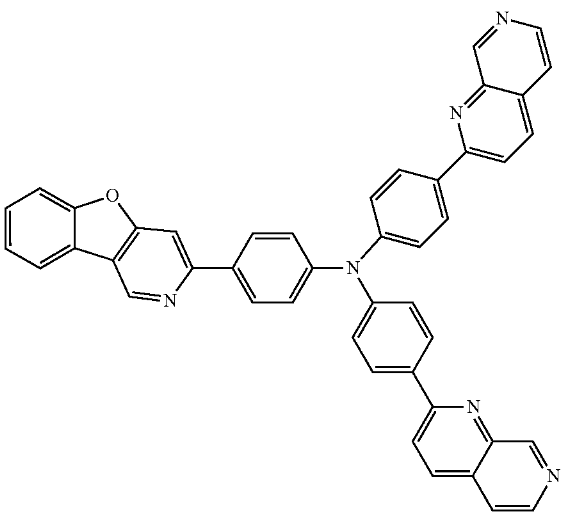
-continued
M173
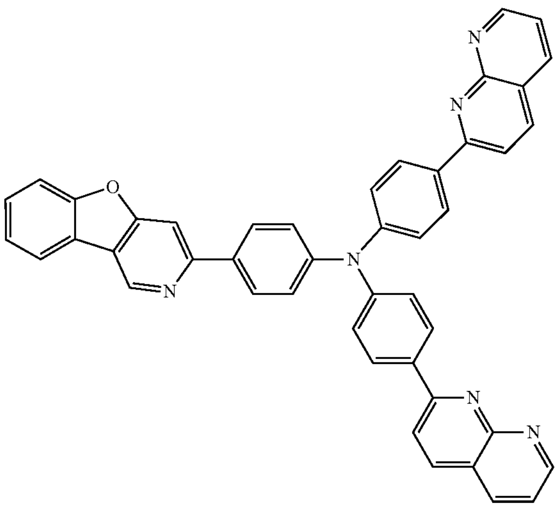
M174
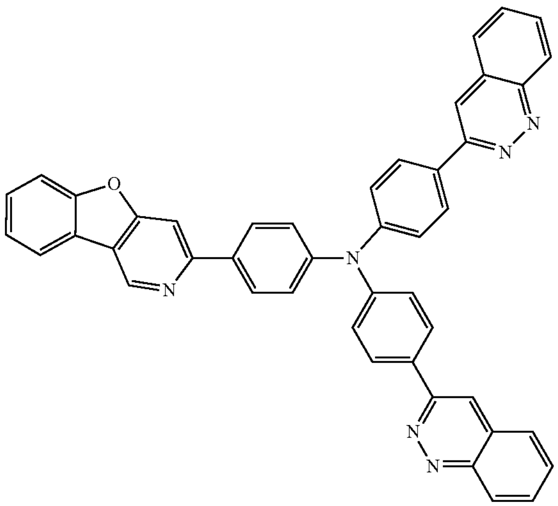
M175
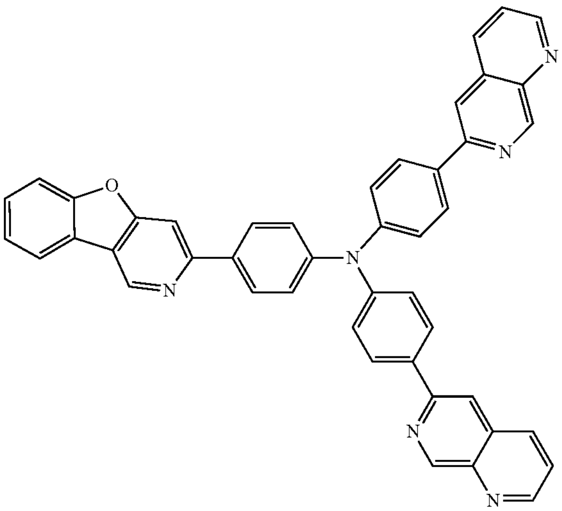

-continued
M176
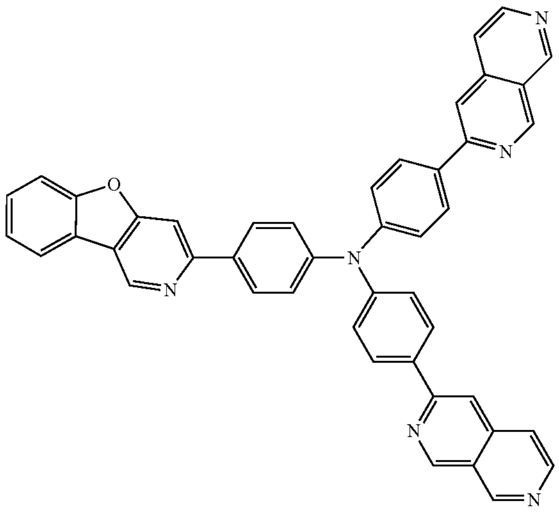
M177
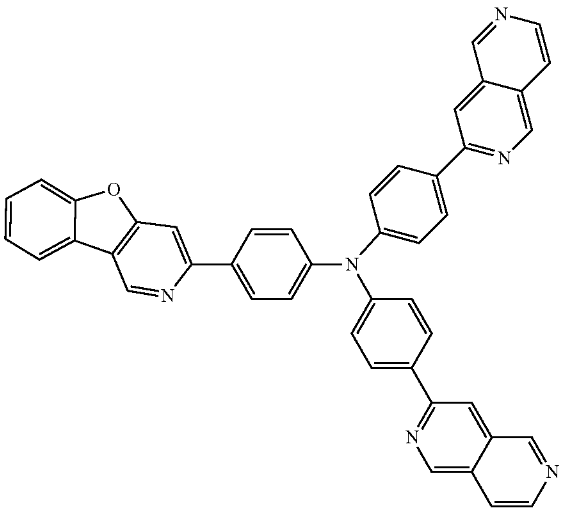
M178
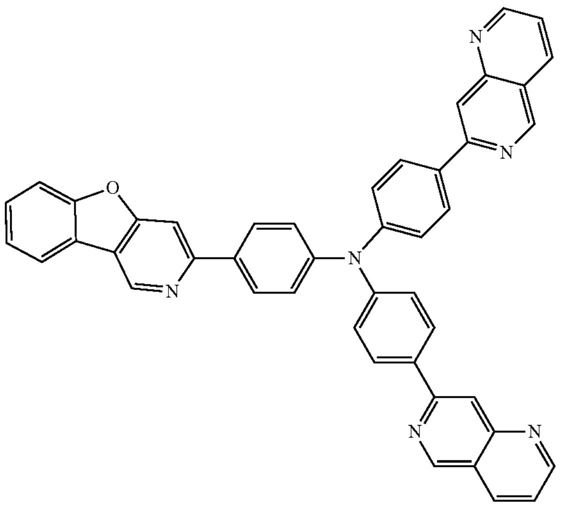
-continued
M179
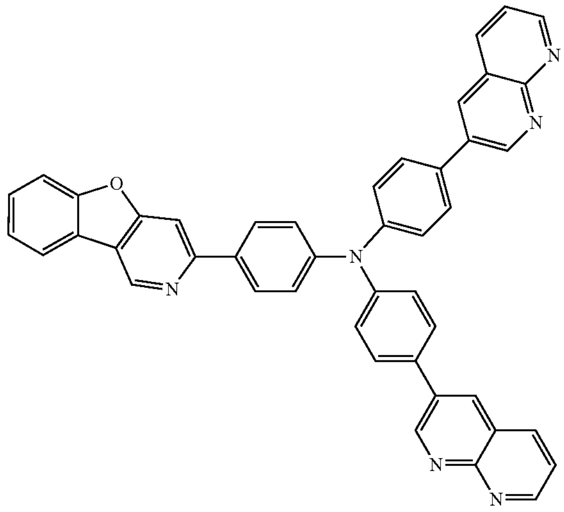
M180
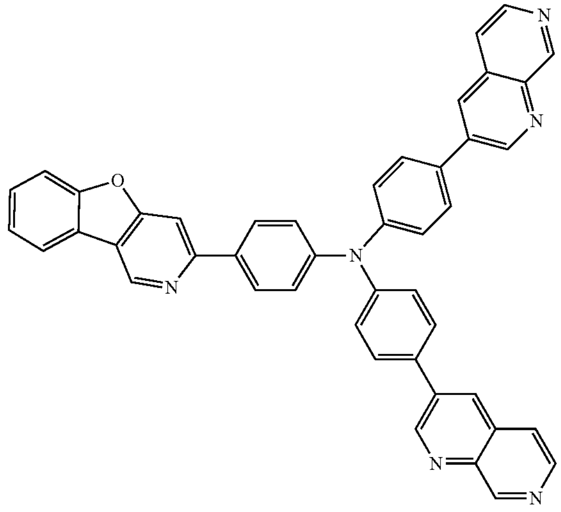
M181
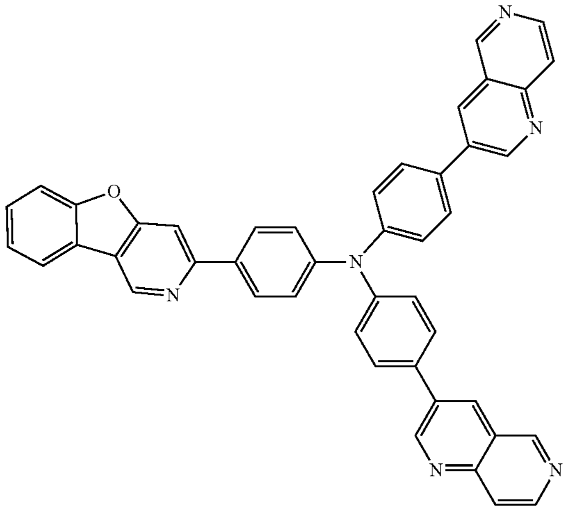

-continued
M182
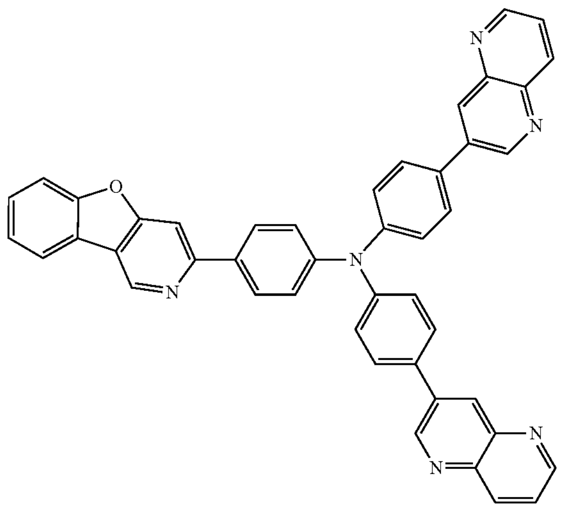
M183
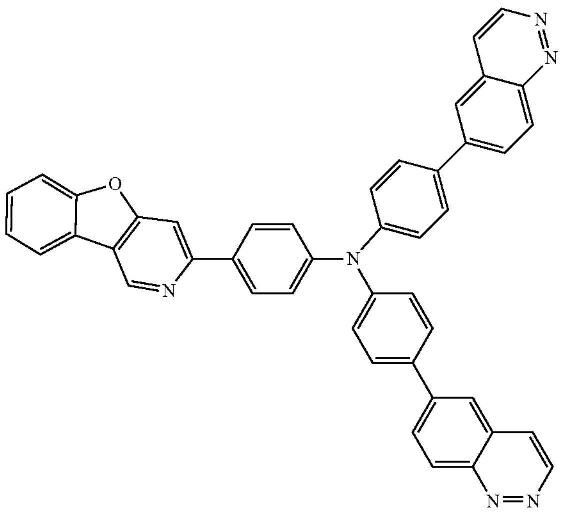
M184
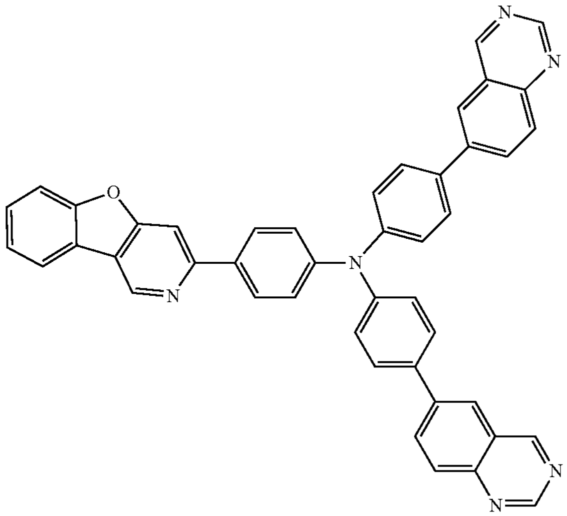
-continued
M185
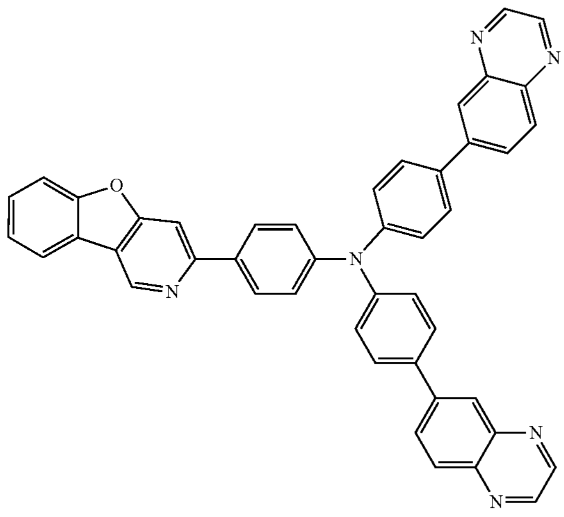
M186
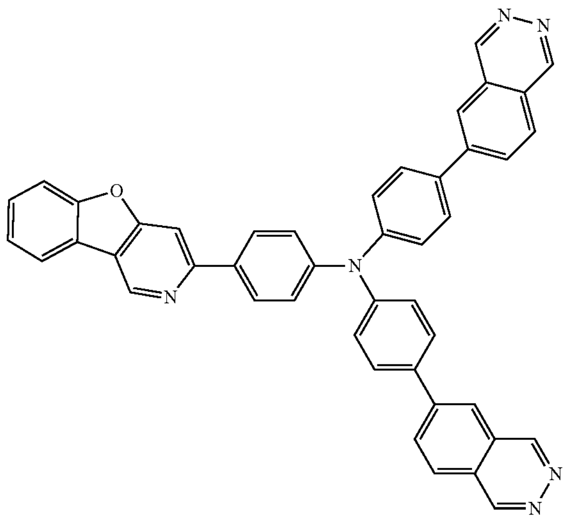
M187
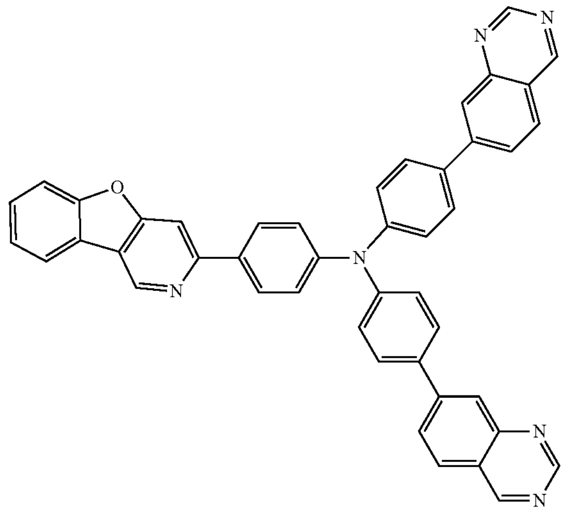

M188
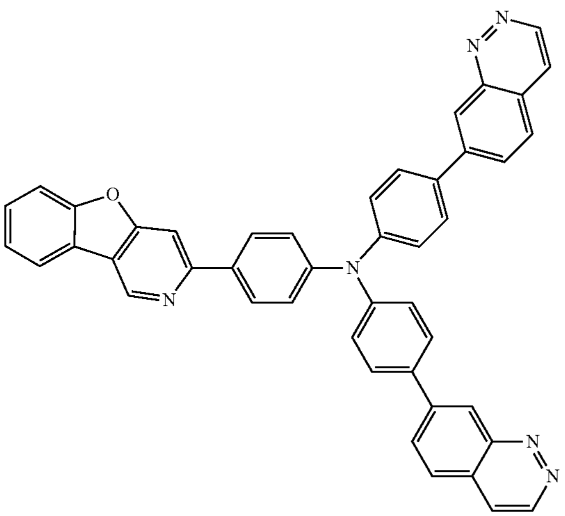
M189
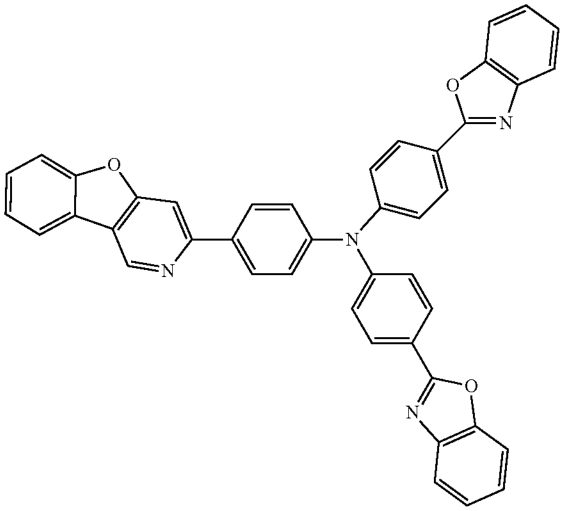
M190
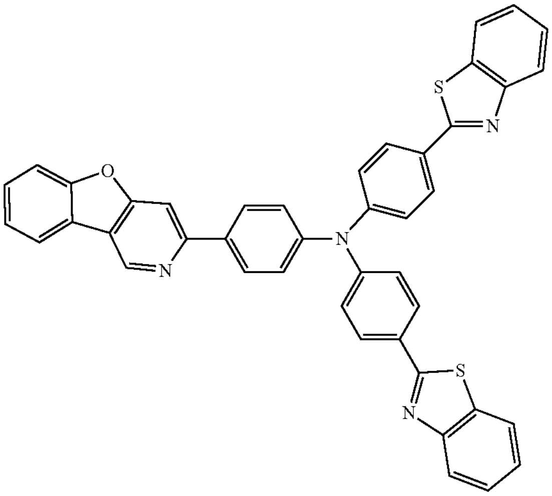
M191
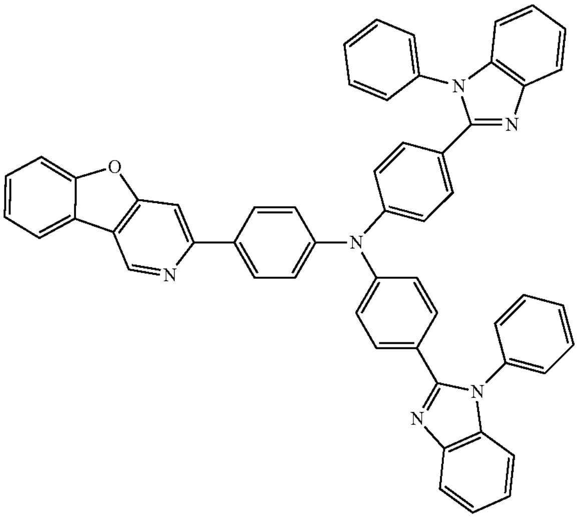
M192
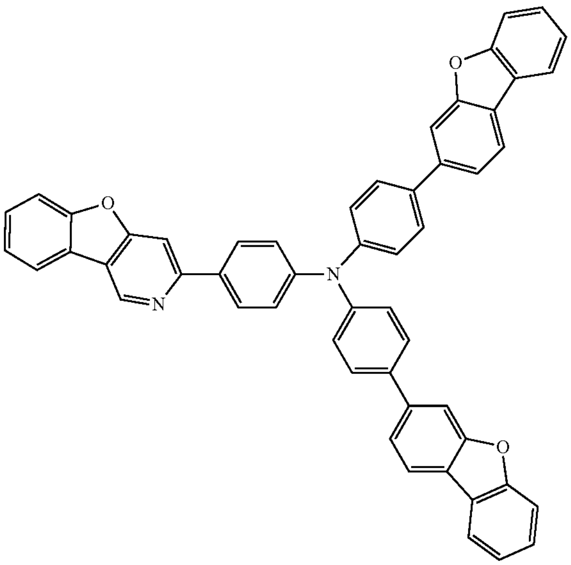

-continued
M193
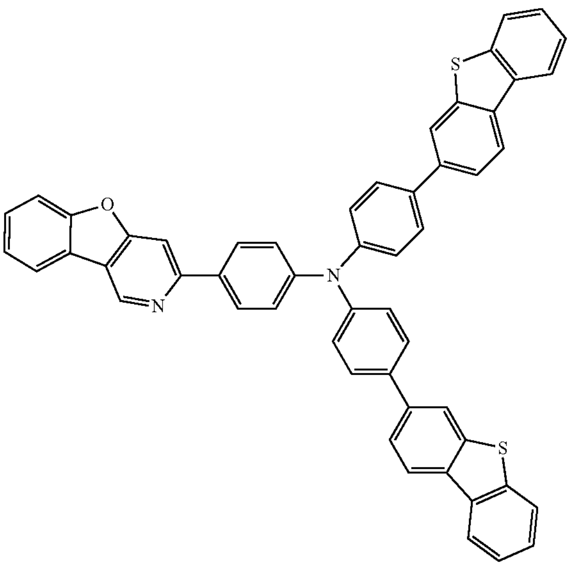
M194
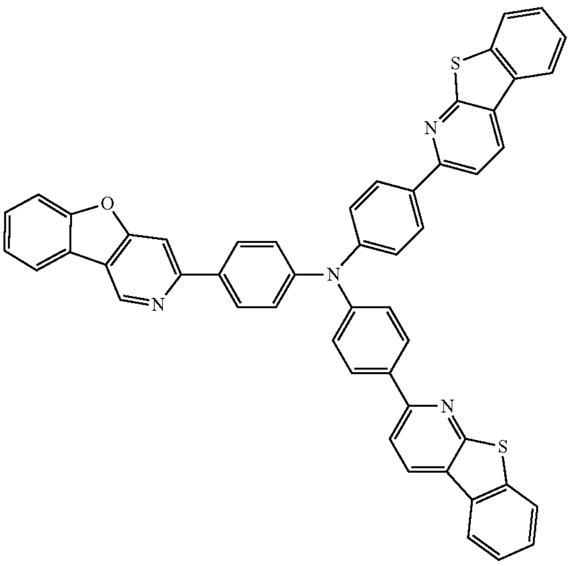
-continued
M195
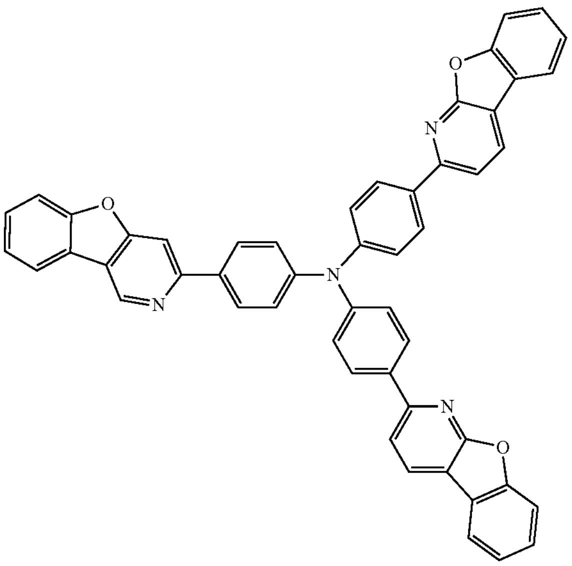
M196
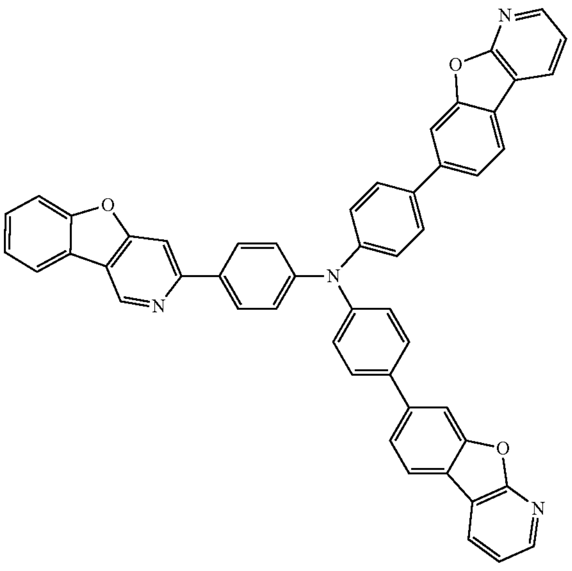

-continued
M197
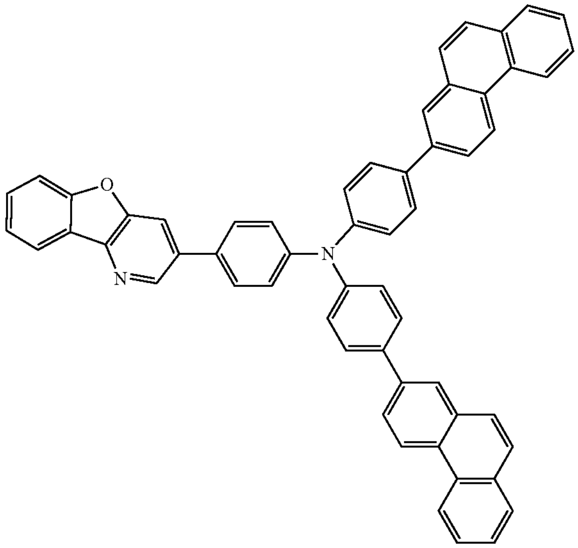
M198
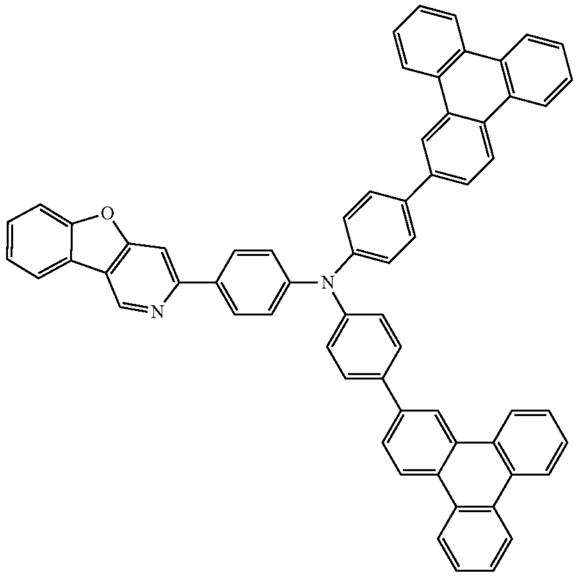
-continued
M199
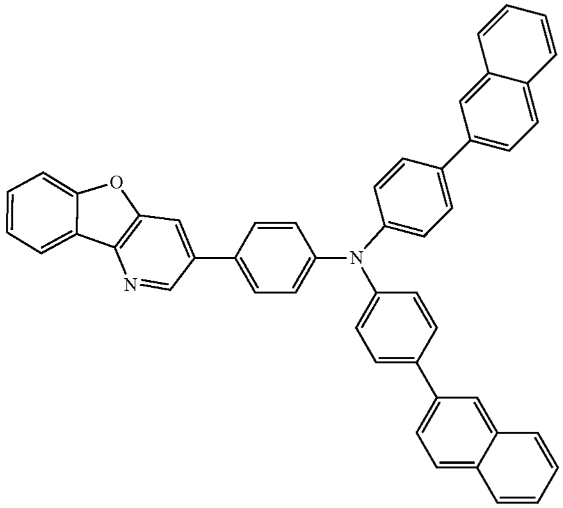
M200
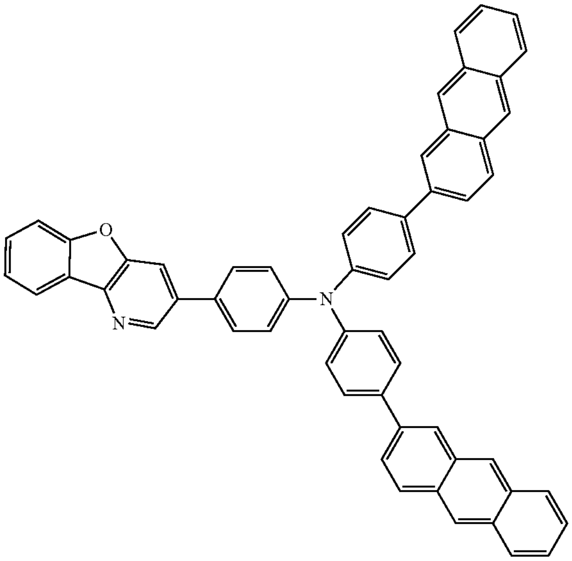
M201
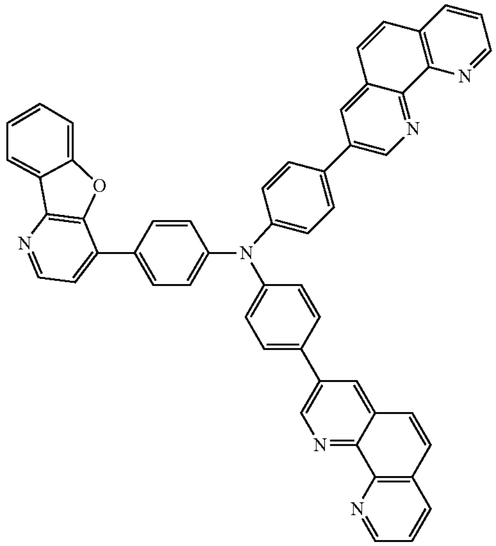

-continued
M202
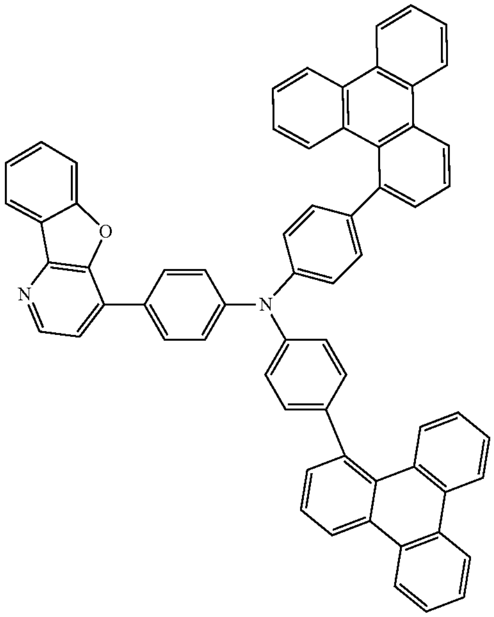
M203
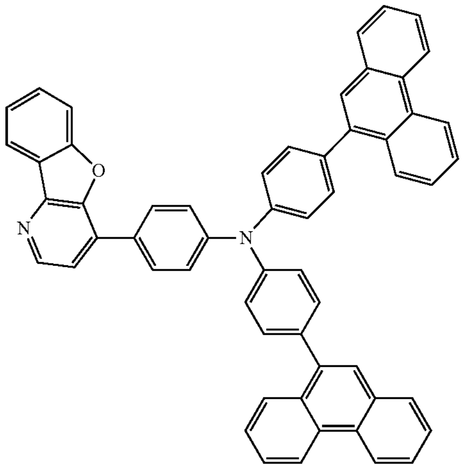
M204
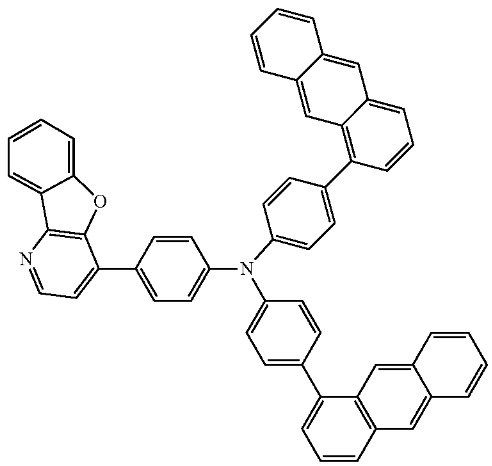
-continued
M205
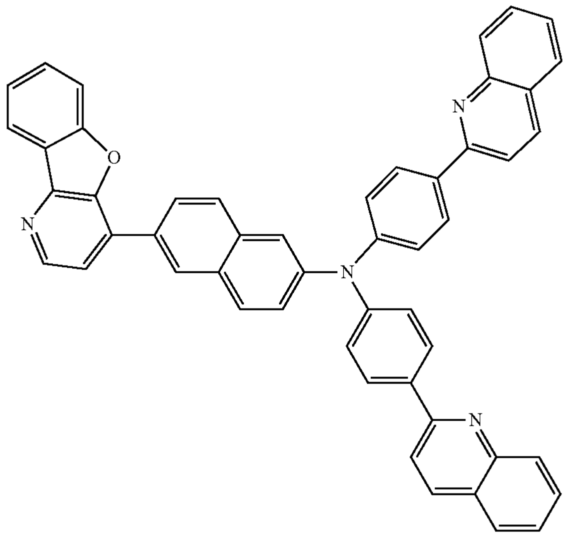
M206
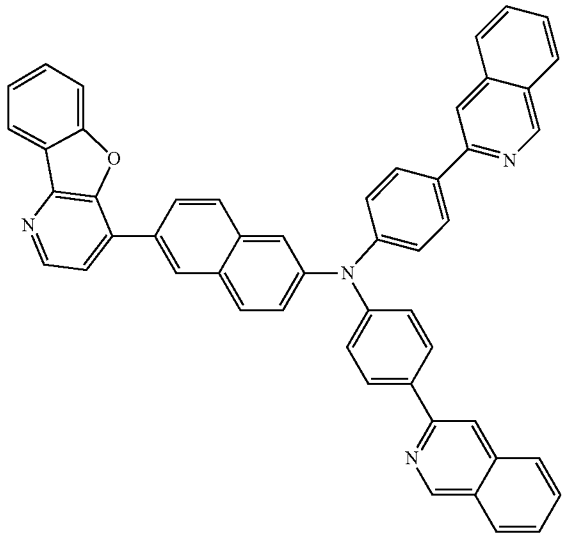
M207
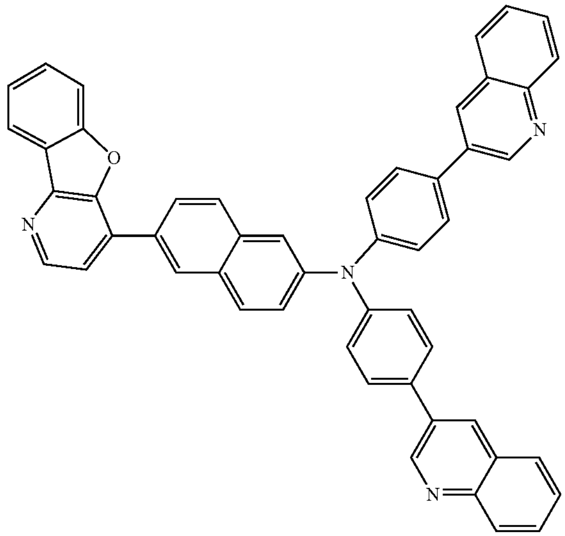

-continued
M208
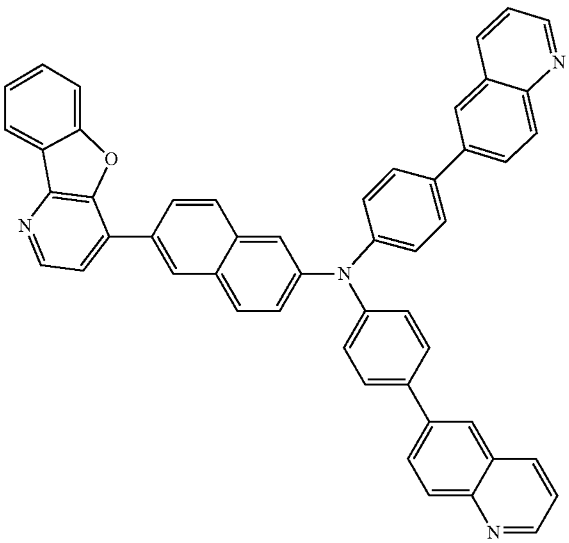
M209
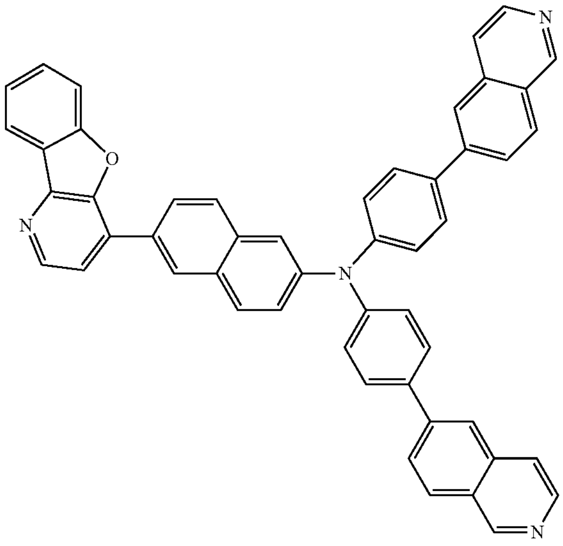
-continued
M210
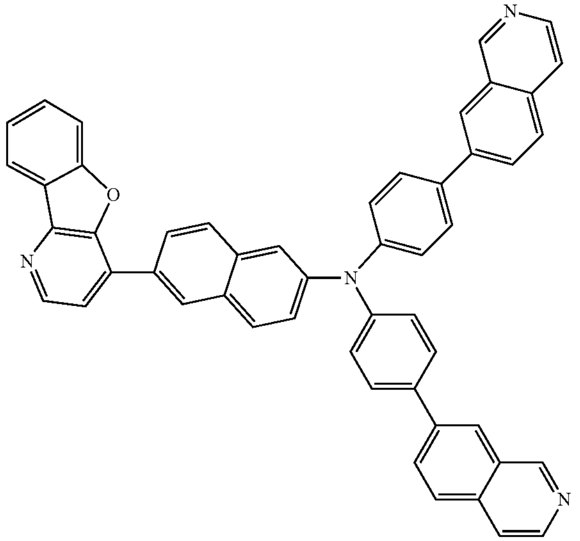
M211
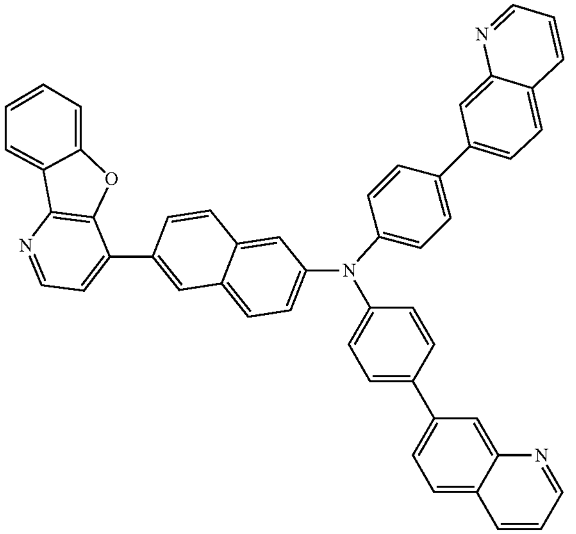

-continued
M212
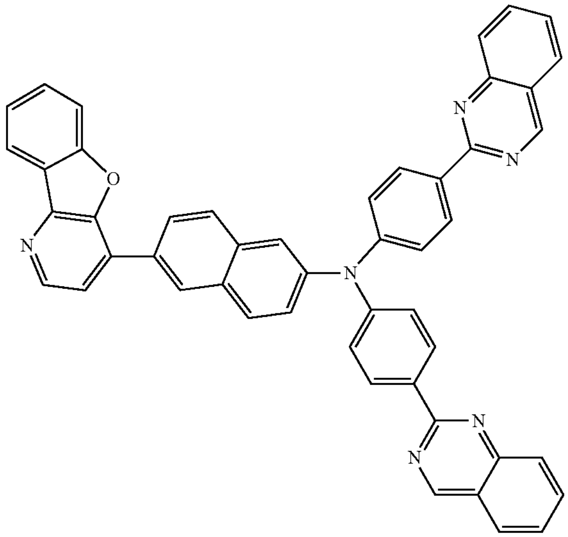
M213
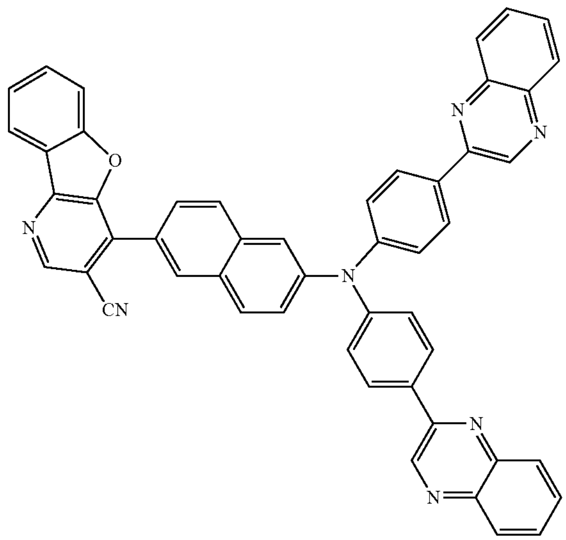
-continued
M214
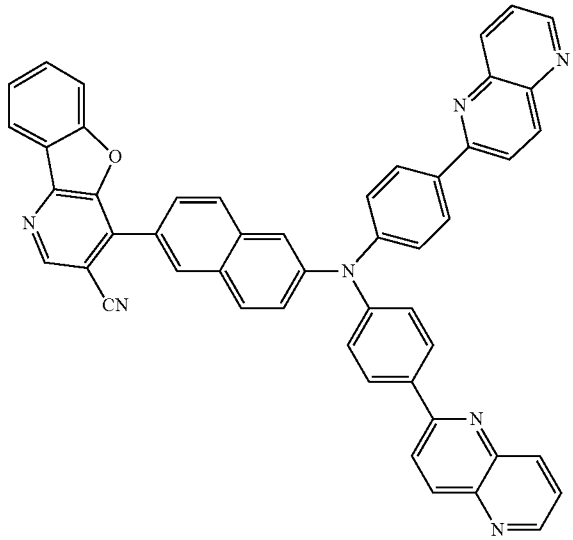
M215
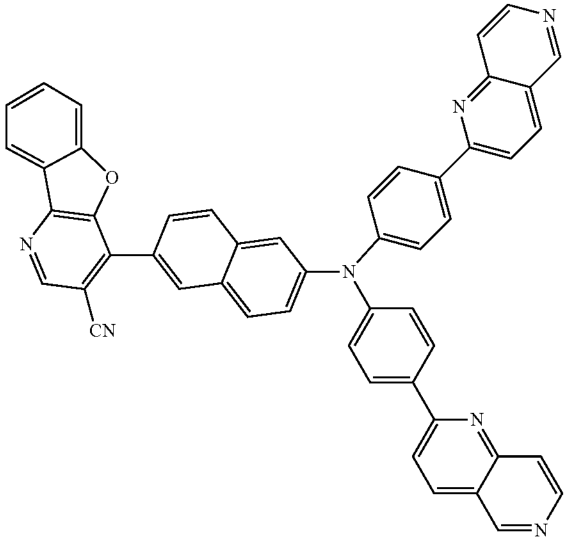

-continued
M216
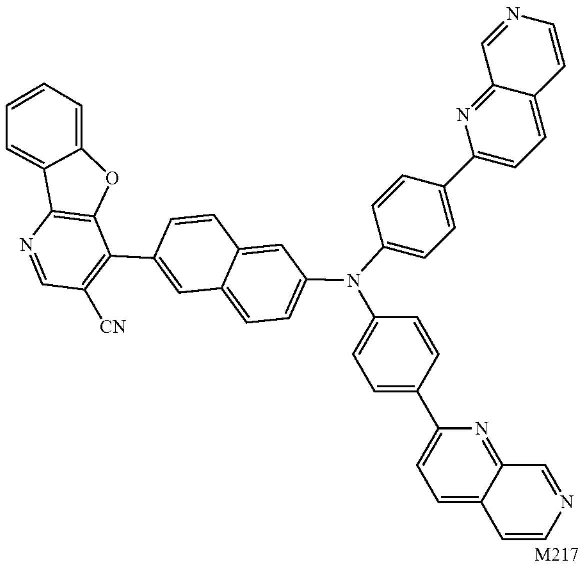
M217
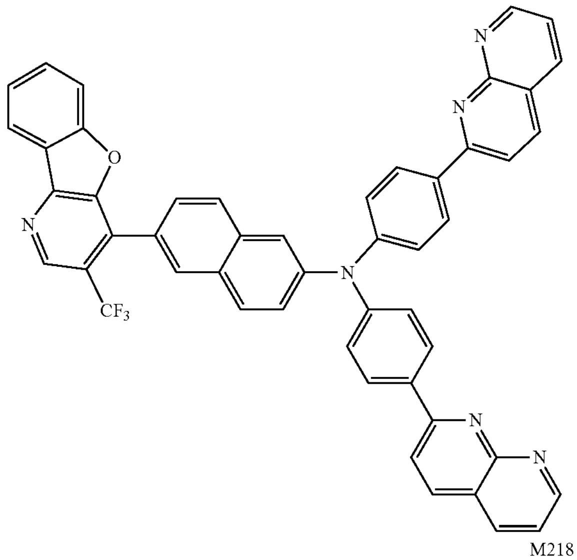
M218
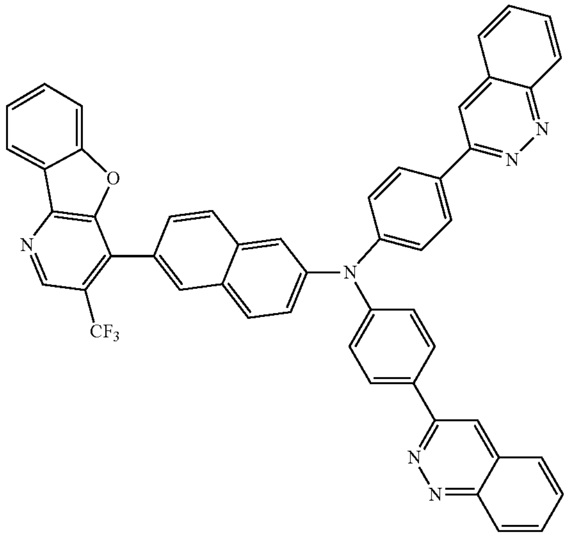
-continued
M219
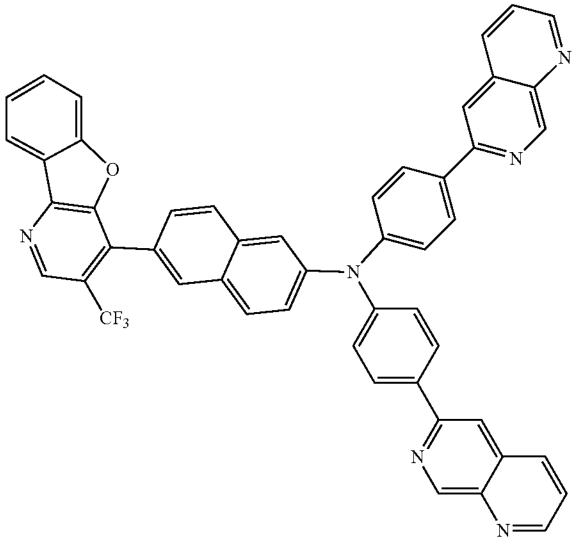
M220
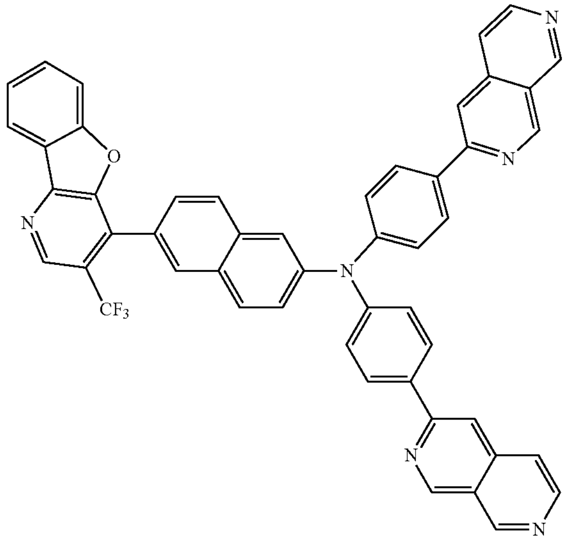

-continued
M221
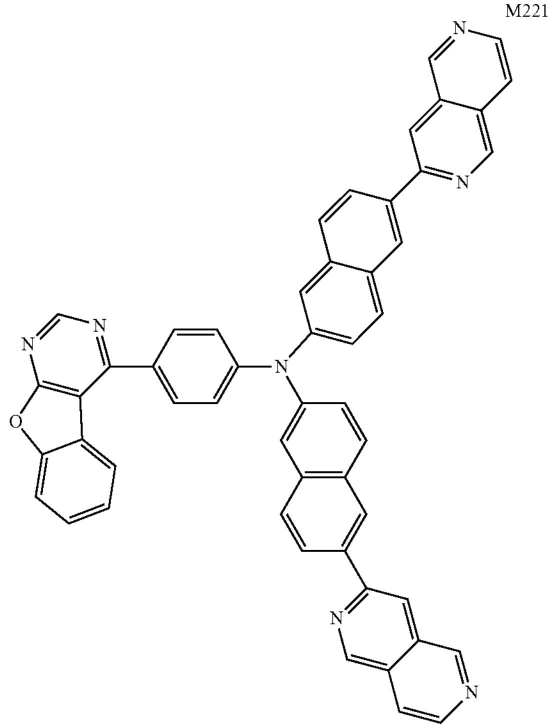
M223
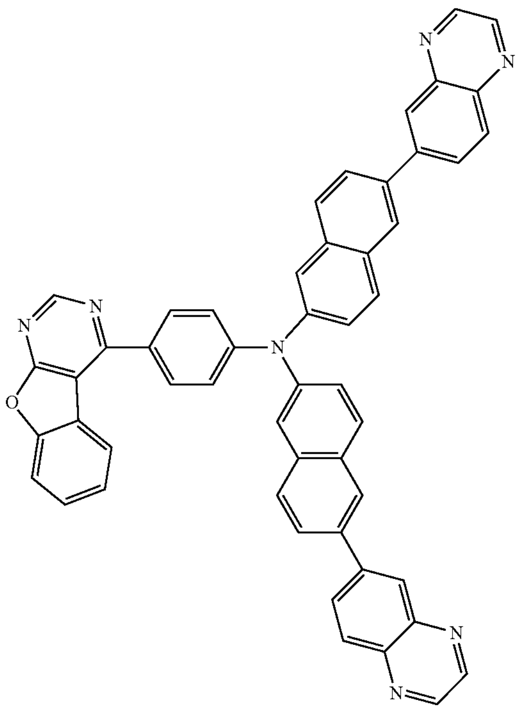
M222
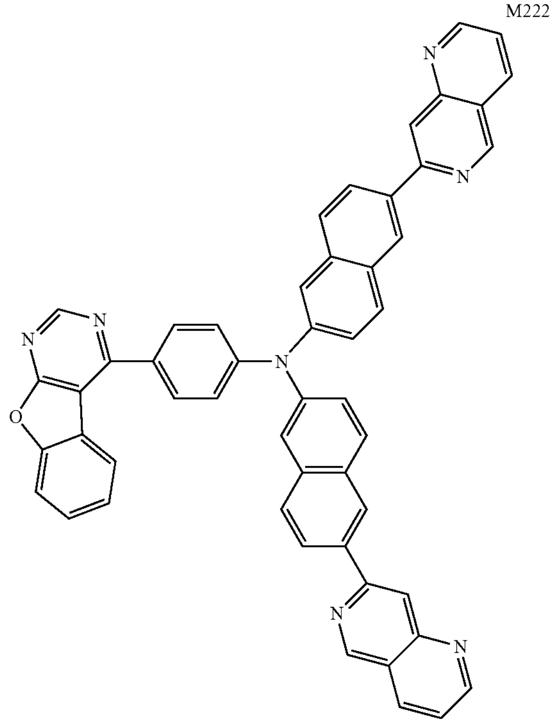
M224
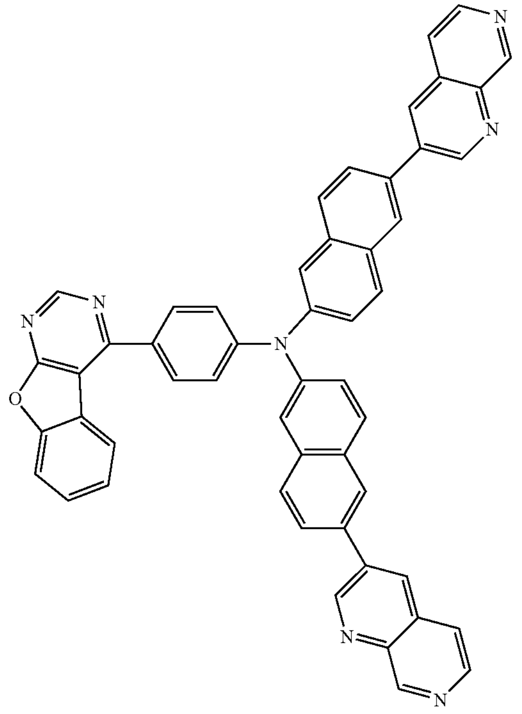

-continued
M225
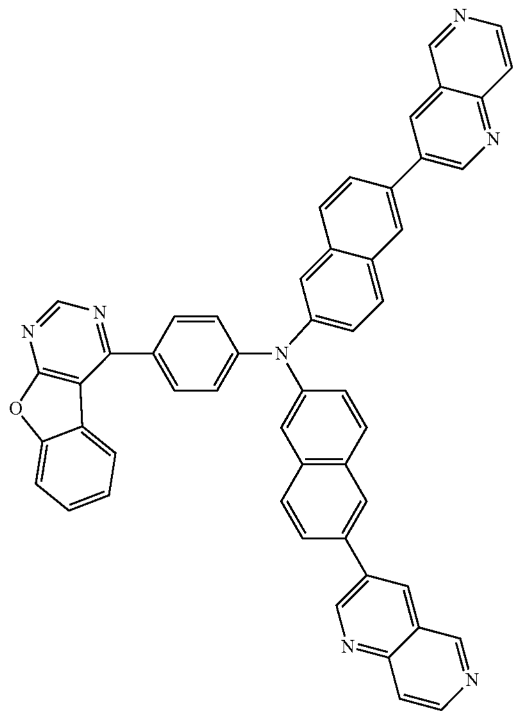
M226
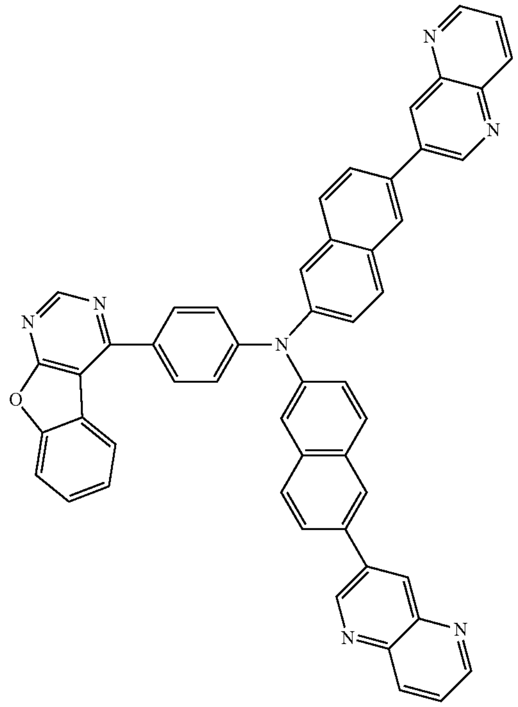
-continued
M227
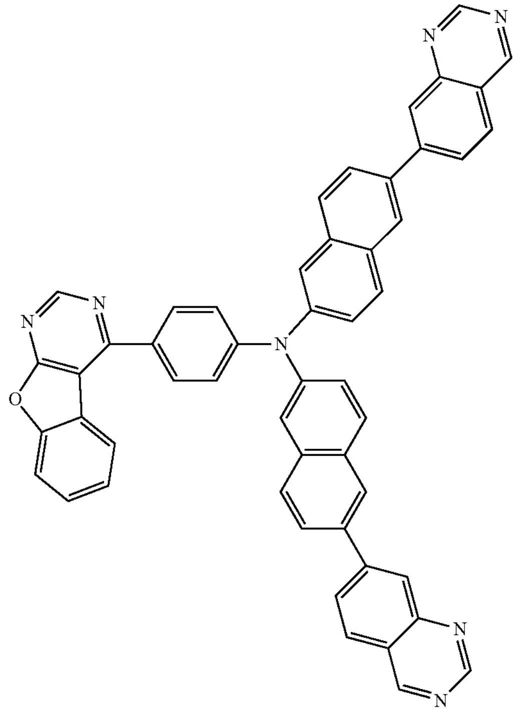
M228
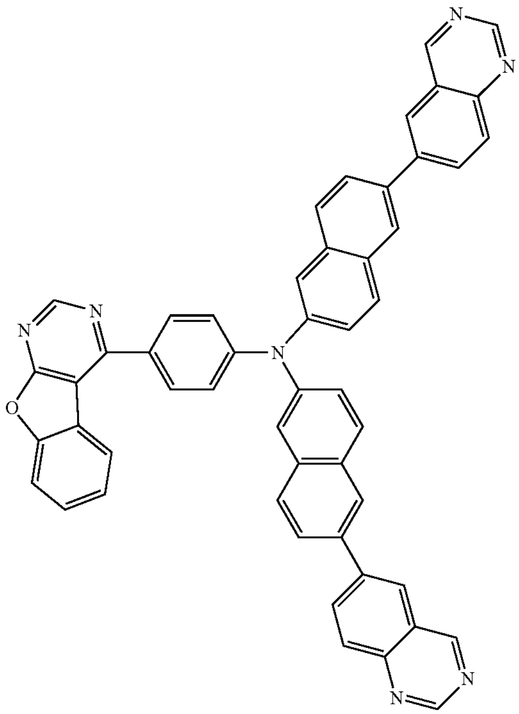

-continued
M229
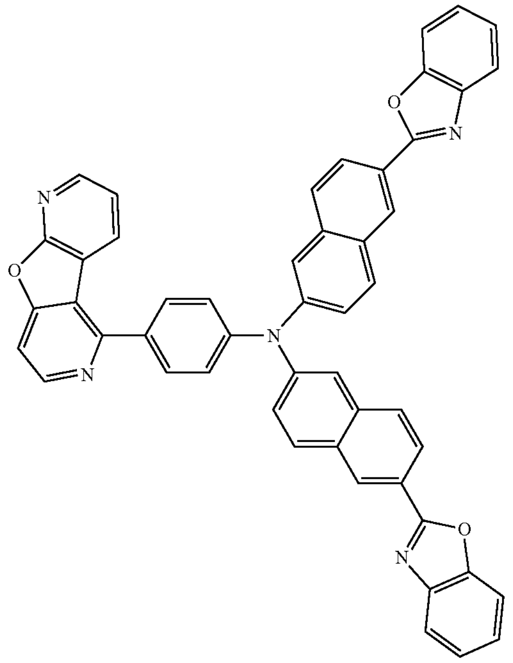
M230
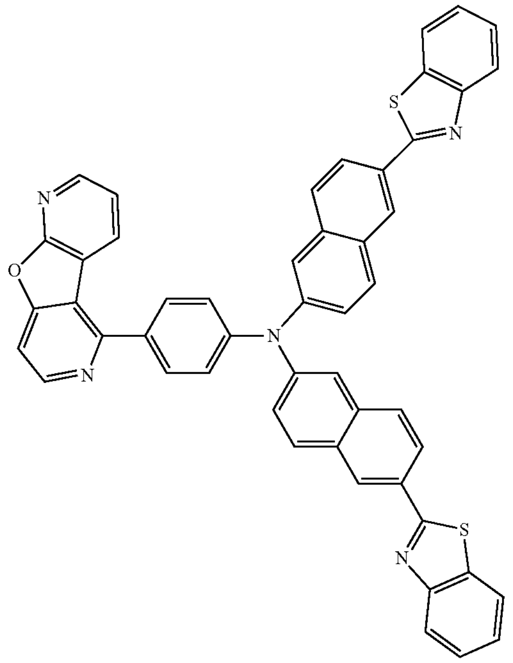
-continued
M231
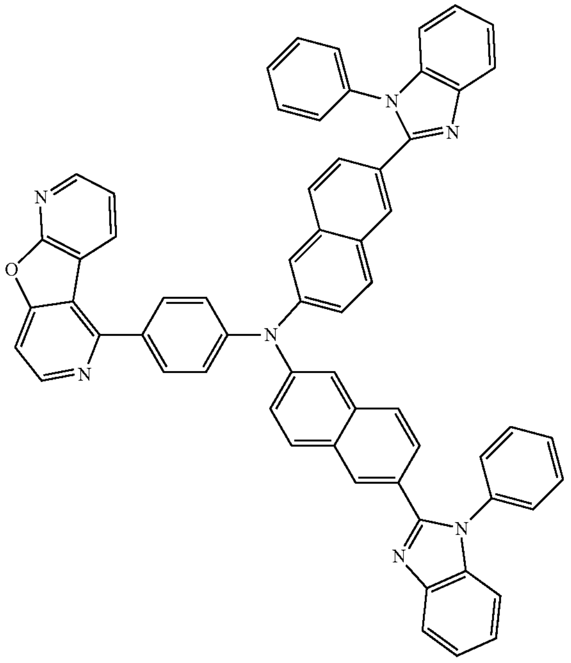
M232
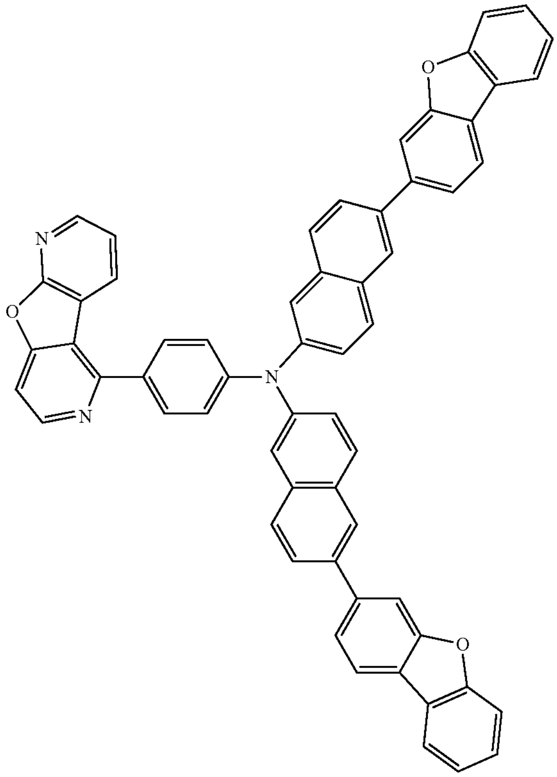

-continued
M233
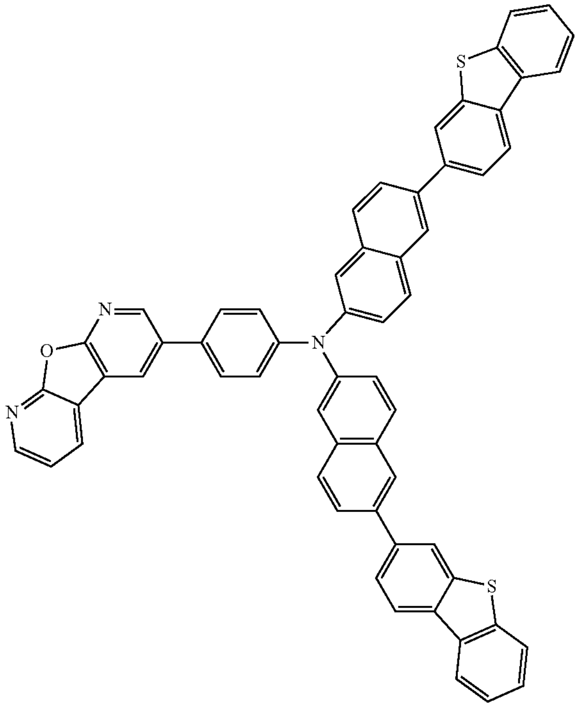
M234
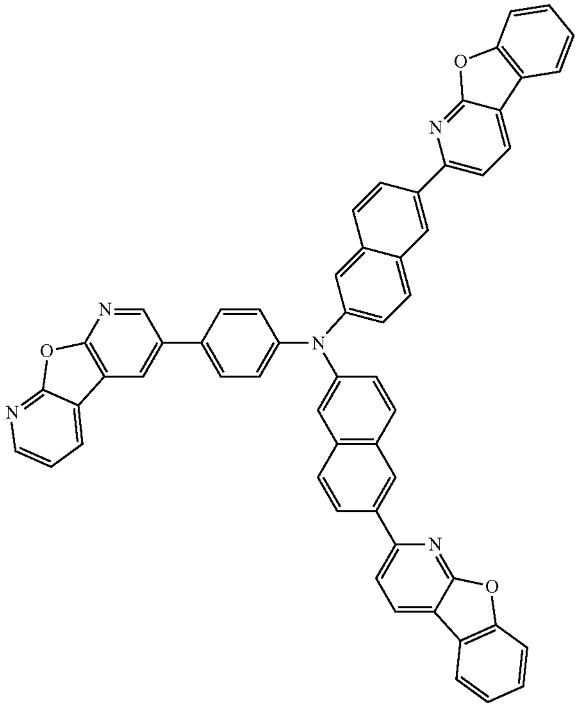
-continued
M235
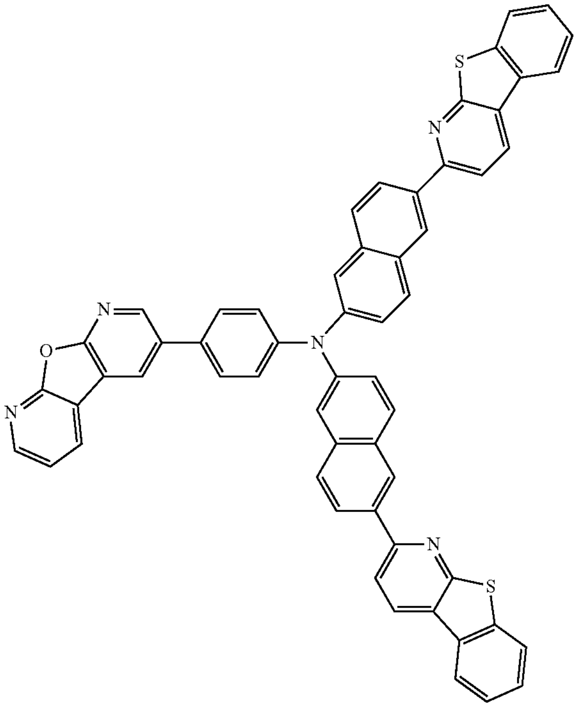
M236
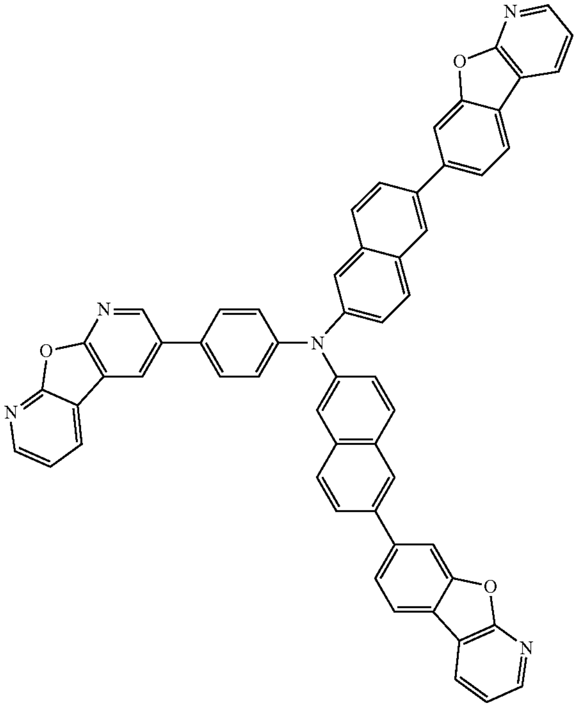

-continued
M237
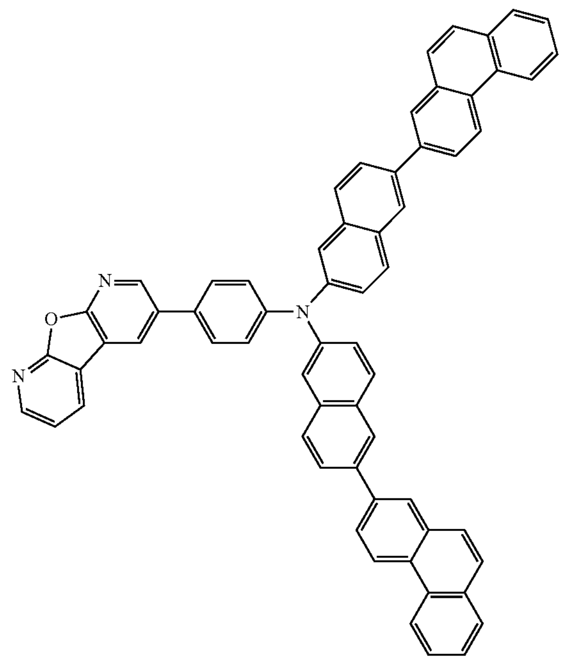
M238
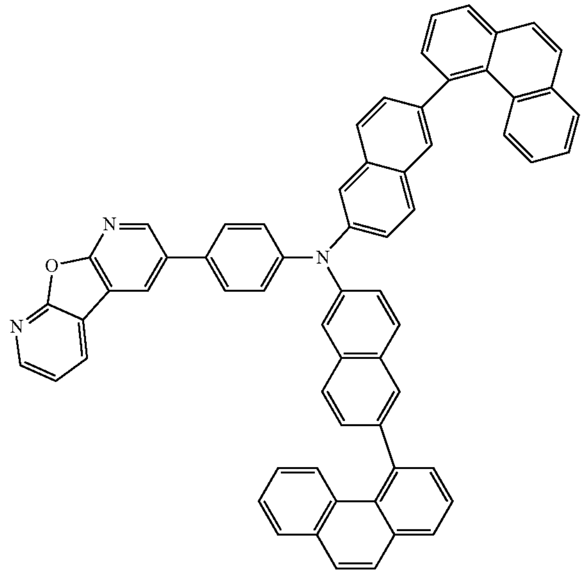
-continued
M239
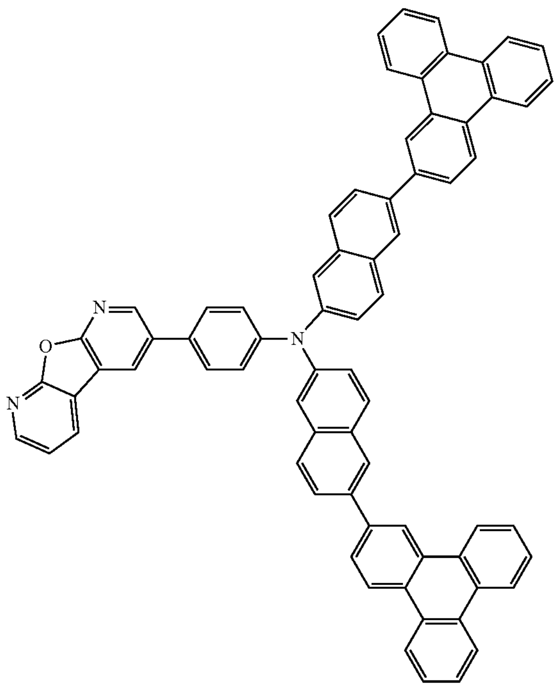
M240
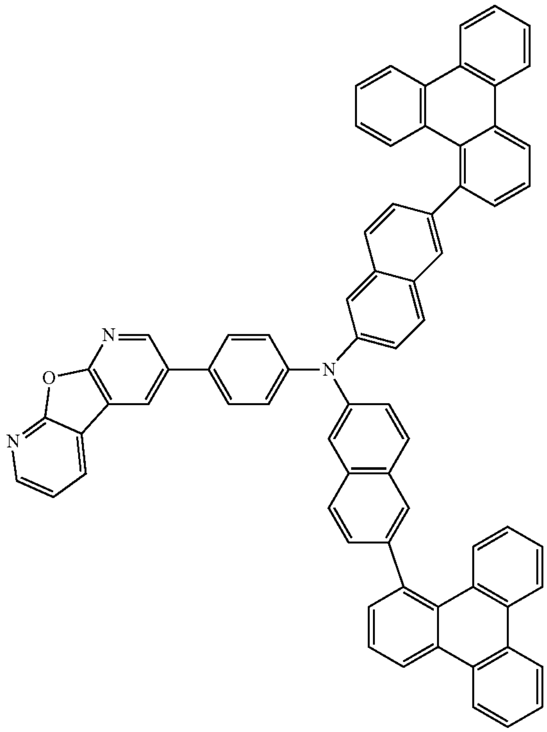

-continued
M241
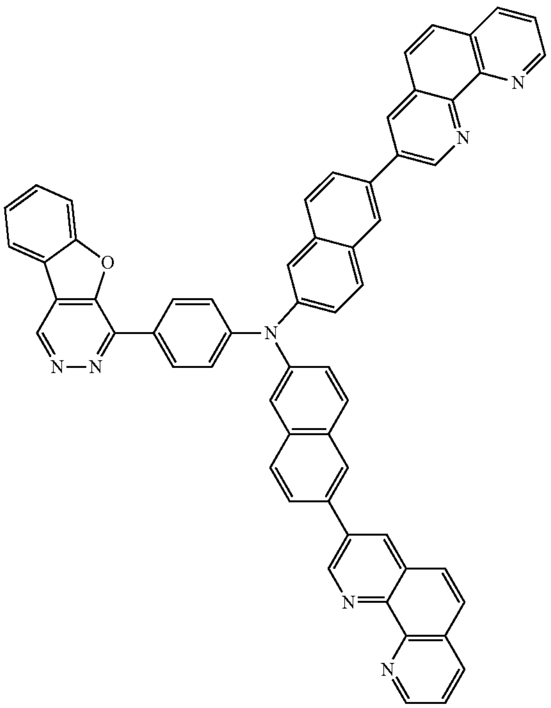
M242
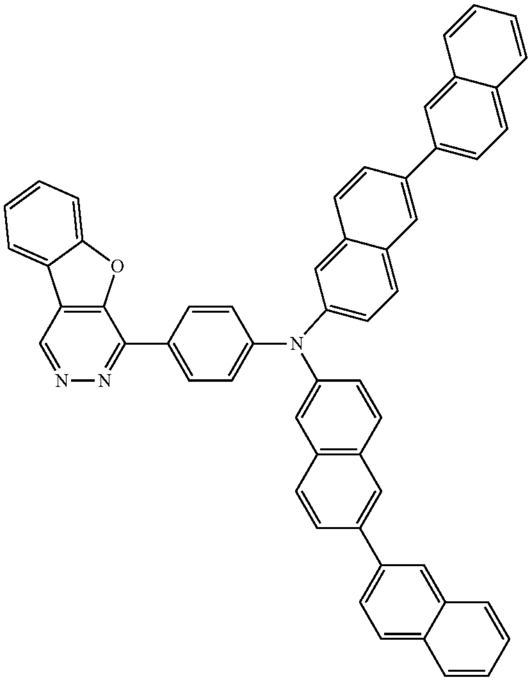
-continued
M243
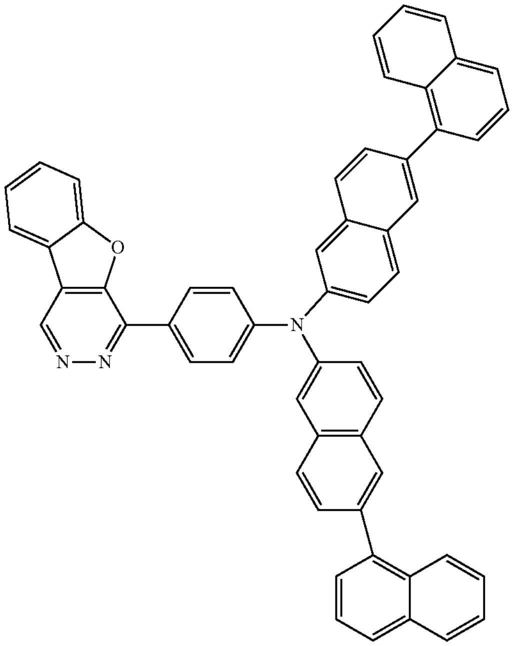
M244
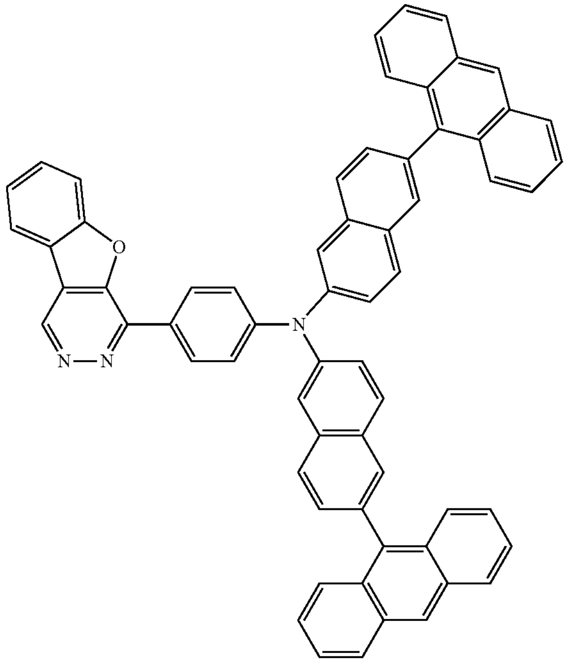

M245
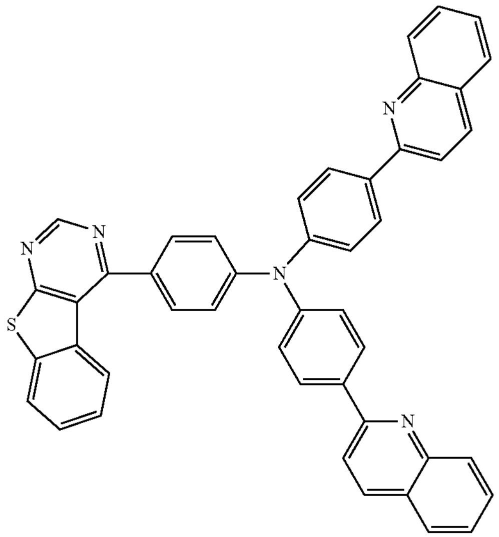
M246
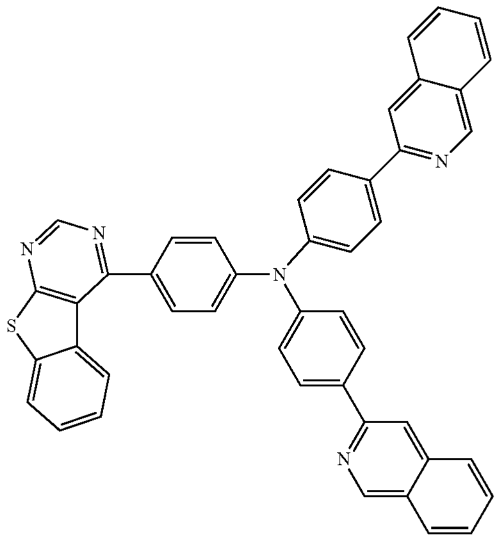
M247
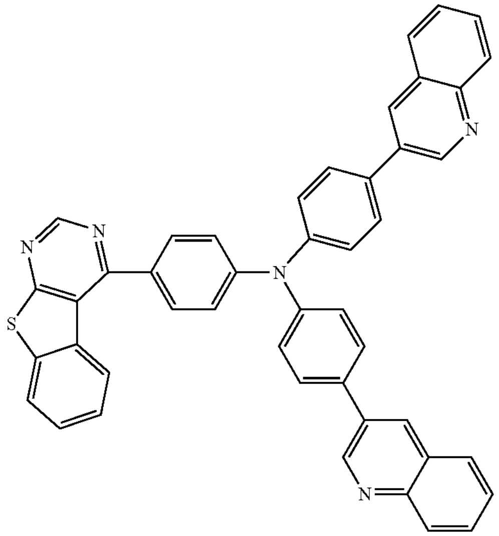
M248
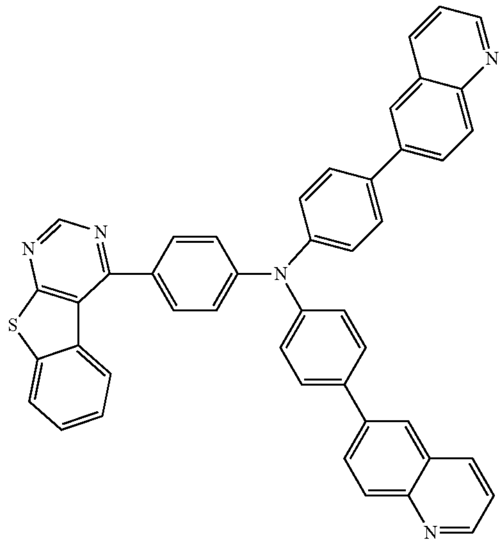
M249
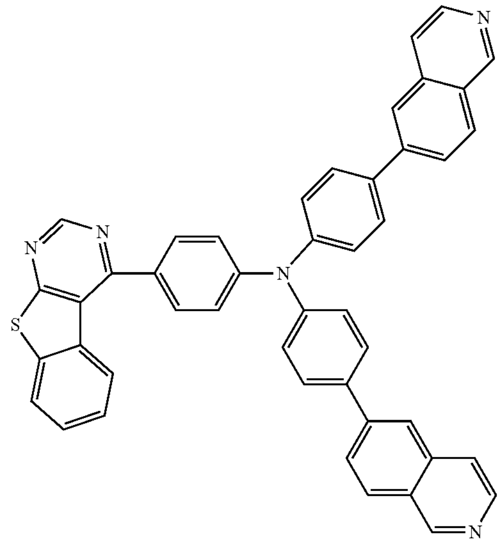
M250
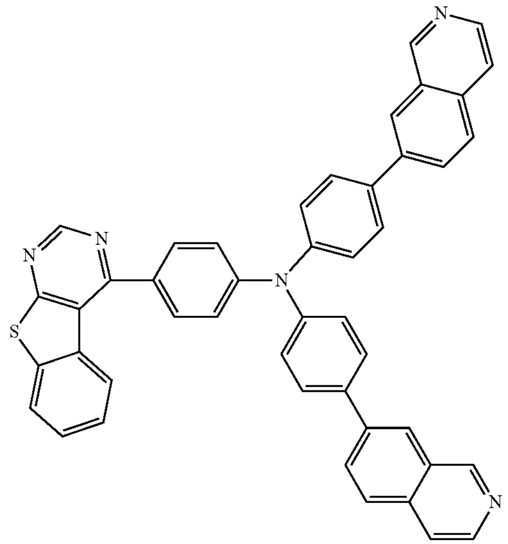

-continued
M251
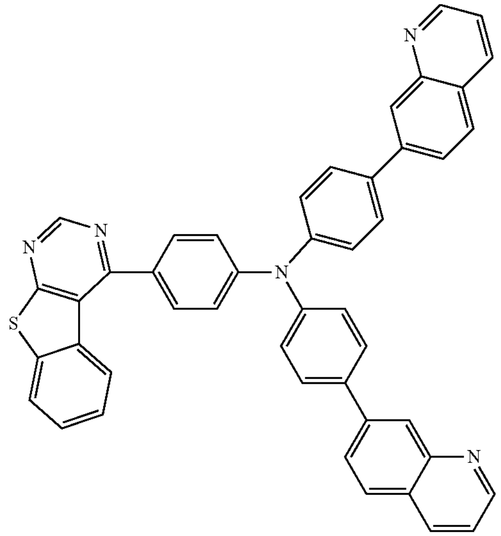
M252
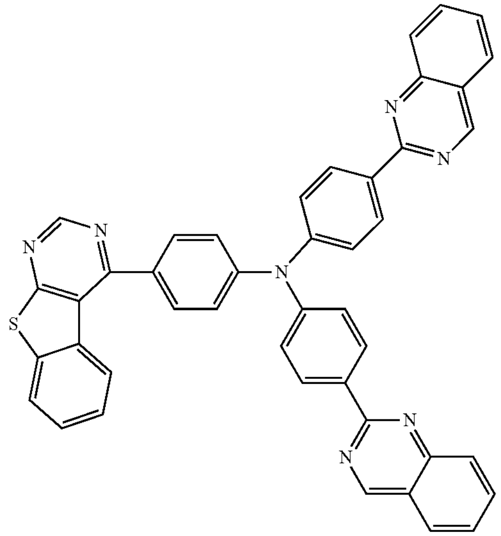
M253
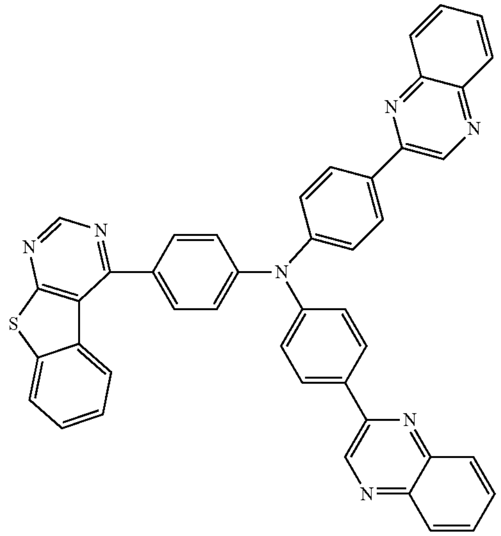
-continued
M254
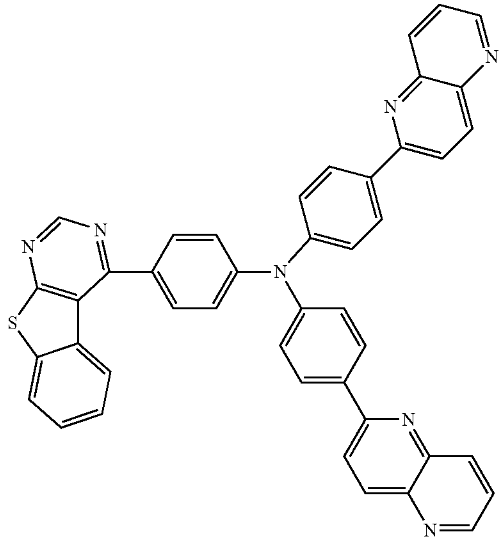
M255
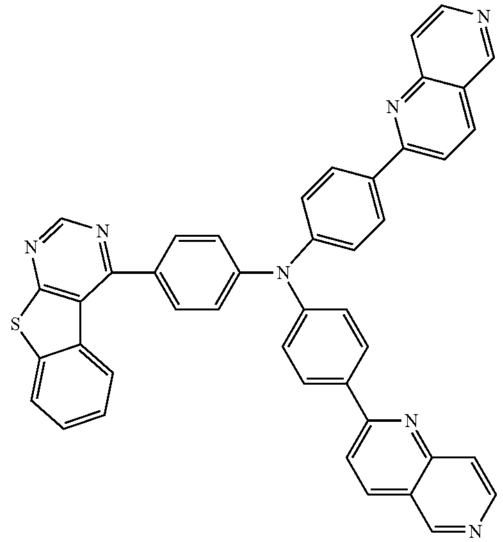
M256
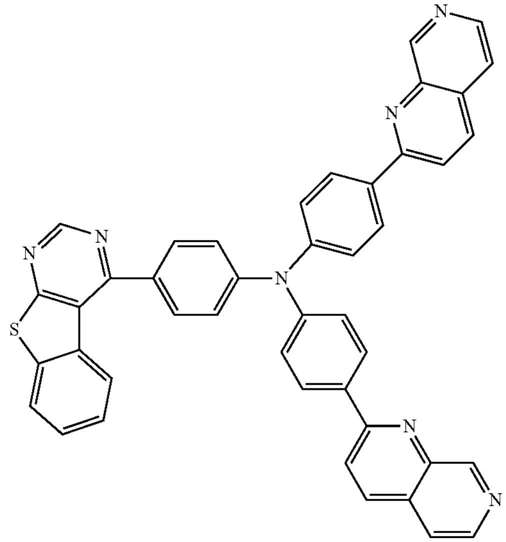

-continued
M257
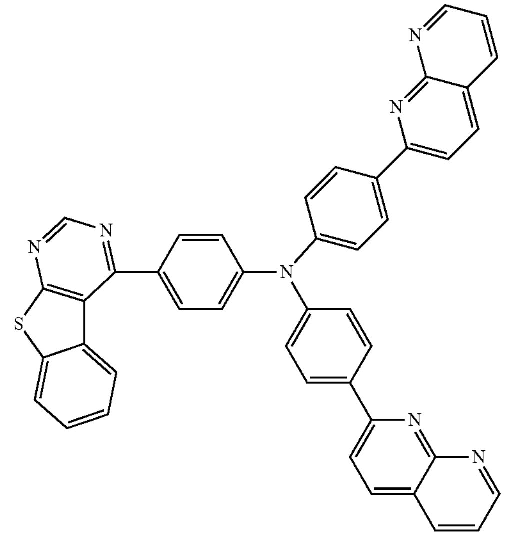
M258
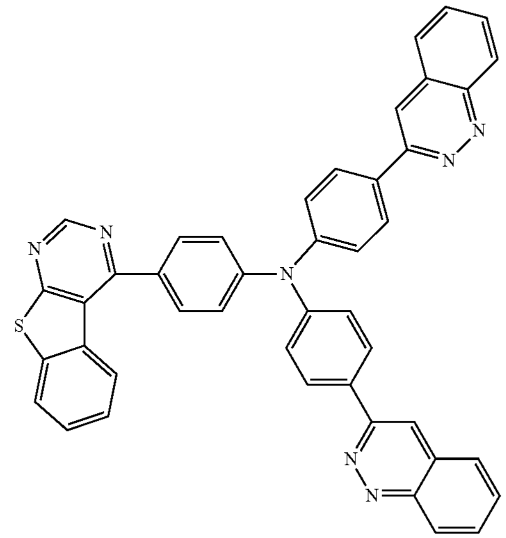
M259
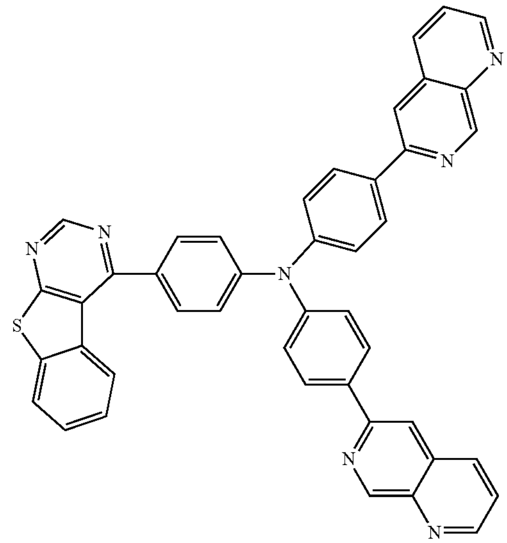
-continued
M260
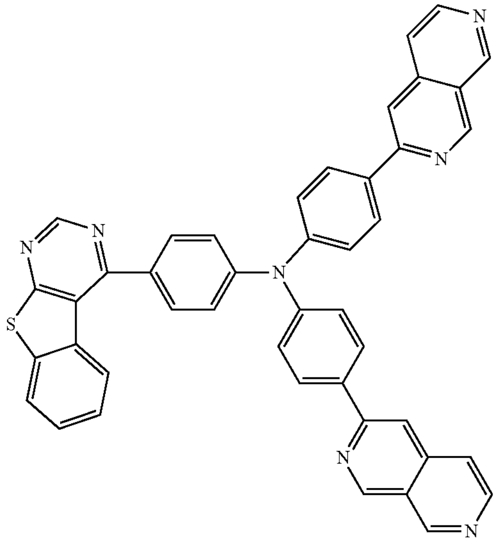
M261
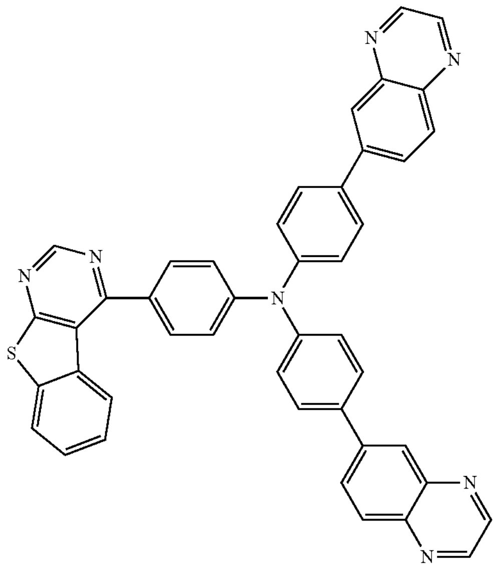

M262
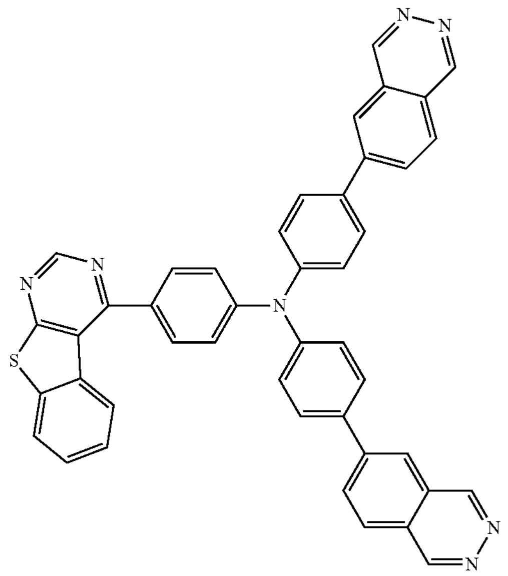
M263
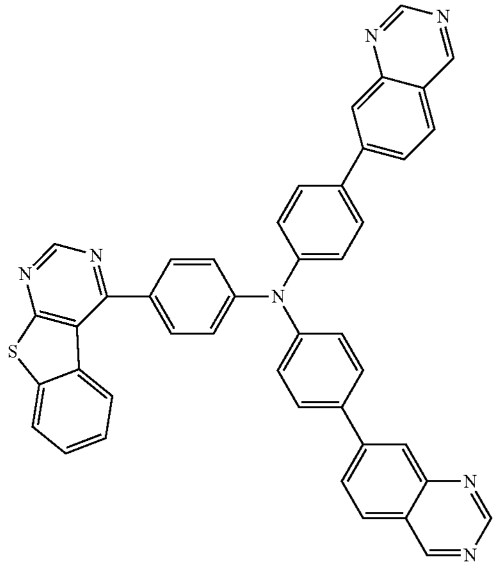
M264
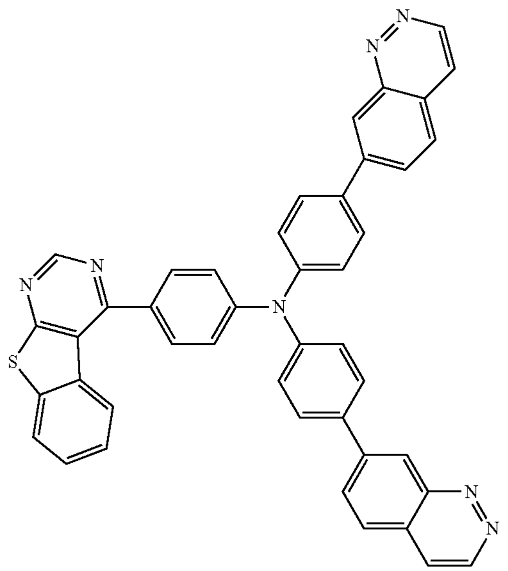
M265
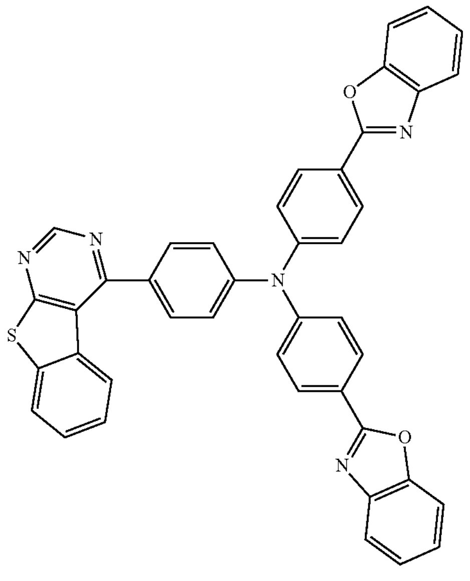

M266
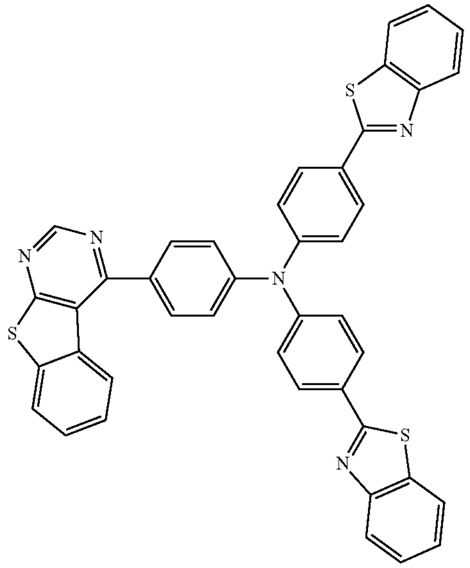
M267
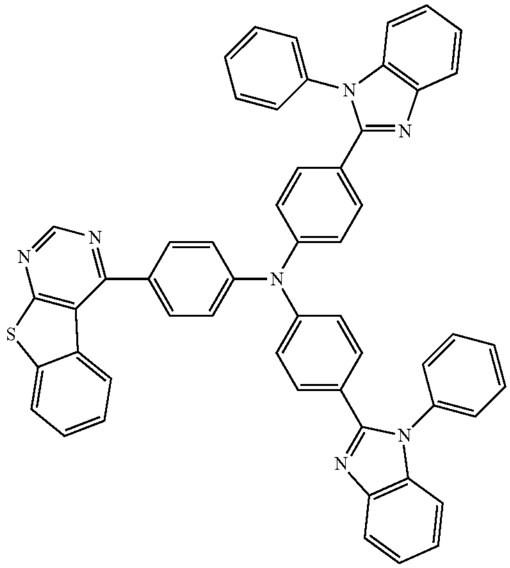
M268
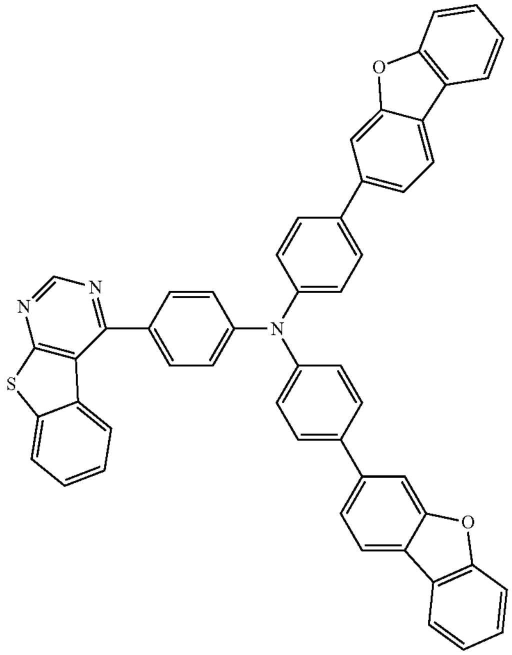
M269
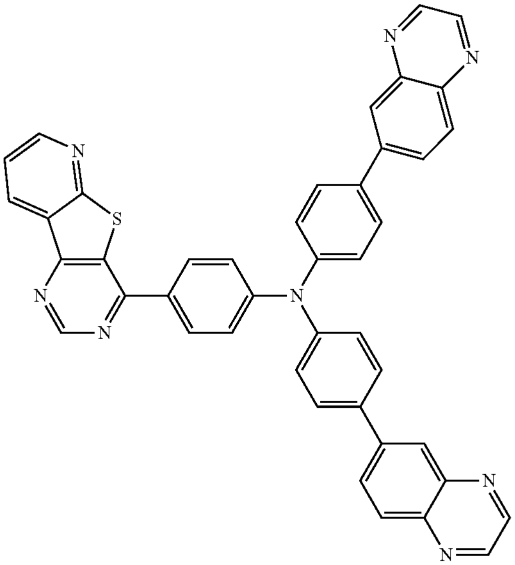

-continued
M270
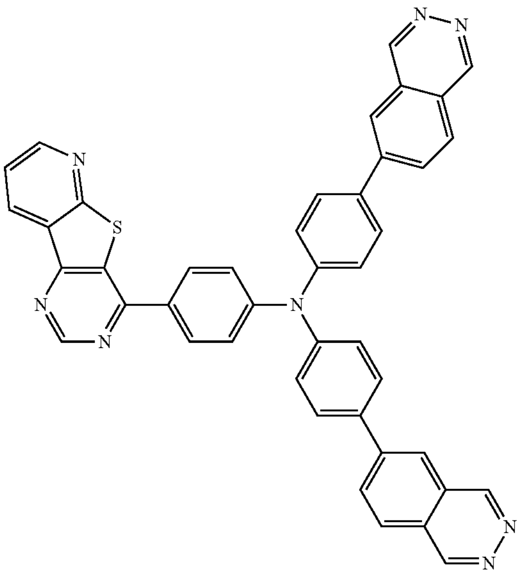
M271
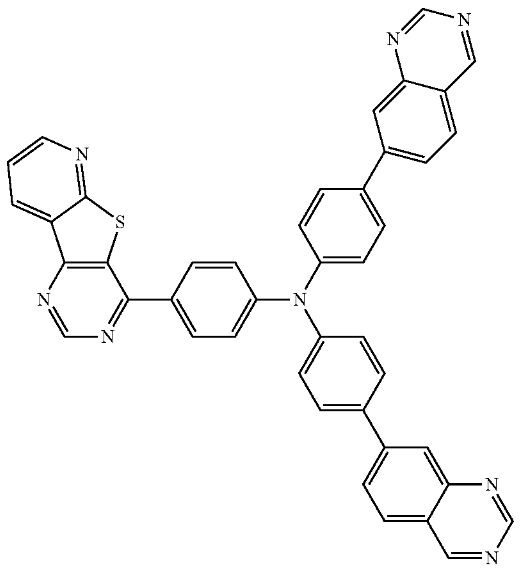
-continued
M272
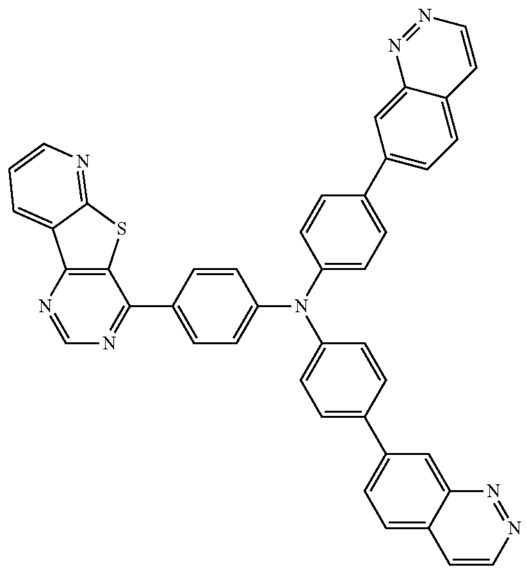
M273
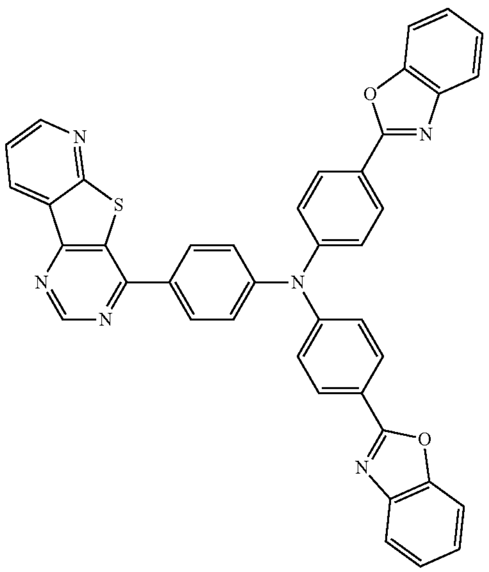

-continued
M274
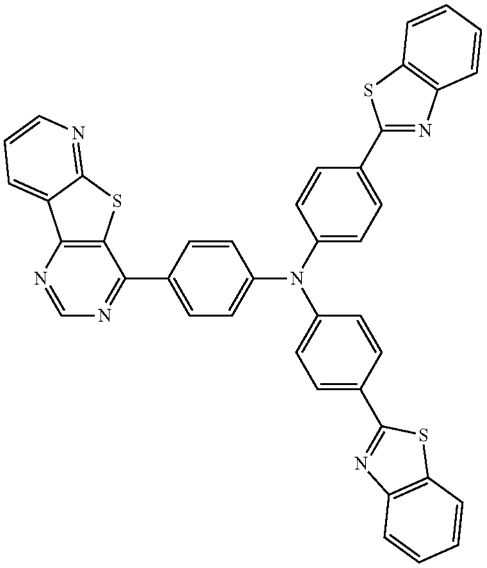
M275
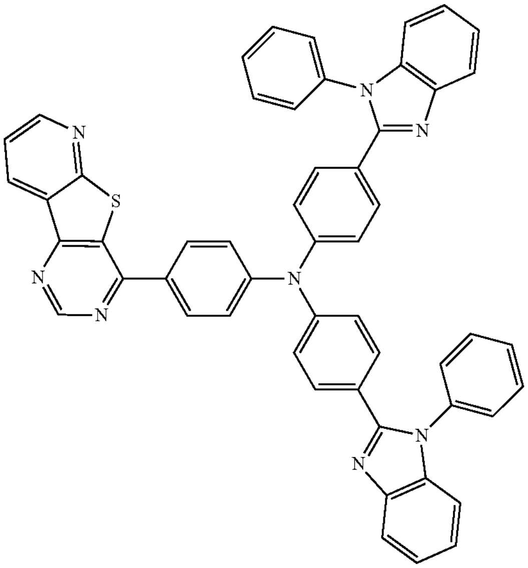
-continued
M276
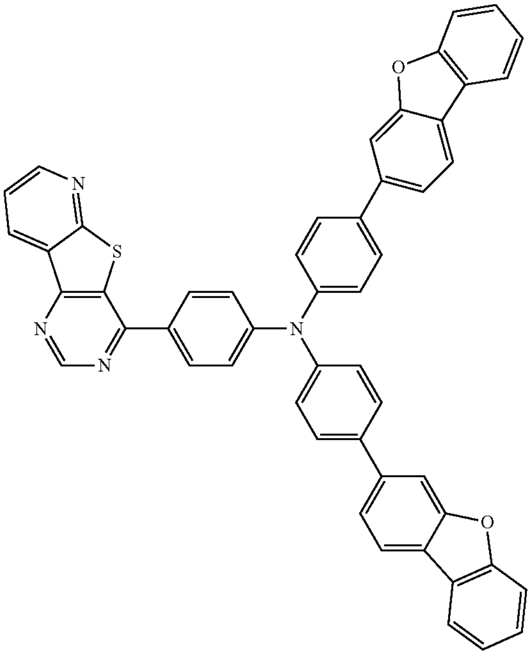
M277
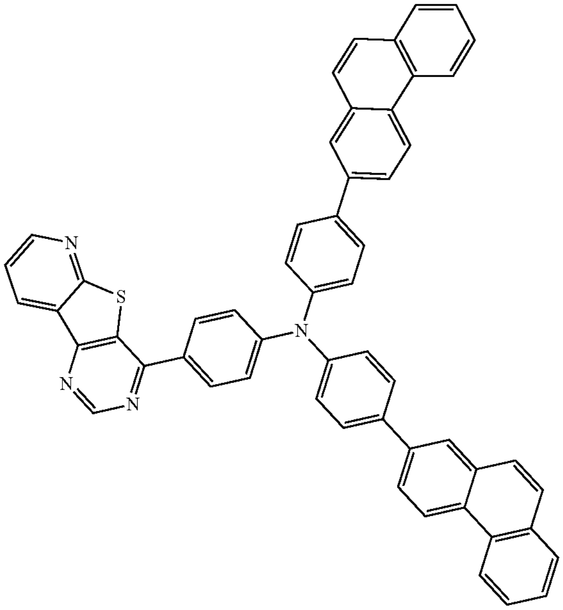

-continued
M278
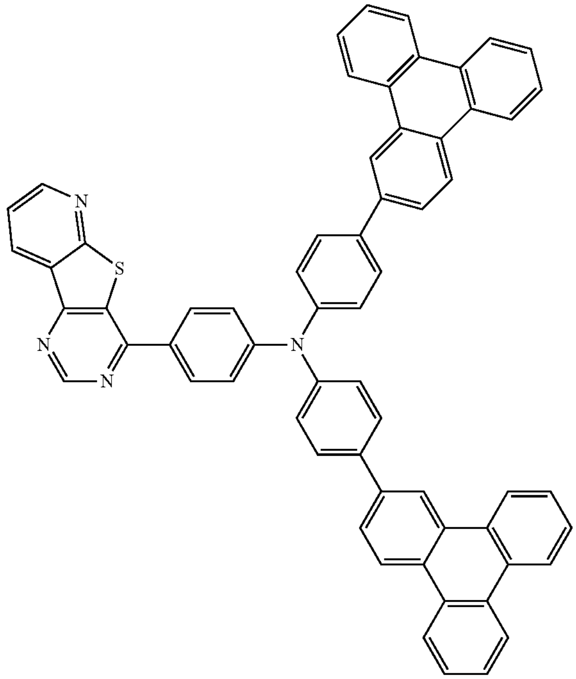
M279
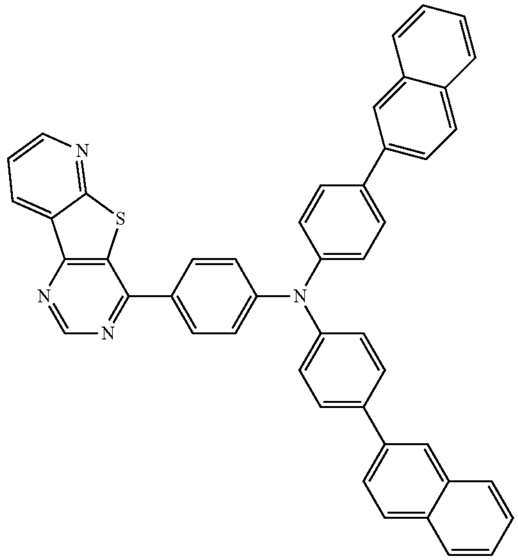
-continued
M280
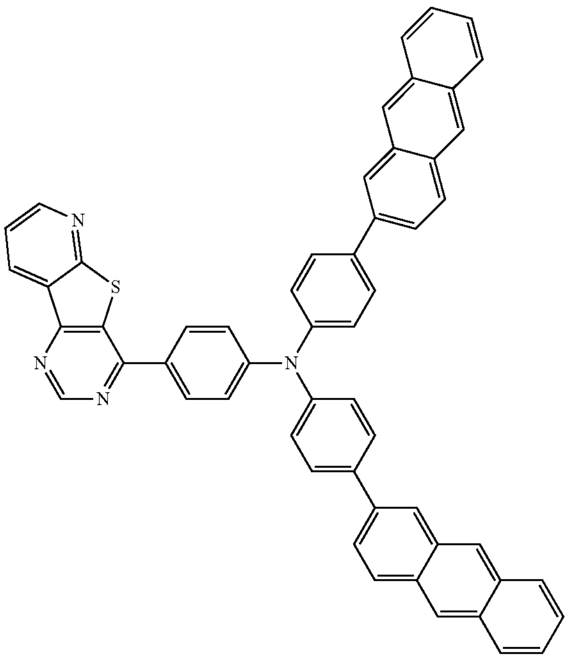
M281
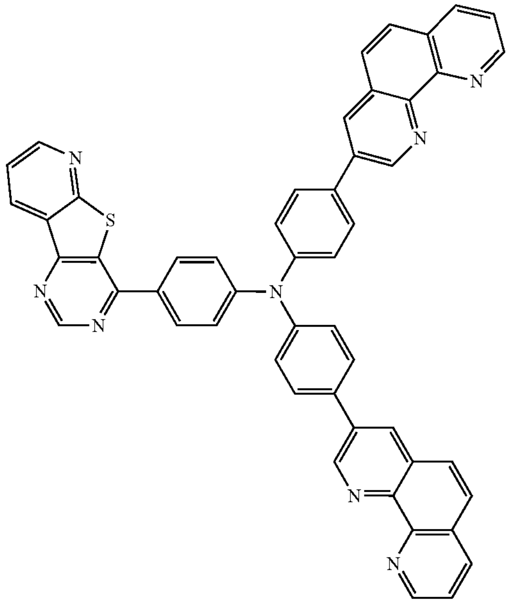

-continued
M282
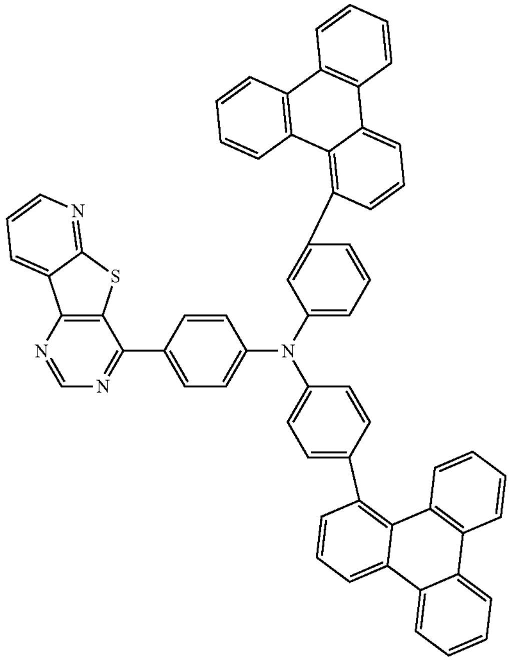
M283
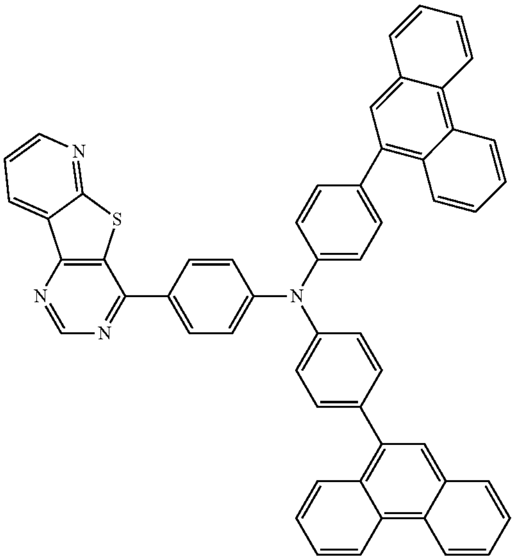
-continued
M284
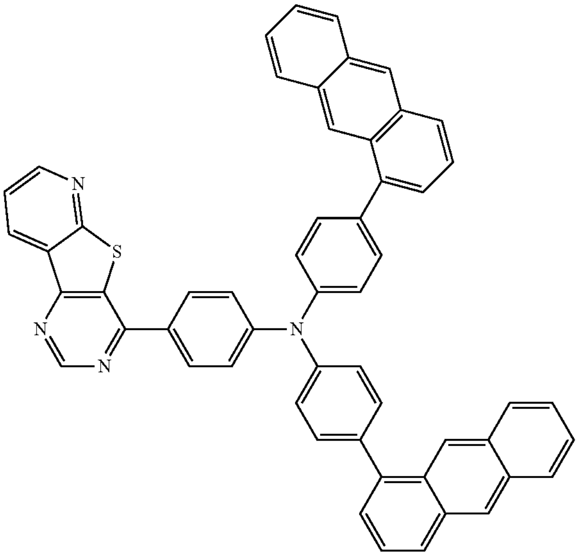
M285
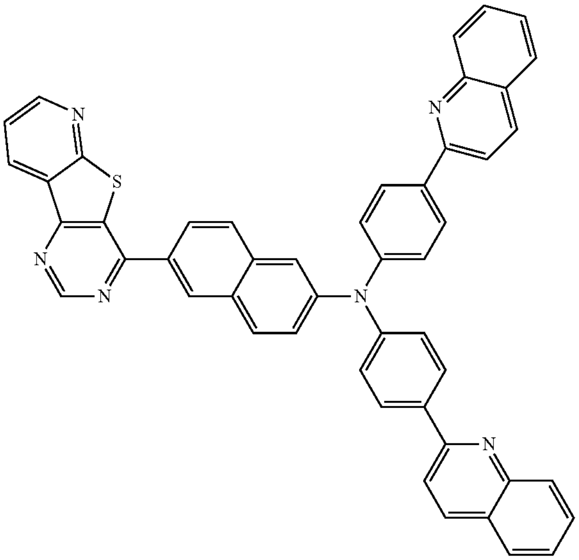

-continued
M286
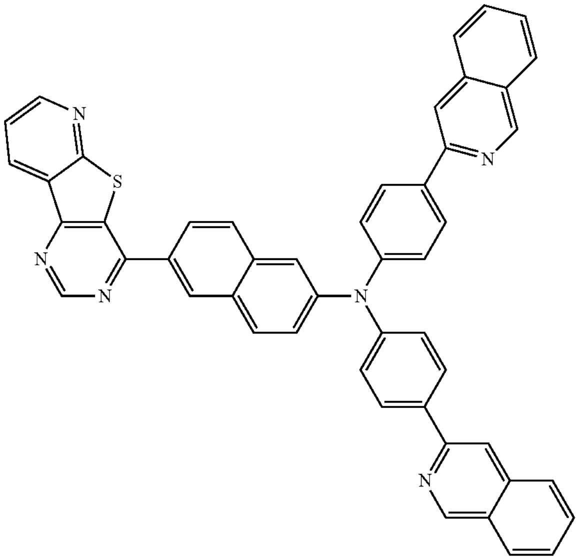
M287
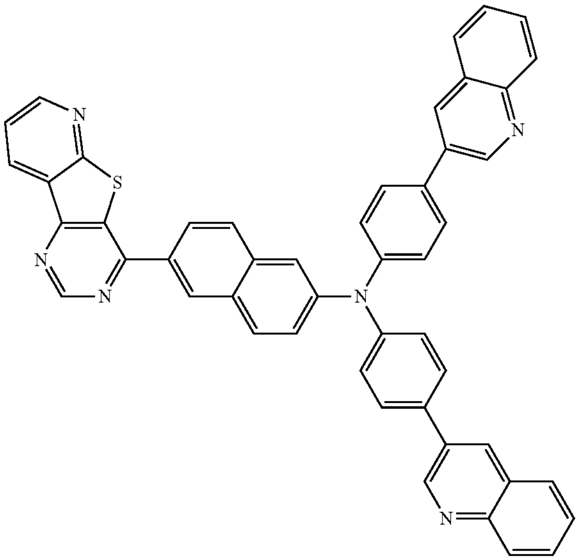
-continued
M288
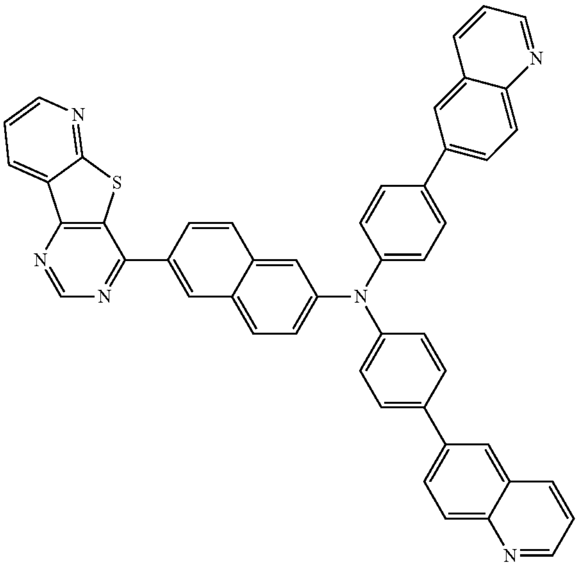
M289
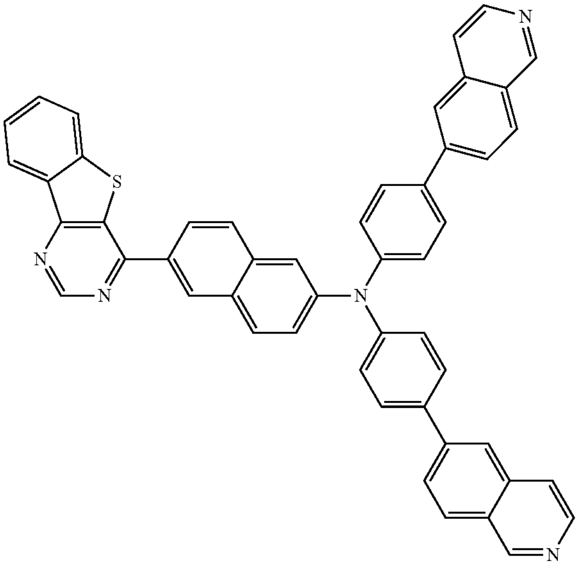

-continued
M290
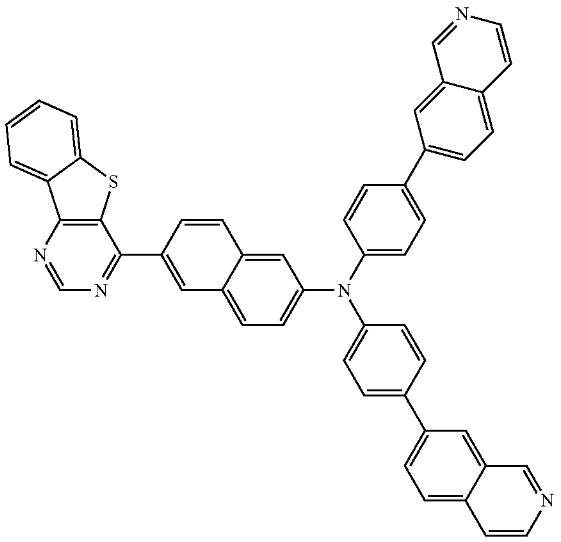
M291
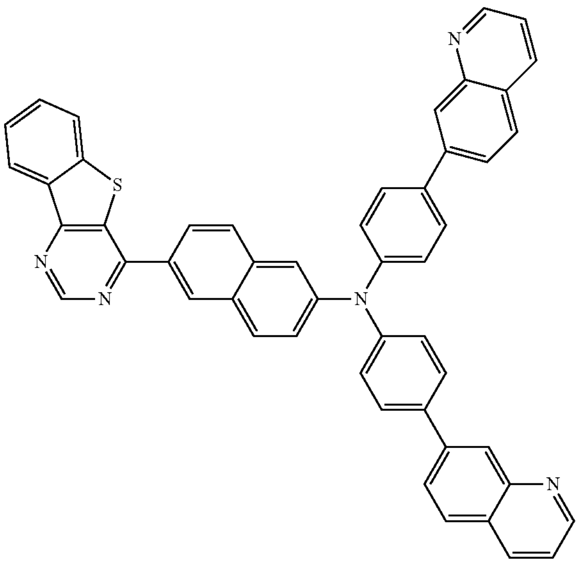
-continued
M292
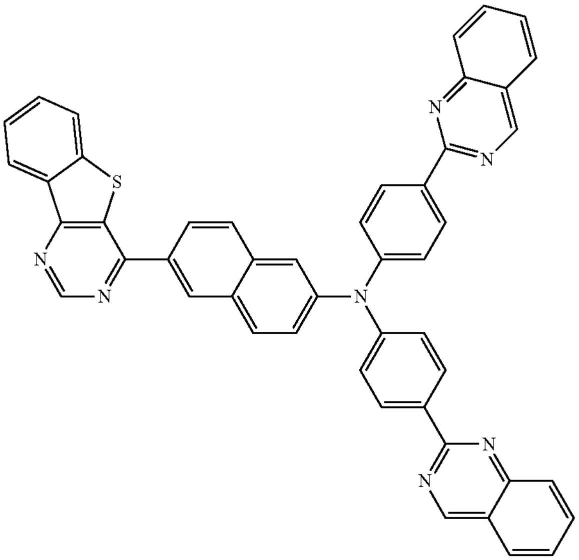
M293
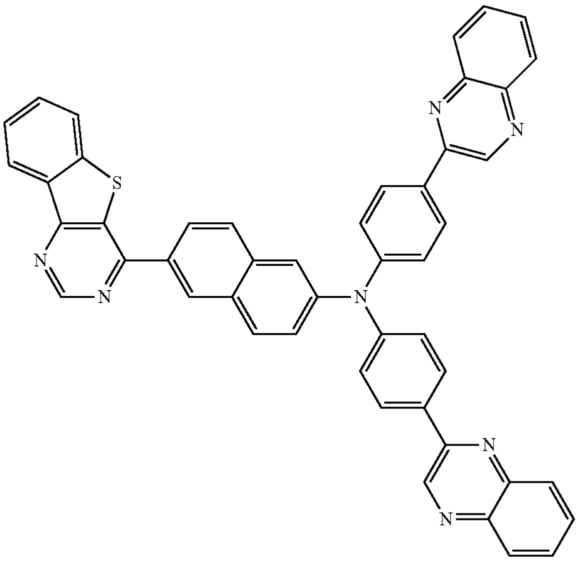

-continued
M294
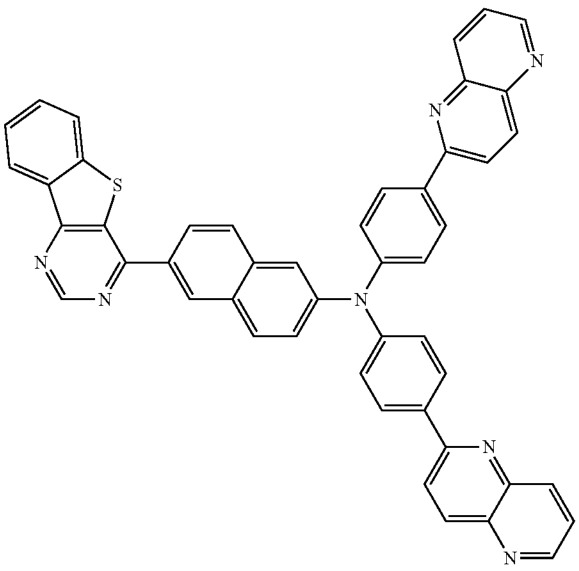
M295
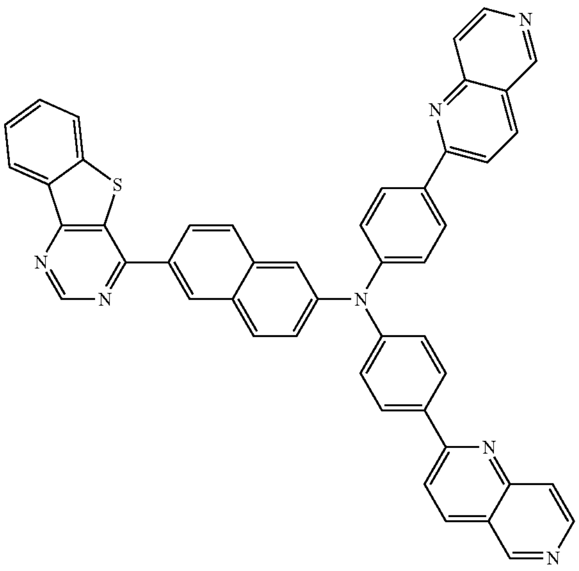
-continued
M296
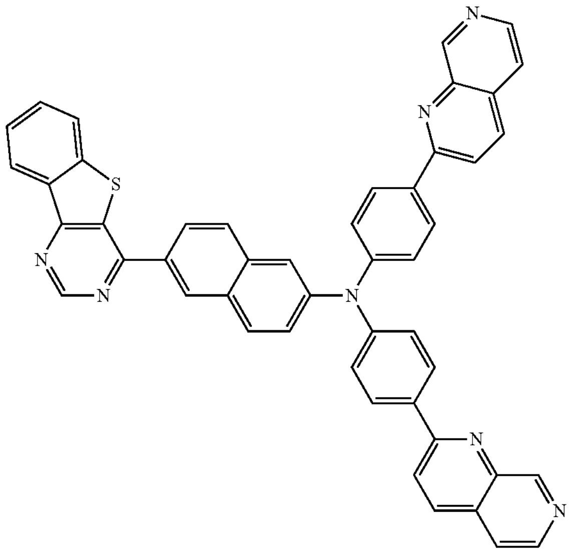
M297
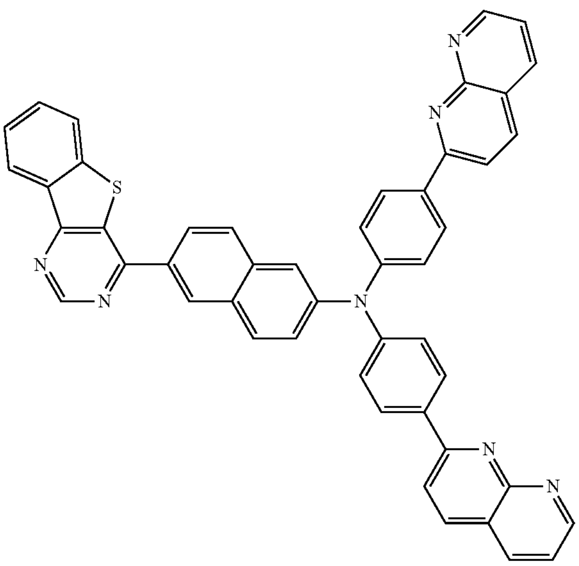

-continued
M298
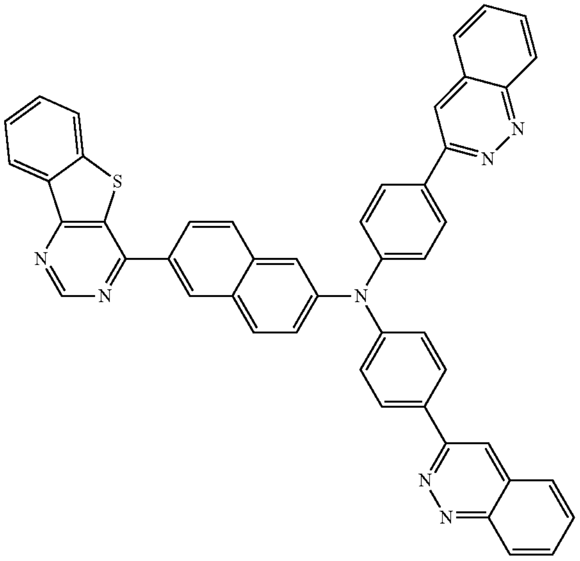
M299
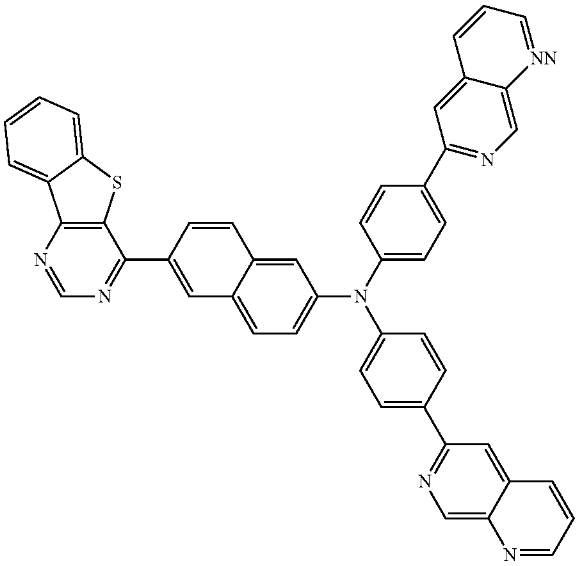
-continued
M300
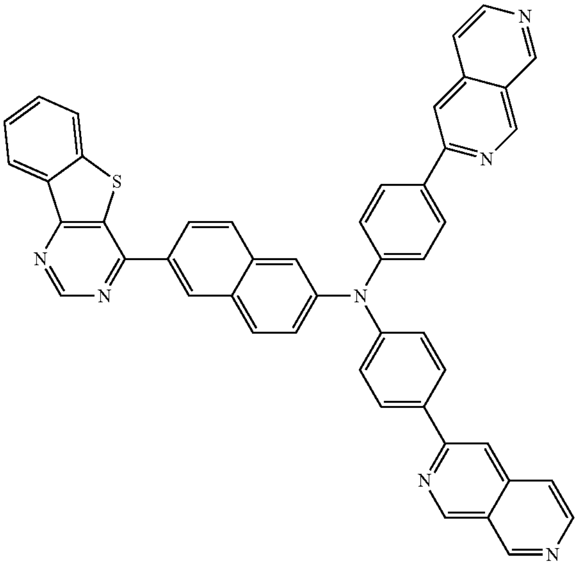
M301
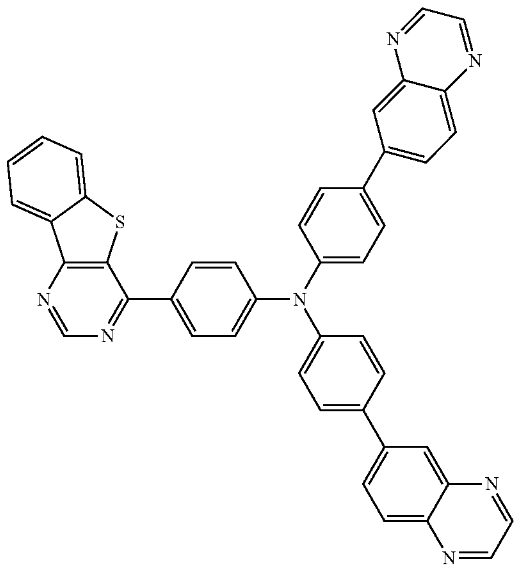

-continued
M302
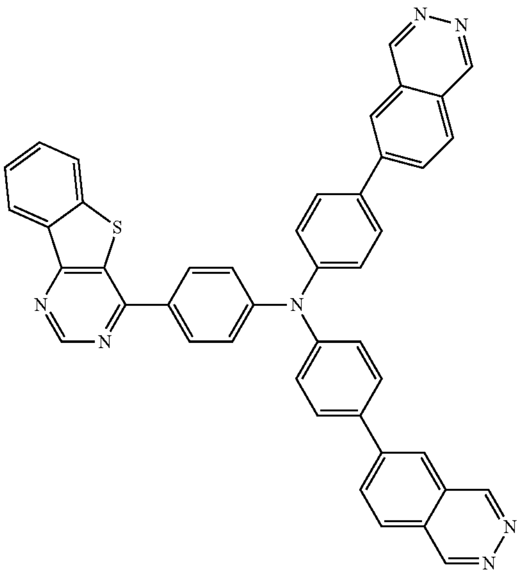
-continued
M304
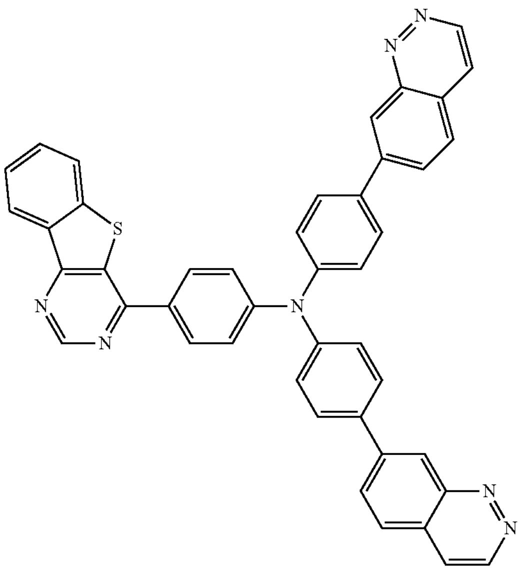
M303
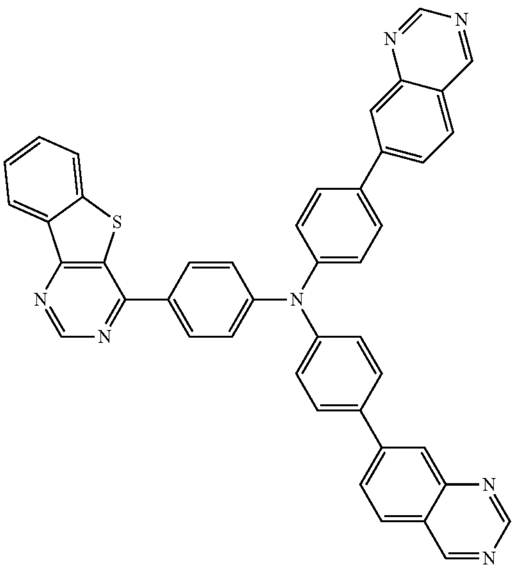
M305
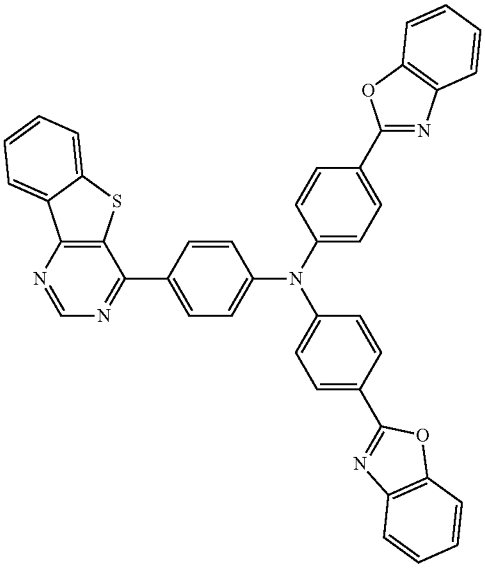

-continued
M306
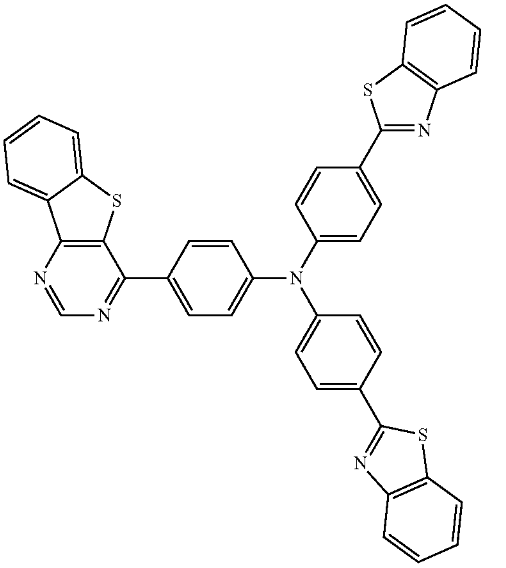
M307
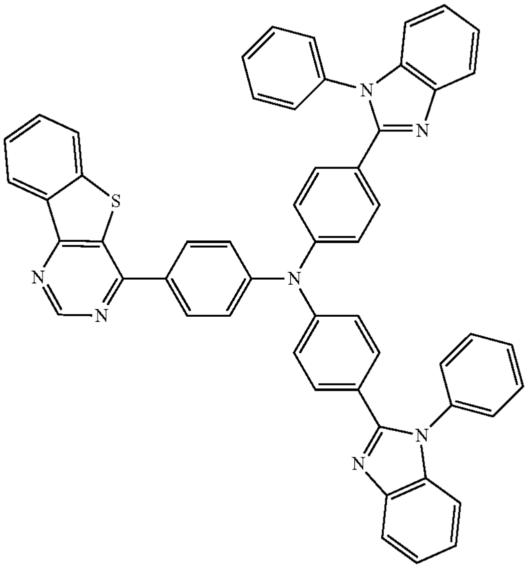
-continued
M308
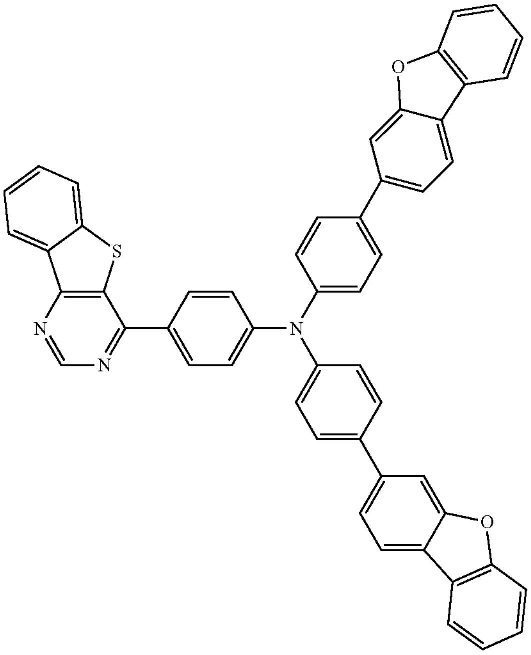
M309
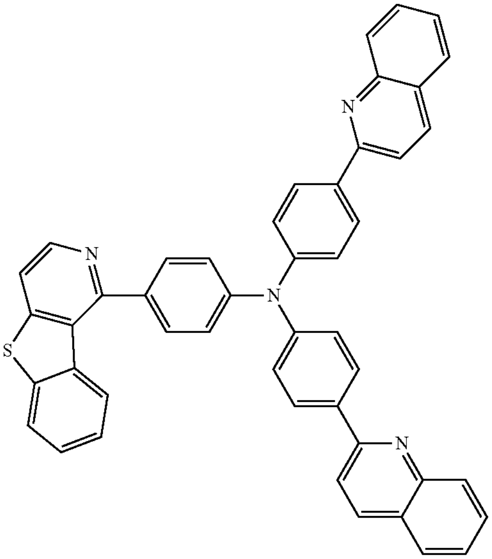

-continued
M310
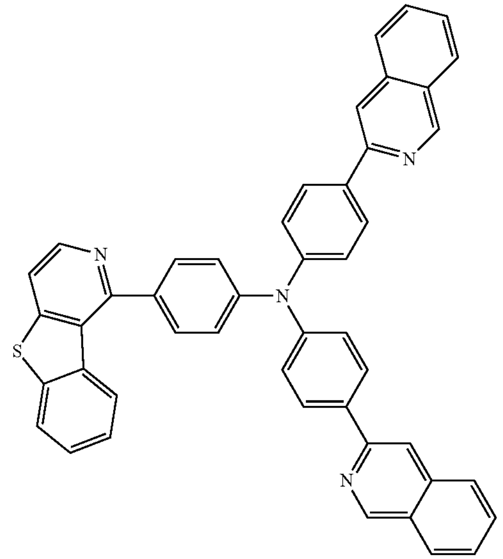
M311
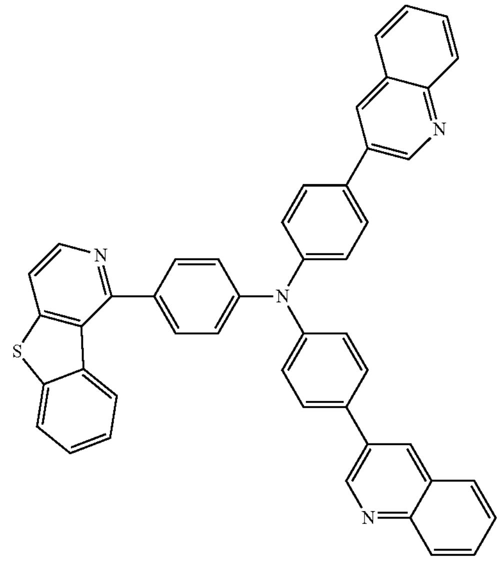
-continued
M312
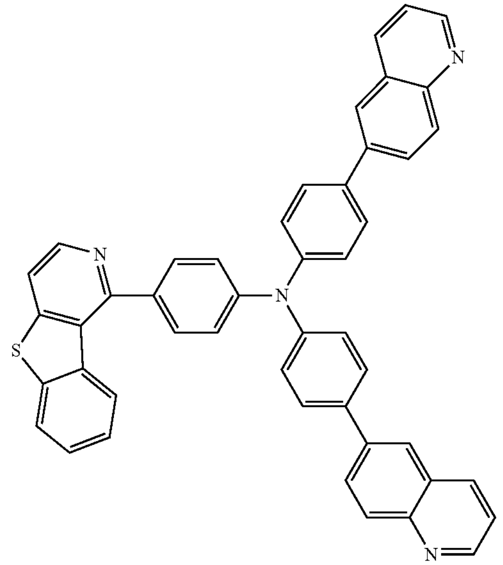
M313
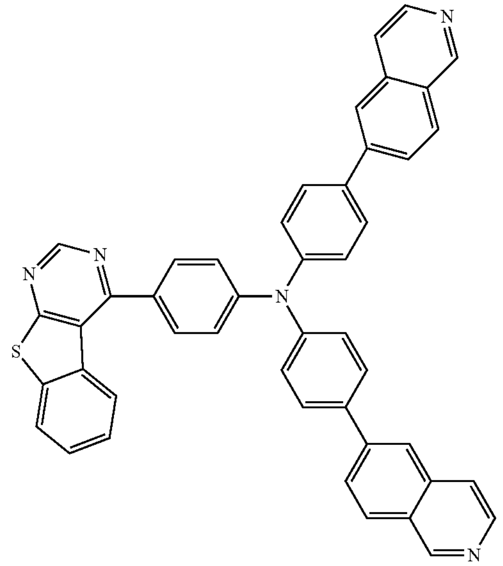

-continued
M314
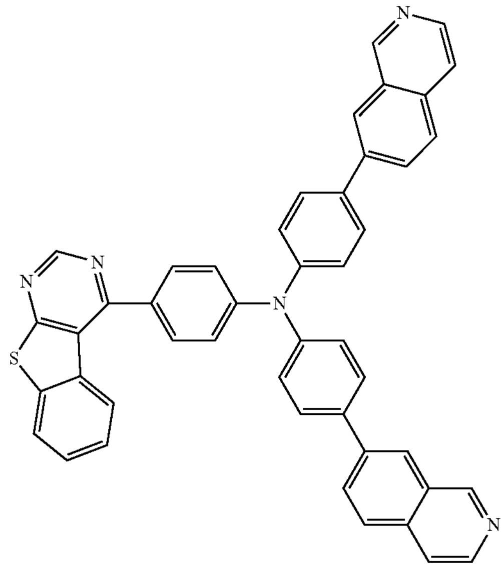
M315
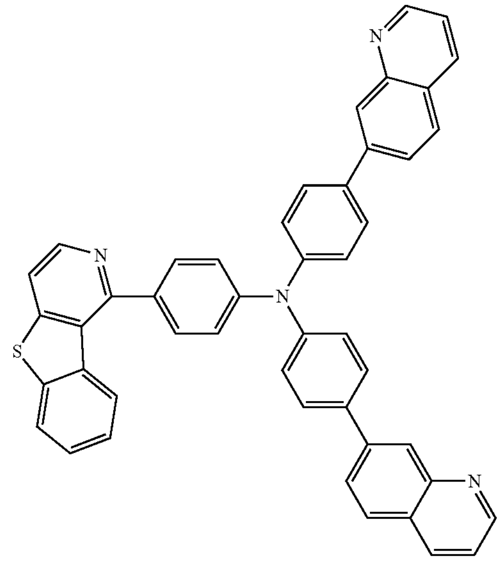
-continued
M316
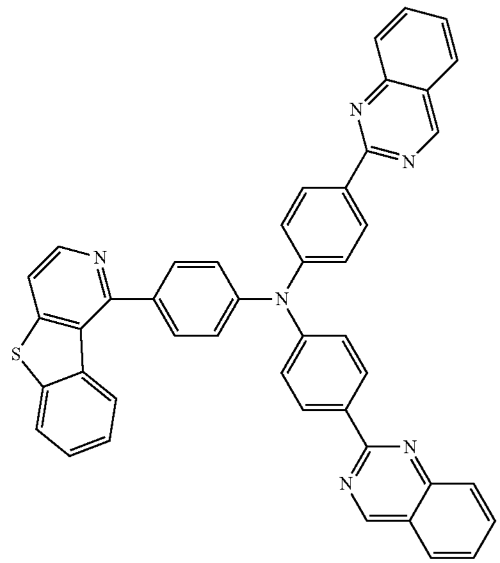
M317
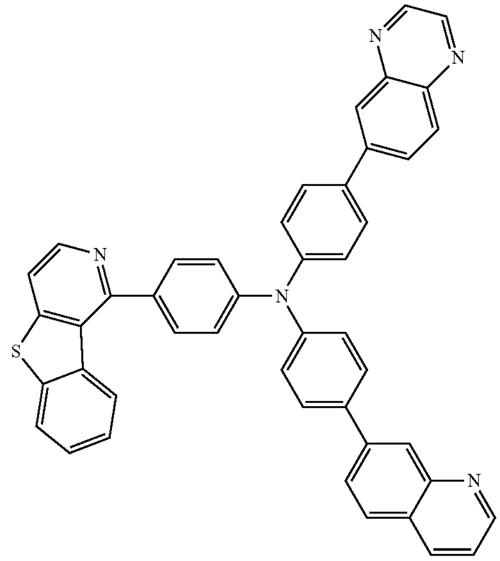

-continued
M318
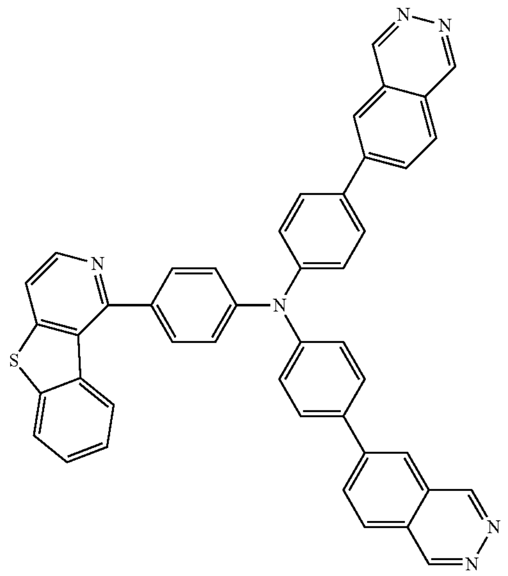
M319
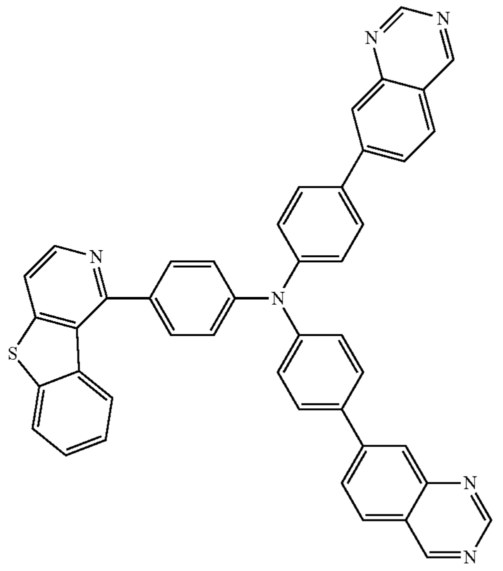
-continued
M320
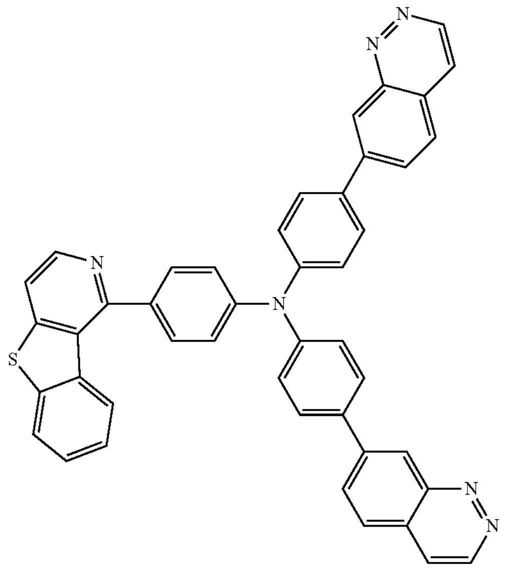
M321
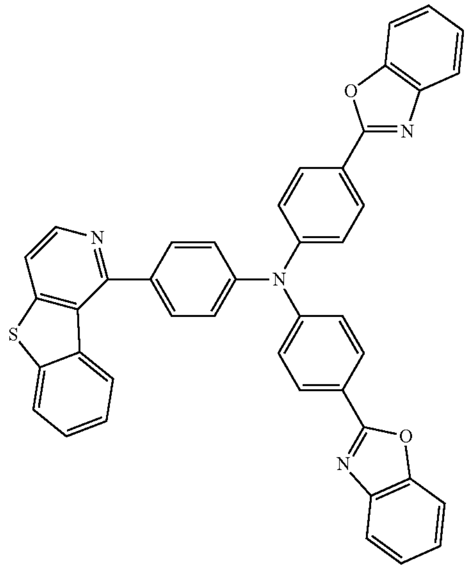

-continued
M322
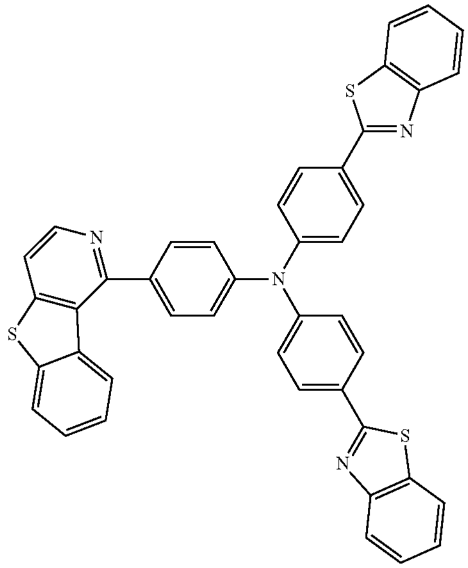
M323
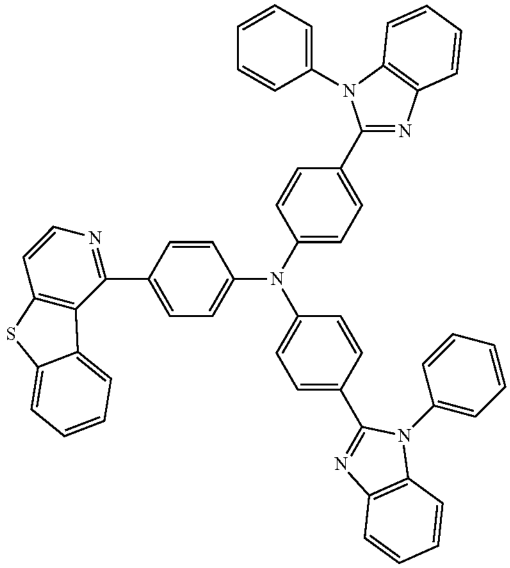
-continued
M324
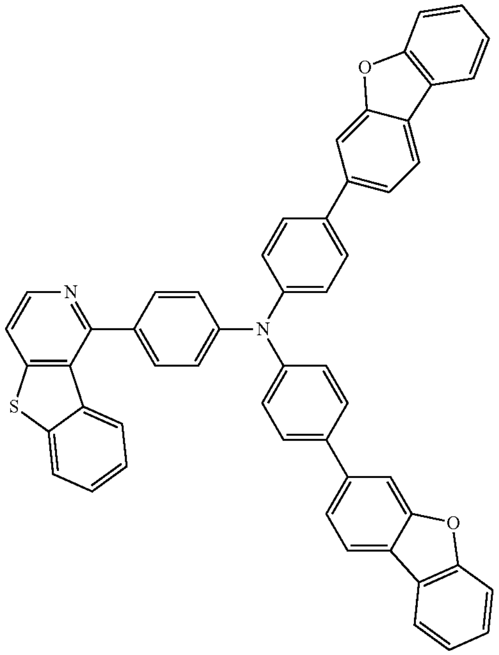
M325
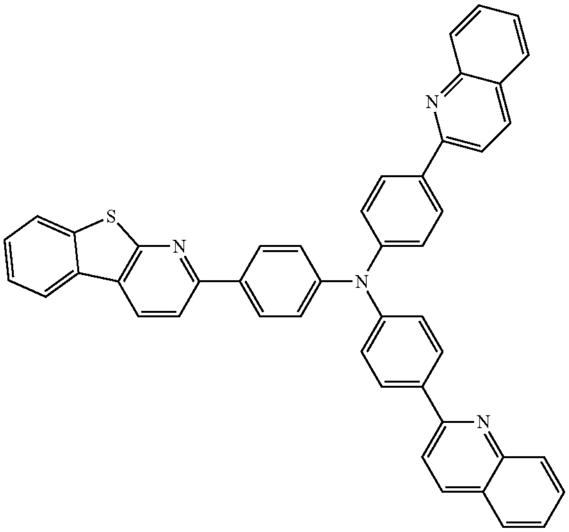

-continued
M326
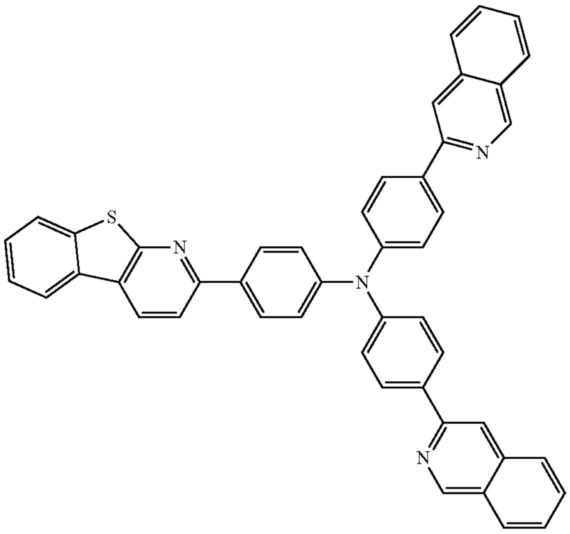
M327
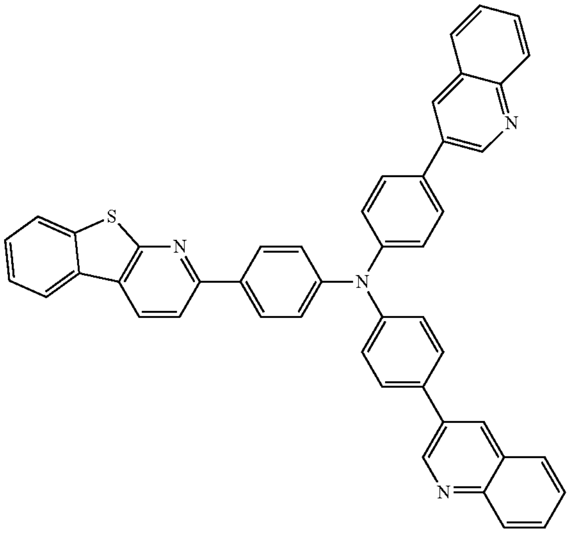
M328
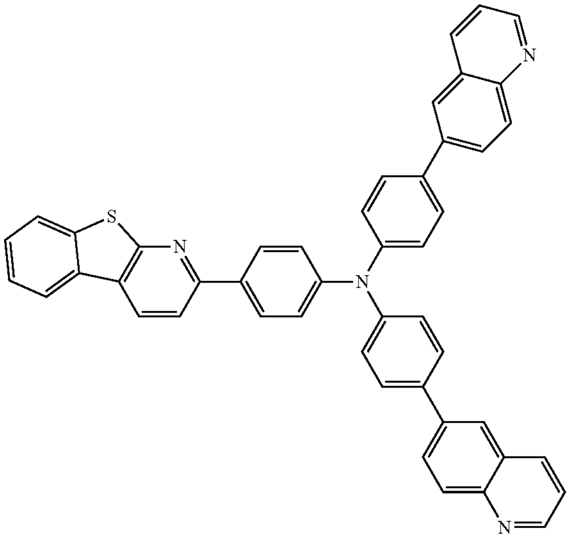
-continued
M329
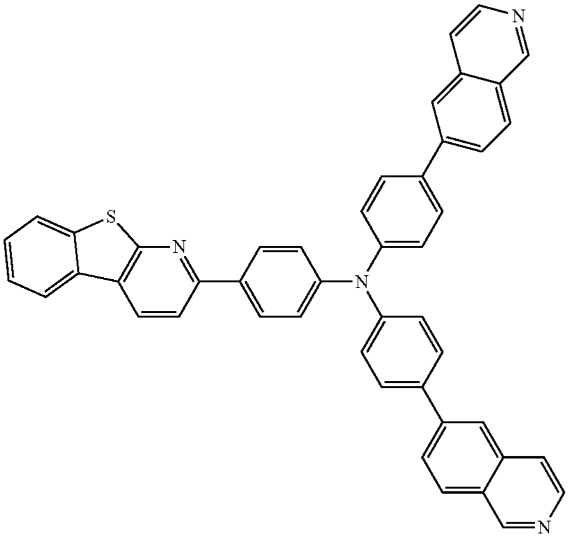
M330
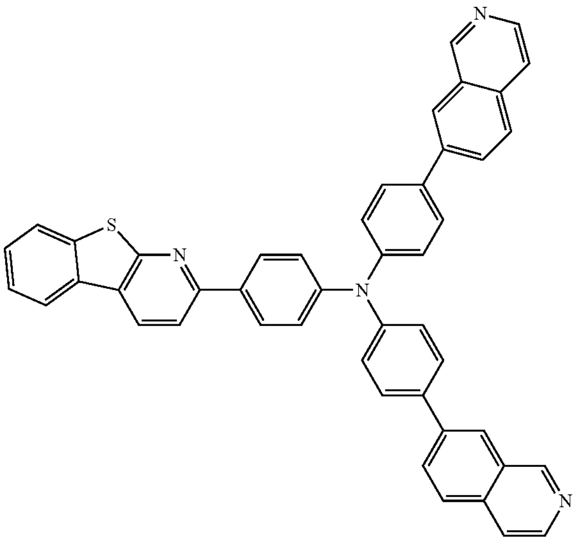
M331
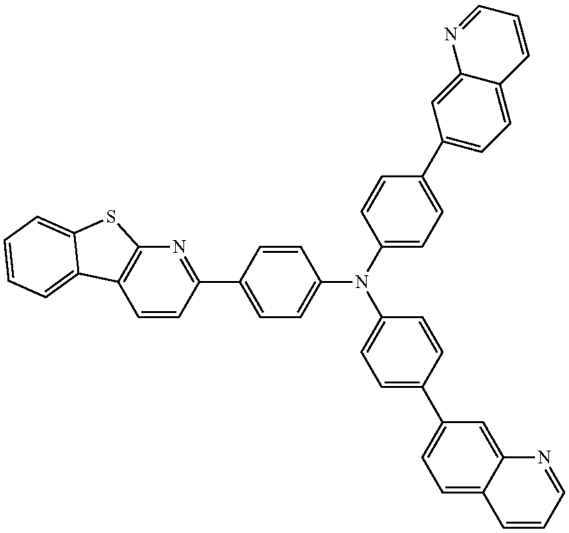

-continued
M332
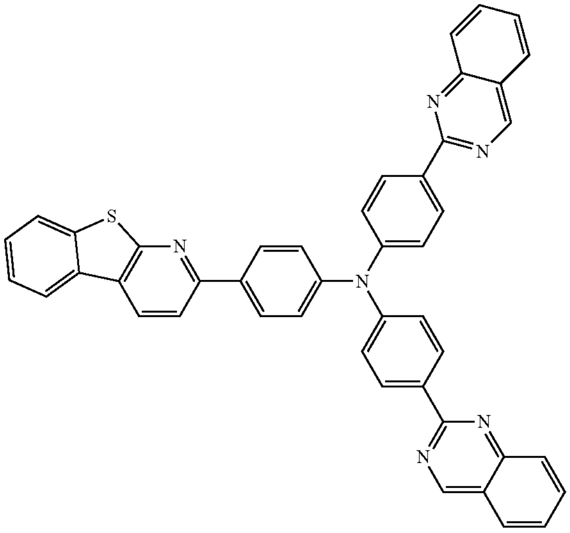
M333
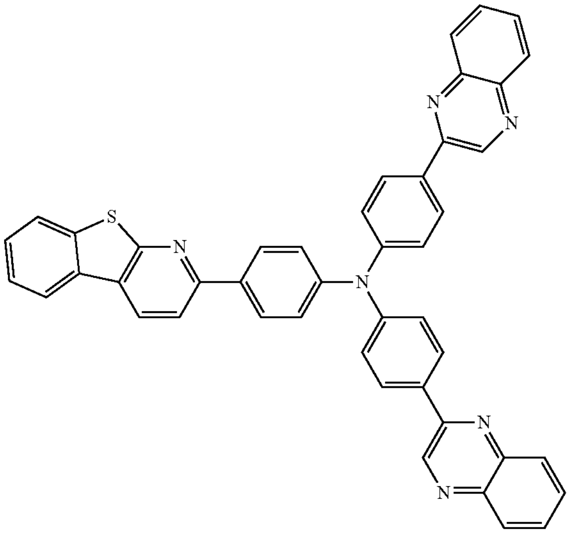
M334
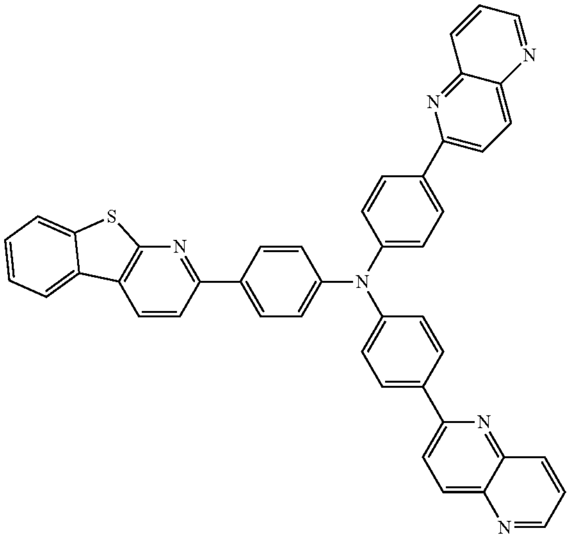
-continued
M335
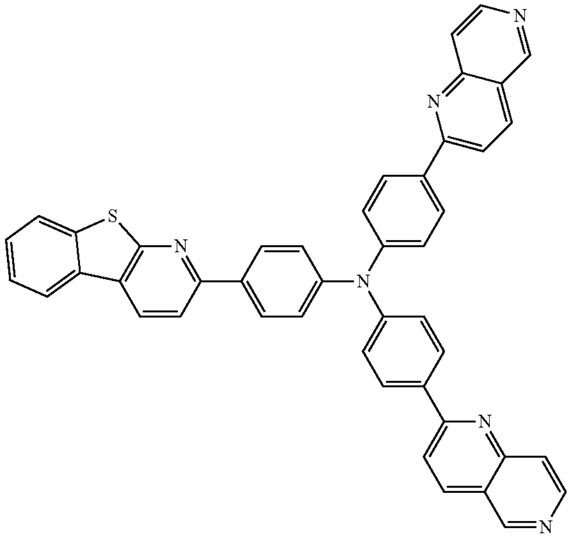
M336
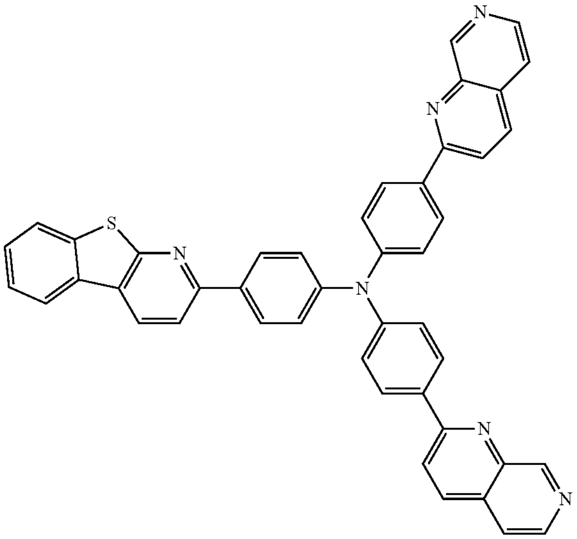
M337
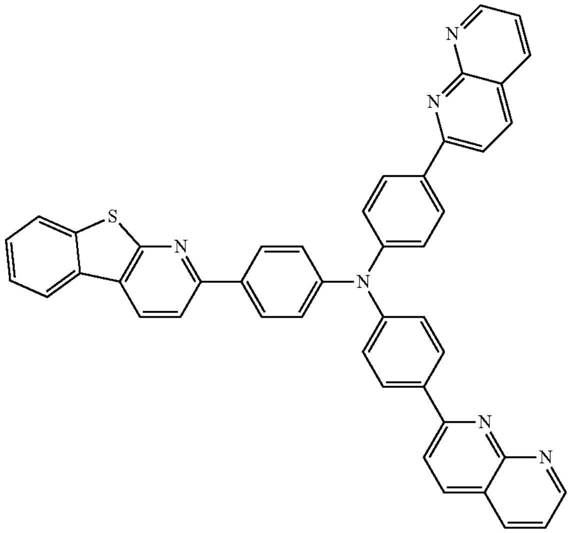

-continued
M338
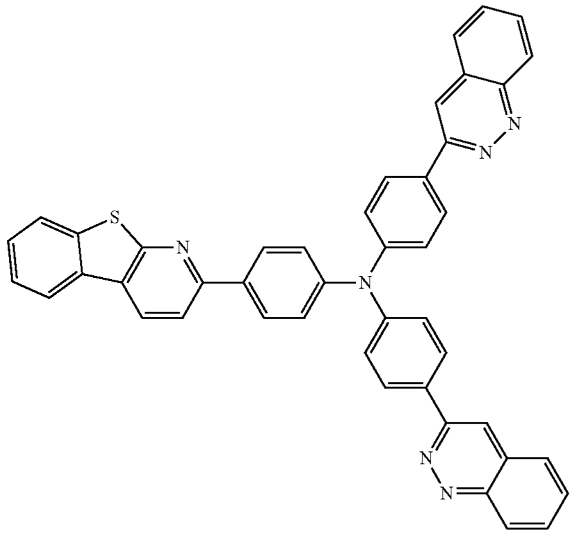
M339
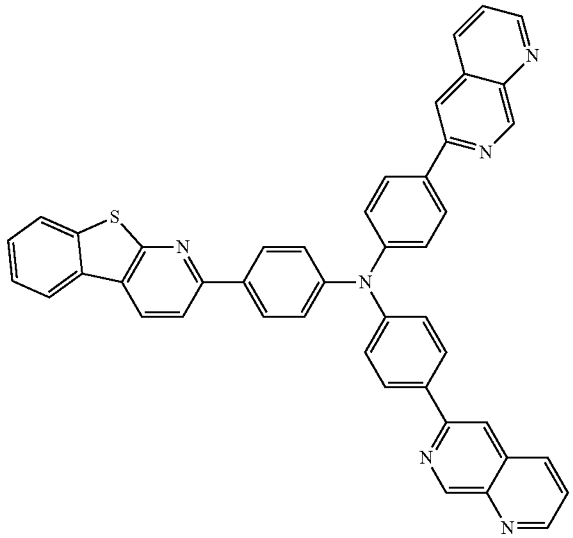
M340
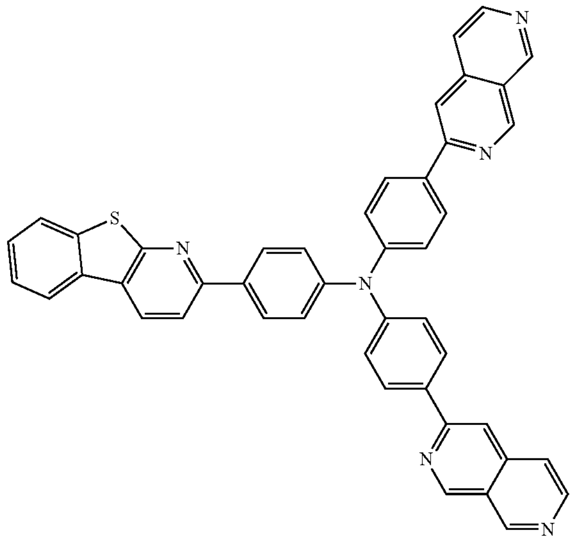
-continued
M341
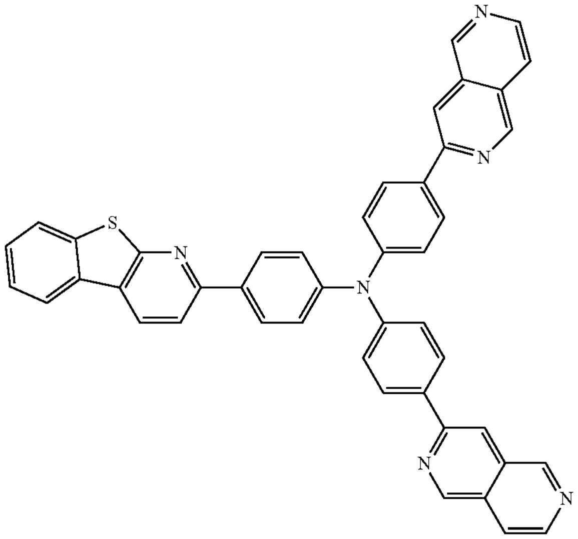
M342
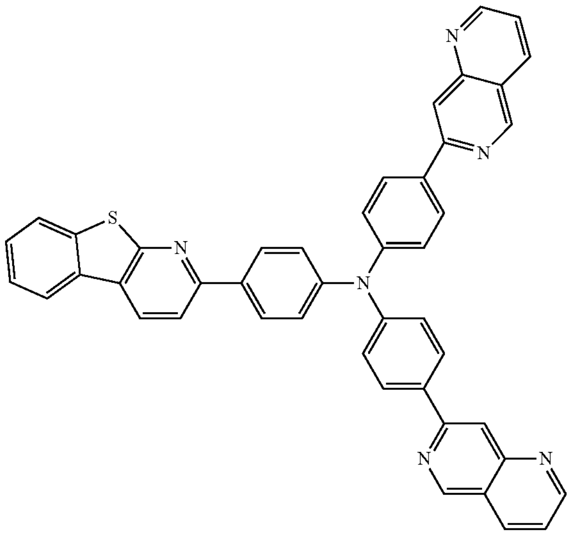
M343
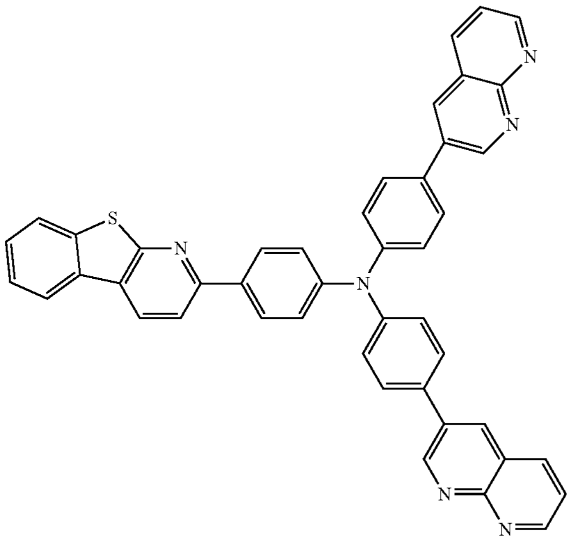

-continued
M344
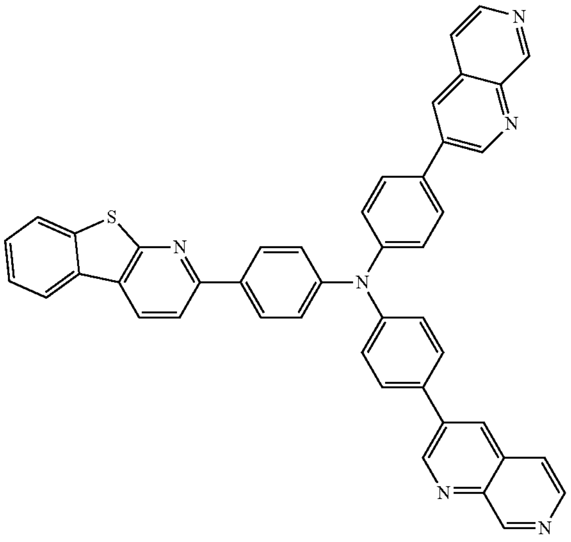
M345
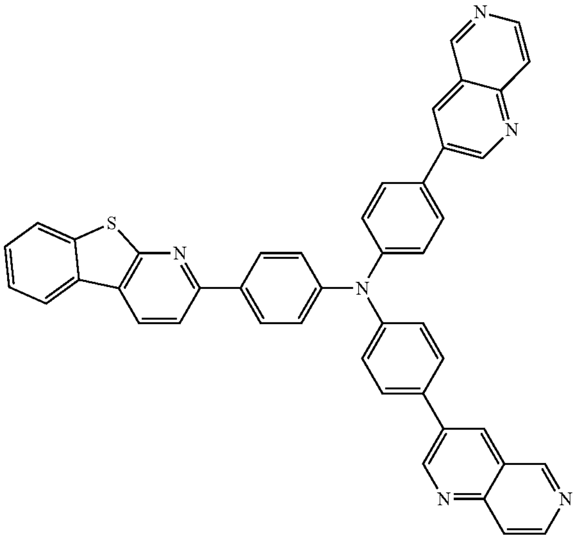
M346
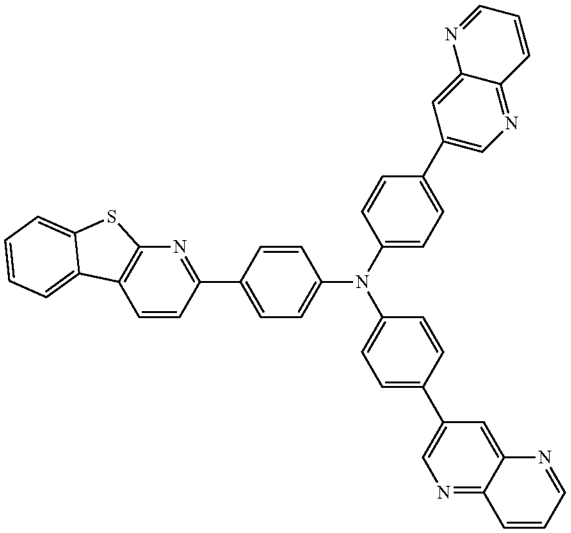
-continued
M347
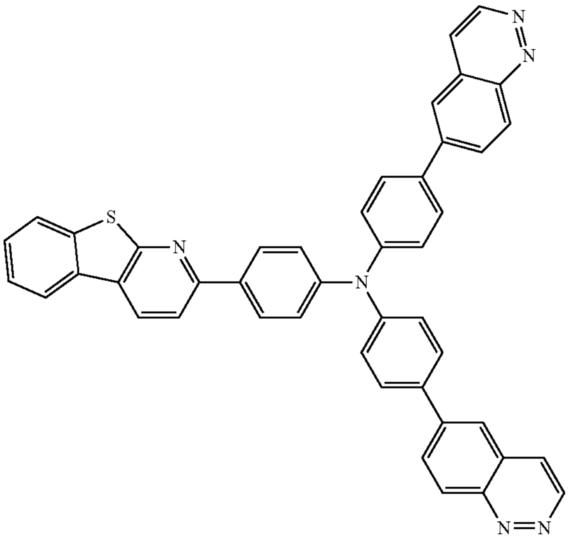
M348
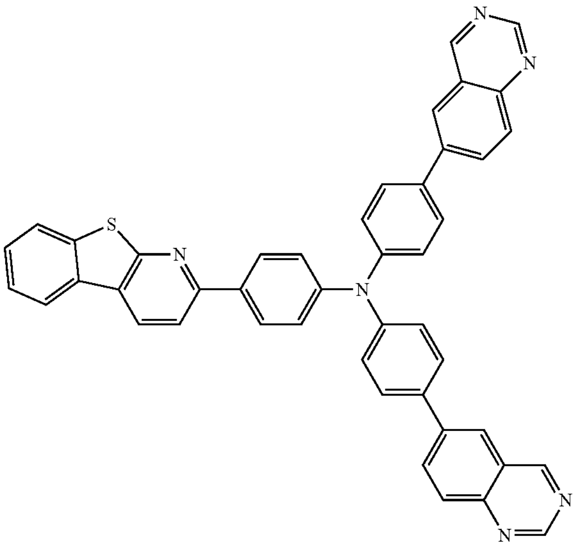

-continued
M349
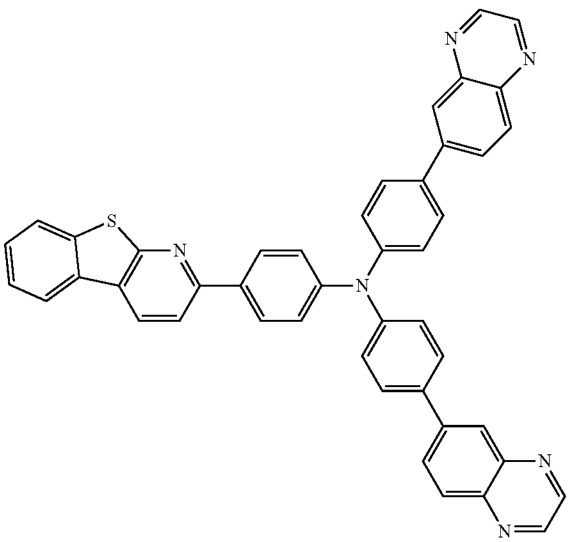
M350
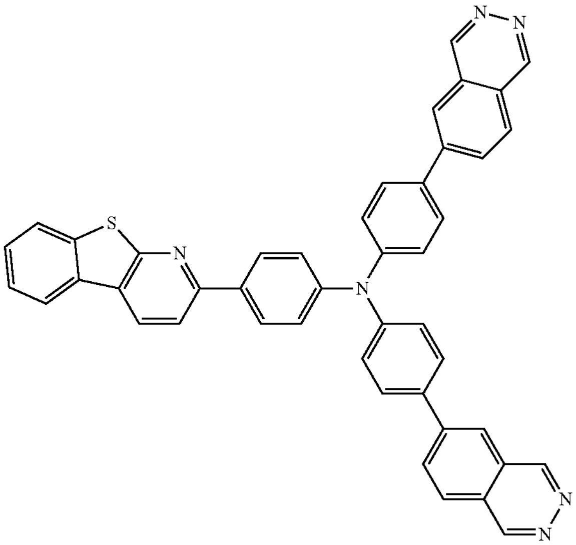
-continued
M351
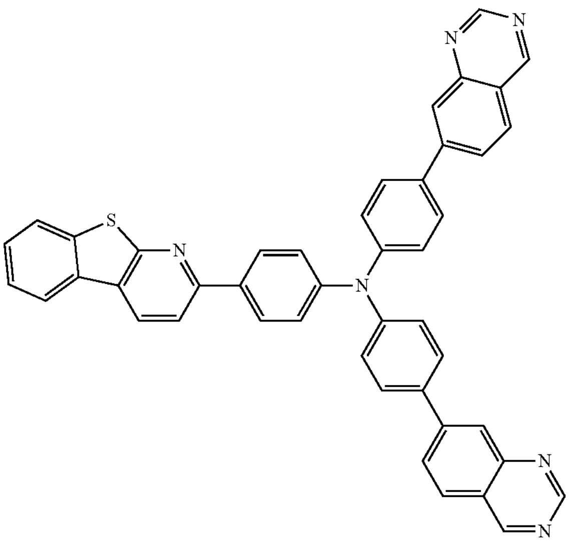
M352
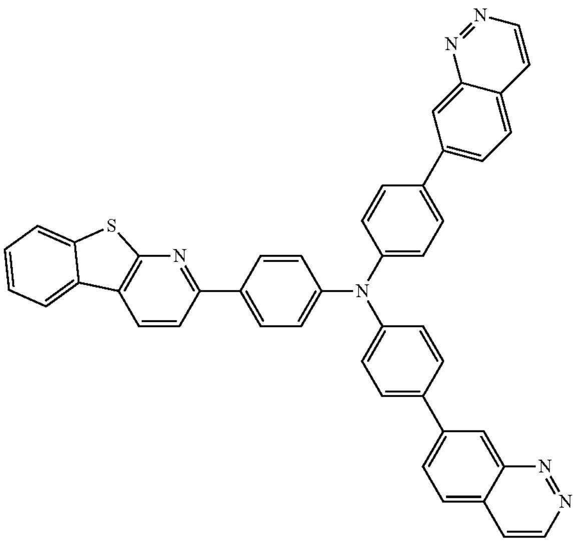

-continued
M353
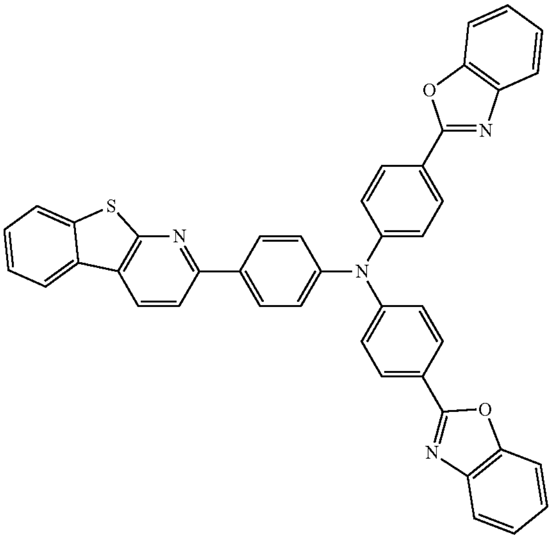
M354
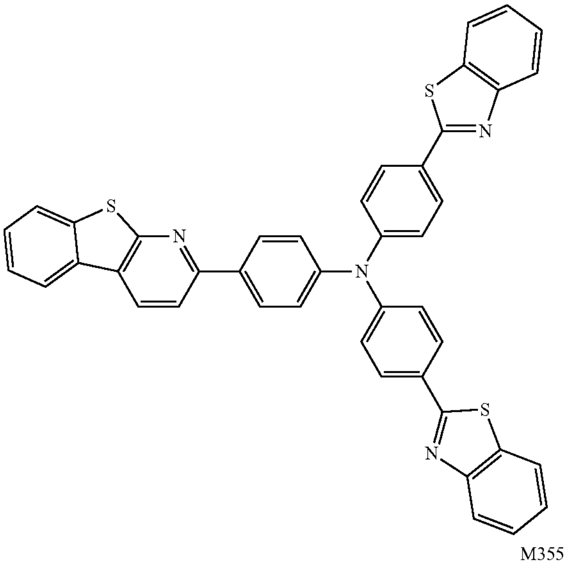
M355
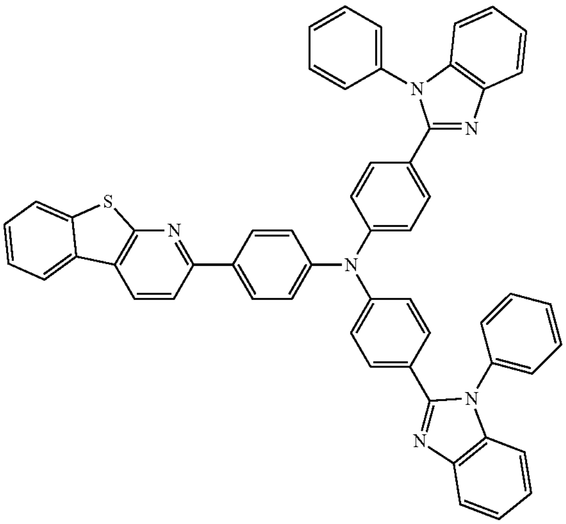
-continued
M356
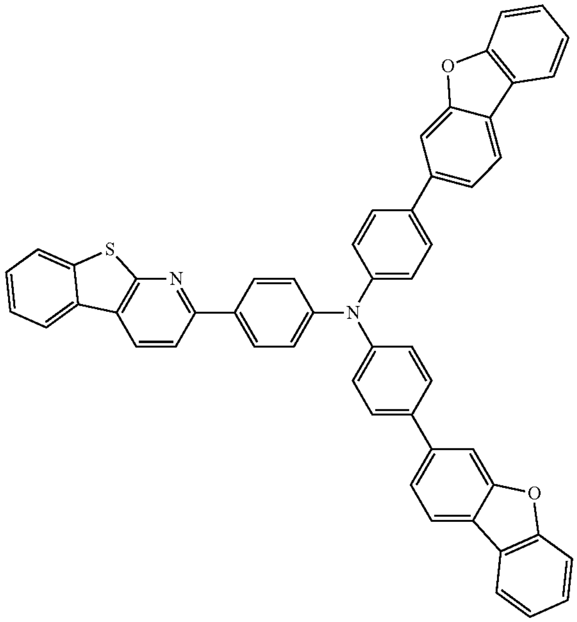
M357
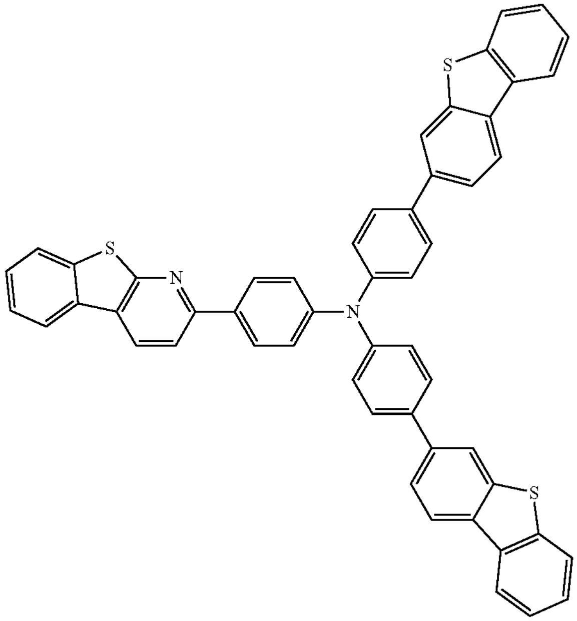

-continued
M358
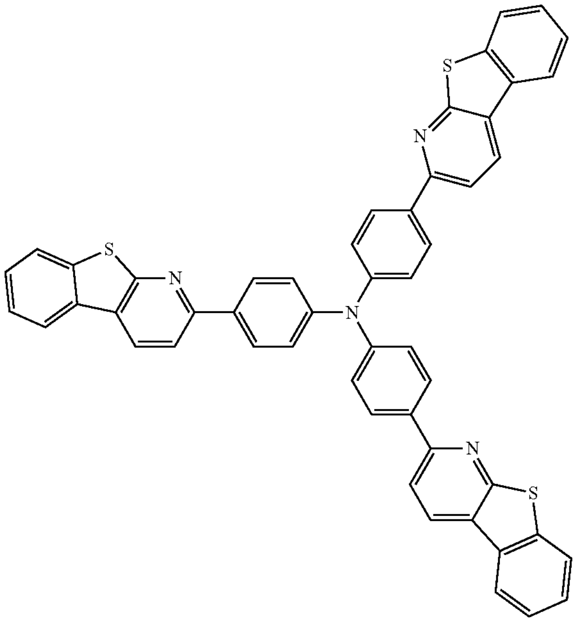
M359
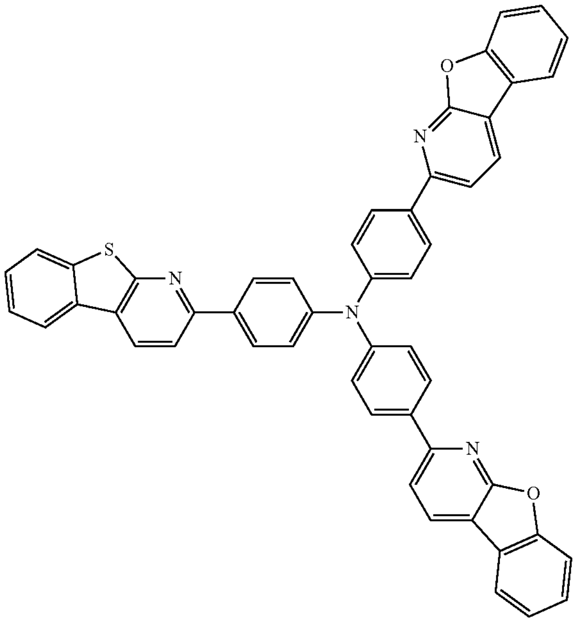
-continued
M360
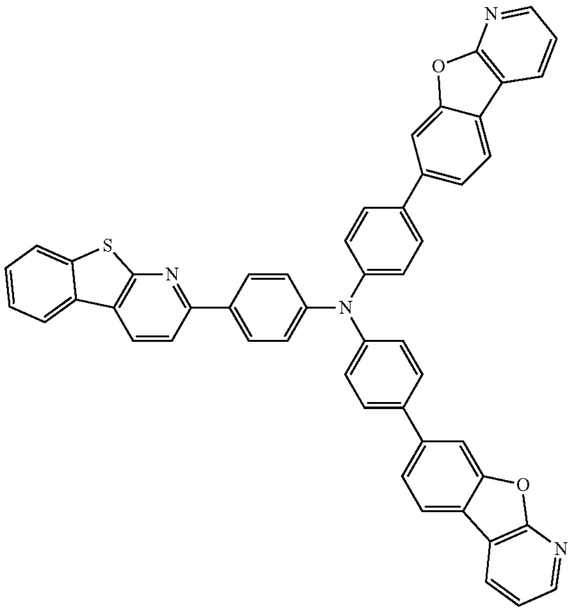
M361
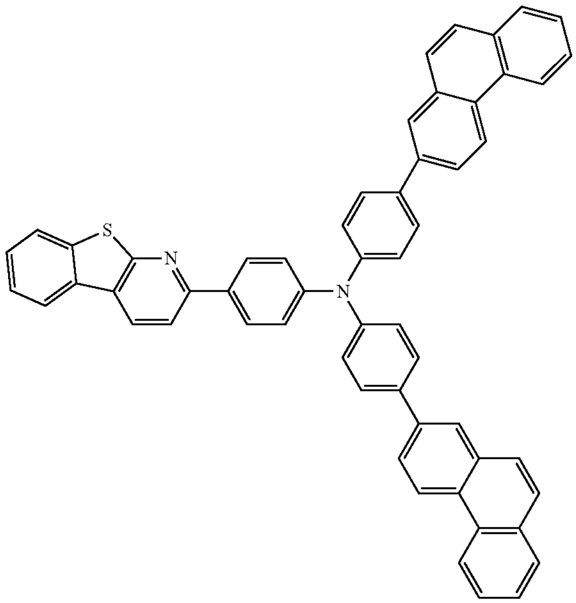

-continued
M362
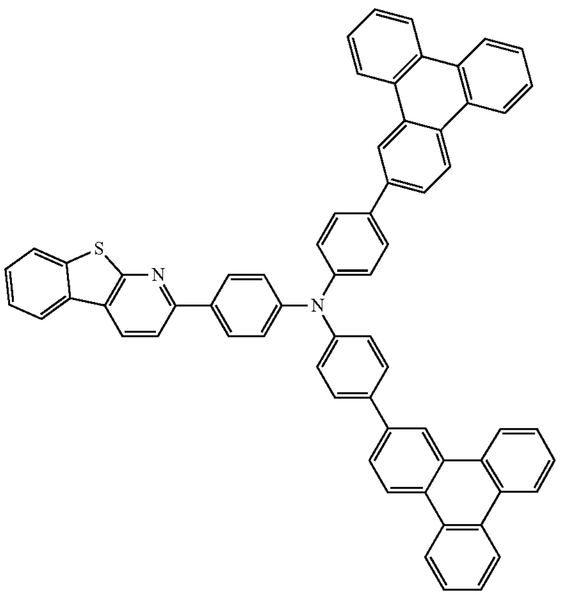
M363
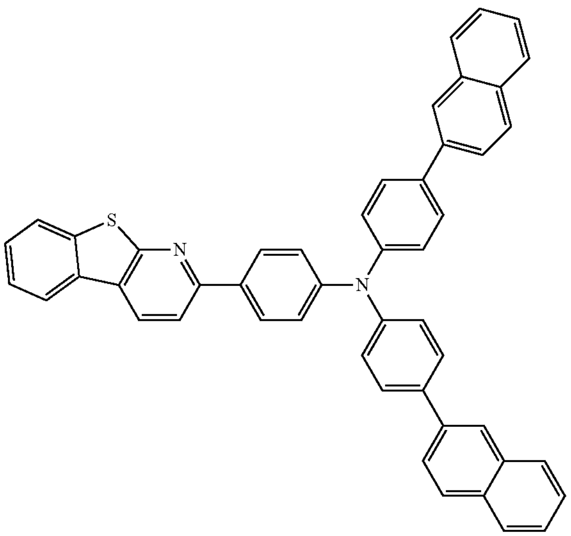
-continued
M364
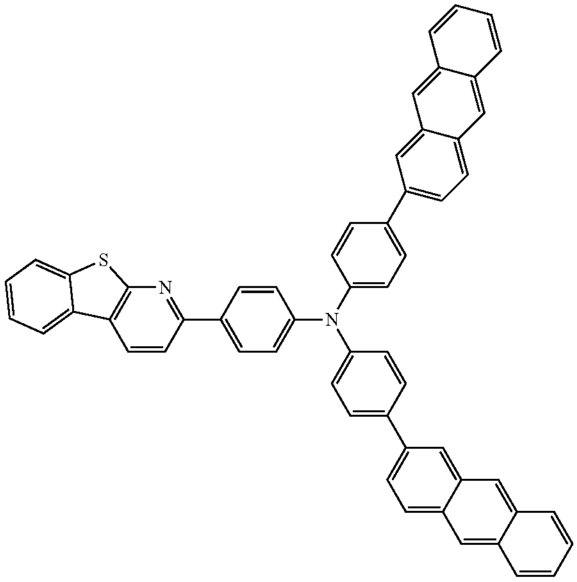
M365
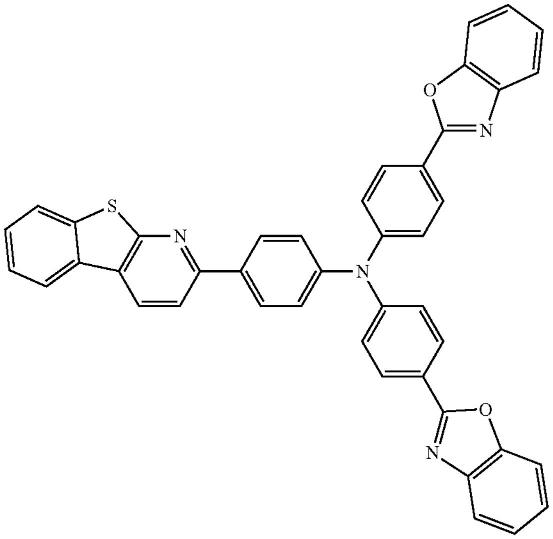

-continued
M366
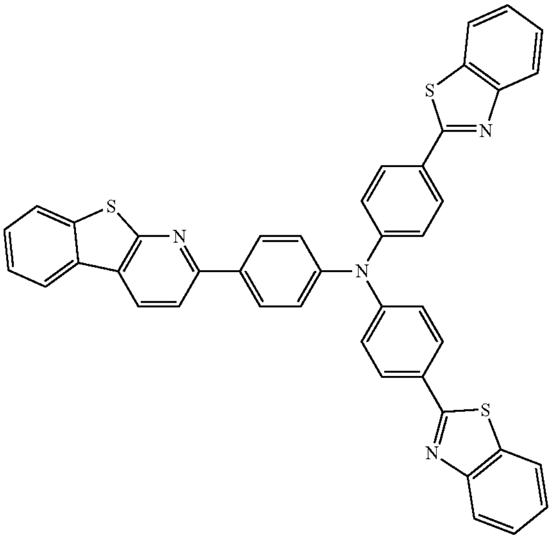
M367
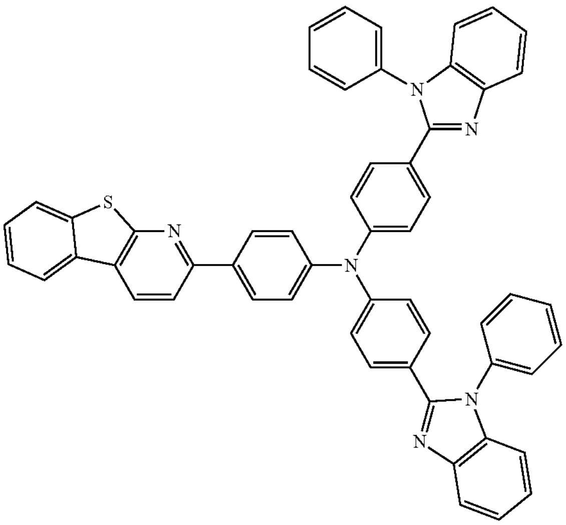
-continued
M368
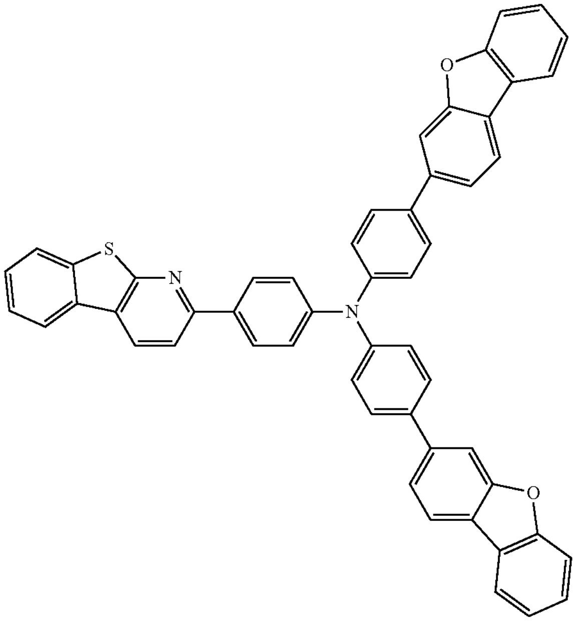
M369
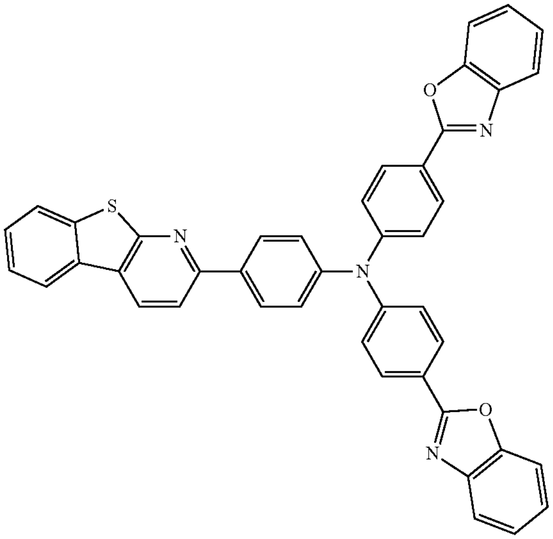

-continued
M370
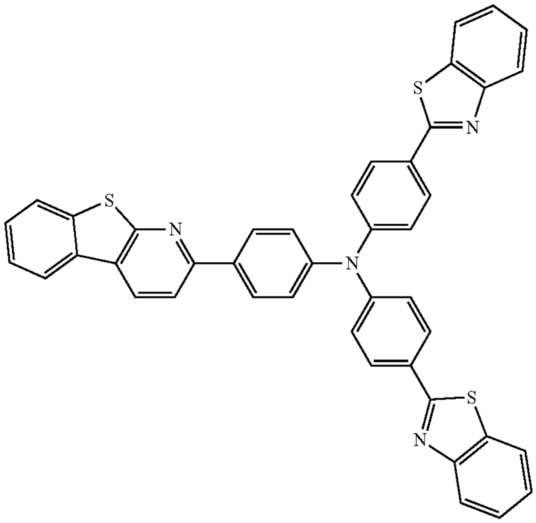
M371
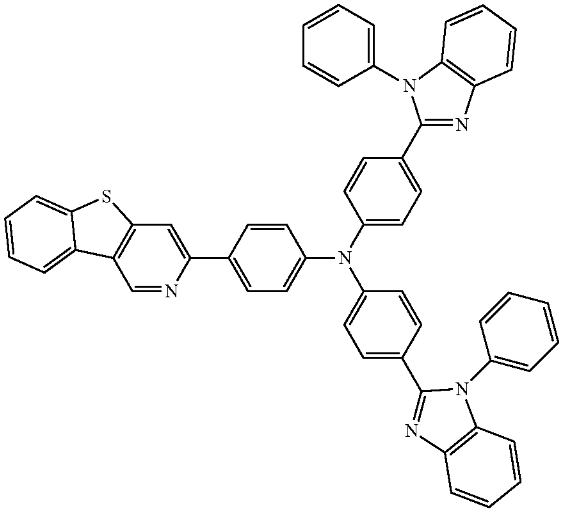
-continued
M372
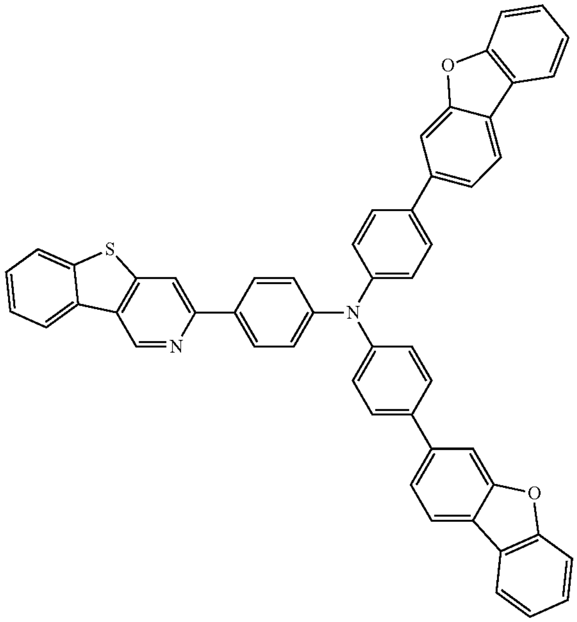
M373
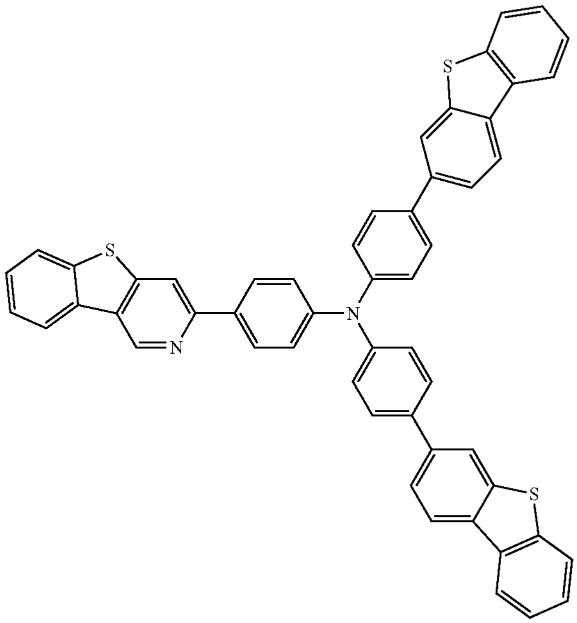

-continued
M374
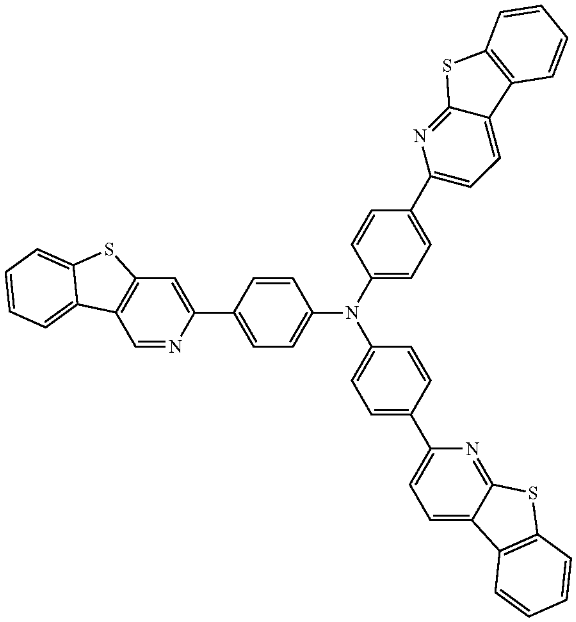
M375
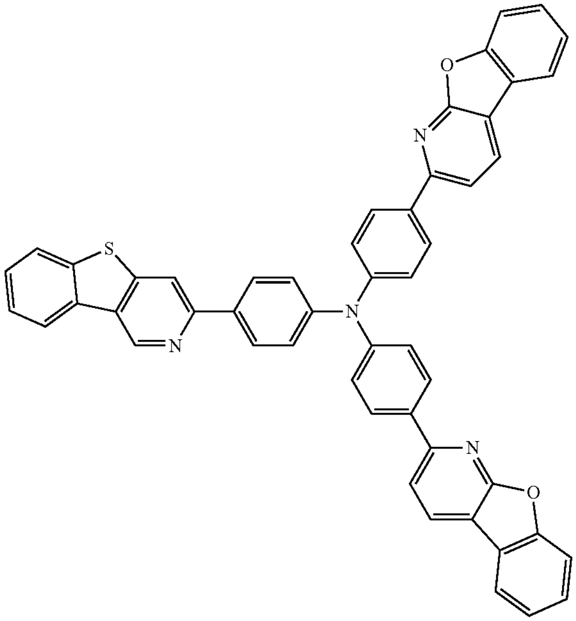
-continued
M376
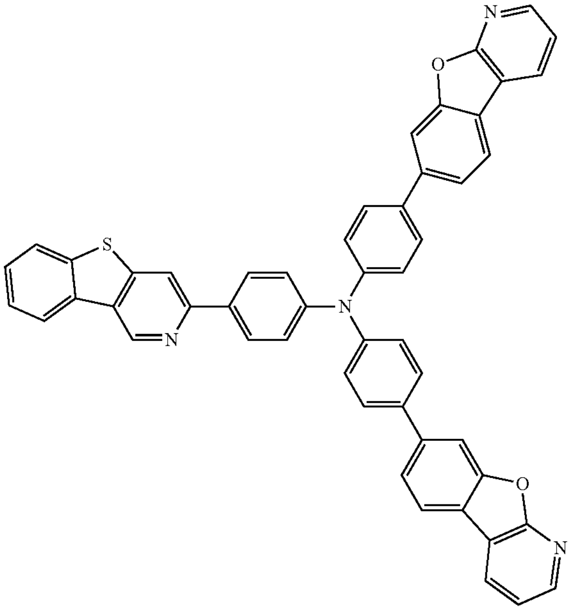
M377
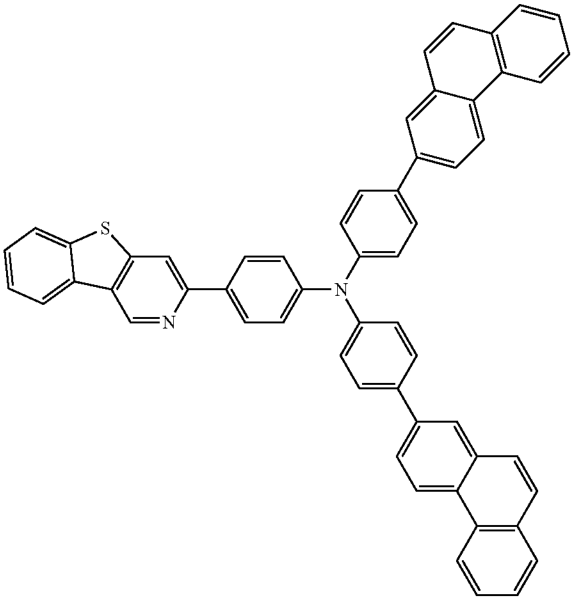

-continued
M378
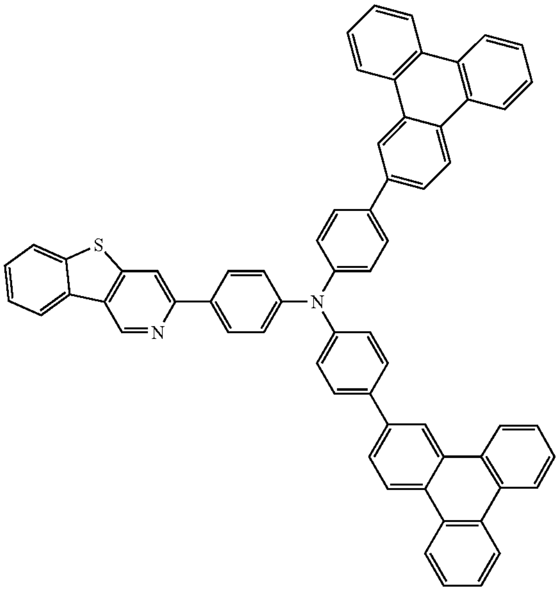
M379
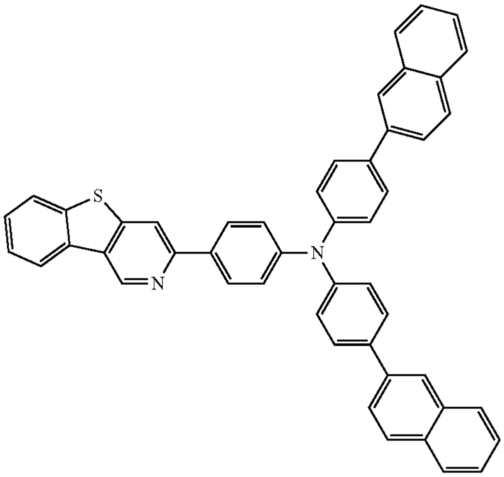
-continued
M380
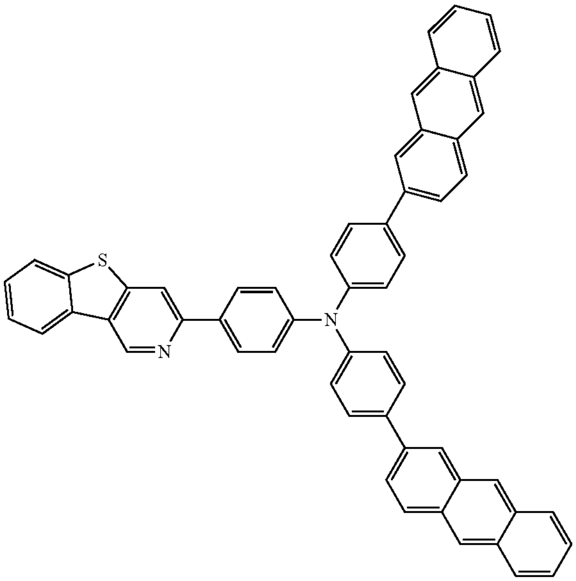
M381
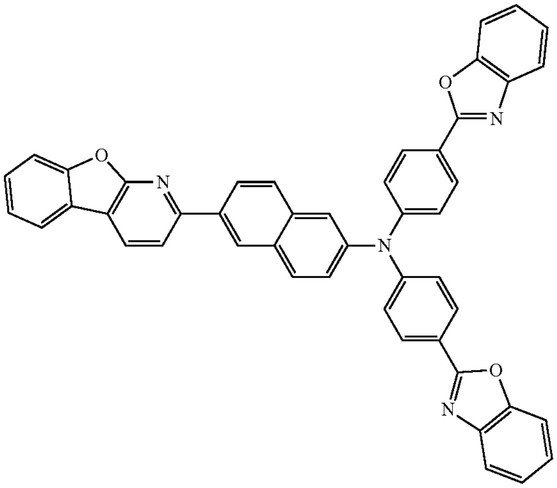
M382
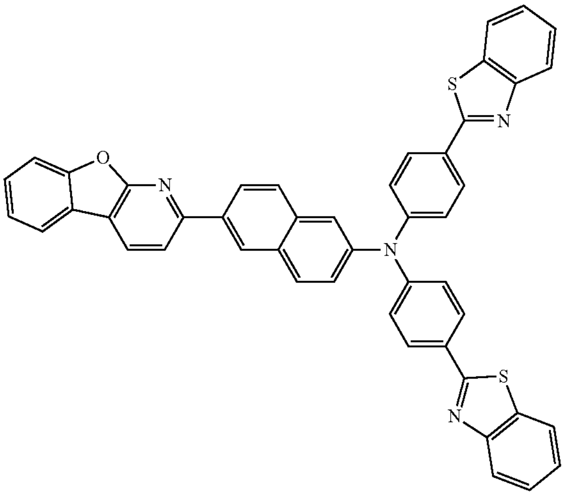

-continued
M383
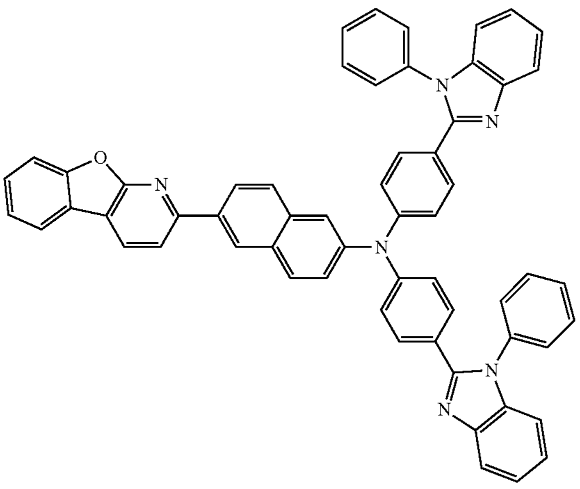
M384
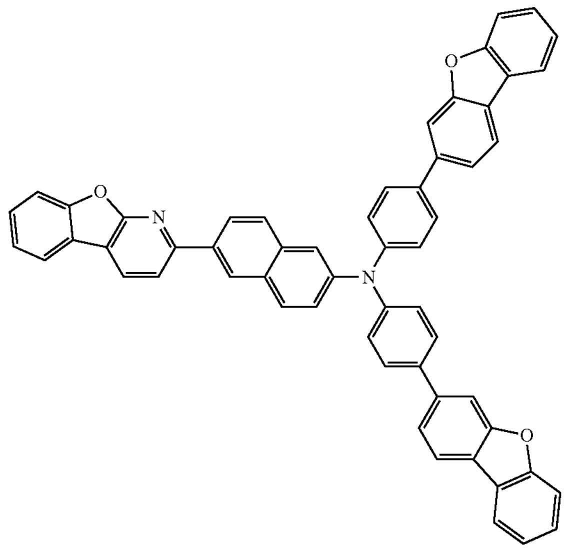
M385
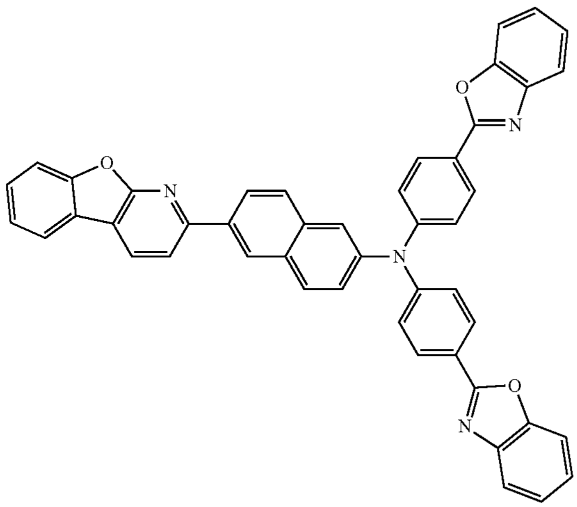
-continued
M386
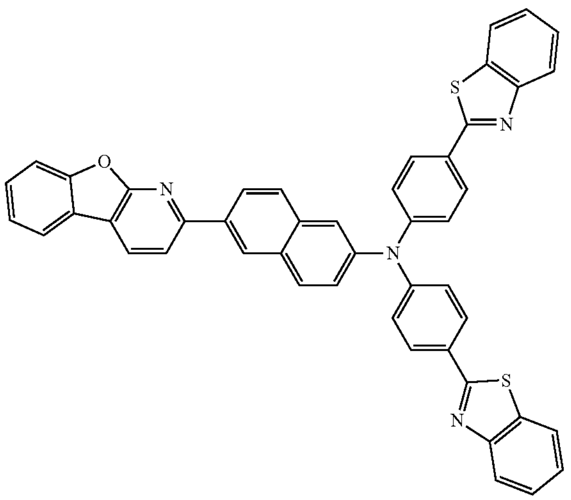
M387
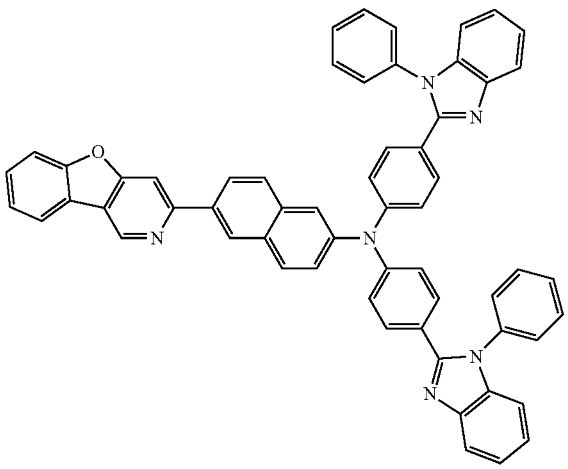
M388
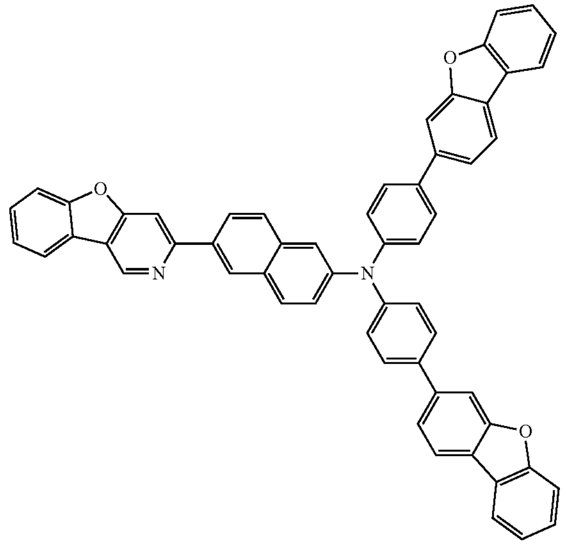

-continued
M389
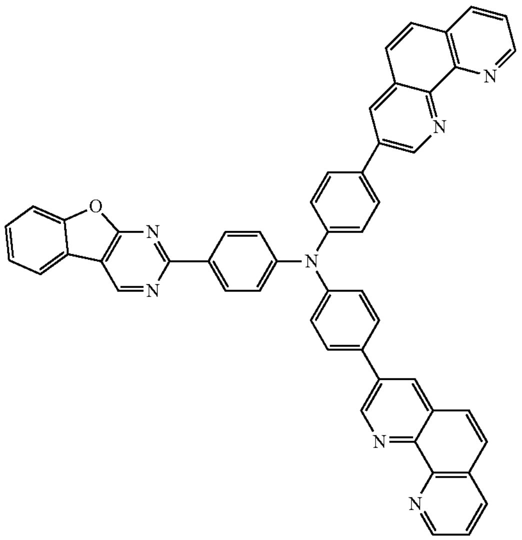
M390
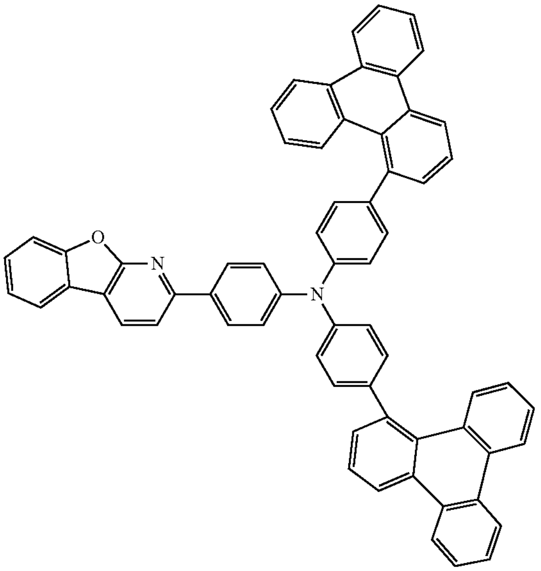
M391
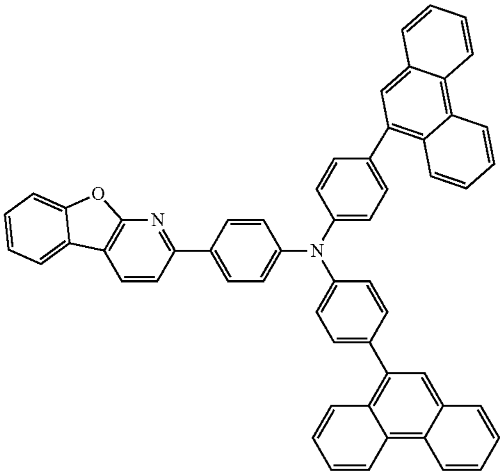
-continued
M392
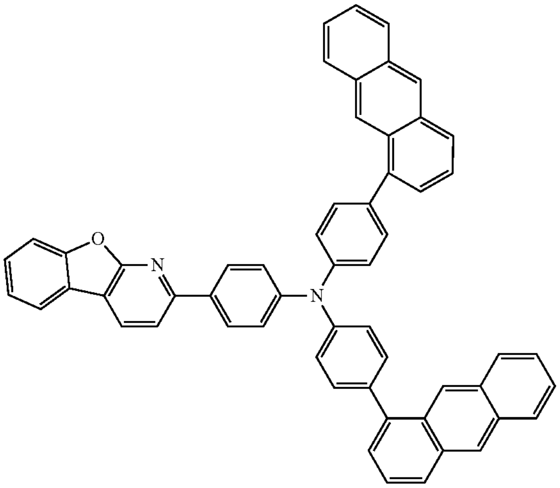
M393
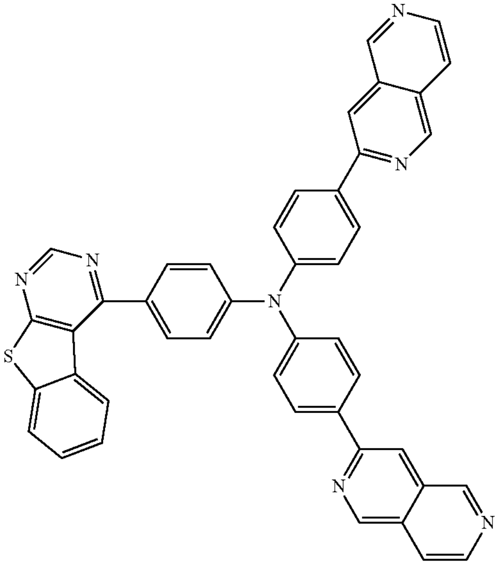
M394
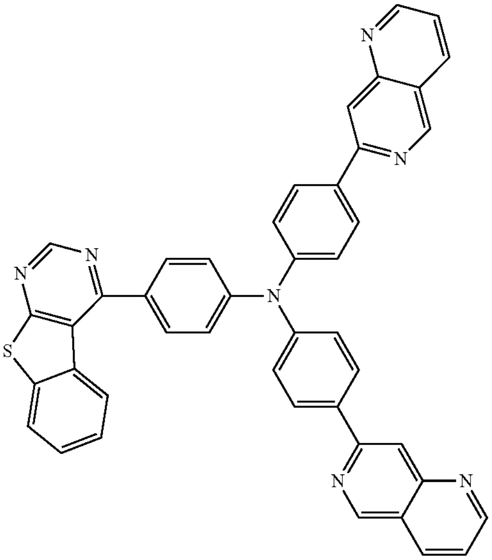

-continued
M395
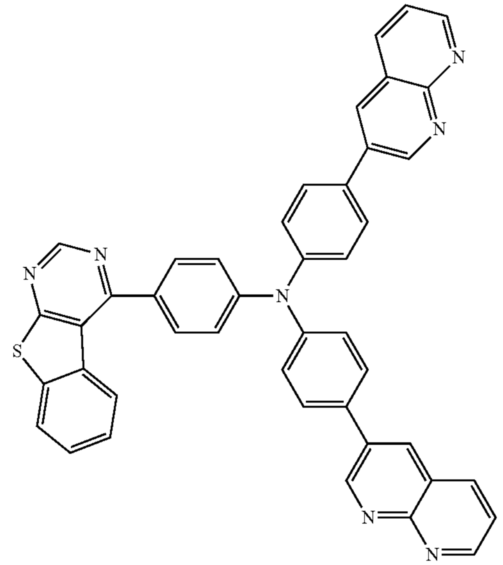
M396
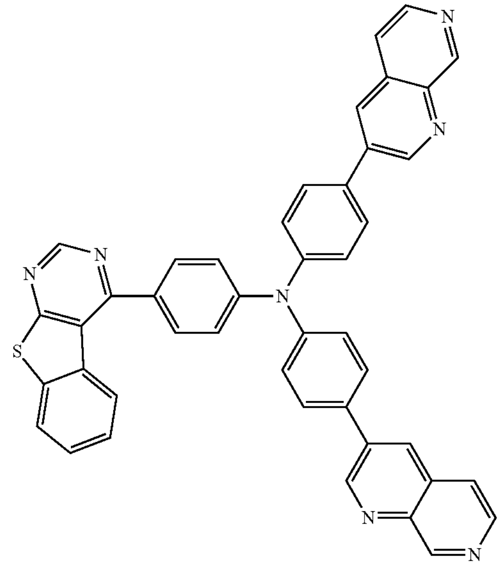
-continued
M397
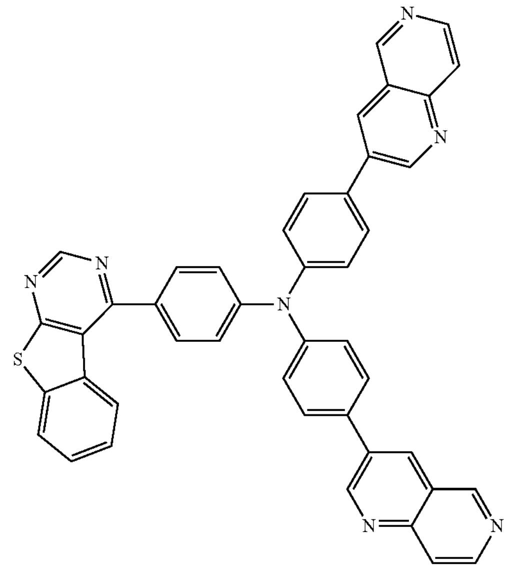
M398
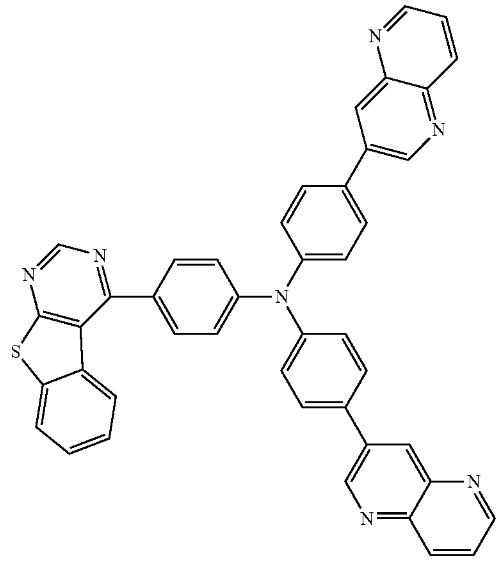

-continued
M399
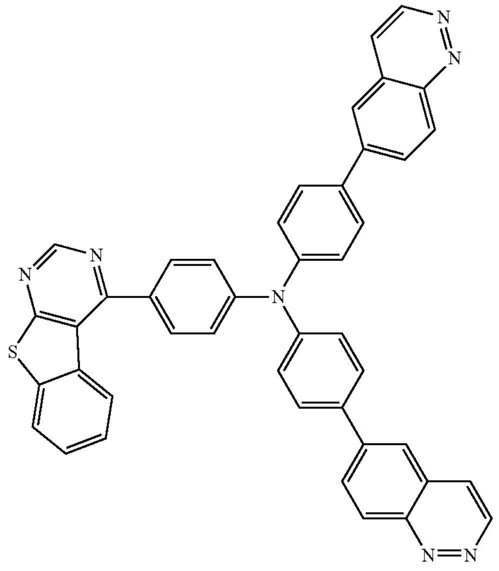
M400
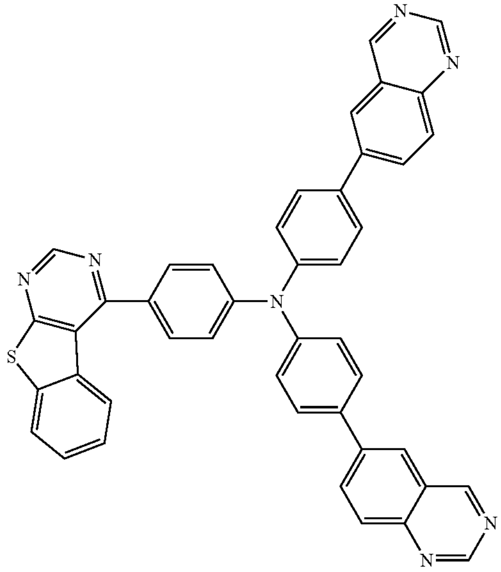
-continued
M401
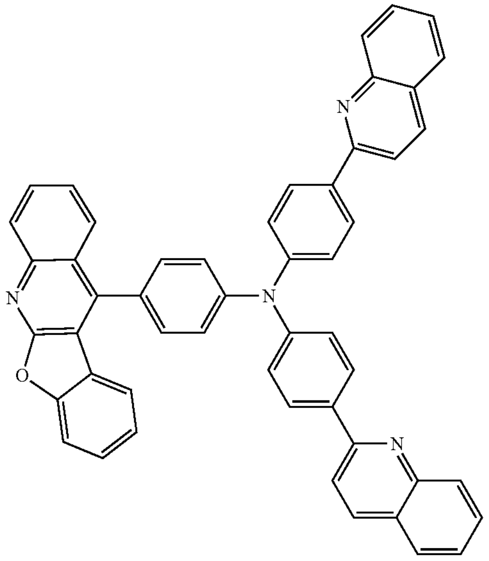
M402
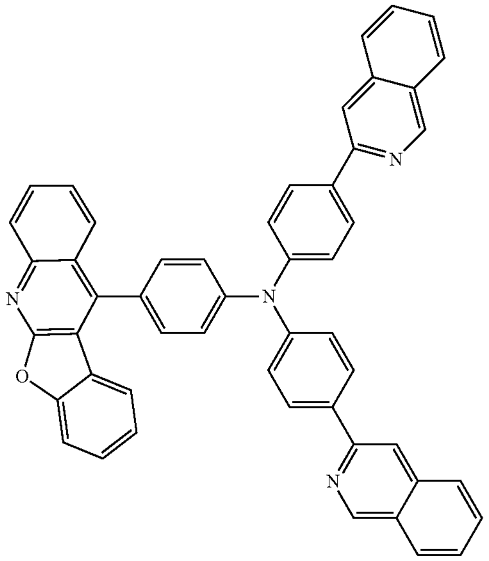

-continued
M403
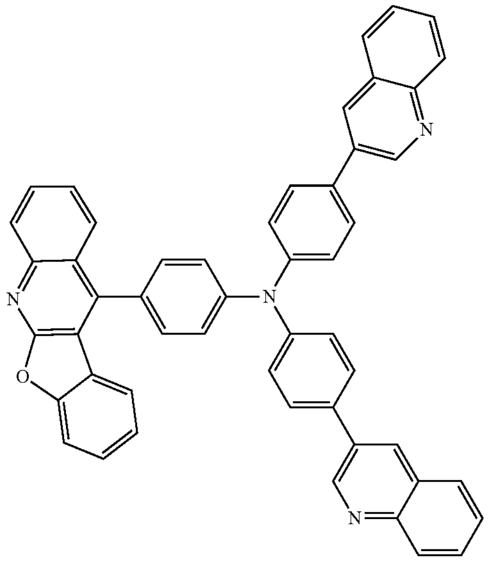
M404
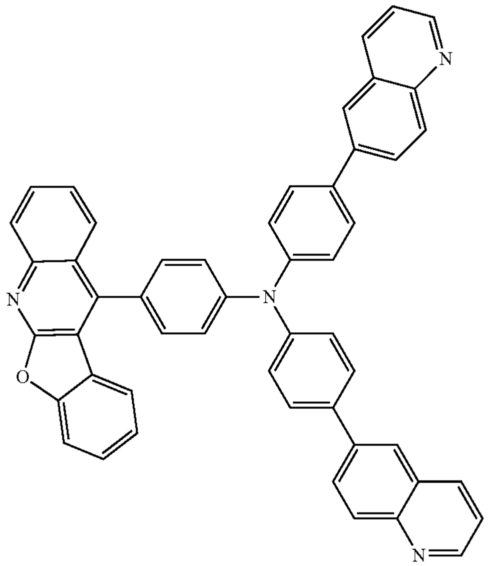
-continued
M405
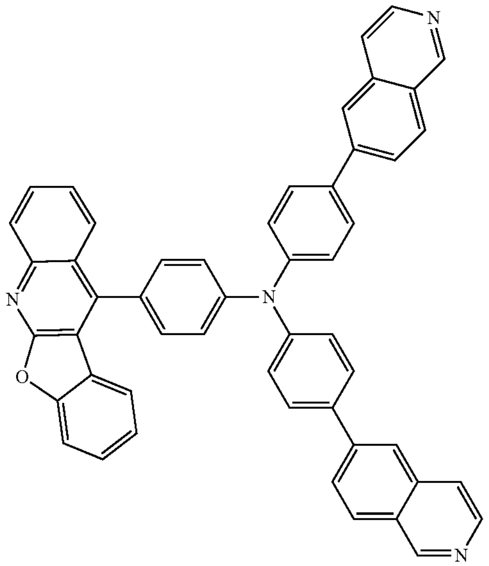
M406
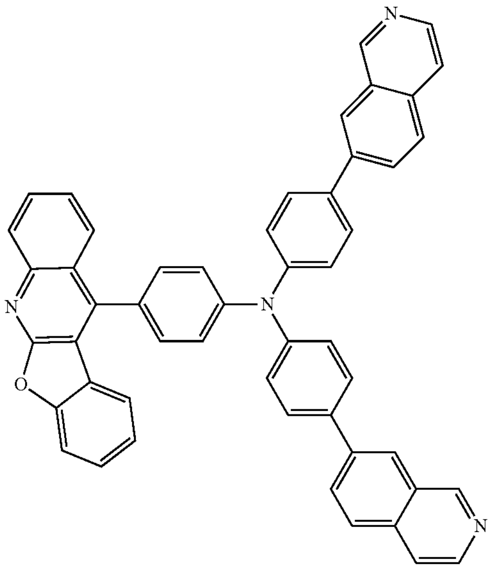

-continued
M407
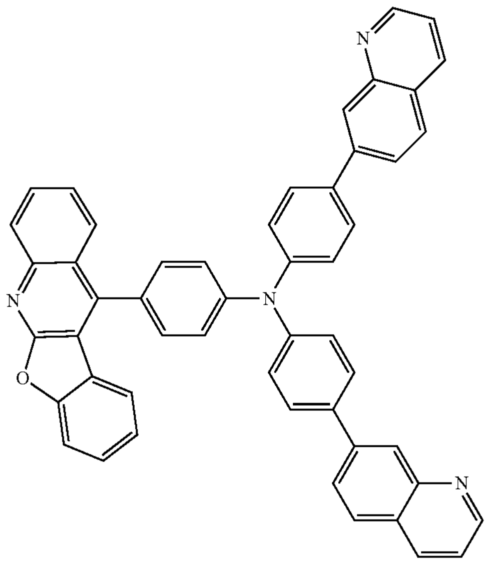
M408
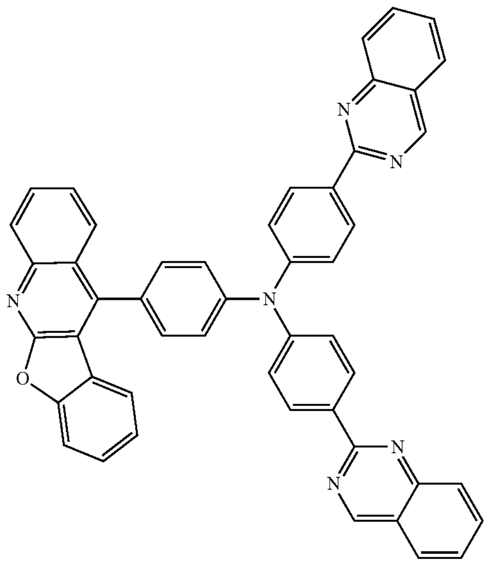
-continued
M409
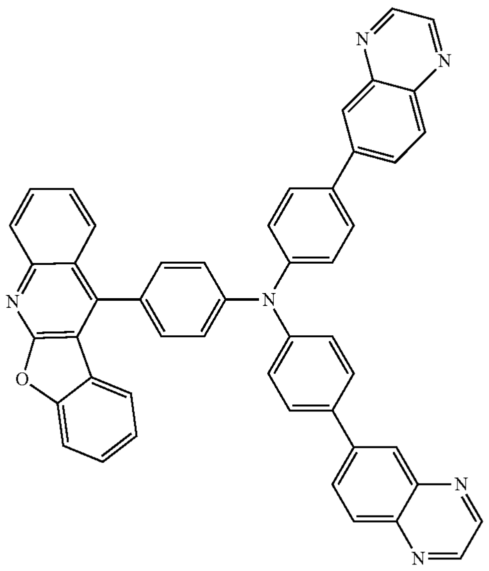
M410
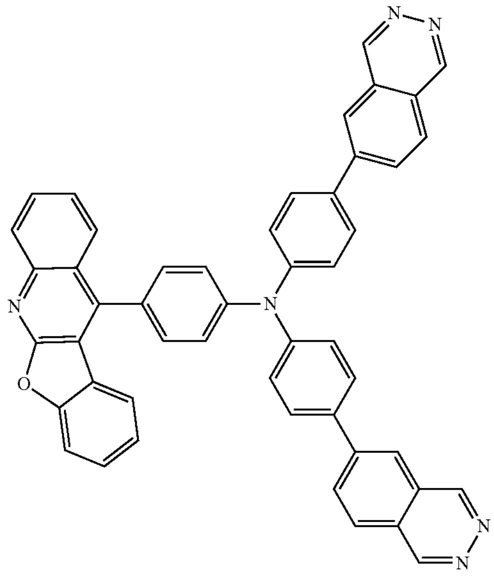

-continued
M411
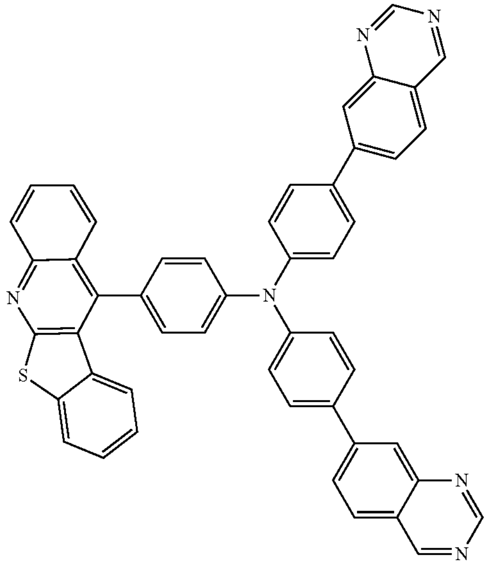
M412
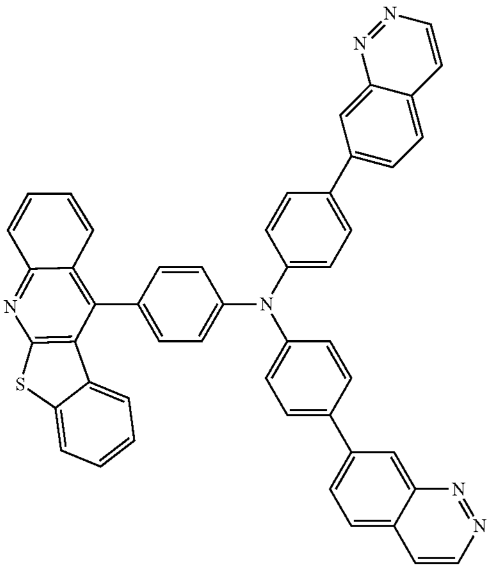
-continued
M413
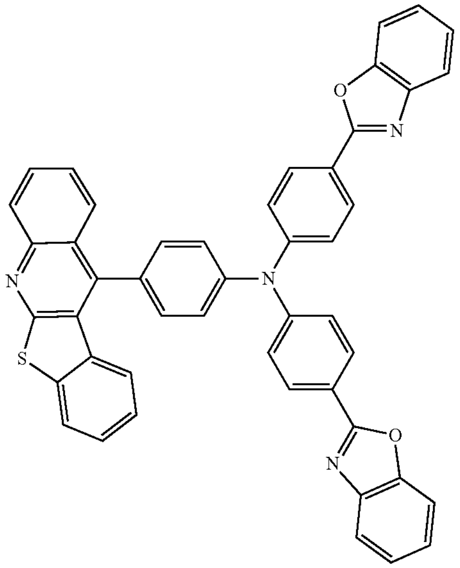
M414
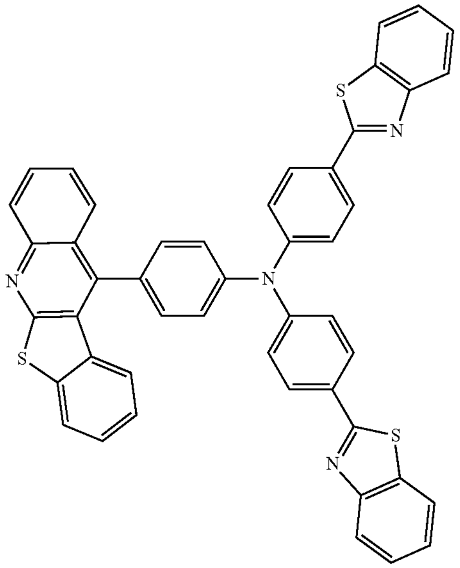

-continued
M415
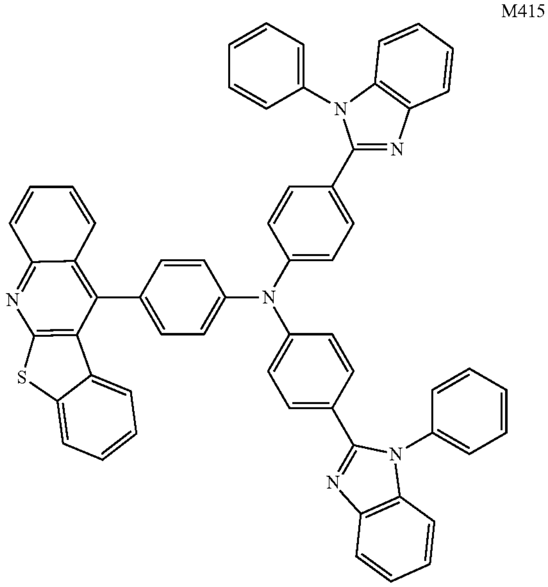
M416
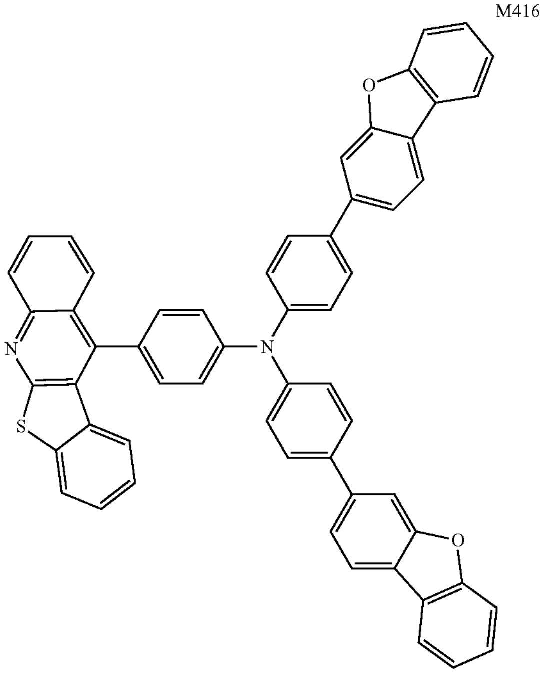
-continued
M417
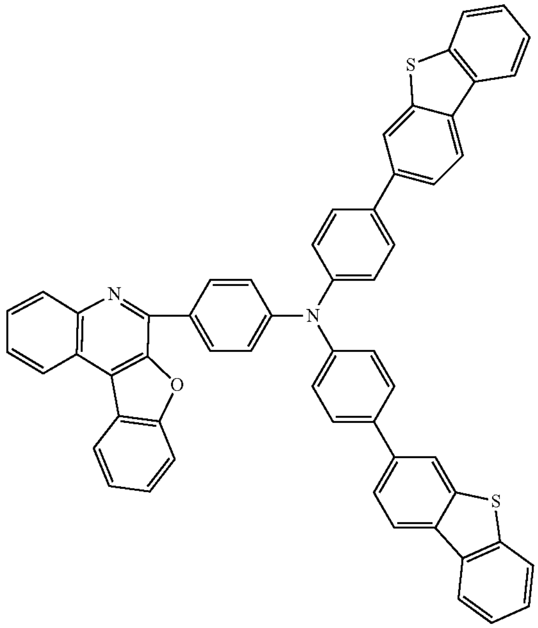
M418
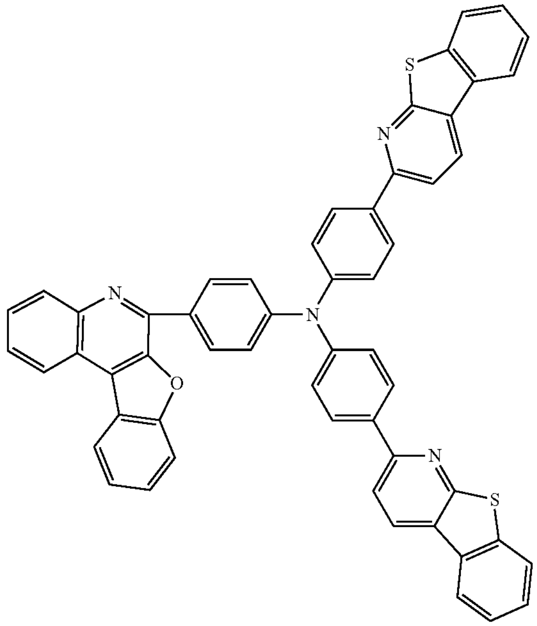

-continued
M419
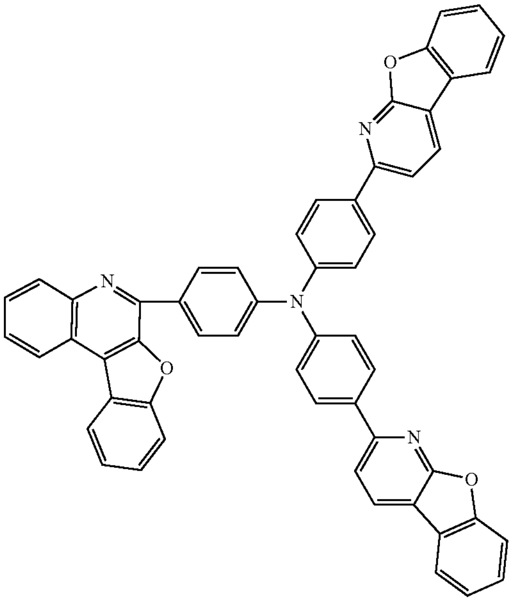
M420
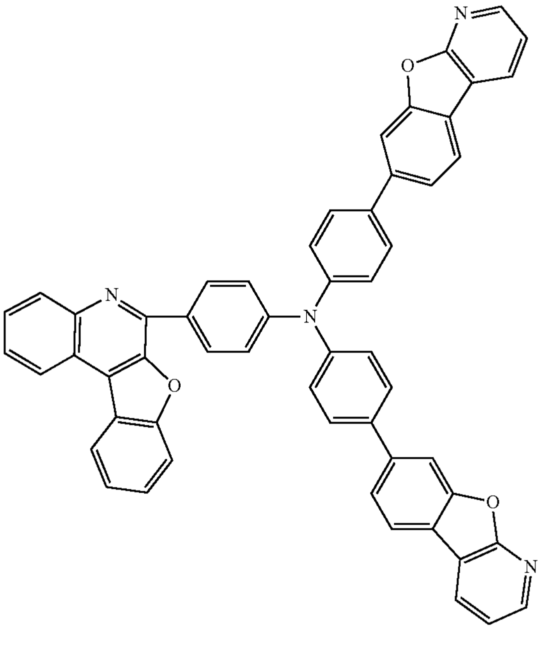
-continued
M421
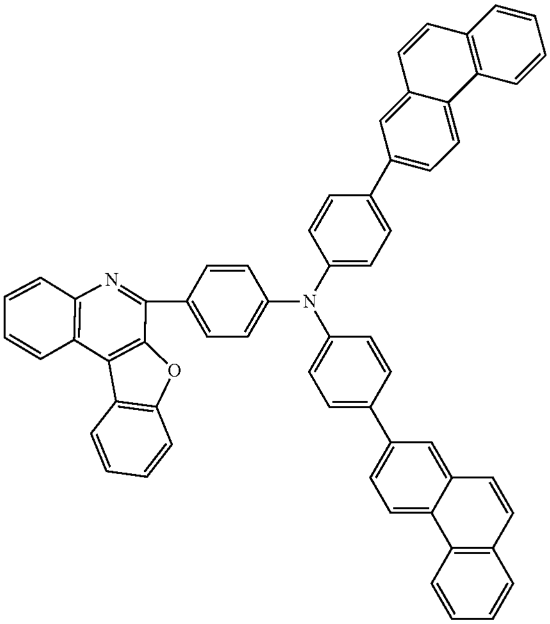
M422
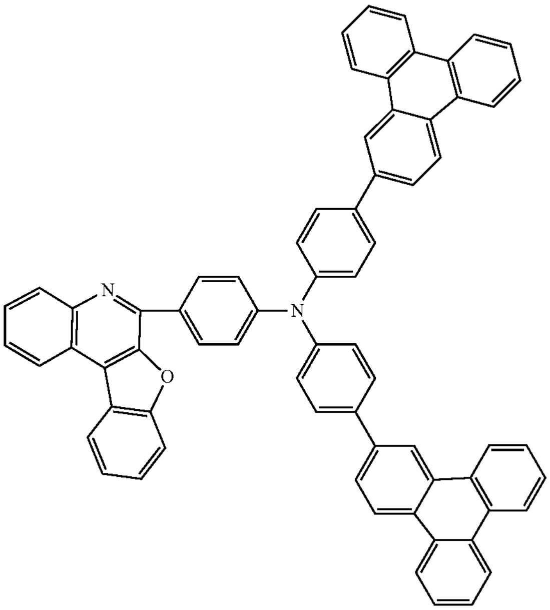

-continued
M423
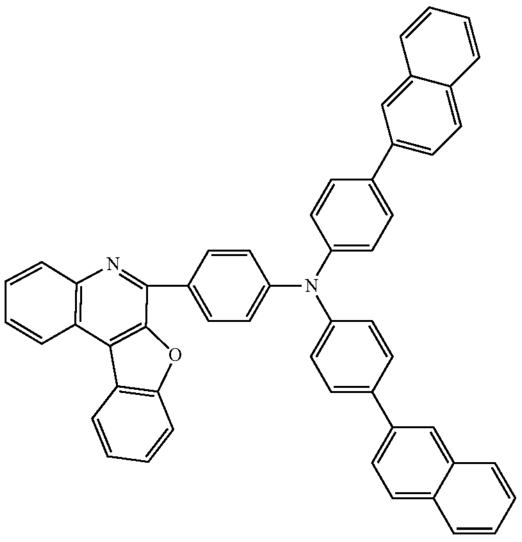
M424
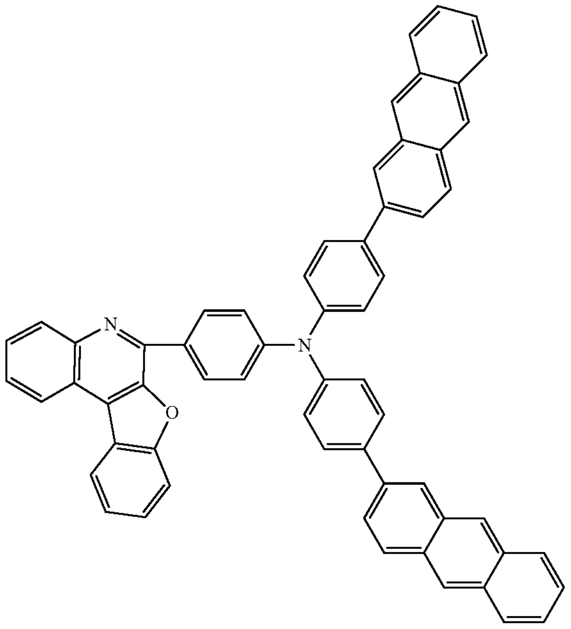
-continued
M425
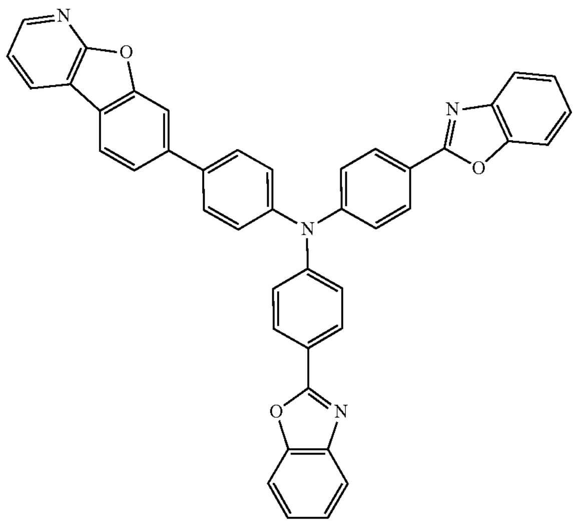
M426
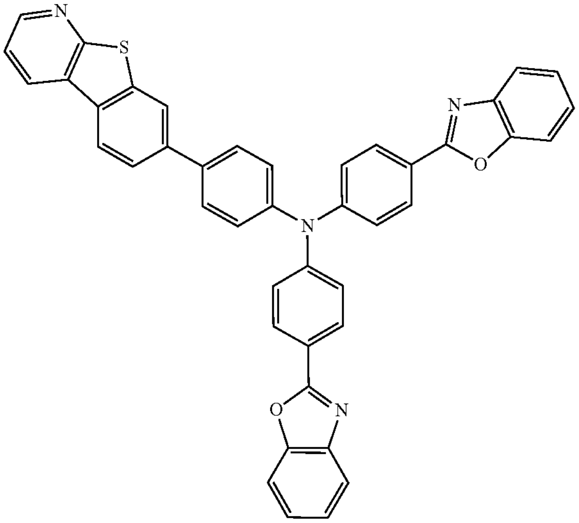
M427
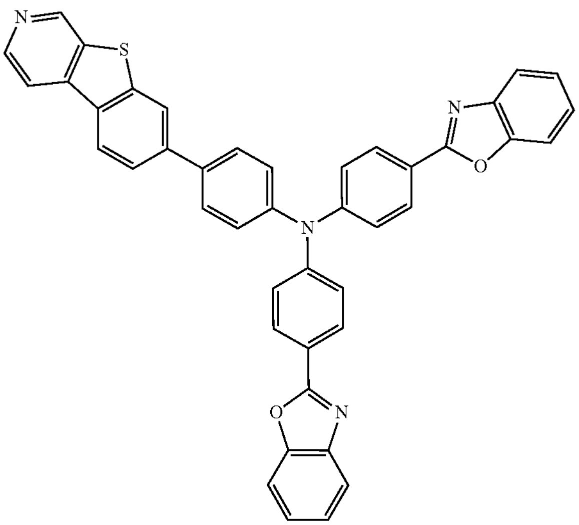

-continued
M428
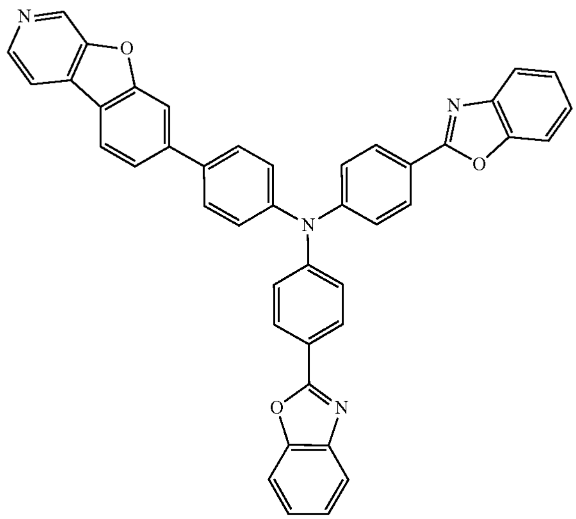
M429
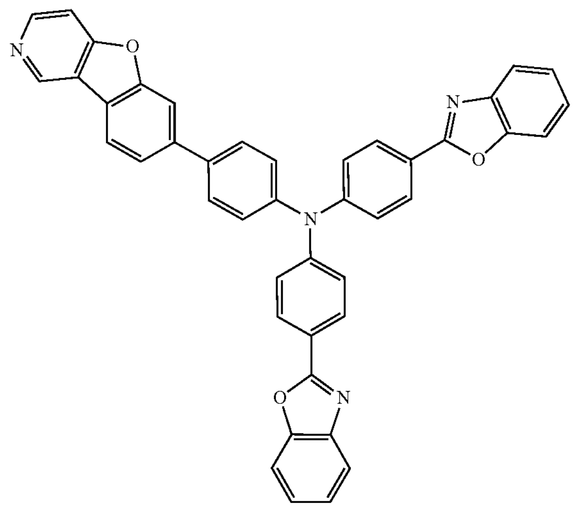
M430
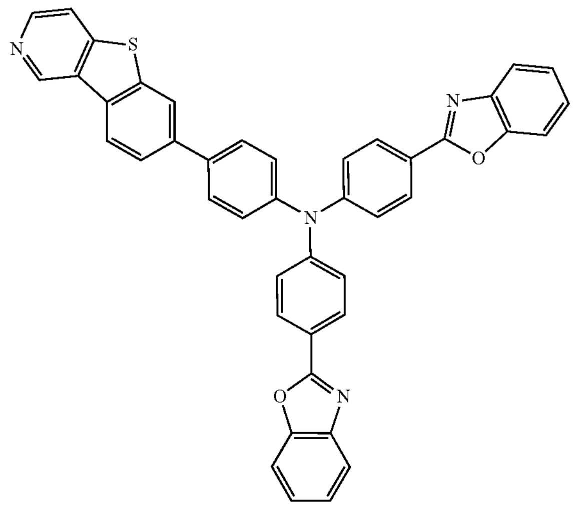
-continued
M431
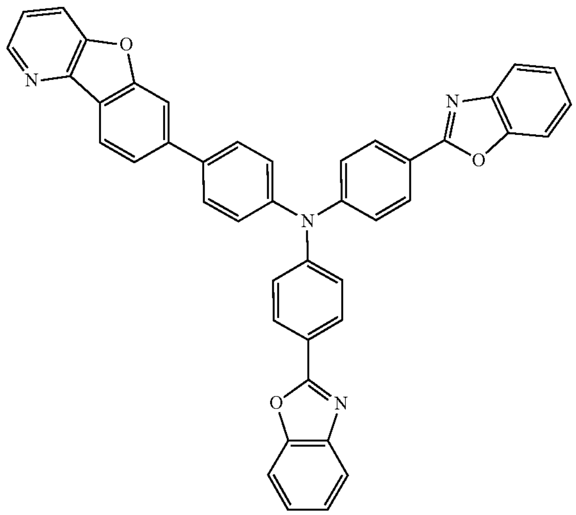
M432
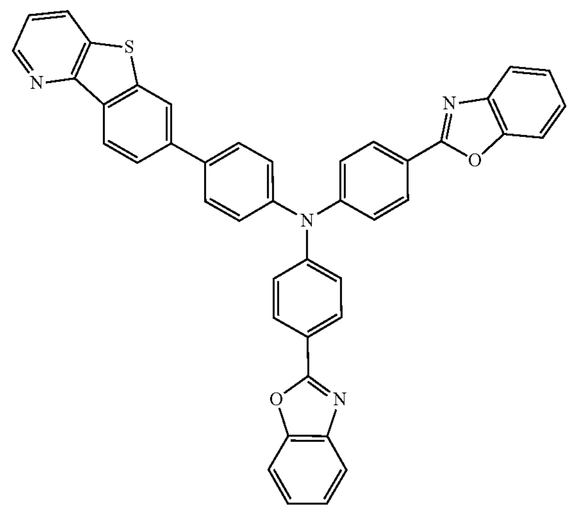
M433
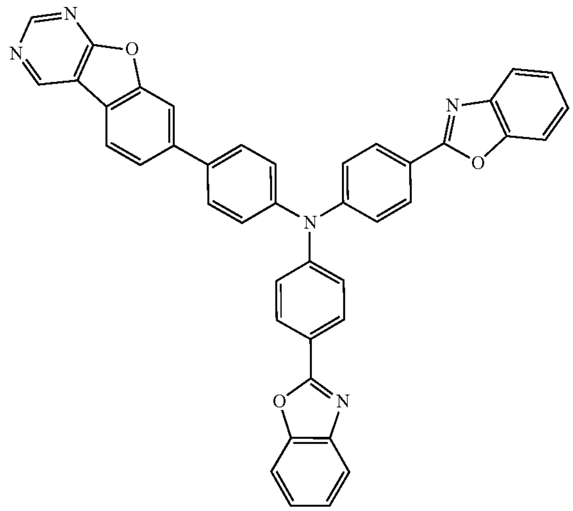

-continued
M434
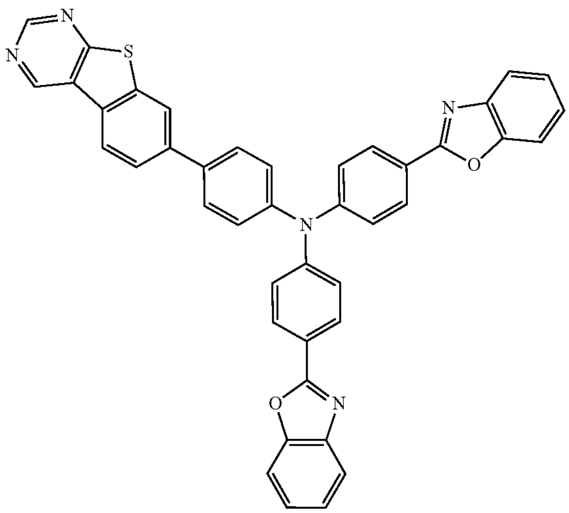
M435
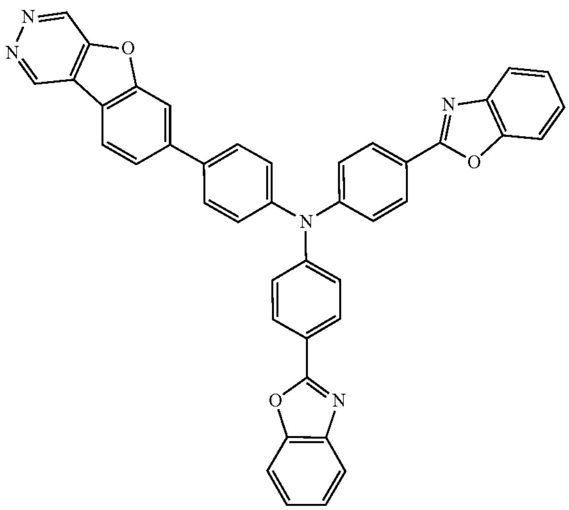
M436
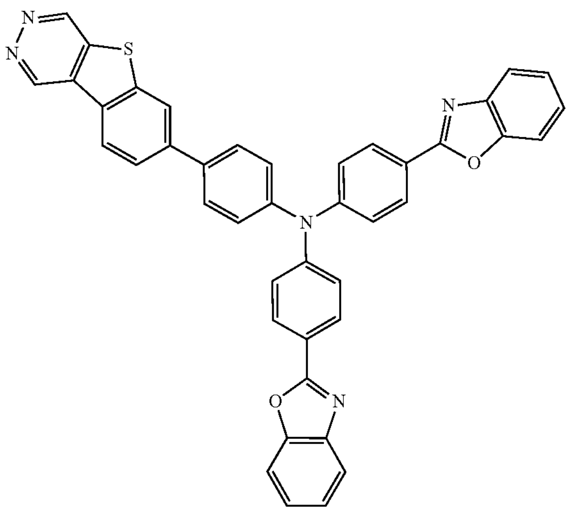
-continued
M437
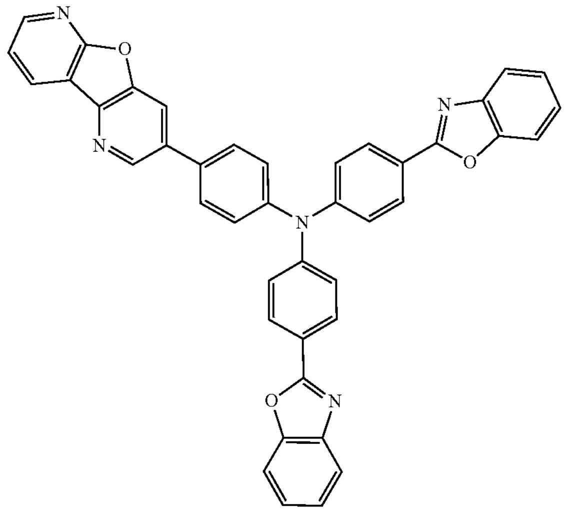
M438
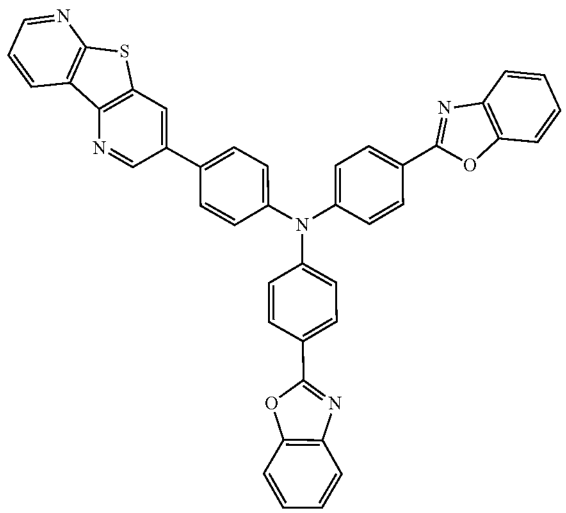
M439
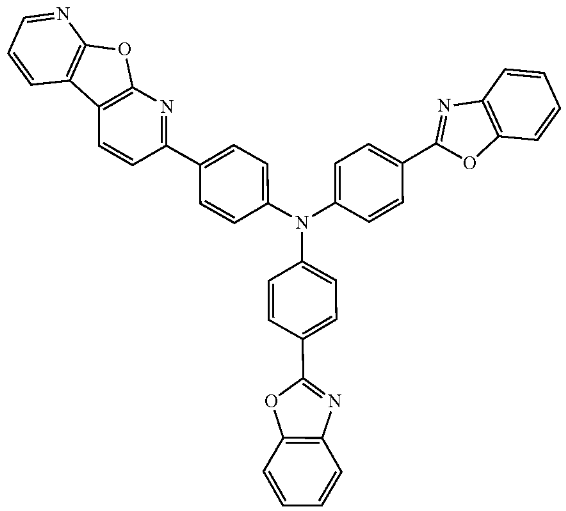

-continued
M440
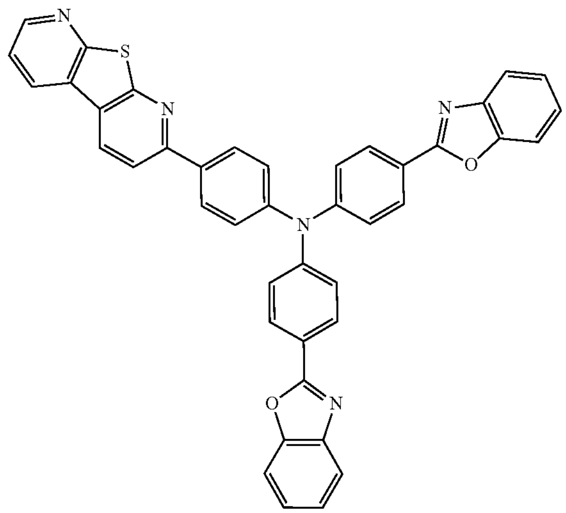
M441
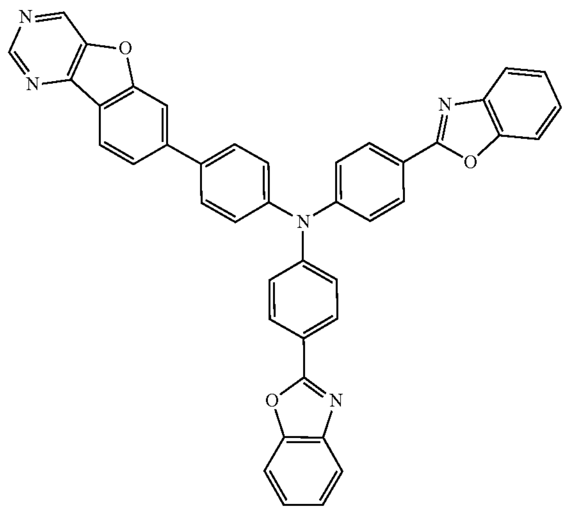
M442
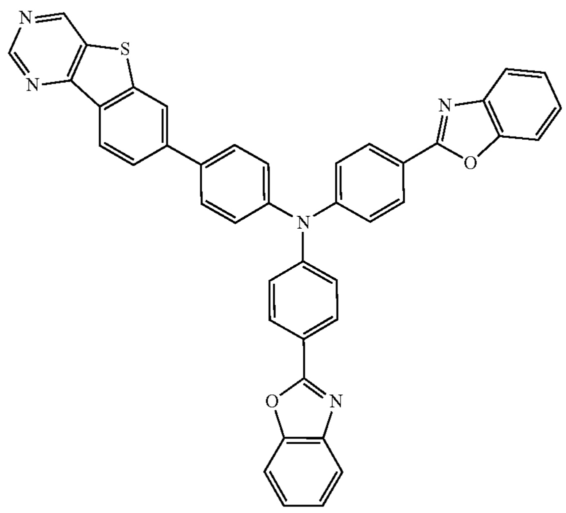
-continued
M443
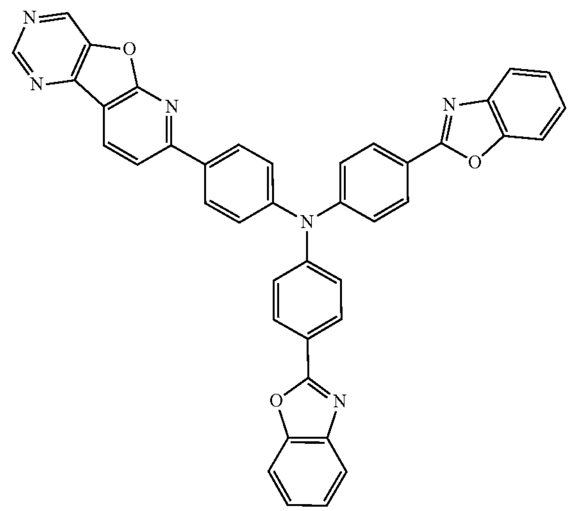
M444
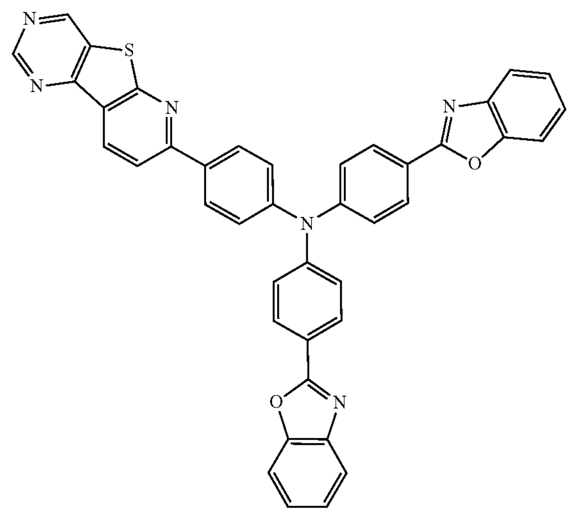
M445
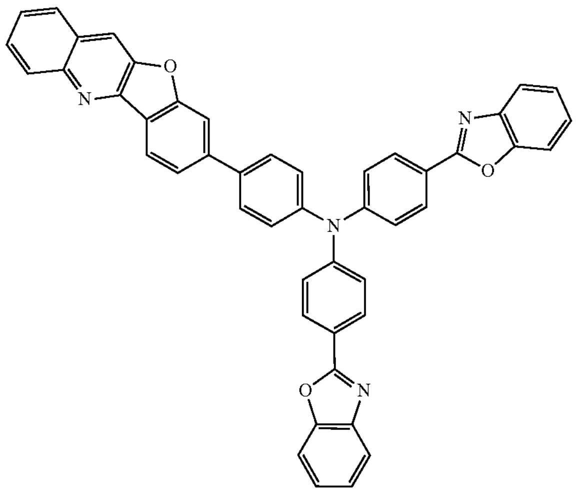

-continued
M446
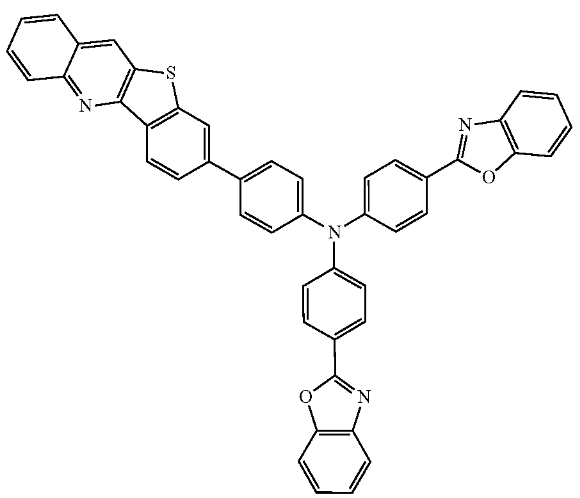
M447
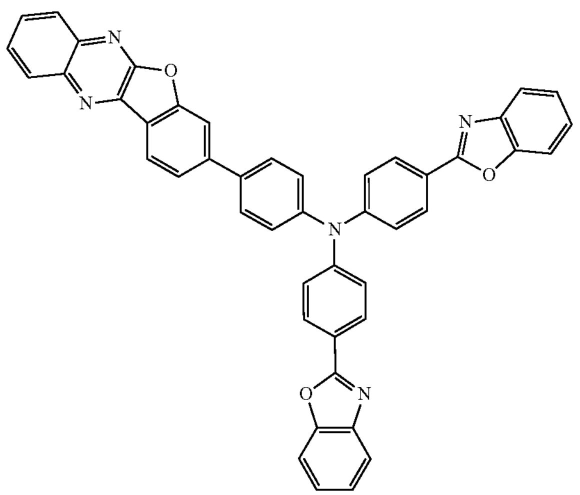
M448
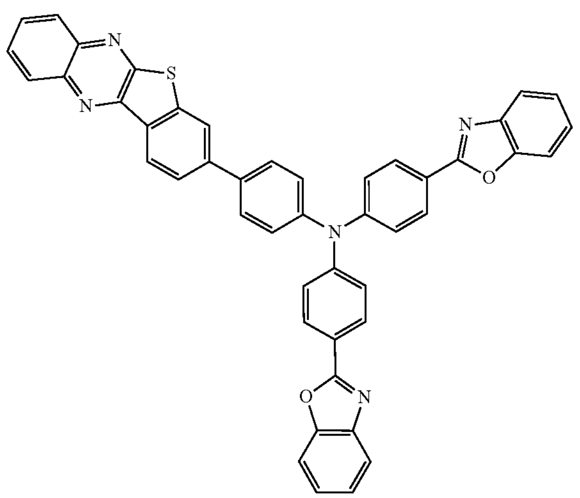
-continued
M449
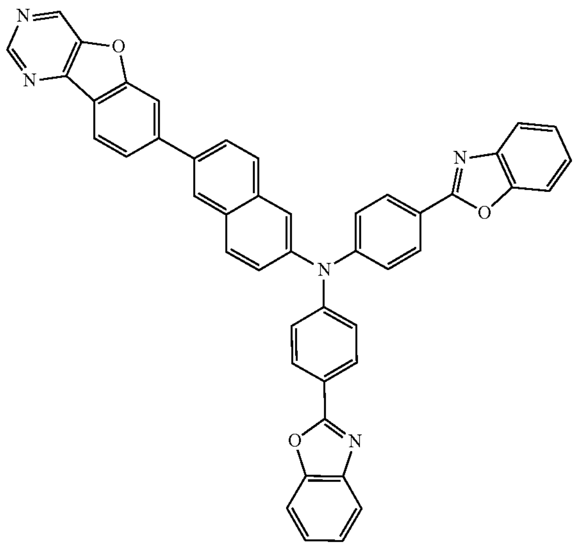
M450
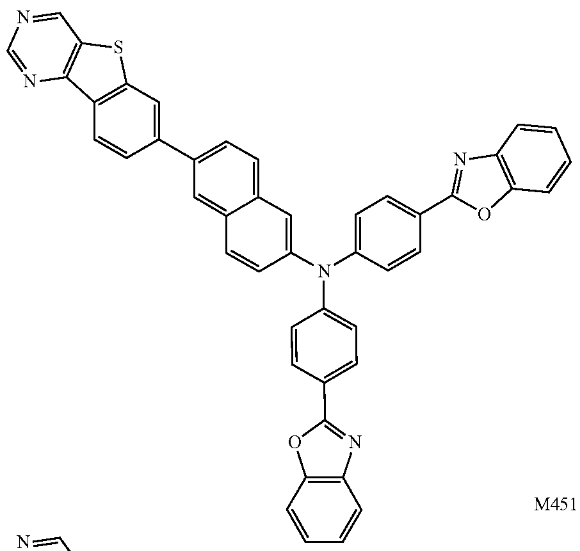
M451
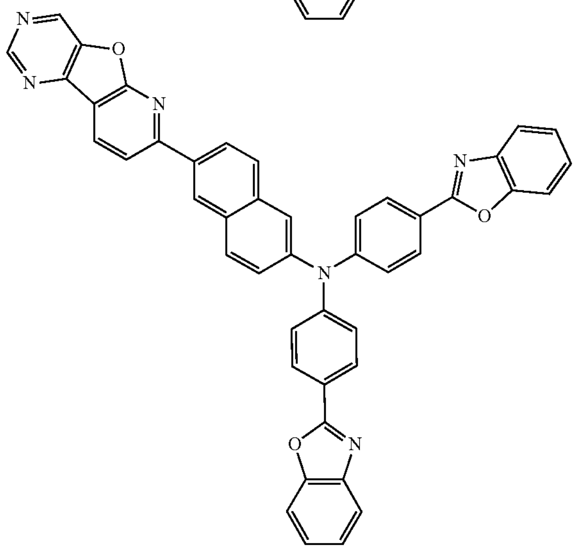

-continued
M452
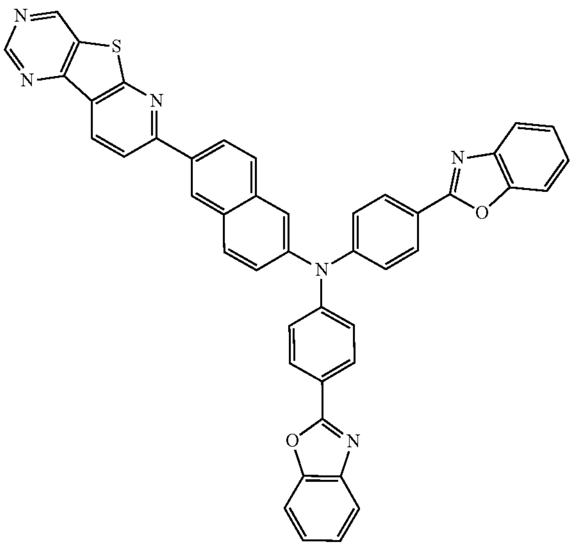
M453
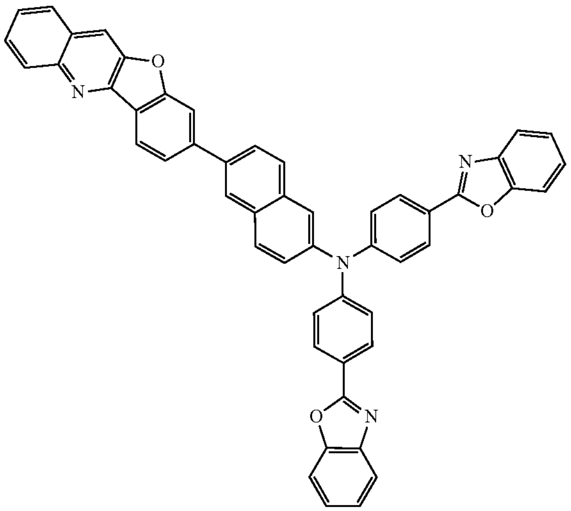
M454
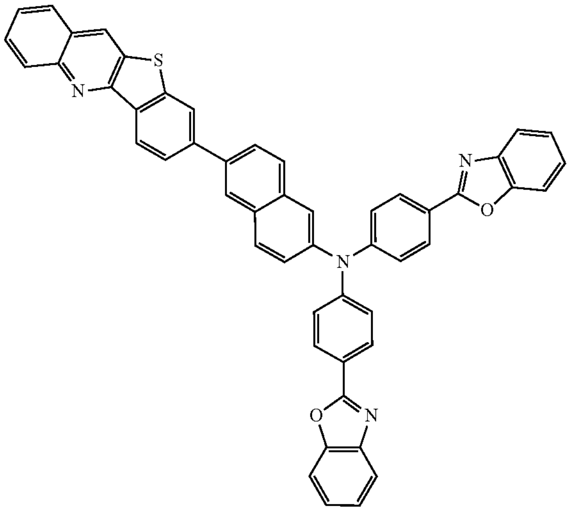
-continued
M455
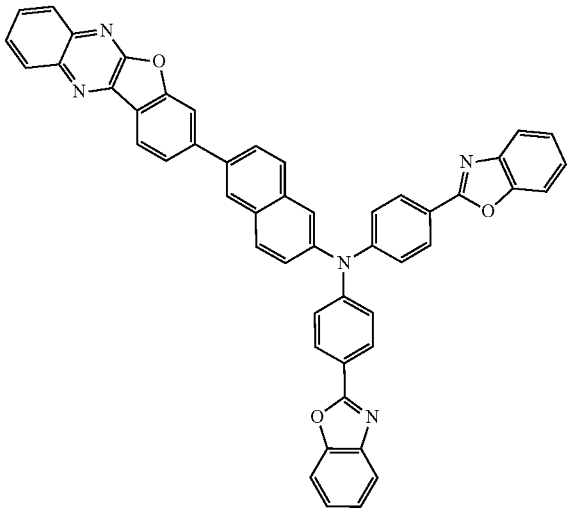
M456
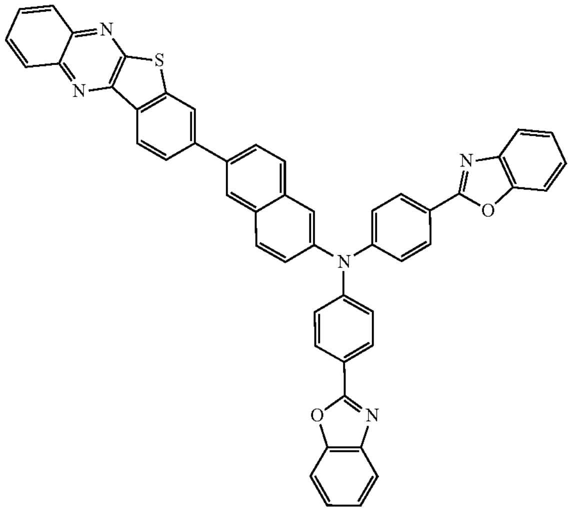
M457
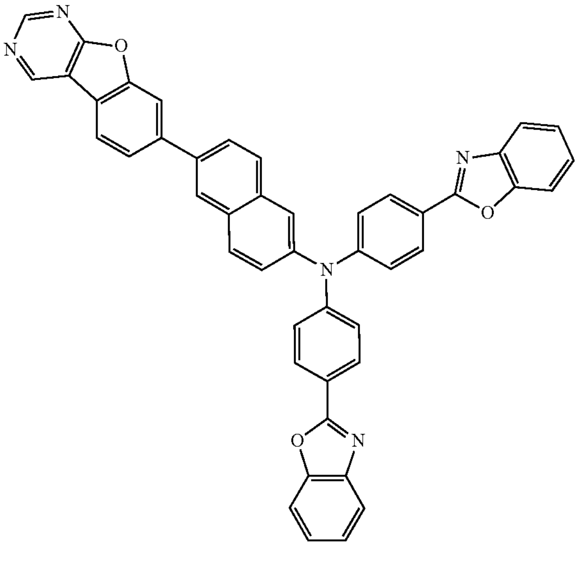

-continued
M458
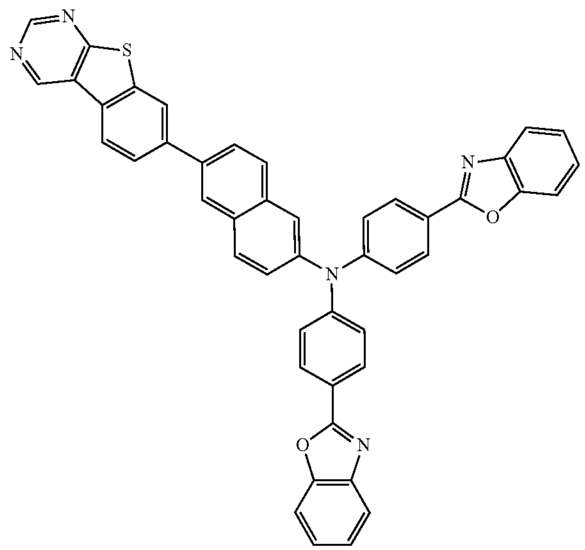
M459
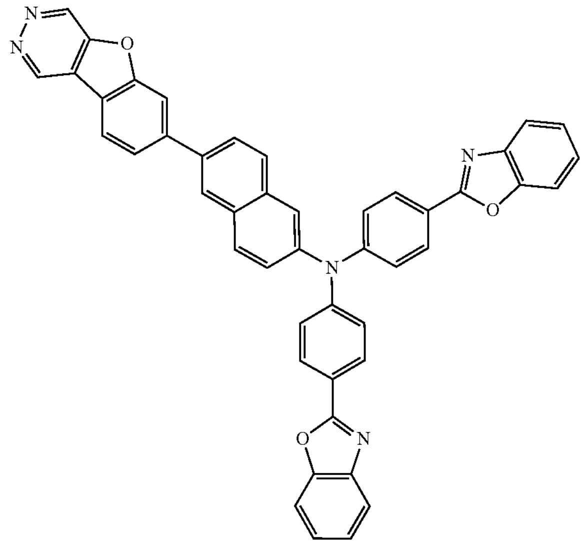
-continued
M460
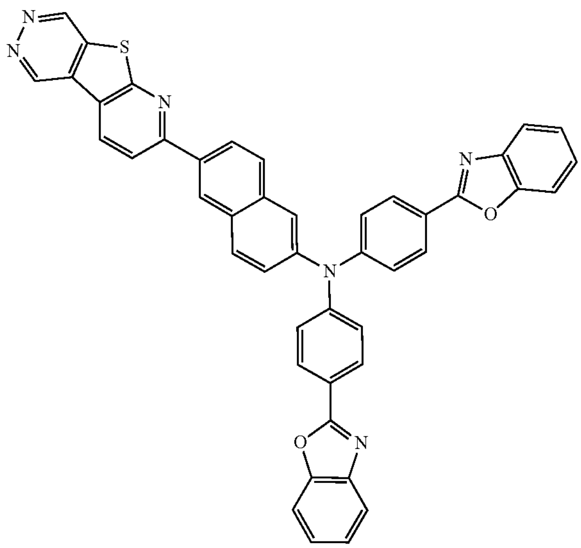
M461
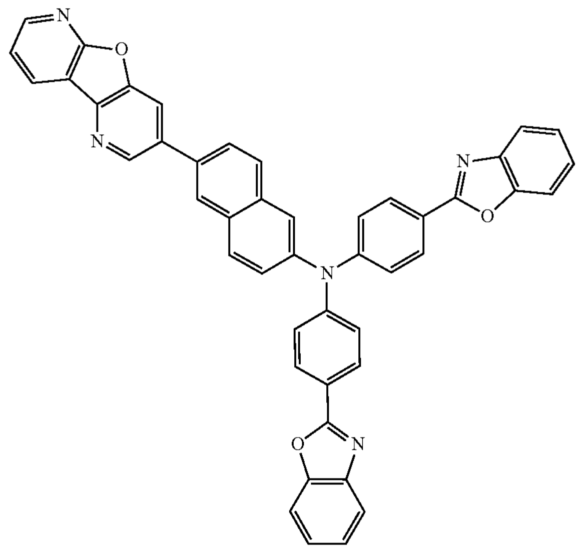

-continued
M462
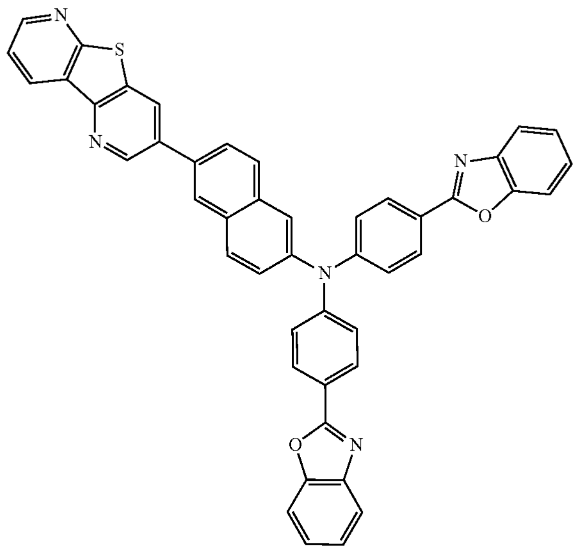
M463
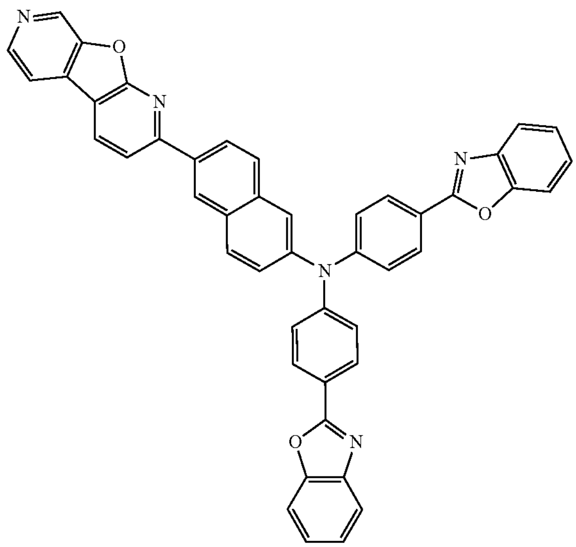
-continued
M464
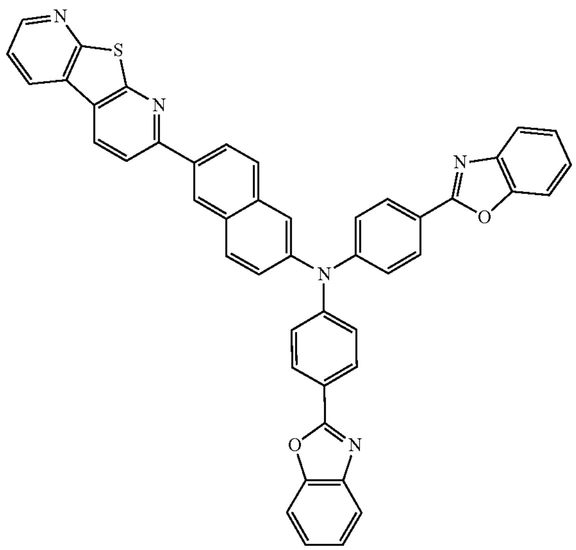
M465
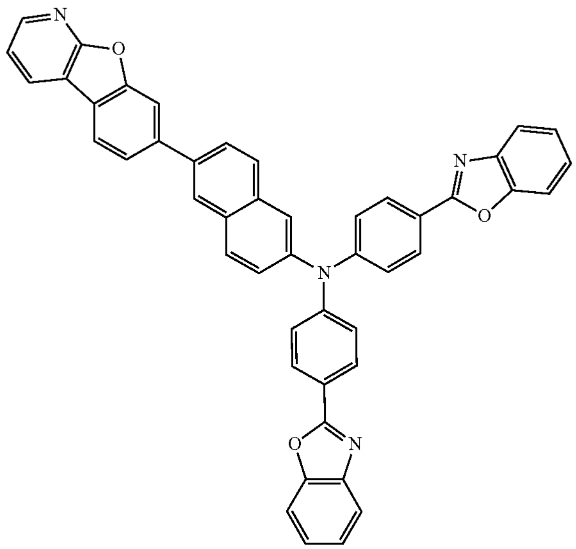

-continued
M466
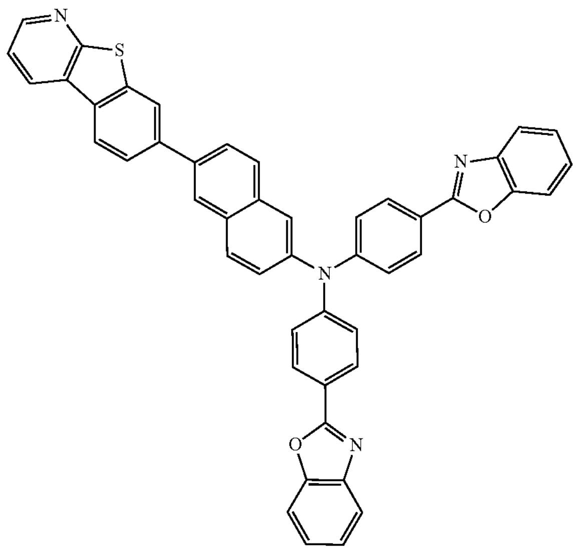
M467
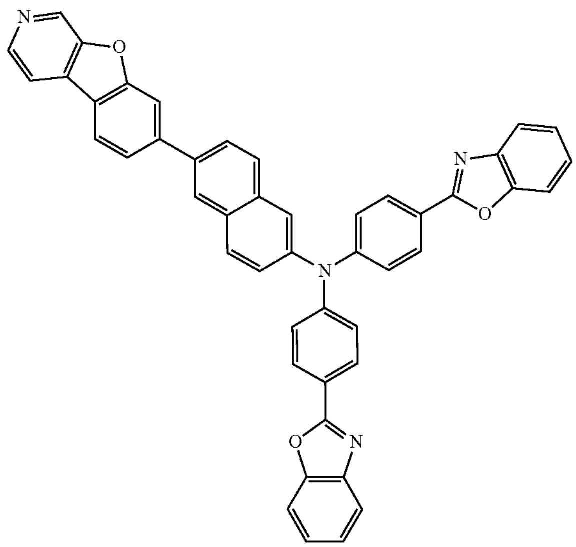
-continued
M468
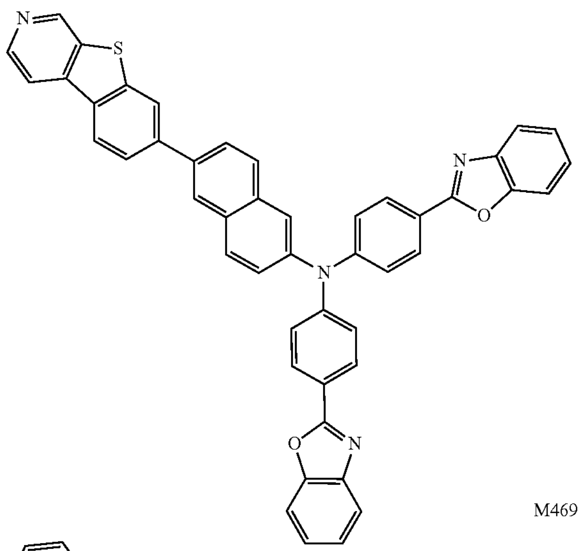
M469
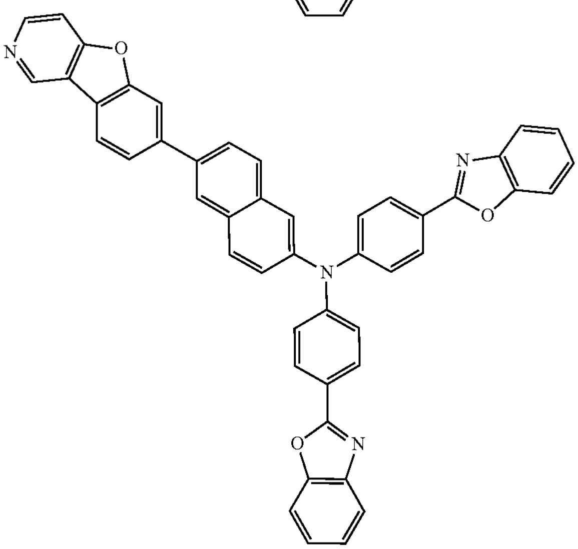
M470
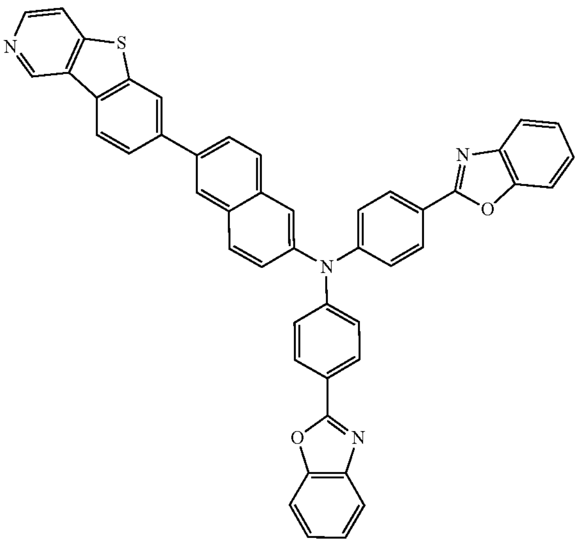

-continued

M471

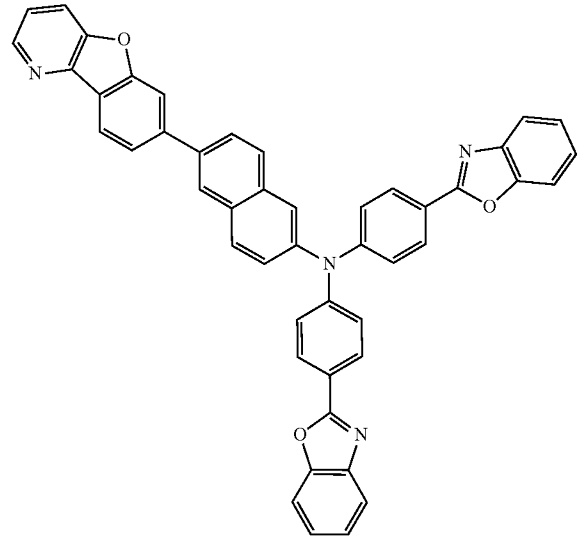

-continued

M472

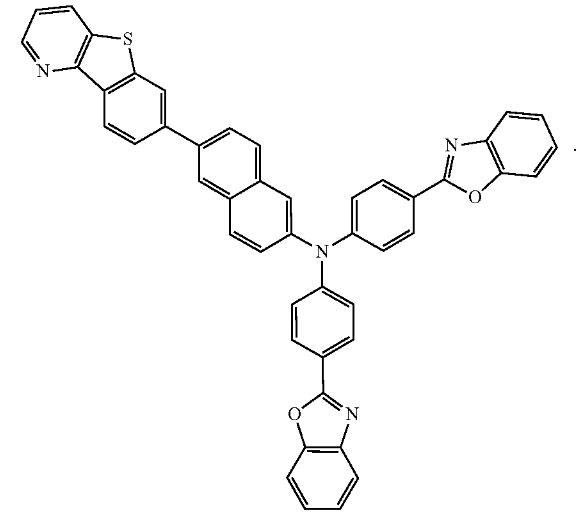

The above disclosed heterocyclic compound in the present disclosure may be prepared by the existing method, and those skilled in the art may select a specific synthesis method according to conventional technical knowledge. The present disclosure may merely provide an exemplary synthesis route, which may not be limited by the present disclosure.

A representative synthetic route of the compound shown in Formula I in the present disclosure may include following:

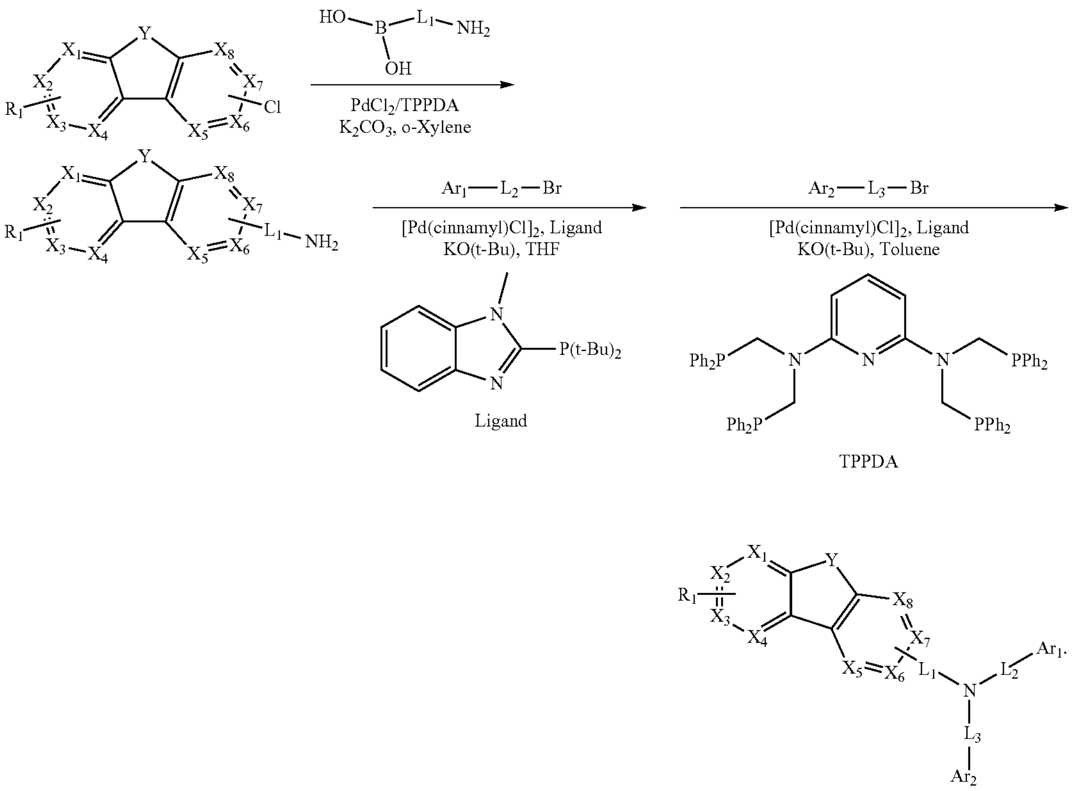

式I

In one embodiment, the above-disclosed compound in the present disclosure may be applied to the CPL layer of a top-emitting OLED device. In another embodiment, the above-disclosed compound may be used as an optical auxiliary layer such as a hole transport layer, an electron blocking layer, etc.

The present disclosure also provides a display panel including an organic light-emitting device. The organic light-emitting device may include an anode, a cathode, and an organic thin layer disposed between the anode and the cathode. The cathode may be covered with a capping layer, and the capping layer may include any one or a combination of at least two of the above-disclosed heterocyclic compounds.

The present disclosure also provides a display panel including an organic light-emitting device. The organic light-emitting device may include an anode, a cathode, and an organic thin layer disposed between the anode and the cathode. The organic thin layer may include a hole transport layer, and the hole transport layer may include any one or a combination of at least two of the above-disclosed heterocyclic compounds.

The present disclosure also provides a display panel including an organic light-emitting device. The organic light-emitting device may include an anode, a cathode, and an organic thin layer disposed between the anode and the cathode. The organic thin layer may include an electron blocking layer, and the electron blocking layer may include any one or a combination of at least two of the above-disclosed heterocyclic compounds.

The organic light-emitting device in the present disclosure may include a substrate, an indium-tin oxide (ITO) anode, a first hole transport layer, a second hole transport layer, an electron blocking layer, a light-emitting layer, a first electron transport layer, a second electron transport layer, a cathode (Mg—Ag electrode, a mass ratio of Mg over Ag may be approximately 1:9), and a capping layer (CPL) that are stacked in sequence.

In one embodiment, the anode material of the organic light-emitting device may be selected from a metal, a metal oxide, and a conductive polymer. The metal may include copper, gold, silver, iron, chromium, nickel, manganese, palladium, and platinum, or an alloy thereof, etc. The metal oxide may include indium oxide, zinc oxide, indium-tin oxide (ITO), indium-zinc oxide (IZO), etc. The conductive polymer may include polyaniline, polypyrrole, poly(3-methylthiophene), etc. In addition to the above materials and combinations that facilitate the hole injection, the anode material may further include any other suitable material.

In one embodiment, the cathode material of the organic light-emitting device may be selected from a metal, and a multilayer metal material. The metal may include aluminum, magnesium, silver, indium, tin, titanium, or an alloy thereof, etc. The multilayer metal material may include LiF/Al, $LiO_2$/Al, $BaF_2$/Al, etc. In addition to the above materials and combinations that facilitate electron injection, the cathode material may further include any other suitable material.

In one embodiment, the organic thin layer of the organic light-emitting device may include at least one light-emitting layer (EML), and may further include other functional layers, including a hole injection layer (HIL), a hole transport layer (HTL), an electron blocking layer (EBL), a hole blocking layer (HBL), an electron transport layer (ETL), and an electron injection layer (EIL).

In one embodiment, the organic light-emitting device may be prepared according to the following method. An anode may be formed on a transparent or an opaque smooth substrate, an organic thin layer may be formed on the anode, and a cathode may be formed on the organic thin layer.

In one embodiment, forming the organic thin layer may include evaporation, sputtering, spin coating, dipping, ion plating, or any other known film formation method.

The present disclosure also provides a display device including the above-disclosed display panel.

In the present disclosure, an organic light-emitting device (OLED device) may be applied to the display device. The organic light-emitting display device may include a mobile phone display, a computer display, a TV display, a smart watch display, a smart car display panel, VR or AR helmet display, or display of various smart devices, etc.

Exemplary Embodiment 1

A synthetic route of compound M001 and detailed preparation method may include following:

M001

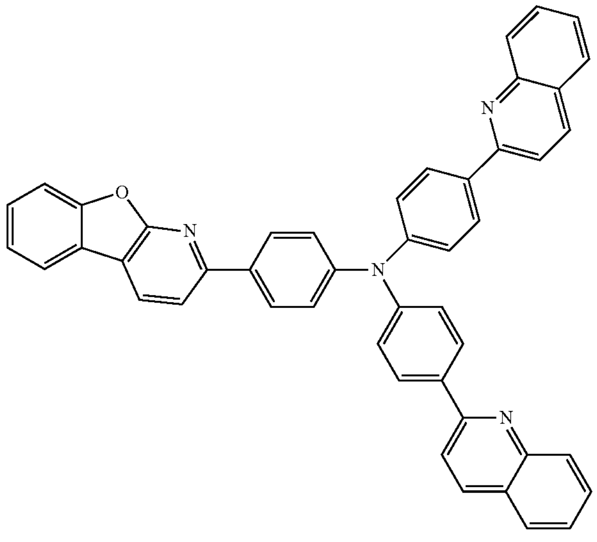

-continued

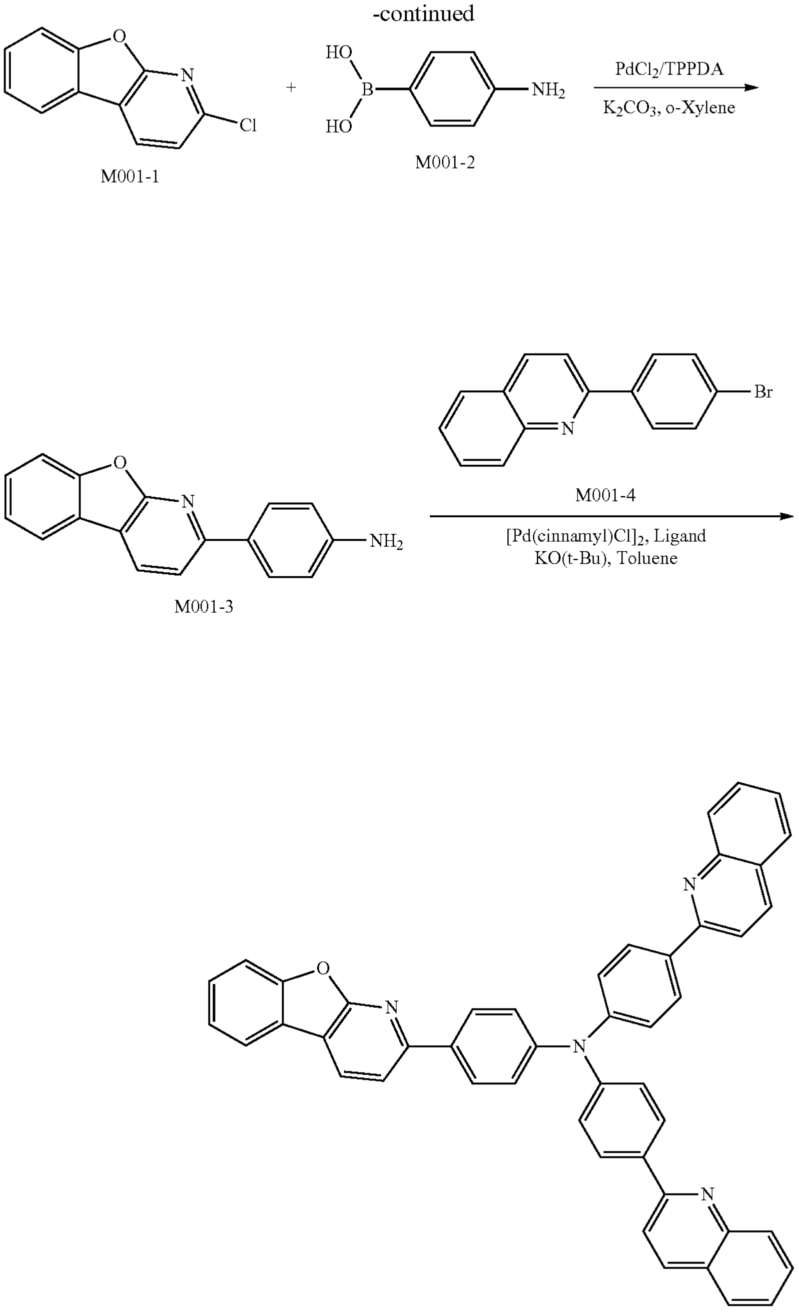

M001

(1) The M001-1 (0.5 mmol), M001-2 (0.75 mmol), $K_2CO_3$ (0.5 mmol), $PdCl_2$ (5×10$^4$ mmol), TPPDA (5×10$^4$ mmol) may be added into 3 mL o-xylene solution and then may be mixed. The mixed solution may be loaded into a 50 mL flask, and may react at 100° C. for 24 hours. After cooling to room temperature, saturated $MgSO_4$ aqueous and ethyl acetate may be slowly added into the mixed solution for extraction three times. Then, solvent may be removed through a rotary evaporator, and a crude product M001-3 may be obtained through column chromatography.

(2) M001-3 (0.5 mmol), M001-4 (1.5 mmol), KO(t-Bu) (0.75 mmol), $[Pd(cinnamyl)Cl]_2$ (2 mol %), Ligand (1.5 mol %) may be added into 3 mL toluene solution and then may be mixed. The mixed solution may be loaded into a 50 mL flask, and may react at 110° C. for 12 hours. After cooling to room temperature, saturated $MgSO_4$ aqueous and ethyl acetate may be slowly added into the mixed solution for extraction three times. Then, solvent may be removed through a rotary evaporator, and a crude product M001 may be obtained through column chromatography.

Through the matrix-assisted laser desorption/ionization time-of-flight mass spectrometry (MALDI-TOF MS (m/z)), the structure of the target product M001 may be obtained as $C_{47}H_{30}N_4O$ with a calculated value of 666.2 and a test value of 666.1.

Elemental analysis: theoretical value C, 84.66, H, 4.54, N, 8.40; test value C, 84.66, H, 4.53, N, 8.40.

Exemplary Embodiment 2

A synthetic route of compound M029 and detailed preparation method may include following:

acetate may be slowly added into the mixed solution for extraction three times. Then, solvent may be removed through a rotary evaporator, and a crude product M029 may be obtained through column chromatography.

M029

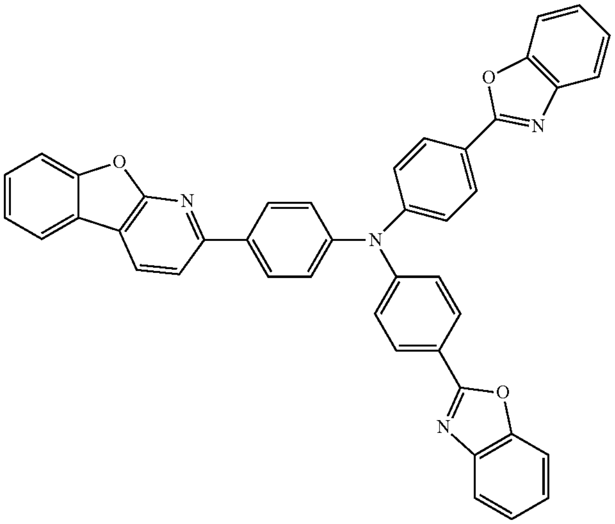

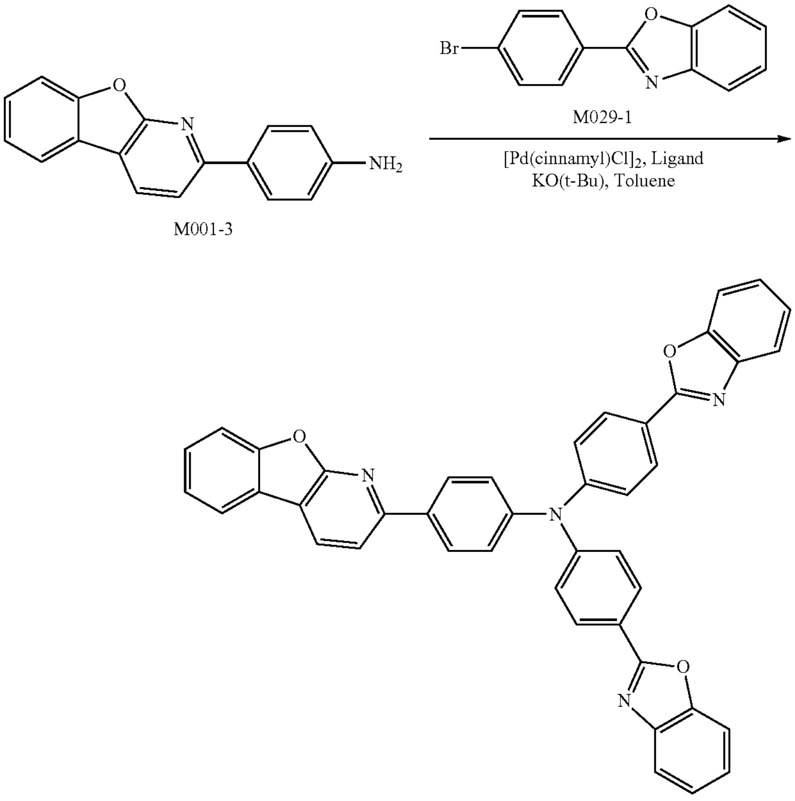

M001-3

M029

(1) M001-3 (0.5 mmol), M029-1 (1.5 mmol), KO(t-Bu) (0.75 mmol), $[Pd(cinnamyl)Cl]_2$ (2 mol %), Ligand (1.5 mol %) may be added into 3 mL toluene solution and then may be mixed. The mixed solution may be loaded into a 50 mL flask, and may react at 110° C. for 12 hours. After cooling to room temperature, saturated $MgSO_4$ aqueous and ethyl Through the matrix-assisted laser desorption/ionization time-of-flight mass spectrometry (MALDI-TOF MS (m/z)), the structure of the target product M029 may be obtained as $C_{43}H_{26}N_4O_3$ with a calculated value of 646.2 and a test value of 646.3.

Elemental analysis: theoretical value C, 79.86, H, 4.05, N, 8.66; test value C, 79.87, H, 4.05, N, 8.66.

Exemplary Embodiment 3

A synthetic route of compound M039 and detailed preparation method may include following:

acetate may be slowly added into the mixed solution for extraction three times. Then, solvent may be removed through a rotary evaporator, and a crude product M039 may be obtained through column chromatography.

M039

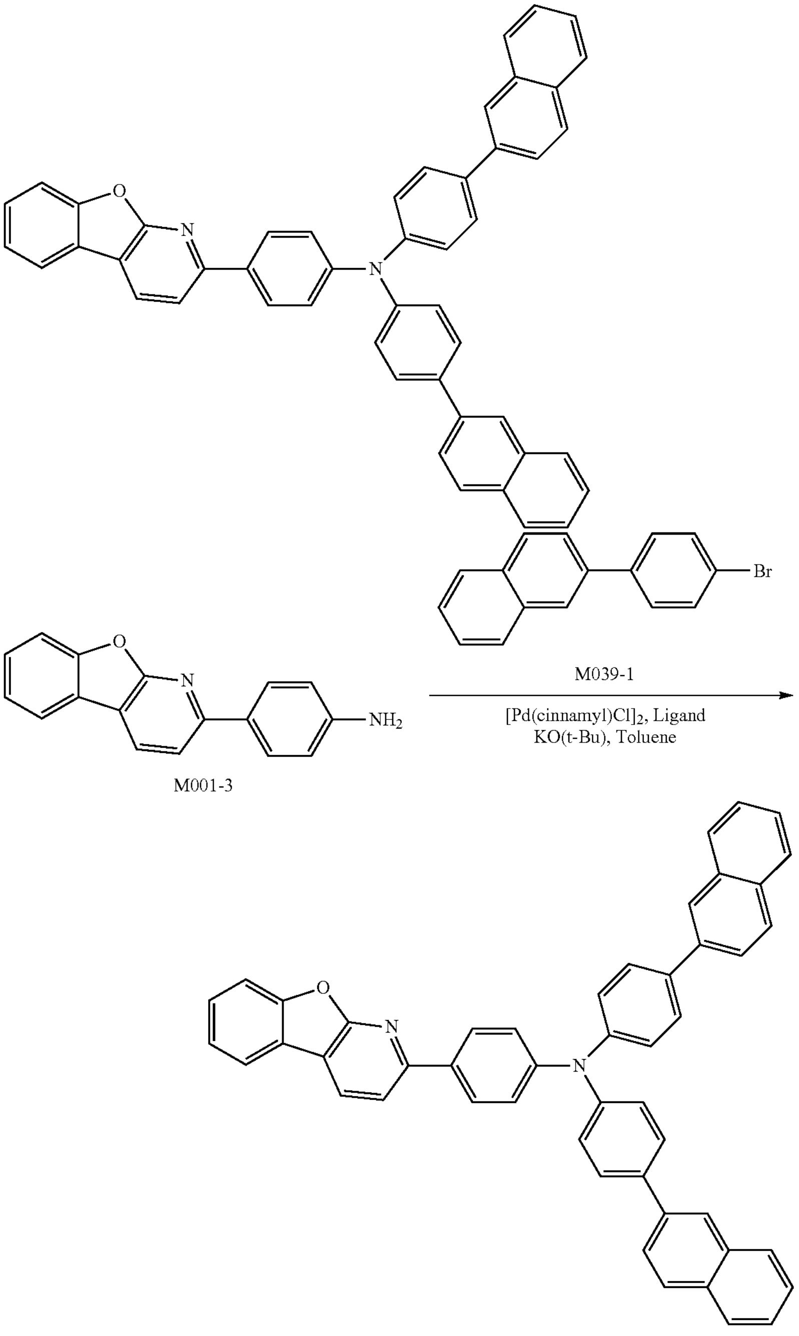

M039

(1) M001-3 (0.5 mmol), M039-1 (1.5 mmol), KO(t-Bu) (0.75 mmol), $[Pd(cinnamyl)Cl]_2$ (2 mol %), Ligand (1.5 mol %) may be added into 3 mL toluene solution and then may be mixed. The mixed solution may be loaded into a 50 mL flask, and may react at 110° C. for 12 hours. After cooling to room temperature, saturated $MgSO_4$ aqueous and ethyl Through the matrix-assisted laser desorption/ionization time-of-flight mass spectrometry (MALDI-TOF MS (m/z)), the structure of the target product M039 may be obtained as $C_{49}H_{32}N_2O$ with a calculated value of 664.2 and a test value of 664.3.

Elemental analysis: theoretical value C, 88.53, H, 4.85, N, 4.21; test value C, 88.53, H, 4.86, N, 4.21.

Exemplary Embodiment 4

A synthetic route of compound M265 and detailed preparation method may include following:

M265

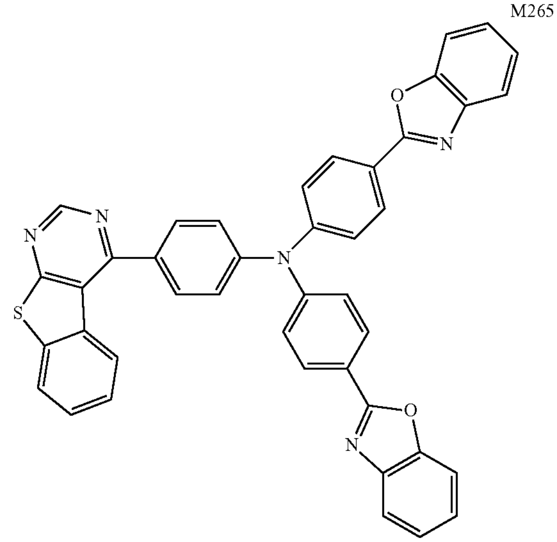

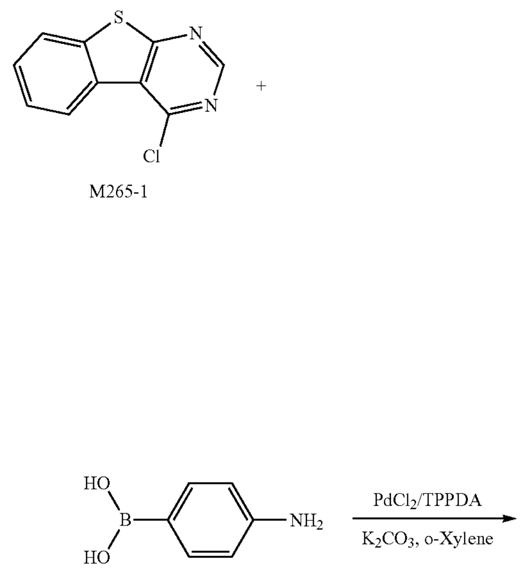

M265-1

M001-2

-continued

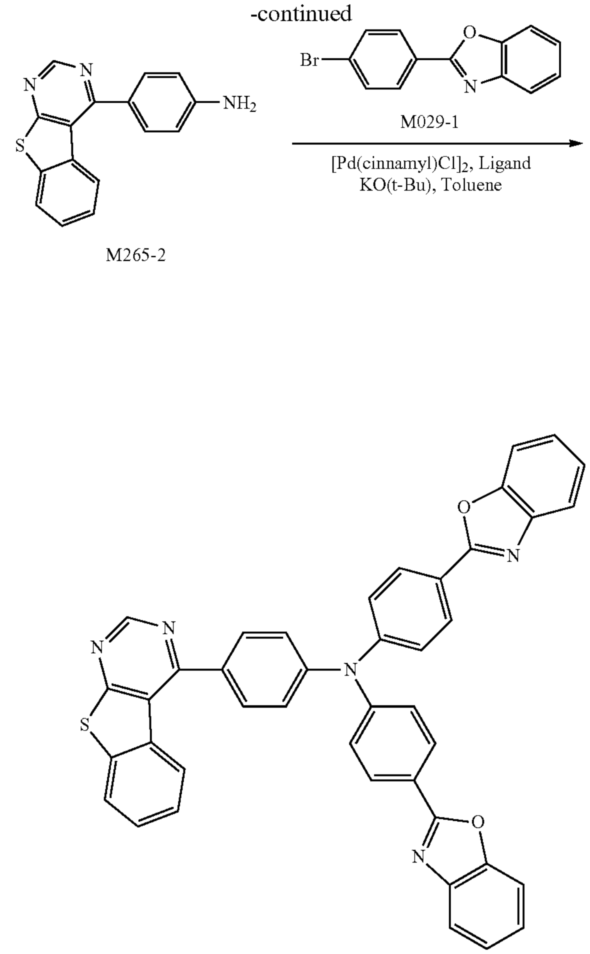

M029-1

M265-2

M265

(1) The M265-1 (0.5 mmol), M001-2 (0.75 mmol), $K_2CO_3$ (0.5 mmol), $PdCl_2$ ($5\times10^4$ mmol), TPPDA ($5\times10^4$ mmol) may be added into 3 mL o-xylene solution and then may be mixed. The mixed solution may be loaded into a 50 mL flask, and may react at 100° C. for 24 hours. After cooling to room temperature, saturated $MgSO_4$ aqueous and ethyl acetate may be slowly added into the mixed solution for extraction three times. Then, solvent may be removed through a rotary evaporator, and a crude product M265-2 may be obtained through column chromatography.

(2) M265-2 (0.5 mmol), M029-1 (1.5 mmol), KO(t-Bu) (0.75 mmol), $[Pd(cinnamyl)Cl]_2$ (2 mol %), Ligand (1.5 mol %) may be added into 3 mL toluene solution and then may be mixed. The mixed solution may be loaded into a 50 mL flask, and may react at 110° C. for 12 hours. After cooling to room temperature, saturated $MgSO_4$ aqueous and ethyl acetate may be slowly added into the mixed solution for extraction three times. Then, solvent may be removed through a rotary evaporator, and a crude product M265 may be obtained through column chromatography.

Through the matrix-assisted laser desorption/ionization time-of-flight mass spectrometry (MALDI-TOF MS (m/z)), the structure of the target product M265 may be obtained as $C_{42}H_{25}N_5O_2S$ with a calculated value of 663.2 and a test value of 663.1.

Elemental analysis: theoretical value C, 76.00, H, 3.80, N, 10.55; test value C, 76.01, H, 3.80, N, 10.55.

Exemplary Embodiment 5

A synthetic route of compound M382 and detailed preparation method may include following:

M382

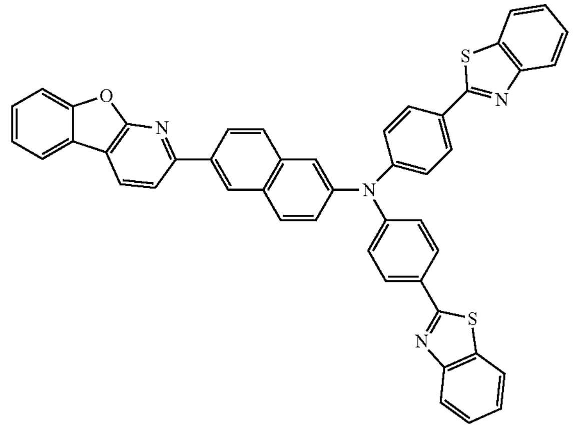

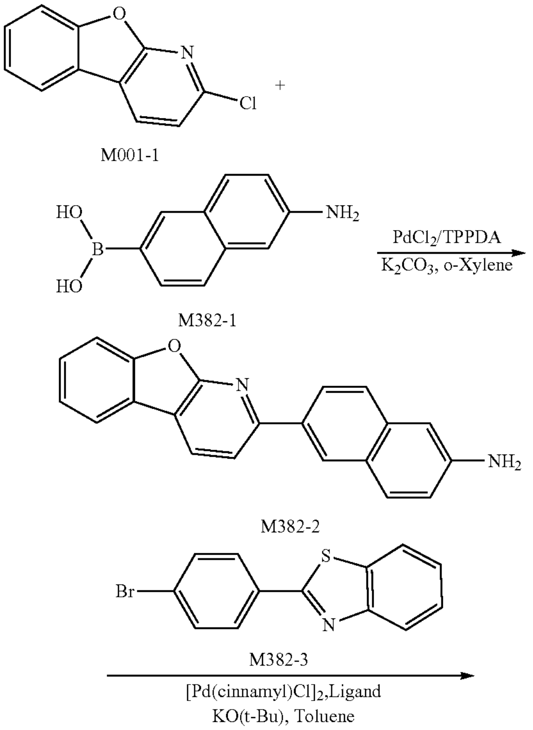

M001-1

M382-1

M382-2

M382-3

-continued

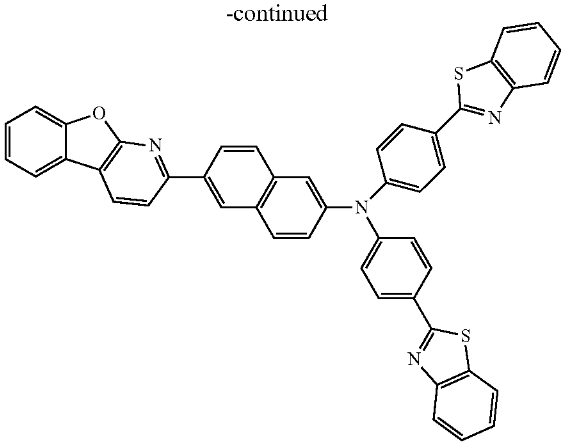

M382

(1) The M001-1 (0.5 mmol), M382-1 (0.75 mmol), $K_2CO_3$ (0.5 mmol), $PdCl_2$ ($5\times10^4$ mmol), TPPDA ($5\times10^4$ mmol) may be added into 3 mL o-xylene solution and then may be mixed. The mixed solution may be loaded into a 50 mL flask, and may react at 100° C. for 24 hours. After cooling to room temperature, saturated $MgSO_4$ aqueous and ethyl acetate may be slowly added into the mixed solution for extraction three times. Then, solvent may be removed through a rotary evaporator, and a crude product M382-2 may be obtained through column chromatography.

(2) The M382-2 (0.5 mmol), M382-3 (1.5 mmol), KO(t-Bu) (0.75 mmol), $[Pd(cinnamyl)Cl]_2$ (2 mol %), Ligand (1.5 mol %) may be added into 3 mL toluene solution and then may be mixed. The mixed solution may be loaded into a 50 mL flask, and may react at 110° C. for 12 hours. After cooling to room temperature, saturated $MgSO_4$ aqueous and ethyl acetate may be slowly added into the mixed solution for extraction three times. Then, solvent may be removed through a rotary evaporator, and a crude product M382 may be obtained through column chromatography.

Through the matrix-assisted laser desorption/ionization time-of-flight mass spectrometry (MALDI-TOF MS (m/z)), the structure of the target product M382 may be obtained as $C_{47}H_{28}N_4OS_2$ with a calculated value of 728.2 and a test value of 728.1.

Elemental analysis: theoretical value C, 77.45, H, 3.87, N, 7.69; test value C, 77.44, The preparation method of the disclosed compounds in the present disclosure used in the specific embodiments may be similar to the above-mentioned method, and may not be repeated herein. The characterization results, such as the results of mass spectrometry and elemental analysis, may be provided and shown in Table 1.

TABLE 1

| | Mass spectrometry results | | Elemental analysis results | |
|---|---|---|---|---|
| Compound | Calculated value | Test value | Theoretical value | Test value |
| M002 | 666.2 | 666.1 | C, 84.66; H, 4.54; N, 8.40; | C, 84.66; H, 4.56; N, 8.40; |
| M008 | 668.2 | 668.1 | C, 80.82; H, 4.22; N, 12.57; | C, 80.80; H, 4.22; N, 12.58; |
| M011 | 668.2 | 668.0 | C, 80.82; H, 4.22; N, 12.57; | C, 80.82; H, 4.22; N, 12.56; |
| M016 | 668.1 | 668.2 | C, 80.82; H, 4.22; N, 12.57; | C, 80.82; H, 4.23; N, 12.57; |
| M021 | 668.2 | 668.1 | C, 80.82; H, 4.22; N, 12.57; | C, 80.83; H, 4.22; N, 12.57; |
| M024 | 668.2 | 668.0 | C, 80.82; H, 4.22; N, 12.57; | C, 80.82; H, 4.22; N, 12.56; |
| M025 | 668.2 | 668.3 | C, 80.82; H, 4.22; N, 12.57; | C, 80.82; H, 4.23; N, 12.57; |
| M032 | 744.2 | 744.1 | C, 85.46; H, 4.33; N, 3.76; | C, 85.47; H, 4.32; N, 3.76; |

TABLE 1-continued

| Compound | Mass spectrometry results Calculated value | Test value | Elemental analysis results Theoretical value | Test value |
|---|---|---|---|---|
| M033 | 776.2 | 776.1 | C, 81.93; H, 4.15; N, 3.61; | C, 81.94; H, 4.15; N, 3.61; |
| M035 | 746.2 | 746.1 | C, 82.02; H, 4.05; N, 7.50; | C, 82.02; H, 4.05; N, 7.51; |
| M036 | 746.2 | 746.3 | C, 82.02; H, 4.05; N, 7.50; | C, 82.02; H, 4.06; N, 7.51; |
| M037 | 764.3 | 764.2 | C, 89.50; H, 4.74; N, 3.66; | C, 89.51; H, 4.74; N, 3.66; |
| M038 | 864.3 | 864.2 | C, 90.25; H, 4.66; N, 3.24; | C, 90.25; H, 4.67; N, 3.24; |
| M042 | 716.3 | 716.1 | C, 85.45; H, 4.50; N, 7.82; | C, 85.44; H, 4.50; N, 7.82; |
| M045 | 716.3 | 716.1 | C, 85.45; H, 4.50; N, 7.82; | C, 85.45; H, 4.51; N, 7.82; |
| M048 | 718.3 | 718.2 | C, 81.88; H, 4.21; N, 11.69; | C, 81.89; H, 4.21; N, 11.69; |
| M056 | 718.3 | 718.2 | C, 81.88; H, 4.21; N, 11.69; | C, 81.88; H, 4.20; N, 11.69; |
| M063 | 718.3 | 718.4 | C, 81.88; H, 4.21; N, 11.69; | C, 81.89; H, 4.20; N, 11.68; |
| M065 | 746.2 | 746.3 | C, 82.02; H, 4.05; N, 7.50; | C, 82.03; H, 4.06; N, 7.50; |
| M068 | 844.3 | 844.2 | C, 86.71; H, 4.29; N, 3.32; | C, 86.71; H, 4.28; N, 3.33; |
| M072 | 846.3 | 846.2 | C, 83.67; H, 4.05; N, 6.62; | C, 83.68; H, 4.05; N, 6.62; |
| M078 | 764.3 | 764.1 | C, 89.50; H, 4.74; N, 3.66; | C, 89.51; H, 4.74; N, 3.66; |
| M081 | 666.2 | 666.0 | C, 84.66; H, 4.54; N, 8.40; | C, 84.66; H, 4.55; N, 8.40; |
| M086 | 666.2 | 666.0 | C, 84.66; H, 4.54; N, 8.40; | C, 84.65; H, 4.55; N, 8.40; |
| M088 | 668.2 | 668.1 | C, 80.82; H, 4.22; N, 12.57; | C, 80.82; H, 4.23; N, 12.57; |
| M092 | 668.2 | 668.0 | C, 80.82; H, 4.22; N, 12.57; | C, 80.81; H, 4.22; N, 12.57; |
| M104 | 668.2 | 668.0 | C, 80.82; H, 4.22; N, 12.57; | C, 80.82; H, 4.22; N, 12.58; |
| M105 | 646.2 | 646.1 | C, 79.86; H, 4.05; N, 8.66; | C, 79.85; H, 4.05; N, 8.67; |
| M113 | 764.3 | 764.2 | C, 89.50; H, 4.74; N, 3.66; | C, 89.50; H, 4.75; N, 3.66; |
| M123 | 716.3 | 716.3 | C, 85.45; H, 4.50; N, 7.82; | C, 85.45; H, 4.51; N, 7.82; |
| M128 | 718.3 | 718.2 | C, 81.88; H, 4.21; N, 11.69; | C, 81.88; H, 4.21; N, 11.69; |
| M136 | 718.3 | 718.1 | C, 81.88; H, 4.21; N, 11.69; | C, 81.88; H, 4.20; N, 11.69; |
| M143 | 768.3 | 768.2 | C, 82.79; H, 4.20; N, 10.93; | C, 82.79; H, 4.21; N, 10.93; |
| M145 | 746.2 | 746.1 | C, 82.02; H, 4.05; N, 7.50; | C, 82.02; H, 4.04; N, 7.50; |
| M158 | 764.3 | 764.2 | C, 89.50; H, 4.74; N, 3.66; | C, 89.51; H, 4.74; N, 3.66; |
| M161 | 666.2 | 666.3 | C, 84.66; H, 4.54; N, 8.40; | C, 84.66; H, 4.54; N, 8.41; |
| M163 | 666.2 | 666.3 | C, 84.66; H, 4.54; N, 8.40; | C, 84.66; H, 4.55; N, 8.41; |
| M167 | 666.2 | 666.3 | C, 84.66; H, 4.54; N, 8.40; | C, 84.64; H, 4.56; N, 8.41; |
| M171 | 668.2 | 668.1 | C, 80.82; H, 4.22; N, 12.57; | C, 80.82; H, 4.23; N, 12.58; |
| M184 | 668.2 | 668.1 | C, 80.82; H, 4.22; N, 12.57; | C, 80.83; H, 4.22; N, 12.57; |
| M189 | 646.2 | 646.1 | C, 79.86; H, 4.05; N, 8.66; | C, 79.86; H, 4.04; N, 8.66; |
| M192 | 744.2 | 744.1 | C, 85.46; H, 4.33; N, 3.76; | C, 85.46; H, 4.33; N, 3.77; |
| M197 | 764.3 | 764.2 | C, 89.50; H, 4.74; N, 3.66; | C, 89.50; H, 4.75; N, 3.66; |
| M198 | 864.3 | 864.2 | C, 90.25; H, 4.66; N, 3.24; | C, 90.25; H, 4.67; N, 3.24; |
| M215 | 743.2 | 743.1 | C, 80.74; H, 3.93; N, 13.18; | C, 80.74; H, 3.93; N, 13.17; |
| M220 | 786.2 | 786.2 | C, 76.33; H, 3.72; N, 10.68; | C, 76.33; H, 3.72; N, 10.69; |
| M228 | 769.3 | 769.2 | C, 81.13; H, 4.06; N, 12.74; | C, 81.13; H, 4.07; N, 12.74; |
| M229 | 747.2 | 747.1 | C, 80.31; H, 3.91; N, 9.37; | C, 80.31; H, 3.90; N, 9.37; |
| M237 | 865.3 | 865.2 | C, 88.76; H, 4.54; N, 4.85; | C, 88.76; H, 4.55; N, 4.85; |
| M242 | 765.3 | 765.2 | C, 87.82; H, 4.61; N, 5.49; | C, 87.83; H, 4.61; N, 5.49; |
| M246 | 683.2 | 683.1 | C, 80.79; H, 4.27; N, 10.24; | C, 80.79; H, 4.28; N, 10.24; |
| M261 | 685.2 | 685.1 | C, 77.06; H, 3.97; N, 14.30; | C, 77.06; H, 3.98; N, 14.30; |
| M274 | 696.1 | 696.2 | C, 70.66; H, 3.47; N, 12.06; | C, 70.66; H, 3.48; N, 12.06; |
| M277 | 782.3 | 782.2 | C, 84.37; H, 4.38; N, 7.16; | C, 84.37; H, 4.39; N, 7.16; |
| M295 | 735.2 | 735.1 | C, 78.35; H, 3.97; N, 13.32; | C, 78.36; H, 3.96; N, 13.32; |
| M305 | 663.2 | 663.1 | C, 76.00; H, 3.80; N, 10.55; | C, 76.01; H, 3.80; N, 10.56; |
| M314 | 682.2 | 682.1 | C, 82.67; H, 4.43; N, 8.21; | C, 82.67; H, 4.45; N, 8.21; |
| M324 | 760.2 | 760.1 | C, 83.66; H, 4.24; N, 3.68; | C, 83.66; H, 4.24; N, 3.69; |
| M340 | 684.2 | 684.1 | C, 78.92; H, 4.12; N, 12.27; | C, 78.90; H, 4.12; N, 12.28; |
| M353 | 662.2 | 662.1 | C, 77.93; H, 3.95; N, 8.45; | C, 77.93; H, 3.96; N, 8.45; |
| M362 | 880.3 | 880.1 | C, 88.61; H, 4.58; N, 3.18; | C, 88.62; H, 4.57; N, 3.18; |
| M381 | 696.2 | 696.1 | C, 81.02; H, 4.05; N, 8.04; | C, 81.02; H, 4.06; N, 8.04; |
| M385 | 696.2 | 696.1 | C, 81.02; H, 4.05; N, 8.04; | C, 81.03; H, 4.05; N, 8.03; |
| M388 | 796.3 | 796.2 | C, 86.13; H, 4.31; N, 3.52; | C, 86.13; H, 4.30; N, 3.52; |
| M400 | 685.2 | 685.1 | C, 77.06; H, 3.97; N, 14.30; | C, 77.06; H, 3.98; N, 14.30; |
| M401 | 716.3 | 716.2 | C, 85.45; H, 4.50; N, 7.82; | C, 85.45; H, 4.51; N, 7.82; |
| M413 | 712.2 | 712.3 | C, 79.19; H, 3.96; N, 7.86; | C, 79.19; H, 3.97; N, 7.86; |
| M416 | 810.2 | 810.3 | C, 84.42; H, 4.23; N, 3.45; | C, 84.42; H, 4.22; N, 3.45; |

The refractive indices of the compounds may be detected, and the results may be shown in Table 2.
TABLE 2
| No. | Structure | Refractive index 460 nm | Refractive index 530 nm | Refractive index 620 nm |
|---|---|---|---|---|
| M001 | 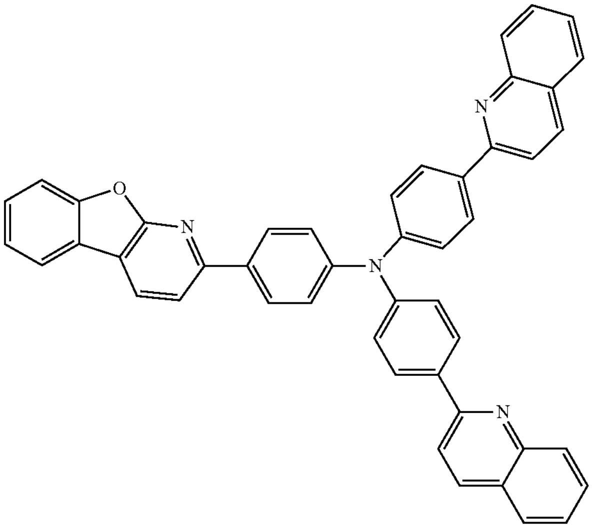 [SMILES: c1ccc2nc(-c3ccc(N(c4ccc(-c5ccc6ccccc6n5)cc4)c4ccc(-c5ccc6c(n5)oc5ccccc56)cc4)cc3)ccc2c1] | 2.29 | 2.14 | 2.06 |
| M002 | 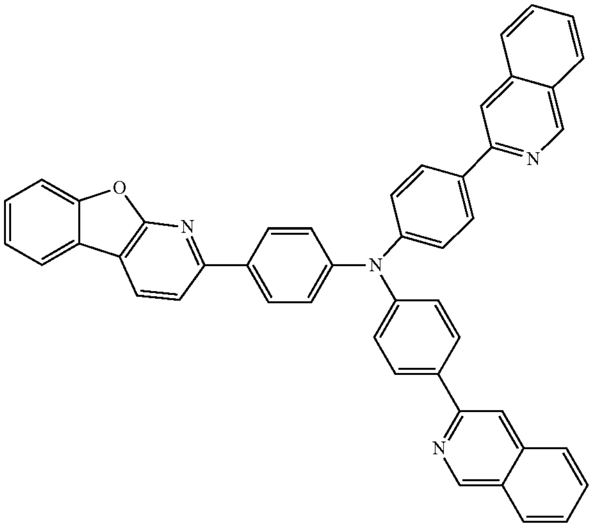 [SMILES: c1ccc2cc(-c3ccc(N(c4ccc(-c5cc6ccccc6cn5)cc4)c4ccc(-c5ccc6c(n5)oc5ccccc56)cc4)cc3)ncc2c1] | 2.30 | 2.15 | 2.07 |

TABLE 2-continued
| No. | Structure | Refractive index 460 nm | Refractive index 530 nm | Refractive index 620 nm |
|---|---|---|---|---|
| M008 | 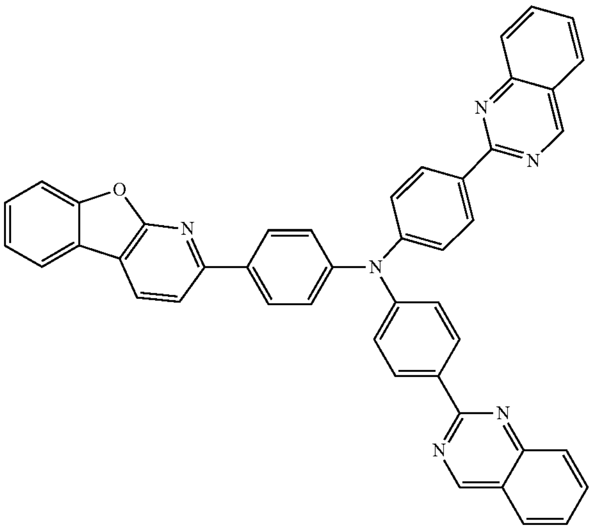 [SMILES: c1ccc2nc(-c3ccc(N(c4ccc(-c5ccc6c(n5)oc5ccccc56)cc4)c4ccc(-c5ncc6ccccc6n5)cc4)cc3)ncc2c1] | 2.34 | 2.18 | 2.08 |
| M011 | 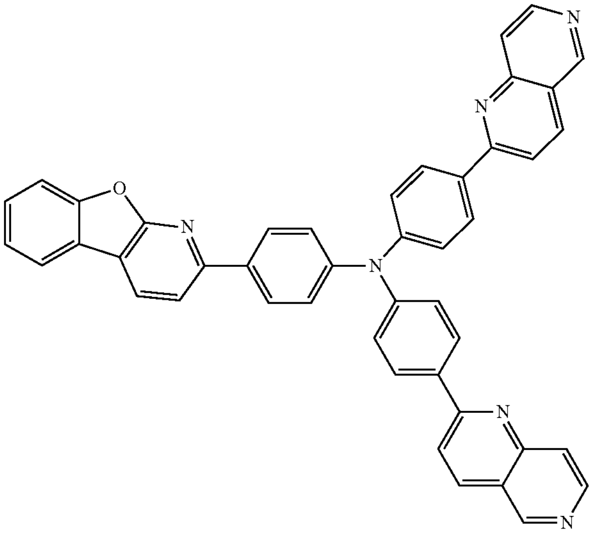 [SMILES: c1ccc2c(c1)oc1nc(-c3ccc(N(c4ccc(-c5ccc6cnccc6n5)cc4)c4ccc(-c5ccc6cnccc6n5)cc4)cc3)ccc12] | 2.28 | 2.13 | 2.05 |

TABLE 2-continued
| No. | Structure | Refractive index 460 nm | Refractive index 530 nm | Refractive index 620 nm |
|---|---|---|---|---|
| M016 | 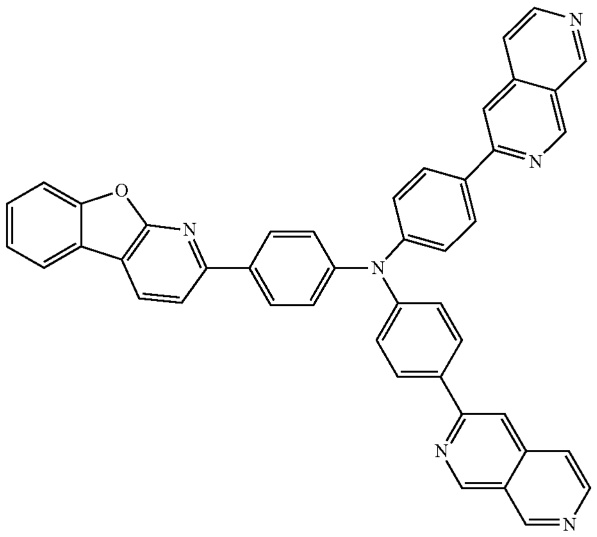 [SMILES: c1ccc2c(c1)oc1nc(-c3ccc(N(c4ccc(-c5cc6ccncc6cn5)cc4)c4ccc(-c5cc6ccncc6cn5)cc4)cc3)ccc12] | 2.29 | 2.14 | 2.06 |
| M021 | 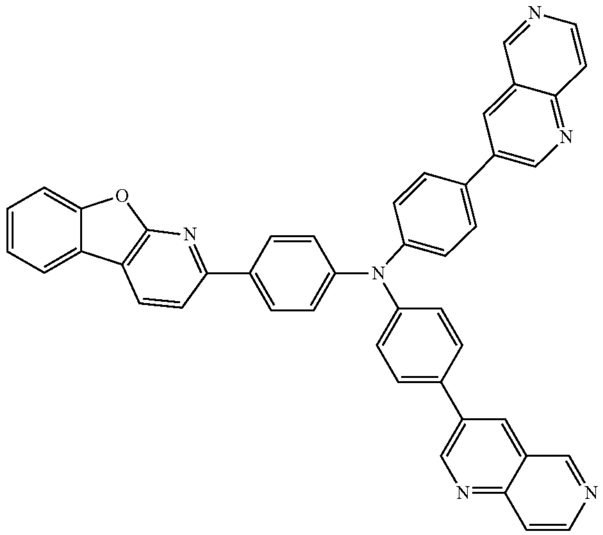 [SMILES: c1ccc2c(c1)oc1nc(-c3ccc(N(c4ccc(-c5cnc6ccncc6c5)cc4)c4ccc(-c5cnc6ccncc6c5)cc4)cc3)ccc12] | 2.18 | 2.07 | 2.00 |

TABLE 2-continued
| No. | Structure | Refractive index 460 nm | Refractive index 530 nm | Refractive index 620 nm |
| --- | --- | --- | --- | --- |
| M024 | 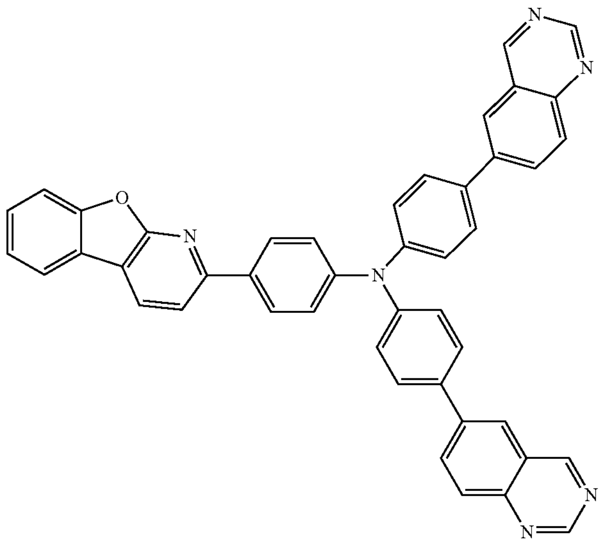 [SMILES: c1ccc2c(c1)oc1nc(-c3ccc(N(c4ccc(-c5ccc6ncncc6c5)cc4)c4ccc(-c5ccc6ncncc6c5)cc4)cc3)ccc12] | 2.18 | 2.07 | 2.00 |
| M025 | 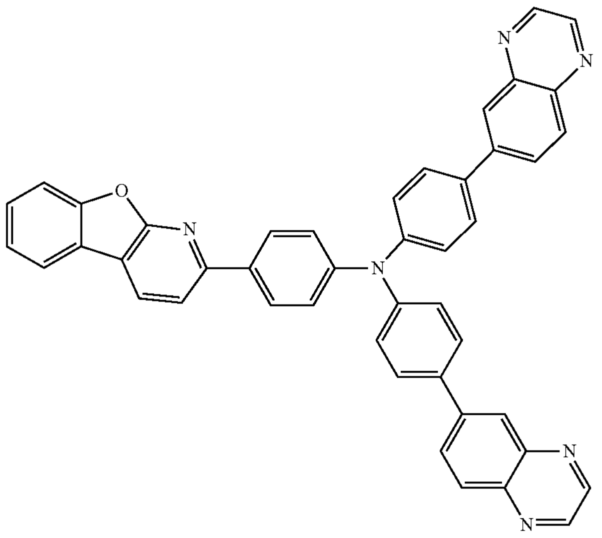 [SMILES: c1ccc2c(c1)oc1nc(-c3ccc(N(c4ccc(-c5ccc6nccnc6c5)cc4)c4ccc(-c5ccc6nccnc6c5)cc4)cc3)ccc12] | 2.22 | 2.10 | 2.03 |

TABLE 2-continued
| No. | Structure | Refractive index 460 nm | Refractive index 530 nm | Refractive index 620 nm |
|---|---|---|---|---|
| M029 | 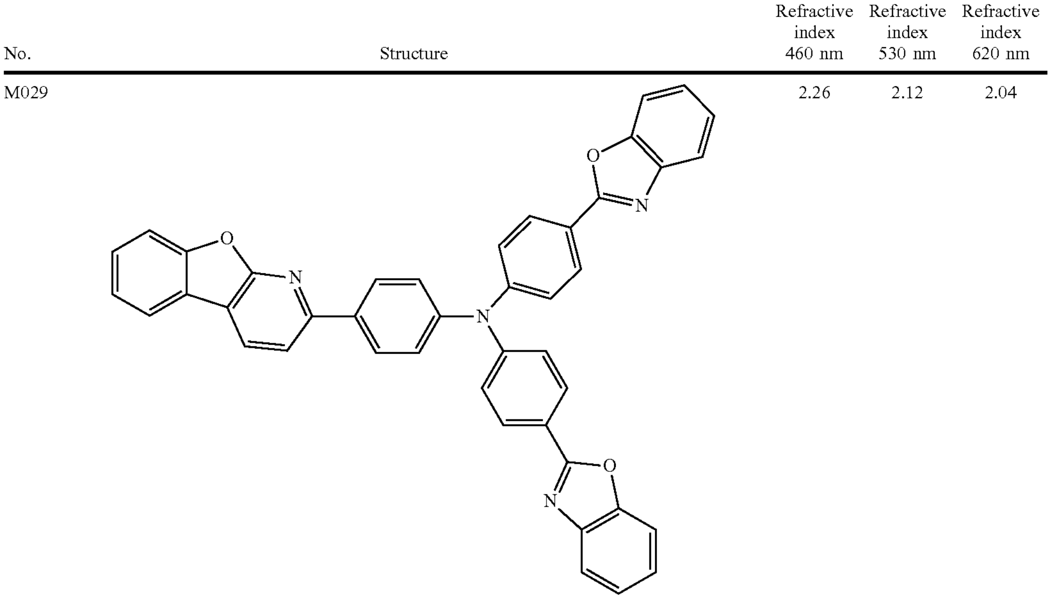 | 2.26 | 2.12 | 2.04 |
| M032 | 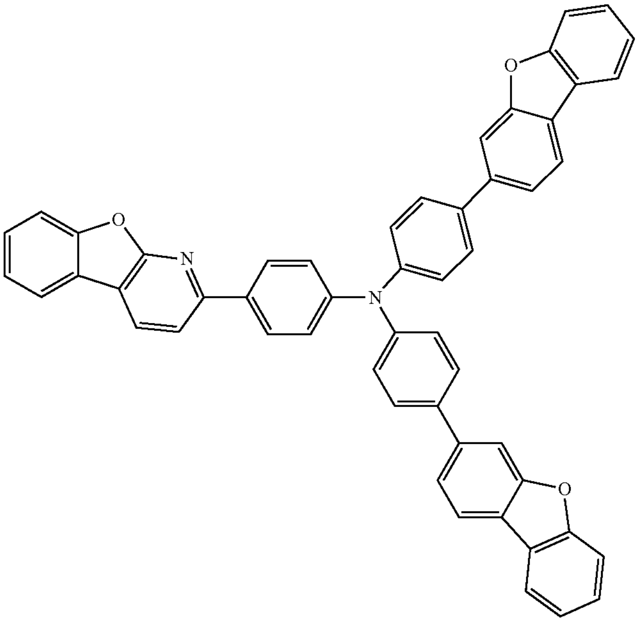 | 2.24 | 2.12 | 2.05 |

TABLE 2-continued
| No. | Structure | Refractive index 460 nm | Refractive index 530 nm | Refractive index 620 nm |
|---|---|---|---|---|
| M033 | 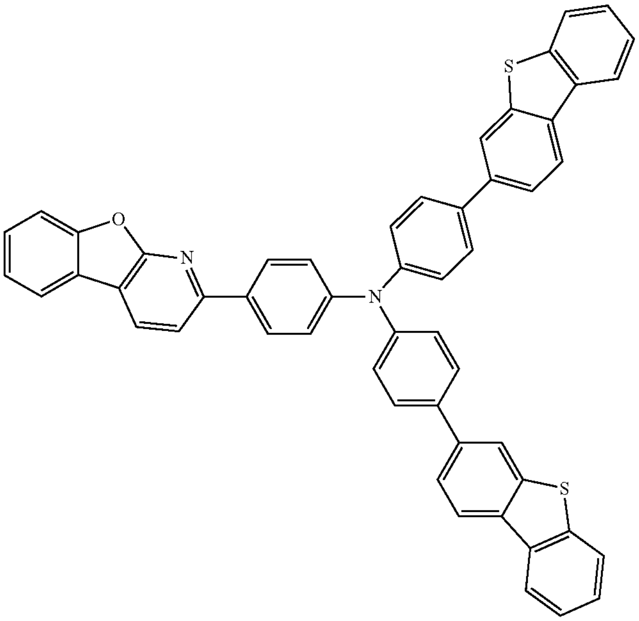 [SMILES: c1ccc2c(c1)oc1nc(-c3ccc(N(c4ccc(-c5ccc6c(c5)sc5ccccc56)cc4)c4ccc(-c5ccc6c(c5)sc5ccccc56)cc4)cc3)ccc12] | 2.24 | 2.12 | 2.05 |
| M035 | 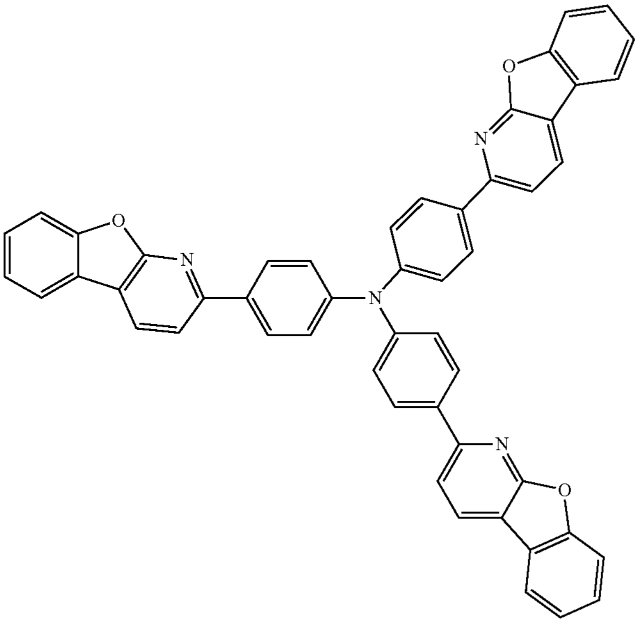 [SMILES: c1ccc2c(c1)oc1nc(-c3ccc(N(c4ccc(-c5ccc6c(n5)oc5ccccc56)cc4)c4ccc(-c5ccc6c(n5)oc5ccccc56)cc4)cc3)ccc12] | 2.38 | 2.21 | 2.11 |

TABLE 2-continued
| No. | Structure | Refractive index 460 nm | Refractive index 530 nm | Refractive index 620 nm |
|---|---|---|---|---|
| M036 | 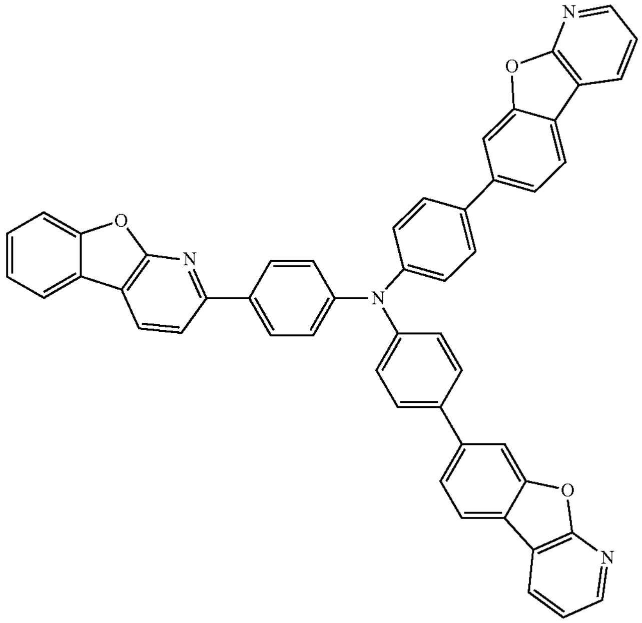 [SMILES: c1ccc2c(c1)oc1nc(-c3ccc(N(c4ccc(-c5ccc6c(c5)oc5ncccc56)cc4)c4ccc(-c5ccc6c(c5)oc5ncccc56)cc4)cc3)ccc12] | 2.25 | 2.12 | 2.05 |
| M037 | 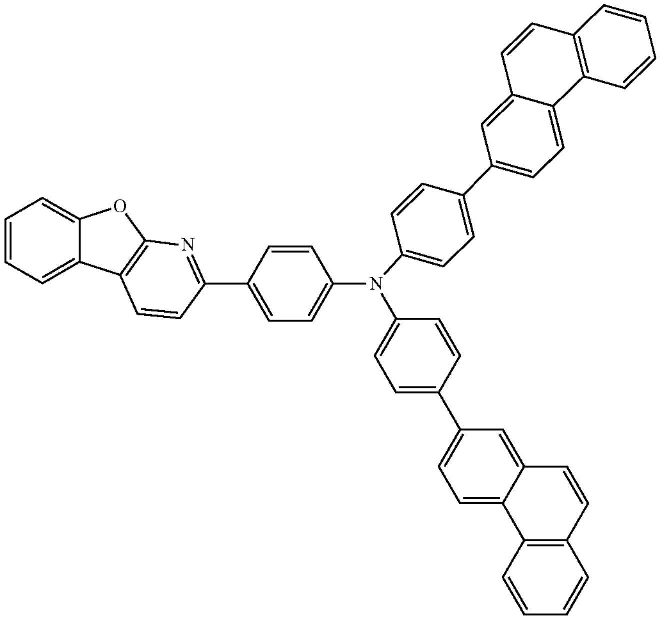 [SMILES: c1ccc2c(c1)ccc1cc(-c3ccc(N(c4ccc(-c5ccc6c(ccc7ccccc76)c5)cc4)c4ccc(-c5ccc6c(n5)oc5ccccc56)cc4)cc3)ccc12] | 2.29 | 2.16 | 2.08 |

TABLE 2-continued
| No. | Structure | Refractive index 460 nm | Refractive index 530 nm | Refractive index 620 nm |
|---|---|---|---|---|
| M038 | 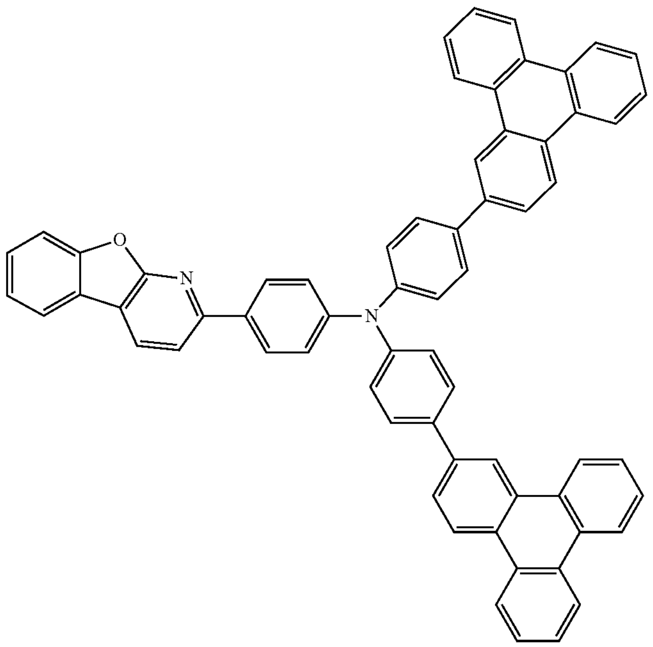 [SMILES: c1ccc2c(c1)oc1nc(-c3ccc(N(c4ccc(-c5ccc6c7ccccc7c7ccccc7c6c5)cc4)c4ccc(-c5ccc6c7ccccc7c7ccccc7c6c5)cc4)cc3)ccc12] | 2.26 | 2.14 | 2.06 |
| M039 | 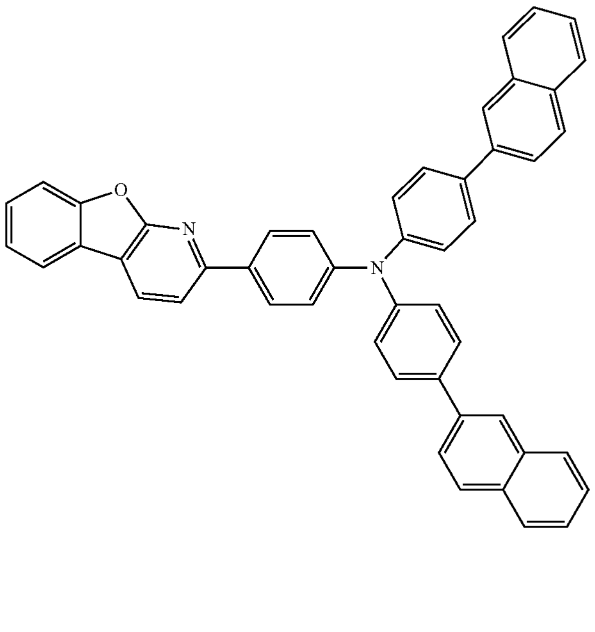 [SMILES: c1ccc2cc(-c3ccc(N(c4ccc(-c5ccc6ccccc6c5)cc4)c4ccc(-c5ccc6c(n5)oc5ccccc56)cc4)cc3)ccc2c1] | 2.19 | 2.07 | 2.00 |

TABLE 2-continued
| No. | Structure | Refractive index 460 nm | Refractive index 530 nm | Refractive index 620 nm |
|---|---|---|---|---|
| M042 | 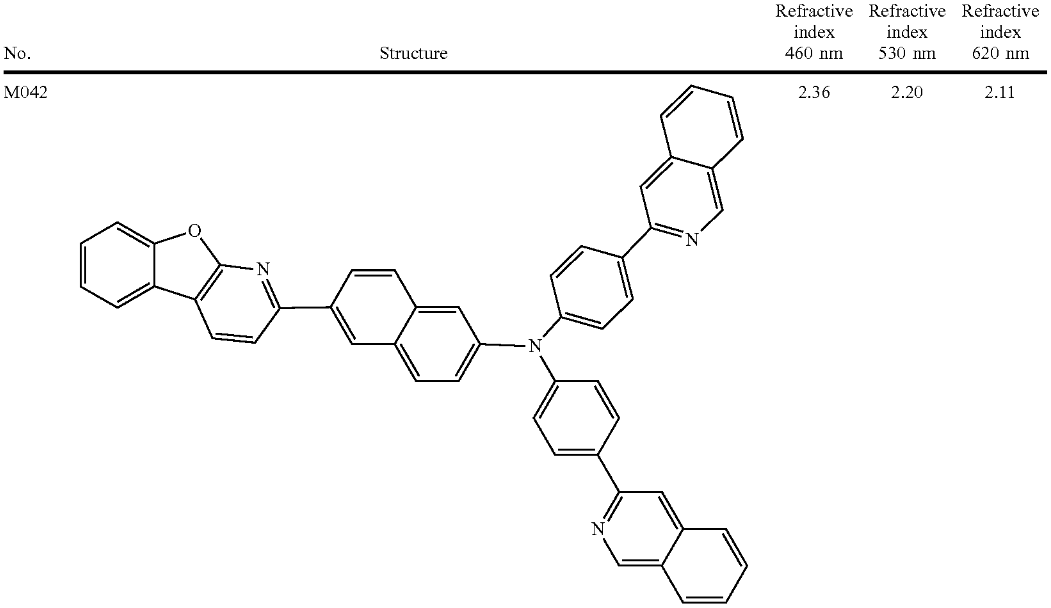 | 2.36 | 2.20 | 2.11 |
| M045 | 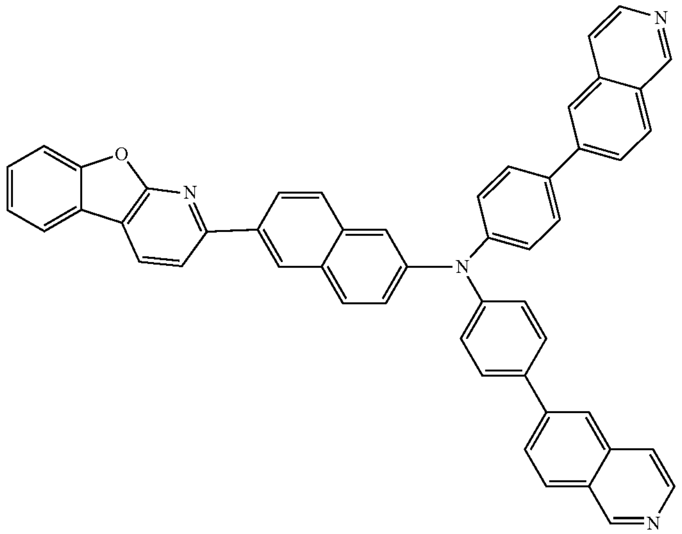 [SMILES: c1ccc2c(c1)oc1nc(-c3ccc4cc(N(c5ccc(-c6ccc7cnccc7c6)cc5)c5ccc(-c6ccc7cnccc7c6)cc5)ccc4c3)ccc12] | 2.24 | 2.12 | 2.05 |
| M048 | 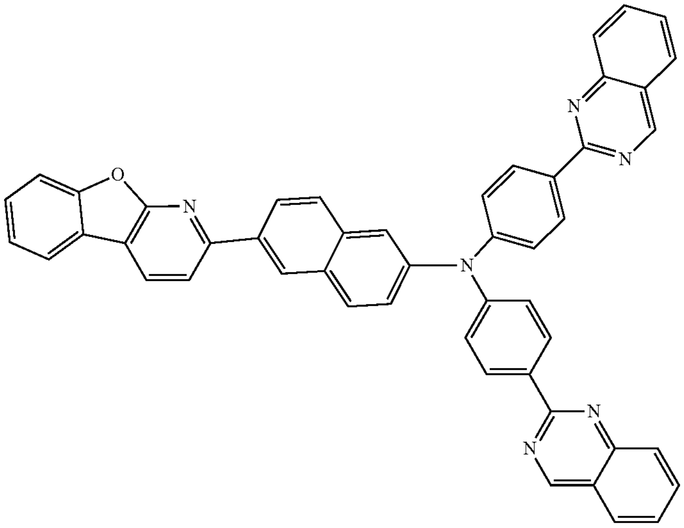 [SMILES: c1ccc2nc(-c3ccc(N(c4ccc(-c5ncc6ccccc6n5)cc4)c4ccc5cc(-c6ccc7c(n6)oc6ccccc67)ccc5c4)cc3)ncc2c1] | 2.40 | 2.23 | 2.12 |

TABLE 2-continued
| No. | Structure | Refractive index 460 nm | Refractive index 530 nm | Refractive index 620 nm |
|---|---|---|---|---|
| M056 | 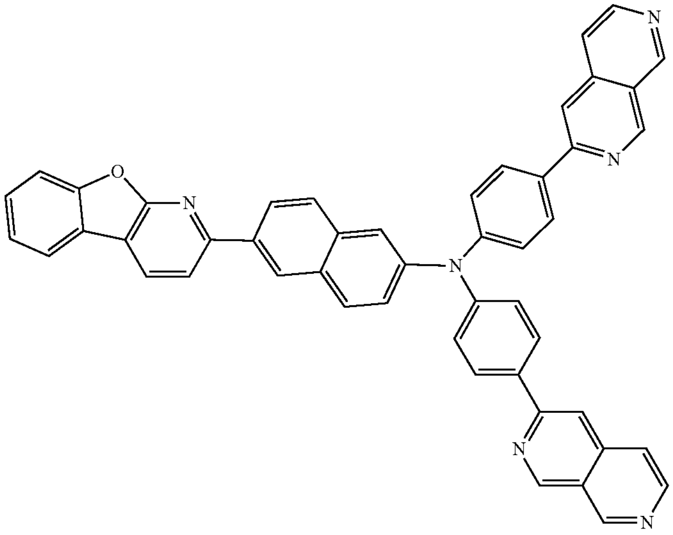 [SMILES: c1ccc2c(c1)oc1nc(-c3ccc4cc(N(c5ccc(-c6cc7ccncc7cn6)cc5)c5ccc(-c6cc7ccncc7cn6)cc5)ccc4c3)ccc12] | 2.35 | 2.19 | 2.10 |
| M063 | 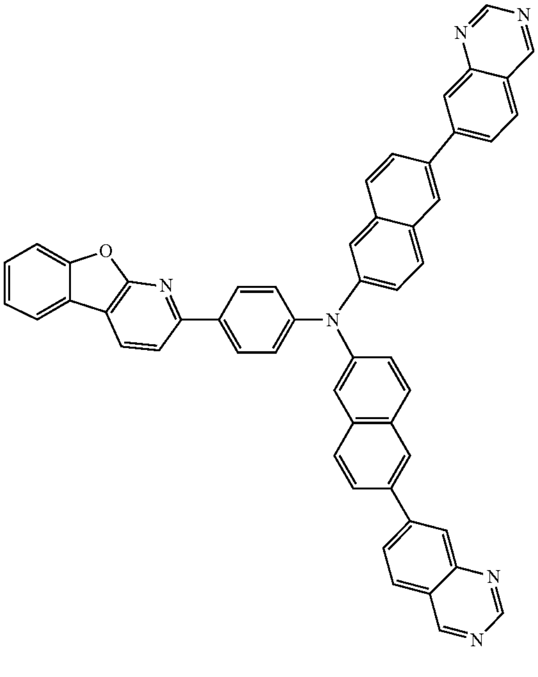 [SMILES: c1ccc2c(c1)oc1nc(-c3ccc(N(c4ccc5cc(-c6ccc7cncnc7c6)ccc5c4)c4ccc5cc(-c6ccc7cncnc7c6)ccc5c4)cc3)ccc12] | 2.32 | 2.18 | 2.10 |

TABLE 2-continued
| No. | Structure | Refractive index 460 nm | Refractive index 530 nm | Refractive index 620 nm |
|---|---|---|---|---|
| M065 | 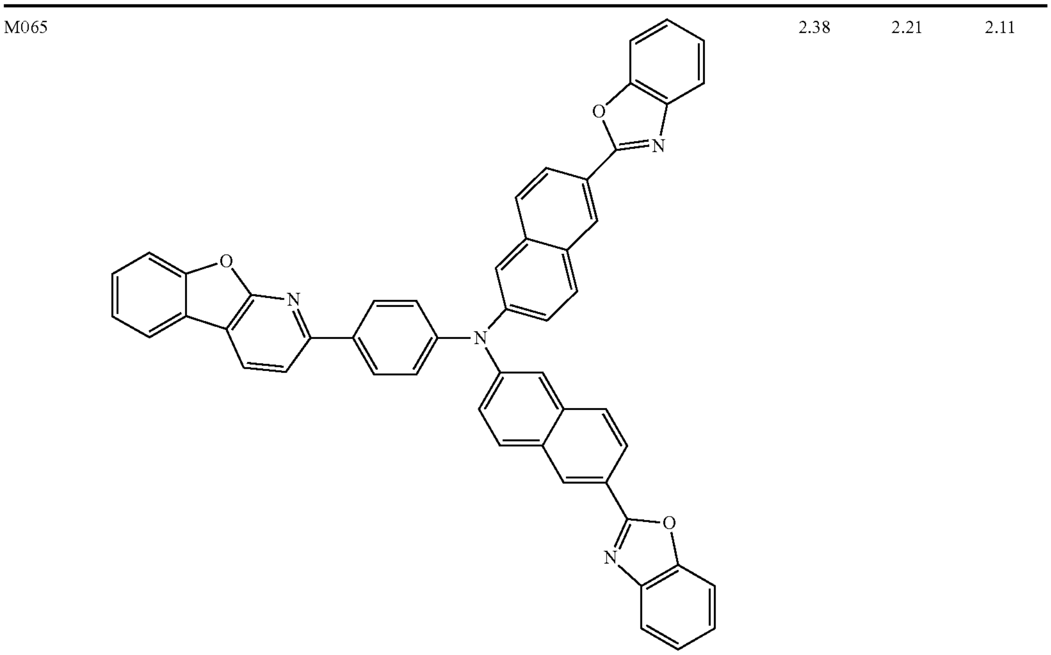 | 2.38 | 2.21 | 2.11 |
| M068 | 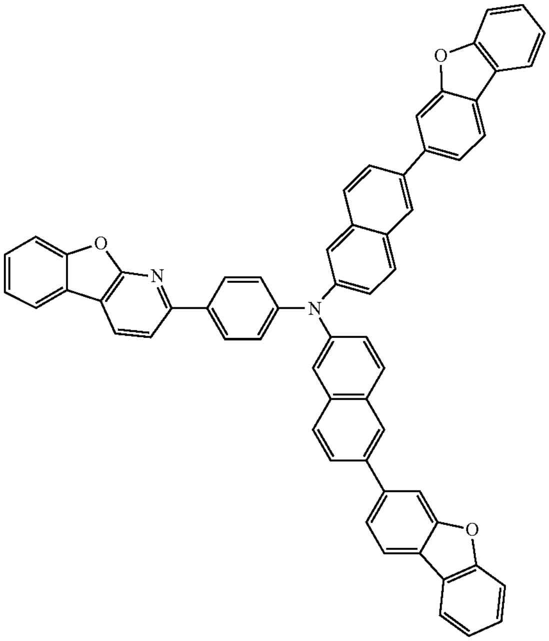 [SMILES: c1ccc2c(c1)oc1cc(-c3ccc4cc(N(c5ccc(-c6ccc7c(n6)oc6ccccc67)cc5)c5ccc6cc(-c7ccc8c(c7)oc7ccccc78)ccc6c5)ccc4c3)ccc12] | 2.36 | 2.21 | 2.12 |

TABLE 2-continued
| No. | Structure | Refractive index 460 nm | Refractive index 530 nm | Refractive index 620 nm |
|---|---|---|---|---|
| M072 | 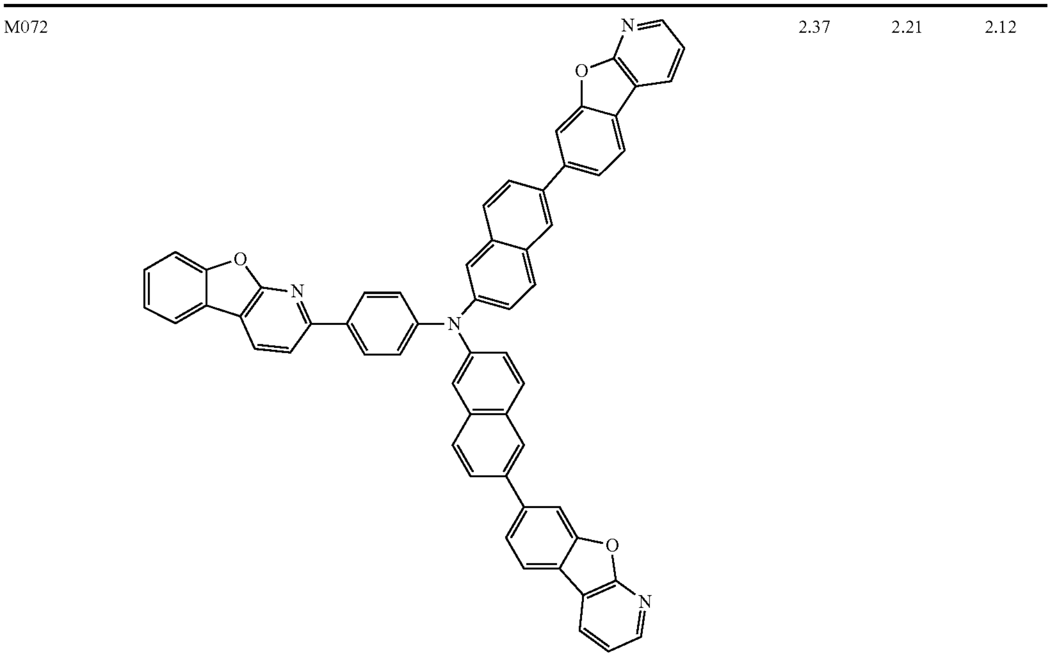 | 2.37 | 2.21 | 2.12 |
| M078 | 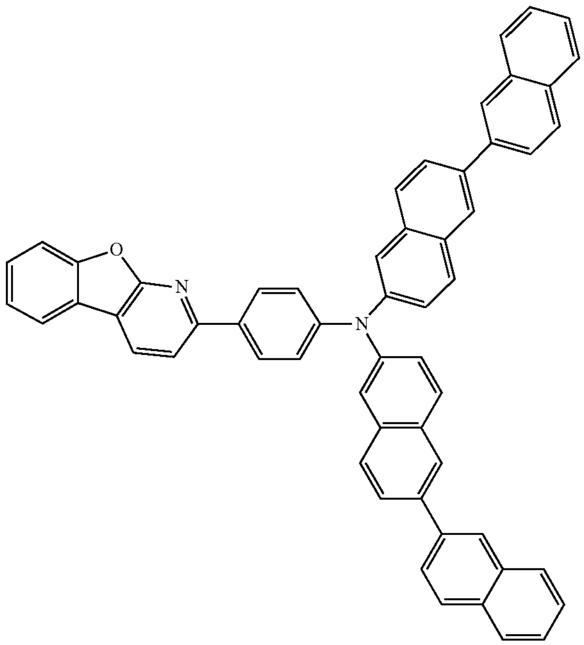 [SMILES: c1ccc2cc(-c3ccc4cc(N(c5ccc(-c6ccc7c(n6)oc6ccccc67)cc5)c5ccc6cc(-c7ccc8ccccc8c7)ccc6c5)ccc4c3)ccc2c1] | 2.34 | 2.19 | 2.11 |

TABLE 2-continued
| No. | Structure | Refractive index 460 nm | Refractive index 530 nm | Refractive index 620 nm |
|---|---|---|---|---|
| M081 | 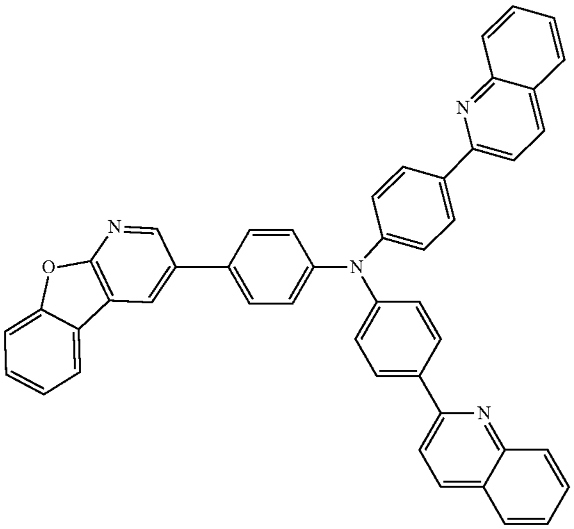 [SMILES: c1ccc2nc(-c3ccc(N(c4ccc(-c5cnc6oc7ccccc7c6c5)cc4)c4ccc(-c5ccc6ccccc6n5)cc4)cc3)ccc2c1] | 2.18 | 2.09 | 2.02 |
| M086 | 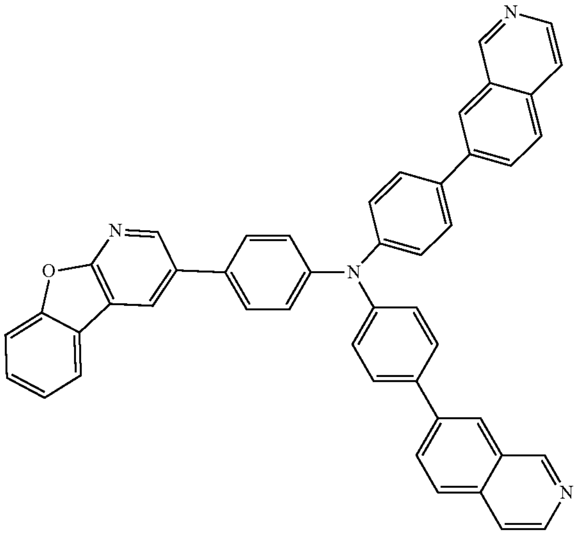 [SMILES: c1ccc2c(c1)oc1ncc(-c3ccc(N(c4ccc(-c5ccc6ccncc6c5)cc4)c4ccc(-c5ccc6ccncc6c5)cc4)cc3)cc12] | 2.09 | 2.03 | 1.98 |

TABLE 2-continued
| No. | Structure | Refractive index 460 nm | Refractive index 530 nm | Refractive index 620 nm |
|---|---|---|---|---|
| M088 | 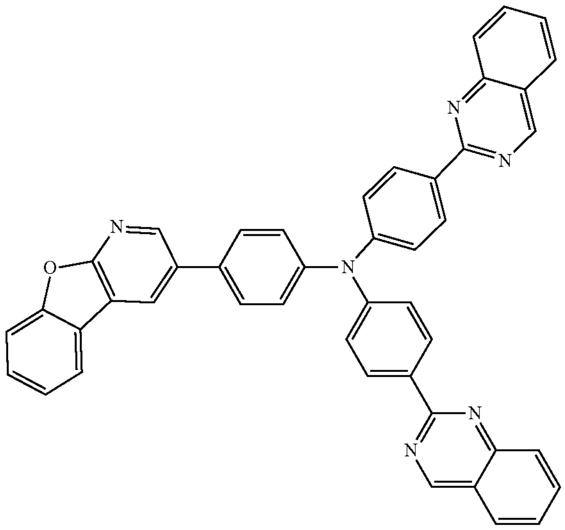 [SMILES: c1ccc2nc(-c3ccc(N(c4ccc(-c5cnc6oc7ccccc7c6c5)cc4)c4ccc(-c5ncc6ccccc6n5)cc4)cc3)ncc2c1] | 2.23 | 2.13 | 2.04 |
| M092 | 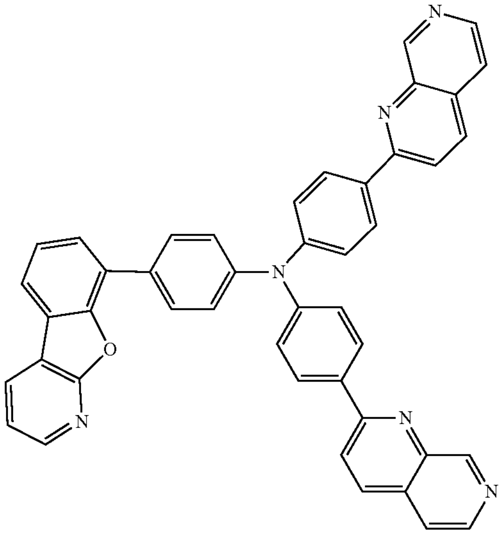 [SMILES: c1cnc2oc3c(-c4ccc(N(c5ccc(-c6ccc7ccncc7n6)cc5)c5ccc(-c6ccc7ccncc7n6)cc5)cc4)cccc3c2c1] | 2.17 | 2.08 | 2.02 |

TABLE 2-continued
| No. | Structure | Refractive index 460 nm | Refractive index 530 nm | Refractive index 620 nm |
|---|---|---|---|---|
| M104 | 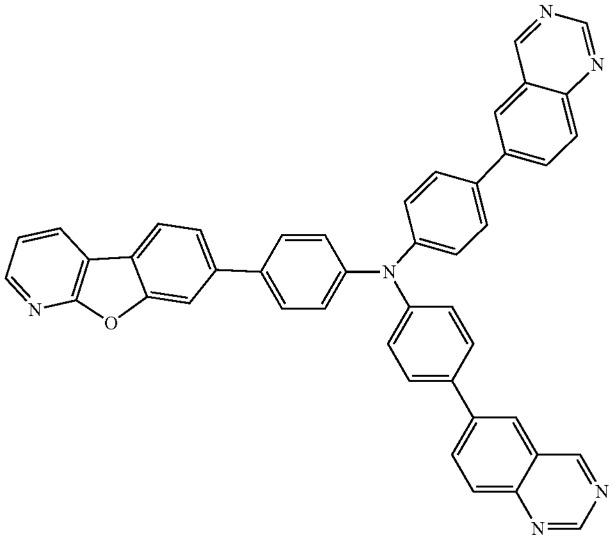 [SMILES: c1cnc2oc3cc(-c4ccc(N(c5ccc(-c6ccc7ncncc7c6)cc5)c5ccc(-c6ccc7ncncc7c6)cc5)cc4)ccc3c2c1] | 2.13 | 2.04 | 1.98 |
| M105 | 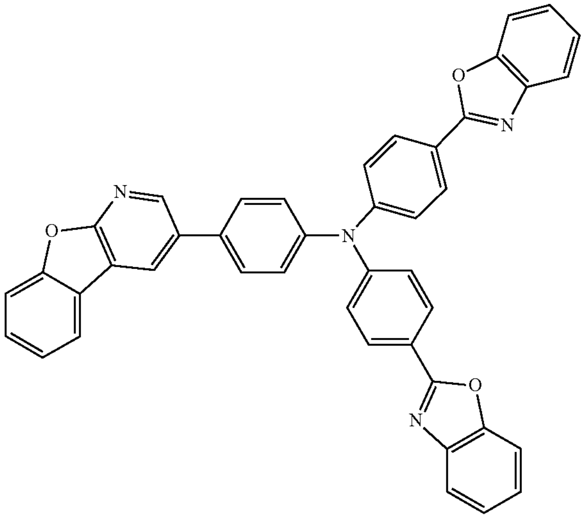 [SMILES: c1ccc2oc(-c3ccc(N(c4ccc(-c5cnc6oc7ccccc7c6c5)cc4)c4ccc(-c5nc6ccccc6o5)cc4)cc3)nc2c1] | 2.15 | 2.04 | 1.98 |

TABLE 2-continued
| No. | Structure | Refractive index 460 nm | Refractive index 530 nm | Refractive index 620 nm |
| --- | --- | --- | --- | --- |
| M113 | 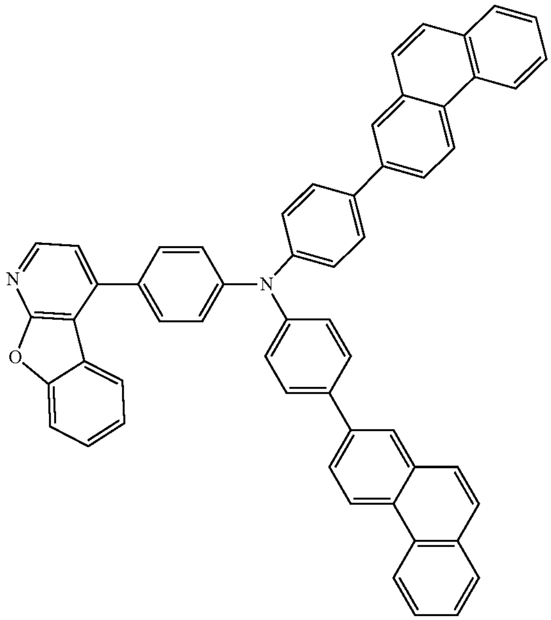 [SMILES: c1ccc2c(c1)ccc1cc(-c3ccc(N(c4ccc(-c5ccc6c(ccc7ccccc76)c5)cc4)c4ccc(-c5ccnc6oc7ccccc7c56)cc4)cc3)ccc12] | 2.12 | 2.03 | 1.98 |
| M123 | 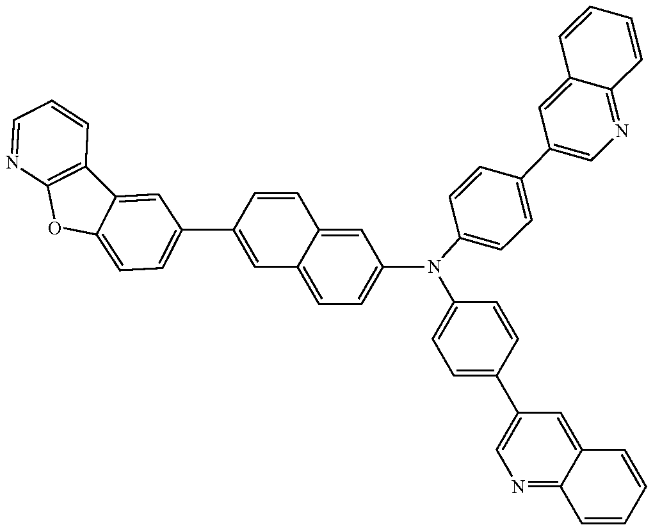 [SMILES: c1ccc2ncc(-c3ccc(N(c4ccc(-c5cnc6ccccc6c5)cc4)c4ccc5cc(-c6ccc7oc8ncccc8c7c6)ccc5c4)cc3)cc2c1] | 2.16 | 2.07 | 2.01 |

TABLE 2-continued
| No. | Structure | Refractive index 460 nm | Refractive index 530 nm | Refractive index 620 nm |
| --- | --- | --- | --- | --- |
| M128 | 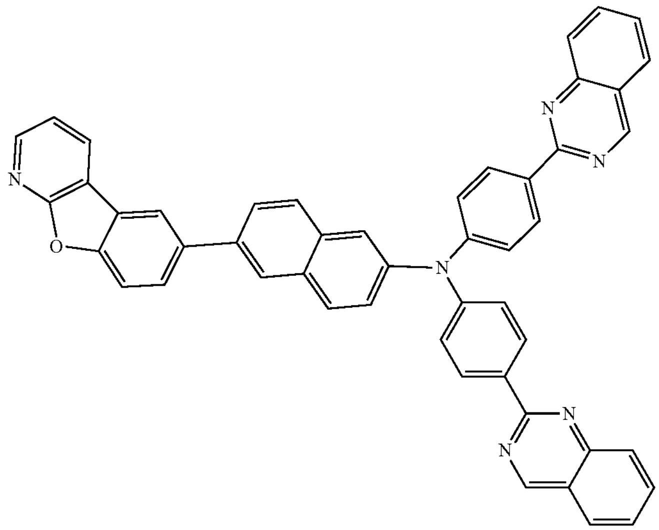 [SMILES: c1ccc2nc(-c3ccc(N(c4ccc(-c5ncc6ccccc6n5)cc4)c4ccc5cc(-c6ccc7oc8ncccc8c7c6)ccc5c4)cc3)ncc2c1] | 2.32 | 2.18 | 2.09 |
| M136 | 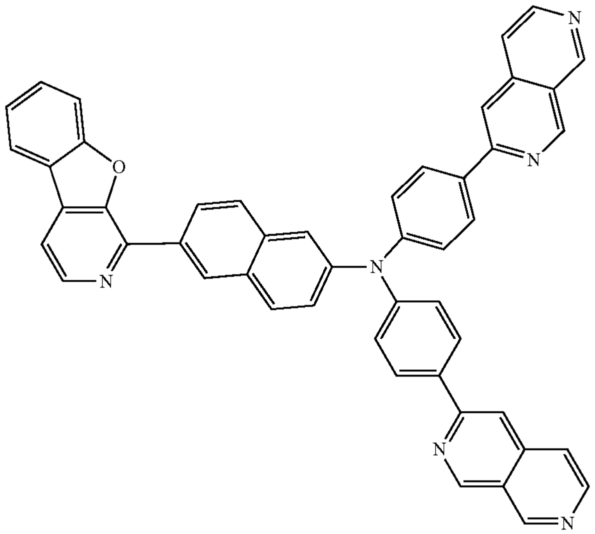 [SMILES: c1ccc2c(c1)oc1c(-c3ccc4cc(N(c5ccc(-c6cc7ccncc7cn6)cc5)c5ccc(-c6cc7ccncc7cn6)cc5)ccc4c3)nccc12] | 2.30 | 2.16 | 2.07 |

TABLE 2-continued
| No. | Structure | Refractive index 460 nm | Refractive index 530 nm | Refractive index 620 nm |
|---|---|---|---|---|
| M143 | 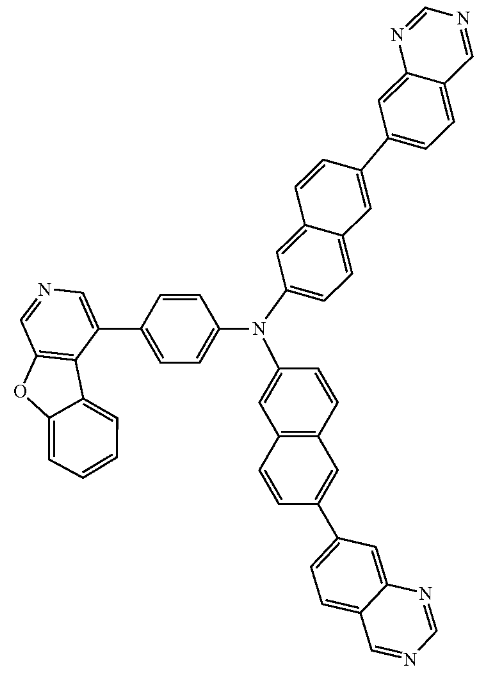 [SMILES: c1ccc2c(c1)oc1cncc(-c3ccc(N(c4ccc5cc(-c6ccc7cncnc7c6)ccc5c4)c4ccc5cc(-c6ccc7cncnc7c6)ccc5c4)cc3)c12] | 2.22 | 2.13 | 2.06 |
| M145 | 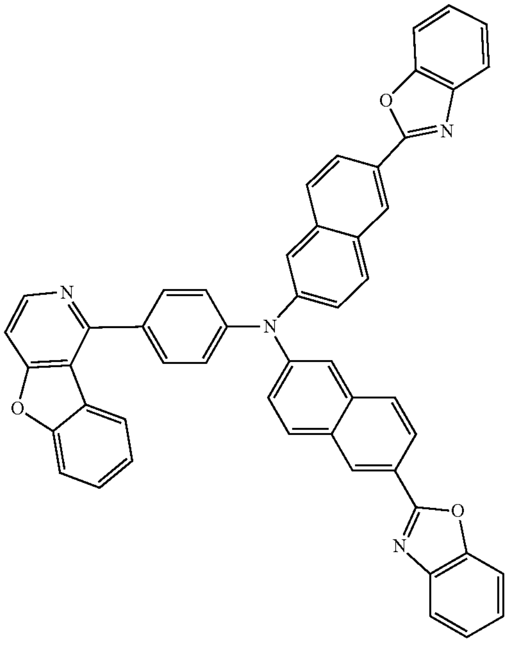 [SMILES: c1ccc2oc(-c3ccc4cc(N(c5ccc(-c6nccc7oc8ccccc8c67)cc5)c5ccc6cc(-c7nc8ccccc8o7)ccc6c5)ccc4c3)nc2c1] | 2.26 | 2.13 | 2.05 |

TABLE 2-continued
| No. | Structure | Refractive index 460 nm | Refractive index 530 nm | Refractive index 620 nm |
|---|---|---|---|---|
| M158 | 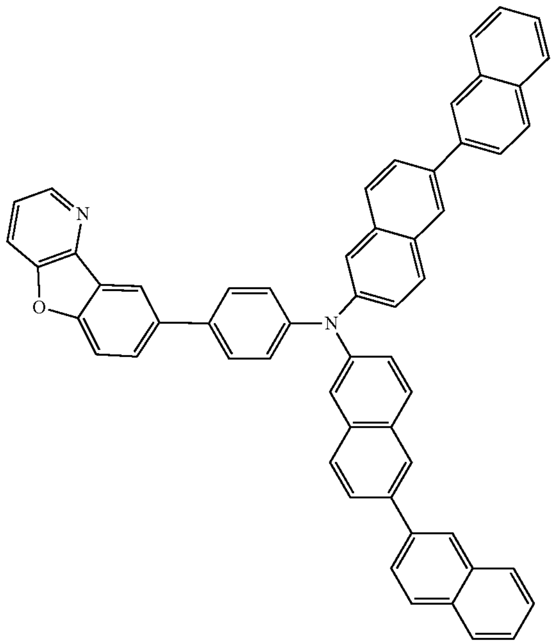 [SMILES: c1ccc2cc(-c3ccc4cc(N(c5ccc(-c6ccc7oc8cccnc8c7c6)cc5)c5ccc6cc(-c7ccc8ccccc8c7)ccc6c5)ccc4c3)ccc2c1] | 2.25 | 2.12 | 2.06 |
| M161 | 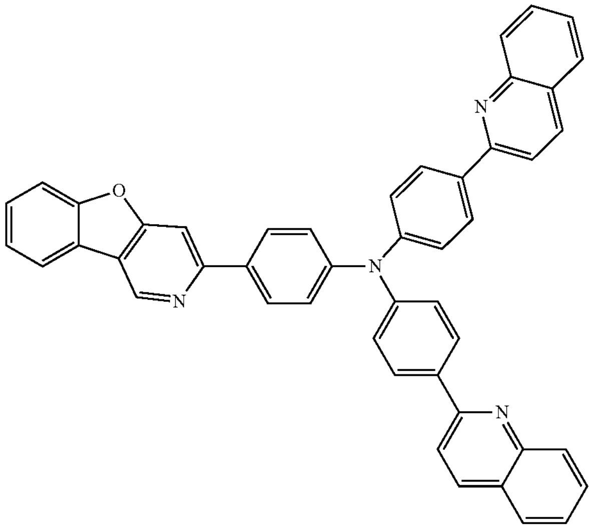 [SMILES: c1ccc2nc(-c3ccc(N(c4ccc(-c5cc6oc7ccccc7c6cn5)cc4)c4ccc(-c5ccc6ccccc6n5)cc4)cc3)ccc2c1] | 2.27 | 2.13 | 2.06 |

TABLE 2-continued
| No. | Structure | Refractive index 460 nm | Refractive index 530 nm | Refractive index 620 nm |
|---|---|---|---|---|
| M163 | 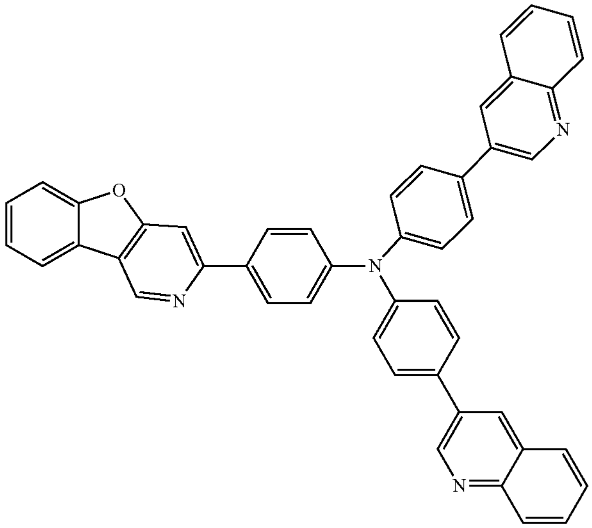 [SMILES: c1ccc2ncc(-c3ccc(N(c4ccc(-c5cnc6ccccc6c5)cc4)c4ccc(-c5cc6oc7ccccc7c6cn5)cc4)cc3)cc2c1] | 2.22 | 2.11 | 2.03 |
| M167 | 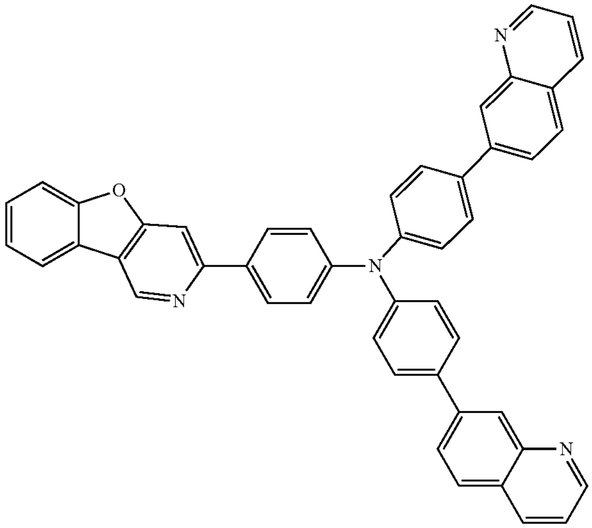 [SMILES: c1cnc2cc(-c3ccc(N(c4ccc(-c5ccc6cccnc6c5)cc4)c4ccc(-c5cc6oc7ccccc7c6cn5)cc4)cc3)ccc2c1] | 2.20 | 2.10 | 2.02 |

TABLE 2-continued
| No. | Structure | Refractive index 460 nm | Refractive index 530 nm | Refractive index 620 nm |
|---|---|---|---|---|
| M171 | 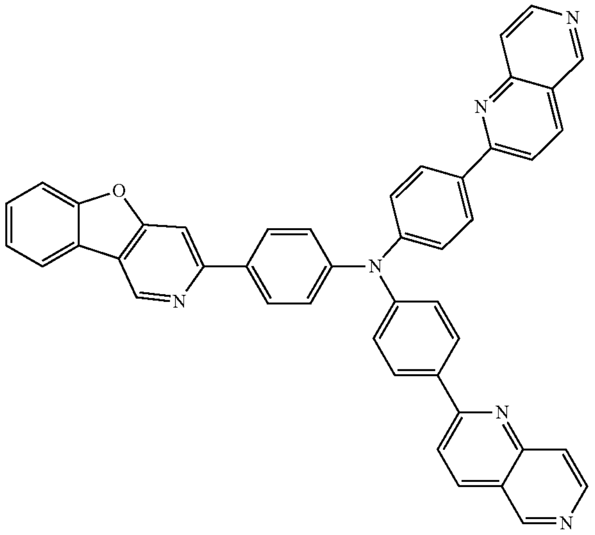 [SMILES: c1ccc2c(c1)oc1cc(-c3ccc(N(c4ccc(-c5ccc6cnccc6n5)cc4)c4ccc(-c5ccc6cnccc6n5)cc4)cc3)ncc12] | 2.26 | 2.12 | 2.04 |
| M184 | 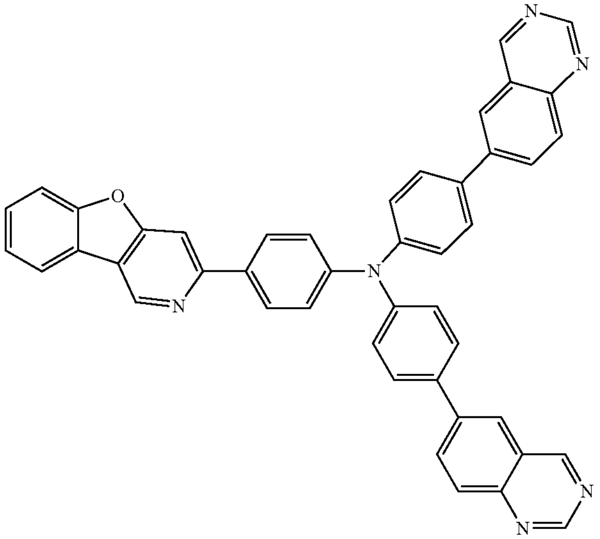 [SMILES: c1ccc2c(c1)oc1cc(-c3ccc(N(c4ccc(-c5ccc6ncncc6c5)cc4)c4ccc(-c5ccc6ncncc6c5)cc4)cc3)ncc12] | 2.16 | 2.06 | 2.00 |

TABLE 2-continued
| No. | Structure | Refractive index 460 nm | Refractive index 530 nm | Refractive index 620 nm |
|---|---|---|---|---|
| M189 | 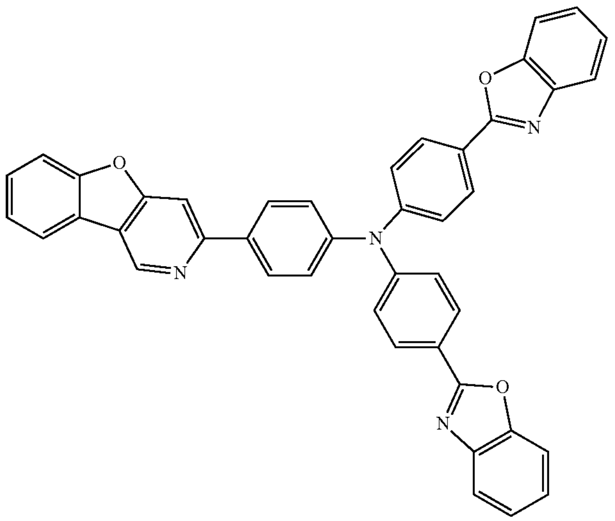 [SMILES: c1ccc2oc(-c3ccc(N(c4ccc(-c5cc6oc7ccccc7c6cn5)cc4)c4ccc(-c5nc6ccccc6o5)cc4)cc3)nc2c1] | 2.24 | 2.12 | 2.04 |
| M192 | 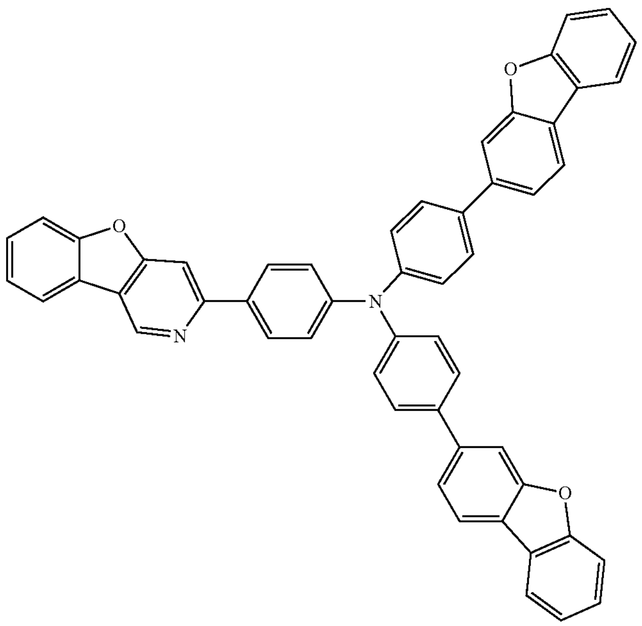 [SMILES: c1ccc2c(c1)oc1cc(-c3ccc(N(c4ccc(-c5ccc6c(c5)oc5ccccc56)cc4)c4ccc(-c5cc6oc7ccccc7c6cn5)cc4)cc3)ccc12] | 2.22 | 2.12 | 2.05 |

TABLE 2-continued
| No. | Structure | Refractive index 460 nm | Refractive index 530 nm | Refractive index 620 nm |
|---|---|---|---|---|
| M197 | 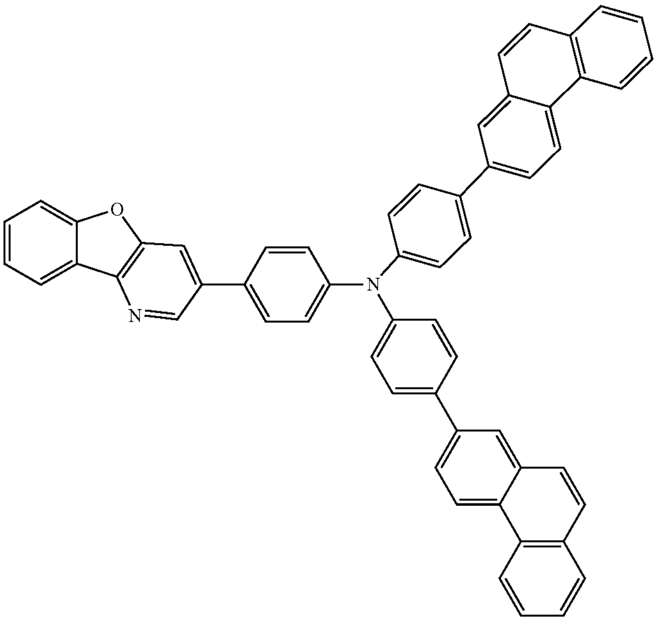 [SMILES: c1ccc2c(c1)ccc1cc(-c3ccc(N(c4ccc(-c5ccc6c(ccc7ccccc76)c5)cc4)c4ccc(-c5cnc6c(c5)oc5ccccc56)cc4)cc3)ccc12] | 2.23 | 2.12 | 2.05 |
| M198 | 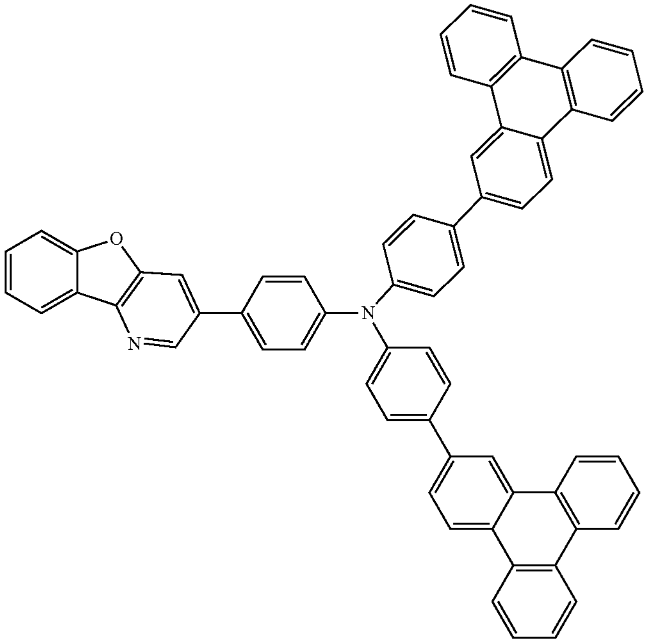 [SMILES: c1ccc2c(c1)oc1cc(-c3ccc(N(c4ccc(-c5ccc6c7ccccc7c7ccccc7c6c5)cc4)c4ccc(-c5ccc6c7ccccc7c7ccccc7c6c5)cc4)cc3)cnc12] | 2.20 | 2.10 | 2.03 |

TABLE 2-continued
| No. | Structure | Refractive index 460 nm | Refractive index 530 nm | Refractive index 620 nm |
|---|---|---|---|---|
| M215 | 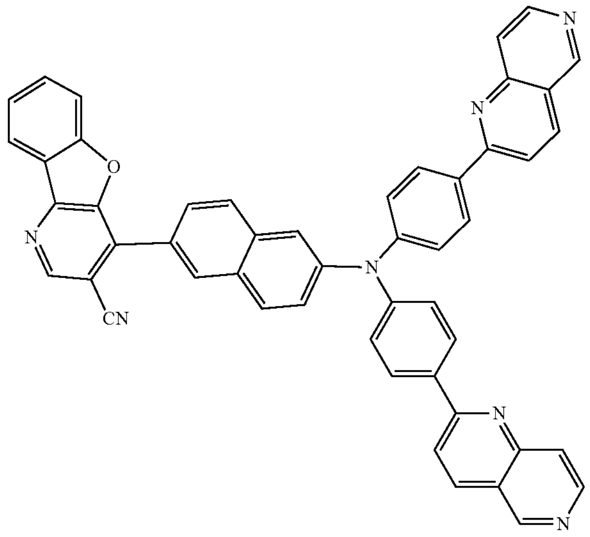 [SMILES: N#Cc1cnc2c(oc3ccccc32)c1-c1ccc2cc(N(c3ccc(-c4ccc5cnccc5n4)cc3)c3ccc(-c4ccc5cnccc5n4)cc3)ccc2c1] | 2.22 | 2.10 | 2.03 |
| M220 | 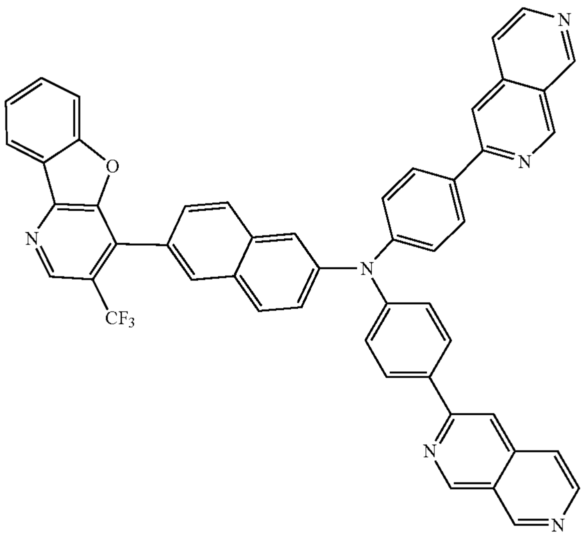 [SMILES: FC(F)(F)c1cnc2c(oc3ccccc32)c1-c1ccc2cc(N(c3ccc(-c4cc5ccncc5cn4)cc3)c3ccc(-c4cc5ccncc5cn4)cc3)ccc2c1] | 2.16 | 2.05 | 1.98 |

TABLE 2-continued
| No. | Structure | Refractive index 460 nm | Refractive index 530 nm | Refractive index 620 nm |
|---|---|---|---|---|
| M228 | 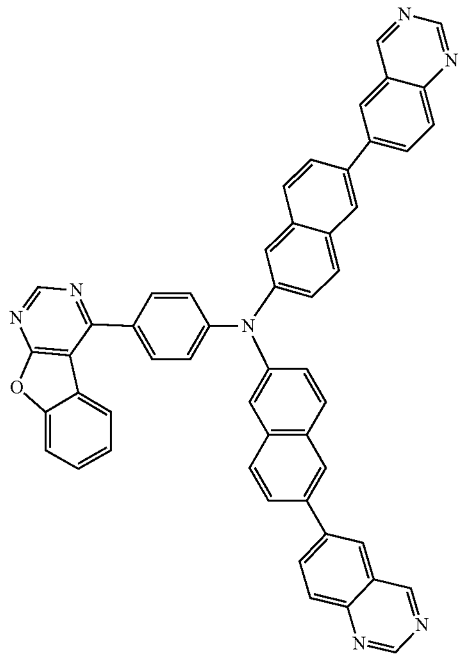 [SMILES: c1ccc2c(c1)oc1ncnc(-c3ccc(N(c4ccc5cc(-c6ccc7ncncc7c6)ccc5c4)c4ccc5cc(-c6ccc7ncncc7c6)ccc5c4)cc3)c12] | 2.17 | 2.08 | 2.02 |
| M229 | 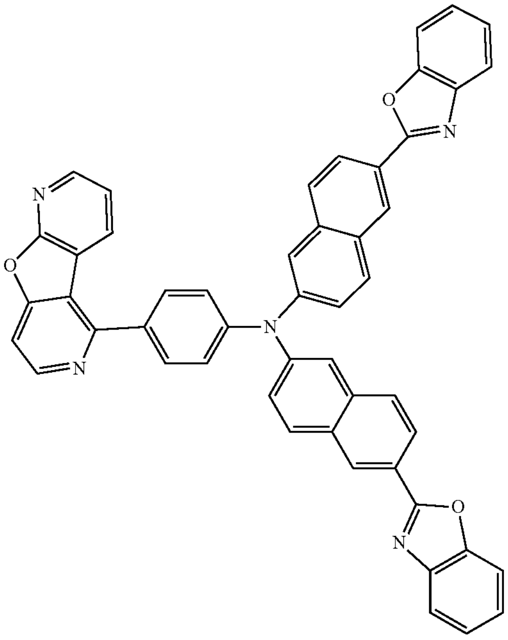 [SMILES: c1ccc2oc(-c3ccc4cc(N(c5ccc(-c6nccc7oc8ncccc8c67)cc5)c5ccc6cc(-c7nc8ccccc8o7)ccc6c5)ccc4c3)nc2c1] | 2.26 | 2.12 | 2.05 |

TABLE 2-continued
| No. | Structure | Refractive index 460 nm | Refractive index 530 nm | Refractive index 620 nm |
|---|---|---|---|---|
| M237 | 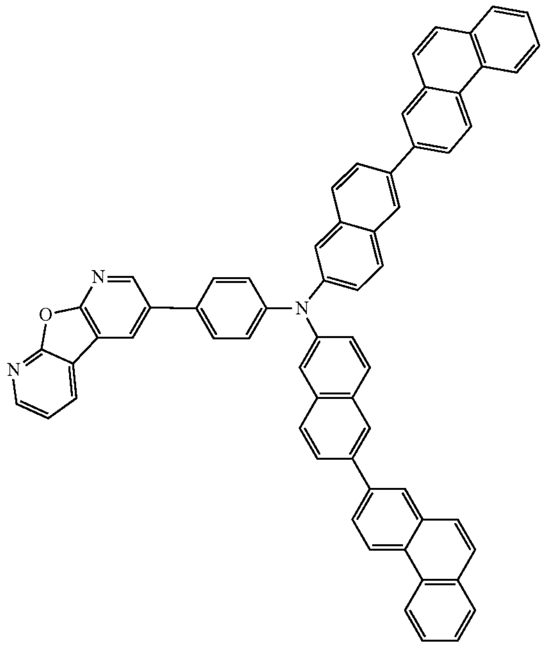 [SMILES: c1ccc2c(c1)ccc1cc(-c3ccc4cc(N(c5ccc(-c6cnc7oc8ncccc8c7c6)cc5)c5ccc6cc(-c7ccc8c(ccc9ccccc98)c7)ccc6c5)ccc4c3)ccc12] | 2.30 | 2.18 | 2.10 |
| M242 | 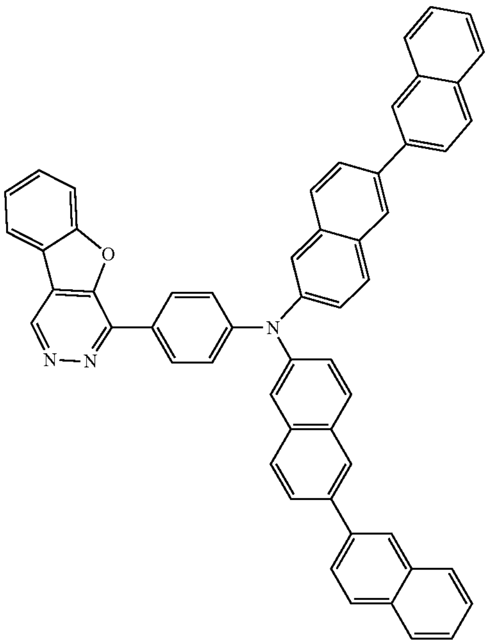 [SMILES: c1ccc2cc(-c3ccc4cc(N(c5ccc(-c6nncc7c6oc6ccccc67)cc5)c5ccc6cc(-c7ccc8ccccc8c7)ccc6c5)ccc4c3)ccc2c1] | 2.26 | 2.14 | 2.07 |

TABLE 2-continued
| No. | Structure | Refractive index 460 nm | Refractive index 530 nm | Refractive index 620 nm |
|---|---|---|---|---|
| M246 | 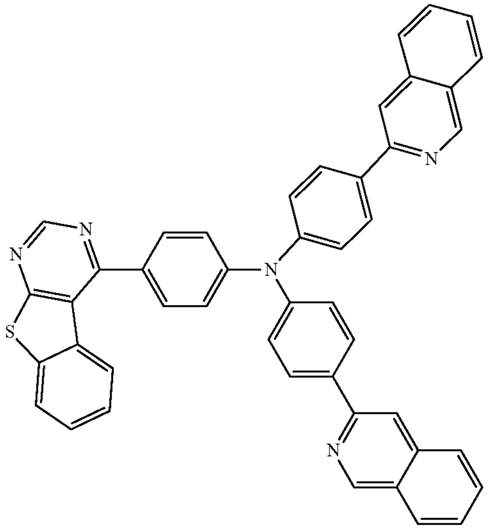 [SMILES: c1ccc2cc(-c3ccc(N(c4ccc(-c5cc6ccccc6cn5)cc4)c4ccc(-c5ncnc6sc7ccccc7c56)cc4)cc3)ncc2c1] | 2.17 | 2.05 | 2.00 |
| M261 | 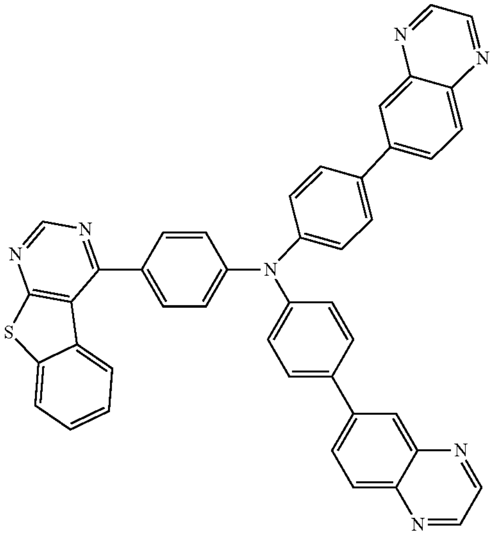 [SMILES: c1ccc2c(c1)sc1ncnc(-c3ccc(N(c4ccc(-c5ccc6nccnc6c5)cc4)c4ccc(-c5ccc6nccnc6c5)cc4)cc3)c12] | 2.09 | 2.00 | 1.96 |

TABLE 2-continued
| No. | Structure | Refractive index 460 nm | Refractive index 530 nm | Refractive index 620 nm |
|---|---|---|---|---|
| M265 | 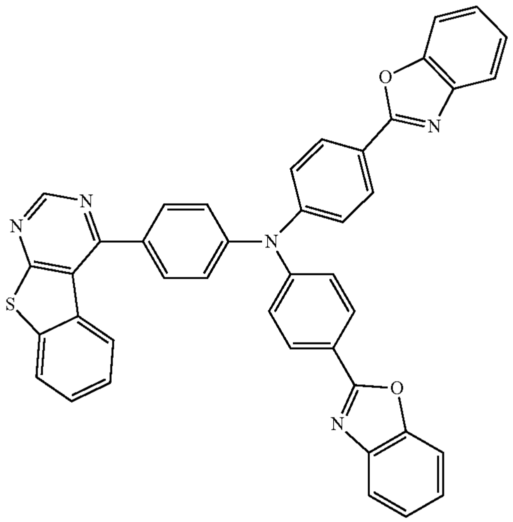 [SMILES: c1ccc2oc(-c3ccc(N(c4ccc(-c5nc6ccccc6o5)cc4)c4ccc(-c5ncnc6sc7ccccc7c56)cc4)cc3)nc2c1] | 2.13 | 2.02 | 1.97 |
| M274 | 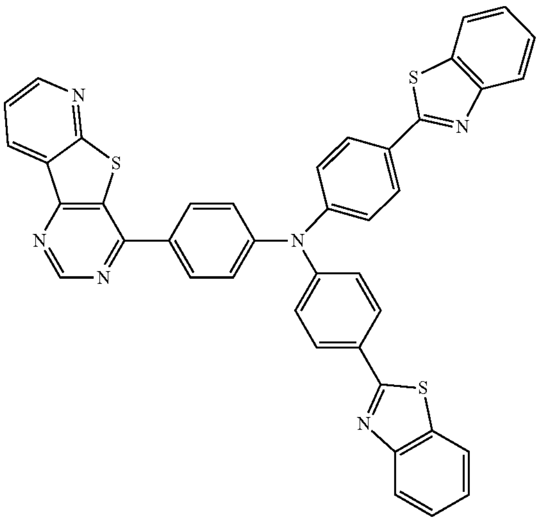 [SMILES: c1ccc2sc(-c3ccc(N(c4ccc(-c5nc6ccccc6s5)cc4)c4ccc(-c5ncnc6c5sc5ncccc56)cc4)cc3)nc2c1] | 2.24 | 2.10 | 2.03 |

TABLE 2-continued
| No. | Structure | Refractive index 460 nm | Refractive index 530 nm | Refractive index 620 nm |
|---|---|---|---|---|
| M277 | 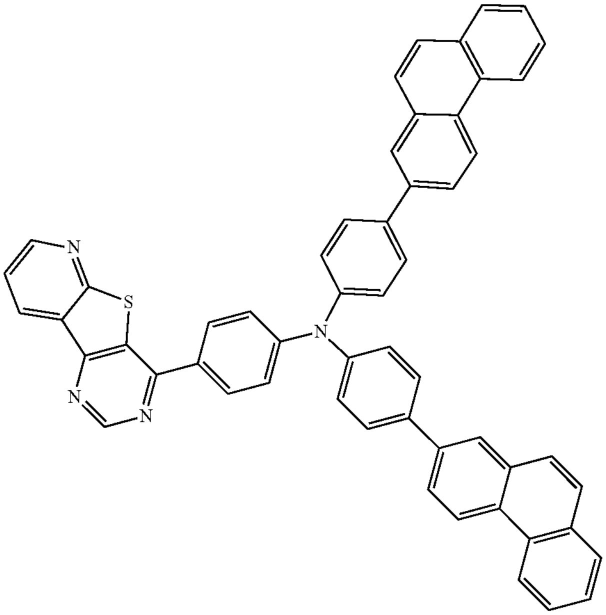 [SMILES: c1ccc2c(c1)ccc1cc(-c3ccc(N(c4ccc(-c5ccc6c(ccc7ccccc76)c5)cc4)c4ccc(-c5ncnc6c5sc5ncccc56)cc4)cc3)ccc12] | 2.22 | 2.11 | 2.04 |
| M295 | 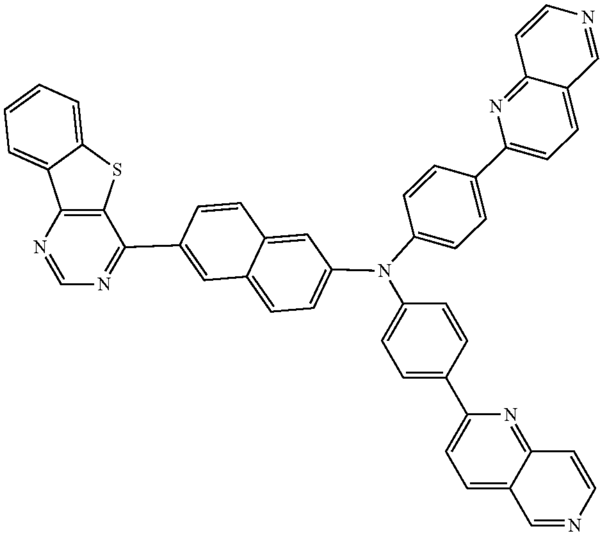 [SMILES: c1ccc2c(c1)sc1c(-c3ccc4cc(N(c5ccc(-c6ccc7cnccc7n6)cc5)c5ccc(-c6ccc7cnccc7n6)cc5)ccc4c3)ncnc12] | 2.27 | 2.13 | 2.05 |

TABLE 2-continued
| No. | Structure | Refractive index 460 nm | Refractive index 530 nm | Refractive index 620 nm |
|---|---|---|---|---|
| M305 | 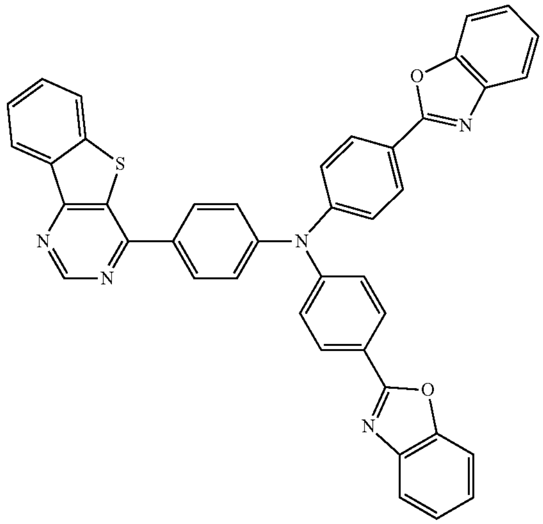 [SMILES: c1ccc2oc(-c3ccc(N(c4ccc(-c5nc6ccccc6o5)cc4)c4ccc(-c5ncnc6c5sc5ccccc56)cc4)cc3)nc2c1] | 2.18 | 2.06 | 1.99 |
| M314 | 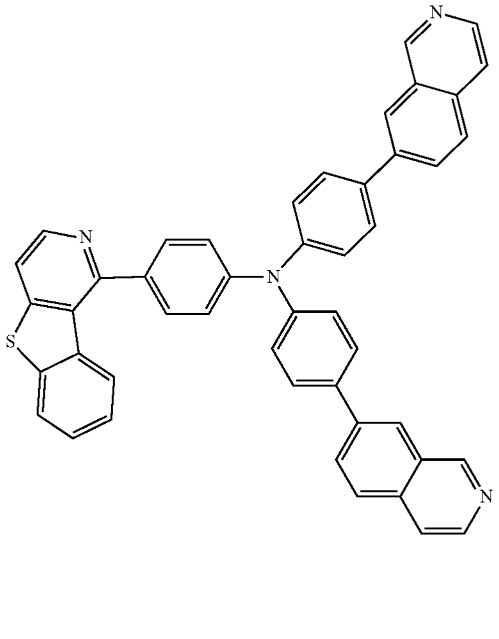 [SMILES: c1ccc2c(c1)sc1ccnc(-c3ccc(N(c4ccc(-c5ccc6ccncc6c5)cc4)c4ccc(-c5ccc6ccncc6c5)cc4)cc3)c12] | 2.07 | 1.99 | 1.95 |

TABLE 2-continued
| No. | Structure | Refractive index 460 nm | Refractive index 530 nm | Refractive index 620 nm |
|---|---|---|---|---|
| M324 | 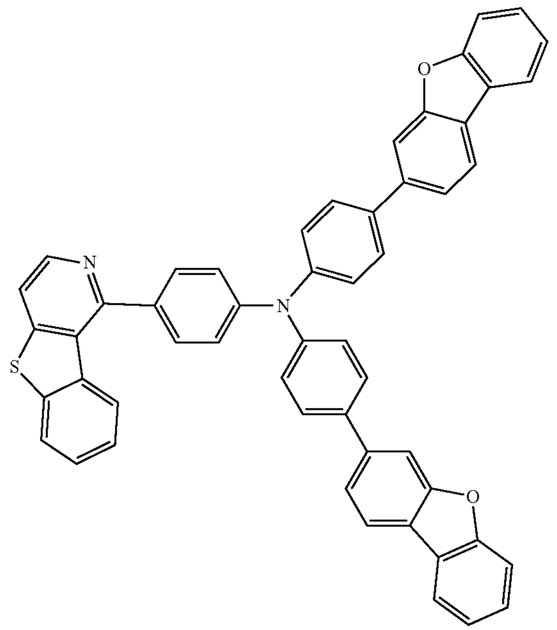 [SMILES: c1ccc2c(c1)oc1cc(-c3ccc(N(c4ccc(-c5ccc6c(c5)oc5ccccc56)cc4)c4ccc(-c5nccc6sc7ccccc7c56)cc4)cc3)ccc12] | 2.11 | 2.02 | 1.97 |
| M340 | 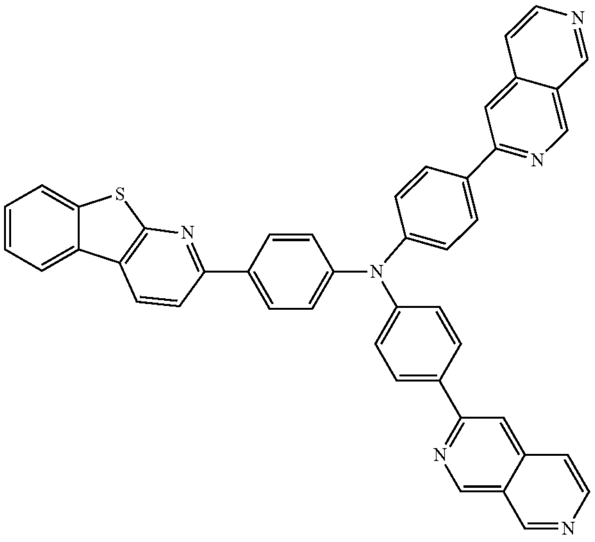 [SMILES: c1ccc2c(c1)sc1nc(-c3ccc(N(c4ccc(-c5cc6ccncc6cn5)cc4)c4ccc(-c5cc6ccncc6cn5)cc4)cc3)ccc12] | 2.28 | 2.14 | 2.06 |

TABLE 2-continued
| No. | Structure | Refractive index 460 nm | Refractive index 530 nm | Refractive index 620 nm |
|---|---|---|---|---|
| M353 | 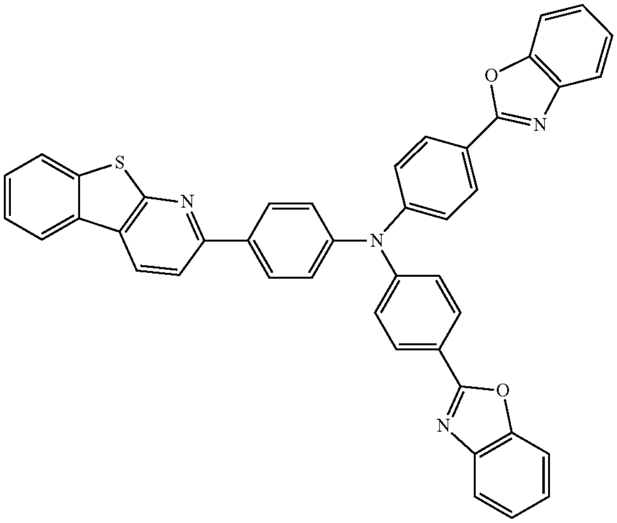 [SMILES: c1ccc2oc(-c3ccc(N(c4ccc(-c5ccc6c(n5)sc5ccccc56)cc4)c4ccc(-c5nc6ccccc6o5)cc4)cc3)nc2c1] | 2.26 | 2.12 | 2.04 |
| M362 | 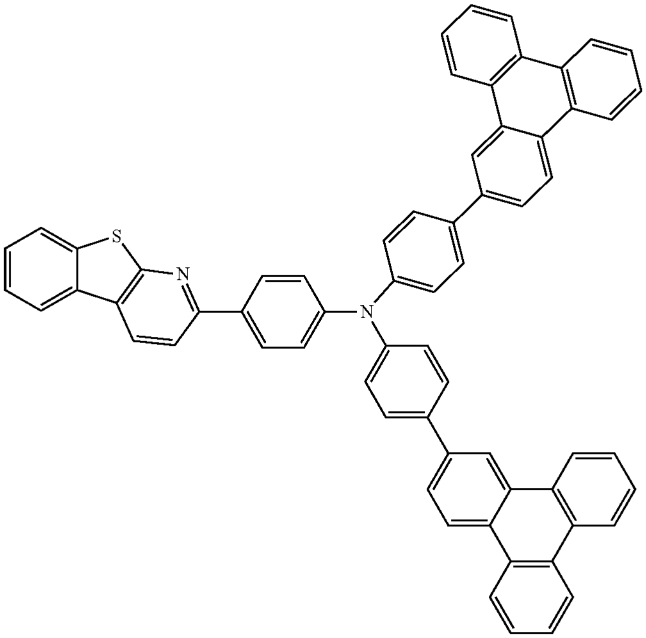 [SMILES: c1ccc2c(c1)sc1nc(-c3ccc(N(c4ccc(-c5ccc6c7ccccc7c7ccccc7c6c5)cc4)c4ccc(-c5ccc6c7ccccc7c7ccccc7c6c5)cc4)cc3)ccc12] | 2.32 | 2.19 | 2.11 |

TABLE 2-continued
| No. | Structure | Refractive index 460 nm | Refractive index 530 nm | Refractive index 620 nm |
|---|---|---|---|---|
| M381 | 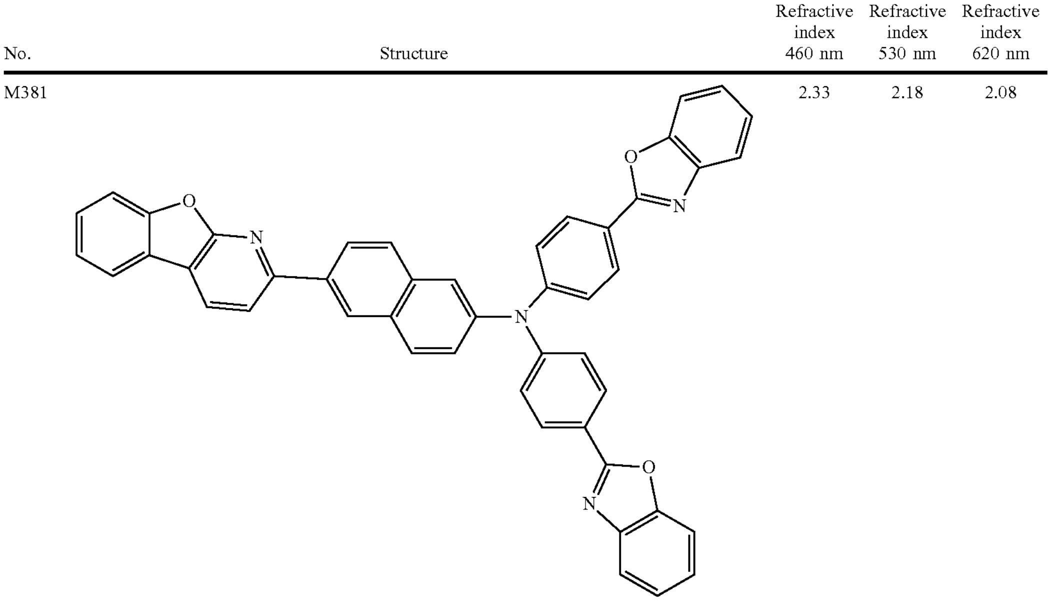 | 2.33 | 2.18 | 2.08 |
| M382 | 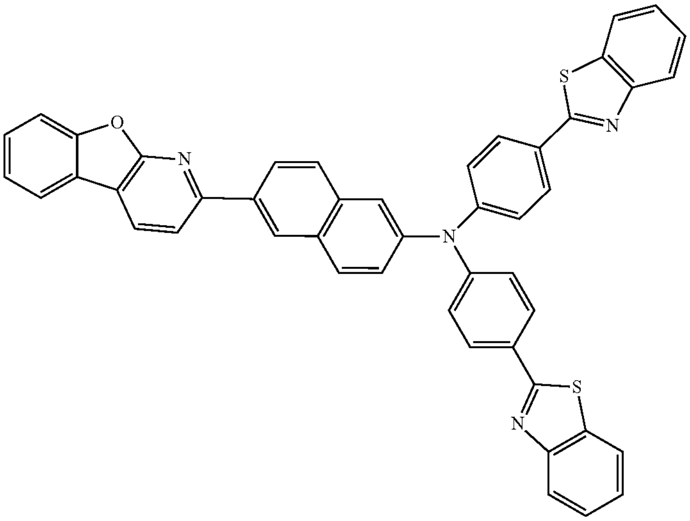 [SMILES: c1ccc2sc(-c3ccc(N(c4ccc(-c5nc6ccccc6s5)cc4)c4ccc5cc(-c6ccc7c(n6)oc6ccccc67)ccc5c4)cc3)nc2c1] | 2.38 | 2.21 | 2.11 |
| M385 | 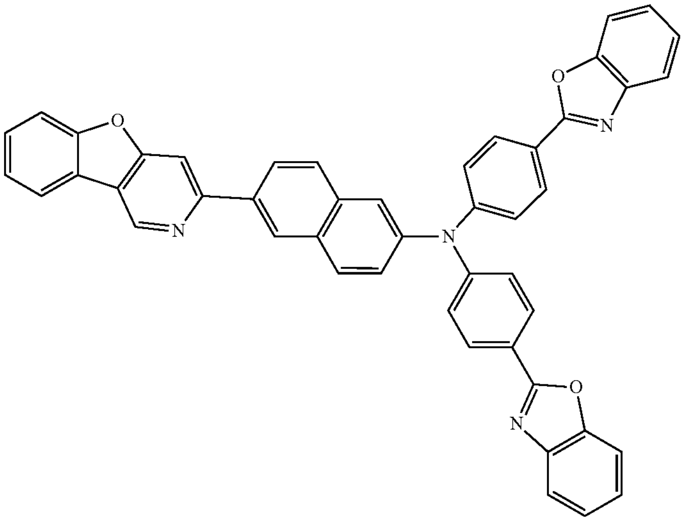 [SMILES: c1ccc2oc(-c3ccc(N(c4ccc(-c5nc6ccccc6o5)cc4)c4ccc5cc(-c6cc7oc8ccccc8c7cn6)ccc5c4)cc3)nc2c1] | 2.31 | 2.16 | 2.08 |

TABLE 2-continued
| No. | Structure | Refractive index 460 nm | Refractive index 530 nm | Refractive index 620 nm |
|---|---|---|---|---|
| M388 | 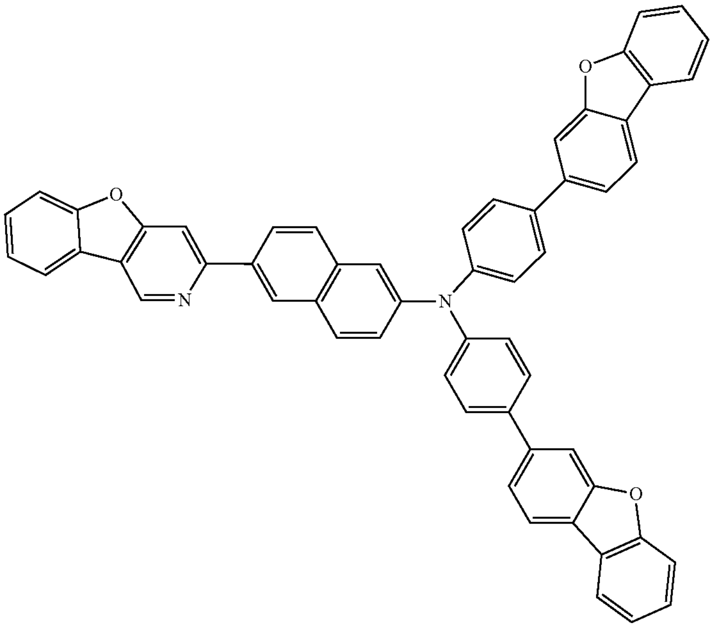 [SMILES: c1ccc2c(c1)oc1cc(-c3ccc(N(c4ccc(-c5ccc6c(c5)oc5ccccc56)cc4)c4ccc5cc(-c6cc7oc8ccccc8c7cn6)ccc5c4)cc3)ccc12] | 2.29 | 2.16 | 2.08 |
| M401 | 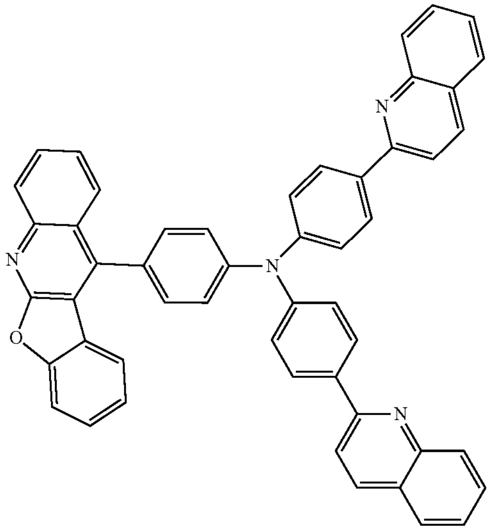 [SMILES: c1ccc2nc(-c3ccc(N(c4ccc(-c5ccc6ccccc6n5)cc4)c4ccc(-c5c6ccccc6nc6oc7ccccc7c56)cc4)cc3)ccc2c1] | 2.14 | 2.04 | 1.98 |

TABLE 2-continued
| No. | Structure | Refractive index 460 nm | Refractive index 530 nm | Refractive index 620 nm |
| --- | --- | --- | --- | --- |
| M413 | 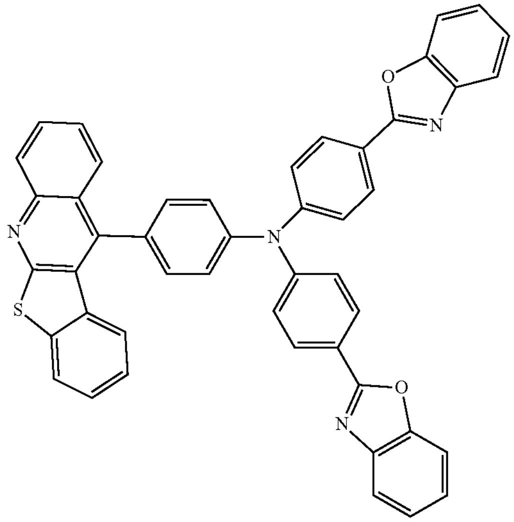 [SMILES: c1ccc2oc(-c3ccc(N(c4ccc(-c5nc6ccccc6o5)cc4)c4ccc(-c5c6ccccc6nc6sc7ccccc7c56)cc4)cc3)nc2c1] | 2.10 | 2.01 | 1.96 |
| M416 | 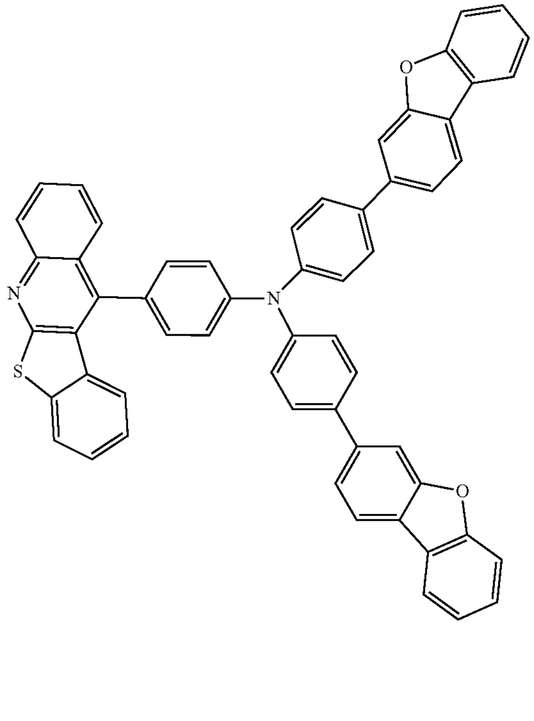 [SMILES: c1ccc2c(-c3ccc(N(c4ccc(-c5ccc6c(c5)oc5ccccc56)cc4)c4ccc(-c5ccc6c(c5)oc5ccccc56)cc4)cc3)c3c(nc2c1)sc1ccccc13] | 2.10 | 2.02 | 1.97 |

TABLE 2-continued
| No. | Structure | Refractive index 460 nm | Refractive index 530 nm | Refractive index 620 nm |
| --- | --- | --- | --- | --- |
| Ref 1 | 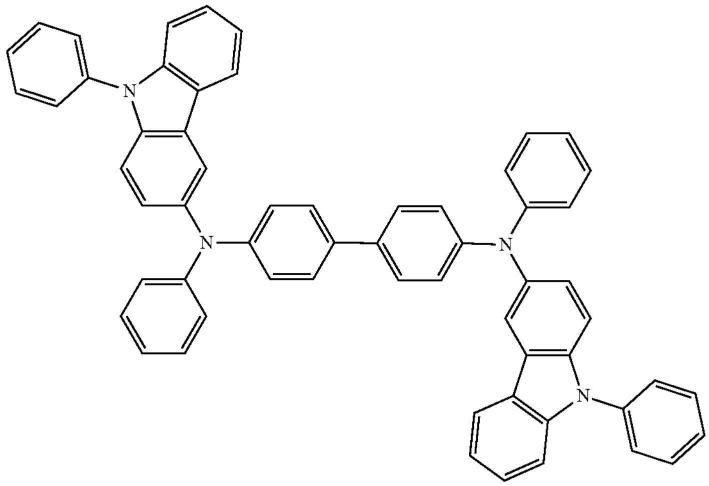 Ref 1 | 2.03 | 1.95 | 1.90 |
| Ref 2 | 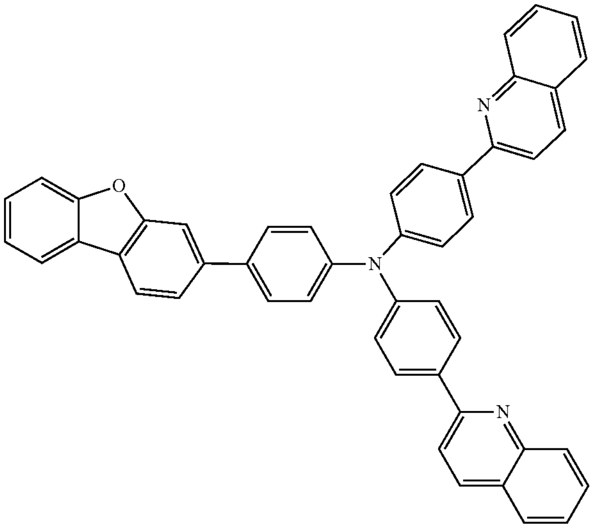 Ref 2 | 2.21 | 2.10 | 2.03 |

TABLE 2-continued

| No. | Structure | Refractive index 460 nm | Refractive index 530 nm | Refractive index 620 nm |
|---|---|---|---|---|
| Ref 3 | 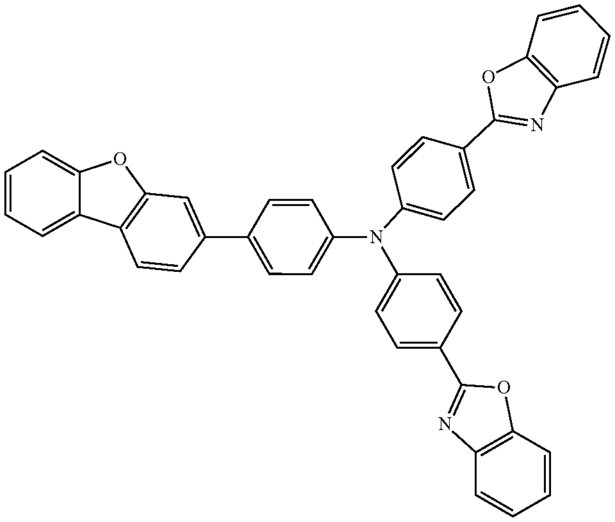 Ref 3 | 2.20 | 2.08 | 2.01 |
| Ref 4 | 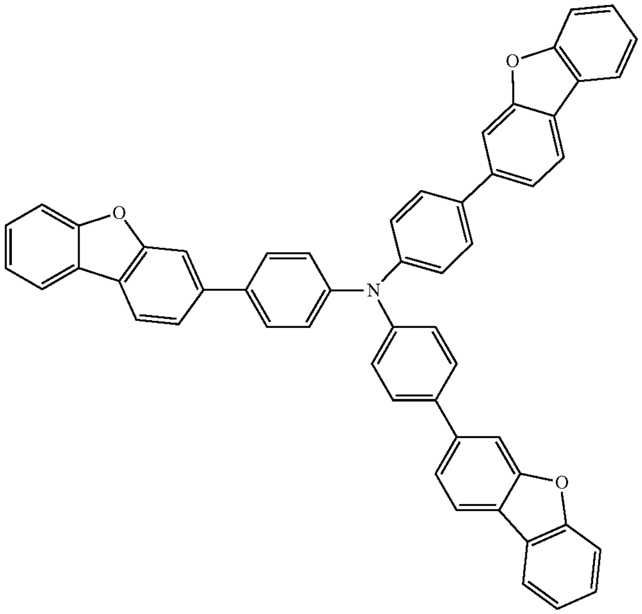 Ref 4 | 2.18 | 2.08 | 2.02 |

According to the data in Table 1, compared with a commonly used capping layer material Ref 1 in the industry, the compounds in the present disclosure may have higher refractive indices in the entire visible wavelength range. Therefore, when the above compounds are used as capping layer materials in an OLED device of the blue, green and red light-emitting devices, a substantially high light-emitting efficiency may be expected.

Application Embodiment 1A

The present application embodiment provides an OLED device. The figure illustrates a schematic diagram of an organic light-emitting device consistent with various disclosed embodiments of the present disclosure. Referring to the Figure, the OLED device may include a substrate 1, an anode 2, a hole injection layer 3, a first hole transport layer 4, a second hole transport layer 5, a light-emitting layer 6, an electron transport layer 7, an electron injection layer 8, a cathode 9 and a capping layer 10 that are stacked in sequence.

The structure of the OLED blue-light device may include: ITO (10 nm)/compound 1:compound 2 (3:97 mass ratio) (5 nm)/compound 3 (100 nm)/compound 4 (5 nm)/compound 5:compound 6 (97:3 mass ratio) (30 nm)/compound 7 (5 nm)/compound 8:compound 9 (1:1 mass ratio) (30 nm)/Mg:Ag (10:90 mass ratio) (10 nm)/M001 (70 nm).

The preparation method of the OLED device may include following.

1) A glass substrate having a size of 50 mm×50 mm×0.7 mm may be provided. The glass substrate may be sonicated in isopropanol and deionized water for 30 minutes, respectively, and then may be exposed to ozone for approximately 10 minutes for cleaning, to obtain the substrate 1. The obtained glass substrate with a 10 nm indium tin oxide (ITO) anode may be mounted on a vacuum deposition apparatus.

2) The hole injection layer material compound 2 and the p-doped material compound 1 may be co-evaporated on the ITO anode 2 through a vacuum evaporation, to form the hole injection layer 3 with a doping ratio of approximately 3% (mass ratio) and a thickness of approximately 5 nm.

3) The hole transport layer material compound 3 may be evaporated on the hole injection layer 3 through a vacuum evaporation, to form the first hole transport layer 4 with a thickness of approximately 100 nm.

4) The hole transport layer material compound 4 may be evaporated on the first hole transport layer 4 through a vacuum evaporation, to form the second hole transport layer 5 with a thickness of approximately 5 nm.

5) The compound 5 as a host material and the compound 6 as a doping material may be co-evaporated on the second hole transport layer 5 through a vacuum evaporation, to form the light-emitting layer 6 with a doping ratio of approximately 3% (mass ratio) and a thickness of approximately 30 nm.

6) The electron transport material compound 7 may be evaporated on the light-emitting layer 6 through a vacuum evaporation, to form the electron transport layer 7 with a thickness of approximately 5 nm.

7) The electron transport material compound 8 and the compound 9 may be co-evaporated on the electron transport layer 7 through a vacuum evaporation, to form the electron injection layer 8 with a doping mass ratio of approximately 1:1 and a thickness of approximately 30 nm.

8) Magnesium-silver electrode may be evaporated on the electron injection layer 8 through a vacuum evaporation, to form the cathode 9 with a Mg:Ag mass ratio of approximately 1:9 and a thickness of approximately 10 nm.

9) The compound M001 may be evaporated on the cathode 9 through a vacuum evaporation, to form the capping layer 10 with a thickness of approximately 70 nm.

The structure of the compounds used in the OLED device may have the following structures.

Compound 1

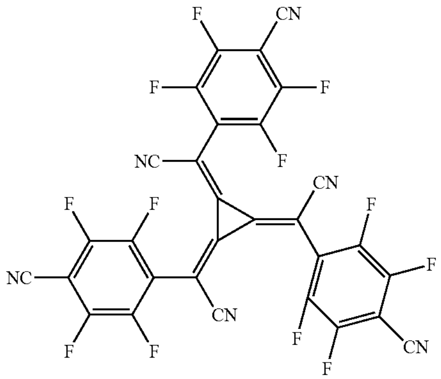

-continued

Compound 2

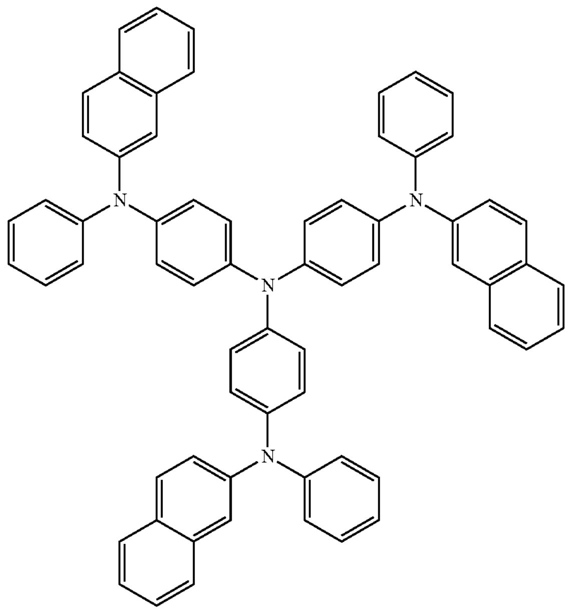

Compound 3

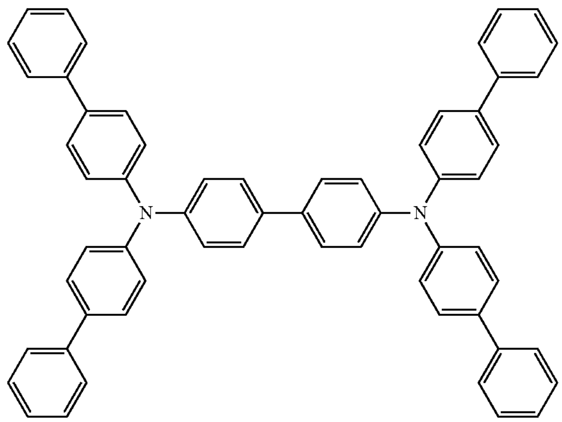

Compound 4

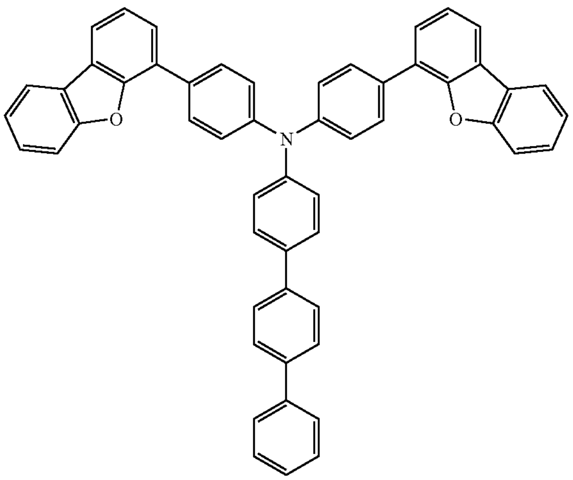

-continued

Compound 5

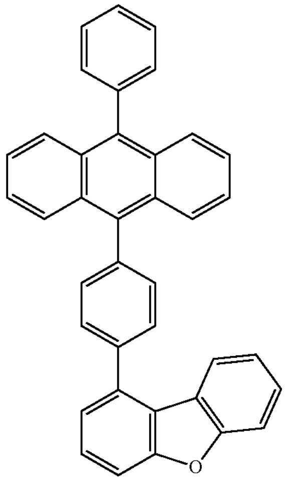

Compound 6

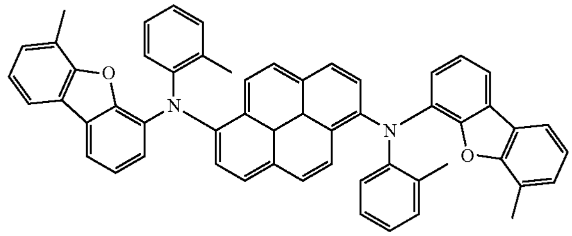

Compound 7

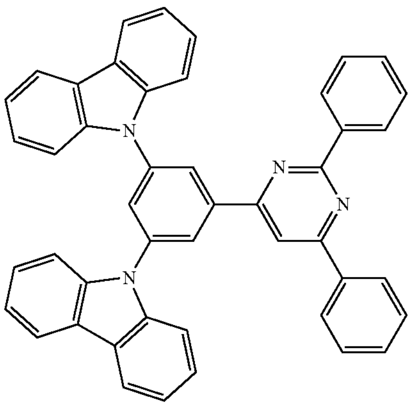

Compound 8

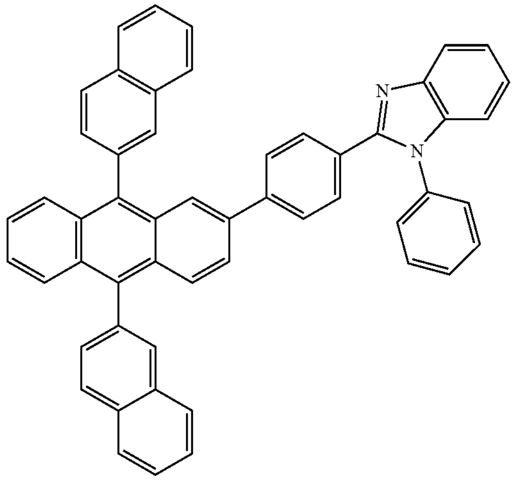

-continued

Compound 9

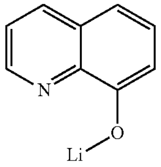

C1

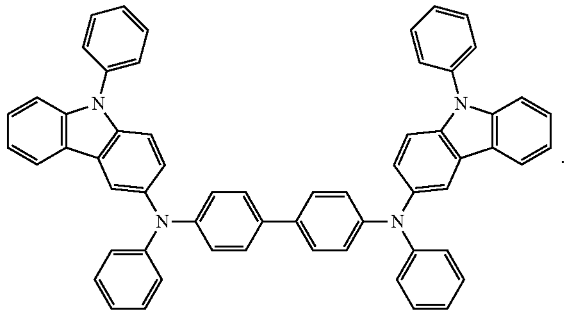

Application Embodiment 1B

The present application embodiment provides an OLED device. The preparation method of the OLED device in the present application embodiment may be the same as the preparation method of the OLED device in the application embodiment 1A, while the OLED device in the present embodiment may have the following device structure.

The structure of the OLED green-light device may include: ITO (10 nm)/compound 1:compound 2 (3:97 mass ratio) (5 nm)/compound 3 (140 nm)/compound 4 (5 nm)/CBP:Ir (ppy)$_3$ (9:1 mass ratio) (40 nm)/compound 7 (5 nm)/compound 8:compound 9 (1:1 mass ratio) (30 nm)/Mg:Ag (10:90 mass ratio) (10 nm)/M001 (70 nm).

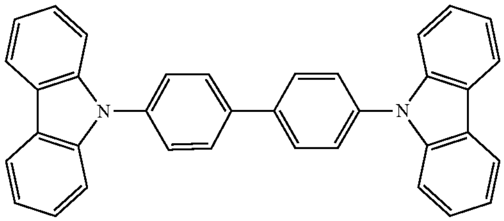

CBP

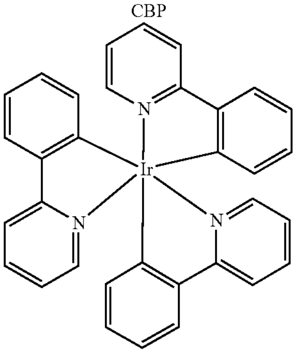

Ir(ppy)$_3$

Application Embodiment 1C

The present application embodiment provides an OLED device. The preparation method of the OLED device in the present application embodiment may be the same as the preparation method of the OLED device in the application embodiment 1A, while the OLED device in the present embodiment may have the following device structure.

The structure of the OLED red-light device may include: ITO (10 nm)/compound 1:compound 2 (3:97 mass ratio) (5 nm)/compound 3 (190 nm)/compound 4 (5 nm)/CBP:Ir(piq)$_2$(acac) (96:4 mass ratio) (40 nm)/compound 7 (5 nm)/compound 8:compound 9 (1:1 mass ratio) (30 nm)/Mg:Ag (10:90 mass ratio) (10 nm)/M001 (70 nm).

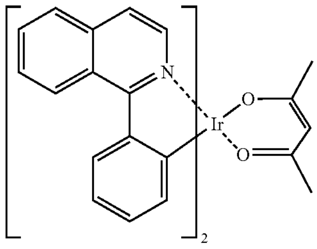

Ir(piq)$_2$(acac)

The difference between application embodiments 2 (A,B,C)-72 (A,B,C) and application embodiments 1(A,B,C) may include that the compound M001 may be replaced with the compounds in Table 3.

Comparative Embodiment 1

The difference between the present comparative embodiment and application embodiments 1(A,B,C) may include that the organic compound M001 in step (9) may be replaced with an equivalent amount of the comparative compound Ref 1. The other preparation steps in the present comparative embodiment may be the same as the preparation steps in the application embodiment 1A.

Ref 1

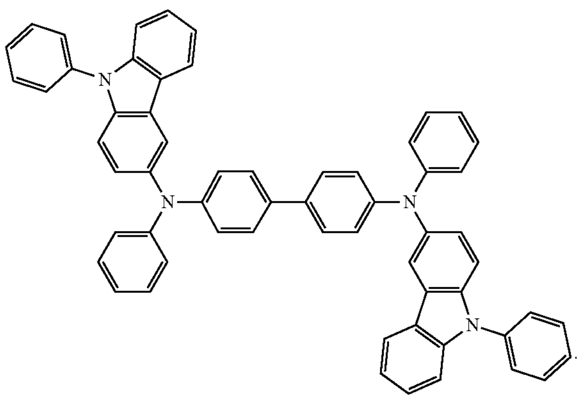

Comparative Embodiment 2

The difference between the present comparative embodiment and application embodiments 1(A,B,C) may include that the organic compound M001 in step (9) may be replaced with an equivalent amount of the comparative compound Ref 2. The other preparation steps in the present comparative embodiment may be the same as the preparation steps in the application embodiment 1A.

Ref 2

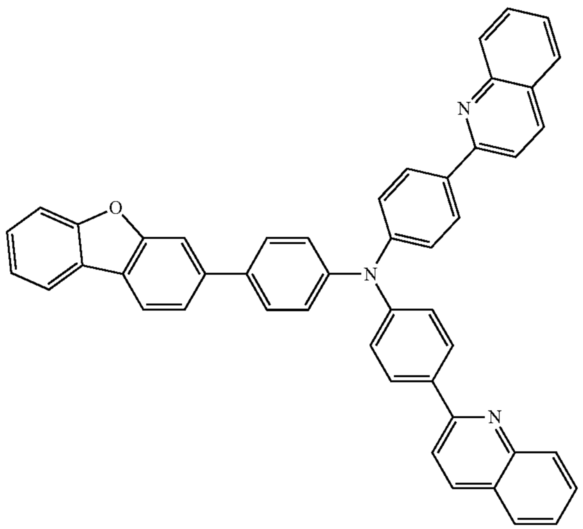

m

Comparative Embodiment 3

The difference between the present comparative embodiment and application embodiments 1(A,B,C) may include that the organic compound M001 in step (9) may be replaced with an equivalent amount of the comparative compound Ref 3. The other preparation steps in the present comparative embodiment may be the same as the preparation steps in the application embodiment 1A.

Ref 3

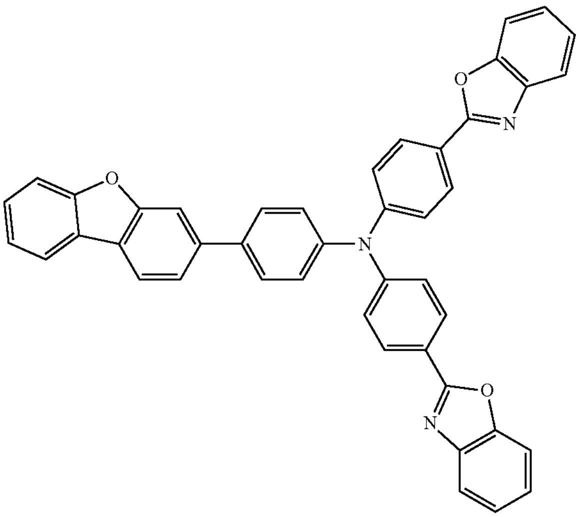

Comparative Embodiment 4

The difference between the present comparative embodiment and application embodiments 1(A,B,C) may include that the organic compound M001 in step (9) may be replaced with an equivalent amount of the comparative compound Ref 4. The other preparation steps in the present comparative embodiment may be the same as the preparation steps in the application embodiment 1A.

Ref 4

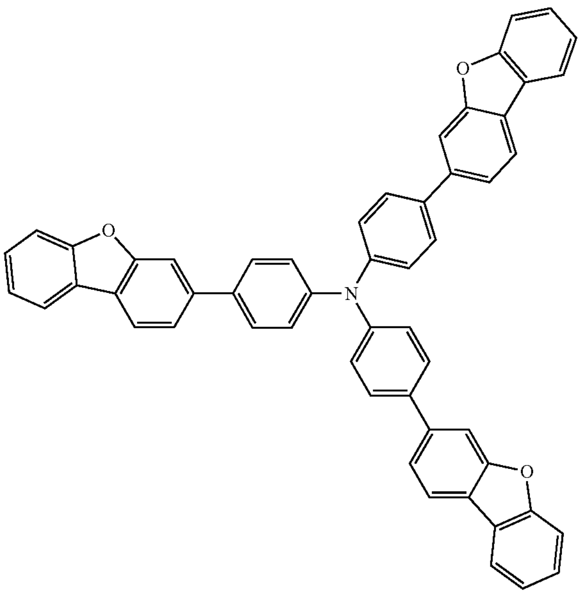

Performance evaluation of the OLED device

A Keithley 2365A digital nano-voltmeter may be used to test the current of the OLED device at a different voltage, and then the current may be divided by the light-emitting area to obtain a current density of the OLED device at the different voltage. The brightness and radiant energy flux density of the OLED device at the different voltage may be tested using a Konicaminolta CS-2000 spectroradiometer. According to the current density and brightness of the OLED device at the different voltage, the operating driving voltage and current efficiency (Cd/A) under a same current density (10 mA/cm$^2$) may be obtained. The service lifetime of the OLED device may be obtained by measuring the duration when the brightness of the OLED device reaches 95% of the initial brightness (under a test condition of 50 mA/cm$^2$). The specific data may be shown in Table 3.

TABLE 3

| Device performance data sheet | | | | |
|---|---|---|---|---|
| No. | CPL material | Blue-light current efficiency (based on Comparative Embodiment 1A) | Green-light current efficiency (based on Comparative Embodiment 1B) | Red-light current efficiency (based on Comparative Embodiment 1C) |
| Application Embodiment 1A/1B/1C | M001 | 106% | 112% | 112% |
| Application Embodiment 2A/2B/2C | M002 | 106% | 113% | 113% |
| Application Embodiment 3A/3B/3C | M008 | 107% | 114% | 113% |
| Application Embodiment 4A/4B/4C | M011 | 106% | 111% | 110% |
| Application Embodiment 5A/5B/5C | M016 | 106% | 111% | 111% |
| Application Embodiment 6A/6B/6C | M021 | 104% | 107% | 108% |

TABLE 3-continued

| Device performance data sheet | | | | |
|---|---|---|---|---|
| No. | CPL material | Blue-light current efficiency (based on Comparative Embodiment 1A) | Green-light current efficiency (based on Comparative Embodiment 1B) | Red-light current efficiency (based on Comparative Embodiment 1C) |
| Application Embodiment 7A/7B/7C | M024 | 104% | 108% | 107% |
| Application Embodiment 8A/8B/8C | M025 | 105% | 109% | 109% |
| Application Embodiment 9A/9B/9C | M029 | 106% | 110% | 110% |
| Application Embodiment 10A/10B/10C | M032 | 106% | 111% | 110% |
| Application Embodiment 11A/11B/11C | M033 | 106% | 110% | 111% |
| Application Embodiment 12A/12B/12C | M035 | 107% | 114% | 114% |
| Application Embodiment 13A/13B/13C | M036 | 106% | 110% | 112% |
| Application Embodiment 14A/14B/14C | M037 | 106% | 112% | 113% |
| Application Embodiment 15A/15B/15C | M038 | 106% | 111% | 112% |
| Application Embodiment 16A/16B/16C | M039 | 105% | 108% | 108% |
| Application Embodiment 17A/17B/17C | M042 | 107% | 113% | 114% |
| Application Embodiment 18A/18B/18C | M045 | 106% | 111% | 112% |
| Application Embodiment 19A/19B/19C | M048 | 107% | 115% | 115% |
| Application Embodiment 20A/20B/20C | M056 | 107% | 113% | 113% |
| Application Embodiment 21A/21B/21C | M063 | 107% | 114% | 114% |
| Application Embodiment 22A/22B/22C | M065 | 107% | 113% | 114% |
| Application Embodiment 23A/23B/23C | M068 | 107% | 113% | 115% |
| Application Embodiment 24A/24B/24C | M072 | 107% | 114% | 115% |
| Application Embodiment 25A/25B/25C | M078 | 107% | 113% | 114% |
| Application Embodiment 26A/26B/26C | M081 | 105% | 110% | 109% |
| Application Embodiment 27A/27B/27C | M086 | 104% | 107% | 106% |
| Application Embodiment 28A/28B/28C | M088 | 106% | 112% | 111% |
| Application Embodiment 29A/29B/29C | M092 | 105% | 109% | 110% |
| Application Embodiment 30A/30B/30C | M104 | 105% | 109% | 107% |

TABLE 3-continued

| Device performance data sheet | | | | |
|---|---|---|---|---|
| No. | CPL material | Blue-light current efficiency (based on Comparative Embodiment 1A) | Green-light current efficiency (based on Comparative Embodiment 1B) | Red-light current efficiency (based on Comparative Embodiment 1C) |
| Application Embodiment 31A/31B/31C | M105 | 105% | 108% | 107% |
| Application Embodiment 32A/32B/32C | M113 | 104% | 107% | 107% |
| Application Embodiment 33A/33B/33C | M123 | 105% | 109% | 110% |
| Application Embodiment 34A/34B/34C | M128 | 107% | 113% | 114% |
| Application Embodiment 35A/35B/35C | M136 | 106% | 113% | 112% |
| Application Embodiment 36A/36B/36C | M143 | 106% | 112% | 111% |
| Application Embodiment 37A/37B/37C | M145 | 106% | 111% | 112% |
| Application Embodiment 38A/38B/38C | M158 | 106% | 111% | 112% |
| Application Embodiment 39A/39B/39C | M161 | 106% | 112% | 111% |
| Application Embodiment 40A/40B/40C | M163 | 106% | 111% | 110% |
| Application Embodiment 41A/41B/41C | M167 | 105% | 110% | 110% |
| Application Embodiment 42A/42B/42C | M171 | 106% | 112% | 111% |
| Application Embodiment 43A/43B/43C | M184 | 105% | 109% | 110% |
| Application Embodiment 44A/44B/44C | M189 | 106% | 111% | 112% |
| Application Embodiment 45A/45B/45C | M192 | 106% | 111% | 112% |
| Application Embodiment 46A/46B/46C | M197 | 106% | 112% | 112% |
| Application Embodiment 47A/47B/47C | M198 | 105% | 111% | 110% |
| Application Embodiment 48A/48B/48C | M215 | 106% | 111% | 110% |
| Application Embodiment 49A/49B/49C | M220 | 105% | 108% | 107% |
| Application Embodiment 50A/50B/50C | M228 | 105% | 109% | 110% |
| Application Embodiment 51A/51B/51C | M229 | 106% | 112% | 111% |
| Application Embodiment 52A/52B/52C | M237 | 106% | 113% | 113% |
| Application Embodiment 53A/53B/53C | M242 | 106% | 111% | 112% |
| Application Embodiment 54A/54B/54C | M246 | 105% | 109% | 107% |

TABLE 3-continued

| Device performance data sheet | | | | |
|---|---|---|---|---|
| No. | CPL material | Blue-light current efficiency (based on Comparative Embodiment 1A) | Green-light current efficiency (based on Comparative Embodiment 1B) | Red-light current efficiency (based on Comparative Embodiment 1C) |
| Application Embodiment 55A/55B/55C | M261 | 104% | 106% | 105% |
| Application Embodiment 56A/56B/56C | M265 | 104% | 106% | 105% |
| Application Embodiment 57A/57B/57C | M274 | 106% | 110% | 109% |
| Application Embodiment 58A/58B/58C | M277 | 105% | 109% | 109% |
| Application Embodiment 59A/59B/59C | M295 | 106% | 111% | 112% |
| Application Embodiment 60A/60B/60C | M305 | 105% | 109% | 107% |
| Application Embodiment 61A/61B/61C | M314 | 104% | 106% | 105% |
| Application Embodiment 62A/62B/62C | M324 | 104% | 106% | 106% |
| Application Embodiment 63A/63B/63C | M340 | 106% | 112% | 112% |
| Application Embodiment 64A/64B/64C | M353 | 106% | 111% | 110% |
| Application Embodiment 65A/65B/65C | M362 | 107% | 113% | 114% |
| Application Embodiment 66A/66B/66C | M381 | 107% | 113% | 113% |
| Application Embodiment 67A/67B/67C | M382 | 107% | 113% | 114% |
| Application Embodiment 68A/68B/68C | M385 | 107% | 113% | 114% |
| Application Embodiment 69A/69B/69C | M388 | 106% | 114% | 113% |
| Application Embodiment 70A/70B/70C | M401 | 104% | 106% | 105% |
| Application Embodiment 71A/71B/71C | M413 | 104% | 106% | 106% |
| Application Embodiment 72A/72B/72C | M416 | 104% | 106% | 106% |
| Comparative Embodiment 1A/1B/1C | Ref | 100% | 100% | 100% |
| Comparative Embodiment 2A/2B/2C | Ref 2 | 105% | 109% | 109% |
| Comparative Embodiment 3A/3B/3C | Ref 3 | 105% | 108% | 108% |
| Comparative Embodiment 4A/4B/4C | Ref 4 | 105% | 109% | 109% |

As can be seen from the above-disclosed embodiments and comparative embodiments, compared with the conventional commercial capping layer material compound Ref1, the compounds in the present disclosure may realize substantially high luminescence when being applied to blue-light, green-light and red-light devices. The light-emitting efficiency of blue-light device is increased by 4%-7%, the light-emitting efficiency of green-light device is increased by 6%-14%, and the light-emitting efficiency of red-light device is increased by 5%-15%. Therefore, the compounds in the present disclosure may have excellent light extraction ability when being used as capping layer materials, and may effectively improve the light-emitting efficiency of the OLED device.

Compared with Ref2, Ref3, and Ref4, M001, M029, M032, and M192 in the present disclosure may improve the refractive indices of the capping layer for the blue-light, green-light, and red-light wavelength regions merely by replacing carbon atoms with nitrogen atoms, thereby effectively improving the blue-light, green-light and red-light light-emitting efficiency of the OLED device. Further, the synthesis of the nitrogen heterocycle may be simple, and the cost may be low, which may be suitable for mass production.

The description of the disclosed embodiments is provided to illustrate the present disclosure to those skilled in the art. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments illustrated herein but is to be accorded the widest scope consistent with the principles and novel features disclosed herein.

What is claimed is:

1. A heterocyclic compound of Formula I:

Formula I

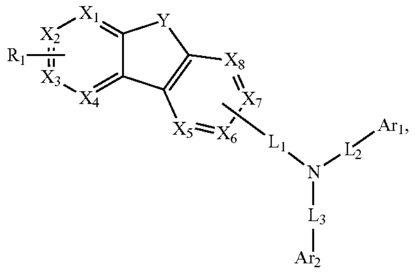

wherein Y is selected from O or S; at least three of $X_1$, $X_2$, $X_3$, $X_4$, $X_5$, $X_6$, $X_7$ and $X_8$ are a N atom and the at least three N atoms are positioned at different rings, and rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group to be condensed with a ring including X1, X2, X3, and X4, and one of X5 through X8 is bonded to the L1-N(L2Ar1)(L3Ar2) group, and one of X1 through X4 is bonded to R1; and $R_2$ is selected from a hydrogen atom, a deuterium atom, a substituted or unsubstituted C1-C5 alkyl group, a halogen, a cyano group, or an amino group.

2. The heterocyclic compound according to claim 1, wherein:

$R_2$ is selected from H, D, F, Cl, Br, a cyano group, or a trifluoromethyl group.

3. The heterocyclic compound according to claim 1, wherein:

Formula I includes any one of following structures:

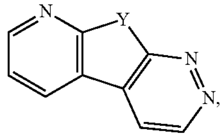, 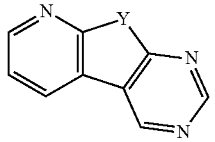,

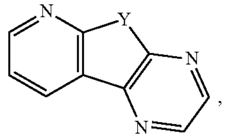, 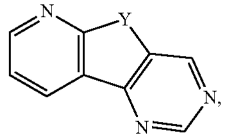,

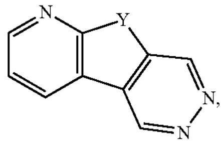, 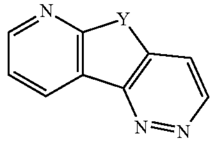,

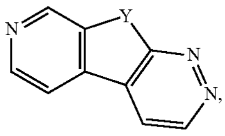, 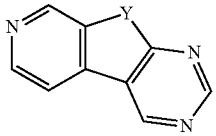,

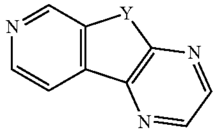, 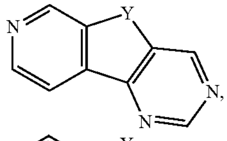,

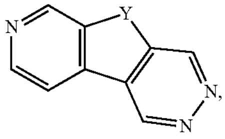, 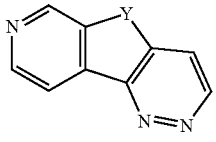,

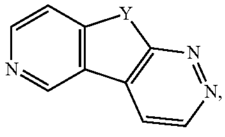, 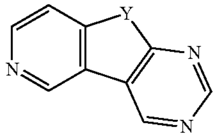,

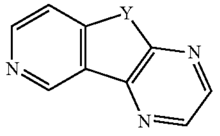, 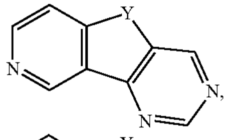,

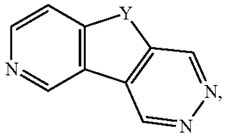, 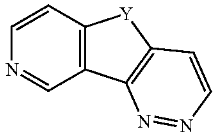,

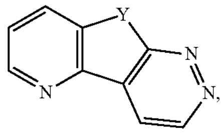, 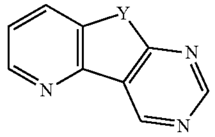,

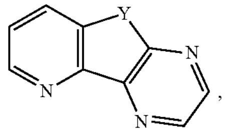, 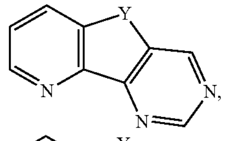,

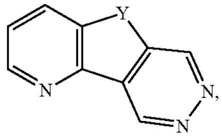, 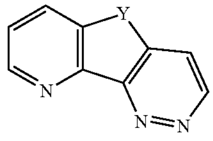;

wherein Y is selected from O or S, and each of the above structures is connected to $L_1$ through any carbon atom.
4. The heterocyclic compound according to claim 1, wherein:
Formula I includes any one of following structures:
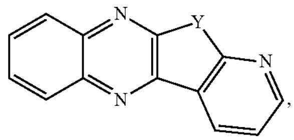
,
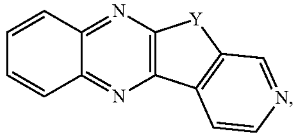
,
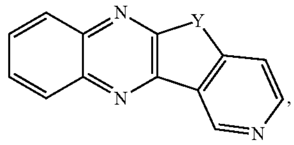
,
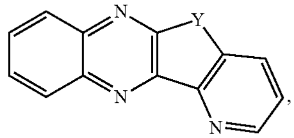
,
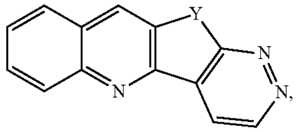
,
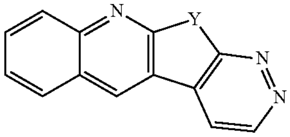
,
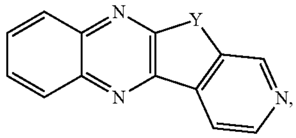
,
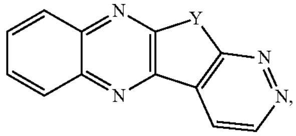
,
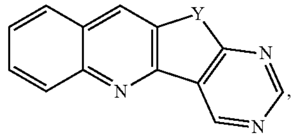
,
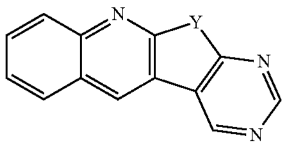
,
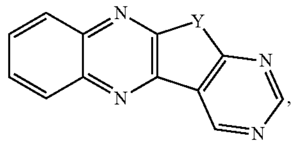
,
-continued
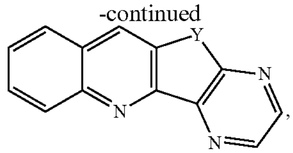
,
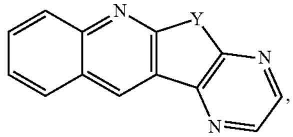
,
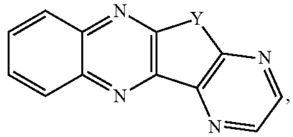
,
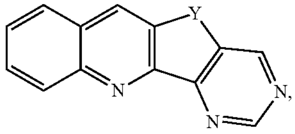
,
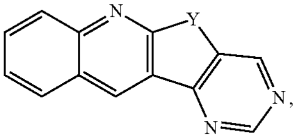
,
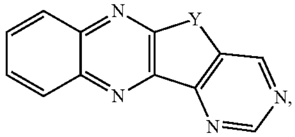
,
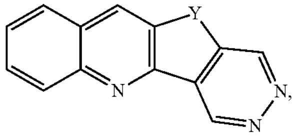
,
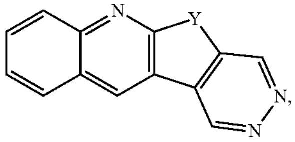
,
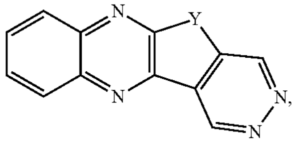
,
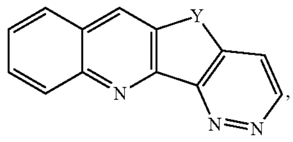
,
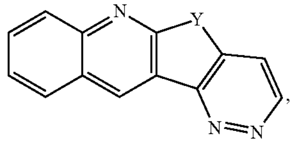
,
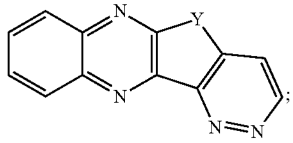
;
wherein Y is selected from O or S, and each of the above structures is connected to $L_1$ through any carbon atom.

5. The heterocyclic compound according to claim 1, wherein:

$L_1$, $L_2$, and $L_3$ are independently selected from substituted or unsubstituted aromatic groups.

6. The heterocyclic compound according to claim 5, wherein:

$L_1$, $L_2$, and $L_3$ are independently selected from phenylene, biphenylene, terphenylene, naphthylene, anthrylene, phenanthrylene, pyrenylene, fluoranthene, triphenylene, or fluorenylene.

7. The heterocyclic compound according to claim 5, wherein:

$L_1$, $L_2$, and $L_3$ are independently selected from any one of following structures:

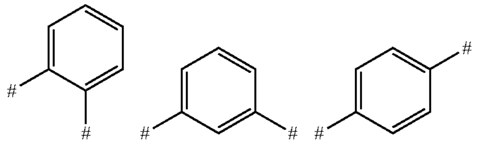
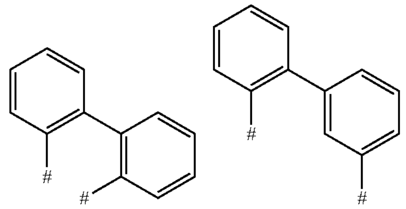
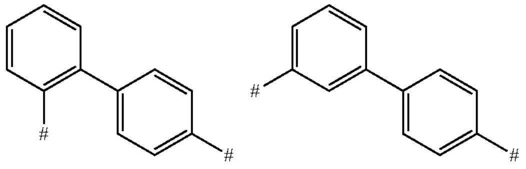
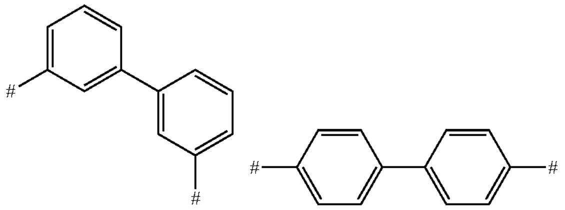
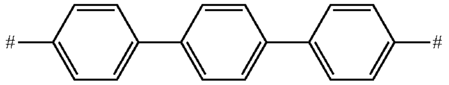
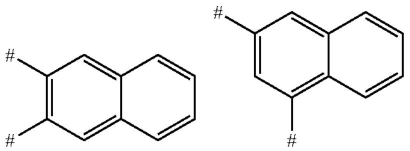
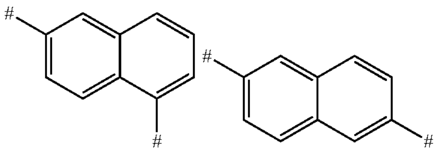
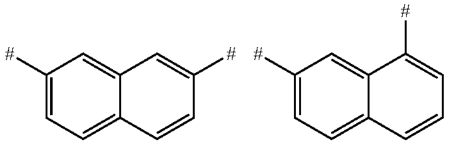

-continued

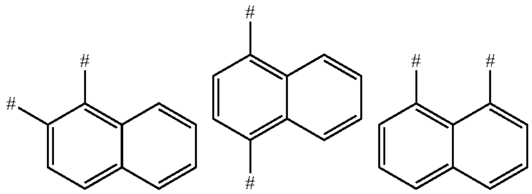
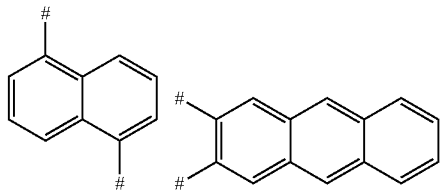
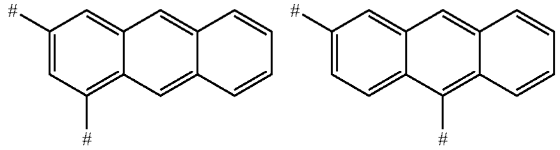
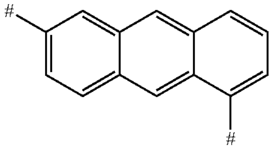
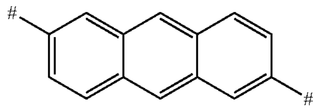
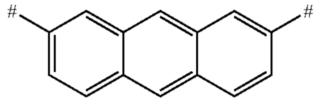
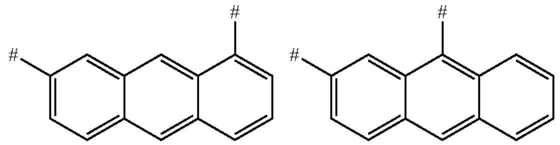
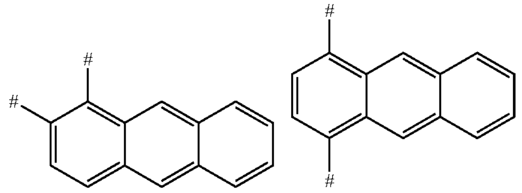
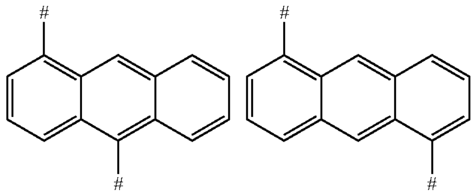
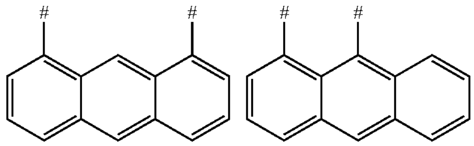

-continued
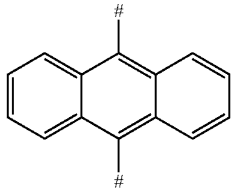
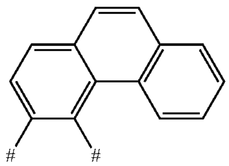
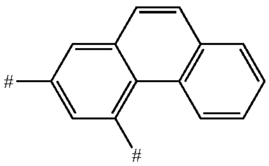
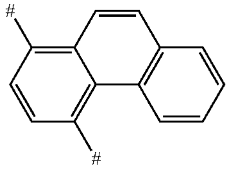
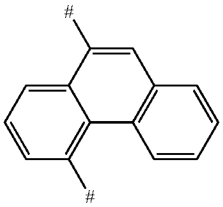
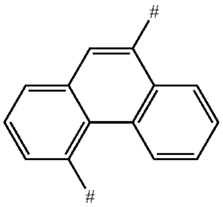
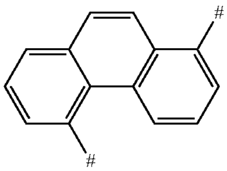
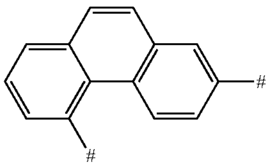
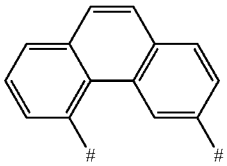
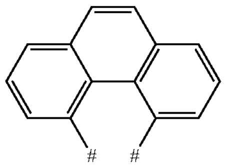
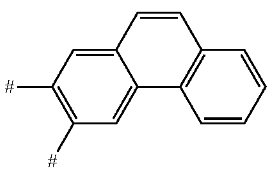
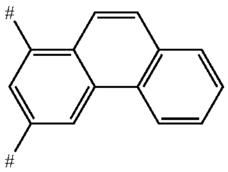
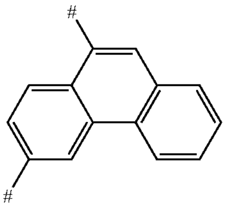
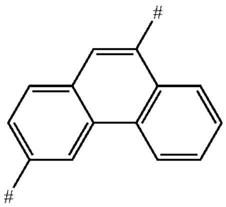
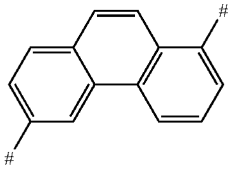
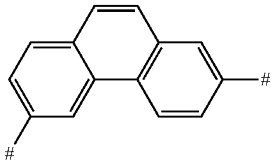
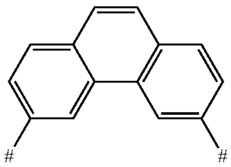
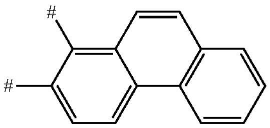
-continued
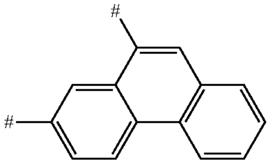
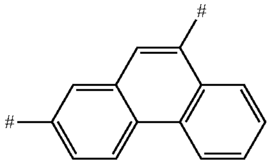
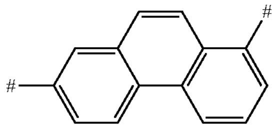
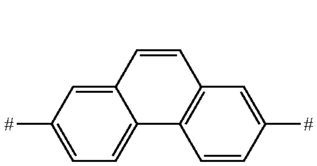
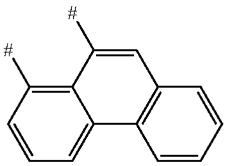
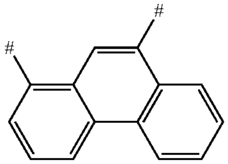
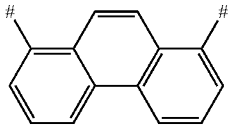
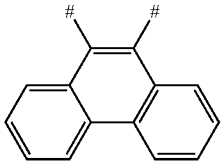
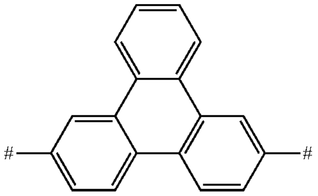
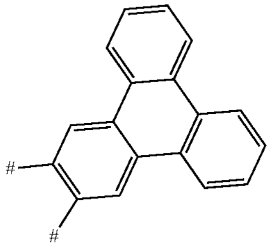
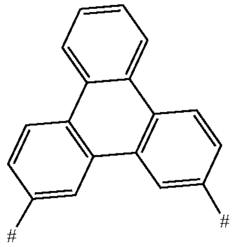
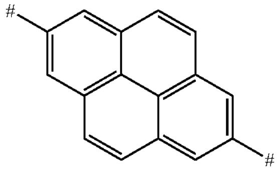
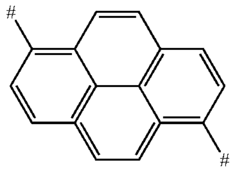
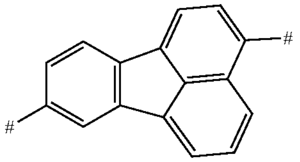
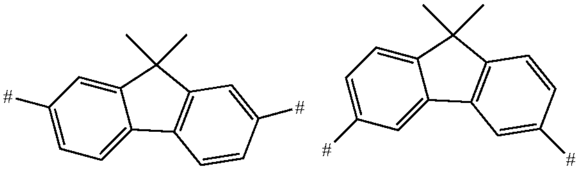

-continued

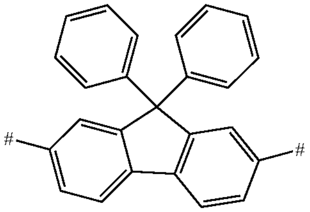

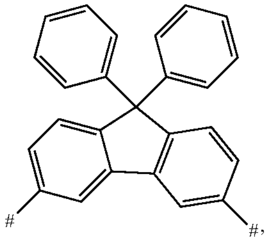

wherein #represents a connection position.

8. The heterocyclic compound according to claim 1, wherein:

$Ar_1$ and $Ar_2$ are independently selected from phenyl, biphenyl, terphenyl, naphthyl, anthracenyl, phenanthryl, pyrenyl, fluoranthene, triphenylene, fluorenyl, pyrrolyl, furyl, thienyl, pyridyl, pyrimidinyl, pyridazinyl, triazinyl, benzofuranyl, benzothienyl, dibenzofuranyl, dibenzothienyl, oxazolyl, oxadiazolyl, thiazolyl, thiadiazolyl, benzoxazolyl, benzothiazolyl, imidazolyl, pyrazolyl, indolyl, quinolinyl, isoquinolinyl, purinyl, isoxazolyl, isothiazole, pyrone, pyrazinyl, thienofuranyl, thienopyrrolyl, pyrrolopyridyl, pyridopyrimidinyl, pyrazolooxazolyl, pyrazinopyridazinyl, imidazothiazolyl, or coumarin.

9. The heterocyclic compound according to claim 1, wherein:

$Ar_1$ and $Ar_2$ are independently selected from any one of following structures:

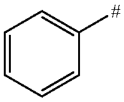
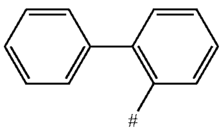

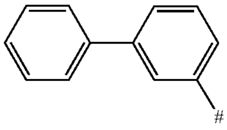
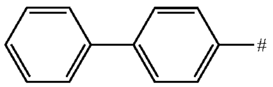

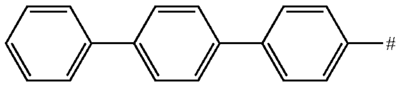

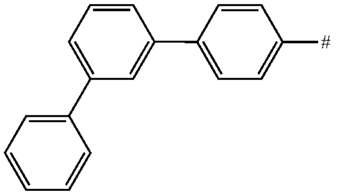

-continued

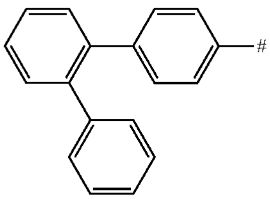
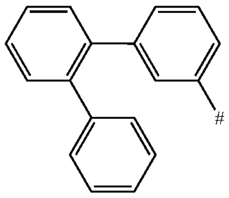

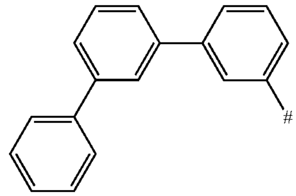

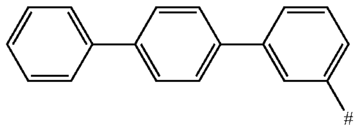

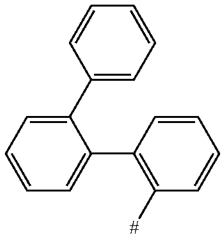
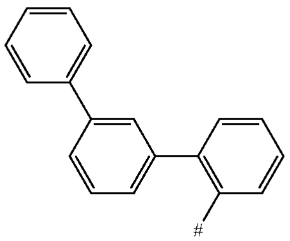

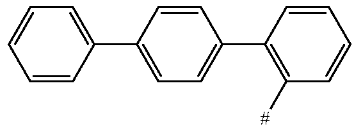

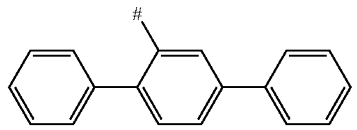

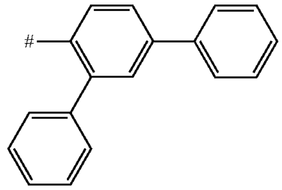
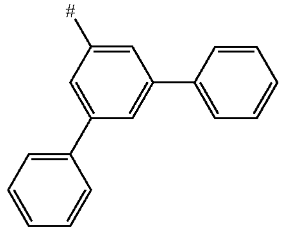

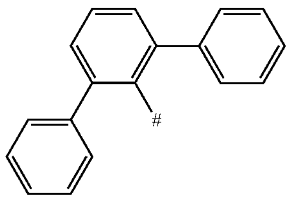
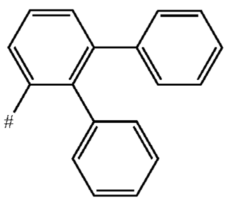

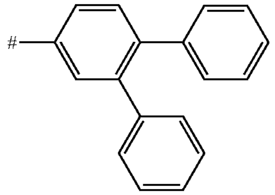
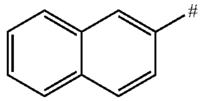

-continued
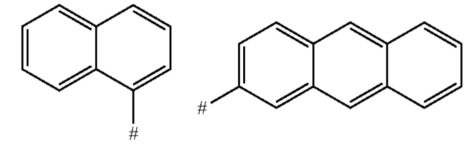
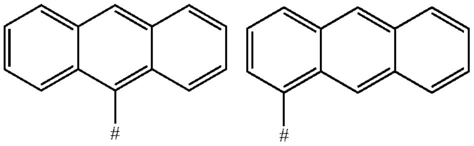
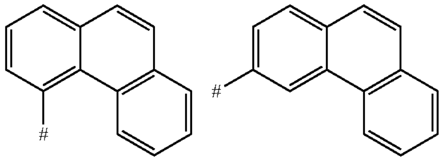
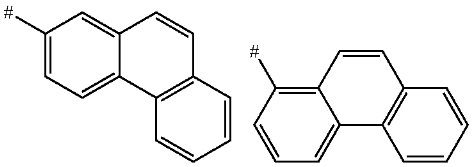
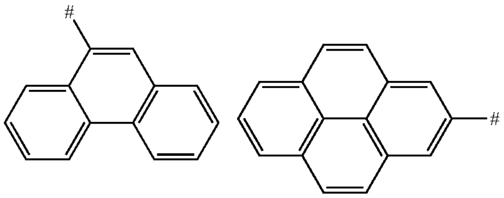
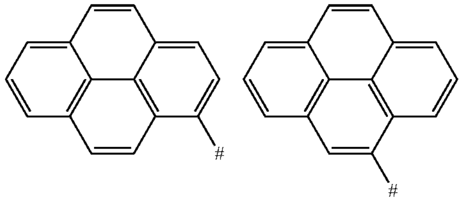
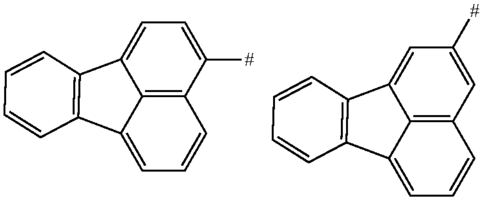
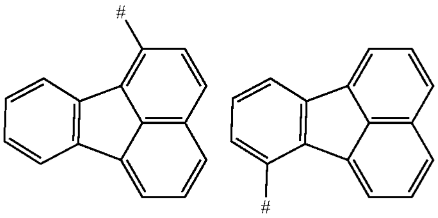
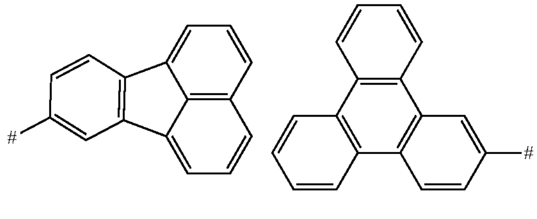
-continued
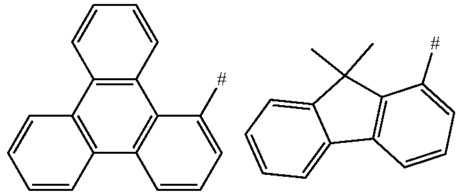
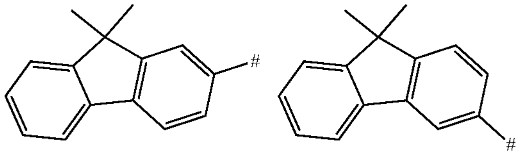
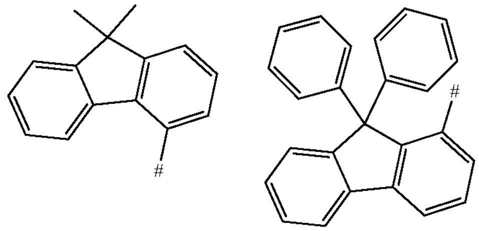
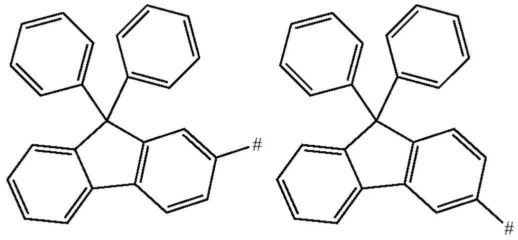
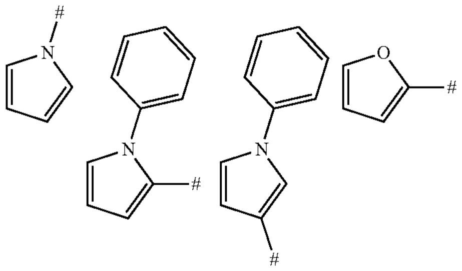
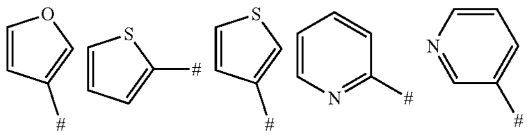
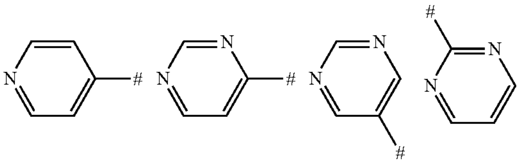
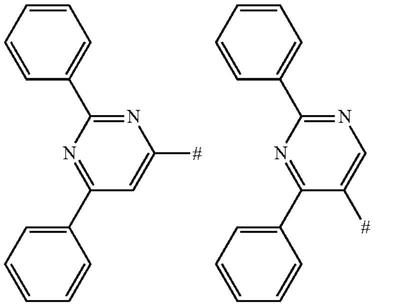

-continued
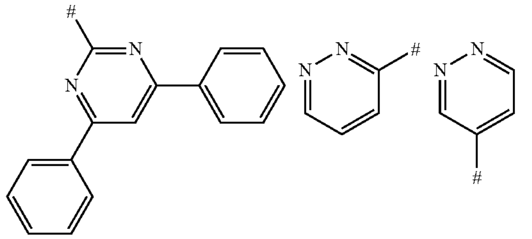
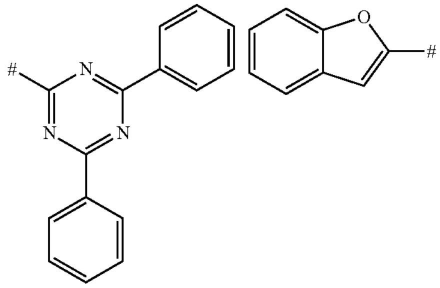
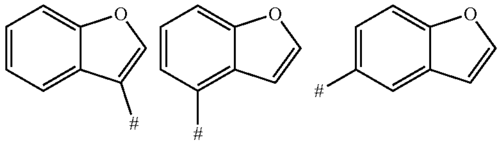
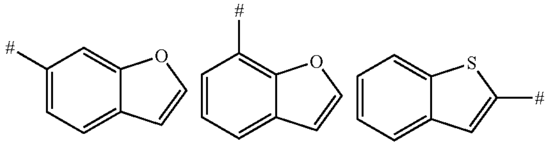
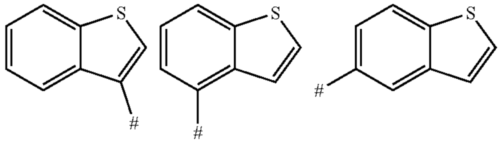
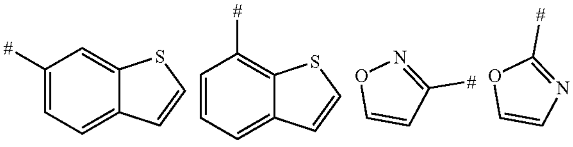
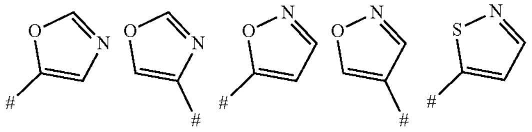
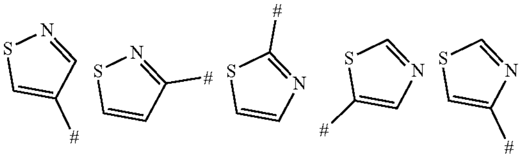
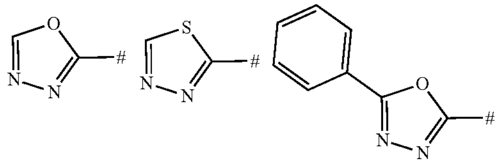
-continued
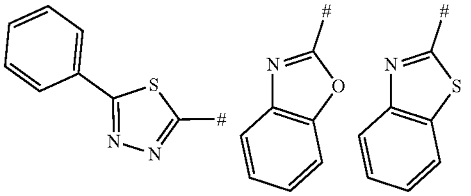
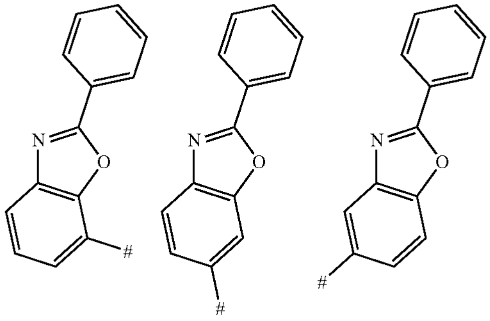
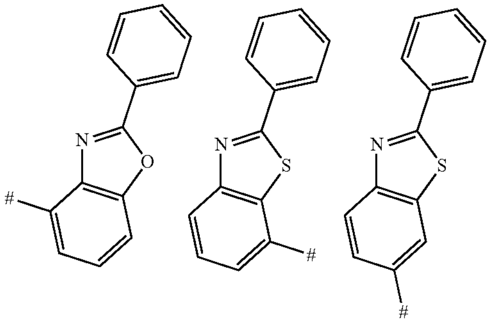
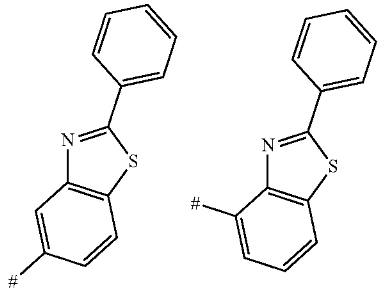
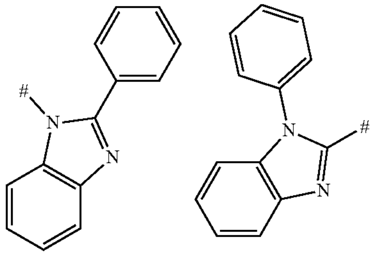
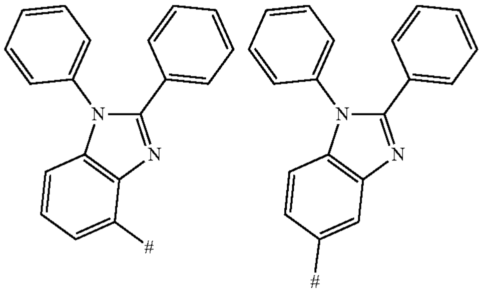

-continued
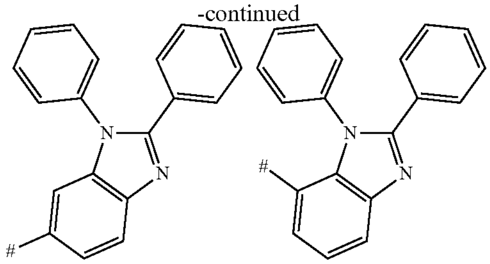
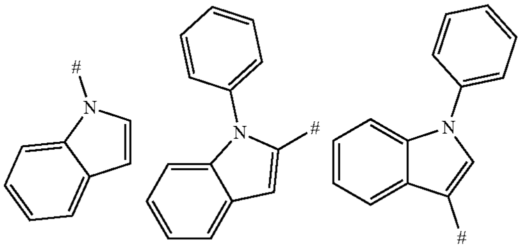
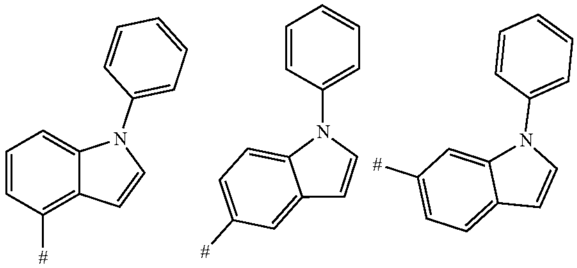
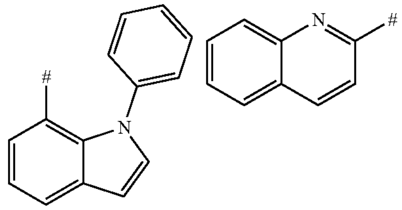
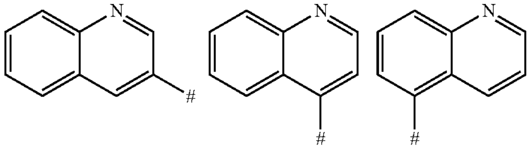
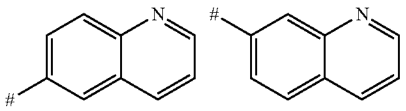
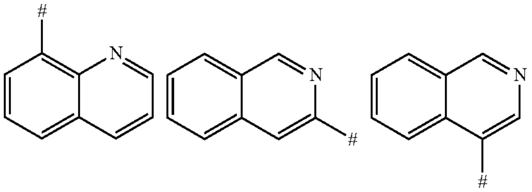
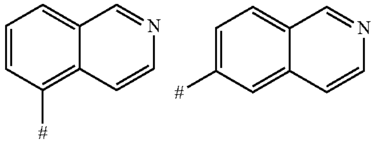
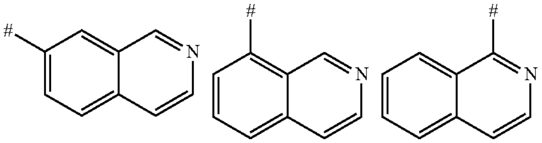
-continued
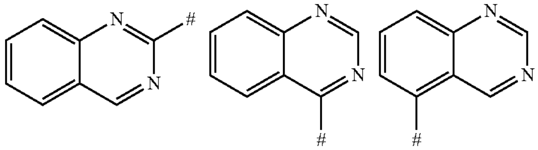
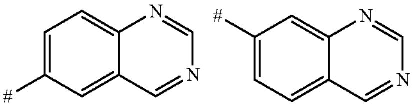
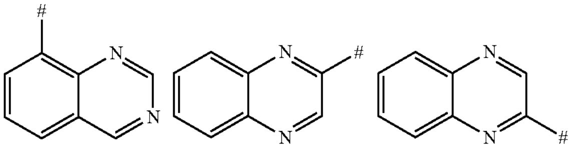
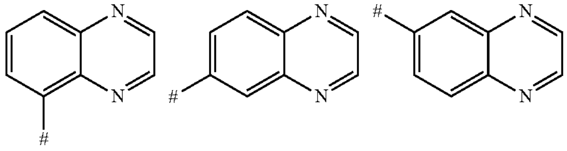
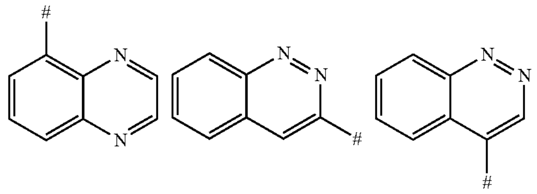
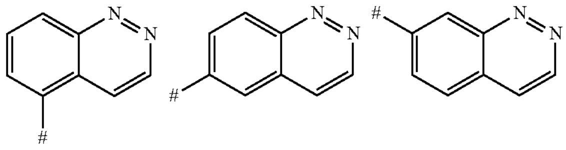
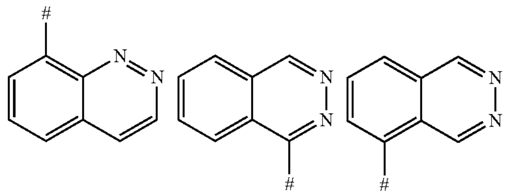
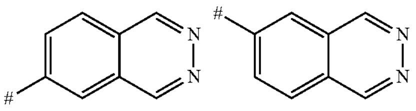
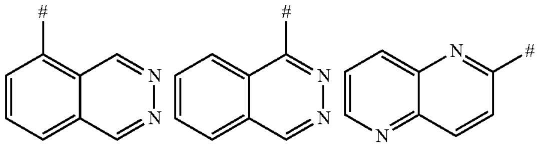
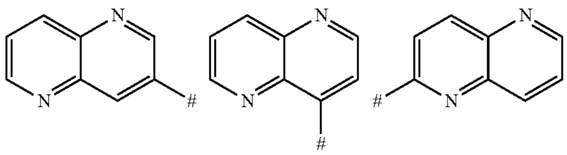
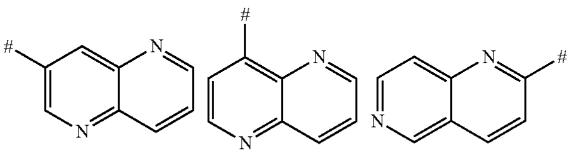

-continued
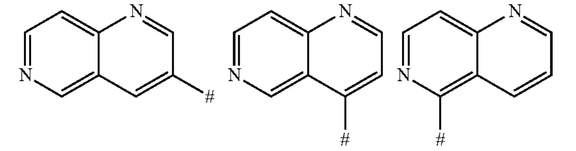
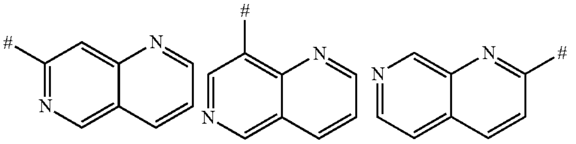
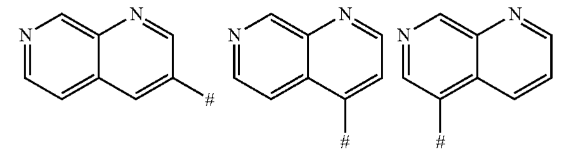
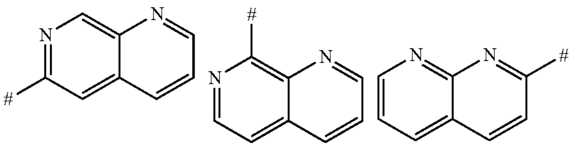
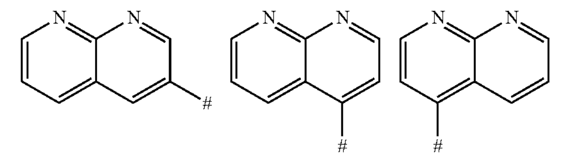
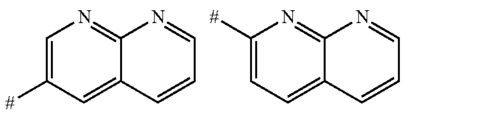
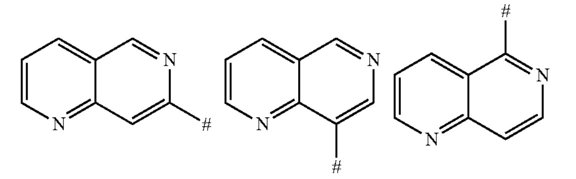
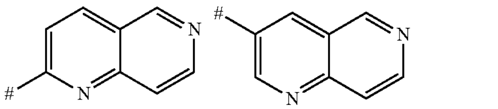
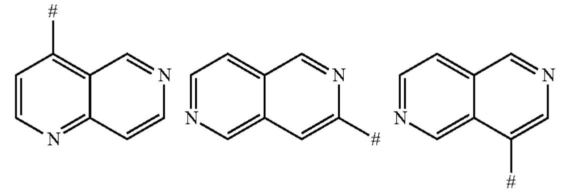
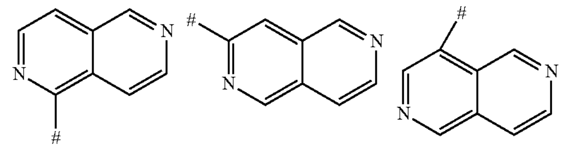
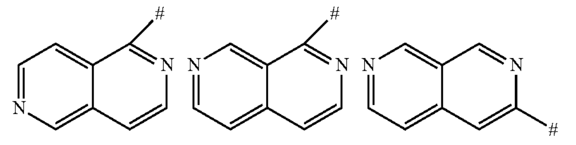
-continued
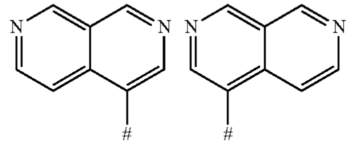
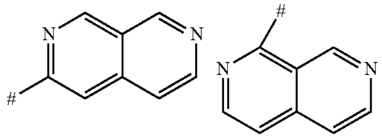
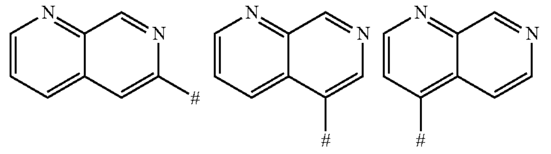
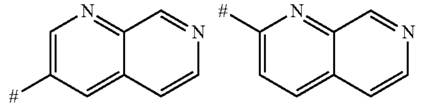
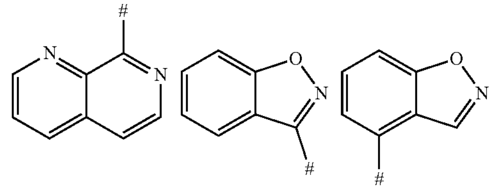
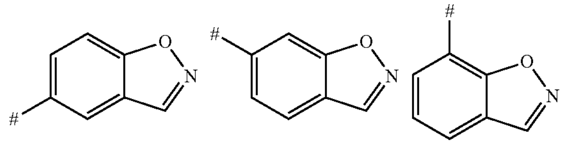
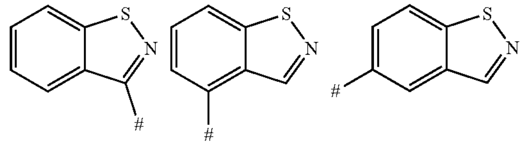
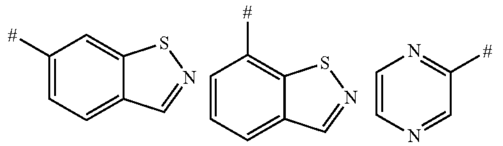
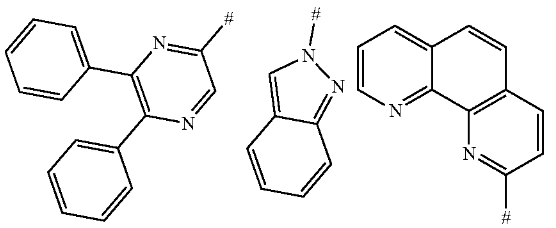
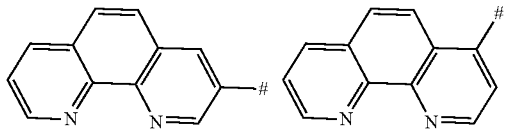
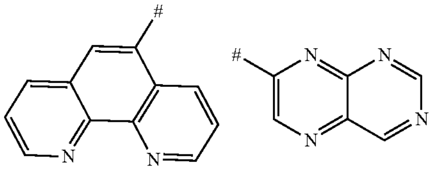

-continued
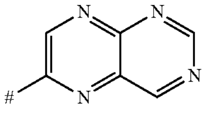
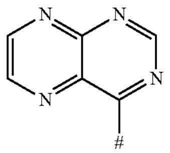
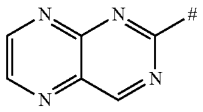
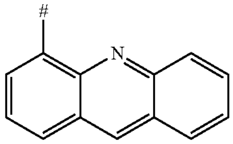
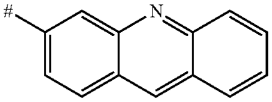
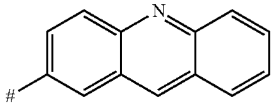
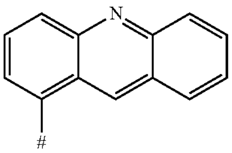
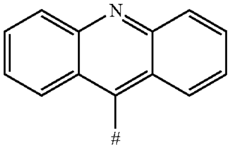
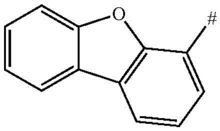
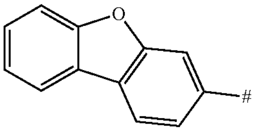
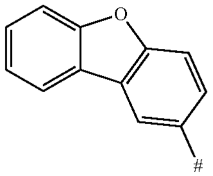
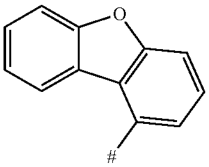
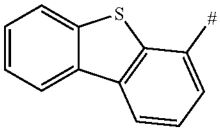
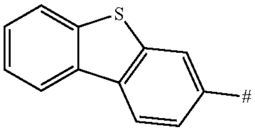
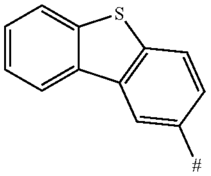
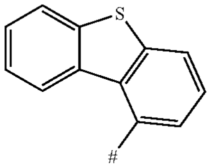
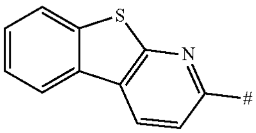
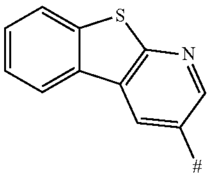
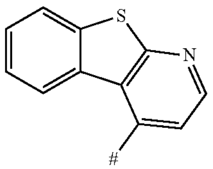
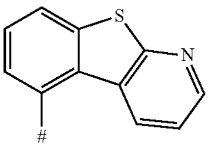
-continued
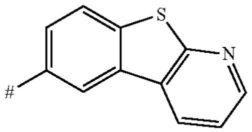
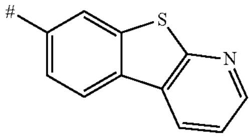
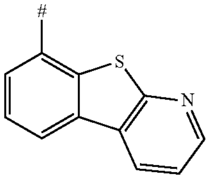
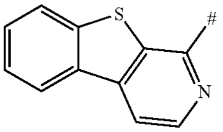
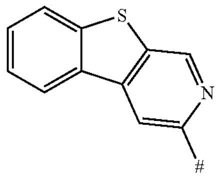
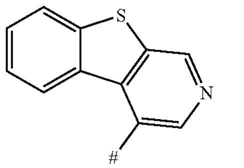
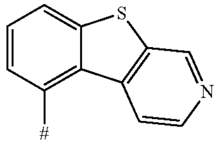
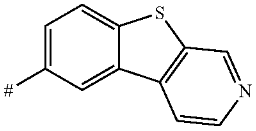
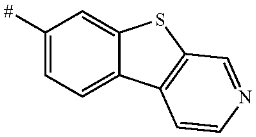
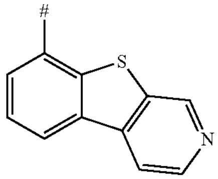
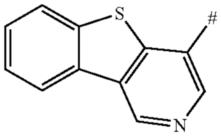
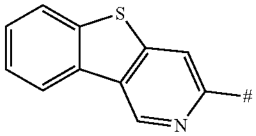
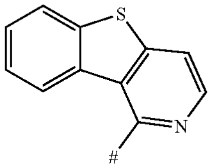
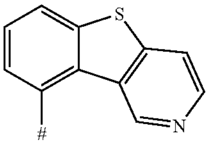
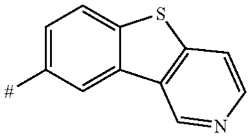
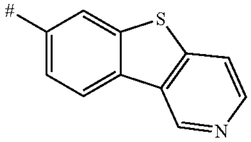
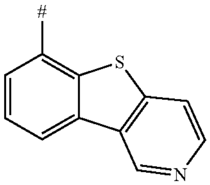
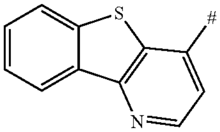
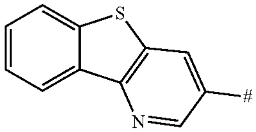
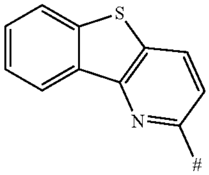

-continued
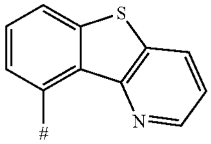
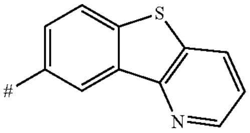
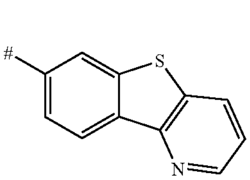
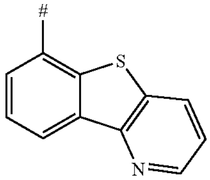
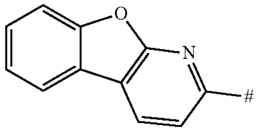
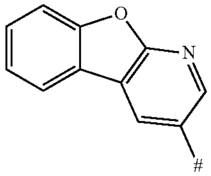
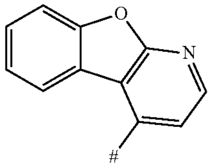
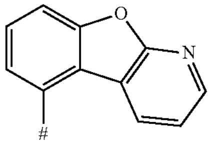
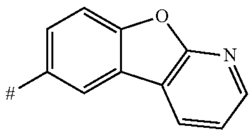
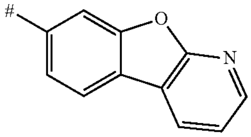
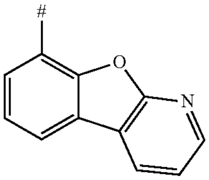
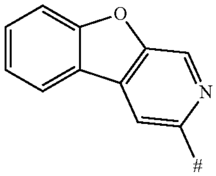
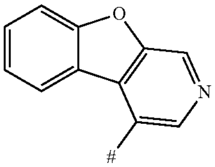
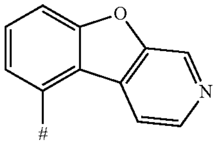
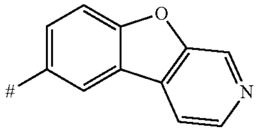
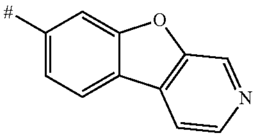
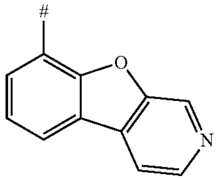
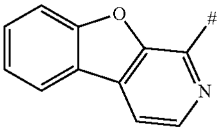
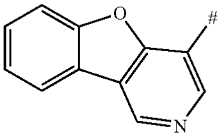
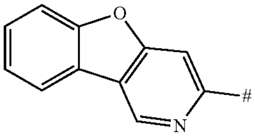
-continued
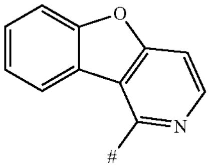
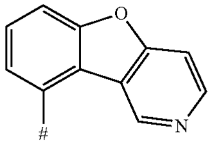
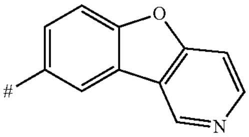
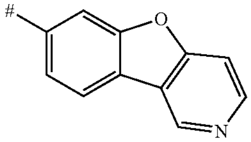
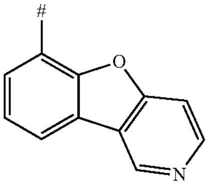
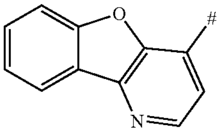
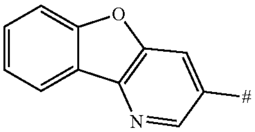
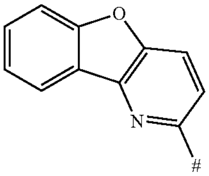
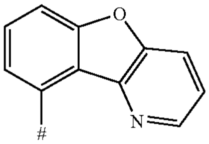
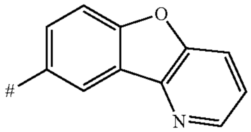
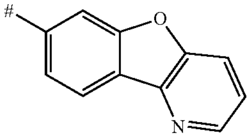
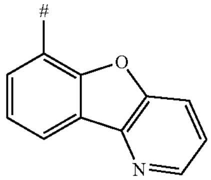
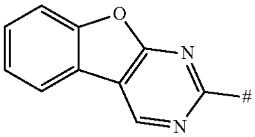
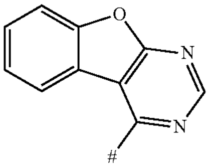
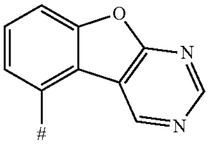
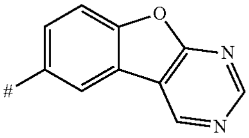
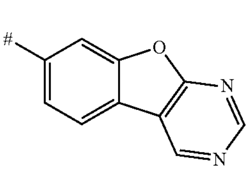
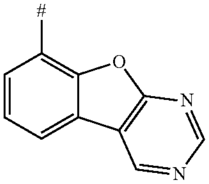
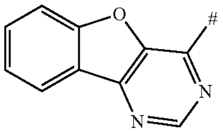
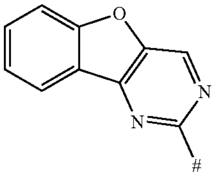

-continued
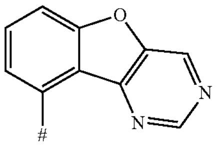
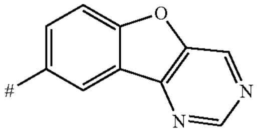
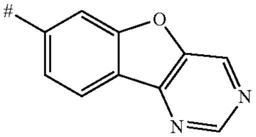
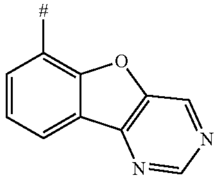
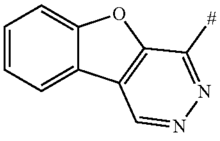
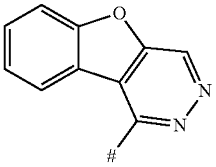
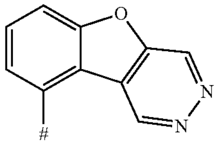
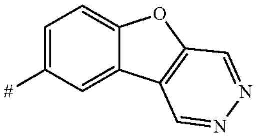
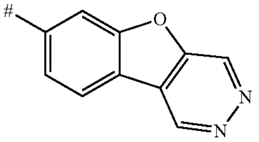
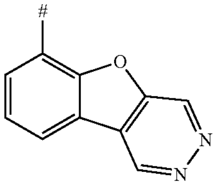
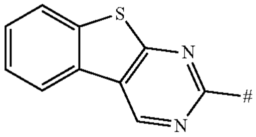
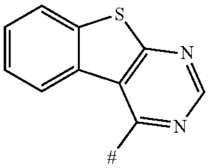
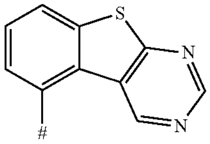
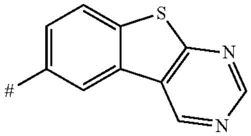
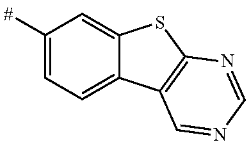
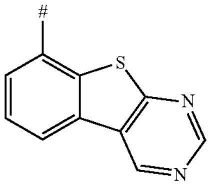
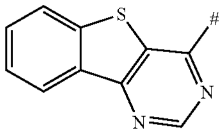
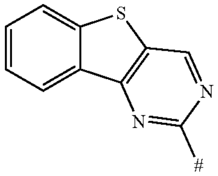
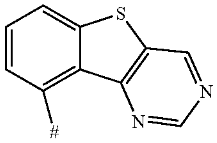
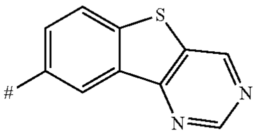
-continued
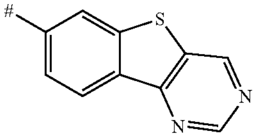
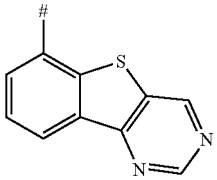
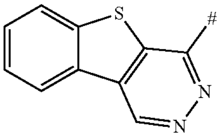
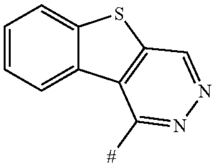
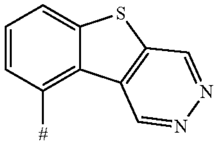
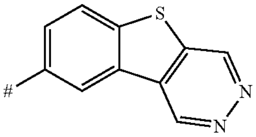
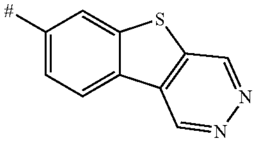
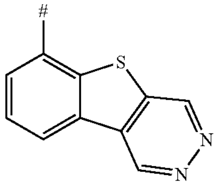
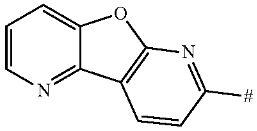
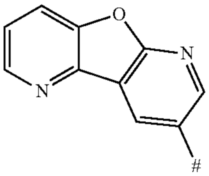
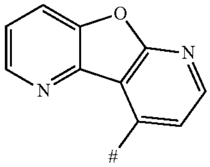
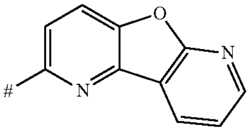
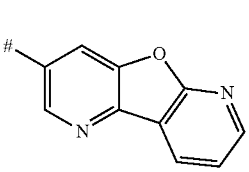
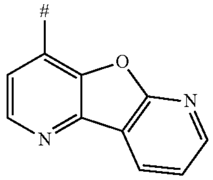
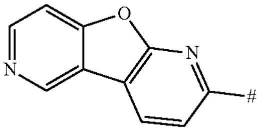
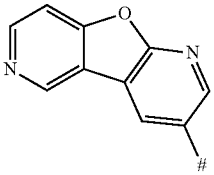
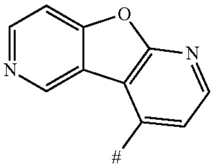
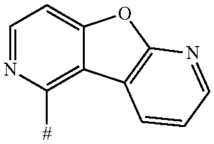
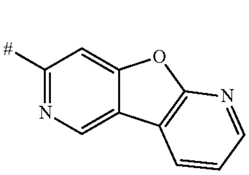
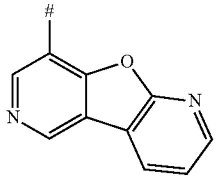

-continued
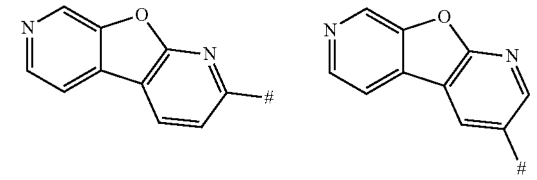
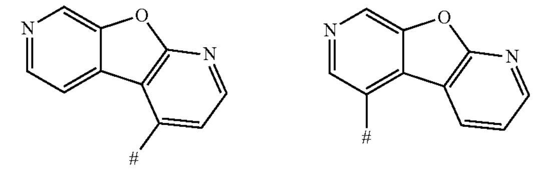
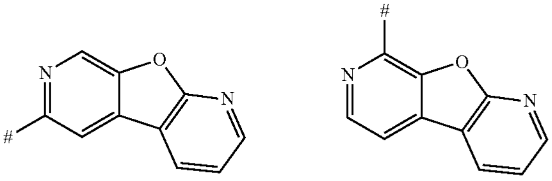
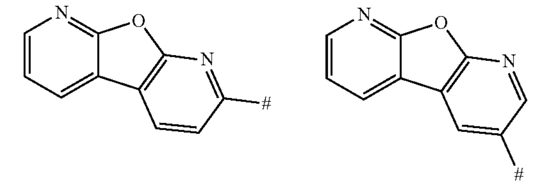
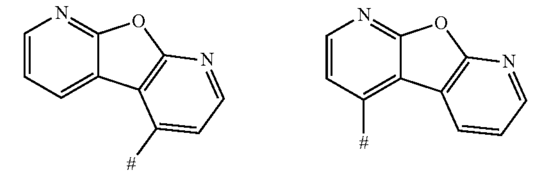
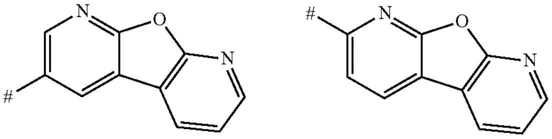
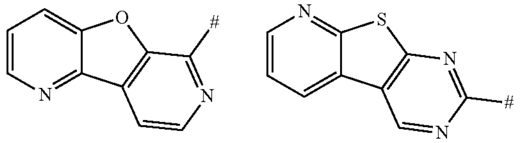
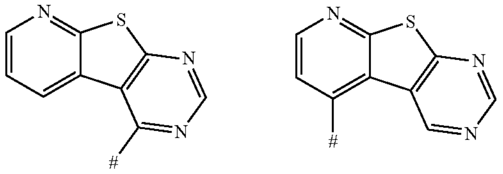
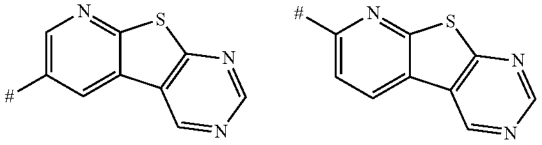
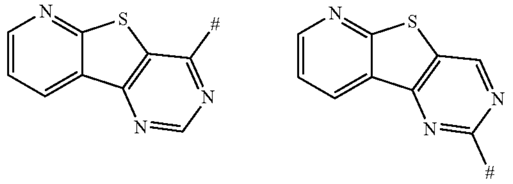
-continued
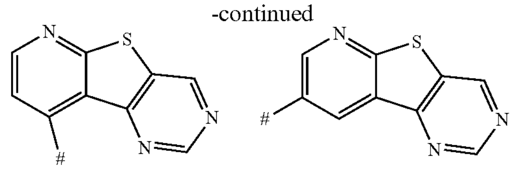
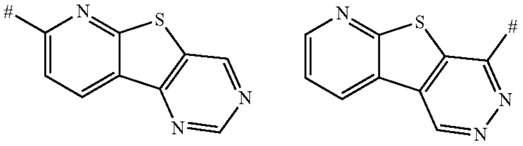
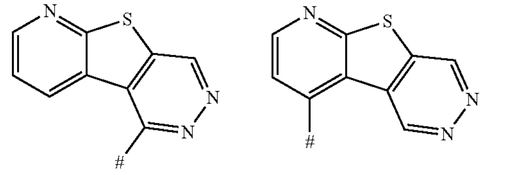
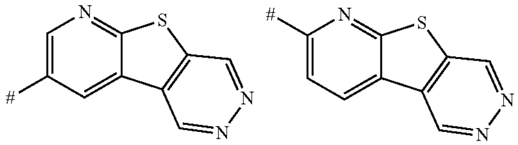
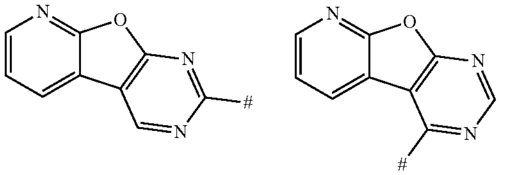
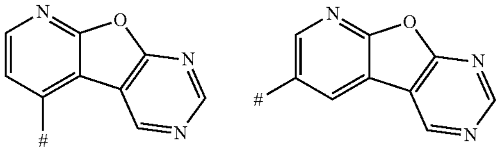
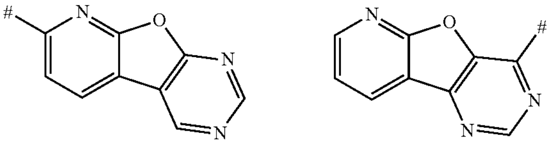
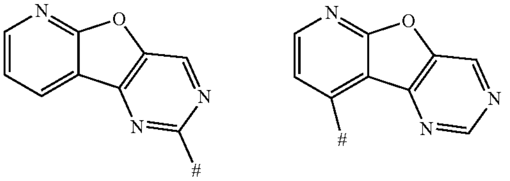
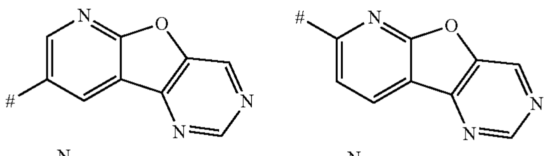
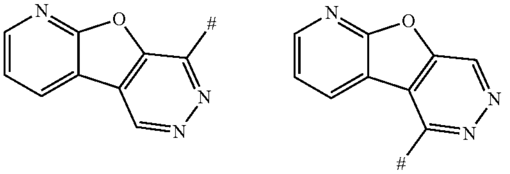
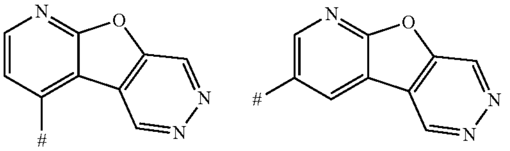

-continued

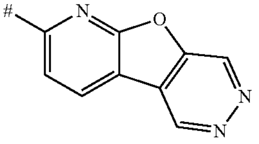

wherein #represents a connection position.

10. A display panel, comprising:

an organic light-emitting device, wherein:

the organic light-emitting device includes an anode, a cathode, and an organic thin layer disposed between the anode and the cathode, and the cathode is covered with a capping layer, and the capping layer includes any one or a combination of at least two of heterocyclic compounds, each heterocyclic compound comprising a structure in Formula I:

Formula I

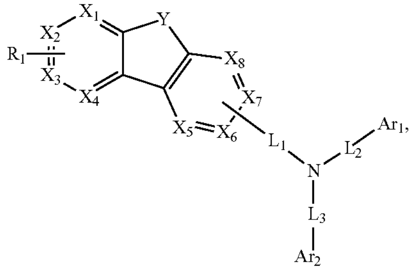

wherein Y is selected from O or S; two of $X_1$, $X_2$, $X_3$, $X_4$, $X_5$, $X_6$, $X_7$ and $X_8$ are a N atom and the two N atoms are positioned within a same ring, and rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group to be condensed with a ring including X1, X2, X3, and X4, and one of X5 through X8 is bonded to the L1-N(L2Ar1)(L3Ar2) group, and one of X1 through X4 is bonded to R1; and $R_2$ is selected from a hydrogen atom, a deuterium atom, a substituted or unsubstituted C1-C5 alkyl group, a halogen, a cyano group, or an amino group.

11. The heterocyclic compound according to claim 10, wherein:

Formula I includes any one of following structures:

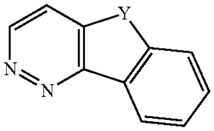
,
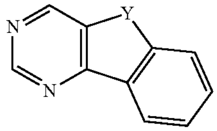
,
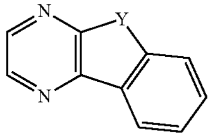
,
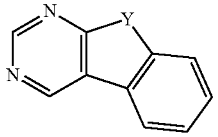
,

-continued

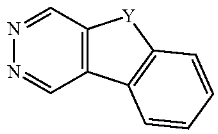
,
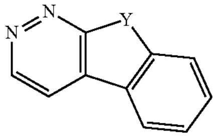
;

wherein Y is selected from O or S, and each of the above structures is connected to $L_1$ through any carbon atom.

12. The heterocyclic compound according to claim 10, wherein:

the heterocyclic compound includes any one of following structures:

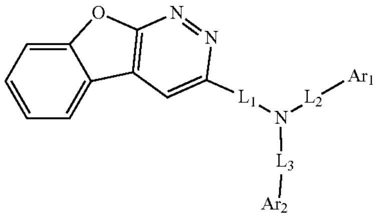

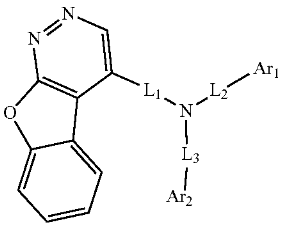

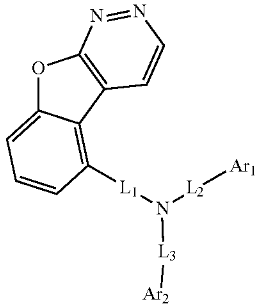

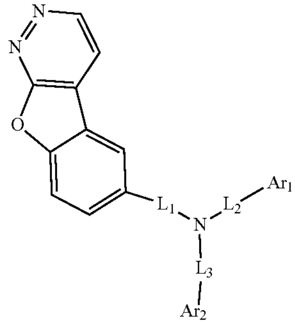

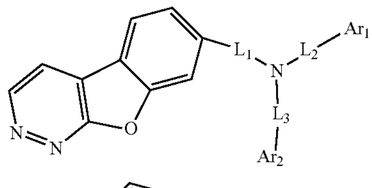

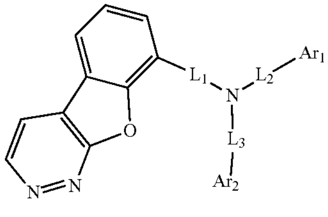

-continued
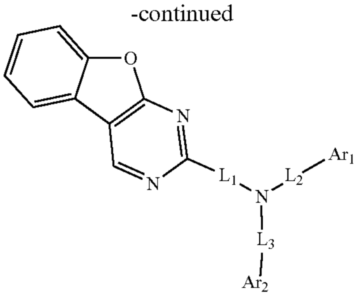
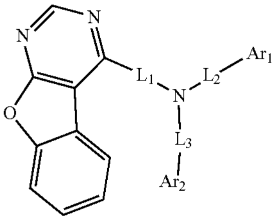
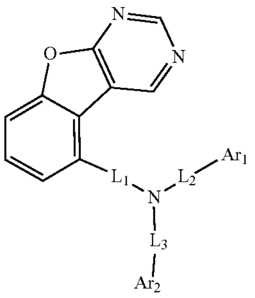
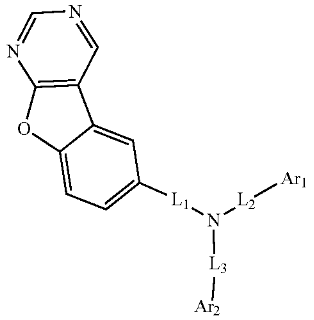
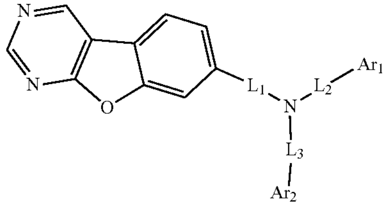
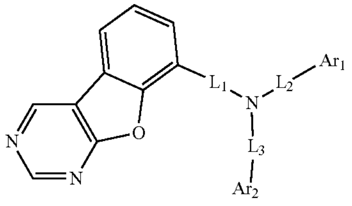
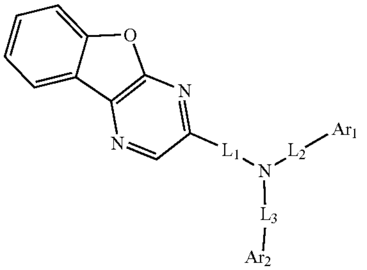
-continued
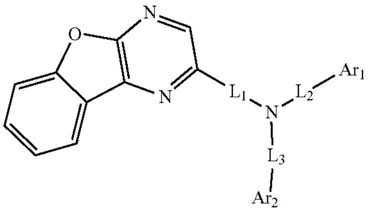
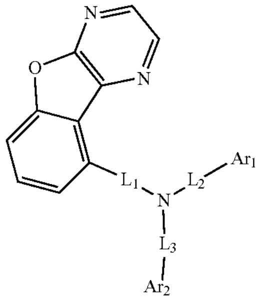
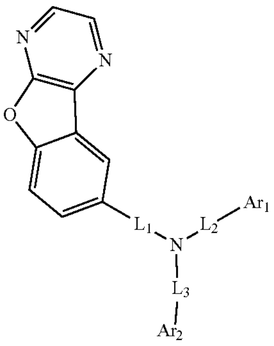
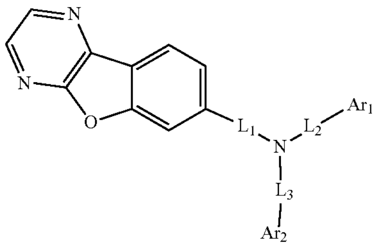
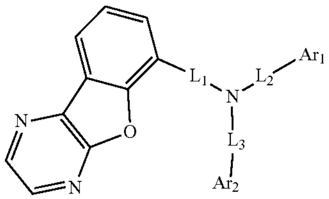
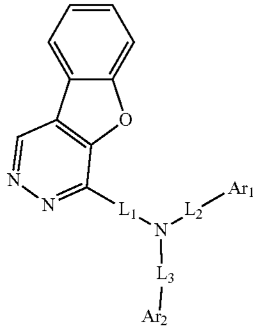
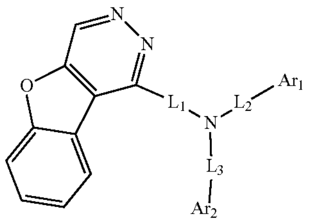
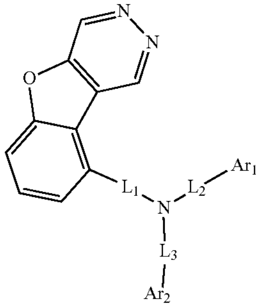

-continued
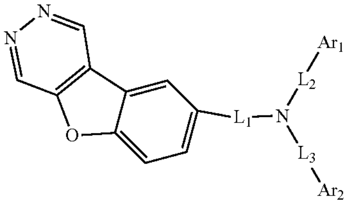
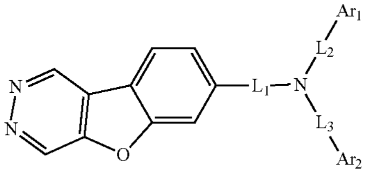
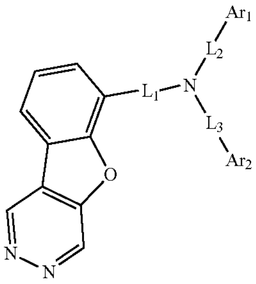
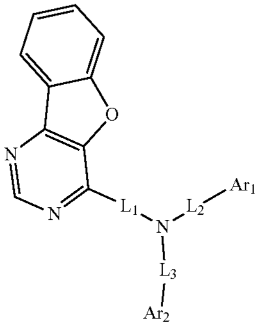
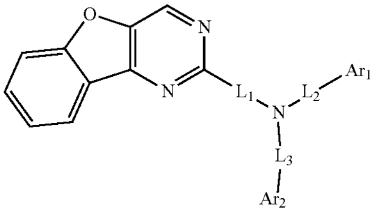
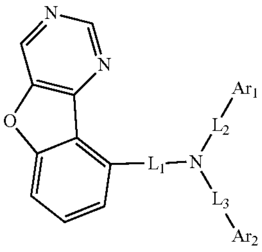
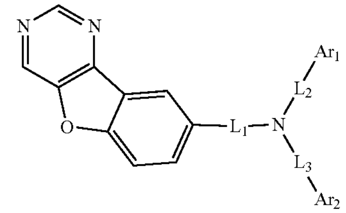
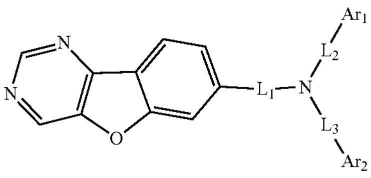
-continued
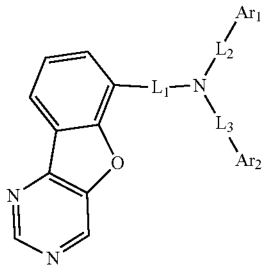
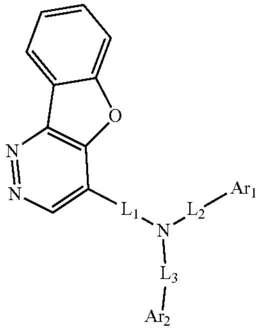
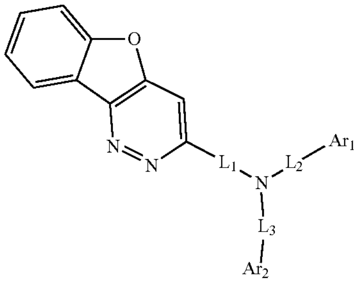
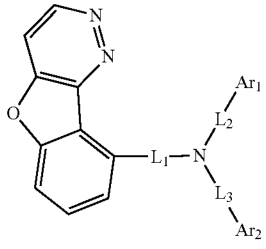
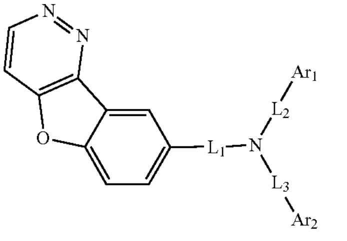
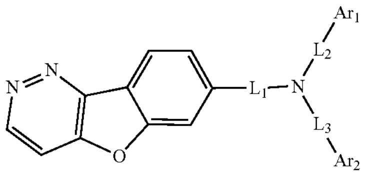

-continued
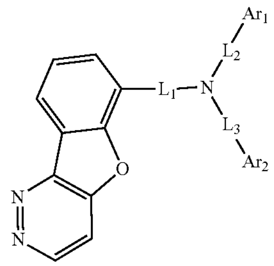
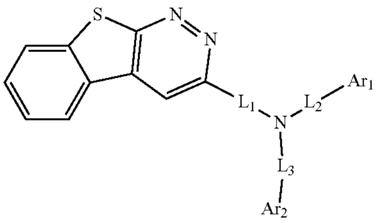
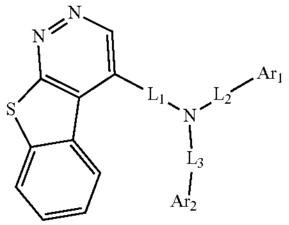
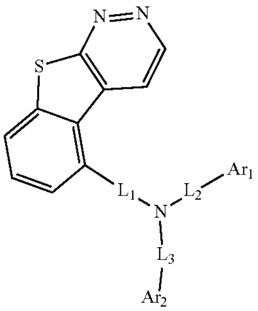
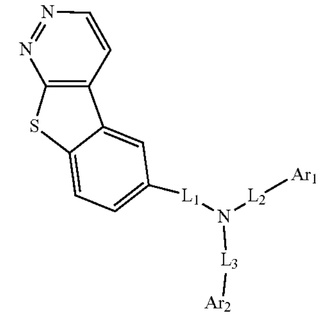
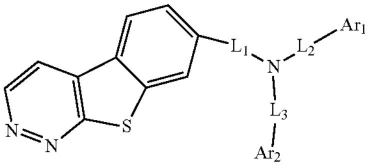
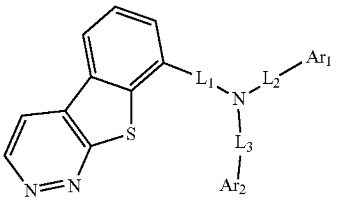
-continued
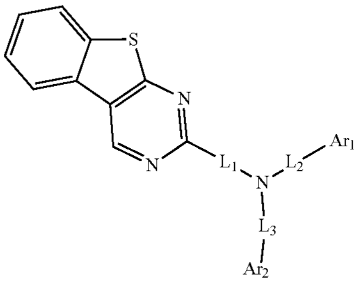
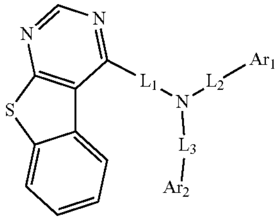
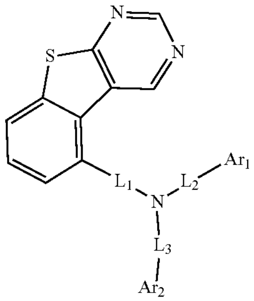
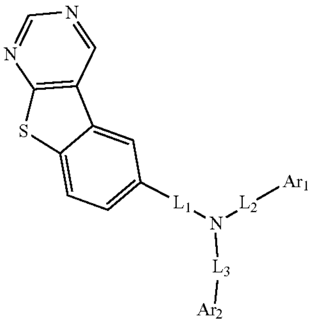
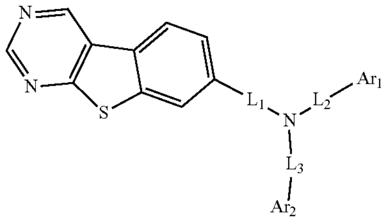
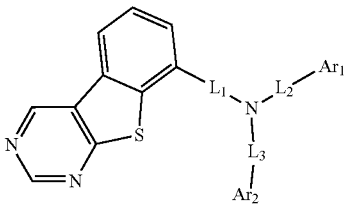
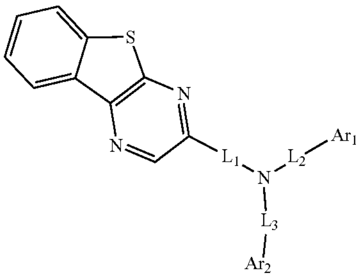

-continued
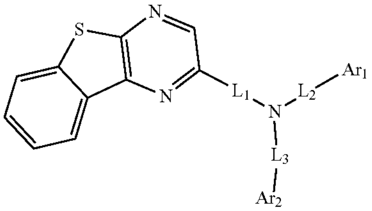
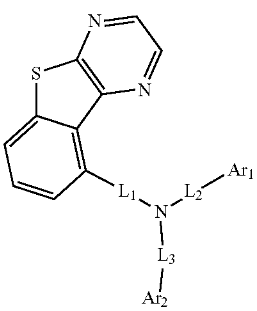
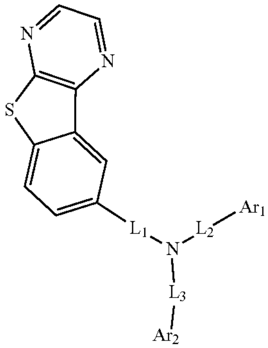
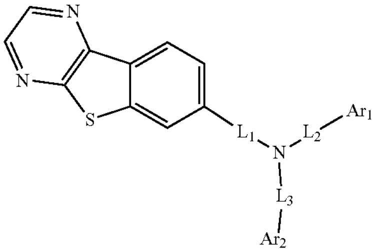
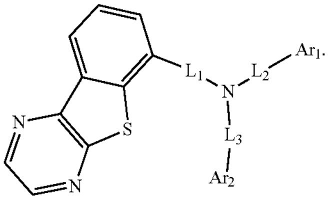
13. The heterocyclic compound according to claim 10, wherein:
the heterocyclic compound includes any one of following structures:
M221
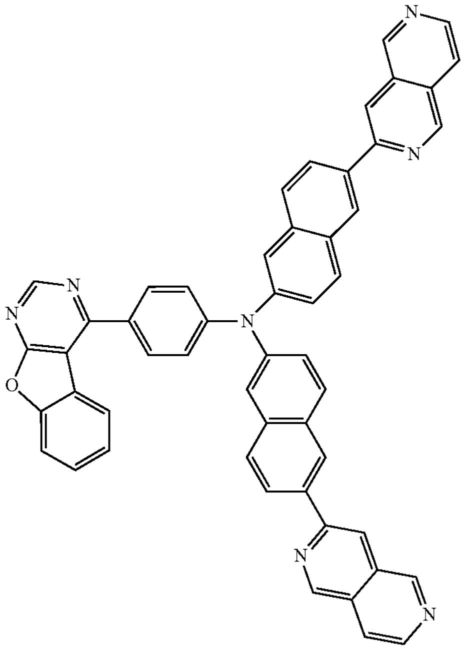
M222
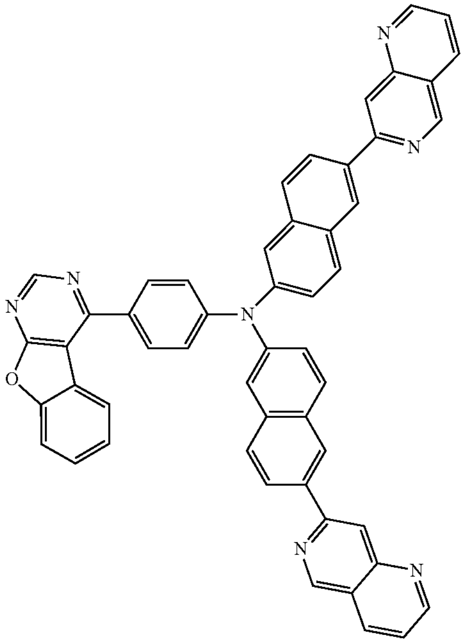

-continued
M223
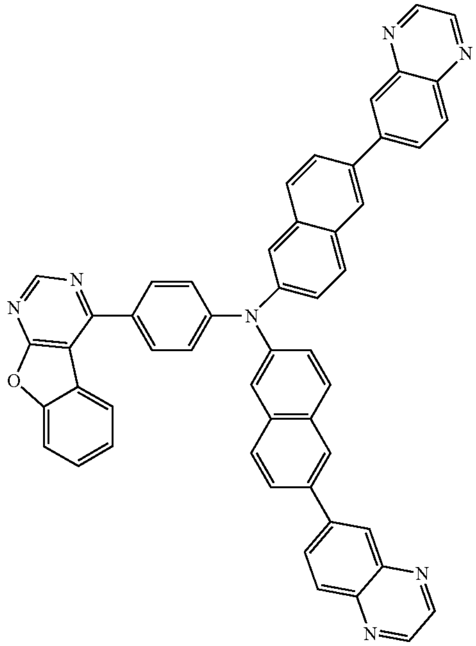
M224
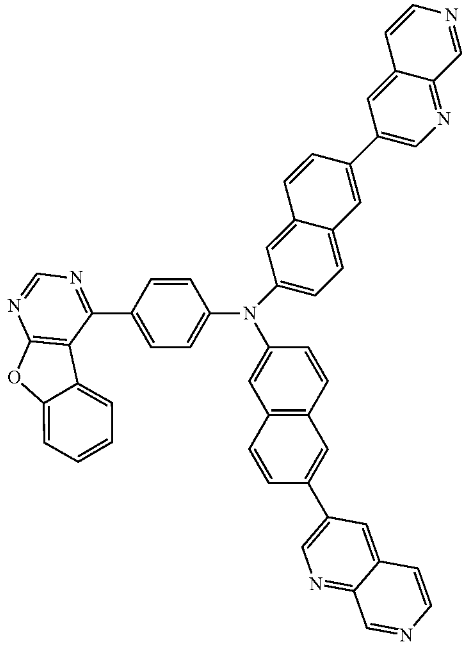
-continued
M225
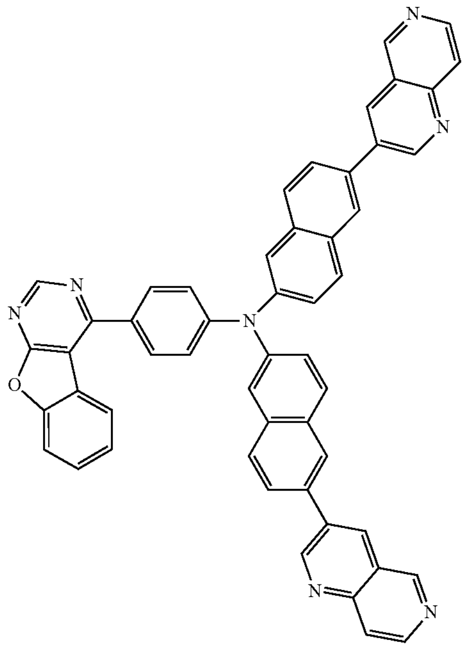
M226
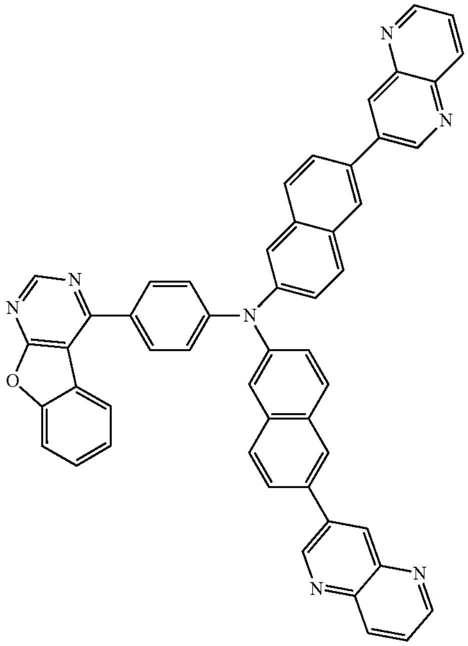

-continued
M227
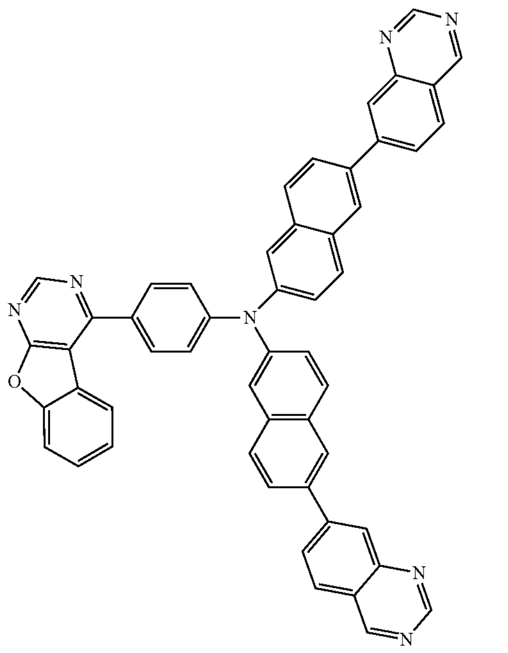
M228
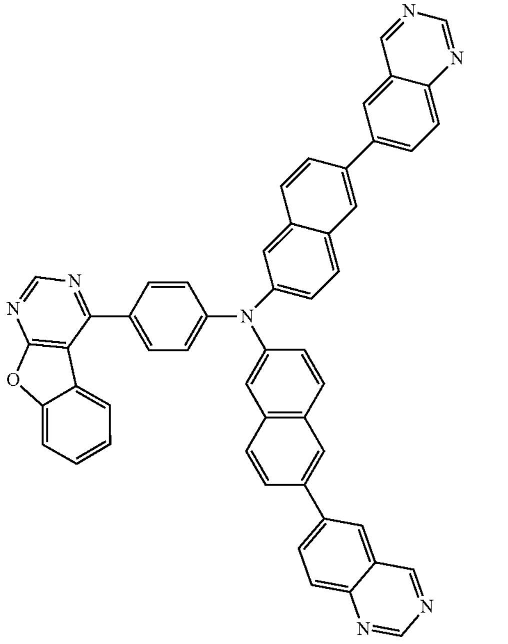
-continued
M241
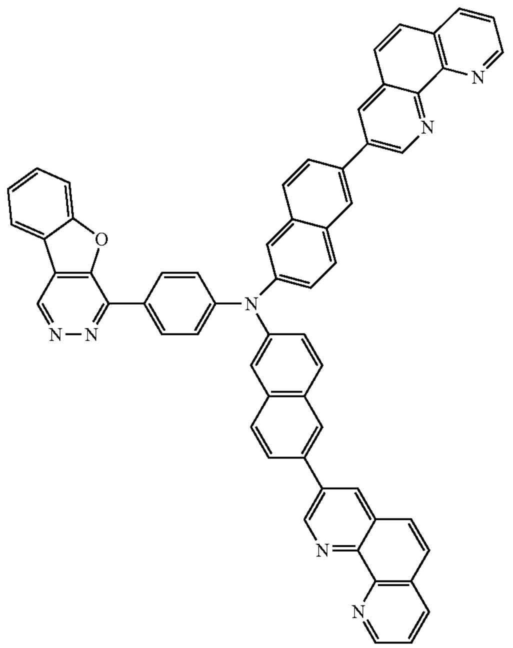
M242
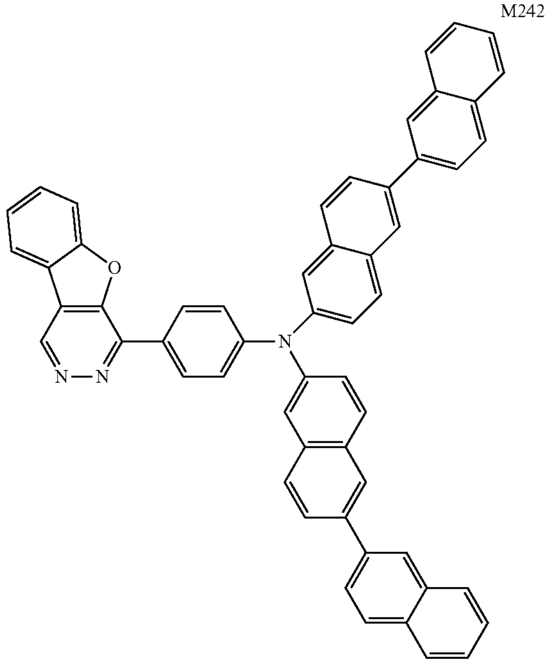

-continued
M243
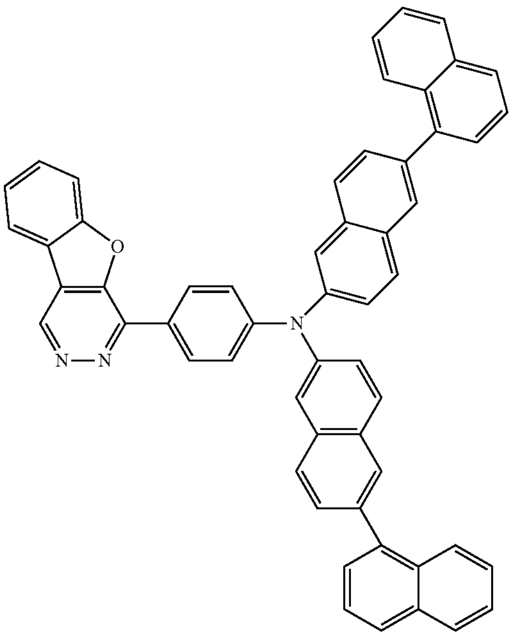
M244
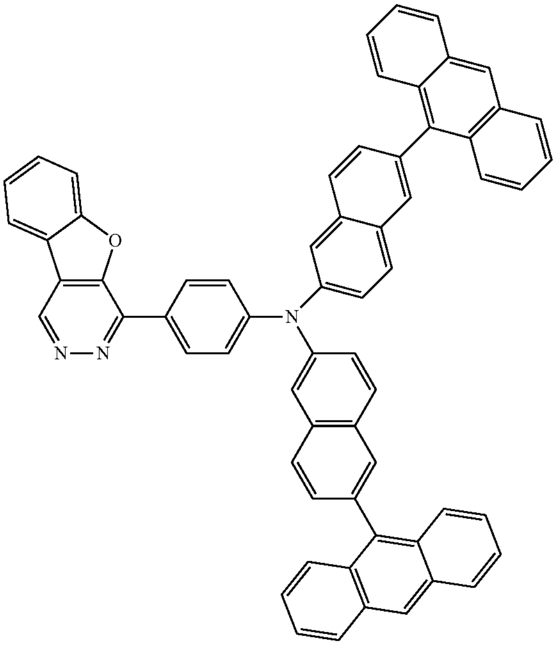
-continued
M245
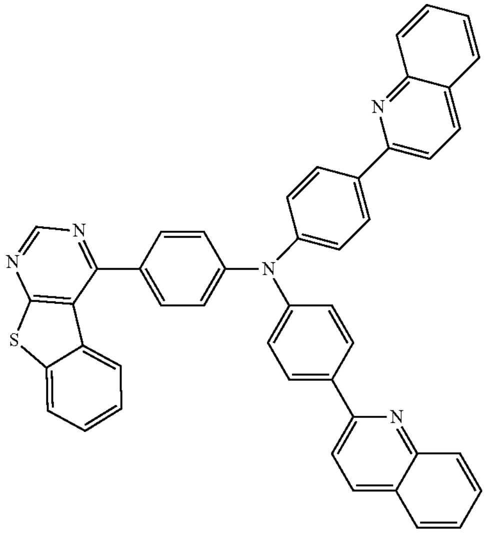
M246
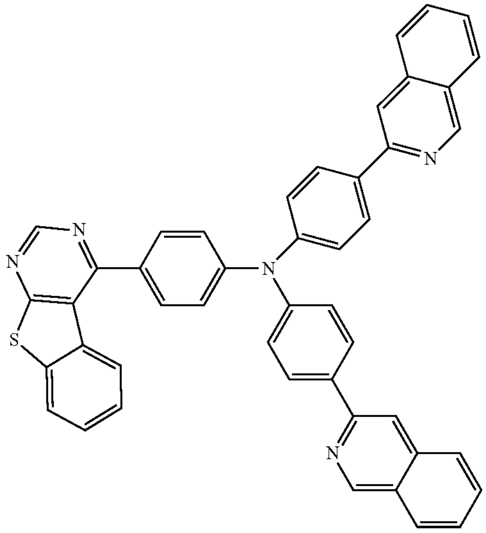
M247
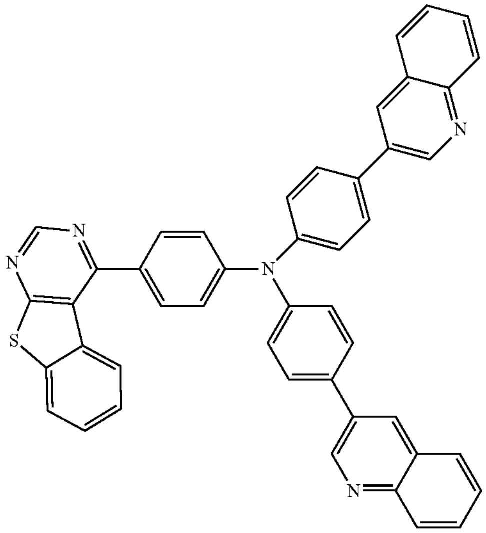

-continued
M248
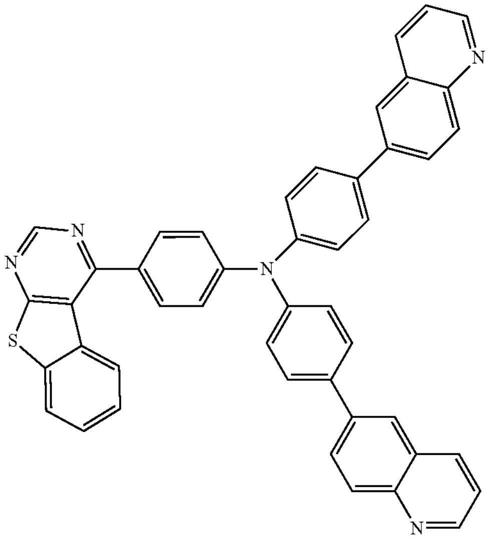
M249
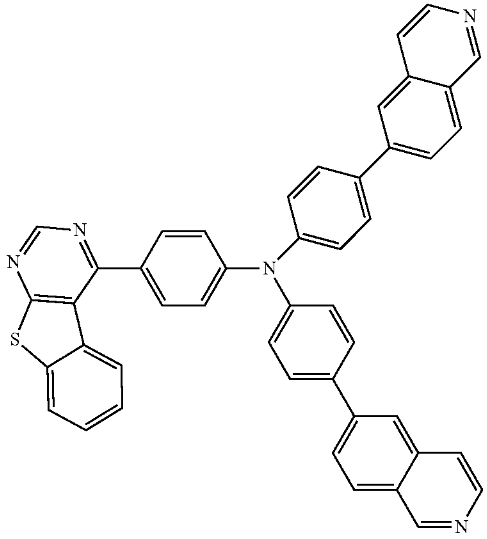
M250
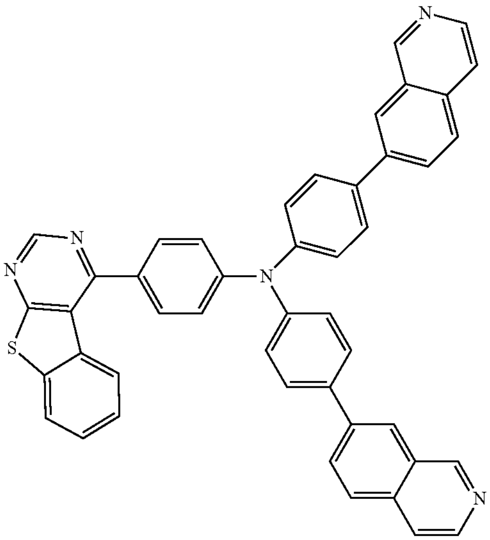
-continued
M251
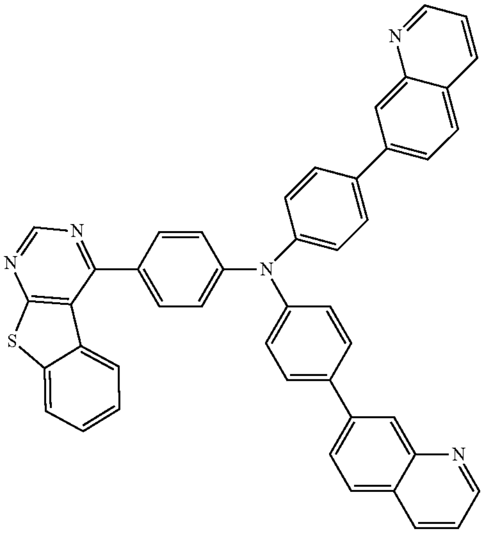
M252
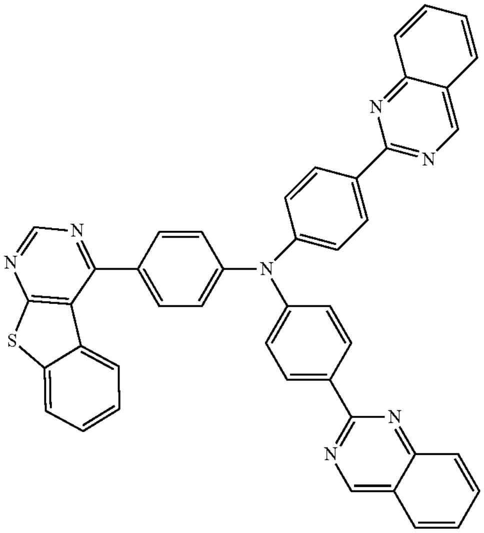
M253
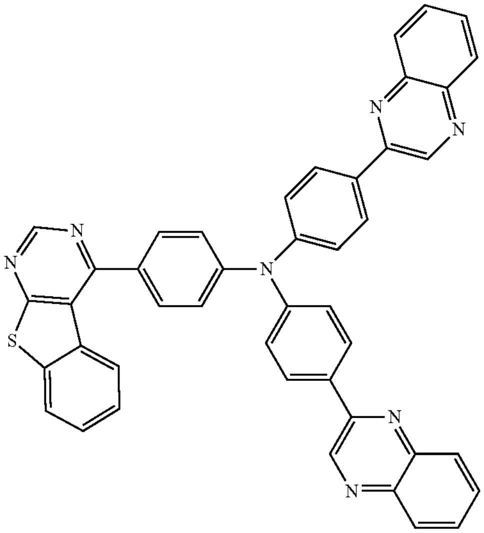

-continued
M254
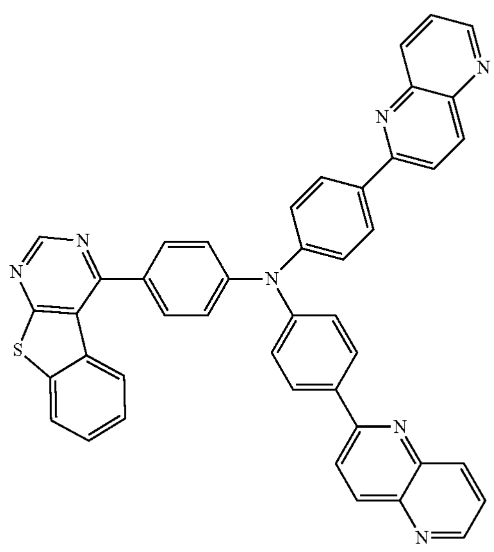
M255
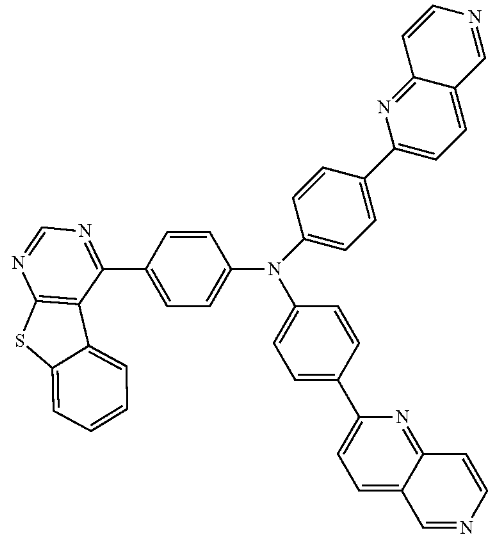
-continued
M256
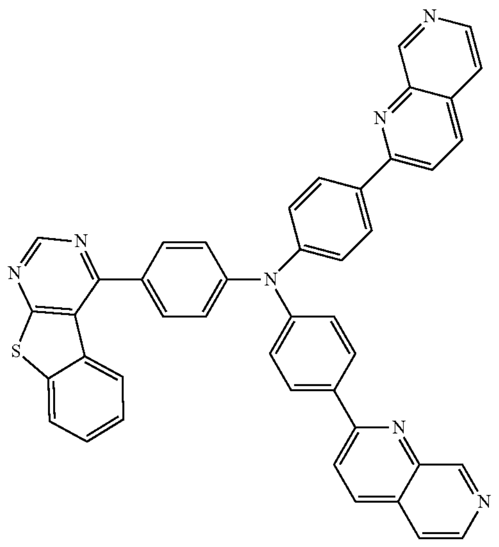
M257
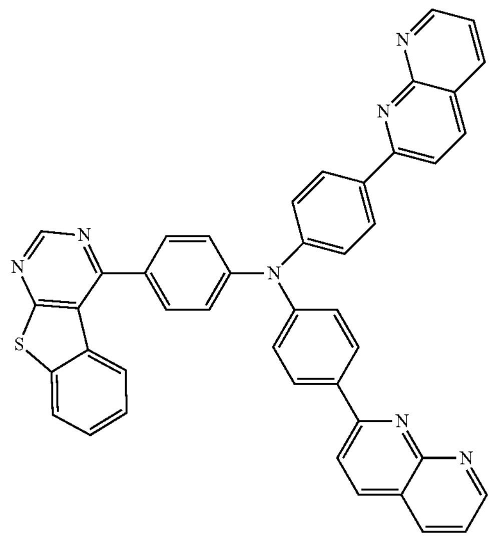
M258
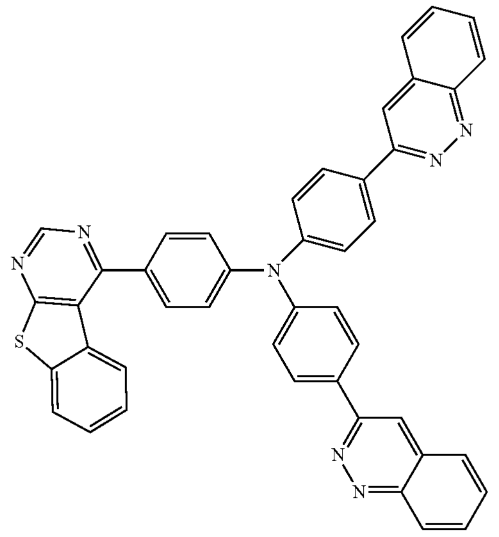

-continued
M259
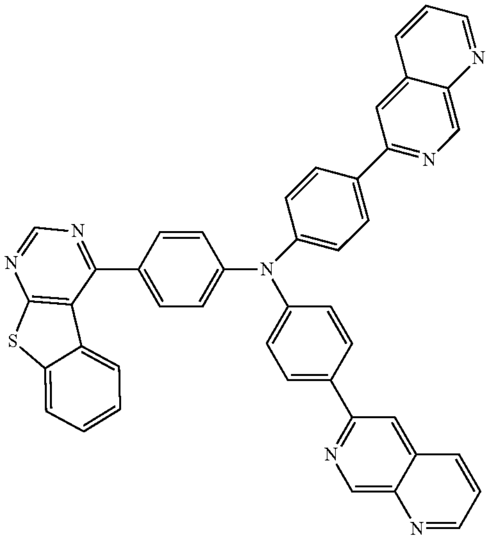
M260
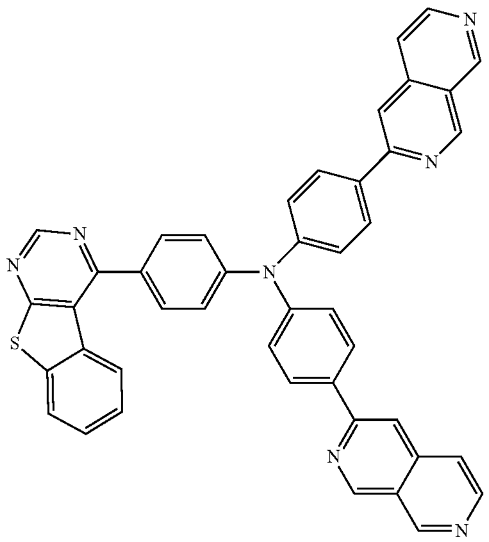
-continued
M253
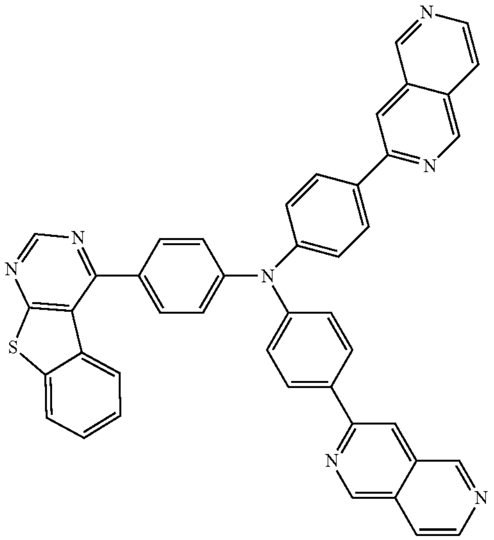
M254
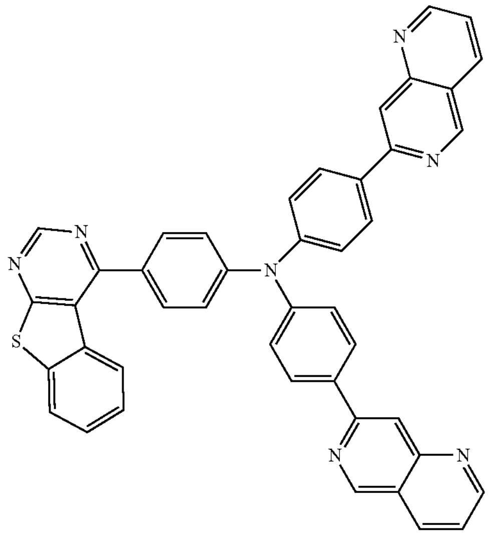
M255
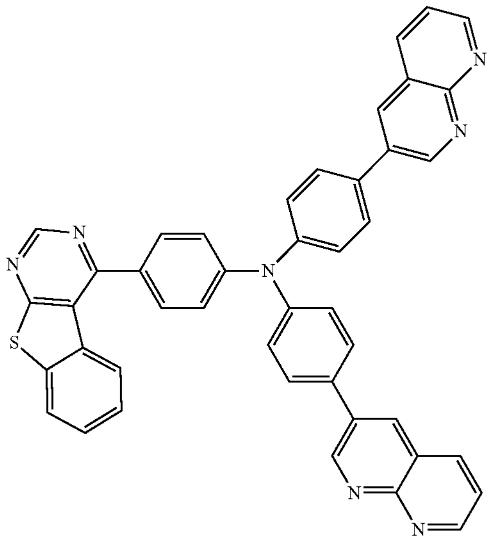

-continued
M256
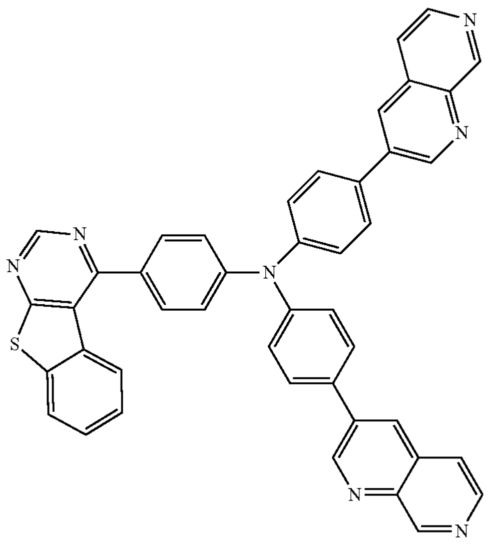
M257
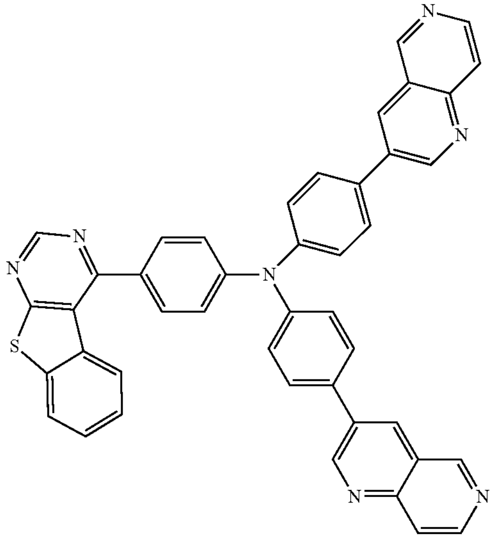
M258
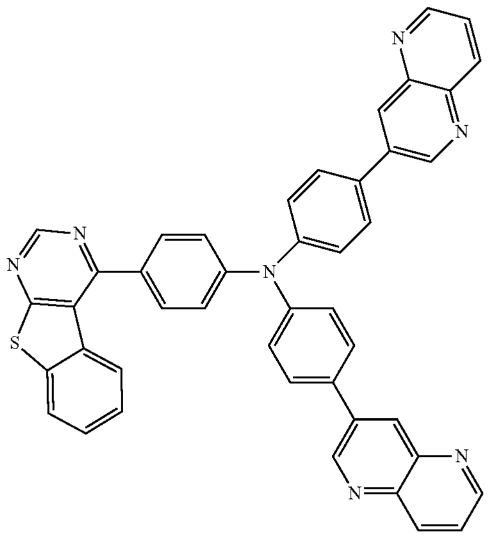
-continued
M259
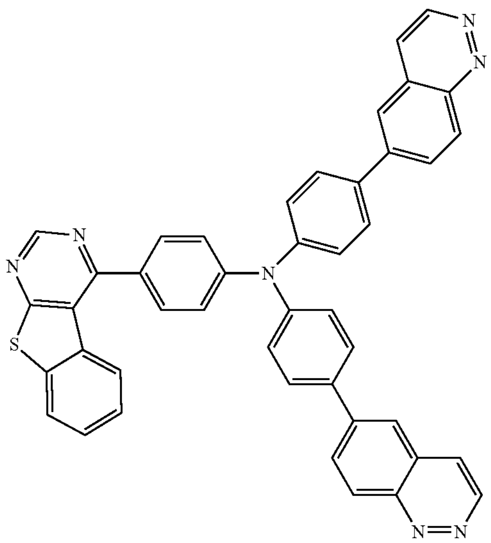
M260
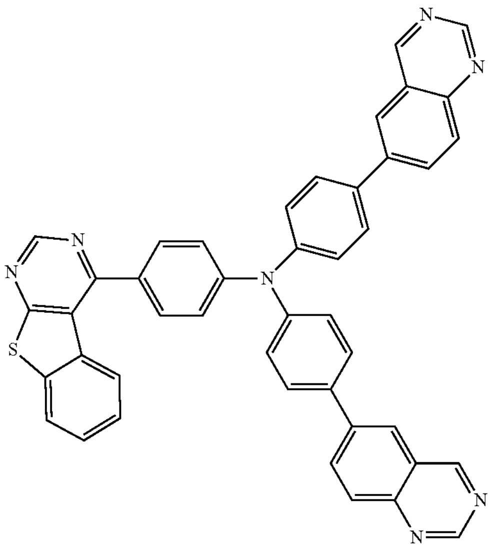

-continued
M261
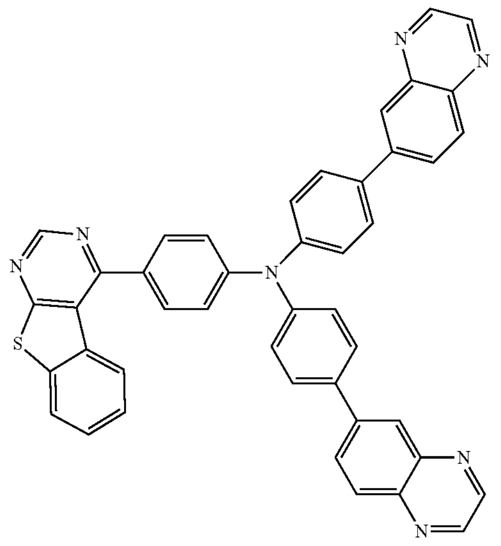
M262
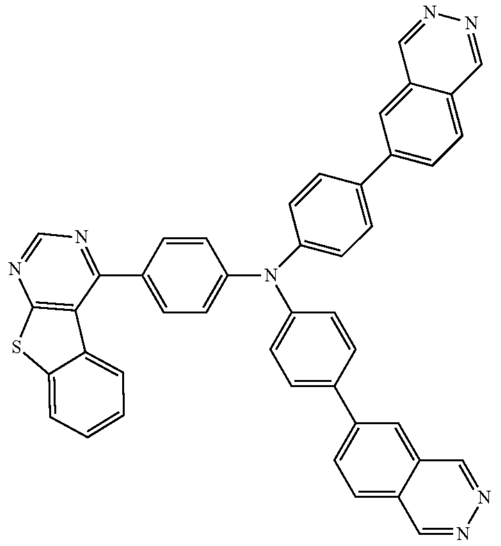
M263
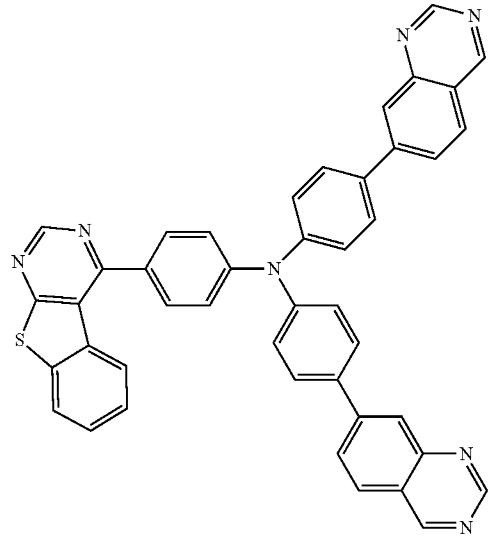
-continued
M264
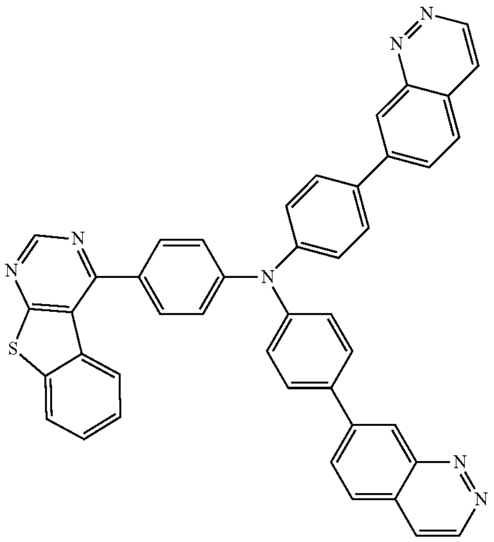
M265
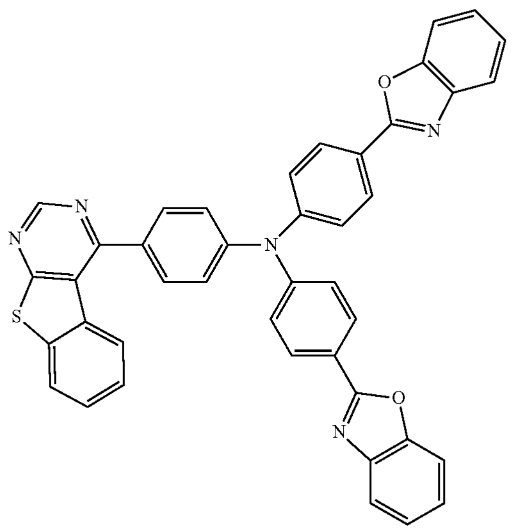
M266
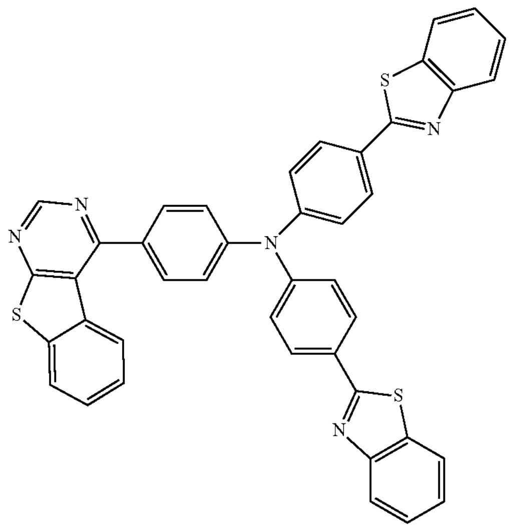

-continued
M267
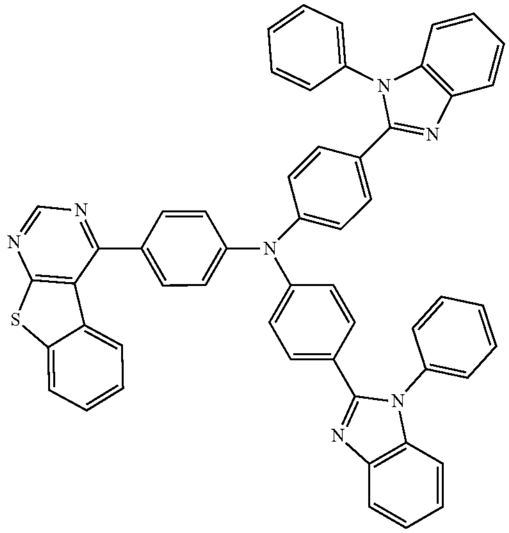
M268
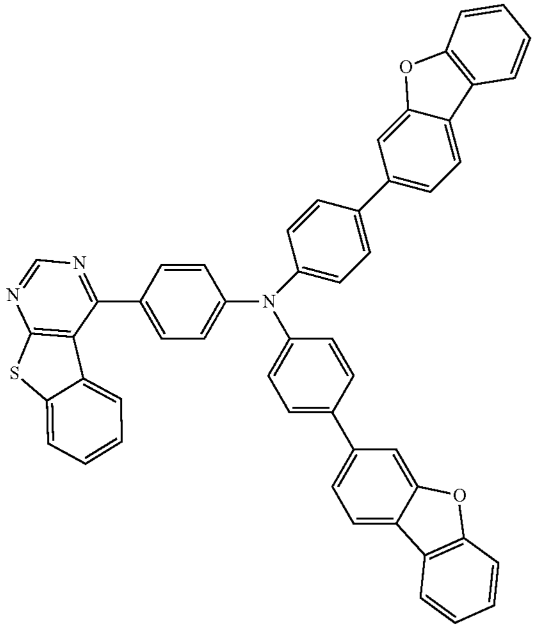
M289
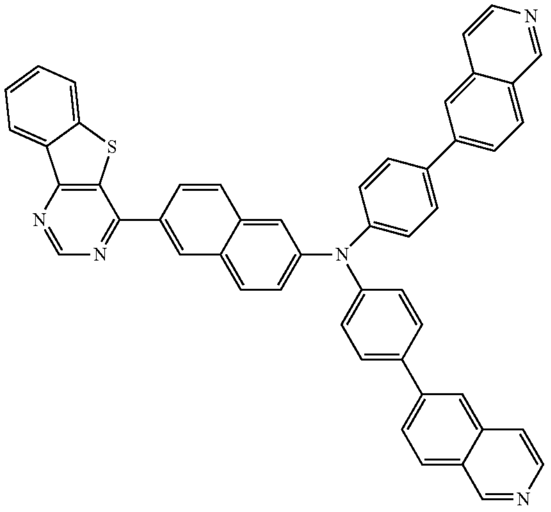
M290
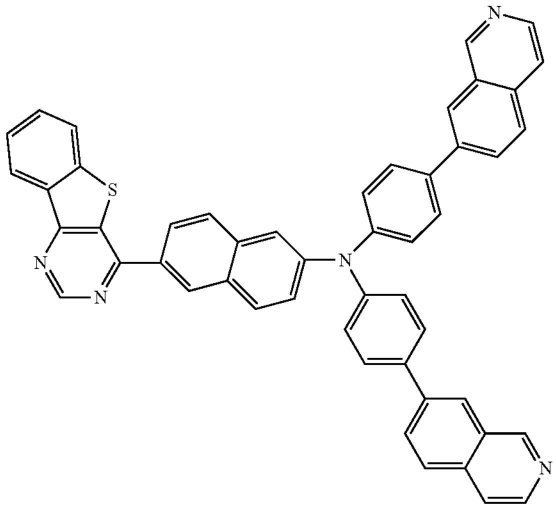
M291
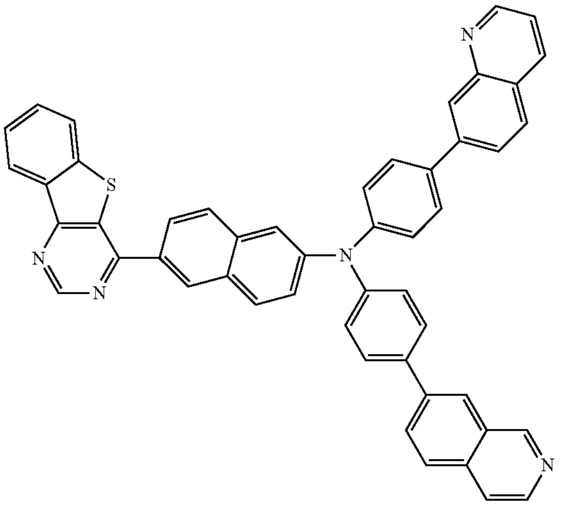

-continued
M292
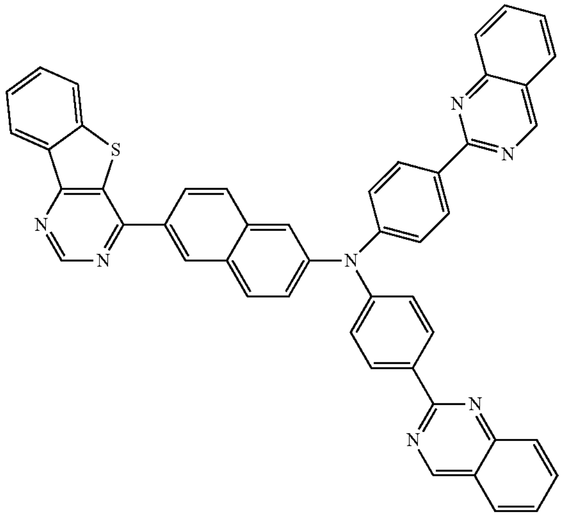
M293
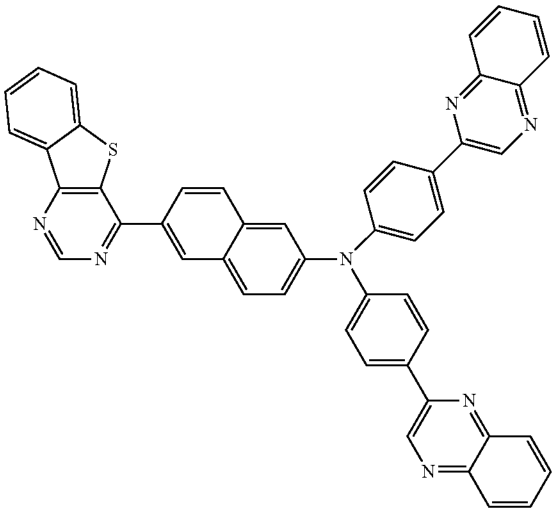
M294
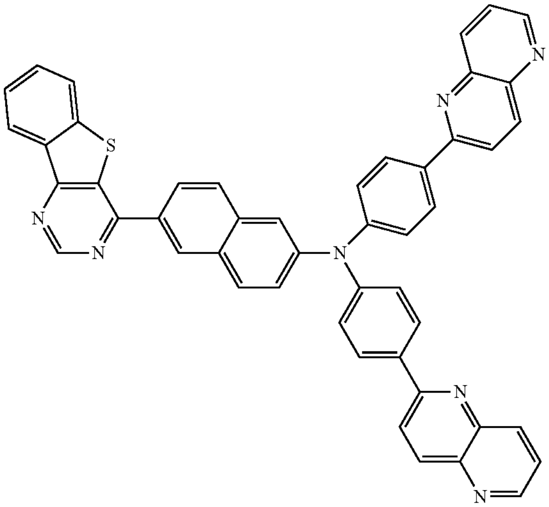
-continued
M295
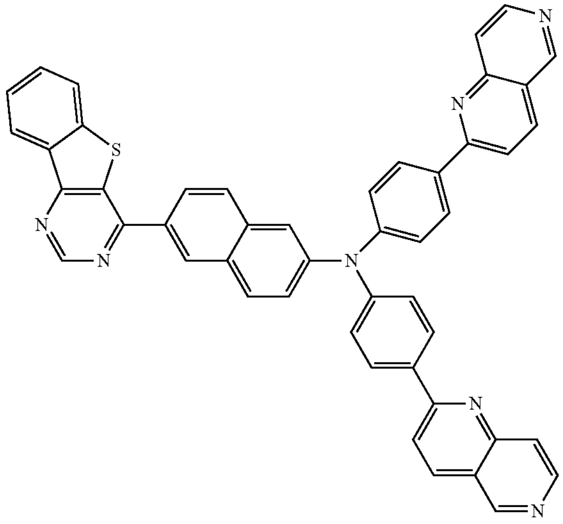
M296
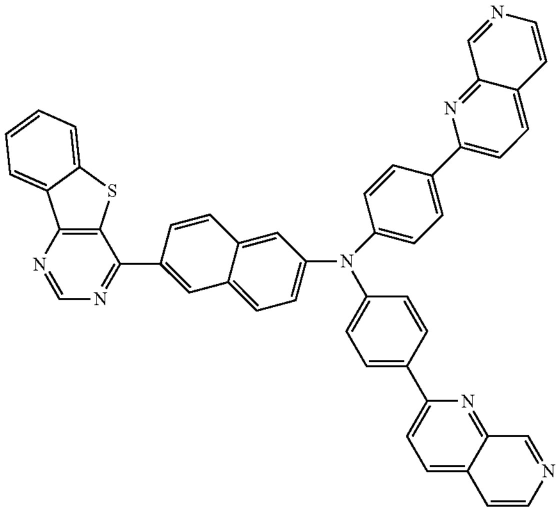
M297
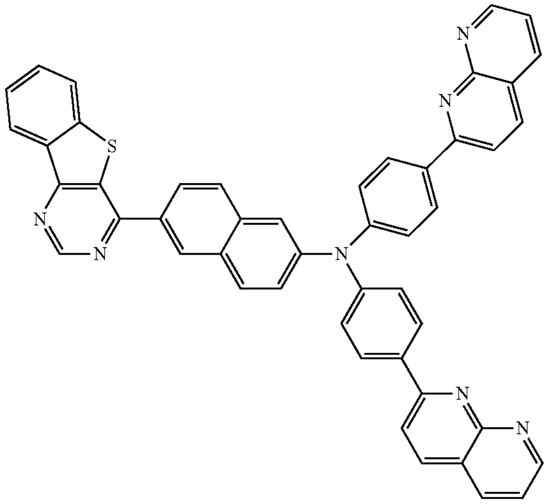

-continued
M298
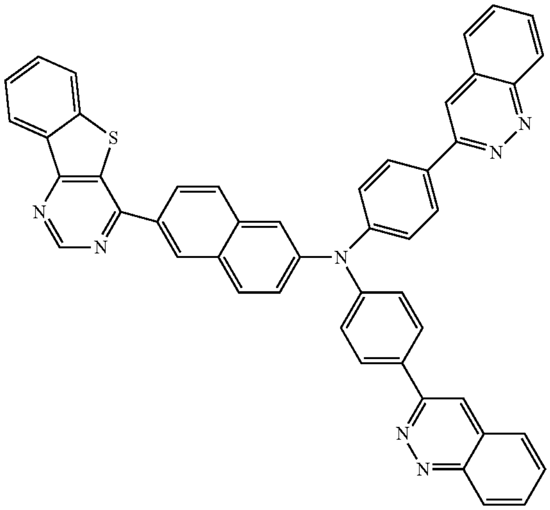
M299
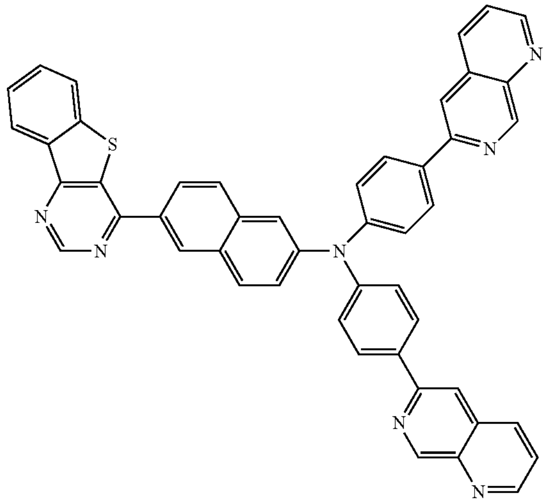
M300
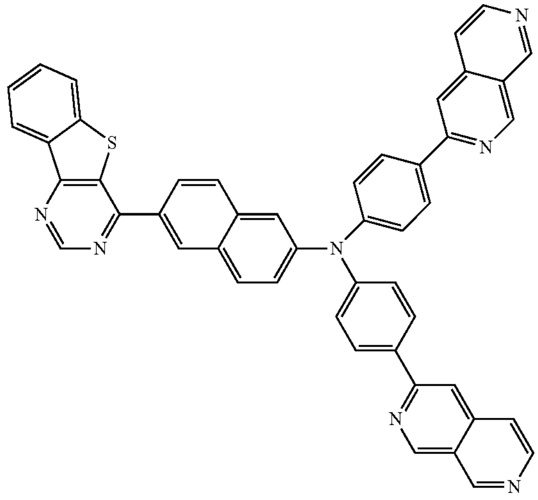
-continued
M301
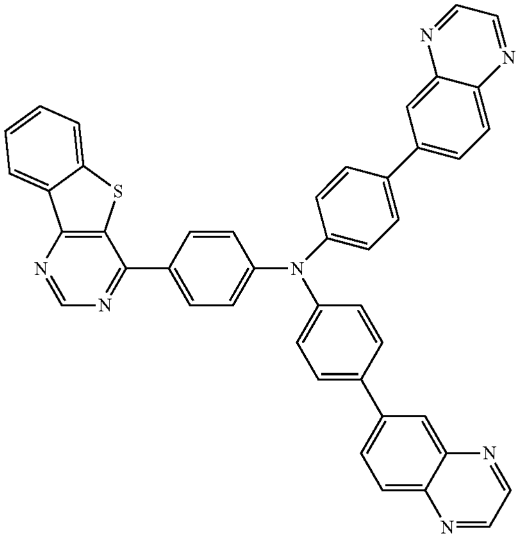
M302
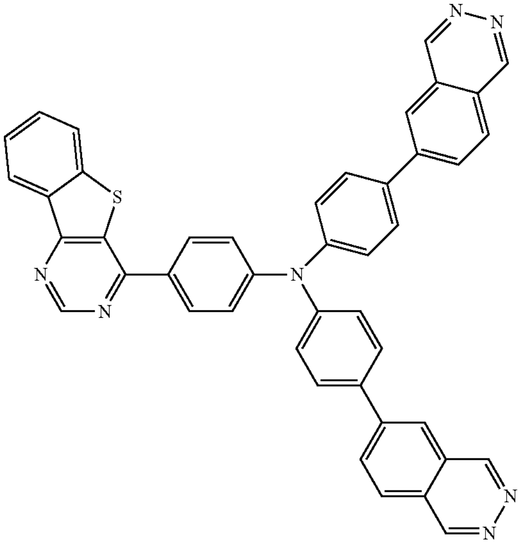

-continued
M303
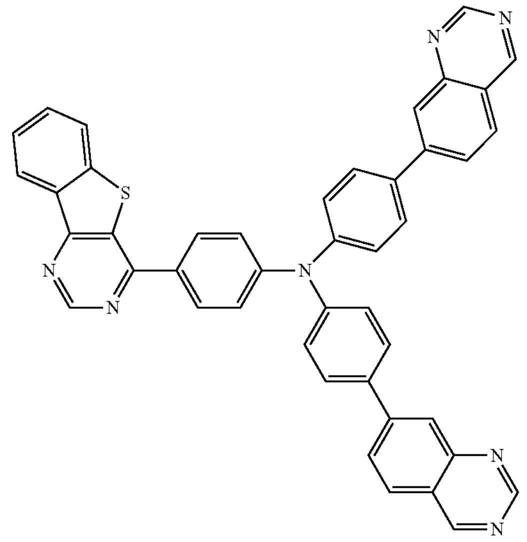
M304
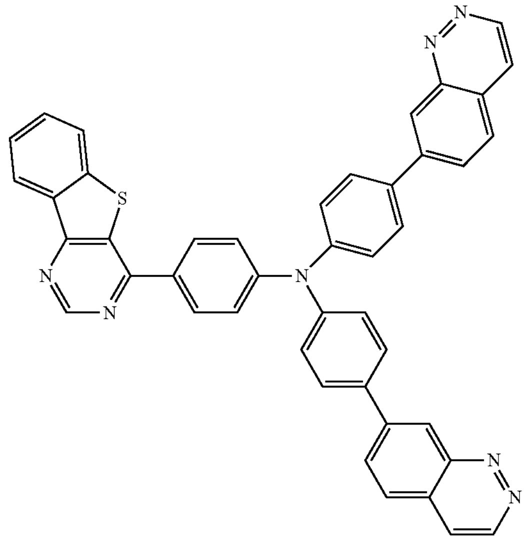
M305
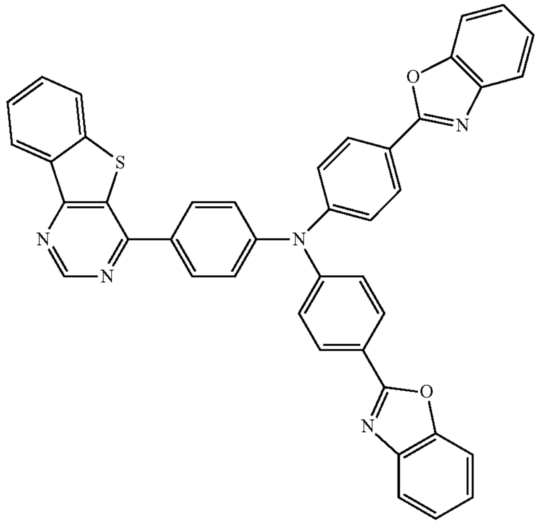
-continued
M306
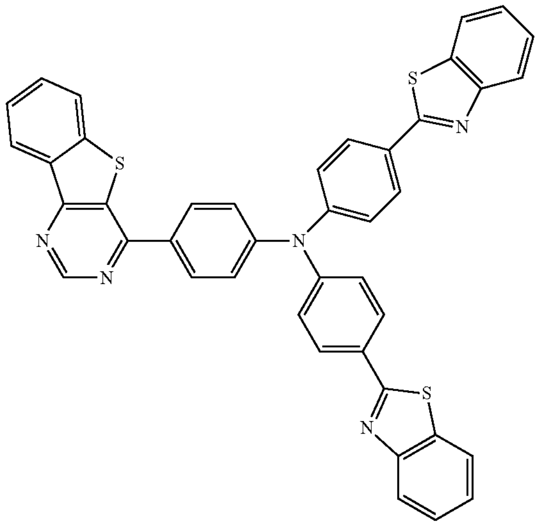
M307
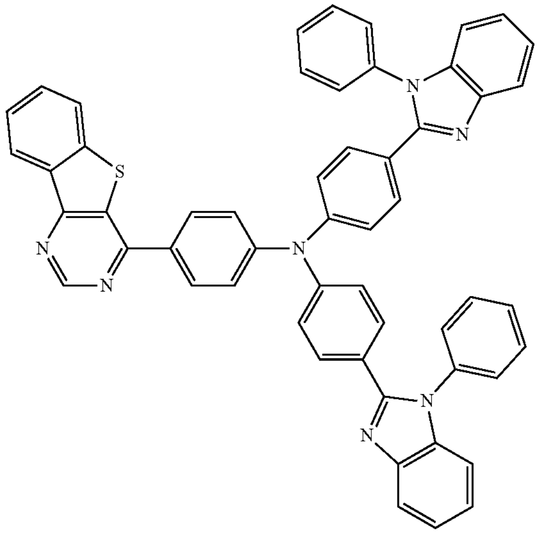

-continued
M308
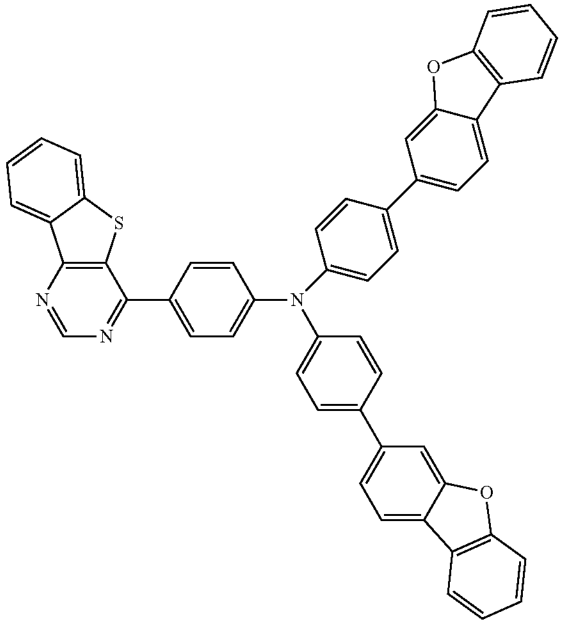
M393
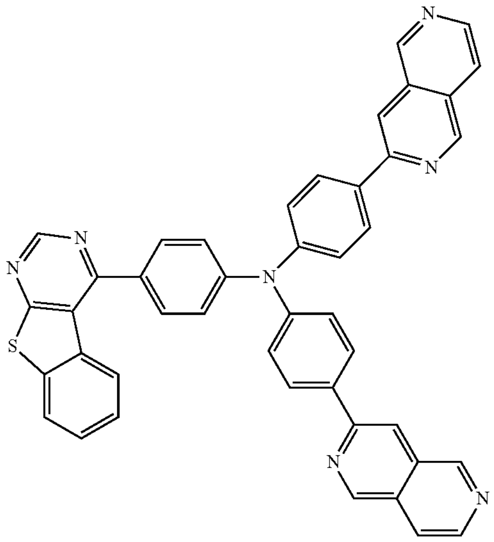
-continued
M394
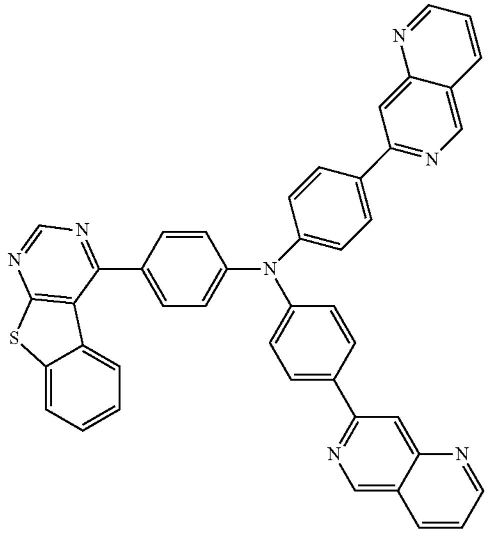
M395
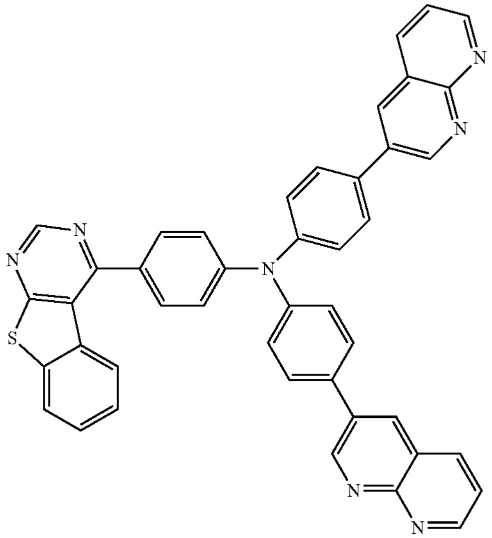
M396
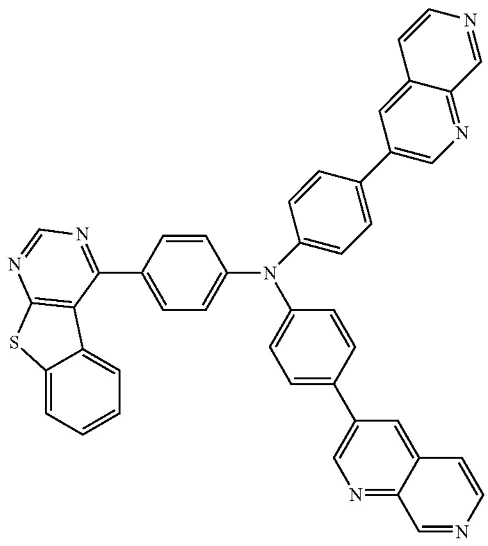

-continued
M397
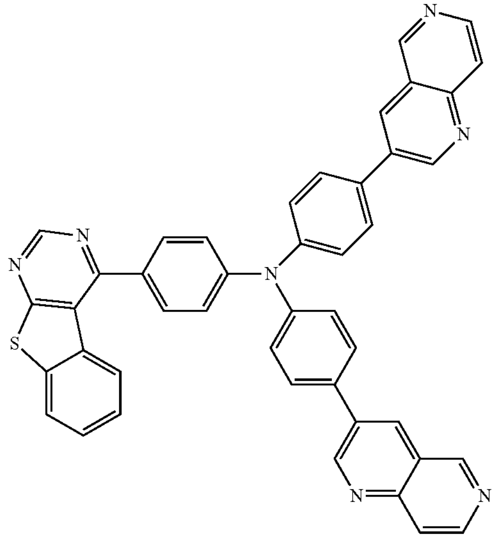
M398
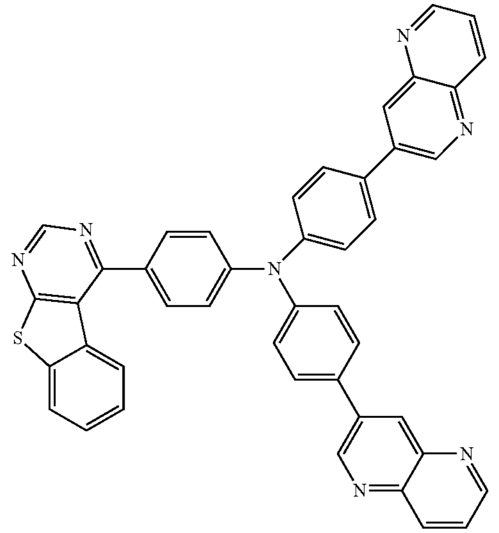
M399
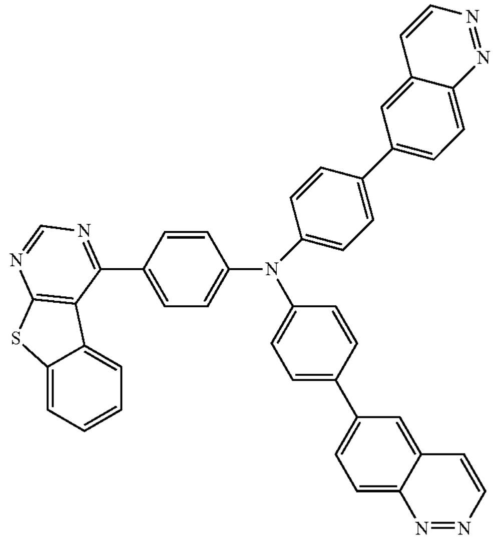
-continued
M400
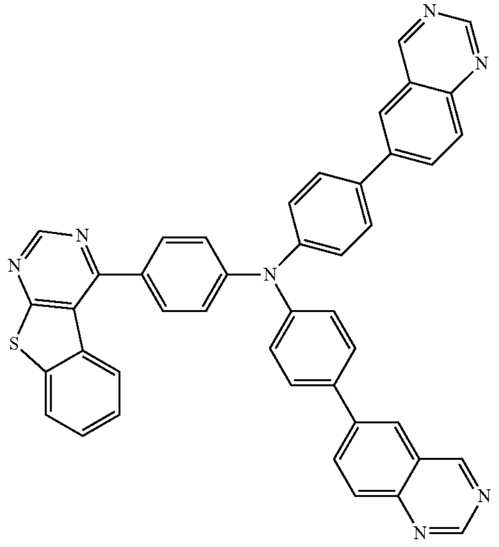
M433
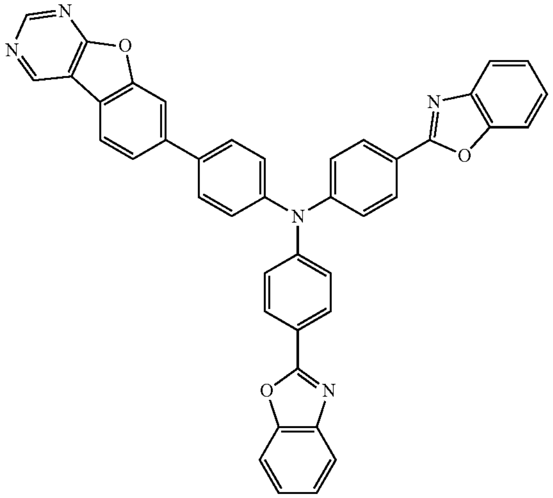
M434
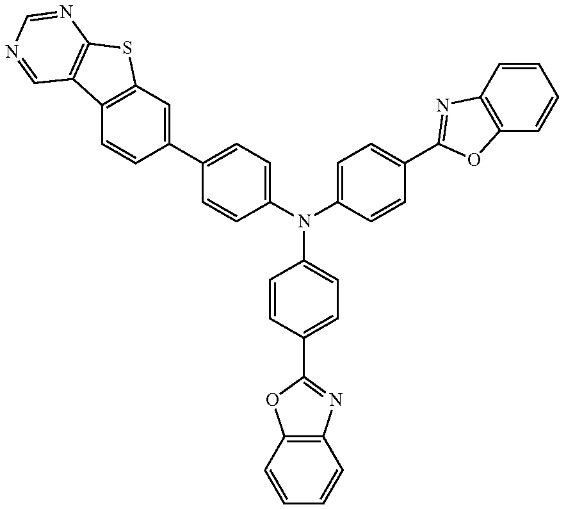

-continued
M435
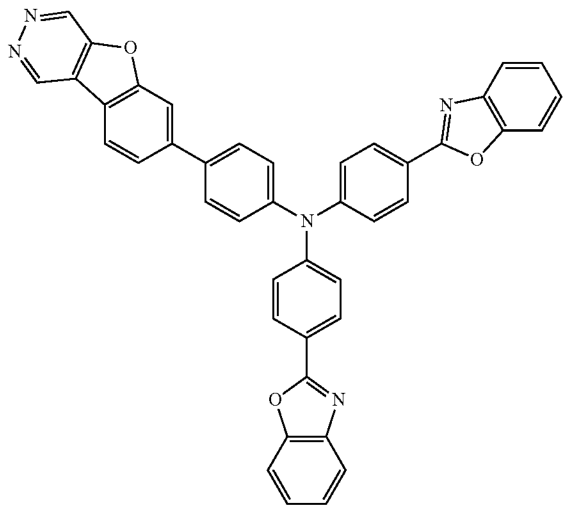
M436
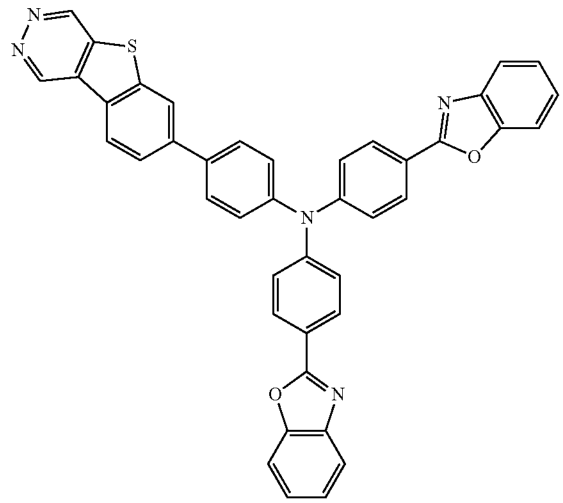
M441
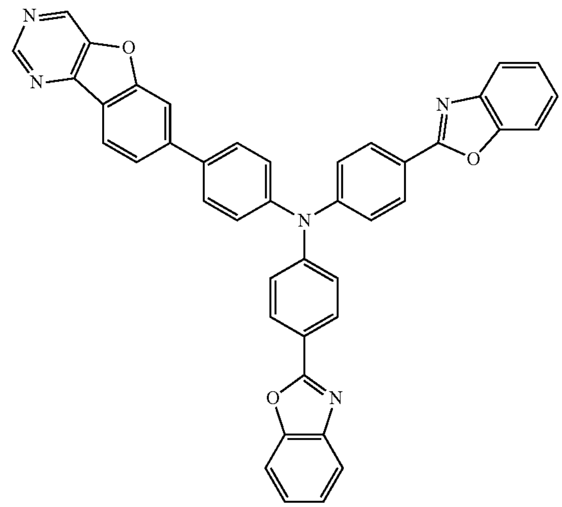
-continued
M442
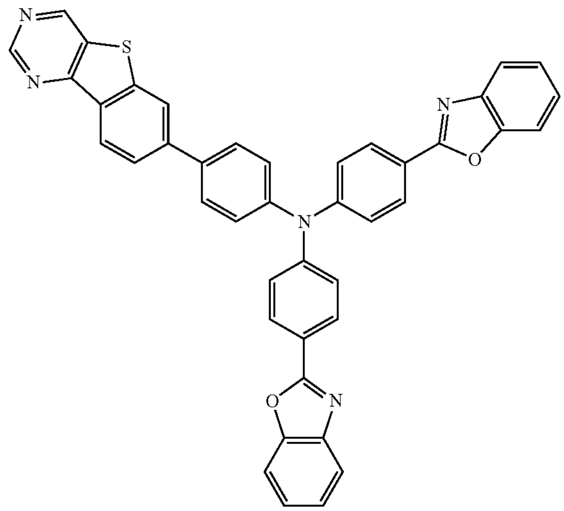
M447
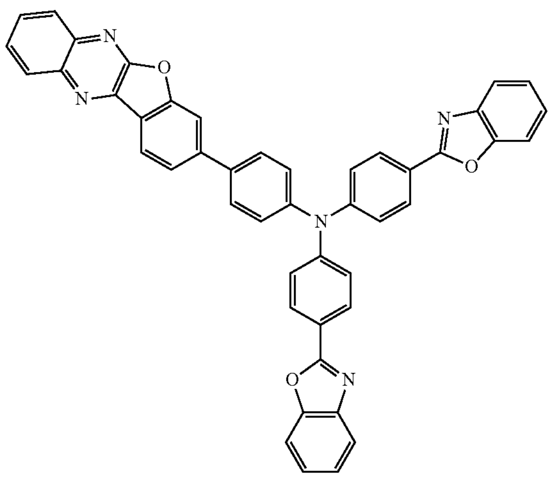
M448
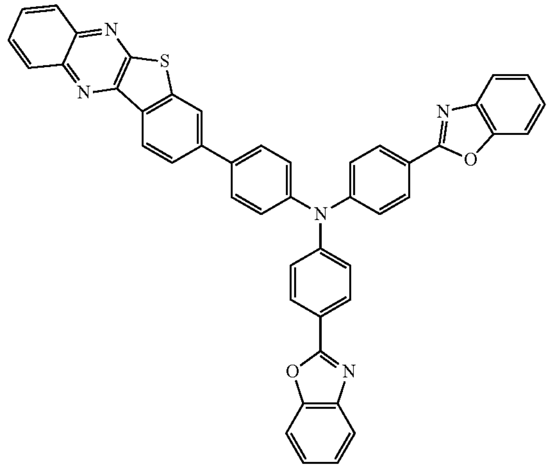

-continued
M449
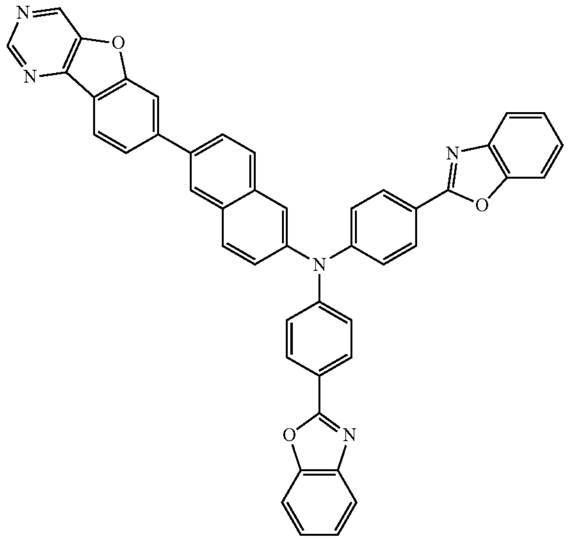
M450
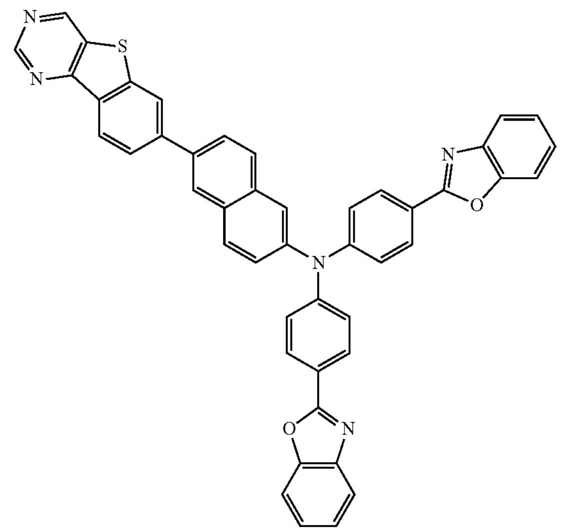
M455
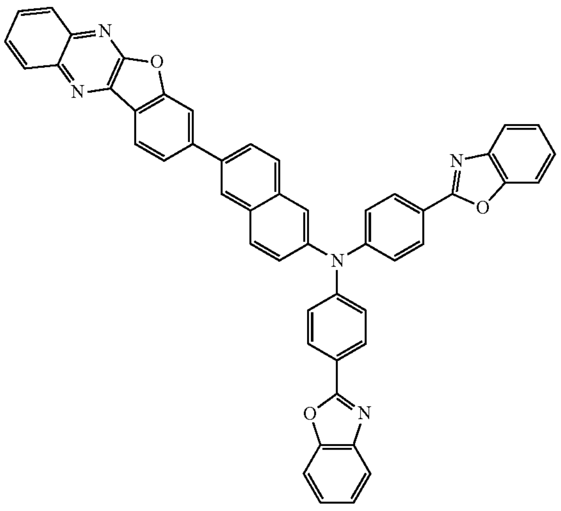
-continued
M456
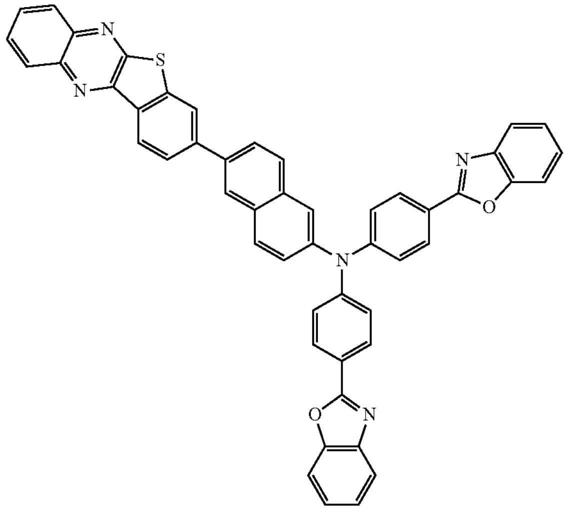
M457
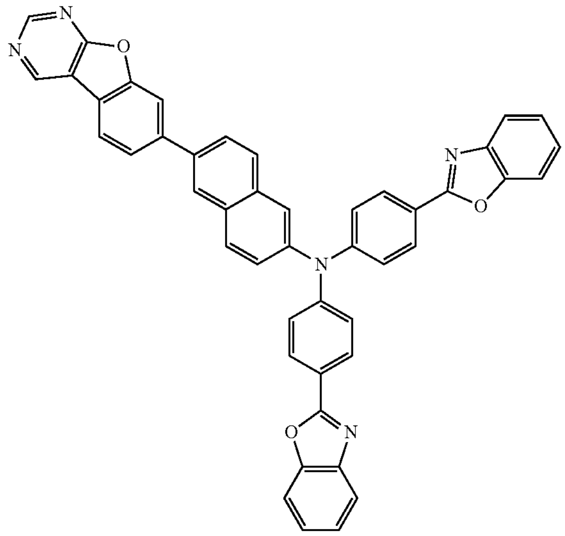
M458
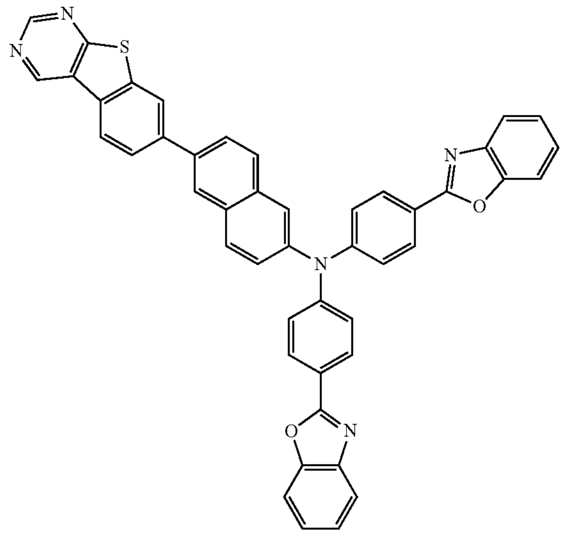

-continued

M459

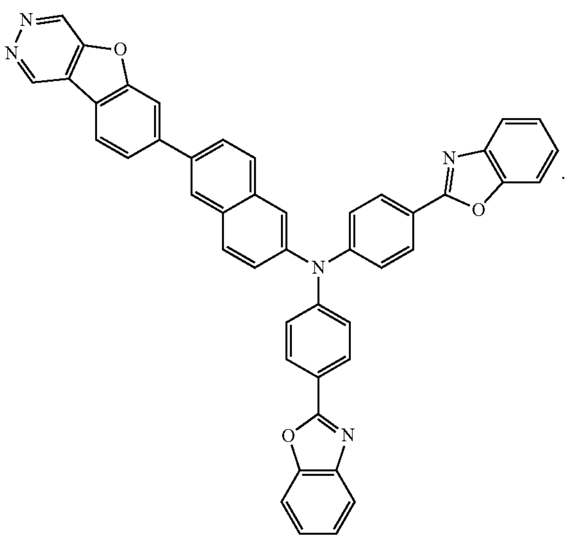

14. The display panel according to claim 10, wherein: the organic thin layer includes a hole transport layer, and the hole transport layer includes any one or a combination of the at least two of heterocyclic compounds, each heterocyclic compound comprising the structure in Formula I:

Formula I

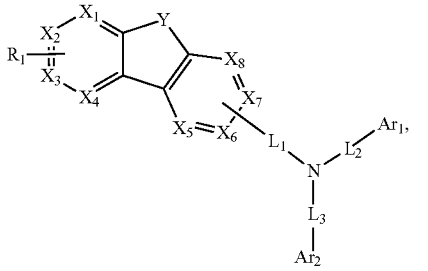

wherein Y is selected from O or S; at least one of $X_1$, $X_2$, $X_3$, $X_4$, $X_5$, $X_6$, $X_7$ and $X_8$ is a N atom, and the rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group condensed with adjacent groups; and $R_2$ is selected from a hydrogen atom, a deuterium atom, a substituted or unsubstituted C1-C5 alkyl group, a halogen, a cyano group, or an amino group.

15. The display panel according to claim 10, wherein: the organic thin layer includes an electron blocking layer, and the electron blocking layer includes any one or a combination of the at least two of the heterocyclic compounds, each heterocyclic compound comprising the structure in Formula I:

Formula I

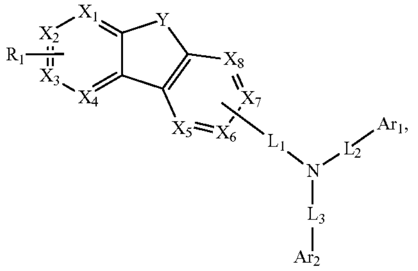

wherein Y is selected from O or S; at least one of $X_1$, $X_2$, $X_3$, $X_4$, $X_5$, $X_6$, $X_7$ and $X_8$ is a N atom, and the rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group condensed with adjacent groups; and $R_2$ is selected from a hydrogen atom, a deuterium atom, a substituted or unsubstituted C1-C5 alkyl group, a halogen, a cyano group, or an amino group.

16. A display device, comprising:

a display panel, the display panel including an organic light-emitting device, wherein:

the organic light-emitting device includes an anode, a cathode, and an organic thin layer disposed between the anode and the cathode, and the cathode is covered with a capping layer, and the capping layer includes any one or a combination of at least two of heterocyclic compounds, each heterocyclic compound comprising a structure in Formula I:

Formula I

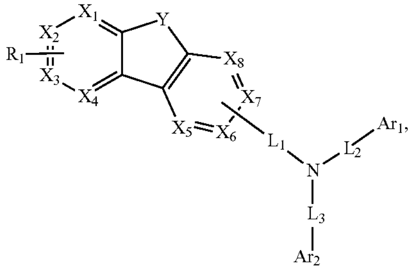

wherein Y is selected from O or S; two of $X_1$, $X_2$, $X_3$, $X_4$, $X_5$, $X_6$, $X_7$ and $X_8$ are a N atom and the two N atoms are positioned within a same ring, and rest are $CR_2$; $L_1$, $L_2$, and $L_3$ are independently selected from single bond, substituted or unsubstituted aromatic groups; $Ar_1$ and $Ar_2$ are independently selected from substituted or unsubstituted aromatic groups or heteroaryl groups; $R_1$ is selected from a hydrogen atom, a deuterium atom, or an aromatic group or a heteroaryl group to be condensed with a ring including X1, X2, X3, and X4, and one of X5 through X8 is bonded to the L1-N(L2Ar1)(L3Ar2) group, and one of X1 through X4 is bonded to R1; and $R_2$ is selected from a hydrogen atom, a deuterium atom, a substituted or unsubstituted C1-C5 alkyl group, a halogen, a cyano group, or an amino group.

* * * * *